(12) United States Patent
Fan et al.

(10) Patent No.: US 10,934,363 B2
(45) Date of Patent: *Mar. 2, 2021

(54) CHIMERIC ANTIGEN RECEPTORS BASED ON SINGLE DOMAIN ANTIBODIES AND METHODS OF USE THEREOF

(71) Applicant: Legend Biotech USA Inc., New Castle, DE (US)

(72) Inventors: Xiaohu Fan, Edmonton (CA); Chuan-Chu Chou, Westfield, NJ (US); Qiuchuan Zhuang, Jiangsu (CN); Pingyan Wang, Anhui (CN); Lin Wang, Jiangsu (CN); Lei Yang, Anhui (CN); Jiaying Hao, Jiangsu (CN)

(73) Assignee: Legend Biotech USA Inc., Wilmington, DE (US)

( * ) Notice: Subject to any disclaimer, the term of this patent is extended or adjusted under 35 U.S.C. 154(b) by 245 days.

This patent is subject to a terminal disclaimer.

(21) Appl. No.: 15/751,609

(22) PCT Filed: Aug. 10, 2016

(86) PCT No.: PCT/CN2016/094408
§ 371 (c)(1),
(2) Date: Feb. 9, 2018

(87) PCT Pub. No.: WO2017/025038
PCT Pub. Date: Feb. 16, 2017

(65) Prior Publication Data
US 2018/0230225 A1    Aug. 16, 2018

(30) Foreign Application Priority Data

Aug. 11, 2015 (CN) .......................... 201510490002.8
Nov. 2, 2015 (CN) .......................... 201510733585.2

(51) Int. Cl.
| | |
|---|---|
| C07K 16/28 | (2006.01) |
| C07K 14/725 | (2006.01) |
| C07K 14/705 | (2006.01) |
| C07K 16/30 | (2006.01) |
| A61K 35/17 | (2015.01) |
| C12N 5/0783 | (2010.01) |
| C07K 19/00 | (2006.01) |
| C12N 5/10 | (2006.01) |
| C12N 15/62 | (2006.01) |
| C12N 15/63 | (2006.01) |

(52) U.S. Cl.
CPC .......... *C07K 16/2878* (2013.01); *A61K 35/17* (2013.01); *C07K 14/7051* (2013.01); *C07K 14/70517* (2013.01); *C07K 14/70521* (2013.01); *C07K 14/70575* (2013.01); *C07K 14/70578* (2013.01); *C07K 14/70596* (2013.01); *C07K 16/2803* (2013.01); *C07K 16/2887* (2013.01); *C07K 16/2896* (2013.01); *C07K 16/30* (2013.01); *C07K 16/3061* (2013.01); *C07K 19/00* (2013.01); *C12N 5/0636* (2013.01); *C12N 5/10* (2013.01); *C12N 15/62* (2013.01); *C12N 15/63* (2013.01); *C07K 2317/22* (2013.01); *C07K 2317/31* (2013.01); *C07K 2317/35* (2013.01); *C07K 2317/569* (2013.01); *C07K 2317/622* (2013.01); *C07K 2319/02* (2013.01); *C07K 2319/03* (2013.01); *C07K 2319/21* (2013.01); *C07K 2319/30* (2013.01); *C07K 2319/33* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 2010/0136018 A1 | 6/2010 | Dolk et al. | |
| 2012/0034160 A1 | 2/2012 | Ghayur et al. | |
| 2013/0156769 A1 | 6/2013 | Kufer et al. | |
| 2014/0099340 A1* | 4/2014 | June ........................ | A61K 35/17 424/277.1 |
| 2014/0161828 A1* | 6/2014 | Armitage ............ | A61K 39/3955 424/181.1 |
| 2015/0038684 A1* | 2/2015 | Jensen ................... | C07K 14/71 530/391.9 |
| 2016/0046724 A1 | 2/2016 | Brogdon et al. | |
| 2020/0078399 A1 | 3/2020 | Fan et al. | |

FOREIGN PATENT DOCUMENTS

| | | |
|---|---|---|
| CN | 104136458 A | 11/2014 |
| CN | 104379179 A | 2/2015 |
| CN | 104583230 A | 4/2015 |
| CN | 105143263 A | 12/2015 |

(Continued)

OTHER PUBLICATIONS

Deaglio et al., "CD38/CD19: a lipid raft-dependent signaling complex in human B cells," Blood, vol. 109, No. e105, pp. 5390-5398 (2007).

Grada et al., "TanCAR: A Novel Bispecific Chimeric Antigen Receptor for Cancer Immunotherapy," Citation: Molecular Therapy—Nucleic Acids, vol. 2, pp. 1-11 (2013).

Jamnani et al., "T cells expressing VHH-directed oligoclonal chimeric HER2 antigen receptors: Towards tumor-directed oligclonal T cell therapy," Biochimica et Bop[jusoca Acta, vol. 1840, pp. 378-386 (2014).

(Continued)

*Primary Examiner* — Brad Duffy
(74) *Attorney, Agent, or Firm* — Jones Day

(57) ABSTRACT

The present application provides single-domain antibodies, and chimeric antigen receptors comprising one or more antigen binding domains each comprising a single-domain antibody. Further provided are engineered immune effector cells (such as T cells) comprising the chimeric antigen receptors. Pharmaceutical compositions, kits and methods of treating cancer are also provided.

24 Claims, 10 Drawing Sheets

Specification includes a Sequence Listing.

(56) References Cited

FOREIGN PATENT DOCUMENTS

| | | |
|---|---|---|
| CN | 105384825 A | 3/2016 |
| CN | 105658671 A | 6/2016 |
| CN | 105777911 A | 7/2016 |
| EP | 3029067 A1 | 6/2016 |
| JP | 2015-504306 A | 2/2015 |
| JP | 2015-513394 A | 5/2015 |
| WO | WO 1998024893 A2 | 6/1998 |
| WO | WO 2008074867 A2 | 6/2008 |
| WO | WO 2008074867 A3 | 6/2008 |
| WO | WO 2011154453 A1 | 12/2011 |
| WO | 2013123061 A1 | 8/2013 |
| WO | WO 2013126729 A1 | 8/2013 |
| WO | WO 2013154760 A1 | 10/2013 |
| WO | WO 2014011988 A2 | 1/2014 |
| WO | WO 2014011988 A3 | 1/2014 |
| WO | WO 2014089335 A2 | 6/2014 |
| WO | WO 2014089335 A3 | 6/2014 |
| WO | WO 2014122143 A1 | 8/2014 |
| WO | WO 2014153270 A1 | 9/2014 |
| WO | WO 2014165707 A2 | 10/2014 |
| WO | WO 2014165707 A3 | 10/2014 |
| WO | WO 2015052538 A1 | 4/2015 |
| WO | 2015120187 A1 | 8/2015 |
| WO | 2016014789 A2 | 1/2016 |
| WO | WO 2016014565 A2 | 1/2016 |
| WO | WO 2016014565 A3 | 1/2016 |
| WO | 2016094304 A2 | 6/2016 |
| WO | 2017025038 A1 | 2/2017 |
| WO | 2018028647 A1 | 2/2018 |

OTHER PUBLICATIONS

Kalled et al., "The role of BAFF in immune function and implications for autoimmunity," Immunological Review, vol. 204, pp. 43-54 (2015).
Konopleva et al., "Ligation of Cell Surface CD38 Protein with Agonistic Monoclonal Antibody Induces a Cell Growth Signal in Myeloid Leukemia Cells," The Journal of Immunology, vol. 161, pp. 4702-4708 (1998).
Lin et al., "Flow Cytometric Immunophenotypic Analysis of 306 Cases of Multiple Myeloma," Am. J. Clin. Pathol., vol. 121, pp. 482-488 (2004).
Lokhorst et al., "Targeting CD38 with Daratumumab Monotherapy in Multiple Myeloma," The New England Journal of Medicine, vol. 373, pp. 1-13 (2015) Downloaded from nejm.org on Aug. 26, 2015.
Mackay et al., "BAFF and APRIL: A Tutorial on B Cell Survival," Annu. Rev. Immunol., vol. 21, pp. 231-264 (2003).
Neri et al., "Neutralizing B-Cell-Activating Factor Antibody Improves Survival and Inhibits Osteoclastogenesis in a Severe Combined Immunodeficient Human Multiple Myeloma Model," Clin. Cancer Res., vol. 13, No. 19, pp. 5903-5909 (2007).
Novak et al., "Expression of BCMA, TACI, and BAFF-R in multiple myeloma: a mechanism for growth and survival," Blood, vol. 103, No. 2, pp. 689-694 (2004).
Oden et al., "Potent anti-tumor response by targeting B cell maturation antigen (BCMA) in a mouse model of multiple myeloma," Molecular Oncology, vol. 9, pp. 1348-1358 (2015).
Thompson et al., "BAFF Binds to the Tumor Necrosis Factor Receptor-like Molecule B Cell Maturation Antigen and Is Important for Maintaining the Peripheral B Cell Population," J. Exp. Med., vol. 192, No. 1, pp. 129-135 (Jul. 2, 2000).
International Preliminary Report on Patentability dated Feb. 22, 2018 in International Application No. PCT/CN2016/094408.
International Search Report dated Nov. 18, 2016 in International Application No. PCT/CN2016/094408.
Written Opinion dated Nov. 18, 2016 in International Application No. PCT/CN2016/094408.
Hoffmann et al., "Serial Killing of tumor cells by cytotoxic T Cells redirected with a CD19-/CD3-bispecific single-chain antibody construct" Int. J. Cancer, 115, pp. 98-104, 2005.
Hegde et al., "Tandem CAR T cells targeting HER2 and IL 13Ra2 mitigate tumor antigen escape", Journal of Clinical Investigation, 126(8), pp. 3036-3052, 2016.
Int'l Search Report dated Nov. 8, 2017 in Int'l Application No. PCT/CN2017/096938.
Int'l Written Opinion of the Int'l Searching Authority dated Nov. 8, 2017 in Int'l Application No. PCT/CN2017/096938.
Int'l Preliminary Report on Patentability dated Feb. 12, 2019 in Int'l Application No. PCT/CN2017/096938.
International Preliminary Report on Patentability dated Feb. 13, 2018 in International Application No. PCT/CN2016/094408.
Agaugue, et al; "Development of Safer & Optimized CAR-T Cells Using Lentiviral Vectors.", Cancer-Immunotherapy, Cancer Vaccines I, Molecular Therapy, vol. 23, pp. 88 (May 2015).
Chang, et al; "Chimeric antigen receptor-modified T cells against several target antigens in multiple myeloma.", ACCR 106th Annual Meeting, (Apr. 2015).
Ramadoss, et al., "An Anti-B Cell Maturation Antigen Bispecific Antibody for Multiple Myeloma", Journal of the American Chemical Society, vol. 213, pp. 5288-5291, (2015).
Brentjens et al., 2013, "CD19-targeted T cells rapidly induce molecular remissions in adults with chemotherapy-refractory acute lymphoblastic leukemia", Sci Transl Med., 5(177):177ra38 (11 pages).
De Munter et al., 2018, "Nanobody Based Dual Specific CARs", Int J Mol Sci., 19(2):403 (11 pages).
Grupp et al., 2013, "Chimeric antigen receptor-modified T cells for acute lymphoid leukemia", N Engl J Med., 368(16):1509-1518.
Kalos et al., 2011, "T cells with chimeric antigen receptors have potent antitumor effects and can establish memory in patients with advanced leukemia", Sci Transl Med., 3(95):95ra73 (13 pages).
Kijanka et al., 2015, "Nanobody-based cancer therapy of solid tumors", Nanomedicine (Lond), 10(1):161-174.
Liu et al., 2014, "Thermal stability and refolding capability of shark derived single domain antibodies", Mol Immunol., 59(2): 194-199.
Wang et al., 2013, "Construction and selection of camelized human sdAbs library against TNF-α", Military Medical Sciences, 37(5):339-344, English abstract only.
Yan et al., 2015, "Characterization and applications of Nanobodies against human procalcitonin selected from a novel naive Nanobody phage display library", J Nanobiotechnology, 13:33 (11 pages).

\* cited by examiner

CHIMERIC ANTIGEN RECEPTORS BASED ON SINGLE DOMAIN ANTIBODIES AND METHODS OF USE THEREOF

CROSS REFERENCE TO RELATED APPLICATIONS

This application is a Section 371 of international Application No. PCT/CN2016/094408, filed Aug. 10, 2016, which was published on Feb. 16, 2017 under International Publication No. WO 2017/025038 A1, which claims priority under 35 U.S.C. § 119(b) to Chinese Patent Application No. 201510490002.8 filed Aug. 11, 2015, and Chinese Patent Application No. 201510733585.2 filed Nov. 2, 2015. The contents of each application are incorporated herein by reference in its entirety.

REFERENCE TO SEQUENCE LISTING SUBMITTED ELECTRONICALLY

This application contains a sequence listing, which is submitted electronically via. EFS-Web as an ASCII formatted sequence listing with a file name "689296-1US Sequence Listing" and a creation date of Feb. 6, 2018, and having a size of 354 kB. The sequence listing submitted via EFS-Web is part of the specification and is herein incorporated by reference in its entirety.

FIELD OF THE PRESENT APPLICATION

The present invention relates to single-domain antibodies, chimeric antigen receptors, engineered immune effector cells, and methods of use thereof. The present invention further relates to activation and expansion of cells for therapeutic uses, especially for chimeric antigen receptor-based T cell immunotherapy.

BACKGROUND OF THE PRESENT APPLICATION

With the development of tumor immunotherapy and clinical technology, chimeric antigen receptor T cell (CAR-T) immunotherapy is now one of the most promising tumor immunotherapy approaches. Generally, a chimeric antigen receptor (CAR) comprises an extracellular antigen binding domain, a transmembrane domain and an intracellular signaling domain. The extracellular antigen binding domain may comprise a single chain variable fragment (scFv) targeting an identified tumor antigen. CARs can be expressed on the surface of T cells using gene transfection techniques. Upon binding to the target tumor antigen, the CARs can activate the T cells to launch specific anti-tumor response in an antigen-dependent manner without being limited by the availability of major histocompatibility complexes (MHC) specific to the target tumor antigen.

Single-domain antibodies (sdAbs) are different from conventional 4-chain antibodies by having a single monomeric antibody variable domain. For example, camelids and sharks produce single-domain antibodies named heavy chain-only antibodies (HcAbs), which naturally lack light chains. The antigen-binding fragment in each arm of the camelid heavy-chain only antibodies has a single heavy chain variable domain ($V_HH$), which can have high affinity to an antigen without the aid of a light chain. Camelid $V_HH$ is known as the smallest functional antigen-binding fragment with a molecular weight of approximately 15 kD.

The disclosures of all publications, patents, patent applications and published patent applications referred to herein are hereby incorporated herein by reference in their entirety.

BRIEF SUMMARY OF THE PRESENT APPLICATION

The present application provides single-domain antibodies, chimeric antigen receptors (CARs) based on single-domain antibodies (such as $V_HH$ fragments), engineered immune effector cells, and methods of use thereof in cancer immunotherapy.

One aspect of the present application provides an anti-CD19 sdAb comprising the CDR regions of SEQ ID NO: 76. In some embodiments, the anti-CD19 sdAb comprises a CDR1 comprising the amino acid sequence of SEQ ID NO: 1, a CDR2 comprising the amino acid sequence of SEQ ID NO:2, and a CDR3 comprising the amino acid sequence of SEQ ID NO:3. In some embodiments, the anti-CD19 sdAb comprises a $V_HH$ domain comprising the amino acid sequence of SEQ ID NO: 76.

In some embodiments, there is provided an anti-CD19 heavy-chain only antibody (HcAb) or an antigen binding protein comprising any one of the anti-CD19 sdAbs described above.

One aspect of the present application provides a CD19 chimeric antigen receptor comprising: (a) an extracellular antigen binding domain comprising an anti-CD19 sdAb (such as any one of the anti-CD19 sdAbs described above); (b) a transmembrane domain; and (c) an intracellular signaling domain. In some embodiments, the CAR is monospecific. In some embodiments, the CAR is monovalent. In some embodiments, the CAR is multivalent (such as bivalent or trivalent). In some embodiments, the CAR is multispecific (such as bispecific).

One aspect of the present application provides an anti-CD20 sdAb comprising the CDR regions of SEQ ID NO: 77. In some embodiments, the anti-CD20 sdAb comprises a CDR1 comprising the amino acid sequence of SEQ ID NO:4, a CDR2 comprising the amino acid sequence of SEQ ID NO:5, and a CDR3 comprising the amino acid sequence of SEQ ID NO:6. In some embodiments, the anti-CD20 sdAb comprises a $V_HH$ domain comprising the amino acid sequence of SEQ ID NO: 77.

In some embodiments, there is provided an anti-CD20 heavy-chain only antibody (HCAB) or an antigen binding protein comprising any one of the anti-CD20 sdAbs described above.

One aspect of the present application provides a CD20 chimeric antigen receptor comprising: (a) an extracellular antigen binding domain comprising an anti-CD20 sdAb (such as any one of the anti-CD20 sdAbs described above); (b) a transmembrane domain; and (c) an intracellular signaling domain. In some embodiments, the CAR is monospecific. In some embodiments, the CAR is monovalent. In some embodiments, the CAR is multivalent (such as bivalent or trivalent). In some embodiments, the CAR is multispecific (such as bispecific).

One aspect of the present application provides an anti-BCMA sdAb comprising the CDR regions of any one of SEQ ID NOs: 78-88. In some embodiments, the anti-BCMA sdAb comprises any one of the following:
(1) a CDR1 comprising the amino acid sequence of SEQ ID NO:7; a CDR2 comprising the amino acid sequence of SEQ ID NO: 18; and a CDR3 comprising the amino acid sequence of SEQ ID NO:29;

(2) a CDR1 comprising the amino acid sequence of SEQ ID NO:8; a CDR2 comprising the amino acid sequence of SEQ ID NO: 19; and a CDR3 comprising the amino acid sequence of SEQ ID NO:30;
(3) a CDR1 comprising the amino acid sequence of SEQ ID NO:9; a CDR2 comprising the amino acid sequence of SEQ ID NO:20; and a CDR3 comprising the amino acid sequence of SEQ ID NO:31;
(4) a CDR1 comprising the amino acid sequence of SEQ ID NO: 10; a CDR2 comprising the amino acid sequence of SEQ ID NO:21; and a CDR3 comprising the amino acid sequence of SEQ ID NO:32;
(5) a CDR1 comprising the amino acid sequence of SEQ ID NO: 11; a CDR2 comprising the amino acid sequence of SEQ ID NO:22; and a CDR3 comprising the amino acid sequence of SEQ ID NO:33;
(6) a CDR1 comprising the amino acid sequence of SEQ ID NO:12; a CDR2 comprising the amino acid sequence of SEQ ID NO:23; and a CDR3 comprising the amino acid sequence of SEQ ID NO:34;
(7) a CDR1 comprising the amino acid sequence of SEQ ID NO:13; a CDR2 comprising the amino acid sequence of SEQ ID NO:24; and a CDR3 comprising the amino acid sequence of SEQ ID NO:35;
(8) a CDR1 comprising the amino acid sequence of SEQ ID NO:14; a CDR2 comprising the amino acid sequence of SEQ ID NO:25; and a CDR3 comprising the amino acid sequence of SEQ ID NO:36;
(9) a CDR1 comprising the amino acid sequence of SEQ ID NO:15; a CDR2 comprising the amino acid sequence of SEQ ID NO:26; and a CDR3 comprising the amino acid sequence of SEQ ID NO:37;
(10) a CDR1 comprising the amino acid sequence of SEQ ID NO: 16; a CDR2 comprising the amino acid sequence of SEQ ID NO:27; and a CDR3 comprising the amino acid sequence of SEQ ID NO:38; or
(11) a CDR1 comprising the amino acid sequence of SEQ ID NO: 17; a CDR2 comprising the amino acid sequence of SEQ ID NO:28; and a CDR3 comprising the amino acid sequence of SEQ ID NO:39.

In some embodiments, the anti-BCMA sdAb comprises a $V_HH$ domain comprising an amino acid sequence selected from the group consisting of SEQ ID NO:78-88.

In some embodiments, there is provided an anti-BCMA heavy-chain only antibody (HCAB) or an antigen binding protein comprising any one of the anti-BCMA sdAbs described above.

One aspect of the present application provides a BCMA chimeric antigen receptor comprising: (a) an extracellular antigen binding domain comprising an anti-BCMA sdAb (such as any one of the anti-BCMA sdAbs described above); (b) a transmembrane domain; and (c) an intracellular signaling domain. In some embodiments, the CAR is monospecific. In some embodiments, the CAR is monovalent. In some embodiments, the CAR is multivalent (such as bivalent or trivalent). In some embodiments, the CAR is multispecific (such as bispecific).

One aspect of the present application provides an anti-CD38 sdAb comprising the CDR regions of any one of SEQ ID NOs: 89-100. In some embodiments, the anti-CD38 sdAb comprises any one of the following:
(1) a CDR1 comprising the amino acid sequence of SEQ ID NO:40; a CDR2 comprising the amino acid sequence of SEQ ID NO:52; and a CDR3 comprising the amino acid sequence of SEQ ID NO:64;
(2) a CDR1 comprising the amino acid sequence of SEQ ID NO:41; a CDR2 comprising the amino acid sequence of SEQ ID NO:53; and a CDR3 comprising the amino acid sequence of SEQ ID NO:65;
(3) a CDR1 comprising the amino acid sequence of SEQ ID NO:42; a CDR2 comprising the amino acid sequence of SEQ ID NO:54; and a CDR3 comprising the amino acid sequence of SEQ ID NO:66;
(4) a CDR1 comprising the amino acid sequence of SEQ ID NO:43; a CDR2 comprising the amino acid sequence of SEQ ID NO:55; and a CDR3 comprising the amino acid sequence of SEQ ID NO:67;
(5) a CDR1 comprising the amino acid sequence of SEQ ID NO:44; a CDR2 comprising the amino acid sequence of SEQ ID NO:56; and a CDR3 comprising the amino acid sequence of SEQ ID NO:68;
(6) a CDR1 comprising the amino acid sequence of SEQ ID NO:45; a CDR2 comprising the amino acid sequence of SEQ ID NO:57; and a CDR3 comprising the amino acid sequence of SEQ ID NO:69;
(7) a CDR1 comprising the amino acid sequence of SEQ ID NO:46; a CDR2 comprising the amino acid sequence of SEQ ID NO:58; and a CDR3 comprising the amino acid sequence of SEQ ID NO:70;
(8) a CDR1 comprising the amino acid sequence of SEQ ID NO:47; a CDR2 comprising the amino acid sequence of SEQ ID NO:59; and a CDR3 comprising the amino acid sequence of SEQ ID NO:71;
(9) a CDR1 comprising the amino acid sequence of SEQ ID NO:48; a CDR2 comprising the amino acid sequence of SEQ ID NO:60; and a CDR3 comprising the amino acid sequence of SEQ ID NO:72;
(10) a CDR1 comprising the amino acid sequence of SEQ ID NO:49; a CDR2 comprising the amino acid sequence of SEQ ID NO:61; and a CDR3 comprising the amino acid sequence of SEQ ID NO:73;
(11) a CDR1 comprising the amino acid sequence of SEQ ID NO: 50; a CDR2 comprising the amino acid sequence of SEQ ID NO:62; and a CDR3 comprising the amino acid sequence of SEQ ID NO:74; or
(12) a CDR1 comprising the amino acid sequence of SEQ ID NO:51; a CDR2 comprising the amino acid sequence of SEQ ID NO:63; and a CDR3 comprising the amino acid sequence of SEQ ID NO:75.

In some embodiments, the anti-CD38 sdAb comprises a $V_HH$ domain comprising an amino acid sequence selected from the group consisting of SEQ ID NO:89-100.

In some embodiments, there is provided an anti-BCMA heavy-chain only antibody (HCAB) or an antigen binding protein comprising any one of the anti-BCMA sdAbs described above.

One aspect of the present application provides a CD38 chimeric antigen receptor comprising: (a) an extracellular antigen binding domain comprising an anti-CD38 sdAb (such as any one of the anti-CD38 sdAbs described above); (b) a transmembrane domain; and (c) an intracellular signaling domain. In some embodiments, the CAR is monospecific. In some embodiments, the CAR is monovalent. In some embodiments, the CAR is multivalent (such as bivalent or trivalent). In some embodiments, the CAR is multispecific (such as bispecific).

One aspect of the present application provides a CD22 chimeric antigen receptor comprising: (a) an extracellular antigen binding domain comprising an anti-CD22 sdAb; (b) a transmembrane domain; and (c) an intracellular signaling domain. In some embodiments, the CAR is monospecific. In some embodiments, the CAR is monovalent. In some embodiments, the CAR is multivalent (such as bivalent or trivalent). In some embodiments, the CAR is multispecific (such as bispecific).

One aspect of the present application provides a chimeric antigen receptor (CAR) comprising a polypeptide comprising: (a) an extracellular antigen binding domain comprising a first single-domain antibody (sdAb) specifically binding to a first antigen and a second single-domain antibody (sdAb) specifically binding to a second antigen; (b) a transmembrane domain; and (c) an intracellular signaling domain. In some embodiments, the first sdAb is located at the N-terminus of the second sdAb. In some embodiments, the first sdAb is located at the C-terminus of the second sdAb.

In some embodiments according to any one of the CARs provided above, the first antigen and the second antigen are selected from the group consisting of CD19, CD20, CD22, CD33, CD38, BCMA, CS1, ROR1, GPC3, CD123, IL-13R, CD138, c-Met, EGFRvIII, GD-2, NY-ESO-1, MAGE A3, and glycolipid F77. In some embodiments, the first sdAb is an anti-BCMA sdAb, such as any one of the BCMA sdAbs described above. In some embodiments, the CAR comprises an extracellular antigen binding domain comprising at least two copies (such as 2, 3, or more copies) of an anti-BCMA sdAb. In some embodiments, the first sdAb is an anti-CD19 sdAb, such as any one of the anti-CD19 sdAbs described above. In some embodiments, the first sdAb is an anti-CD20 sdAb, such as any one of the anti-CD20 sdAbs described above. In some embodiments, the first sdAb is an anti-CD38 sdAb, such as any one of the anti-CD38 sdAbs described above. In some embodiments, the CAR comprises an extracellular antigen binding domain comprising at least two copies (such as 2, 3, or more copies) of an anti-CD38 sdAb. In some embodiments, the first sdAb is an anti-CD22 sdAb.

In some embodiments according to any one of the CARs provided above, the first antigen is different from the second antigen. In some embodiments, the CAR is multispecific, such as bispecific. In some embodiments, the first sdAb is an anti-BCMA sdAb, and the second sdAb is an anti-CD38 sdAb. In some embodiments, the first sdAb is an anti-BCMA sdAb, and the second sdAb is an anti-CD19 sdAb. In some embodiments, the first sdAb is an anti-CD19 sdAb, and the second sdAb is an anti-CD20 sdAb. In some embodiments, the first sdAb is an anti-CD19 sdAb, and the second sdAb is an anti-CD22 sdAb.

In some embodiments according to any one of the monospecific CARs provided above, the first antigen is the same as the second antigen. In some embodiments, the CAR is bivalent or trivalent. In some embodiments, the first sdAb and the second sdAb specifically bind to the same epitope. In some embodiments, the first sdAb is the same as the second sdAb. In some embodiments, the first sdAb and the second sdAb specifically bind to different epitopes.

In some embodiments according to any one of the CARs provided above, the first sdAb and/or the second sdAb are camelid, chimeric, human, or humanized.

In some embodiments according to any one of the CARs provided above, the first sdAb and the second sdAb are directly fused to each other via a peptide bond. In some embodiments, the first sdAb and the second sdAb are fused to each other via a peptide linker. In some embodiments, the peptide linker is no more than about 50 (such as no more than about any one 35, 25, 20, 15, 10, or 5) amino acids long. In some embodiments, the peptide linker comprises an amino acid sequence selected from SEQ ID NOs: 144-151.

In some embodiments according to any one of the CARs (including CD19 CARs, CD20 CARs, BCMA CARs, CD38 CARs, and CD22 CARs) provided above, the transmembrane domain is derived from a molecule selected from the group consisting of CD8a, CD4, CD28, CD137, CD80, CD86, CD152 and PD1. In some embodiments, the transmembrane domain is derived from CD8 or CD28. In some embodiments, the transmembrane domain comprises the amino acid sequence of SEQ ID NO: 132 or SEQ ID NO: 133.

In some embodiments according to any one of the CARs (including CD19 CARs, CD20 CARs, BCMA CARs, CD38 CARs, and CD22 CARs) provided above, the intracellular signaling domain comprises a primary intracellular signaling domain of an immune effector cell (such as a T cell). In some embodiments, the primary intracellular signaling domain is derived from CD3ζ. In some embodiments, the primary intracellular signaling domain comprises the amino acid sequence of SEQ ID NO: 140 or SEQ ID NO: 141.

In some embodiments according to any one of the CARs (including CD19 CARs, CD20 CARs, BCMA CARs, CD38 CARs, and CD22 CARs) provided above, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the co-stimulatory signaling domain comprises a cytoplasmic domain of CD28 and/or a cytoplasmic domain of CD137. In some embodiments, the co-stimulatory signaling domain comprises the amino acid sequence of SEQ ID NO: 136 and/or SEQ ID NO: 137.

In some embodiments according to any one of the CARs (including CD19 CARs, CD20 CARs, BCMA CARs, CD38 CARs, and CD22 CARs) provided above, the CAR further comprises a hinge domain located between the C-terminus of the extracellular antigen binding domain and the N-terminus of the transmembrane domain. In some embodiments, the hinge domain is derived from CD8a. In some embodiments, the hinge domain comprises the amino acid sequence of SEQ ID NO: 130.

In some embodiments, the CAR further comprises a signal peptide located at the N-terminus of the polypeptide. In some embodiments, the signal peptide is derived from a molecule selected from the group consisting of CD8α, GM-CSF receptor α, and IgG1 heavy chain. In some embodiments, the signal peptide is derived from CD8α. In some embodiments, the signal peptide comprises the amino acid sequence of SEQ ID NO: 127.

One aspect of the present application provides a chimeric antigen receptor of any one listed in Tables 4, 5, and 6. In some embodiments, the CAR comprises an amino acid sequence selected from the group consisting of SEQ ID NOs: 152-174, 198-201, 206-216, 248-249, 257-260, and 265-270.

One aspect of the present application provides a polypeptide comprising an amino acid sequence selected from the group consisting of SEQ ID NOs: 76-100, 152-174, 198-201, 206-216, 248-249, 257-260, and 265-270.

One aspect of the present application provides an isolated nucleic acid comprising a nucleic acid sequence encoding any one of the CARs (including CD19 CARs, CD20 CARs, BCMA CARs, CD38 CARs, and CD22 CARs) provided above. In some embodiments, the nucleic acid sequence is selected from the group consisting of SEQ ID NOs: 175-197, 202-205, 217-227, 250-251, 261-264, and 271-276. In some embodiments, the isolated nucleic acid further comprises a second nucleic acid sequence encoding a second CAR, wherein the nucleic acid sequence encoding the CAR is operably linked to the second nucleic acid sequence via a third nucleic acid sequence encoding a self-cleaving peptide, such as a T2A, P2A, or F2A peptide. In some embodiments, the third nucleic acid sequence is SEQ ID NO: 256. In some embodiments, the isolated nucleic acid is a DNA molecule. In some embodiments, the isolated nucleic acid is an RNA molecule.

One aspect of the present application provides a vector comprising any one of the isolated nucleic acids described above. In some embodiments, the vector is an expression vector. In some embodiments, the vector is a viral vector. In some embodiments, the vector is a lentiviral vector.

One aspect of the present application provides an engineered immune effector cell, comprising any one of the CARs (including CD19 CARs, CD20 CARs, BCMA CARs, CD38 CARs, and CD22 CARs) provided above, or any one of the isolated nucleic acids described above, or any one of the vectors described above. In some embodiments, the engineered immune effector cell comprises or expresses two or more CARs (including CD19 CARs, CD20 CARs, BCMA CARs, CD38 CARs, and CD22 CARs) described above, wherein the two or more CARs specifically bind to different antigens. In some embodiments, the immune effector cell is a T cell, an NK cell, a peripheral blood mononuclear cell (PBMC), a hematopoietic stem cell, a pluripotent stem cell, or an embryonic stem cell. In some embodiments, the immune effector cell is a T cell.

One aspect of the present application provides a pharmaceutical composition comprising any one of the engineered immune effector cells described above and a pharmaceutically acceptable carrier. Further provided is a method of treating cancer in an individual, comprising administering to the individual an effective amount of any one of the pharmaceutical compositions described above. In some embodiments, the engineered immune effector cell is autologous. In some embodiments, the engineered immune effector cell is allogenic. In some embodiments, the cancer is a liquid cancer. In some embodiments, the cancer is multiple myeloma, acute lymphoblastic leukemia, or chronic lymphocytic leukemia. In some embodiments, the cancer is a solid cancer, such as glioblastoma.

One aspect of the present application provides a pharmaceutical composition comprising any one of the anti-CD19 sdAbs, anti-CD20 sdAbs, anti-CD38 sdAbs or anti-BCMA sdAbs described above and a pharmaceutically acceptable carrier. In some embodiments, there is provided a method of treating a disease (such as cancer) in an individual, comprising administering to the individual an effective amount of the pharmaceutical composition.

Also provided are methods of use, kits, and articles of manufacture comprising any one of the single-domain antibodies, CARs, engineered immune effector cells, isolated nucleic acids, or vectors described above.

DETAILED DESCRIPTION OF THE PRESENT APPLICATION

Figure 1A:
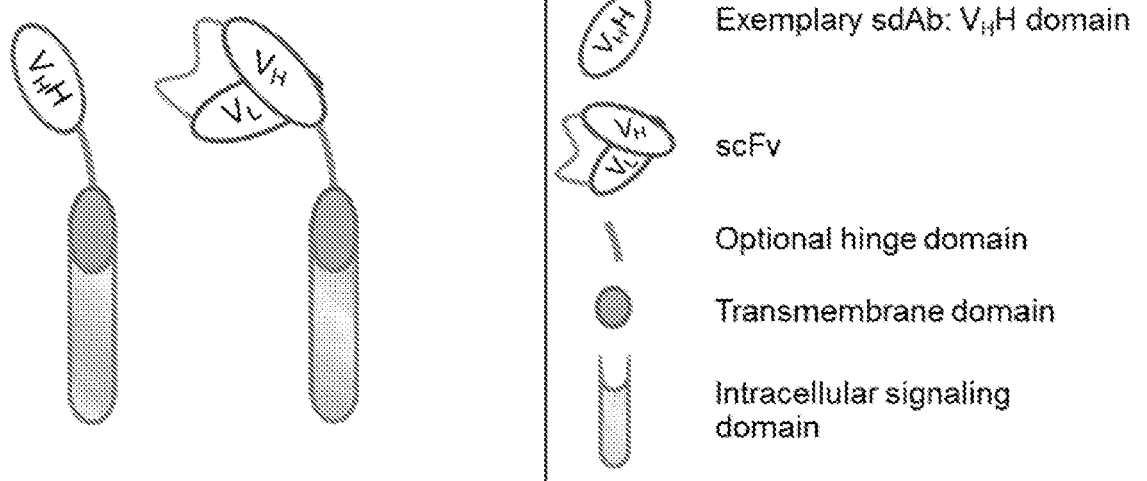
FIG. 1A compares the structures of a $V_HH$-based CAR and a conventional scFv-based CAR. The schematic structure on the left shows an exemplary monospecific monovalent CAR having an extracellular antigen binding domain comprising a $V_HH$ domain. The schematic structure on the right shows an exemplary monospecific monovalent CAR having an extracellular antigen binding domain comprising a scFv domain.
Figure 1B:
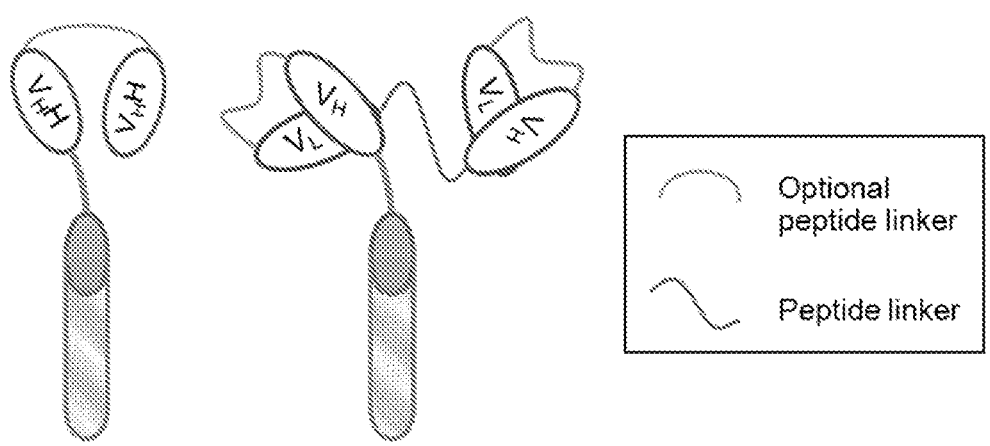
FIG. 1B compares the structures of a $V_HH$-based CAR having two antigen binding sites and a conventional scFv-based CAR having two antigen binding sites. The schematic structure on the left is an exemplary CAR having an extracellular antigen binding domain comprising two $V_HH$ domains. The two $V_HH$ domains may be the same or different. The schematic structure on the right shows an exemplary CAR having an extracellular antigen binding domain comprising two scFv domains. The two scFv domains may be the same or different.
Figure 1C:
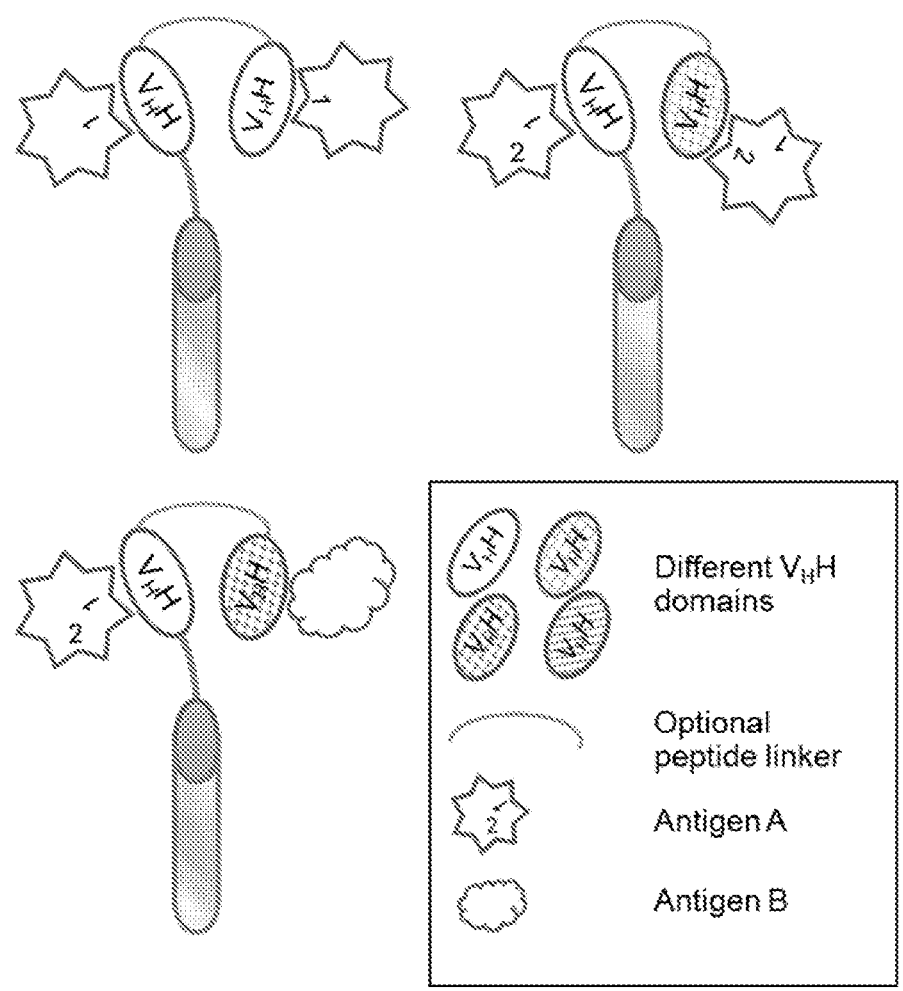
FIG. 1C shows schematic structures of exemplary bivalent and bispecific $V_HH$-based CARs. The schematic structure in the top left panel shows an exemplary monospecific, bivalent CAR having an extracellular antigen binding domain comprising two identical $V_HH$ domains, each of which specifically binds to epitope 1 of antigen A. The schematic structure in the top right panel shows an exemplary monospecific, bivalent CAR having an extracellular antigen binding domain comprising a first $V_HH$ domain specifically binding to epitope 1 of antigen A, and a second $V_HH$ domain specifically binding to epitope 2 of antigen A. Epitope 1 and epitope 2 of antigen A may be different in their structures and/or sequences. The schematic structure in the bottom left panel shows an exemplary bispecific CAR having an extracellular antigen binding domain comprising a first $V_HH$ domain specifically binding to antigen A, and a second $V_HH$ domain specifically binding to antigen B. Antigen A and antigen B are different antigens.
Figure 1D:
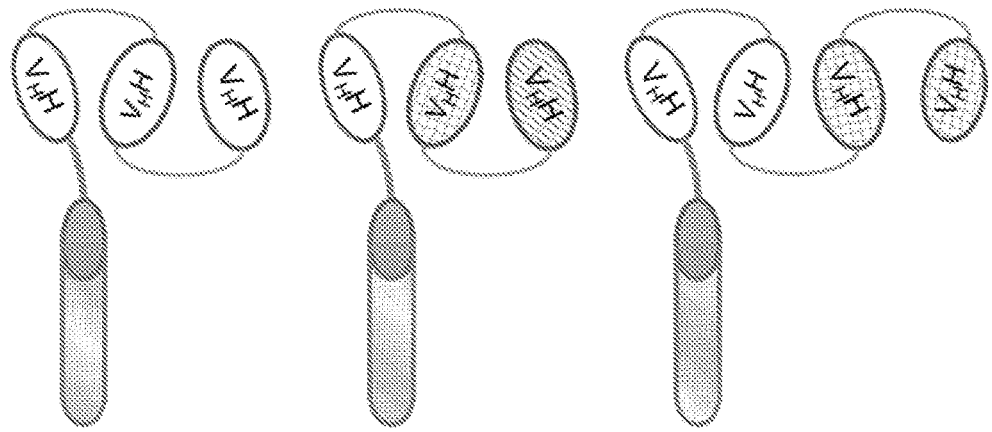
FIG. 1D shows schematic structures of exemplary $V_HH$-based CARs having three or more $V_HH$ domains. The CARs may have a plurality of $V_HH$ domains fused to each other directly or via peptide linkers. The $V_HH$ domains may be the same or different. Different $V_HH$ domains may specifically bind to different epitopes on the same antigen or different antigens.

The present application provides monospecific, multispecific (such as bispecific), and multivalent (such as bivalent or trivalent) chimeric antigen receptors comprising single-domain antibody (sdAb) based extracellular antigen binding domains. Unlike antigen binding fragments derived from conventional four-chain antibodies, sdAbs only contain a single variable domain, such as $V_HH$. Thus, sdAbs are much smaller in size than antigen binding fragments such as scFvs that are currently used as extracellular antigen binding domains in CARs. Also, as there is no need for pairing of the heavy chain and light chain during folding of the sdAbs, misfolding of the extracellular antigen binding domain can be reduced in engineered immune cells expressing CARs based on sdAbs. CARs having extracellular antigen binding domains comprising multiple copies of an sdAb or multiple sdAbs targeting different epitopes or antigens can be conveniently constructed and produced recombinantly, thereby providing an efficient platform for preparation and screening of multivalent and multispecific CARs. Additionally, the small footprint of sdAbs may allow access of the CARs to hidden antigen targets and epitopes in tumor tissues.

Multispecific and multivalent CARs may have improved efficacy over monospecific monovalent CARs for cancer immunotherapy. Cancer cells are unstable genetically, which allows them to escape from targeted therapies by mutating or losing genes encoding the target antigens. By targeting two or more different epitopes or antigens on cancer cells, multivalent or multispecific CARs can make it more difficult for cancer cells to completely escape from targeting by engineered immune effector cells (such as T cells) expressing the CARs. Owing to their small size, tandemly fused single-domain antibodies, which are used as extracellular antigen binding domains in the multivalent or multispecific CARs of the present application, can preserve their individual structural integrity and binding affinity to target antigens, thereby allowing effective targeting of each epitope or antigen by the CARs. Engineered immune effector cells expressing the multivalent or multispecific CARs or co-expressing two or more chimeric antigen receptors that target different tumor antigens may overcome tumor immune escape mechanisms that are due to abnormalities in protein-antigen processing and presentation.

Accordingly, one aspect of the present application provides a multispecific (such as bispecific) chimeric antigen receptor (CAR) comprising a polypeptide comprising: (a) an extracellular antigen binding domain comprising a first single-domain antibody (sdAb) specifically binding to a first antigen and a second single-domain antibody (sdAb) specifically binding to a second antigen; (b) a transmembrane domain; and (c) an intracellular signaling domain, wherein the first antigen is different from the second antigen. In some embodiments, the first antigen is BCMA, and the second antigen is CD38. In some embodiments, the first antigen is CD19, and the second antigen is BCMA. In some embodiments, the first antigen is CD19, and the second antigen is CD20. In some embodiments, the first antigen is CD19, and the second antigen is CD22.

In another aspect, there is provided a multivalent chimeric antigen receptor (CAR) comprising a polypeptide comprising: (a) an extracellular antigen binding domain comprising a plurality of a single-domain antibody (sdAb) specifically binding to an antigen; (b) a transmembrane domain; and (c) an intracellular signaling domain.

In another aspect, there is provided a multivalent chimeric antigen receptor (CAR) comprising a polypeptide comprising: (a) an extracellular antigen binding domain comprising a first single-domain antibody specifically binding to a first epitope of an antigen, and a second single-domain antibody specifically binds a second epitope of the antigen; (b) a transmembrane domain; and (c) an intracellular signaling domain, wherein the first epitope is different from the second epitope.

Further provided are novel anti-CD19, anti-CD20, anti-BCMA, and anti-CD38 single-domain antibodies and chimeric antigen receptors comprising any one of the sdAbs.

Engineered immune effector cells (such as T cells) comprising the CARs, pharmaceutical compositions, kits, articles of manufacture and methods of treating cancer using the engineered immune effectors cells or the single-domain antibodies are also described herein.

I. Definitions

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Current Protocols in Molecular Biology or Current Protocols in Immunology, John Wiley & Sons, New York, N.Y. (2009); Ausubel et al, Short Protocols in Molecular Biology, $3^{rd}$ ed., Wiley & Sons, 1995; Sambrook and Russell, Molecular Cloning: A Laboratory Manual (3rd Edition, 2001); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R Freshney, ed., 1986); Perbal, A Practical Guide to Molecular Cloning (1984) and other like references.

The term "antibody" includes monoclonal antibodies (including full length 4-chain antibodies or full length heavy-chain only antibodies which have an immunoglobulin Fc region), antibody compositions with polyepitopic specificity, multispecific antibodies (e.g., bispecific antibodies, diabodies, and single-chain molecules), as well as antibody fragments (e.g., Fab, F(ab')$_2$, and Fv). The term "immunoglobulin" (Ig) is used interchangeably with "antibody"

herein. Antibodies contemplated herein include single-domain antibodies, such as heavy chain only antibodies.

The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for p and F isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see e.g., *Basic and Clinical Immunology*, 8th Edition, Daniel P. Sties, Abba I. Terr and Tristram G. Parsolw (eds), Appleton & Lange, Norwalk, Conn., 1994, page 71 and Chapter 6. The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG and IgM, having heavy chains designated α, δ, ε, γ and μ, respectively. The γ and α classes are further divided into subclasses on the basis of relatively minor differences in the $C_H$ sequence and function, e.g., humans express the following subclasses: IgG1, IgG2A, IgG2B, IgG3, IgG4, IgA1 and IgA2.

The term "heavy chain-only antibody" or "HCAb" refers to a functional antibody, which comprises heavy chains, but lacks the light chains usually found in 4-chain antibodies. Camelid animals (such as camels, llamas, or alpacas) are known to produce HCAbs.

The term "single-domain antibody" or "sdAb" refers to a single antigen-binding polypeptide having three complementary determining regions (CDRs). The sdAb alone is capable of binding to the antigen without pairing with a corresponding CDR-containing polypeptide. In some cases, single-domain antibodies are engineered from camelid HCAbs, and their heavy chain variable domains are referred herein as "$V_H$Hs". Some $V_H$Hs may also be known as Nanobodies. Camelid sdAb is one of the smallest known antigen-binding antibody fragments (see, e.g., Hamers-Casterman et al., Nature 363:446-8 (1993); Greenberg et al., Nature 374:168-73 (1995); Hassanzadeh-Ghassabeh et al., Nanomedicine (Lond), 8:1013-26 (2013)). A basic $V_H$H has the following structure from the N-terminus to the C-terminus: FR1-CDR1-FR2-CDR2-FR3-CDR3-FR4, in which FR1 to FR4 refer to framework regions 1 to 4, respectively, and in which CDR1 to CDR3 refer to the complementarity determining regions 1 to 3.

An "isolated" antibody is one that has been identified, separated and/or recovered from a component of its production environment (e.g., natural or recombinant). Preferably, the isolated polypeptide is free of association with all other components from its production environment. Contaminant components of its production environment, such as that resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (1) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant cells since at least one component of the antibody's natural environment will not be present. Ordinarily, however, an isolated polypeptide or antibody will be prepared by at least one purification step.

The "variable region" or "variable domain" of an antibody refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites. Heavy-chain only antibodies from the Camelid species have a single heavy chain variable region, which is referred to as "$V_H$H". $V_H$H is thus a special type of $V_H$.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen binding site of antibodies (see Kabat et al., *Sequences of Immunological Interest*, Fifth Edition, National Institute of Health, Bethesda, Md. (1991)). The constant domains are not involved directly in the binding of antibody to an antigen, but exhibit various effector functions, such as participation of the antibody in antibody-dependent cellular toxicity.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture or recombinantly, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present application may be made by a variety of techniques, including, for example, the hybridoma method (e.g., Kohler and Milstein., Nature, 256: 495-97 (1975); Hongo et al., Hybridoma, 14 (3): 253-260 (1995), Harlow et al., Antibodies: A Laboratory Manual, (Cold Spring Harbor Laboratory Press, 2$^{nd}$ ed. 1988); Hammerling et al., in: Monoclonal Antibodies and T-Cell Hybridomas 563-681 (Elsevier, N.Y., 1981)), recombinant DNA methods (see, e.g., U.S. Pat. No. 4,816,567), phage-display technologies (see, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., Proc. Natl. Acad. Sci. USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; and 5,661,016; Marks et al., Bio/Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996); and Lonberg and Huszar, Intern. Rev. Immunol. 13: 65-93 (1995).

The term "naked antibody" refers to an antibody that is not conjugated to a cytotoxic moiety or radiolabel.

The terms "full-length antibody," "intact antibody" or "whole antibody" are used interchangeably to refer to an antibody in its substantially intact form, as opposed to an antibody fragment. Specifically, full-length 4-chain antibodies include those with heavy and light chains including an Fc region. Full-length heavy-chain only antibodies include the heavy chain (such as $V_HH$) and an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, preferably the antigen binding and/or the variable region of the intact antibody. Examples of antibody fragments include Fab, Fab', F(ab')$_2$ and Fv fragments; diabodies; linear antibodies (see U.S. Pat. No. 5,641,870, Example 2; Zapata et al., Protein Eng. 8(10): 1057-1062 [1995]); single-chain antibody molecules; single-domain antibodies (such as $V_HH$), and multispecific antibodies formed from antibody fragments. Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of the sFv, see Pluckthun in The Pharmacology of Monoclonal Antibodies, vol. 113, Rosenburg and Moore eds., Springer-Verlag, New York, pp. 269-315 (1994).

"Functional fragments" of the antibodies described herein comprise a portion of an intact antibody, generally including the antigen binding or variable region of the intact antibody or the Fc region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., Proc. Natl. Acad. Sci. USA 90: 6444-6448 (1993).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, 81:6851-6855 (1984)). Chimeric antibodies of interest herein include PRIMATTZFD® antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., camelid) antibodies are chimeric antibodies that contain minimal sequence derived from non-human immunoglobulin. In some embodiments, a humanized antibody is a human immunoglobulin (recipient antibody) in which residues from an HVR (hereinafter defined) of the recipient are replaced by residues from an HVR of a non-human species (donor antibody) such as mouse, rat, rabbit or non-human primate having the desired specificity, affinity, and/or capacity. In some instances, framework ("FR") residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, etc. The number of these amino acid substitutions in the FR is typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, for example, Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is an antibody that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.*, 227: 381 (1991); Marks et al., *J. Mol. Biol.*, 222:581 (1991). Also available for the preparation of human monoclonal antibodies are methods described in Cole et al., *Monoclonal Antibodies and Cancer Therapy*, Alan R Liss, p. 77 (1985); Boerner et al., *J. Immunol.*, 147(1):86-95 (1991). See also van Dijk and van de Winkel, *Curr. Opin. Pharmacol.*, 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA*, 103:3557-3562 (2006) regarding human antibodies generated via a human B-cell hybridoma technology.

The term "hypervariable region," "HVR," or "HV," when used herein refers to the regions of an antibody variable domain which are hypervariable in sequence and/or form structurally defined loops. Generally, single-domain antibodies comprise three HVRs (or CDRs): HVR1 (or CDR1), HVR2 (or CDR2), and HVR3 (or CDR3). HVR3 displays the most diversity of the three HVRs, and is believed to play a unique role in conferring fine specificity to antibodies. See, e.g., Hamers-Casterman et al., *Nature* 363:446-448 (1993); Sheriff et al., *Nature Struct. Biol.* 3:733-736 (1996).

The term "Complementarity Determining Region" or "CDR" are used to refer to hypervariable regions as defined by the Kabat system. See Kabat et al., *Sequences of Proteins of Immunological Interest*, 5th Ed. Public Health Service, National Institutes of Health, Bethesda, Md. (1991)

A number of HVR delineations are in use and are encompassed herein. The Kabat Complementarity Determining Regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk, *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below in Table 1.

TABLE 1

HVR delineations.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B (Kabat Numbering) | H26-H32 | H30-H35B |
| H1 | H31-H35 | H26-H35 (Chothia Numbering) | H26-H32 | H30-H35 |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the $V_L$ and 26-35 (H1), 50-65 or 49-65 (H2) and 93-102, 94-102, or 95-102 (H3) in the $V_H$. The variable domain residues are numbered according to Kabat et al., supra, for each of these definitions.

The amino acid residues of a single-domain antibody (such as $V_H H$) are numbered according to the general numbering for $V_H$ domains given by Kabat et al. ("Sequence of proteins of immunological interest", US Public Health Services, NIH Bethesda, Md., Publication No. 91), as applied to $V_H H$ domains from Camelids in the article of Riechmann and Muyldermans, J. Immunol. Methods 2000 Jun. 23; 240 (1-2): 185-195. According to this numbering, FR1 of a $V_H H$ comprises the amino acid residues at positions 1-30, CDR1 of a $V_H H$ comprises the amino acid residues at positions 31-35, FR2 of a $V_H H$ comprises the amino acids at positions 36-49, CDR2 of a $V_H H$ comprises the amino acid residues at positions 50-65, FR3 of a $V_HH$ comprises the amino acid residues at positions 66-94, CDR3 of a $V_HH$ comprises the amino acid residues at positions 95-102, and FR4 of a $V_HH$ comprises the amino acid residues at positions 103-113. In this respect, it should be noted that—as is well known in the art for $V_H$ domains and for $V_HH$ domains—the total number of amino acid residues in each of the CDR's may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering).

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

Unless indicated otherwise herein, the numbering of the residues in an immunoglobulin heavy chain is that of the EU index as in Kabat et al., supra. The "EU index as in Kabat" refers to the residue numbering of the human IgG1 EU antibody.

"Framework" or "FR" residues are those variable-domain residues other than the HVR residues as herein defined.

A "human consensus framework" or "acceptor human framework" is a framework that represents the most commonly occurring amino acid residues in a selection of human immunoglobulin $V_L$ or $V_H$ framework sequences. Generally, the selection of human immunoglobulin $V_L$ or $V_H$ sequences is from a subgroup of variable domain sequences. Generally, the subgroup of sequences is a subgroup as in Kabat et al., *Sequences of Proteins of Immunological Interest*, 5$^{th}$ Ed. Public Health Service, National Institutes of Health, Bethesda, Md. (1991). Examples include for the $V_L$, the subgroup may be subgroup kappa I, kappa II, kappa III or kappa IV as in Kabat et al., supra. Additionally, for the VH, the subgroup may be subgroup I, subgroup II, or subgroup II as in Kabat et al. Alternatively, a human consensus framework can be derived from the above in which particular residues, such as when a human framework residue is selected based on its homology to the donor framework by aligning the donor framework sequence with a collection of various human framework sequences. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less.

An "amino-acid modification" at a specified position, e.g. of the Fc region, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

An "affinity-matured" antibody is one with one or more alterations in one or more HVRs thereof that result in an improvement in the affinity of the antibody for antigen, compared to a parent antibody that does not possess those alteration(s). In some embodiments, an affinity-matured antibody has nanomolar or even picomolar affinities for the target antigen. Affinity-matured antibodies are produced by procedures known in the art. For example, Marks et al., *Bio/Technology* 10:779-783 (1992) describes affinity maturation by $V_H$- and $V_L$-domain shuffling. Random mutagenesis of HVR and/or framework residues is described by, for example: Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

As use herein, the term "specifically binds," "specifically recognizes," or is "specific for" refers to measurable and reproducible interactions such as binding between a target and an antigen binding protein (such as a CAR or an sdAb), which is determinative of the presence of the target in the presence of a heterogeneous population of molecules including biological molecules. For example, an antigen binding protein (such as a CAR or an sdAb) that specifically binds a target (which can be an epitope) is an antigen binding protein (such as a CAR or an sdAb) that binds this target with greater affinity, avidity, more readily, and/or with greater duration than it binds other targets. In some embodiments, the extent of binding of an antigen binding protein (such as a CAR or an sdAb) to an unrelated target is less than about 10% of the binding of the antigen binding protein (such as a CAR or an sdAb) to the target as measured, e.g., by a radioimmunoassay (RIA). In some embodiments, an antigen binding protein (such as a CAR or an sdAb) that specifically binds a target has a dissociation constant (Kd) of ≤1 µM, ≤100 nM, ≤10 nM, ≤1 nM, or ≤0.1 nM. In some embodiments, an antigen binding protein (such as a CAR or an sdAb) specifically binds an epitope on a protein that is conserved among the protein from different species. In some embodiments, specific binding can include, but does not require exclusive binding.

The term "specificity" refers to selective recognition of an antigen binding protein (such as a CAR or an sdAb) for a particular epitope of an antigen. Natural antibodies, for example, are monospecific. The term "multispecific" as used herein denotes that an antigen binding protein (such as a CAR or an sdAb) has two or more antigen-binding sites of which at least two bind a different antigen or a different epitope of the same antigen. "Bispecific" as used herein denotes that an antigen binding protein (such as a CAR or an sdAb) has two different antigen-binding specificities. The term "monospecific" CAR as used herein denotes an antigen binding protein (such as a CAR or an sdAb) that has one or more binding sites each of which bind the same epitope of the same antigen.

The term "valent" as used herein denotes the presence of a specified number of binding sites in an antigen binding protein (such as a CAR or an sdAb). A natural antibody for example or a full length antibody has two binding sites and is bivalent. As such, the terms "trivalent", "tetravalent", "pentavalent" and "hexavalent" denote the presence of two binding site, three binding sites, four binding sites, five binding sites, and six binding sites, respectively, in an antigen binding protein (such as a CAR or an sdAb).

"Antibody effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptors); and B cell activation. "Reduced or minimized" antibody effector function means that which is reduced by at least 50% (alternatively 60%, 65%, 70%, 75%, 80%, 85%, 90%, 95%, 96%, 97%, 98%, 99%) from the wild type or unmodified antibody. The determination of antibody effector function is readily determinable and measurable by one of ordinary skill in the art. In a preferred embodiment, the antibody effector functions of complement binding, complement dependent cytotoxicity and antibody dependent cytotoxicity are affected. In some embodiments, effector function is eliminated through a mutation in the constant region that eliminated glycosylation, e.g., "effectorless mutation." In one aspect, the effector-less mutation is an N297A or DANA mutation (D265A+N297A) in the $C_H2$ region. Shields et al., *J. Biol. Chem.* 276 (9): 6591-6604 (2001). Alternatively, additional mutations resulting in reduced or eliminated effector function include: K322A and L234A/L235A (LALA). Alternatively, effector function can be reduced or eliminated through production techniques, such as expression in host cells that do not glycosylate (e.g., *E. coli*.) or in which result in an altered glycosylation pattern that is ineffective or less effective at promoting effector function (e.g., Shinkawa et al., *J. Biol. Chem.* 278(5): 3466-3473 (2003).

"Antibody-dependent cell-mediated cytotoxicity" or ADCC refers to a form of cytotoxicity in which secreted Ig bound onto Fc receptors (FcRs) present on certain cytotoxic cells (e.g., natural killer (NK) cells, neutrophils and macrophages) enable these cytotoxic effector cells to bind specifically to an antigen-bearing target cell and subsequently kill the target cell with cytotoxins. The antibodies "arm" the cytotoxic cells and are required for killing of the target cell by this mechanism. The primary cells for mediating ADCC, NK cells, express FcγRIII only, whereas monocytes express FcγRI, FcγRII and FcγRIII. Fc expression on hematopoietic cells is summarized in Table 3 on page 464 of Ravetch and Kinet, *Annu. Rev. Immunol.* 9: 457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and natural killer (NK) cells. Alternatively, or additionally, ADCC activity of the molecule of interest may be assessed in vivo, e.g., in an animal model such as that disclosed in Clynes et al., *PNAS USA* 95:652-656 (1998).

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies described herein include human IgG1, IgG2 (IgG2A, IgG2B), IgG3 and IgG4.

"Binding affinity" generally refers to the strength of the sum total of non-covalent interactions between a single binding site of a molecule (e.g., an antibody or a CAR) and its binding partner (e.g., an antigen). Unless indicated otherwise, as used herein, "binding affinity" refers to intrinsic binding affinity that reflects a 1:1 interaction between members of a binding pair (e.g., antibody and antigen, or CAR and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present application. Specific illustrative and exemplary embodiments for measuring binding affinity are described in the following.

A "blocking" antibody or an "antagonist" antibody is one that inhibits or reduces a biological activity of the antigen it binds. In some embodiments, blocking antibodies or antagonist antibodies substantially or completely inhibit the biological activity of the antigen.

An "agonist" or activating antibody is one that enhances or initiates signaling by the antigen to which it binds. In some embodiments, agonist antibodies cause or activate signaling without the presence of the natural ligand.

"Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

"Chimeric antigen receptor" or "CAR" as used herein refers to genetically engineered receptors, which can be used to graft one or more antigen specificity onto immune effector cells, such as T cells. Some CARs are also known as "artificial T-cell receptors," "chimeric T cell receptors," or "chimeric immune receptors." In some embodiments, the CAR comprises an extracellular antigen binding domain specific for one or more antigens (such as tumor antigens), a transmembrane domain, and an intracellular signaling domain of a T cell and/or other receptors. "CAR-T" refers to a T cell that expresses a CAR.

An "isolated" nucleic acid molecule encoding a CAR or an sdAb described herein is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

As used herein, the term "autologous" is meant to refer to any material derived from the same individual to whom it is later to be re-introduced into the individual.

"Allogeneic" refers to a graft derived from a different individual of the same species.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

As used herein, the expressions "cell", "cell line", and "cell culture" are used interchangeably and all such designations include progeny. Thus, the words "transfectants" and "transfected cells" include the primary subject cell and cultures derived there from without regard for the number of transfers. It is also understood that all progeny may not be precisely identical in DNA content, due to deliberate or inadvertent mutations. Variant progeny that have the same function or biological activity as screened for in the originally transformed cell are included.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. Also encompassed by "treatment" is a reduction of pathological consequence of cancer. The methods of the present application contemplate any one or more of these aspects of treatment.

As used herein, an "individual" or a "subject" refers to a mammal, including, but not limited to, human, bovine, horse, feline, canine, rodent, or primate. In some embodiments, the individual is a human.

The term "effective amount" used herein refers to an amount of an agent, such as a single-domain antibody, an engineered immune effector cell, or a pharmaceutical composition thereof, sufficient to treat a specified disorder, condition or disease such as ameliorate, palliate, lessen, and/or delay one or more of its symptoms. In reference to cancer, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay recurrence. An effective amount can be administered in one or more administrations. The effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

"Adjuvant setting" refers to a clinical setting in which an individual has had a history of cancer, and generally (but not necessarily) been responsive to therapy, which includes, but is not limited to, surgery (e.g., surgery resection), radiotherapy, and chemotherapy. However, because of their history of cancer, these individuals are considered at risk of development of the disease. Treatment or administration in the "adjuvant setting" refers to a subsequent mode of treatment. The degree of risk (e.g., when an individual in the adjuvant setting is considered as "high risk" or "low risk") depends upon several factors, most usually the extent of disease when first treated.

"Neoadjuvant setting" refers to a clinical setting in which the method is carried out before the primary/definitive therapy.

As used herein, "delaying" the development of cancer means to defer, hinder, slow, retard, stabilize, and/or postpone development of the disease. This delay can be of varying lengths of time, depending on the history of the disease and/or individual being treated. As is evident to one skilled in the art, a sufficient or significant delay can, in effect, encompass prevention, in that the individual does not develop the disease. A method that "delays" development of cancer is a method that reduces probability of disease development in a given time frame and/or reduces the extent of the disease in a given time frame, when compared to not using the method. Such comparisons are typically based on clinical studies, using a statistically significant number of individuals. Cancer development can be detectable using standard methods, including, but not limited to, computerized axial tomography (CAT Scan), Magnetic Resonance Imaging (MRI), abdominal ultrasound, clotting tests, arteriography, or biopsy. Development may also refer to cancer progression that may be initially undetectable and includes occurrence, recurrence, and onset.

The term "pharmaceutical formulation" refers to a preparation that is in such form as to permit the biological activity of the active ingredient to be effective, and that contains no additional components that are unacceptably toxic to a subject to which the formulation would be administered. Such formulations are sterile. A "sterile" formulation is aseptic or free from all living microorganisms and their spores.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugars such as sucrose, mannitol, trehalose or sorbitol; salt-forming counterions such as sodium; metal complexes (e.g. Zn-protein complexes); and/or nonionic surfactants such as TWEEN™, polyethylene glycol (PEG), and PLURONICS™ or polyethylene glycol (PEG).

The "diluent" of interest herein is one which is pharmaceutically acceptable (safe and non-toxic for administration to a human) and is useful for the preparation of a liquid formulation, such as a formulation reconstituted after lyophilization. Exemplary diluents include sterile water, bacteriostatic water for injection (BWFI), a pH buffered solution (e.g. phosphate-buffered saline), sterile saline solution, Ringer's solution or dextrose solution. In an alternative embodiment, diluents can include aqueous solutions of salts and/or buffers.

A "preservative" is a compound which can be added to the formulations herein to reduce bacterial activity. The addition of a preservative may, for example, facilitate the production of a multi-use (multiple-dose) formulation. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. The most preferred preservative herein is benzyl alcohol.

A "stable" formulation is one in which the protein therein essentially retains its physical and chemical stability and integrity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993). Stability can be measured at a selected temperature for a selected time period. For rapid screening, the formulation may be kept at 40° C. for 2 weeks to 1 month, at which time stability is measured. Where the formulation is to be stored at 2-8° C., generally the formulation should be stable at 30° C. or 40° C. for at least 1 month and/or stable at 2-8° C. for at least 2 years. Where the formulation is to be stored at 30° C., generally the formulation should be stable for at least 2 years at 30° C. and/or stable at 40° C. for at least 6 months. For example, the extent of aggregation during storage can be used as an indicator of protein stability. Thus, a "stable" formulation may be one wherein less than about 10% and preferably less than about 5% of the protein are present as an aggregate in the formulation. In other embodiments, any increase in aggregate formation during storage of the formulation can be determined.

A "reconstituted" formulation is one which has been prepared by dissolving a lyophilized protein or antibody formulation in a diluent such that the protein is dispersed throughout. The reconstituted formulation is suitable for administration (e.g. subcutaneous administration) to a patient to be treated with the protein of interest and, In some embodiments of the present application, may be one which is suitable for parenteral or intravenous administration.

An "isotonic" formulation is one which has essentially the same osmotic pressure as human blood. Isotonic formulations will generally have an osmotic pressure from about 250 to 350 mOsm. The term "hypotonic" describes a formulation with an osmotic pressure below that of human blood. Correspondingly, the term "hypertonic" is used to describe a formulation with an osmotic pressure above that of human blood. Isotonicity can be measured using a vapor pressure or ice-freezing type osmometer, for example. The formulations of the present invention are hypertonic as a result of the addition of salt and/or buffer.

It is understood that embodiments of the present application described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat cancer of type X means the method is used to treat cancer of types other than X.

The term "about X-Y" used herein has the same meaning as "about X to about Y."

As used herein and in the appended claims, the singular forms "a," "or," and "the" include plural referents unless the context clearly dictates otherwise.

II. Single-Domain Antibodies

The present application in one aspect provides single-domain antibodies, antigen-binding fragments thereof, and antigen binding proteins comprising any one of the single-domain antibodies. Exemplary single-domain antibodies are listed in Table 2 below.

TABLE 2

Exemplary single-domain antibodies.

| Ab | Ex. AA SEQ ID | Ex. NA SEQ ID | CDR1 | CDR2 | CDR3 |
|---|---|---|---|---|---|
| \multicolumn{6}{c}{Exemplary Anti-CD19 single-domain antibodies} |
| CD19 VHH | 76 | 101 | INRMG (SEQ ID NO: 1) | SITVRGITNYADSVKG (SEQ ID NO: 2) | VSSNRDPDY (SEQ ID NO: 3) |
| \multicolumn{6}{c}{Exemplary Anti-CD20 single-domain antibodies} |
| CD20 VHH | 77 | 102 | IGTMG (SEQ ID NO: 4) | AIRWSTGGTRYADSVKG (SEQ ID NO: 5) | DRLSLDLSGRYHYNPAVYDY (SEQ ID NO: 6) |
| \multicolumn{6}{c}{Exemplary Anti-BCMA single-domain antibodies} |
| 269A3 7346 | 78 | 103 | SGFTLDYYAIG (SEQ ID NO: 7) | CISRSDGSTYYADSVKG (SEQ ID NO: 18) | AGADCSGYLRDYEF (SEQ ID NO: 29) |
| 269A3 7348 | 79 | 104 | SGRTFSTYGMA (SEQ ID NO: 8) | SKASMNYSGRTYYADSVKG (SEQ ID NO: 19) | AGTGCSTYGCFDAQTIDY (SEQ ID NO: 30) |
| 269A3 7917 | 80 | 105 | SGRTFTMG (SEQ ID NO: 9) | AISLSPTLAYYAESVKG (SEQ ID NO: 20) | ADRKSVMSIRPDY (SEQ ID NO: 31) |
| 269A3 7355 | 81 | 106 | SGGIFVINAMG (SEQ ID NO: 10) | SIRGLGRTNYDDSVKG (SEQ ID NO: 21) | VYVTLLGGVNRDY (SEQ ID NO: 32) |
| 269A3 7915 | 82 | 107 | SGRTFSSIVMG (SEQ ID NO: 11) | AIMWNDGITYLQDSVKG (SEQ ID NO: 22) | ASKGRYSEYEY (SEQ ID NO: 33) |
| 269A3 7936 | 83 | 108 | SGFTFDRAVIV (SEQ ID NO: 12) | FIKPSDGTIYYIDSLKG (SEQ ID NO: 23) | ASPEDWYTDWIDWSIYR (SEQ ID NO: 34) |
| 269A3 7953 | 84 | 109 | STYTVNSDVMG (SEQ ID NO: 13) | AIMWNDGITYLQDSVKG (SEQ ID NO: 24) | ASKGRYSEYEY (SEQ ID NO: 35) |
| 269A3 7965 | 85 | 110 | SGATLTNDEIMA (SEQ ID NO: 14) | AIDWSGRTTNYADPVEG (SEQ ID NO: 25) | VLRAWISYDNDY (SEQ ID NO: 36) |
| 269A3 7972 | 86 | 111 | SGGTLSKNTVA (SEQ ID NO: 15) | SITWDGRTTYYADSVKG (SEQ ID NO: 26) | DLGKWPAGPADY (SEQ ID NO: 37) |
| 269A3 7353 | 87 | 112 | SEHTFSSHVMG (SEQ ID NO: 16) | VIGWRDISTSYADSVKG (SEQ ID NO: 27) | ARRIDAADFDS (SEQ ID NO: 38) |

TABLE 2-continued

Exemplary single-domain antibodies.

| Ab | Ex. AA SEQ ID | Ex. NA SEQ ID | CDR1 | CDR2 | CDR3 |
|---|---|---|---|---|---|
| 269A3 7948 | 88 | 113 | SGRAFSTYFMA (SEQ ID NO: 17) | GIAWSGGSTAYADS VKG (SEQ ID NO: 28) | SRGIEVEEF GA (SEQ ID NO: 39) |

Exemplary Anti-CD38 single-domain antibodies

| Ab | Ex. AA SEQ ID | Ex. NA SEQ ID | CDR1 | CDR2 | CDR3 |
|---|---|---|---|---|---|
| 38A37 333 | 89 | 114 | SGLTFSSYPMM (SEQ ID NO: 40) | RISDSGGYTNYDDS VKG (SEQ ID NO: 52) | ILGLPT (SEQ ID NO: 64) |
| 38A37 336 | 90 | 115 | SGFTFSSNWM Y (SEQ ID NO: 41) | TISTDGRGTYYKDS VKG (SEQ ID NO: 53) | KEPRVLMAYLRNLG DFGS (SEQ ID NO: 65) |
| 38A37 699 | 91 | 116 | SGRIFSINAMG (SEQ ID NO: 42) | AISTAGSTNYGDSV KG (SEQ ID NO: 54) | LNFPPYVY (SEQ ID NO: 66) |
| 38A37 331 | 92 | 117 | SGSIFKVFRVF AMS (SEQ ID NO: 43) | SISSGETTTYADSVK G (SEQ ID NO: 55) | ADHTFTGDF (SEQ ID NO: 67) |
| 38A37 717 | 93 | 118 | TGKVFSIYDMG (SEQ ID NO: 44) | EITSSGTTHYDDFVS G (SEQ ID NO: 56) | NHVFGGSY (SEQ ID NO: 68) |
| 38A37 719 | 94 | 119 | SASIFTRLPMG (SEQ ID NO: 45) | GIVPSGRINYADSVK G (SEQ ID NO: 57) | ADTFPLPT (SEQ ID NO: 69) |
| 38A37 330 | 95 | 120 | SGRAYATMA (SEQ ID NO: 46) | EILRVSGDTTYYTDS VKG (SEQ ID NO: 58) | GPYGILAAARVSNP GNYDY (SEQ ID NO: 70) |
| 38A37 334 | 96 | 121 | SGLTFSSYIMG (SEQ ID NO: 47) | EISSGGMTSYADSV KG (SEQ ID NO: 59) | APERGSIWYSRYEY KY (SEQ ID NO: 71) |
| 38A37 730 | 97 | 122 | SQGIFTINAMG (SEQ ID NO: 48) | EVSSGGRTDYADSV KG (SEQ ID NO: 60) | VSGWHVEVGDRIV (SEQ ID NO: 72) |
| 38A37 340 | 98 | 123 | SGRTFSSYAMA (SEQ ID NO: 49) | SISTSGGITDYADSV KG (SEQ ID NO: 61) | ARTWYLRTSLQYD Y (SEQ ID NO: 73) |
| 38A37 731 | 99 | 124 | SGTIVSISTMG (SEQ ID NO: 50) | TITRRGRTNYTDSV KG (SEQ ID NO: 62) | AEVQLDIWASAYDY (SEQ ID NO: 74) |
| 38A37 326 | 100 | 125 | SGRTYAMG (SEQ ID NO: 51) | TISGAGNTKYADSV KG (SEQ ID NO: 63) | AGKWFPAANEY (SEQ ID NO: 75) |

Anti-CD19 Single-Domain Antibodies

In one aspect, the present application provides isolated single-domain antibodies that specifically bind to CD19, such as human CD19. In some embodiments, the anti-CD19 single-domain antibody modulates CD19 activity. In some embodiments, the anti-CD19 single-domain antibody is an antagonist antibody.

In some embodiments, there is provided an anti-CD19 single-domain antibody comprising one, two, or all three CDRs of the amino acid sequence of SEQ ID NO: 76. In some embodiments, the anti-CD19 single-domain antibody is camelid. In some embodiments, the anti-CD19 single-domain antibody is humanized. In some embodiments, the anti-CD19 single-domain antibody comprises an acceptor human framework, e.g., a human immunoglobulin framework or a human consensus framework.

In some embodiments, there is provided an anti-CD19 single-domain antibody comprising at least one, at least two, or all three CDRs selected from (a) a CDR1 comprising the amino acid sequence of SEQ ID NO: 1; (b) a CDR2 comprising the amino acid sequence of SEQ ID NO: 2; and (c) a CDR3 comprising the amino acid sequence of SEQ ID NO: 3. In some embodiments, the anti-CD19 single-domain antibody is camelid. In some embodiments, the anti-CD19 single-domain antibody is humanized. In some embodiments, the anti-CD19 single-domain antibody comprises an acceptor human framework, e.g., a human immunoglobulin framework or a human consensus framework.

In some embodiments, there is provided an anti-CD19 single-domain antibody comprising three CDRs comprising: (a) a CDR1 having at least about any one of 85%, 86%, 87%, 88%, 89%, 90%, 91%, 92%, 93%, 94%, 95%, 96%, 97%, 98%, 99%, or 100% sequence identity to the amino acid sequence of SEQ ID NO: 1; (b) a CDR2 having at least about any one of 85%, 86%, 87%, 88%, 89%, 90%, 91%, 92%, 93%, 94%, 95%, 96%, 97%, 98%, 99%, or 100% sequence identity to the amino acid sequence of SEQ ID NO:2; and (c) a CDR3 having at least about any one of 85%, 86%, 87%, 88%, 89%, 90%, 91%, 92%, 93%, 94%, 95%, 96%, 97%, 98%, 99%, or 100% sequence identity to the amino acid sequence of SEQ ID NO:3. In some embodiments, the anti-CD19 single-domain antibody is camelid. In some embodiments, the anti-CD19 antibody is humanized. In some embodiments, a CDR having at least about any one of 85%, 86%, 87%, 88%, 89%, 90%, 91%, 92%, 93%, 94%, 95%, 96%, 97%, 98%, or 99% identity contains substitutions (e.g., conservative substitutions), insertions, or deletions relative to the reference sequence, but the anti-CD19 single-domain antibody comprising that sequence retains the ability to bind to CD19. In some embodiments, the anti-CD19 antibody is affinity matured. In some embodiments, the anti-CD19 single-domain antibody is camelid. In some embodiments, the anti-CD19 single-domain antibody is humanized. In some embodiments, the anti-CD19 single-domain antibody comprises an acceptor human framework, e.g., a human immunoglobulin framework or a human consensus framework.

In some embodiments, there is provided an anti-CD19 single-domain antibody comprising three CDRs comprising: (a) a CDR1 comprising the amino acid sequence of SEQ ID NO: 1; (b) a CDR2 comprising the amino acid sequence of SEQ ID NO: 2; and (c) a CDR3 comprising the amino acid sequence of SEQ ID NO: 3. In some embodiments, the anti-CD19 single-domain antibody is camelid. In some embodiments, the anti-CD19 antibody is humanized. In some embodiments, the anti-CD19 single-domain antibody comprises an acceptor human framework, e.g., a human immunoglobulin framework or a human consensus framework.

In some embodiments, there is provided an anti-CD19 single-domain antibody comprising a $V_HH$ domain having at least about any one of 85%, 86%, 87%, 88%, 89%, 90%, 91%, 92%, 93%, 94%, 95%, 96%, 97%, 98%, 99%, or 100% sequence identity to the amino acid sequence of SEQ ID NO: 76. In some embodiments, a $V_HH$ sequence having at least about any one of 85%, 86%, 87%, 88%, 89%, 90%, 91%, 92%, 93%, 94%, 95%, 96%, 97%, 98%, or 99% identity contains substitutions (e.g., conservative substitutions), insertions, or deletions relative to the reference sequence, but the anti-CD19 single-domain antibody comprising that sequence retains the ability to bind to CD19. In some embodiments, a total of 1 to 10 amino acids have been substituted, inserted and/or deleted in the amino acid sequence of SEQ ID NO: 76. In some embodiments, substitutions, insertions, or deletions occur in regions outside the CDRs (i.e., in the FRs). Optionally, the anti-CD19 single-domain antibody comprises the amino acid sequence of SEQ ID NO: 76, including post-translational modifications of that sequence. In some embodiments, the anti-CD19 single-domain antibody is camelid. In some embodiments, the anti-CD19 antibody is humanized. In some embodiments, the anti-CD19 single-domain antibody comprises an acceptor human framework, e.g., a human immunoglobulin framework or a human consensus framework.

In some embodiments, there is provided an anti-CD19 single-domain antibody comprising a $V_HH$ domain having the amino acid sequence of SEQ ID NO: 76. In some embodiments, there is provided a polypeptide comprising the amino acid sequence of SEQ ID NO: 76.

In some embodiments, functional epitopes can be mapped by combinatorial alanine scanning. In this process, a combinatorial alanine-scanning strategy can be used to identify amino acids in the CD19 protein that are necessary for interaction with the anti-CD19 single-domain antibodies. In some embodiments, the epitope is conformational and crystal structure of the anti-CD19 single-domain antibody bound to CD19 may be employed to identify the epitopes. In some embodiments, the present application provides an antibody that specifically binds to the same epitope as any one of the anti-CD19 single-domain antibodies provided herein. For example, in some embodiments, an antibody is provided that binds to the same epitope as an anti-CD19 single-domain antibody comprising the amino acid sequence of SEQ ID NO: 76.

In some embodiments, the present application provides an anti-CD19 antibody, or antigen binding fragment thereof, that specifically binds to CD19 competitively with any one of the anti-CD19 single-domain antibodies described herein. In some embodiments, competitive binding may be determined using an ELISA assay. For example, in some embodiments, an antibody is provided that specifically binds to CD19 competitively with an anti-CD19 single-domain antibody comprising the amino acid sequence of SEQ ID NO:76.

In some embodiments, there is provided an anti-CD19 antibody or antigen binding protein comprising any one of the anti-CD19 single-domain antibodies described above. In some embodiments, the anti-CD19 antibody is a monoclonal antibody, including a camelid, chimeric, humanized or human antibody. In some embodiments, the anti-CD19 antibody is an antibody fragment, e.g., a $V_HH$ fragment. In some embodiments, the anti-CD19 antibody is a full-length heavy-chain only antibody comprising an Fc region of any antibody class or isotype, such as IgG1 or IgG4. In some embodiments, the Fc region has reduced or minimized effector function.

In some embodiments, the anti-CD19 antibody (such as anti-CD19 single-domain antibody) or antigen binding protein according to any of the above embodiments may incorporate any of the features, singly or in combination, as described in Sections 1-7 of "Features of antibodies" below.

In some embodiments, there is provided an isolated nucleic acid encoding any one of the anti-CD19 antibodies (such as anti-CD19 single-domain antibodies) described above. In some embodiments, an isolated nucleic acid encoding an anti-CD19 single-domain antibody is provided wherein the nucleic acid comprises a sequence having at least about any one of 85%, 86%, 87%, 88%, 89%, 90%, 91%, 92%, 93%, 94%, 95%, 96%, 97%, 98%, 99%, or 100% sequence identity to the nucleic acid sequence of SEQ ID NO: 101. In some embodiments, there is provided an isolated nucleic acid comprising the nucleic acid sequence of SEQ ID NO: 101. In some embodiments, a vector (e.g., expression vector) comprising such nucleic acid are provided. In some embodiments, a host cell comprising such nucleic acid is provided. In some embodiments, a method of making an anti-CD19 antibody is provided, wherein the method comprises culturing a host cell comprising a nucleic acid encoding the anti-CD19 antibody, as provided above, under conditions suitable for expression of the anti-CD19 antibody, and optionally recovering the anti-CD19 antibody from the host cell (or host cell culture medium).

Anti-CD20 Single-Domain Antibodies

In one aspect, the present application provides isolated single-domain antibodies that specifically bind to CD20, such as human CD20. In some embodiments, the anti-CD20 single-domain antibody modulates CD20 activity. In some embodiments, the anti-CD20 single-domain antibody is an antagonist antibody.

In some embodiments, there is provided an anti-CD20 single-domain antibody comprising one, two, or all three CDRs of the amino acid sequence of SEQ ID NO: 77. In some embodiments, the anti-CD20 single-domain antibody is camelid. In some embodiments, the anti-CD20 single-domain antibody is humanized. In some embodiments, the anti-CD20 single-domain antibody comprises an acceptor human framework, e.g., a human immunoglobulin framework or a human consensus framework.

In some embodiments, there is provided an anti-CD20 single-domain antibody comprising at least one, at least two, or all three CDRs selected from (a) a CDR1 comprising the amino acid sequence of SEQ ID NO: 4; (b) a CDR2 comprising the amino acid sequence of SEQ ID NO: 5; and (c) a CDR3 comprising the amino acid sequence of SEQ ID NO: 6. In some embodiments, the anti-CD20 single-domain antibody is camelid. In some embodiments, the anti-CD20 single-domain antibody is humanized. In some embodiments, the anti-CD20 single-domain antibody comprises an acceptor human framework, e.g., a human immunoglobulin framework or a human consensus framework.

In some embodiments, there is provided an anti-CD20 single-domain antibody comprising three CDRs comprising: (a) a CDR1 having at least about any one of 85%, 86%, 87%, 88%, 89%, 90%, 91%, 92%, 93%, 94%, 95%, 96%, 97%, 98%, 99%, or 100% sequence identity to the amino acid sequence of SEQ ID NO:4; (b) a CDR2 having at least about any one of 85%, 86%, 87%, 88%, 89%, 90%, 91%, 92%, 93%, 94%, 95%, 96%, 97%, 98%, 99%, or 100% sequence identity to the amino acid sequence of SEQ ID NO: 5; and (c) a CDR3 having at least about any one of 85%, 86%, 87%, 88%, 89%, 90%, 91%, 92%, 93%, 94%, 95%, 96%, 97%, 98%, 99%, or 100% sequence identity to the amino acid sequence of SEQ ID NO:6. In some embodiments, the anti-CD20 single-domain antibody is camelid. In some embodiments, the anti-CD20 antibody is humanized. In some embodiments, a CDR having at least about any one of 85%, 86%, 87%, 88%, 89%, 90%, 91%, 92%, 93%, 94%, 95%, 96%, 97%, 98%, or 99% identity contains substitutions (e.g., conservative substitutions), insertions, or deletions relative to the reference sequence, but the anti-CD20 single-domain antibody comprising that sequence retains the ability to bind to CD20. In some embodiments, the anti-CD20 single-domain antibody is affinity matured. In some embodiments, the anti-CD20 single-domain antibody is camelid. In some embodiments, the anti-CD20 single-domain antibody is humanized. In some embodiments, the anti-CD20 single-domain antibody comprises an acceptor human framework, e.g., a human immunoglobulin framework or a human consensus framework.

In some embodiments, there is provided an anti-CD20 single-domain antibody comprising three CDRs comprising: (a) a CDR1 comprising the amino acid sequence of SEQ ID NO: 4; (b) a CDR2 comprising the amino acid sequence of SEQ ID NO: 5; and (c) a CDR3 comprising the amino acid sequence of SEQ ID NO; 6. In some embodiments, the anti-CD20 single-domain antibody is camelid. In some embodiments, the anti-CD20 single-domain antibody is humanized. In some embodiments, the anti-CD20 single-domain antibody comprises an acceptor human framework, e.g., a human immunoglobulin framework or a human consensus framework.

In some embodiments, there is provided an anti-CD20 single-domain antibody comprising a $V_HH$ domain having at least about any one of 85%, 86%, 87%, 88%, 89%, 90%, 91%, 92%, 93%, 94%, 95%, 96%, 97%, 98%, 99%, or 100% sequence identity to the amino acid sequence of SEQ ID NO: 77. In some embodiments, a $V_HH$ sequence having at least about any one of 85%, 86%, 87%, 88%, 89%, 90%, 91%, 92%, 93%, 94%, 95%, 96%, 97%, 98%, or 99% identity contains substitutions (e.g., conservative substitutions), insertions, or deletions relative to the reference sequence, but the anti-CD20 single-domain antibody comprising that sequence retains the ability to bind to CD20. In some embodiments, a total of 1 to 10 amino acids have been substituted, inserted and/or deleted in the amino acid sequence of SEQ ID NO: 77. In some embodiments, substitutions, insertions, or deletions occur in regions outside the CDRs (i.e., in the FRs). Optionally, the anti-CD20 single-domain antibody comprises the amino acid sequence of SEQ ID NO: 77, including post-translational modifications of that sequence.

In some embodiments, there is provided an isolated anti-CD20 single-domain antibody comprising a $V_HH$ domain having the amino acid sequence of SEQ ID NO: 77. In some embodiments, there is provided a polypeptide comprising the amino acid sequence of SEQ ID NO: 77.

In some embodiments, functional epitopes can be mapped by combinatorial alanine scanning. In this process, a combinatorial alanine-scanning strategy can be used to identify amino acids in the CD20 protein that are necessary for interaction with anti-CD20 single-domain antibodies. In some embodiments, the epitope is conformational and crystal structure of the anti-CD20 single-domain antibody bound to CD20 may be employed to identify the epitopes. In some embodiments, the present application provides an antibody that specifically binds to the same epitope as any one of the anti-CD20 single-domain antibodies provided herein. For example, in some embodiments, an antibody is provided that binds to the same epitope as an anti-CD20 single-domain antibody comprising the amino acid sequence of SEQ ID NO: 77.

In some embodiments, the present application provides an anti-CD20 antibody, or antigen binding fragment thereof, that specifically binds to CD20 competitively with any one of the anti-CD20 single-domain antibodies described herein. In some embodiments, competitive binding may be determined using an ELISA assay. For example, in some embodiments, an antibody is provided that specifically binds to CD20 competitively with an anti-CD20 single-domain antibody comprising the amino acid sequence of SEQ ID NO: 77.

In some embodiments, there is provided an anti-CD20 antibody or antigen binding protein comprising any one of the anti-CD20 single-domain antibodies described above. In some embodiments, the anti-CD20 antibody is a monoclonal antibody, including a camelid, chimeric, humanized or human antibody. In some embodiments, the anti-CD20 antibody is an antibody fragment, e.g., a $V_HH$ fragment. In some embodiments, the anti-CD20 antibody is a full-length heavy-chain only antibody comprising an Fc region of any antibody class or isotype, such as IgG1 or IgG4. In some embodiments, the Fc region has reduced or minimized effector function.

In some embodiments, the anti-CD20 antibody (such as anti-CD20 single-domain antibody) or antigen binding protein according to any of the above embodiments may incorporate any of the features, singly or in combination, as described in Sections 1-7 of "Features of antibodies" below.

In some embodiments, there is provided an isolated nucleic acid encoding any one of the anti-CD20 antibodies (such as anti-CD20 single-domain antibodies) described above. In some embodiments, an isolated nucleic acid encoding an anti-CD20 single-domain antibody is provided wherein the nucleic acid comprises a sequence having at least about any one of 85%, 86%, 87%, 88%, 89%, 90%, 91%, 92%, 93%, 94%, 95%, 96%, 97%, 98%, 99%, or 100% sequence identity to the nucleic acid sequence of SEQ ID NO: 102. In some embodiments, there is provided an isolated nucleic acid comprising the nucleic acid sequence of SEQ ID NO: 102. In some embodiments, a vector (e.g., expression vector) comprising such nucleic acid are provided. In some embodiments, a host cell comprising such nucleic acid is provided. In some embodiments, a method of making an anti-CD20 antibody is provided, wherein the method comprises culturing a host cell comprising a nucleic acid encoding the anti-CD20 antibody, as provided above, under conditions suitable for expression of the anti-CD20 antibody, and optionally recovering the anti-CD20 antibody from the host cell (or host cell culture medium).

Anti-BCMA Single-Domain Antibodies

In one aspect, the present application provides isolated single-domain antibodies that specifically bind to BCMA, such as human BCMA. In some embodiments, the anti-BCMA single-domain antibody modulates BCMA activity. In some embodiments, the anti-BCMA single-domain antibody is an antagonist antibody.

B cell mature antigen (BCMA), also known as CD269, is a member of the tumor necrosis factor receptor superfamily, namely TNFRSF17 (Thompson et al., J. Exp. Medicine, 192 (1):129-135, 2000). Human BCMA is almost exclusively expressed in plasma cells and multiple myelomia cells (see e.g. Novak et al., Blood, 103(2): 689-694, 2004; Neri et al., Clinical Cancer Research, 73(19):5903-5909; Felix et al., Mol. Oncology, 9(7): 1348-58, 2015). BCMA can bind B-cell activating factor (BAFF) and a proliferation including ligand (APRIL) (e.g. Mackay et al., 2003 and Kalled et al., Immunological Review, 204: 43-54, 2005). BCMA can be a suitable tumor antigen target for immunotherapeutic agents against multiple myelomia. Antibodies of high affinity can block the binding between BCMA and its native ligands BAFF and APRIL. The anti-BCMA single-domain antibodies can be used in combination with cell immunotherapy using CAR-T cells, for example, to enhance cytotoxic effects against tumor cells.

In some embodiments, there is provided an anti-BCMA single-domain antibody comprising one, two, or all three CDRs of the amino acid sequence of SEQ ID NO: 78. In some embodiments, there is provided an anti-BCMA single-domain antibody comprising one, two, or all three CDRs of the amino acid sequence of SEQ ID NO: 79. In some embodiments, there is provided an anti-BCMA single-domain antibody comprising one, two, or all three CDRs of the amino acid sequence of SEQ ID NO: 80. In some embodiments, there is provided an anti-BCMA single-domain antibody comprising one, two, or all three CDRs of the amino acid sequence of SEQ ID NO: 81. In some embodiments, there is provided an anti-BCMA single-domain antibody comprising one, two, or all three CDRs of the amino acid sequence of SEQ ID NO: 82. In some embodiments, there is provided an anti-BCMA single-domain antibody comprising one, two, or all three CDRs of the amino acid sequence of SEQ ID NO: 83. In some embodiments, there is provided an anti-BCMA single-domain antibody comprising one, two, or all three CDRs of the amino acid sequence of SEQ ID NO: 84. In some embodiments, there is provided an anti-BCMA single-domain antibody comprising one, two, or all three CDRs of the amino acid sequence of SEQ ID NO: 85. In some embodiments, there is provided an anti-BCMA single-domain antibody comprising one, two, or all three CDRs of the amino acid sequence of SEQ ID NO: 86. In some embodiments, there is provided an anti-BCMA single-domain antibody comprising one, two, or all three CDRs of the amino acid sequence of SEQ ID NO: 87. In some embodiments, there is provided an anti-BCMA single-domain antibody comprising one, two, or all three CDRs of the amino acid sequence of SEQ ID NO: 88. In some embodiments, the anti-BCMA single-domain antibody is camelid. In some embodiments, the anti-BCMA single-domain antibody is humanized. In some embodiments, the anti-BCMA single-domain antibody comprises an acceptor human framework, e.g., a human immunoglobulin framework or a human consensus framework.

In some embodiments, there is provided an anti-BCMA single-domain antibody comprising at least one, at least two, or all three CDRs selected from (a) a CDR1 comprising an amino acid sequence selected from SEQ ID NO: 7-17; (b) a CDR2 comprising an amino acid sequence selected from SEQ ID NO: 18-28; and (c) a CDR3 comprising an amino acid sequence selected from SEQ ID NO: 29-39. In some embodiments, the anti-BCMA single-domain antibody is camelid. In some embodiments, the anti-BCMA single-domain antibody is humanized. In some embodiments, the anti-BCMA single-domain antibody comprises an acceptor human framework, e.g., a human immunoglobulin framework or a human consensus framework.

In some embodiments, there is provided an anti-BCMA single-domain antibody comprising three CDRs comprising: (a) a CDR1 having at least about any one of 85%, 86%, 87%, 88%, 89%, 90%, 91%, 92%, 93%, 94%, 95%, 96%, 97%, 98%, 99%, or 100% sequence identity to an amino acid sequence selected from SEQ ID NO:7-17; (b) a CDR2 having at least about any one of 85%, 86%, 87%, 88%, 89%, 90%, 91%, 92%, 93%, 94%, 95%, 96%, 97%, 98%, 99%, or 100% sequence identity to an amino acid sequence selected from SEQ ID NO: 18-28; and (c) a CDR3 having at least about any one of 85%, 86%, 87%, 88%, 89%, 90%, 91%, 92%, 93%, 94%, 95%, 96%, 97%, 98%, 99%, or 100% sequence identity to an amino acid sequence selected from SEQ ID NO:29-39. In some embodiments, a CDR having at least about any one of 85%, 86%, 87%, 88%, 89%, 90°/c, 91%, 92/%, 93%, 94%, 95%, 96%, 97%, 98%, or 99% identity contains substitutions (e.g., conservative substitutions), insertions, or deletions relative to the reference sequence, but the anti-BCMA single-domain antibody comprising that sequence retains the ability to bind to BCMA. In some embodiments, the anti-BCMA single-domain antibody is affinity matured. In some embodiments, the anti-BCMA single-domain antibody is camelid. In some embodiments, the anti-BCMA single-domain antibody is humanized. In some embodiments, the anti-BCMA single-domain antibody comprises an acceptor human framework, e.g., a human immunoglobulin framework or a human consensus framework.

In some embodiments, there is provided an anti-BCMA single-domain antibody comprising three CDRs comprising: (a) a CDR1 comprising the amino acid sequence of SEQ ID NO: 7; (b) a CDR2 comprising the amino acid sequence of SEQ ID NO: 18; and (c) a CDR3 comprising the amino acid sequence of SEQ ID NO: 29. In some embodiments, the anti-BCMA single-domain antibody is camelid. In some embodiments, the anti-BCMA single-domain antibody is humanized. In some embodiments, the anti-BCMA single-domain antibody comprises an acceptor human framework, e.g., a human immunoglobulin framework or a human consensus framework.

In some embodiments, there is provided an anti-BCMA single-domain antibody comprising three CDRs comprising: (a) a CDR1 comprising the amino acid sequence of SEQ ID NO: 8; (b) a CDR2 comprising the amino acid sequence of SEQ ID NO: 19; and (c) a CDR3 comprising the amino acid sequence of SEQ ID NO: 30. In some embodiments, the anti-BCMA single-domain antibody is camelid. In some embodiments, the anti-BCMA single-domain antibody is humanized. In some embodiments, the anti-BCMA single-domain antibody comprises an acceptor human framework, e.g., a human immunoglobulin framework or a human consensus framework.

In some embodiments, there is provided an anti-BCMA single-domain antibody comprising three CDRs comprising: (a) a CDR1 comprising the amino acid sequence of SEQ ID NO: 9; (b) a CDR2 comprising the amino acid sequence of SEQ ID NO: 20; and (c) a CDR3 comprising the amino acid sequence of SEQ ID NO: 31. In some embodiments, the anti-BCMA single-domain antibody is camelid. In some embodiments, the anti-BCMA single-domain antibody is humanized. In some embodiments, the anti-BCMA single-domain antibody comprises an acceptor human framework, e.g., a human immunoglobulin framework or a human consensus framework.

In some embodiments, there is provided an anti-BCMA single-domain antibody comprising three CDRs comprising: (a) a CDR1 comprising the amino acid sequence of SEQ ID NO: 10; (b) a CDR2 comprising the amino acid sequence of SEQ ID NO: 21; and (c) a CDR3 comprising the amino acid sequence of SEQ ID NO: 32. In some embodiments, the anti-BCMA single-domain antibody is camelid. In some embodiments, the anti-BCMA single-domain antibody is humanized. In some embodiments, the anti-BCMA single-domain antibody comprises an acceptor human framework, e.g., a human immunoglobulin framework or a human consensus framework.

In some embodiments, there is provided an anti-BCMA single-domain antibody comprising three CDRs comprising: (a) a CDR1 comprising the amino acid sequence of SEQ ID NO: 11; (b) a CDR2 comprising the amino acid sequence of SEQ ID NO: 22; and (c) a CDR3 comprising the amino acid sequence of SEQ ID NO: 33. In some embodiments, the anti-BCMA single-domain antibody is camelid. In some embodiments, the anti-BCMA single-domain antibody is humanized. In some embodiments, the anti-BCMA single-domain antibody comprises an acceptor human framework, e.g., a human immunoglobulin framework or a human consensus framework.

In some embodiments, there is provided an anti-BCMA single-domain antibody comprising three CDRs comprising: (a) a CDR1 comprising the amino acid sequence of SEQ ID NO: 12; (b) a CDR2 comprising the amino acid sequence of SEQ ID NO: 23; and (c) a CDR3 comprising the amino acid sequence of SEQ ID NO: 34. In some embodiments, the anti-BCMA single-domain antibody is camelid. In some embodiments, the anti-BCMA single-domain antibody is humanized. In some embodiments, the anti-BCMA single-domain antibody comprises an acceptor human framework, e.g., a human immunoglobulin framework or a human consensus framework.

In some embodiments, there is provided an anti-BCMA single-domain antibody comprising three CDRs comprising: (a) a CDR1 comprising the amino acid sequence of SEQ ID NO: 13; (b) a CDR2 comprising the amino acid sequence of SEQ ID NO: 24; and (c) a CDR3 comprising the amino acid sequence of SEQ ID NO: 35. In some embodiments, the anti-BCMA single-domain antibody is camelid. In some embodiments, the anti-BCMA single-domain antibody is humanized. In some embodiments, the anti-BCMA single-domain antibody comprises an acceptor human framework, e.g., a human immunoglobulin framework or a human consensus framework.

In some embodiments, there is provided an anti-BCMA single-domain antibody comprising three CDRs comprising: (a) a CDR1 comprising the amino acid sequence of SEQ ID NO: 14; (b) a CDR2 comprising the amino acid sequence of SEQ ID NO: 25; and (c) a CDR3 comprising the amino acid sequence of SEQ ID NO: 36. In some embodiments, the anti-BCMA single-domain antibody is camelid. In some embodiments, the anti-BCMA single-domain antibody is humanized. In some embodiments, the anti-BCMA single-domain antibody comprises an acceptor human framework, e.g., a human immunoglobulin framework or a human consensus framework.

In some embodiments, there is provided an anti-BCMA single-domain antibody comprising three CDRs comprising: (a) a CDR1 comprising the amino acid sequence of SEQ ID NO: 15; (b) a CDR2 comprising the amino acid sequence of SEQ ID NO: 26; and (c) a CDR3 comprising the amino acid sequence of SEQ ID NO: 37. In some embodiments, the anti-BCMA single-domain antibody is camelid. In some embodiments, the anti-BCMA single-domain antibody is humanized. In some embodiments, the anti-BCMA single-domain antibody comprises an acceptor human framework, e.g., a human immunoglobulin framework or a human consensus framework.

In some embodiments, there is provided an anti-BCMA single-domain antibody comprising three CDRs comprising: (a) a CDR1 comprising the amino acid sequence of SEQ ID NO: 16; (b) a CDR2 comprising the amino acid sequence of SEQ ID NO: 27; and (c) a CDR3 comprising the amino acid sequence of SEQ ID NO: 38. In some embodiments, the anti-BCMA single-domain antibody is camelid. In some embodiments, the anti-BCMA single-domain antibody is humanized. In some embodiments, the anti-BCMA single-domain antibody comprises an acceptor human framework, e.g., a human immunoglobulin framework or a human consensus framework.

In some embodiments, there is provided an anti-BCMA single-domain antibody comprising three CDRs comprising: (a) a CDR1 comprising the amino acid sequence of SEQ ID NO: 17; (b) a CDR2 comprising the amino acid sequence of SEQ ID NO: 28; and (c) a CDR3 comprising the amino acid sequence of SEQ ID NO: 39. In some embodiments, the anti-BCMA single-domain antibody is camelid. In some embodiments, the anti-BCMA single-domain antibody is humanized. In some embodiments, the anti-BCMA single-domain antibody comprises an acceptor human framework, e.g., a human immunoglobulin framework or a human consensus framework.

In some embodiments, there is provided an anti-BCMA single-domain antibody comprising a $V_HH$ domain having at least about any one of 85%, 86%, 87%, 88%, 89%, 90%, 91%, 92%, 93%, 94%, 95%, 96%, 97%, 98%, 99%, or 100% sequence identity to an amino acid sequence selected from SEQ ID NO: 78-88. In some embodiments, a $V_HH$ sequence having at least about any one of 85%, 86%, 87%, 88%, 89%, 90%, 91%, 92%, 93%, 94%, 95%, 96%, 97%, 98%, or 99% identity contains substitutions (e.g., conservative substitutions), insertions, or deletions relative to the reference sequence, but the anti-BCMA single-domain antibody comprising that sequence retains the ability to bind to BCMA. In some embodiments, a total of 1 to 10 amino acids have been substituted, inserted and/or deleted in an amino acid sequence selected from SEQ ID NO: 78-88. In some embodiments, substitutions, insertions, or deletions occur in regions outside the CDRs (i.e., in the FRs). Optionally, the anti-BCMA single-domain antibody comprises an amino acid sequence selected from SEQ ID NO: 78-88, including post-translational modifications of that sequence.

In some embodiments, there is provided an isolated anti-BCMA single-domain antibody comprising a $V_HH$ domain having the amino acid sequence of SEQ ID NO: 78. In some embodiments, there is provided a polypeptide comprising the amino acid sequence of SEQ ID NO: 78. In some embodiments, there is provided an isolated anti-BCMA single-domain antibody comprising a $V_HH$ domain having the amino acid sequence of SEQ ID NO: 79. In some embodiments, there is provided a polypeptide comprising the amino acid sequence of SEQ ID NO: 79. In some embodiments, there is provided an isolated anti-BCMA single-domain antibody comprising a $V_HH$ domain having the amino acid sequence of SEQ ID NO: 80. In some embodiments, there is provided a polypeptide comprising the amino acid sequence of SEQ ID NO: 80. In some embodiments, there is provided an isolated anti-BCMA single-domain antibody comprising a $V_HH$ domain having the amino acid sequence of SEQ ID NO: 81. In some embodiments, there is provided a polypeptide comprising the amino acid sequence of SEQ ID NO: 81. In some embodiments, there is provided an isolated anti-BCMA single-domain antibody comprising a $V_HH$ domain having the amino acid sequence of SEQ ID NO: 82. In some embodiments, there is provided a polypeptide comprising the amino acid sequence of SEQ ID NO: 82. In some embodiments, there is provided an isolated anti-BCMA single-domain antibody comprising a $V_HH$ domain having the amino acid sequence of SEQ ID NO: 83. In some embodiments, there is provided a polypeptide comprising the amino acid sequence of SEQ ID NO: 83. In some embodiments, there is provided an isolated anti-BCMA single-domain antibody comprising a $V_HH$ domain having the amino acid sequence of SEQ ID NO: 84. In some embodiments, there is provided a polypeptide comprising the amino acid sequence of SEQ ID NO: 84. In some embodiments, there is provided an isolated anti-BCMA single-domain antibody comprising a $V_HH$ domain having the amino acid sequence of SEQ ID NO: 85. In some embodiments, there is provided a polypeptide comprising the amino acid sequence of SEQ ID NO: 85. In some embodiments, there is provided an isolated anti-BCMA single-domain antibody comprising a $V_HH$ domain having the amino acid sequence of SEQ ID NO: 86. In some embodiments, there is provided a polypeptide comprising the amino acid sequence of SEQ ID NO: 86. In some embodiments, there is provided an isolated anti-BCMA single-domain antibody comprising a $V_HH$ domain having the amino acid sequence of SEQ ID NO: 87. In some embodiments, there is provided a polypeptide comprising the amino acid sequence of SEQ ID NO: 87. In some embodiments, there is provided an isolated anti-BCMA single-domain antibody comprising a $V_HH$ domain having the amino acid sequence of SEQ ID NO: 88. In some embodiments, there is provided a polypeptide comprising the amino acid sequence of SEQ ID NO: 88.

In some embodiments, functional epitopes can be mapped by combinatorial alanine scanning. In this process, a combinatorial alanine-scanning strategy can be used to identify amino acids in the BCMA protein that are necessary for interaction with anti-BCMA single-domain antibodies. In some embodiments, the epitope is conformational and crystal structure of anti-BCMA single-domain antibody bound to BCMA may be employed to identify the epitopes. In some embodiments, the present application provides an antibody that specifically binds to the same epitope as any of the anti-BCMA single-domain antibodies provided herein. For example, in some embodiments, an antibody is provided that binds to the same epitope as an anti-BCMA single-domain antibody comprising the amino acid sequence of SEQ ID NO: 78. In some embodiments, an antibody is provided that binds to the same epitope as an anti-BCMA single-domain antibody comprising the amino acid sequence of SEQ ID NO: 79. In some embodiments, an antibody is provided that binds to the same epitope as an anti-BCMA single-domain antibody comprising the amino acid sequence of SEQ ID NO: 80. In some embodiments, an antibody is provided that binds to the same epitope as an anti-BCMA single-domain antibody comprising the amino acid sequence of SEQ ID NO: 81. In some embodiments, an antibody is provided that binds to the same epitope as an anti-BCMA single-domain antibody comprising the amino acid sequence of SEQ ID NO: 82. In some embodiments, an antibody is provided that binds to the same epitope as an anti-BCMA single-domain antibody comprising the amino acid sequence of SEQ ID NO: 83. In some embodiments, an antibody is provided that binds to the same epitope as an anti-BCMA single-domain antibody comprising the amino acid sequence of SEQ ID NO: 84. In some embodiments, an antibody is provided that binds to the same epitope as an anti-BCMA single-domain antibody comprising the amino acid sequence of SEQ ID NO: 85. In some embodiments, an antibody is provided that binds to the same epitope as an anti-BCMA single-domain antibody comprising the amino acid sequence of SEQ ID NO: 86. In some embodiments, an antibody is provided that binds to the same epitope as an anti-BCMA single-domain antibody comprising the amino acid sequence of SEQ ID NO: 87. In some embodiments, an antibody is provided that binds to the same epitope as an anti-BCMA single-domain antibody comprising the amino acid sequence of SEQ ID NO: 88.

In some embodiments, the present application provides an anti-BCMA antibody, or antigen binding fragment thereof, that specifically binds to BCMA competitively with any one of the anti-BCMA single-domain antibodies described herein. In some embodiments, competitive binding may be determined using an ELISA assay. For example, in some embodiments, an antibody is provided that specifically binds to BCMA competitively with an anti-BCMA single-domain antibody comprising the amino acid sequence of SEQ ID NO:78. In some embodiments, an antibody is provided that specifically binds to BCMA competitively with an anti-BCMA single-domain antibody comprising the amino acid sequence of SEQ ID NO:79. In some embodiments, an antibody is provided that specifically binds to BCMA competitively with an anti-BCMA single-domain antibody comprising the amino acid sequence of SEQ ID NO:80. In some embodiments, an antibody is provided that specifically binds to BCMA competitively with an anti-BCMA single-domain antibody comprising the amino acid sequence of SEQ ID NO:81. In some embodiments, an antibody is provided that specifically binds to BCMA competitively with an anti-BCMA single-domain antibody comprising the amino acid sequence of SEQ ID NO:82. In some embodiments, an antibody is provided that specifically binds to BCMA competitively with an anti-BCMA single-domain antibody comprising the amino acid sequence of SEQ ID NO:83. In some embodiments, an antibody is provided that specifically binds to BCMA competitively with an anti-BCMA single-domain antibody comprising the amino acid sequence of SEQ ID NO:84. In some embodiments, an antibody is provided that specifically binds to BCMA competitively with an anti-BCMA single-domain antibody comprising the amino acid sequence of SEQ ID NO:85. In some embodiments, an antibody is provided that specifically binds to BCMA competitively with an anti-BCMA single-domain antibody comprising the amino acid sequence of SEQ ID NO:86. In some embodiments, an antibody is provided that specifically binds to BCMA competitively with an anti-BCMA single-domain antibody comprising the amino acid sequence of SEQ ID NO:87. In some embodiments, an antibody is provided that specifically binds to BCMA competitively with an anti-BCMA single-domain antibody comprising the amino acid sequence of SEQ ID NO:88.

In some embodiments, there is provided an anti-BCMA antibody or antigen binding protein comprising any one of the anti-BCMA single-domain antibodies described above. In some embodiments, the anti-BCMA antibody is a monoclonal antibody, including a camelid, chimeric, humanized or human antibody. In some embodiments, the anti-BCMA antibody is an antibody fragment, e.g., a $V_H H$ fragment. In some embodiments, the anti-BCMA antibody is a full-length heavy-chain only antibody comprising an Fc region of any antibody class or isotype, such as IgG1 or IgG4. In some embodiments, the Fc region has reduced or minimized effector function.

In some embodiments, the anti-BCMA antibody (such as anti-BCMA single-domain antibody) or antigen binding protein according to any of the above embodiments may incorporate any of the features, singly or in combination, as described in Sections 1-7 of "Features of antibodies" below.

In some embodiments, there is provided an isolated nucleic acid encoding any one of the anti-BCMA antibodies (such as anti-BCMA single-domain antibodies) described above. In some embodiments, an isolated nucleic acid encoding an anti-BCMA single-domain antibody is provided wherein the nucleic acid comprises a sequence having at least about any one of 85%, 86%, 87%, 88%, 89%, 90%, 91%, 92%, 93%, 94%, 95%, 96%, 97%, 98%, 99%, or 100% sequence identity to a nucleic acid sequence selected from the group consisting of SEQ ID NO: 103-113. In some embodiments, there is provided an isolated nucleic acid comprising a nucleic acid sequence selected from the group consisting of SEQ ID NO: 103-113. In some embodiments, a vector (e.g., expression vector) comprising such nucleic acid are provided. In some embodiments, a host cell comprising such nucleic acid is provided. In some embodiments, a method of making an anti-BCMA antibody is provided, wherein the method comprises culturing a host cell comprising a nucleic acid encoding the anti-BCMA antibody, as provided above, under conditions suitable for expression of the anti-BCMA antibody, and optionally recovering the anti-BCMA antibody from the host cell (or host cell culture medium).

Anti-CD38 Single-Domain Antibodies

In one aspect, the present application provides isolated single-domain antibodies that specifically bind to CD38, such as human CD38. In some embodiments, the anti-CD38 single-domain antibody modulates CD38 activity. In some embodiments, the anti-CD38 single-domain antibody is an antagonist antibody.

CD38 is a type II transmembrane glycoprotein that associates with cell-surface receptors, regulates cytoplasmic $Ca^{2+}$ flux, and mediates signal transduction in lymphoid and myeloid (Konopleva et al., J Immunol, 161:4702-8, 1998; Deaglio et al., Blood, 109:5390-8, 2007). Human CD38 is highly and uniformly expressed on myeloma cells and is expressed at relatively low levels on normal lymphoid and myeloid cells and in some tissues of non-hematopoietic origin, which makes it a potential target in the treatment of myeloma (See, for example, Lin et al., *Am J Clin Pathol,* 2004, 121:482; H. M. Lokhorst et al., *New Eng. J. Med.,* 2015, 373:13).

In some embodiments, there is provided an anti-CD38 single-domain antibody comprising one, two, or all three CDRs of the amino acid sequence of SEQ ID NO: 89. In some embodiments, there is provided an anti-CD38 single-domain antibody comprising one, two, or all three CDRs of the amino acid sequence of SEQ ID NO: 90. In some embodiments, there is provided an anti-CD38 single-domain antibody comprising one, two, or all three CDRs of the amino acid sequence of SEQ ID NO: 91. In some embodiments, there is provided an anti-CD38 single-domain antibody comprising one, two, or all three CDRs of the amino acid sequence of SEQ ID NO: 92. In some embodiments, there is provided an anti-CD38 single-domain antibody comprising one, two, or all three CDRs of the amino acid sequence of SEQ ID NO: 93. In some embodiments, there is provided an anti-CD38 single-domain antibody comprising one, two, or all three CDRs of the amino acid sequence of SEQ ID NO: 94. In some embodiments, there is provided an anti-CD38 single-domain antibody comprising one, two, or all three CDRs of the amino acid sequence of SEQ ID NO: 95. In some embodiments, there is provided an anti-CD38 single-domain antibody comprising one, two, or all three CDRs of the amino acid sequence of SEQ ID NO: 96. In some embodiments, there is provided an anti-CD38 single-domain antibody comprising one, two, or all three CDRs of the amino acid sequence of SEQ ID NO: 97. In some embodiments, there is provided an anti-CD38 single-domain antibody comprising one, two, or all three CDRs of the amino acid sequence of SEQ ID NO: 98. In some embodiments, there is provided an anti-CD38 single-domain antibody comprising one, two, or all three CDRs of the amino acid sequence of SEQ ID NO: 99. In some embodiments, there is provided an anti-CD38 single-domain antibody comprising one, two, or all three CDRs of the amino acid sequence of SEQ ID NO: 100. In some embodiments, the anti-CD38 single-domain antibody is camelid. In some embodiments, the anti-CD38 single-domain antibody is humanized. In some embodiments, the anti-CD38 single-domain antibody comprises an acceptor human framework, e.g., a human immunoglobulin framework or a human consensus framework.

In some embodiments, there is provided an anti-CD38 single-domain antibody comprising at least one, at least two, or all three CDRs selected from (a) a CDR1 comprising an amino acid sequence selected from SEQ ID NO: 40-51; (b) a CDR2 comprising an amino acid sequence selected from SEQ ID NO: 52-63; and (c) a CDR3 comprising an amino acid sequence selected from SEQ ID NO: 64-75. In some embodiments, the anti-CD38 single-domain antibody is camelid. In some embodiments, the anti-CD38 single-domain antibody is humanized. In some embodiments, the anti-CD38 single-domain antibody comprises an acceptor human framework, e.g., a human immunoglobulin framework or a human consensus framework.

In some embodiments, there is provided an anti-CD38 single-domain antibody comprising three CDRs comprising: (a) a CDR1 having at least about any one of 85%, 86%, 87%, 88%, 89%, 90%, 91%, 92%, 93%, 94%, 95%, 96%, 97%, 98%, 99%, or 100% sequence identity to an amino acid sequence selected from SEQ ID NO:40-51; (b) a CDR2 having at least about any one of 85%, 86%, 87%, 88%, 89%, 90%, 91%, 92%, 93%, 94%, 95%, 96%, 97%, 98%, 99%, or 100% sequence identity to an amino acid sequence selected from SEQ ID NO:52-63; and (c) a CDR3 having at least about any one of 85%, 86%, 87%, 88%, 89%, 90%, 91%, 92%, 93%, 94%, 95%, 96%, 97%, 98%, 99%, or 100% sequence identity to an amino acid sequence selected from SEQ ID NO:64-75. In some embodiments, a CDR having at least about any one of 85%, 86%, 87%, 88%, 89%, 90%, 91%, 92%, 93%, 94%, 95%, 96%, 97%, 98%, or 99% identity contains substitutions (e.g., conservative substitutions), insertions, or deletions relative to the reference sequence, but the anti-CD38 single-domain antibody comprising that sequence retains the ability to bind to CD38. In some embodiments, the anti-CD38 single-domain antibody is camelid. In some embodiments, the anti-CD38 single-domain antibody is humanized. In some embodiments, the anti-CD38 single-domain antibody comprises an acceptor human framework, e.g., a human immunoglobulin framework or a human consensus framework. In some embodiments, the anti-CD38 single-domain antibody is affinity matured.

In some embodiments, there is provided an anti-CD38 single-domain antibody comprising three CDRs comprising: (a) a CDR1 comprising the amino acid sequence of SEQ ID NO: 40: (b) a CDR2 comprising the amino acid sequence of SEQ ID NO: 52; and (c) a CDR3 comprising the amino acid sequence of SEQ ID NO: 64. In some embodiments, the anti-CD38 single-domain antibody is camelid. In some embodiments, the anti-CD38 single-domain antibody is humanized. In some embodiments, the anti-CD38 single-domain antibody comprises an acceptor human framework, e.g., a human immunoglobulin framework or a human consensus framework.

In some embodiments, there is provided an anti-CD38 single-domain antibody comprising three CDRs comprising: (a) a CDR1 comprising the amino acid sequence of SEQ ID NO: 41; (b) a CDR2 comprising the amino acid sequence of SEQ ID NO: 53; and (c) a CDR3 comprising the amino acid sequence of SEQ ID NO: 65. In some embodiments, the anti-CD38 single-domain antibody is camelid. In some embodiments, the anti-CD38 single-domain antibody is humanized. In some embodiments, the anti-CD38 single-domain antibody comprises an acceptor human framework, e.g., a human immunoglobulin framework or a human consensus framework.

In some embodiments, there is provided an anti-CD38 single-domain antibody comprising three CDRs comprising: (a) a CDR1 comprising the amino acid sequence of SEQ ID NO: 42; (b) a CDR2 comprising the amino acid sequence of SEQ ID NO: 54; and (c) a CDR3 comprising the amino acid sequence of SEQ ID NO: 66. In some embodiments, the anti-CD38 single-domain antibody is camelid. In some embodiments, the anti-CD38 single-domain antibody is humanized. In some embodiments, the anti-CD38 single-domain antibody comprises an acceptor human framework, e.g., a human immunoglobulin framework or a human consensus framework.

In some embodiments, there is provided an anti-CD38 single-domain antibody comprising three CDRs comprising: (a) a CDR1 comprising the amino acid sequence of SEQ ID NO: 43; (b) a CDR2 comprising the amino acid sequence of SEQ ID NO: 55; and (c) a CDR3 comprising the amino acid sequence of SEQ ID NO: 67. In some embodiments, the anti-CD38 single-domain antibody is camelid. In some embodiments, the anti-CD38 single-domain antibody is humanized. In some embodiments, the anti-CD38 single-domain antibody comprises an acceptor human framework, e.g., a human immunoglobulin framework or a human consensus framework.

In some embodiments, there is provided an anti-CD38 single-domain antibody comprising three CDRs comprising: (a) a CDR1 comprising the amino acid sequence of SEQ ID NO: 44; (b) a CDR2 comprising the amino acid sequence of SEQ ID NO: 56; and (c) a CDR3 comprising the amino acid sequence of SEQ ID NO: 68. In some embodiments, the anti-CD38 single-domain antibody is camelid. In some embodiments, the anti-CD38 single-domain antibody is humanized. In some embodiments, the anti-CD38 single-domain antibody comprises an acceptor human framework, e.g., a human immunoglobulin framework or a human consensus framework.

In some embodiments, there is provided an anti-CD38 single-domain antibody comprising three CDRs comprising: (a) a CDR1 comprising the amino acid sequence of SEQ ID NO: 45; (b) a CDR2 comprising the amino acid sequence of SEQ ID NO: 57; and (c) a CDR3 comprising the amino acid sequence of SEQ ID NO: 69. In some embodiments, the anti-CD38 single-domain antibody is camelid. In some embodiments, the anti-CD38 single-domain antibody is humanized. In some embodiments, the anti-CD38 single-domain antibody comprises an acceptor human framework, e.g., a human immunoglobulin framework or a human consensus framework.

In some embodiments, there is provided an anti-CD38 single-domain antibody comprising three CDRs comprising: (a) a CDR1 comprising the amino acid sequence of SEQ ID NO: 46; (b) a CDR2 comprising the amino acid sequence of SEQ ID NO: 58; and (c) a CDR3 comprising the amino acid sequence of SEQ ID NO: 70. In some embodiments, the anti-CD38 single-domain antibody is camelid. In some embodiments, the anti-CD38 single-domain antibody is humanized. In some embodiments, the anti-CD38 single-domain antibody comprises an acceptor human framework, e.g., a human immunoglobulin framework or a human consensus framework.

In some embodiments, there is provided an anti-CD38 single-domain antibody comprising three CDRs comprising: (a) a CDR1 comprising the amino acid sequence of SEQ ID NO: 47; (b) a CDR2 comprising the amino acid sequence of SEQ ID NO: 59; and (c) a CDR3 comprising the amino acid sequence of SEQ ID NO: 71. In some embodiments, the anti-CD38 single-domain antibody is camelid. In some embodiments, the anti-CD38 single-domain antibody is humanized. In some embodiments, the anti-CD38 single-domain antibody comprises an acceptor human framework, e.g., a human immunoglobulin framework or a human consensus framework.

In some embodiments, there is provided an anti-CD38 single-domain antibody comprising three CDRs comprising: (a) a CDR1 comprising the amino acid sequence of SEQ ID NO: 48; (b) a CDR2 comprising the amino acid sequence of SEQ ID NO: 60; and (c) a CDR3 comprising the amino acid sequence of SEQ ID NO: 72. In some embodiments, the anti-CD38 single-domain antibody is camelid. In some embodiments, the anti-CD38 single-domain antibody is humanized. In some embodiments, the anti-CD38 single-domain antibody comprises an acceptor human framework, e.g., a human immunoglobulin framework or a human consensus framework.

In some embodiments, there is provided an anti-CD38 single-domain antibody comprising three CDRs comprising: (a) a CDR1 comprising the amino acid sequence of SEQ ID NO: 49; (b) a CDR2 comprising the amino acid sequence of SEQ ID NO: 61; and (c) a CDR3 comprising the amino acid sequence of SEQ ID NO: 73. In some embodiments, the anti-CD38 single-domain antibody is camelid. In some embodiments, the anti-CD38 single-domain antibody is humanized. In some embodiments, the anti-CD38 single-domain antibody comprises an acceptor human framework, e.g., a human immunoglobulin framework or a human consensus framework.

In some embodiments, there is provided an anti-CD38 single-domain antibody comprising three CDRs comprising: (a) a CDR1 comprising the amino acid sequence of SEQ ID NO: 50; (b) a CDR2 comprising the amino acid sequence of SEQ ID NO: 62; and (c) a CDR3 comprising the amino acid sequence of SEQ ID NO: 74. In some embodiments, the anti-CD38 single-domain antibody is camelid. In some embodiments, the anti-CD38 single-domain antibody is humanized. In some embodiments, the anti-CD38 single-domain antibody comprises an acceptor human framework, e.g., a human immunoglobulin framework or a human consensus framework.

In some embodiments, there is provided an anti-CD38 single-domain antibody comprising three CDRs comprising: (a) a CDR1 comprising the amino acid sequence of SEQ ID NO: 51; (b) a CDR2 comprising the amino acid sequence of SEQ ID NO: 63; and (c) a CDR3 comprising the amino acid sequence of SEQ ID NO: 75. In some embodiments, the anti-CD38 single-domain antibody is camelid. In some embodiments, the anti-CD38 single-domain antibody is humanized. In some embodiments, the anti-CD38 single-domain antibody comprises an acceptor human framework, e.g., a human immunoglobulin framework or a human consensus framework.

In some embodiments, there is provided an anti-CD38 single-domain antibody comprising a $V_HH$ domain having at least about any one of 85%, 86%, 87%, 88%, 89%, 90%, 91%, 92%, 93%, 94%, 95%, 96%, 97%, 98%, 99%, or 100% sequence identity to an amino acid sequence selected from SEQ ID NO: 89-100. In some embodiments, a $V_HH$ sequence having at least about any one of 85%, 86%, 87%, 88%, 89%, 90%, 91%, 92%, 93%, 94%, 95%, 96%, 97%, 98%, or 99% identity contains substitutions (e.g., conservative substitutions), insertions, or deletions relative to the reference sequence, but the anti-CD38 single-domain antibody comprising that sequence retains the ability to bind to CD38. In some embodiments, a total of 1 to 10 amino acids have been substituted, inserted and/or deleted in an amino acid sequence selected from SEQ ID NO: 89-100. In some embodiments, substitutions, insertions, or deletions occur in regions outside the CDRs (i.e., in the FRs). Optionally, the anti-CD38 single-domain antibody comprises an amino acid sequence selected from SEQ ID NO: 89-100, including post-translational modifications of that sequence.

In some embodiments, there is provided an isolated anti-CD38 single-domain antibody comprising a $V_HH$ domain having the amino acid sequence of SEQ ID NO: 89.

In some embodiments, there is provided a polypeptide comprising the amino acid sequence of SEQ ID NO: 89. In some embodiments, there is provided an isolated anti-CD38 single-domain antibody comprising a $V_HH$ domain having the amino acid sequence of SEQ ID NO: 90. In some embodiments, there is provided a polypeptide comprising the amino acid sequence of SEQ ID NO: 90. In some embodiments, there is provided an isolated anti-CD38 single-domain antibody comprising a $V_HH$ domain having the amino acid sequence of SEQ ID NO: 91. In some embodiments, there is provided a polypeptide comprising the amino acid sequence of SEQ ID NO: 91. In some embodiments, there is provided an isolated anti-CD38 single-domain antibody comprising a $V_HH$ domain having the amino acid sequence of SEQ ID NO: 92. In some embodiments, there is provided a polypeptide comprising the amino acid sequence of SEQ ID NO: 92. In some embodiments, there is provided an isolated anti-CD38 single-domain antibody comprising a $V_HH$ domain having the amino acid sequence of SEQ ID NO: 93. In some embodiments, there is provided a polypeptide comprising the amino acid sequence of SEQ ID NO: 93. In some embodiments, there is provided an isolated anti-CD38 single-domain antibody comprising a $V_HH$ domain having the amino acid sequence of SEQ ID NO: 94. In some embodiments, there is provided a polypeptide comprising the amino acid sequence of SEQ ID NO: 94. In some embodiments, there is provided an isolated anti-CD38 single-domain antibody comprising a $V_HH$ domain having the amino acid sequence of SEQ ID NO: 95. In some embodiments, there is provided a polypeptide comprising the amino acid sequence of SEQ ID NO: 95. In some embodiments, there is provided an isolated anti-CD38 single-domain antibody comprising a $V_HH$ domain having the amino acid sequence of SEQ ID NO: 96. In some embodiments, there is provided a polypeptide comprising the amino acid sequence of SEQ ID NO: 96. In some embodiments, there is provided an isolated anti-CD38 single-domain antibody comprising a $V_HH$ domain having the amino acid sequence of SEQ ID NO: 97. In some embodiments, there is provided a polypeptide comprising the amino acid sequence of SEQ ID NO: 97. In some embodiments, there is provided an isolated anti-CD38 single-domain antibody comprising a $V_HH$ domain having the amino acid sequence of SEQ ID NO: 98. In some embodiments, there is provided a polypeptide comprising the amino acid sequence of SEQ ID NO: 98. In some embodiments, there is provided an isolated anti-CD38 single-domain antibody comprising a $V_HH$ domain having the amino acid sequence of SEQ ID NO: 99. In some embodiments, there is provided a polypeptide comprising the amino acid sequence of SEQ ID NO: 99. In some embodiments, there is provided an isolated anti-CD38 single-domain antibody comprising a $V_HH$ domain having the amino acid sequence of SEQ ID NO: 100. In some embodiments, there is provided a polypeptide comprising the amino acid sequence of SEQ ID NO: 100.

In some embodiments, functional epitopes can be mapped by combinatorial alanine scanning. In this process, a combinatorial alanine-scanning strategy can be used to identify amino acids in the CD38 protein that are necessary for interaction with the anti-CD38 single-domain antibodies. In some embodiments, the epitope is conformational and crystal structure of anti-CD38 single-domain antibody bound to CD38 may be employed to identify the epitopes. In some embodiments, the present application provides an antibody that specifically binds to the same epitope as any of the anti-CD38 single-domain antibodies provided herein. For example, in some embodiments, an antibody is provided that binds to the same epitope as an anti-CD38 single-domain antibody comprising the amino acid sequence of SEQ ID NO: 89. In some embodiments, an antibody is provided that binds to the same epitope as an anti-CD38 single-domain antibody comprising the amino acid sequence of SEQ ID NO: 90. In some embodiments, an antibody is provided that binds to the same epitope as an anti-CD38 single-domain antibody comprising the amino acid sequence of SEQ ID NO: 91. In some embodiments, an antibody is provided that binds to the same epitope as an anti-CD38 single-domain antibody comprising the amino acid sequence of SEQ ID NO: 92. In some embodiments, an antibody is provided that binds to the same epitope as an anti-CD38 single-domain antibody comprising the amino acid sequence of SEQ ID NO: 93. In some embodiments, an antibody is provided that binds to the same epitope as an anti-CD38 single-domain antibody comprising the amino acid sequence of SEQ ID NO: 94. In some embodiments, an antibody is provided that binds to the same epitope as an anti-CD38 single-domain antibody comprising the amino acid sequence of SEQ ID NO: 95. In some embodiments, an antibody is provided that binds to the same epitope as an anti-CD38 single-domain antibody comprising the amino acid sequence of SEQ ID NO: 96. In some embodiments, an antibody is provided that binds to the same epitope as an anti-CD38 single-domain antibody comprising the amino acid sequence of SEQ ID NO: 97. In some embodiments, an antibody is provided that binds to the same epitope as an anti-CD38 single-domain antibody comprising the amino acid sequence of SEQ ID NO: 98. In some embodiments, an antibody is provided that binds to the same epitope as an anti-CD38 single-domain antibody comprising the amino acid sequence of SEQ ID NO: 99. In some embodiments, an antibody is provided that binds to the same epitope as an anti-CD38 single-domain antibody comprising the amino acid sequence of SEQ ID NO: 100.

In some embodiments, the present application provides an anti-CD38 antibody, or antigen binding fragment thereof, that specifically binds to CD38 competitively with any one of the anti-CD38 single-domain antibodies described herein. In some embodiments, competitive binding may be determined using an ELISA assay. For example, in some embodiments, an antibody is provided that specifically binds to CD38 competitively with an anti-CD38 single-domain antibody comprising the amino acid sequence of SEQ ID NO:89. In some embodiments, an antibody is provided that specifically binds to CD38 competitively with an anti-CD38 single-domain antibody comprising the amino acid sequence of SEQ ID NO:90. In some embodiments, an antibody is provided that specifically binds to CD38 competitively with an anti-CD38 single-domain antibody comprising the amino acid sequence of SEQ ID NO:91. In some embodiments, an antibody is provided that specifically binds to CD38 competitively with an anti-CD38 single-domain antibody comprising the amino acid sequence of SEQ ID NO:92. In some embodiments, an antibody is provided that specifically binds to CD38 competitively with an anti-CD38 single-domain antibody comprising the amino acid sequence of SEQ ID NO:93. In some embodiments, an antibody is provided that specifically binds to CD38 competitively with an anti-CD38 single-domain antibody comprising the amino acid sequence of SEQ ID NO:94. In some embodiments, an antibody is provided that specifically binds to CD38 competitively with an anti-CD38 single-domain antibody comprising the amino acid sequence of SEQ ID NO:95. In some embodiments, an antibody is provided that specifically binds to CD38 competitively with an anti-CD38 single-domain antibody comprising the amino acid sequence of SEQ ID NO:96. In some embodiments, an antibody is provided that specifically binds to CD38 competitively with an anti-CD38 single-domain antibody comprising the amino acid sequence of SEQ ID NO:97. In some embodiments, an antibody is provided that specifically binds to CD38 competitively with an anti-CD38 single-domain antibody comprising the amino acid sequence of SEQ ID NO:98. In some embodiments, an antibody is provided that specifically binds to CD38 competitively with an anti-CD38 single-domain antibody comprising the amino acid sequence of SEQ ID NO:99. In some embodiments, an antibody is provided that specifically binds to CD38 competitively with an anti-CD38 single-domain antibody comprising the amino acid sequence of SEQ ID NO: 100.

In some embodiments, there is provided an anti-CD38 antibody or antigen binding protein comprising any one of the anti-CD38 single-domain antibodies described above. In some embodiments, the anti-CD38 antibody is a monoclonal antibody, including a camelid, chimeric, humanized or human antibody. In some embodiments, the anti-CD38 antibody is an antibody fragment, e.g., a $V_HH$ fragment. In some embodiments, the anti-CD38 antibody is a full-length heavy-chain only antibody comprising an Fc region of any antibody class or isotype, such as IgG1 or IgG4. In some embodiments, the Fc region has reduced or minimized effector function.

In some embodiments, the anti-CD38 antibody (such as anti-CD38 single-domain antibody) or antigen binding protein according to any of the above embodiments may incorporate any of the features, singly or in combination, as described in Sections 1-7 of "Features of antibodies" below.

In some embodiments, there is provided an isolated nucleic acid encoding any one of the anti-CD38 antibodies (such as anti-CD38 single-domain antibodies) described above. In some embodiments, an isolated nucleic acid encoding an anti-CD38 single-domain antibody is provided wherein the nucleic acid comprises a sequence having at least about any one of 85%, 86%, 87%, 88%, 89%, 90%, 91%, 92%, 93%, 94%, 95%, 96%, 97%, 98%, 99%, or 100% sequence identity to a nucleic acid sequence selected from the group consisting of SEQ ID NO: 114-125. In some embodiments, there is provided an isolated nucleic acid comprising a nucleic acid sequence selected from the group consisting of SEQ ID NO: 114-125. In some embodiments, a vector (e.g., expression vector) comprising such nucleic acid are provided. In some embodiments, a host cell comprising such nucleic acid is provided. In some embodiments, a method of making an anti-CD38 antibody is provided, wherein the method comprises culturing a host cell comprising a nucleic acid encoding the anti-CD38 antibody, as provided above, under conditions suitable for expression of the anti-CD38 antibody, and optionally recovering the anti-CD38 antibody from the host cell (or host cell culture medium).

Features of Antibodies
1. Antibody Affinity

In some embodiments, an antibody provided herein has a dissociation constant (Kd) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

In some embodiments, Kd is measured by a radiolabeled antigen binding assay (RIA) performed with the Fab version or $V_HH$ fragment of an antibody of interest and its antigen as described by the following assay. For example, solution binding affinity of Fabs for antigen is measured by equilibrating Fab with a minimal concentration of ($^{125}$I-labeled antigen in the presence of a titration series of unlabeled antigen, then capturing bound antigen with an anti-Fab antibody-coated plate (see, e.g., Chen et al., *J. Mol. Biol.* 293:865-881 (1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

In some embodiments, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab or V$_H$H of the antibody of interest (0.78 nM to 500 nM) are injected in PBS with 0.05% polysorbate 20 (TWEEN-20™) surfactant (PBST) at 25° C. at a flow rate of approximately 25 μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ M$^{-1}$ s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In some embodiments, an antibody provided herein is an antibody fragment. Antibody fragments include, but are not limited to, Fab, Fab', Fab'-SH, F(ab')$_2$, Fv, and scFv fragments, V$_H$H, and other fragments described below. For a review of certain antibody fragments, see Hudson et al. *Nat. Med.* 9:129-134 (2003). For a review of scFv fragments, see, e.g., Plückthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In some embodiments, the antibody provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a camelid species, such as llama) and a human constant region. In a further example, a chimeric antibody is a "class switched" antibody in which the class or subclass has been changed from that of the parent antibody. Chimeric antibodies include antigen-binding fragments thereof.

In some embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285

(1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

In some embodiments, the single-domain antibodies are modified, such as humanized, without diminishing the native affinity of the domain for antigen and while reducing its immunogenicity with respect to a heterologous species. For example, the amino acid residues of the antibody variable domain ($V_HH$) of an llama antibody can be determined, and one or more of the Camelid amino acids, for example, in the framework regions, are replaced by their human counterpart as found in the human consensus sequence, without that polypeptide losing its typical character, i.e. the humanization does not significantly affect the antigen binding capacity of the resulting polypeptide. Humanization of Camelid single-domain antibodies requires the introduction and mutagenesis of a limited amount of amino acids in a single polypeptide chain. This is in contrast to humanization of scFv, Fab', (Fab')2 and IgG, which requires the introduction of amino acid changes in two chains, the light and the heavy chain and the preservation of the assembly of both chains.

Single-domain antibodies comprising a $V_HH$ domain can be humanized to have human-like sequences. In some embodiments, the FR regions of the $V_HH$ domain used herein comprise at least about any one of 50%, 60%, 70%, 80%, 90%, 95% or more of amino acid sequence homology to human $V_H$ framework regions. One exemplary class of humanized $V_HH$ domains is characterized in that the $V_HH$s carry an amino acid from the group consisting of glycine, alanine, valine, leucine, isoleucine, proline, phenylalanine, tyrosine, tryptophan, methionine, serine, threonine, asparagine, or glutamine at position 45, such as, for example, L45 and a tryptophan at position 103, according to the Kabat numbering. As such, polypeptides belonging to this class show a high amino acid sequence homology to human $V_H$ framework regions and said polypeptides might be administered to a human directly without expectation of an unwanted immune response therefrom, and without the burden of further humanization.

Another exemplary class of humanized Camelid single-domain antibodies has been described in WO 03/035694 and contains hydrophobic FR2 residues typically found in conventional antibodies of human origin or from other species, but compensating this loss in hydrophilicity by the charged arginine residue on position 103 that substitutes the conserved tryptophan residue present in $V_H$ from double-chain antibodies. As such, peptides belonging to these two classes show a high amino acid sequence homology to human $V_H$ framework regions and said peptides might be administered to a human directly without expectation of an unwanted immune response therefrom, and without the burden of further humanization.

4. Human Antibodies

In some embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008). Transgenic mice or rats capable of producing fully human single-domain antibodies are known in the art. See, e.g., US20090307787A1, U.S. Pat. No. 8,754,287, US20150289489A1, US20100122358A1, and WO2004049794.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3): 185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

One technique for obtaining $V_HH$ sequences directed against a particular antigen or target involves suitably immunizing a transgenic mammal that is capable of expressing heavy chain antibodies (i.e. so as to raise an immune response and/or heavy chain antibodies directed against said antigen or target), obtaining a suitable biological sample from said transgenic mammal that contains (nucleic acid sequences encoding) said $V_HH$ sequences (such as a blood sample, serum sample or sample of B-cells), and then generating $V_HH$ sequences directed against said antigen or target, starting from said sample, using any suitable technique known per se (such as any of the methods described herein or a hybridoma technique). For example, for this purpose, the heavy chain antibody-expressing mice and the further methods and techniques described in WO 02/085945, WO 04/049794 and WO 06/008548 and Janssens et al., Proc. Natl. Acad. Sci. USA. 2006 Oct. 10;

103(41):15130-5 can be used. For example, such heavy chain antibody expressing mice can express heavy chain antibodies with any suitable (single) variable domain, such as (single) variable domains from natural sources (e.g. human (single) variable domains, Camelid (single) variable domains or shark (single) variable domains), as well as for example synthetic or semi-synthetic (single) variable domains.

5. Library-Derived Antibodies

Antibodies of the present application may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); *Fellouse, Proc. Natl. Acad. Sci. USA* 101(34): 12467-12472 (2004); and Lee et al., *J. Immunol. Methods* 284(1-2): 119-132 (2004). Methods for constructing single-domain antibody libraries have been described, for example, see U.S. Pat. No. 7,371,849.

In certain phage display methods, repertoires of $V_H$ and $V_L$ genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In some embodiments, an antibody provided herein is a multispecific antibody, e.g. a bispecific antibody. Multispecific antibodies are antibodies that have binding specificities for at least two different sites. In some embodiments, one of the binding specificities is for an antigen selected from the group consisting of CD19, CD20, BCMA, and CD38, and the other is for any other antigen. In some embodiments, bispecific antibodies may bind to two different epitopes of an antigen selected from the group consisting of CD19, CD20, BCMA, and CD38. Bispecific antibodies may also be used to localize cytotoxic agents to cells which express an antigen selected from the group consisting of CD19, CD20, BCMA, and CD38.

Bispecific antibodies can be prepared as full length antibodies or antibody fragments. Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g., Gruber et al., *J. Immunol.,* 152:5368 (1994)); and preparing trispecific antibodies as described, e.g., in Tutt et al. *J. Immunol.* 147: 60 (1991); and creating polypeptides comprising tandem single-domain antibodies (see, e.g, U.S. Patent Application No. 20110028695; and Conrath et al. *J. Biol. Chem.,* 2001; 276(10):7346-50). Engineered antibodies with three or more functional antigen binding sites, including "Octopus antibodies," are also included herein (see, e.g., US 2006/0025576A1).

7. Antibody Variants

In some embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleic acid sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In some embodiments, antibody variants having one or more amino acid substitutions are provided. Sites of interest for substitutional mutagenesis include the HVRs and FRs. Conservative substitutions are shown in Table 3 under the heading of "Preferred substitutions." More substantial changes are provided in Table 3 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 3

Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |

TABLE 3-continued

Amino Acid Substitutions

| Original Residue | Exemplary Substitutions | Preferred Substitutions |
|---|---|---|
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant $V_H$ or $V_L$ being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In some embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or CDRs. In some embodiments of the variant $V_HH$ sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

b) Glycosylation Variants

In some embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the present application may be made in order to create antibody variants with certain improved properties.

In some embodiments, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g., complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Patent Application No. US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4): 680-688 (2006); and WO2003/085107).

Antibody variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In some embodiments, one or more amino acid modifications may be introduced into the Fc region of an antibody provided herein, thereby generating an Fc region variant. The Fc region variant may comprise a human Fc region sequence (e.g., a human IgG, IgG2, IgG3 or IgG4 Fc region) comprising an amino acid modification (e.g. a substitution) at one or more amino acid positions.

In some embodiments, the present application contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., Proc. Nat'l *Acad. Sci.* USA 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In some embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

d) Cysteine Engineered Antibody Variants

In some embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In some embodiments, any one or more of the following residues may be substituted with cysteine: A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In some embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In some embodiments, conjugates of an antibody and nonproteinaceous moiety that may be selectively heated by exposure to radiation are provided. In some embodiments, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Methods of Preparation

The antibodies (such as single-domain antibodies) described herein may be prepared using any methods known in the art or as described herein.

Methods of preparing single-domain antibodies have been described. See, for example, Els Pardon et al, *Nature Protocol*, 2014; 9(3): 674. Single-domain antibodies (such as $V_H$Hs) may be obtained using methods known in the art such as by immunizing a Camelid species (such as camel or llama) and obtaining hybridomas therefrom, or by cloning a library of single-domain antibodies using molecular biology techniques known in the art and subsequent selection by ELISA with individual clones of unselected libraries or by using phage display.

For recombinant production of the single-domain antibodies, the nucleic acids encoding the single-domain antibodies are isolated and inserted into a replicable vector for further cloning (amplification of the DNA) or for expression. DNA encoding the single-domain antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian) origin.

1. Polyclonal Antibodies

Polyclonal antibodies are generally raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are independently lower alkyl groups. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The animals are immunized against the antigen, immunogenic conjugates, or derivatives by combining, e.g., 100 μg or 5 μg or the protein or conjugate (for rabbits or mice, respectively) with 3 volumes of Freund's complete adjuvant and injecting the solution intradermally at multiple sites. One month later, the animals are boosted with ⅕ to ¹/₁₀ the original amount of peptide or conjugate in Freund's complete adjuvant by subcutaneous injection at multiple sites. Seven to fourteen days later, the animals are bled and the serum is assayed for antibody titer. Animals are boosted until the titer plateaus. Conjugates also can be made in recombinant cell culture as protein fusions. Also, aggregating agents such as alum are suitable to enhance the immune response.

2. Monoclonal Antibodies

Monoclonal antibodies are obtained from a population of substantially homogeneous antibodies, i.e., the individual antibodies comprising the population are identical except for possible naturally occurring mutations and/or post-translational modifications (e.g., isomerizations, amidations) that may be present in minor amounts. Thus, the modifier "monoclonal" indicates the character of the antibody as not being a mixture of discrete antibodies.

For example, the monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986).

The immunizing agent will typically include the antigenic protein or a fusion variant thereof. Generally either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. Goding, *Monoclonal Antibodies: Principles and Practice*, Academic Press (1986), pp. 59-103.

Immortalized cell lines are usually transformed mammalian cells, particularly myeloma cells of rodent, bovine and human origin. Usually, rat or mouse myeloma cell lines are employed. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which are substances that prevent the growth of HGPRT-deficient cells.

Preferred immortalized myeloma cells are those that fuse efficiently, support stable high-level production of antibody by the selected antibody-producing cells, and are sensitive to a medium such as HAT medium. Among these, preferred are murine myeloma lines, such as those derived from MOPC-21 and MPC-11 mouse tumors available from the Salk Institute Cell Distribution Center, San Diego, Calif. USA, and SP-2 cells (and derivatives thereof, e.g., X63-Ag8-653) available from the American Type Culture Collection, Manassas, Va. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The culture medium in which the hybridoma cells are cultured can be assayed for the presence of monoclonal antibodies directed against the desired antigen. Preferably, the binding affinity and specificity of the monoclonal antibody can be determined by immunoprecipitation or by an in vitro binding assay, such as radioimmunoassay (RIA) or enzyme-linked assay (ELISA). Such techniques and assays are known in the in art. For example, binding affinity may be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as tumors in a mammal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Monoclonal antibodies may also be made by recombinant DNA methods, such as those described in U.S. Pat. No. 4,816,567, and as described above. DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, in order to synthesize monoclonal antibodies in such recombinant host cells. Review articles on recombinant expression in bacteria of DNA encoding the antibody include Skerra et al., *Curr. Opinion in Inmmunol.*, 5:256-262 (1993) and Plückthun, *Immunol. Revs.* 130:151-188 (1992).

In a further embodiment, antibodies can be isolated from antibody phage libraries generated using the techniques described in McCafferty et al., *Nature*, 348:552-554 (1990). Clackson et al., *Nature*, 352:624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nucl. Acids Res.*, 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., *Proc. Natl Acad. Sci. USA,* 81:6851 (1984)), or by covalently joining to the immunoglobulin coding sequence all or part of the coding sequence for a non-immunoglobulin polypeptide. Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

The monoclonal antibodies described herein may by monovalent, the preparation of which is well known in the art. For example, one method involves recombinant expression of immunoglobulin light chain and a modified heavy chain. The heavy chain is truncated generally at any point in the Fc region so as to prevent heavy chain crosslinking. Alternatively, the relevant cysteine residues may be substituted with another amino acid residue or are deleted so as to prevent crosslinking. In vitro methods are also suitable for preparing monovalent antibodies. Digestion of antibodies to produce fragments thereof, particularly Fab fragments, can be accomplished using routine techniques known in the art.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

3. Recombinant Production in Prokaryotic Cells a) Vector Construction

Polynucleic acid sequences encoding the antibodies of the present application can be obtained using standard recombinant techniques. Desired polynucleic acid sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as GEM™-11 may be utilized in making a recombinant vector which can be used to transform susceptible host cells such as *E. coli* LE392.

The expression vector of the present application may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the present application. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the—galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleic acid sequences have been published, thereby enabling a skilled worker operably to ligate them to cistrons encoding the target light and heavy chains (Siebenlist et al. (1980) *Cell* 20: 269) using linkers or adaptors to supply any required restriction sites.

In one aspect, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In some embodiments of the present application, the signal sequences used in both cistrons of the expression system are STII signal sequences or variants thereof.

In some embodiments, the production of the antibodies according to the present application can occur in the cytoplasm of the host cell, and therefore does not require the presence of secretion signal sequences within each cistron. In some embodiments, polypeptide components, such as the polypeptide encoding the $V_H$ domain of the first antigen binding portion optionally fused to the second antigen binding portion, and the polypeptide encoding the $V_L$ domain of the first antigen binding portion optionally fused to the second antigen binding portion, are expressed, folded and assembled to form functional antibodies within the cytoplasm. Certain host strains (e.g., the *E. coli* trxB⁻ strains) provide cytoplasm conditions that are favorable for disulfide bond formation, thereby permitting proper folding and assembly of expressed protein subunits. Proba and Pluckthun *Gene*, 159:203 (1995).

The present invention provides an expression system in which the quantitative ratio of expressed polypeptide components can be modulated in order to maximize the yield of secreted and properly assembled the antibodies of the present application. Such modulation is accomplished at least in part by simultaneously modulating translational strengths for the polypeptide components. One technique for modulating translational strength is disclosed in Simmons et al., U.S. Pat. No. 5,840,523. It utilizes variants of the translational initiation region (TIR) within a cistron. For a given TIR, a series of amino acid or nucleic acid sequence variants can be created with a range of translational strengths, thereby providing a convenient means by which to adjust this factor for the desired expression level of the specific chain. TIR variants can be generated by conventional mutagenesis techniques that result in codon changes which can alter the amino acid sequence, although silent changes in the nucleic acid sequence are preferred. Alterations in the TIR can include, for example, alterations in the number or spacing of Shine-Dalgarno sequences, along with alterations in the signal sequence. One method for generating mutant signal sequences is the generation of a "codon bank" at the beginning of a coding sequence that does not change the amino acid sequence of the signal sequence (i.e., the changes are silent). This can be accomplished by changing the third nucleotide position of each codon; additionally, some amino acids, such as leucine, serine, and arginine, have multiple first and second positions that can add complexity in making the bank. This method of mutagenesis is described in detail in Yansura et al. (1992) *METHODS: A Companion to Methods in Enzymol.* 4:151-158.

Preferably, a set of vectors is generated with a range of TIR strengths for each cistron therein. This limited set provides a comparison of expression levels of each chain as well as the yield of the desired protein products under various TIR strength combinations. TIR strengths can be determined by quantifying the expression level of a reporter gene as described in detail in Simmons et al. U.S. Pat. No. 5,840,523. Based on the translational strength comparison, the desired individual TIRs are selected to be combined in the expression vector constructs of the present application.

b) Prokaryotic Host Cells

Prokaryotic host cells suitable for expressing the antibodies of the present application include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium*, *Serratia marcescans*, *Klebsiella*, *Proteus*, *Shigella*, *Rhizobia*, *Vitreoscilla*, or *Paracoccus*. In some embodiments, gram-negative cells are used. In one embodiment, *E. coli* cells are used as hosts for the invention. Examples of *E. coli* strains include strain W3110 (Bachmann, *Cellular and Molecular Biology*, vol. 2 (Washington, D.C.: American Society for Microbiology, 1987), pp. 1190-1219; ATCC Deposit No. 27,325) and derivatives thereof, including strain 33D3 having genotype W3110 AfhuA (AtonA) ptr3 lac Iq lacL8 AompT A(nmpc-fepE) degP41 kan$^R$ (U.S. Pat. No. 5,639,635). Other strains and derivatives thereof, such as *E. coli* 294 (ATCC 31,446), *E. coli* B, *E. coli* 1776 (ATCC 31,537) and *E. coli* RV308(ATCC 31,608) are also suitable. These examples are illustrative rather than limiting. Methods for constructing derivatives of any of the above-mentioned bacteria having defined genotypes are known in the art and described in, for example, Bass et al., *Proteins*, 8:309-314 (1990). It is generally necessary to select the appropriate bacteria taking into consideration replicability of the replicon in the cells of a bacterium. For example, *E. coli*, *Serratia*, or *Salmonella* species can be suitably used as the host when well known plasmids such as pBR322, pBR325, pACYC177, or pKN410 are used to supply the replicon.

Typically the host cell should secrete minimal amounts of proteolytic enzymes, and additional protease inhibitors may desirably be incorporated in the cell culture.

c) Protein Production

Host cells are transformed with the above-described expression vectors and cultured in conventional nutrient media modified as appropriate for inducing promoters, selecting transformants, or amplifying the genes encoding the desired sequences. Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the antibodies of the present application are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector of the present application, protein expression is induced under conditions suitable for the activation of the promoter. In one aspect of the present application, PhoA promoters are used for controlling transcription of the polypeptides. Accordingly, the transformed host cells are cultured in a phosphate-limiting medium for induction. Preferably, the phosphate-limiting medium is the C.R.A.P medium (see, e.g., Simmons et al., *J. Immunol. Methods* (2002), 263:133-147). A variety of other inducers may be used, according to the vector construct employed, as is known in the art.

The expressed antibodies of the present application are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

Alternatively, protein production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

During the fermentation process, induction of protein expression is typically initiated after the cells have been grown under suitable conditions to a desired density, e.g., an $OD_{550}$ of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the antibodies of the present application, various fermentation conditions can be modified. For example, to improve the proper assembly and folding of the secreted polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) *J Bio Chem* 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun (2000) J. Biol. Chem. 275: 17106-17113; Arie et al. (2001) *Mol. Microbiol.* 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly et al. (1998), supra; Georgiou et al., U.S. Pat. No. 5,264,365; Georgiou et al., U.S. Pat. No. 5,508,192; Hara et al., *Microbial Drug Resistance,* 2:63-72 (1996).

*E. coli* strains deficient for proteolytic enzymes and transformed with plasmids overexpressing one or more chaperone proteins may be used as host cells in the expression system encoding the antibodies of the present application.

d) Protein Purification

The antibodies produced herein are further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the antibodies comprising an Fc region of the present application. Protein A is a 41 kD cell wall protein from *Staphylococcus aureas* which binds with a high affinity to the Fc region of antibodies. Lindmark et al (1983) *J. Immunol. Meth.* 62:1-13. The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants. The solid phase is then washed to remove contaminants nonspecifically bound to the solid phase. Finally the antibodies of interest is recovered from the solid phase by elution.

4. Recombinant Production in Eukaryotic Cells

For Eukaryotic expression, the vector components generally include, but are not limited to, one or more of the following, a signal sequence, an origin of replication, one or more marker genes, and enhancer element, a promoter, and a transcription termination sequence.

a) Signal Sequence Component

A vector for use in a eukaryotic host may also an insert that encodes a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available.

The DNA for such precursor region is ligated in reading frame to DNA encoding the antibodies of the present application.

b) Origin of Replication

Generally, the origin of replication component is not needed for mammalian expression vectors (the SV40 origin may typically be used only because it contains the early promoter).

c) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up nucleic acid encoding the antibodies of the present application, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with the polypeptide encoding-DNA sequences, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

d) Promoter Component

Expression and cloning vectors usually contain a promoter that is recognized by the host organism and is operably linked to the nucleic acid encoding the desired polypeptide sequences. Virtually all eukaryotic genes have an AT-rich region located approximately 25 to 30 based upstream from the site where transcription is initiated. Another sequence found 70 to 80 bases upstream from the start of the transcription of many genes is a CNCAAT region where N may be any nucleotide. A the 3' end of most eukaryotic is an AATAAA sequence that may be the signal for addition of the poly A tail to the 3' end of the coding sequence. All of these sequences may be inserted into eukaryotic expression vectors.

Other promoters suitable for use with prokaryotic hosts include the phoA promoter,—lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the antibodies.

Polypeptide transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heatshock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., *Nature* 297:598-601 (1982) on expression of human-interferon cDNA in mouse cells under the control of a thymidine kinase promoter from herpes simplex virus. Alternatively, the Rous Sarcoma Virus long terminal repeat can be used as the promoter.

e) Enhancer Element Component

Transcription of a DNA encoding the antibodies of the present application by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature* 297:17-18 (1982) on enhancing elements for activation of eukaryotic promoters. The enhancer may be spliced into the vector at a position 5' or 3' to the polypeptide encoding sequence, but is preferably located at a site 5' from the promoter.

f) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the polypeptide-encoding mRNA. One useful transcription termination component is the bovine growth hormone polyadenylation region. See WO94/11026 and the expression vector disclosed therein.

g) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for antibodies production and cultured in conventional nutrient media modified as appropriate for inducing promoters, selecting transformants, or amplifying the genes encoding the desired sequences.

h) Culturing the Host Cells

The host cells used to produce the antibodies of the present application may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. No. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

i) Protein Purification

When using recombinant techniques, the antibodies can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The protein composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify the antibodies that are based on human immunoglobulins containing 1, 2, or 4 heavy chains (Lindmark et al., *J. Immunol. Meth.* 62:1-13 (1983)). Protein G is recommended for all mouse isotypes and for human 3 (Guss et al., *EMBO J.* 5:15671575 (1986)). The matrix to which the affinity ligand is attached is most often agarose, but other matrices are available. Mechanically stable matrices such as controlled pore glass or poly(styrene-divinyl)benzene allow for faster flow rates and shorter processing times than can be achieved with agarose. Where the antibody comprises a $C_H3$ domain, the Bakerbond ABXTMresin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Immunoconjugates

In some embodiments, the present application also provides immunoconjugates comprising any of the antibodies (such as single-domain antibodies) described herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In some embodiments, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In some embodiments, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In some embodiments, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo- SMCC, and sulfo-SMPB, and SVSB (succinimidyl-(4-vinylsulfone)benzoate) which are commercially available (e.g., from Pierce Biotechnology, Inc., Rockford, Ill., U.S.A).

Methods and Compositions for Diagnostics and Detection

In some embodiments, any of the antibodies (such as single-domain antibodies) provided herein is useful for detecting the presence of the corresponding antigen (such as CD19, CD20, BCMA, or CD38) in a biological sample. The term "detecting" as used herein encompasses quantitative or qualitative detection. In certain embodiments, a biological sample is blood, serum or other liquid samples of biological origin. In some embodiments, a biological sample comprises a cell or tissue.

In some embodiments, an anti-CD19 antibody (such as any one of the anti-CD19 single-domain antibodies described herein) for use in a method of diagnosis or detection is provided. In a further aspect, a method of detecting the presence of CD19 in a biological sample is provided. In certain embodiments, the method comprises detecting the presence of CD19 protein in a biological sample. In certain embodiments, CD19 is human CD19. In certain embodiments, the method comprises contacting the biological sample with an anti-CD19 antibody as described herein under conditions permissive for binding of the anti-CD19 antibody to CD19, and detecting whether a complex is formed between the anti-CD19 antibody and CD19. Such method may be an in vitro or in vivo method. In some embodiments, an anti-CD19 antibody is used to select subjects eligible for therapy with an anti-CD19 antibody, e.g. where CD19 is a biomarker for selection of patients.

In some embodiments, an anti-CD20 antibody (such as any one of the anti-CD20 single-domain antibodies described herein) for use in a method of diagnosis or detection is provided. In a further aspect, a method of detecting the presence of CD20 in a biological sample is provided. In certain embodiments, the method comprises detecting the presence of CD20 protein in a biological sample. In certain embodiments, CD20 is human CD20. In certain embodiments, the method comprises contacting the biological sample with an anti-CD20 antibody as described herein under conditions permissive for binding of the anti-CD20 antibody to CD20, and detecting whether a complex is formed between the anti-CD20 antibody and CD20. Such method may be an in vitro or in vivo method. In some embodiments, an anti-CD20 antibody is used to select subjects eligible for therapy with an anti-CD20 antibody, e.g. where CD20 is a biomarker for selection of patients.

In some embodiments, an anti-BCMA antibody (such as any one of the anti-BCMA single-domain antibodies described herein) for use in a method of diagnosis or detection is provided. In a further aspect, a method of detecting the presence of BCMA in a biological sample is provided. In certain embodiments, the method comprises detecting the presence of BCMA protein in a biological sample. In certain embodiments, BCMA is human BCMA. In certain embodiments, the method comprises contacting the biological sample with an anti-BCMA antibody as described herein under conditions permissive for binding of the anti-BCMA antibody to BCMA, and detecting whether a complex is formed between the anti-BCMA antibody and BCMA. Such method may be an in vitro or in vivo method. In some embodiments, an anti-BCMA antibody is used to select subjects eligible for therapy with an anti-BCMA antibody, e.g. where BCMA is a biomarker for selection of patients.

In some embodiments, an anti-CD38 antibody (such as any one of the anti-CD38 single-domain antibodies described herein) for use in a method of diagnosis or detection is provided. In a further aspect, a method of detecting the presence of CD38 in a biological sample is provided. In certain embodiments, the method comprises detecting the presence of CD38 protein in a biological sample. In certain embodiments, CD38 is human CD38. In certain embodiments, the method comprises contacting the biological sample with an anti-CD38 antibody as described herein under conditions permissive for binding of the anti-CD38 antibody to CD38, and detecting whether a complex is formed between the anti-CD38 antibody and CD38. Such method may be an in vitro or in vivo method. In some embodiments, an anti-CD38 antibody is used to select subjects eligible for therapy with an anti-CD38 antibody, e.g. where CD38 is a biomarker for selection of patients.

In certain embodiments, labeled antibodies (such as anti-CD19, anti-CD20, anti-BCMA, or anti-CD38 single-domain antibodies) are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

III. Chimeric Antigen Receptors

One aspect of the present application provides a chimeric antigen receptor (CAR) comprising an extracellular antigen binding domain comprising one or more single-domain antibodies (such as $V_HHs$). Any one of the single-domain antibodies described in Section II can be used in the CARs described herein. Exemplary CARs comprising one or more $V_HH$ domains (i.e., $V_HH$-based CARs) are illustrated and compared with conventional CARs comprising scFvs (i.e., scFv-based CARs) in FIGS. 1A-1D. One of skill in the art would recognize that the $V_HH$ domains in the exemplary CARs of FIGS. 1A-1D may be substituted with other sdAbs.

In some embodiments, there is provided a chimeric antigen receptor (CAR) comprising a polypeptide comprising: (a) an extracellular antigen binding domain comprising a single-domain antibody (sdAb) specifically binding to an antigen (such as a tumor antigen); (b) a transmembrane domain; and (c) an intracellular signaling domain. In some embodiments, the antigen is selected from the group consisting of CD19, CD20, CD22, CD33, CD38, BCMA, CS1, ROR1, GPC3, CD123, IL-13R, CD138, c-Met, EGFRvIII, GD-2, NY-ESO-1, MAGE A3, and glycolipid F77. In some embodiments, the sdAb is camelid, chimeric, human, or humanized. In some embodiments, the transmembrane domain is selected from the group consisting of CD8α, CD4, CD28, CD137, CD80, CD86, CD152 and PD1. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the CAR further comprises a hinge domain (such as a CD8α hinge domain) located between the C-terminus of the extracellular antigen binding domain and the N-terminus of the transmembrane domain. In some embodiments, the CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD28 transmembrane domain, a co-stimulatory signaling domain derived from CD28, and a primary intracellular signaling domain derived from CD3ζ. In some embodiments, the polypeptide comprises from the N-terminus to the C-terminus: a CD8α signal peptide, the extracellular antigen binding domain, a CD8α hinge domain, a CD28 transmembrane domain, a first co-stimulatory signaling domain derived from CD28, a second co-stimulatory signaling domain derived from CD137, and a primary intracellular signaling domain derived from CD3ζ. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ. In some embodiments, the CAR is monospecific. In some embodiments, the CAR is monovalent. In some embodiments, the CAR is multivalent, such as bivalent or trivalent. In some embodiments, the CAR is multispecific, such as bispecific.

Chimeric Antigen Receptors of Specific Targets

In some embodiments, the present application provides CARs comprising an extracellular antigen binding domain comprising any one of the anti-CD19, anti-CD20, anti-BCMA, or anti-CD38 single-domain antibodies described herein. The CARs can be monospecific or multispecific (such as bispecific or of higher number of specificities), and the CARs can be monovalent or multivalent (such as bivalent, trivalent, or of higher number of valencies). A list of exemplary monospecific chimeric antigen receptors, exemplary sequences, constructs and vectors thereof are shown in Table 4.

Tables 4, 5, and 6 listed in the "III. Chimeric antigen receptor" section use the following abbreviations: Ex.: exemplary; Vec.: vector; AA: amino acid sequence of CAR; NA: nucleic acid sequence of CAR; SP: signal peptide; Extracellular: extracellular antigen binding domain; sdAb: single-domain antibody; TM: transmembrane domain; CO1: co-stimulatory signaling domain 1; CO2: co-stimulatory signaling domain 2; Prim.: primary intracellular signaling domain. Domains are listed from the left to the right of each row that corresponds to the order of the domains from the N-terminus to the C-terminus of the CAR polypeptide.

1. CD19 CAR

In some embodiments, there is provided a CAR targeting CD19 (also referred herein as "CD19 CAR") comprising a polypeptide comprising: (a) an extracellular antigen binding domain comprising an anti-CD19 sdAb; (b) a transmembrane domain; and (c) an intracellular signaling domain. In some embodiments, the anti-CD19 sdAb is camelid, chimeric, human, or humanized. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the CD19 CAR further comprises a hinge domain (such as a CD8α hinge domain) located between the C-terminus of the extracellular antigen binding domain and the N-terminus of the transmembrane domain. In some embodiments, the CD19 CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD28 transmembrane domain, a co-stimulatory signaling domain derived from CD28, and a primary intracellular signaling domain derived from CD3ζ. In some embodiments, the CD19 CAR is monospecific. In some embodiments, the CD19 CAR is monovalent. In some embodiments, the CD19 CAR is multispecific, such as bispecific. In some embodiments, the CD19 CAR is multivalent, such as bivalent or trivalent.

In some embodiments, there is provided a CD19 CAR comprising a polypeptide comprising: (a) an extracellular antigen binding domain comprising an anti-CD19 sdAb; (b) a transmembrane domain; and (c) an intracellular signaling domain, wherein the anti-CD19 sdAb comprises the amino acid sequence of SEQ ID NO: 1, a CDR2 comprising the amino acid sequence of SEQ ID NO:2, and a CDR3 comprising the amino acid sequence of SEQ ID NO:3. In some embodiments, the anti-CD19 sdAb is camelid, chimeric, human, or humanized. In some embodiments, the anti-CD19 sdAb further comprises an FR1 comprising the amino acid sequence of SEQ ID NO: 240, an FR2 comprising the amino acid sequence of SEQ ID NO: 241, an FR3 comprising the amino acid sequence of SEQ ID NO: 242, and/or an FR4 comprising the amino acid sequence of SEQ ID NO: 243. In some embodiments, the anti-CD19 sdAb comprises a $V_HH$ domain comprising the amino acid sequence of SEQ ID NO: 76. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the CD19 CAR further comprises a hinge domain (such as a CD8α hinge domain) located between the C-terminus of the extracellular antigen binding domain and the N-terminus of the transmembrane domain. In some embodiments, the CD19 CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen-binding domain, a CD8α hinge domain, a CD28 transmembrane domain, a co-stimulatory signaling domain derived from CD28, and a primary intracellular signaling domain derived from CD3ζ. In some embodiments, the CD19 CAR is monospecific. In some embodiments, the CD19 CAR is monovalent. In some embodiments, the CD19 CAR is multispecific, such as bispecific. In some embodiments, the CD19 CAR is multivalent, such as bivalent or trivalent.

In some embodiments, there is provided a CD19 CAR comprising a polypeptide having at least about any one of 85%, 86%, 87%, 88%, 89%, 90%, 91%, 92%, 93%, 94%, 95%, 96%, 97%, 98%, 99%, or 100% sequence identity to the amino acid sequence of SEQ ID NO: 248. In some embodiments, there is provided a CD19 CAR comprising the amino acid sequence of SEQ ID NO: 248. Also provided is a polypeptide comprising the amino acid sequence of SEQ ID NO: 248.

In some embodiments, there is provided an isolated nucleic acid encoding any of the CD19 CARs provided herein. In some embodiments, there is provided an isolated nucleic acid having at least about any one of 85%, 86%, 87%, 88%, 89%, 90%, 91%, 92%, 93%, 94%, 95%, 96%, 97%, 98%, 99%, or 100% sequence identity to the nucleic acid sequence of SEQ ID NO: 250. In some embodiments, there is provided an isolated nucleic acid comprising the nucleic acid sequence of SEQ ID NO: 250. In some embodiments, the isolated nucleic acid is a DNA. In some embodiments, the isolated nucleic acid is a RNA. In some embodiments, there is provided a vector comprising any one of the nucleic acids encoding the CD19 CARs described above. In some embodiments, the vector is an expression vector. In some embodiments, the vector is a viral vector, such as a lentiviral vector.

2. CD20 CAR

In some embodiments, there is provided a CAR targeting CD20 (also referred herein as "CD20 CAR") comprising a polypeptide comprising: (a) an extracellular antigen binding domain comprising an anti-CD20 sdAb; (b) a transmembrane domain; and (c) an intracellular signaling domain. In some embodiments, the anti-CD20 sdAb is camelid, chimeric, human, or humanized. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the CD20 CAR further comprises a hinge domain (such as a CD8α hinge domain) located between the C-terminus of the extracellular antigen binding domain and the N-terminus of the transmembrane domain. In some embodiments, the CD20 CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen-binding domain, a CD8α hinge domain, a CD28 transmembrane domain, a co-stimulatory signaling domain derived from CD28, and a primary intracellular signaling domain derived from CD3ζ. In some embodiments, the CD20 CAR is monospecific. In some embodiments, the CD20 CAR is monovalent. In some embodiments, the CD20 CAR comprises the amino acid sequence of SEQ ID NO: 249. In some embodiments, the CAR is multispecific, such as bispecific. In some embodiments, the CD20 CAR is multivalent, such as bivalent or trivalent.

In some embodiments, there is provided a CD20 CAR comprising a polypeptide comprising: (a) an extracellular antigen binding domain comprising an anti-CD20 sdAb; (b) a transmembrane domain; and (c) an intracellular signaling domain, wherein the anti-CD20 sdAb comprises the amino acid sequence of SEQ ID NO:4, a CDR2 comprising the amino acid sequence of SEQ ID NO:5, and a CDR3 comprising the amino acid sequence of SEQ ID NO:6. In some embodiments, the anti-CD20 sdAb is camelid, chimeric, human, or humanized. In some embodiments, the anti-CD20 sdAb further comprises an FR1 comprising the amino acid sequence of SEQ ID NO: 244, an FR2 comprising the amino acid sequence of SEQ ID NO: 245, an FR3 comprising the amino acid sequence of SEQ ID NO: 246, and/or an FR4 comprising the amino acid sequence of SEQ ID NO: 247. In some embodiments, the anti-CD20 sdAb comprises a $V_HH$ domain comprising the amino acid sequence of SEQ ID NO: 77. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the CD20 CAR further comprises a hinge domain (such as a CD8α hinge domain) located between the C-terminus of the extracellular antigen binding domain and the N-terminus of the transmembrane domain. In some embodiments, the CD20 CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen-binding domain, a CD8α hinge domain, a CD28 transmembrane domain, a co-stimulatory signaling domain derived from CD28, and a primary intracellular signaling domain derived from CD3ζ. In some embodiments, the CD20 CAR is monospecific. In some embodiments, the CD20 CAR is monovalent. In some embodiments, the CD20 CAR comprises the amino acid sequence of SEQ ID NO: 249. In some embodiments, the CAR is multispecific, such as bispecific. In some embodiments, the CD20 CAR is multivalent, such as bivalent or trivalent.

In some embodiments, there is provided a CD20 CAR comprising a polypeptide having at least about any one of 85%, 86%, 87%, 88%, 89%, 90%, 91%, 92%, 93%, 94%, 95%, 96%, 97%, 98%, 99%, or 100% sequence identity to the amino acid sequence of SEQ ID NO: 249. In some embodiments, there is provided a CD20 CAR comprising the amino acid sequence of SEQ ID NO: 249. Also provided is a polypeptide comprising the amino acid sequence of SEQ ID NO: 249.

In some embodiments, there is provided an isolated nucleic acid encoding any of the CD20 CARs provided herein. In some embodiments, there is provided an isolated nucleic acid having at least about any one of 85%, 86%, 87%, 88%, 89%, 90%, 91%, 92%, 93%, 94%, 95%, 96%, 97%, 98%, 99%, or 100% sequence identity to the nucleic acid sequence of SEQ ID NO: 251. In some embodiments, there is provided an isolated nucleic acid comprising the nucleic acid sequence of SEQ ID NO: 251. In some embodiments, the isolated nucleic acid is a DNA. In some embodiments, the isolated nucleic acid is a RNA. In some embodiments, there is provided a vector comprising any one of the nucleic acids encoding the CD20 CARs described above. In some embodiments, the vector is an expression vector. In some embodiments, the vector is a viral vector, such as a lentiviral vector.

3. BCMA CAR

In some embodiments, there is provided a CAR targeting BCMA (also referred herein as "BCMA CAR") comprising a polypeptide comprising: (a) an extracellular antigen binding domain comprising an anti-BCMA sdAb; (b) a transmembrane domain; and (c) an intracellular signaling domain. In some embodiments, the anti-BCMA sdAb is camelid, chimeric, human, or humanized. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the BCMA CAR further comprises a hinge domain (such as a CD8α hinge domain) located between the C-terminus of the extracellular antigen binding domain and the N-terminus of the transmembrane domain. In some embodiments, the BCMA CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen-binding domain, a CD8α hinge domain, a CD28 transmembrane domain, a first co-stimulatory signaling domain derived from CD28, a second co-stimulatory signaling domain derived from CD137, and a primary intracellular signaling domain derived from CD3ζ. In some embodiments, the polypeptide comprises from the N-terminus to the C-terminus: a CD8α signal peptide, the extracellular antigen-binding domain, a CD8α hinge domain, a CD8α transmembrane domain, a co-stimulatory signaling domain derived from CD137, and a primary intracellular signaling domain derived from CD3ζ. In some embodiments, the BCMA CAR is monospecific. In some embodiments, the BCMA CAR is monovalent.

In some embodiments, there is provided a BCMA CAR comprising a polypeptide comprising: (a) an extracellular antigen binding domain comprising an anti-BCMA sdAb; (b) a transmembrane domain; and (c) an intracellular signaling domain, wherein the anti-BCMA sdAb comprises any one of the following:

(1) a CDR1 comprising the amino acid sequence of SEQ ID NO:7; a CDR2 comprising the amino acid sequence of SEQ ID NO: 18; and a CDR3 comprising the amino acid sequence of SEQ ID NO:29;
(2) a CDR1 comprising the amino acid sequence of SEQ ID NO:8; a CDR2 comprising the amino acid sequence of SEQ ID NO: 19; and a CDR3 comprising the amino acid sequence of SEQ ID NO:30;
(3) a CDR1 comprising the amino acid sequence of SEQ ID NO:9; a CDR2 comprising the amino acid sequence of SEQ ID NO:20; and a CDR3 comprising the amino acid sequence of SEQ ID NO:31;
(4) a CDR1 comprising the amino acid sequence of SEQ ID NO: 10; a CDR2 comprising the amino acid sequence of SEQ ID NO:21; and a CDR3 comprising the amino acid sequence of SEQ ID NO:32;
(5) a CDR1 comprising the amino acid sequence of SEQ ID NO: 11; a CDR2 comprising the amino acid sequence of SEQ ID NO:22; and a CDR3 comprising the amino acid sequence of SEQ ID NO:33;
(6) a CDR1 comprising the amino acid sequence of SEQ ID NO: 12; a CDR2 comprising the amino acid sequence of SEQ ID NO:23; and a CDR3 comprising the amino acid sequence of SEQ ID NO:34;
(7) a CDR1 comprising the amino acid sequence of SEQ ID NO: 13; a CDR2 comprising the amino acid sequence of SEQ ID NO:24; and a CDR3 comprising the amino acid sequence of SEQ ID NO:35;
(8) a CDR1 comprising the amino acid sequence of SEQ ID NO: 14; a CDR2 comprising the amino acid sequence of SEQ ID NO:25; and a CDR3 comprising the amino acid sequence of SEQ ID NO:36;
(9) a CDR1 comprising the amino acid sequence of SEQ ID NO:15; a CDR2 comprising the amino acid sequence of SEQ ID NO:26; and a CDR3 comprising the amino acid sequence of SEQ ID NO:37;
(10) a CDR1 comprising the amino acid sequence of SEQ ID NO: 16; a CDR2 comprising the amino acid sequence of SEQ ID NO:27; and a CDR3 comprising the amino acid sequence of SEQ ID NO:38; or
(11) a CDR1 comprising the amino acid sequence of SEQ ID NO: 17; a CDR2 comprising the amino acid sequence of SEQ ID NO:28; and a CDR3 comprising the amino acid sequence of SEQ ID NO:39.

In some embodiments, the anti-BCMA sdAb is camelid, chimeric, human, or humanized. In some embodiments, the anti-BCMA sdAb comprises a $V_HH$ domain comprising an amino acid sequence from the group consisting of SEQ ID NO:78-88. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the BCMA CAR further comprises a hinge domain (such as a CD8α hinge domain) located between the C-terminus of the extracellular antigen binding domain and the N-terminus of the transmembrane domain. In some embodiments, the BCMA CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen-binding domain, a CD8α hinge domain, a CD28 transmembrane domain, a first co-stimulatory signaling domain derived from CD28, a second co-stimulatory signaling domain derived from CD137, and a primary intracellular signaling domain derived from CD3ζ. In some embodiments, the polypeptide comprises from the N-terminus to the C-terminus: a CD8α signal peptide, the extracellular antigen-binding domain, a CD8α hinge domain, a CD8α transmembrane domain, a co-stimulatory signaling domain derived from CD137, and a primary intracellular signaling domain derived from CD3ζ. In some embodiments, the BCMA CAR is monospecific. In some embodiments, the BCMA CAR is monovalent.

In some embodiments, there is provided a BCMA CAR comprising a polypeptide having at least about any one of 85%, 86%, 87%, 88%, 89%, 90%, 91%, 92%, 93%, 94%, 95%, 96%, 97%, 98%, 99%, or 100% sequence identity to an amino acid sequence selected from the group consisting of SEQ ID NO: 152-162, and 257-259. In some embodiments, there is provided a BCMA CAR comprising an amino acid sequence selected from the group consisting of SEQ ID NO: 152-162, and 257-259. Also provided is a polypeptide comprising an amino acid sequence selected from the group consisting of SEQ ID NO: 152-162, and 257-259.

In some embodiments, there is provided an isolated nucleic acid encoding any of the BCMA CARs provided herein. In some embodiments, there is provided an isolated nucleic acid having at least about any one of 85%, 86%, 87%, 88%, 89%, 90%, 91%, 92%, 93%, 94%, 95%, 96%, 97%, 98%, 99%, or 100% sequence identity to a nucleic acid sequence selected from the group consisting of SEQ ID NOs: 175-185, and 261-263. In some embodiments, there is provided an isolated nucleic acid comprising a nucleic acid sequence selected from the group consisting of SEQ ID NO: 175-185, and 261-263. In some embodiments, the isolated nucleic acid is a DNA. In some embodiments, the isolated nucleic acid is an RNA. In some embodiments, there is provided a vector comprising any one of the nucleic acids encoding the BCMA CARs described above. In some embodiments, the vector is an expression vector. In some embodiments, the vector is a viral vector, such as a lentiviral vector.

4. CD38 CAR

In some embodiments, there is provided a CAR targeting CD38 (also referred herein as "CD38 CAR") comprising a polypeptide comprising: (a) an extracellular antigen binding domain comprising an anti-CD38 sdAb; (b) a transmembrane domain; and (c) an intracellular signaling domain. In some embodiments, the anti-CD38 sdAb is camelid, chimeric, human, or humanized. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the CD38 CAR further comprises a hinge domain (such as a CD8α hinge domain) located between the C-terminus of the extracellular antigen binding domain and the N-terminus of the transmembrane domain. In some embodiments, the CD38 CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen-binding domain, a CD8α hinge domain, a CD28 transmembrane domain, a first co-stimulatory signaling domain derived from CD28, a second co-stimulatory signaling domain derived from CD137, and a primary intracellular signaling domain derived from CD3ζ. In some embodiments, the polypeptide comprises from the N-terminus to the C-terminus: a CD8α signal peptide, the extracellular antigen-binding domain, a CD8α hinge domain, a CD8α transmembrane domain, a co-stimulatory signaling domain derived from CD137, and a primary intracellular signaling domain derived from CD3ζ. In some embodiments, the CD38 CAR is monospecific. In some embodiments, the CD38 CAR is monovalent.

In some embodiments, there is provided a CD38 CAR comprising a polypeptide comprising: (a) an extracellular antigen binding domain comprising an anti-CD38 sdAb; (b) a transmembrane domain; and (c) an intracellular signaling domain, wherein the anti-CD38 sdAb comprises any one of the following:

(1) a CDR1 comprising the amino acid sequence of SEQ ID NO:40; a CDR2 comprising the amino acid sequence of SEQ ID NO:52; and a CDR3 comprising the amino acid sequence of SEQ ID NO:64;

(2) a CDR1 comprising the amino acid sequence of SEQ ID NO:41; a CDR2 comprising the amino acid sequence of SEQ ID NO:53; and a CDR3 comprising the amino acid sequence of SEQ ID NO:65;

(3) a CDR1 comprising the amino acid sequence of SEQ ID NO:42; a CDR2 comprising the amino acid sequence of SEQ ID NO:54; and a CDR3 comprising the amino acid sequence of SEQ ID NO:66;

(4) a CDR1 comprising the amino acid sequence of SEQ ID NO:43; a CDR2 comprising the amino acid sequence of SEQ ID NO:55; and a CDR3 comprising the amino acid sequence of SEQ ID NO:67;

(5) a CDR1 comprising the amino acid sequence of SEQ ID NO:44; a CDR2 comprising the amino acid sequence of SEQ ID NO:56; and a CDR3 comprising the amino acid sequence of SEQ ID NO:68;

(6) a CDR1 comprising the amino acid sequence of SEQ ID NO:45; a CDR2 comprising the amino acid sequence of SEQ ID NO:57; and a CDR3 comprising the amino acid sequence of SEQ ID NO:69;

(7) a CDR1 comprising the amino acid sequence of SEQ ID NO:46; a CDR2 comprising the amino acid sequence of SEQ ID NO:58; and a CDR3 comprising the amino acid sequence of SEQ ID NO:70;

(8) a CDR1 comprising the amino acid sequence of SEQ ID NO:47; a CDR2 comprising the amino acid sequence of SEQ ID NO: 59; and a CDR3 comprising the amino acid sequence of SEQ ID NO:71;

(9) a CDR1 comprising the amino acid sequence of SEQ ID NO:48; a CDR2 comprising the amino acid sequence of SEQ ID NO:60; and a CDR3 comprising the amino acid sequence of SEQ ID NO:72;

(10) a CDR1 comprising the amino acid sequence of SEQ ID NO:49; a CDR2 comprising the amino acid sequence of SEQ ID NO:61; and a CDR3 comprising the amino acid sequence of SEQ ID NO:73;

(11) a CDR1 comprising the amino acid sequence of SEQ ID NO: 50; a CDR2 comprising the amino acid sequence of SEQ ID NO:62; and a CDR3 comprising the amino acid sequence of SEQ ID NO:74; or

(12) a CDR1 comprising the amino acid sequence of SEQ ID NO:51; a CDR2 comprising the amino acid sequence of SEQ ID NO:63; and a CDR3 comprising the amino acid sequence of SEQ ID NO:75.

In some embodiments, the anti-CD38 sdAb is camelid, chimeric, human, or humanized. In some embodiments, the anti-CD38 sdAb comprises a $V_HH$ domain comprising an amino acid sequence from the group consisting of SEQ ID NO:89-100. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the CD38 CAR further comprises a hinge domain (such as a CD8α hinge domain) located between the C-terminus of the extracellular antigen binding domain and the N-terminus of the transmembrane domain. In some embodiments, the CD38 CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen-binding domain, a CD8α hinge domain, a CD28 transmembrane domain, a first co-stimulatory signaling domain derived from CD28, a second co-stimulatory signaling domain derived from CD137, and a primary intracellular signaling domain derived from CD3ζ. In some embodiments, the polypeptide comprises from the N-terminus to the C-terminus: a CD8α signal peptide, the extracellular antigen-binding domain, a CD8α hinge domain, a CD8α transmembrane domain, a co-stimulatory signaling domain derived from CD137, and a primary intracellular signaling domain derived from CD3ζ. In some embodiments, the CD38 CAR is monospecific. In some embodiments, the CD38 CAR is monovalent.

In some embodiments, there is provided a CD38 CAR comprising a polypeptide having at least about any one of 85%, 86%, 87%, 88%, 89%, 90%, 91%, 92%, 93%, 94%, 95%, 96%, 97%, 98%, 99%, or 100% sequence identity to an amino acid sequence selected from the group consisting of SEQ ID NO: 163-174, and 260. In some embodiments, there is provided a CD38 CAR comprising an amino acid sequence selected from the group consisting of SEQ ID NO: 163-174, and 260. Also provided is a polypeptide comprising an amino acid sequence selected from the group consisting of SEQ ID NO: 163-174, and 260.

In some embodiments, there is provided an isolated nucleic acid encoding any of the CD38 CARs provided herein. In some embodiments, there is provided an isolated nucleic acid having at least about any one of 85%, 86%, 87%, 88%, 89%, 90%, 91%, 92%, 93%, 94%, 95%, 96%, 97%, 98%, 99%, or 100% sequence identity to a nucleic acid sequence selected from the group consisting of SEQ ID NOs: 186-197, and 264. In some embodiments, there is provided an isolated nucleic acid comprising a nucleic acid sequence selected from the group consisting of SEQ ID NO: 186-197, and 264. In some embodiments, the isolated nucleic acid is a DNA. In some embodiments, the isolated nucleic acid is an RNA. In some embodiments, there is provided a vector comprising any one of the nucleic acids encoding the CD38 CARs described above. In some embodiments, the vector is an expression vector. In some embodiments, the vector is a viral vector, such as a lentiviral vector.

5. CD22 CAR

In some embodiments, there is provided a CAR targeting CD22 (also referred herein as "CD22 CAR") comprising a polypeptide comprising: (a) an extracellular antigen binding domain comprising an anti-CD22 sdAb; (b) a transmembrane domain; and (c) an intracellular signaling domain. In some embodiments, the anti-CD22 sdAb is camelid, chimeric, human, or humanized. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the CD22CAR further comprises a hinge domain (such as a CD8α hinge domain) located between the C-terminus of the extracellular antigen binding domain and the N-terminus of the transmembrane domain. In some embodiments, the CD22 CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen-binding domain, a CD8α hinge domain, a CD28 transmembrane domain, a first co-stimulatory signaling domain derived from CD28, a second co-stimulatory signaling domain derived from CD137, and a primary intracellular signaling domain derived from CD3ζ. In some embodiments, the polypeptide comprises from the N-terminus to the C-terminus: a CD8α signal peptide, the extracellular antigen-binding domain, a CD8α hinge domain, a CD8α transmembrane domain, a co-stimulatory signaling domain derived from CD137, and a primary intracellular signaling domain derived from CD3ζ. In some embodiments, the CD22 CAR is monospecific. In some embodiments, the CD22 CAR is monovalent.

TABLE 4

Exemplary monospecific, monovalent CARs.

| Ex. Vector or CAR name | Ex. AA SEQ ID | Ex. NA SEQ ID | Extracellular | | | | Intracellular signaling | | |
|---|---|---|---|---|---|---|---|---|---|
| | | | SP | sdAb | Hinge | TM | CO1 | CO2 | Prim. |
| BCMA CAR | | | | | | | | | |
| PLVX-hEF1a-269A37346 | 152 | 175 | CD8α | 269A37346 | CD8α | CD28 | CD28 | CD137 | CD3ζ |
| PLVX-hEF1a-269A37348 | 153 | 176 | CD8α | 269A37348 | CD8α | CD28 | CD28 | CD137 | CD3ζ |
| PLVX-hEF1a-269A37917 | 154 | 177 | CD8α | 269A37917 | CD8α | CD28 | CD28 | CD137 | CD3ζ |

TABLE 4-continued

Exemplary monospecific, monovalent CARs.

| Ex. Vector or CAR name | Ex. AA SEQ ID | Ex. NA SEQ ID | Extracellular | | | Intracellular signaling | | |
| --- | --- | --- | --- | --- | --- | --- | --- | --- |
| | | | SP | sdAb | Hinge | TM | CO1 | CO2 | Prim. |
| PLVX-hEF1a-269A37355 | 155 | 178 | CD8α | 269A37355 | CD8α | CD28 | CD28 | CD137 | CD3ζ |
| PLVX-hEF1a-269A37915 | 156 | 179 | CD8α | 269A37915 | CD8α | CD28 | CD28 | CD137 | CD3ζ |
| PLVX-hEF1a-269A37936 | 157 | 180 | CD8α | 269A37936 | CD8α | CD28 | CD28 | CD137 | CD3ζ |
| PLVX-hEF1a-269A37953 | 158 | 181 | CD8α | 269A37953 | CD8α | CD28 | CD28 | CD137 | CD3ζ |
| PLVX-hEF1a-269A37965 | 159 | 182 | CD8α | 269A37965 | CD8α | CD28 | CD28 | CD137 | CD3ζ |
| PLVX-hEF1a-269A37972 | 160 | 183 | CD8α | 269A37972 | CD8α | CD28 | CD28 | CD137 | CD3ζ |
| PLVX-hEF1a-269A37353 | 161 | 184 | CD8α | 269A37353 | CD8α | CD28 | CD28 | CD137 | CD3ζ |
| PLVX-hEF1a-269A37948 | 162 | 185 | CD8α | 269A37948 | CD8α | CD28 | CD28 | CD137 | CD3ζ |
| GSI5011 CAR | 257 | 261 | CD8α | 269A37346 | CD8α | CD8α | CD137 | NA | CD3ζ |
| G5I5019 CAR | 258 | 262 | CD8α | 269A37353 | CD8α | CD8α | CD137 | NA | CD3ζ |
| G5I5020 CAR | 259 | 263 | CD8α | 269A37917 | CD8α | CD8α | CD137 | NA | CD3ζ |
| CD38 CAR | | | | | | | | | |
| PLVX-hEF1a-38A37333 | 163 | 186 | CD8α | 38A37333 | CD8α | CD28 | CD28 | CD137 | CD3ζ |
| PLVX-hEF1a-38A37336 | 164 | 187 | CD8α | 38A37336 | CD8α | CD28 | CD28 | CD137 | CD3ζ |
| PLVX-hEF1a-38A37699 | 165 | 188 | CD8α | 38A37699 | CD8α | CD28 | CD28 | CD137 | CD3ζ |
| PLVX-hEF1a-38A37331 | 166 | 189 | CD8α | 38A37331 | CD8α | CD28 | CD28 | CD137 | CD3ζ |
| PLVX-hEF1a-38A37717 | 167 | 190 | CD8α | 38A37717 | CD8α | CD28 | CD28 | CD137 | CD3ζ |
| PLVX-hEF1a-38A37719 | 168 | 191 | CD8α | 38A37719 | CD8α | CD28 | CD28 | CD137 | CD3ζ |
| PLVX-hEF1a-38A37330 | 169 | 192 | CD8α | 38A37330 | CD8α | CD28 | CD28 | CD137 | CD3ζ |
| PLVX-hEF1a-38A37334 | 170 | 193 | CD8α | 38A37334 | CD8α | CD28 | CD28 | CD137 | CD3ζ |
| PLVX-hEF1a-38A37730 | 171 | 194 | CD8α | 38A37730 | CD8α | CD28 | CD28 | CD137 | CD3ζ |
| PLVX-hEF1a-38A37340 | 172 | 195 | CD8α | 38A37340 | CD8α | CD28 | CD28 | CD137 | CD3ζ |
| PLVX-hEF1a-38A37731 | 173 | 196 | CD8α | 38A37731 | CD8α | CD28 | CD28 | CD137 | CD3ζ |
| PLVX-hEF1a-38A37326 | 174 | 197 | CD8α | 38A37326 | CD8α | CD28 | CD28 | CD137 | CD3ζ |
| CD19 $V_HH$ CAR | 248 | 250 | CD8α | CD19 $V_HH$ | CD8α | CD28 | CD28 | NA | CD3ζ |
| CD20 $V_HH$ CAR | 249 | 251 | CD8α | CD20 $V_HH$ | CD8α | CD28 | CD28 | NA | CD3ζ |
| GSI5012 CAR | 260 | 264 | CD8α | 38A37717 | CD8α | CD8α | CD137 | NA | CD3ζ |

Multivalent Chimeric Antigen Receptors

The present application also provides multivalent CARs that have two or more (such as about any one of 2, 3, 4, 5, 6, or more) antigen binding sites comprising single-domain antibodies. In some embodiments, the multivalent CAR targets a single antigen, and comprises two or more binding sites for the single antigen. In some embodiments, the multivalent CAR targets more than one antigen, and the multivalent CAR comprises two or more binding sites for at least one antigen. The binding sites specific for the same antigen may bind to the same epitope of the antigen or bind to different epitopes of the antigen. The binding sites specific for the same antigen may comprise the same or different single-domain antibodies.

In some embodiments, the present application provides a multivalent (such as bivalent, trivalent, or of higher number of valencies) chimeric antigen receptor comprising a polypeptide comprising: (a) an extracellular antigen binding domain comprising a plurality (such as about any one of 2, 3, 4, 5, 6, or more) of single-domain antibodies (sdAbs) specifically binding to an antigen (such as a tumor antigen); (b) a transmembrane domain; and (c) an intracellular signaling domain. In some embodiments, the antigen is selected from the group consisting of CD19, CD20, CD22, CD33, CD38, BCMA, CS1, ROR1, GPC3, CD123, IL-13R, CD138, c-Met, EGFRvIII, GD-2, NY-ESO-1, MAGE A3, and glycolipid F77. In some embodiments, the plurality of sdAbs is camelid, chimeric, human, or humanized. In some embodiments, the plurality of single-domain antibodies is fused to each other via peptide bonds or peptide linkers. In some embodiments, each peptide linker is no more than about 50 (such as no more than about any one of 35, 25, 20, 15, 10, or 5) amino acids long. In some embodiments, the transmembrane domain is selected from the group consisting of CD8α, CD4, CD28, CD137, CD80, CD86, CD152 and PD1. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the multivalent CAR further comprises a hinge domain (such as a CD8α hinge domain) located between the C-terminus of the extracellular antigen binding domain and the N-terminus of the transmembrane domain. In some embodiments, the multivalent CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ. In some embodiments, the multivalent CAR is monospecific. In some embodiments, the multivalent CAR is multispecific, such as bispecific.

In some embodiments, the present application provides a multivalent (such as bivalent, trivalent, or of higher number of valencies) chimeric antigen receptor comprising a polypeptide comprising: (a) an extracellular antigen binding domain comprising a first single-domain antibody specifically binding to a first epitope of an antigen (such as a tumor antigen), and a second single-domain antibody specifically binding to a second epitope of the antigen; (b) a transmembrane domain; and (c) an intracellular signaling domain, wherein the first epitope and the second epitope are different. In some embodiments, the antigen is selected from the group consisting of CD19, CD20, CD22, CD33, CD38, BCMA, CS1, ROR1, GPC3, CD123, IL-13R, CD138, c-Met, EGFRvIII, GD-2, NY-ESO-1, MAGE A3, and glycolipid F77. In some embodiments, the first sdAb and/or the second sdAb is camelid, chimeric, human, or humanized. In some embodiments, the first single-domain antibody and the second single-domain antibody are fused to each other via a peptide bond or a peptide linker. In some embodiments, the peptide linker is no more than about 50 (such as no more than about any one of 35, 25, 20, 15, 10, or 5) amino acids long. In some embodiments, the transmembrane domain is selected from the group consisting of CD8α, CD4, CD28, CD137, CD80, CD86, CD152 and PD1. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the multivalent CAR further comprises a hinge domain (such as a CD8α hinge domain) located between the C-terminus of the extracellular antigen binding domain and the N-terminus of the transmembrane domain. In some embodiments, the multivalent CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ. In some embodiments, the multivalent CAR is monospecific. In some embodiments, the multivalent CAR is multispecific, such as bispecific.

The multivalent CARs describe herein may be specially suitable for targeting multimeric antigens via synergistic binding by the different antigen binding sites, or for enhancing binding affinity or avidity to the antigen. Any of the single-domain antibodies described herein, such as the anti-CD19, anti-CD20, anti-BCMA, or anti-CD38 antibodies, may be used in the extracellular antigen binding domain of the multivalent CARs described herein. A list of exemplary monospecific multivalent chimeric antigen receptors, exemplary sequences, constructs and vectors thereof are shown in Table 5.

1. Multivalent BCMA CAR

In some embodiments, there is provided a multivalent CAR targeting BCMA (also referred herein as "multivalent BCMA CAR") comprising: (a) an extracellular antigen binding domain comprising a plurality (such as 2, 3, or more) of an anti-BCMA sdAb; (b) a transmembrane domain; and (c) an intracellular signaling domain. In some embodiments, the anti-BCMA sdAb is camelid, chimeric, human, or humanized. In some embodiments, the plurality of the anti-BCMA sdAb is fused to each other via peptide bonds or peptide linkers. In some embodiments, each peptide linker is no more than about 50 (such as no more than about any one of 35, 25, 20, 15, 10, or 5) amino acids long. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the multivalent BCMA CAR further comprises a hinge domain (such as a CD8α hinge domain) located between the C-terminus of the extracellular antigen binding domain and the N-terminus of the transmembrane domain. In some embodiments, the multivalent BCMA CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ. In some embodiments, the multivalent BCMA CAR is bivalent. In some embodiments, the multivalent BCMA CAR is trivalent. Any of the anti-BCMA sdAbs can be used to construct the multivalent BCMA CAR.

In some embodiments, there is provided a multivalent BCMA CAR comprising: (a) an extracellular antigen binding domain comprising a plurality (such as 2, 3, or more) of an anti-BCMA sdAb; (b) a transmembrane domain; and (c) an intracellular signaling domain, wherein the anti-BCMA sdAb comprises a CDR1 comprising the amino acid sequence of SEQ ID NO:7, a CDR2 comprising the amino acid sequence of SEQ ID NO: 18, and a CDR3 comprising the amino acid sequence of SEQ ID NO:29. In some embodiments, the anti-BCMA sdAb is camelid, chimeric, human, or humanized. In some embodiments, the anti-BCMA sdAb comprises a $V_HH$ domain comprising the amino acid sequence of SEQ ID NO:78. In some embodiments, the plurality of anti-BCMA sdAbs is fused to each other via peptide bonds or peptide linkers. In some embodiments, each peptide linker is no more than about 50 (such as no more than about any one of 35, 25, 20, 15, 10, or 5) amino acids long. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the multivalent BCMA CAR further comprises a hinge domain (such as a CD8α hinge domain) located between the C-terminus of the extracellular antigen binding domain and the N-terminus of the transmembrane domain. In some embodiments, the multivalent BCMA CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ. In some embodiments, the multivalent BCMA CAR is bivalent. In some embodiments, the multivalent BCMA CAR is trivalent.

In some embodiments, there is provided a multivalent BCMA CAR comprising: (a) an extracellular antigen binding domain comprising a first anti-BCMA sdAb and a second anti-BCMA sdAb; (b) a transmembrane domain; and (c) an intracellular signaling domain, wherein the first anti-BCMA sdAb and the second anti-BCMA sdAb specifically binds to different epitopes on BCMA. In some embodiments, the first anti-BCMA sdAb is located at the N-terminus of the second anti-BCMA sdAb. In some embodiments, the first anti-BCMA sdAb is located at the C-terminus of the second anti-BCMA sdAb. In some embodiments, the first anti-BCMA sdAb and the second anti-BCMA sdAb is fused to each other via a peptide bond or a peptide linker. In some embodiments, the peptide linker is no more than about 50 (such as no more than about any one of 35, 25, 20, 15, 10, or 5) amino acids long. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the multivalent BCMA CAR further comprises a hinge domain (such as a CD8α hinge domain) located between the C-terminus of the extracellular antigen binding domain and the N-terminus of the transmembrane domain. In some embodiments, the multivalent BCMA CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ. In some embodiments, the multivalent BCMA CAR is bivalent. In some embodiments, the multivalent BCMA CAR is trivalent. In some embodiments, the extracellular antigen binding domain further comprises a third anti-BCMA sdAb that specifically binds to an epitope that is different from the first and the second anti-BCMA sdAb. Any of the anti-BCMA sdAbs can be used to construct the multivalent BCMA CAR.

In some embodiments, there is provided a multivalent BCMA CAR comprising: (a) an extracellular antigen binding domain comprising a first anti-BCMA sdAb and a second anti-BCMA sdAb; (b) a transmembrane domain; and (c) an intracellular signaling domain, wherein the first anti-BCMA sdAb comprises a CDR1 comprising the amino acid sequence of SEQ ID NO: 16, a CDR2 comprising the amino acid sequence of SEQ ID NO:27, and a CDR3 comprising the amino acid sequence of SEQ ID NO:38; and wherein the second anti-BCMA sdAb comprises a CDR1 comprising the amino acid sequence of SEQ ID NO:9, a CDR2 comprising the amino acid sequence of SEQ ID NO:20, and a CDR3 comprising the amino acid sequence of SEQ ID NO:31. In some embodiments, the first anti-BCMA sdAb comprises a $V_HH$ domain comprising the amino acid sequence of SEQ ID NO: 87. In some embodiments, the first anti-BCMA sdAb comprises a $V_HH$ domain comprising the amino acid sequence of SEQ ID NO: 80. In some embodiments, the first anti-BCMA sdAb is located at the N-terminus of the second anti-BCMA sdAb. In some embodiments, the first anti-BCMA sdAb is located at the C-terminus of the second anti-BCMA sdAb. In some embodiments, the first anti-BCMA sdAb and the second anti-BCMA sdAb is fused to each other via a peptide bond or a peptide linker. In some embodiments, the peptide linker is no more than about 50 (such as no more than about any one of 35, 25, 20, 15, 10, or 5) amino acids long. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the multivalent BCMA CAR further comprises a hinge domain (such as a CD8α hinge domain) located between the C-terminus of the extracellular antigen binding domain and the N-terminus of the transmembrane domain. In some embodiments, the multivalent BCMA CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ. In some embodiments, the multivalent BCMA CAR is bivalent.

In some embodiments, there is provided a multivalent BCMA CAR comprising a polypeptide having at least about any one of 85%, 86%, 87%, 88%, 89%, 90%, 91%, 92%, 93%, 94%, 95%, 96%, 97%, 98%, 99%, or 100% sequence identity to an amino acid sequence selected from the group consisting of SEQ ID NOs: 198-199 and 265-270. In some embodiments, there is provided a multivalent BCMA CAR comprising an amino acid sequence selected from the group consisting of SEQ ID NOs: 198-199 and 265-270. Also provided is a polypeptide comprising an amino acid sequence selected from the group consisting of SEQ ID NOs: 198-199 and 265-270.

In some embodiments, there is provided an isolated nucleic acid encoding any of the multivalent BCMA CARs provided herein. In some embodiments, there is provided an isolated nucleic acid having at least about any one of 85%, 86%, 87%, 88%, 89%, 90%, 91%, 92%, 93%, 94%, 95%, 96%, 97%, 98%, 99%, or 100% sequence identity to a nucleic acid sequence selected from the group consisting of SEQ ID NOs: 202-203 and 271-276. In some embodiments, there is provided an isolated nucleic acid comprising a nucleic acid sequence selected from the group consisting of SEQ ID NOs: 202-203 and 271-276. In some embodiments, the isolated nucleic acid is a DNA. In some embodiments, the isolated nucleic acid is an RNA. In some embodiments, there is provided a vector comprising any one of the nucleic acids encoding the multivalent BCMA CARs described above. In some embodiments, the vector is an expression vector. In some embodiments, the vector is a viral vector, such as a lentiviral vector.

2. Multivalent CD38 CAR

In some embodiments, there is provided a multivalent CAR targeting CD38 (also referred herein as "multivalent CD38 CAR") comprising: (a) an extracellular antigen binding domain comprising a plurality (such as 2, 3, or more) of an anti-CD38 sdAb; (b) a transmembrane domain; and (c) an intracellular signaling domain. In some embodiments, the anti-CD38 sdAb is camelid, chimeric, human, or humanized. In some embodiments, the plurality of the anti-CD38 sdAb is fused to each other via peptide bonds or peptide linkers. In some embodiments, each peptide linker is no more than about 50 (such as no more than about any one of 35, 25, 20, 15, 10, or 5) amino acids long. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the multivalent CD38 CAR further comprises a hinge domain (such as a CD8α hinge domain) located between the C-terminus of the extracellular antigen binding domain and the N-terminus of the transmembrane domain. In some embodiments, the multivalent CD38 CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ. In some embodiments, the multivalent CD38 CAR is bivalent. In some embodiments, the multivalent CD38 CAR is trivalent Any of the anti-CD38 sdAbs can be used to construct the multivalent CD38 CAR.

In some embodiments, there is provided a multivalent CD38 CAR comprising: (a) an extracellular antigen binding domain comprising a plurality of anti-CD38 sdAbs; (b) a transmembrane domain; and (c) an intracellular signaling domain, wherein each of the plurality of anti-CD38 sdAbs comprises a CDR1 comprising the amino acid sequence of SEQ ID NO:44, a CDR2 comprising the amino acid sequence of SEQ ID NO:56, and a CDR3 comprising the amino acid sequence of SEQ ID NO:68. In some embodiments, the anti-CD38 sdAb is camelid, chimeric, human, or humanized. In some embodiments, each of the plurality of anti-CD38 sdAbs comprises a $V_H H$ domain comprising the amino acid sequence of SEQ ID NO:93. In some embodiments, the plurality of anti-CD38 sdAbs is fused to each other via peptide bonds or peptide linkers. In some embodiments, each peptide linker is no more than about 50 (such as no more than about any one of 35, 25, 20, 15, 10, or 5) amino acids long. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the multivalent CD38 CAR further comprises a hinge domain (such as a CD8α hinge domain) located between the C-terminus of the extracellular antigen binding domain and the N-terminus of the transmembrane domain. In some embodiments, the multivalent CD38 CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ. In some embodiments, the multivalent CD38 CAR is bivalent. In some embodiments, the multivalent CD38 CAR is trivalent.

In some embodiments, there is provided a multivalent CD38 CAR comprising: (a) an extracellular antigen binding domain comprising a first anti-CD38 sdAb and a second anti-CD38 sdAb; (b) a transmembrane domain; and (c) an intracellular signaling domain, wherein the first anti-CD38 sdAb and the second anti-CD38 sdAb specifically binds to different epitopes on CD38. In some embodiments, the first anti-CD38 sdAb is located at the N-terminus of the second anti-CD38 sdAb. In some embodiments, the first anti-CD38 sdAb is located at the C-terminus of the second anti-CD38 sdAb. In some embodiments, the first anti-CD38 sdAb and the second anti-CD38 sdAb is fused to each other via a peptide bond or a peptide linker. In some embodiments, the peptide linker is no more than about 50 (such as no more than about any one of 35, 25, 20, 15, 10, or 5) amino acids long. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the multivalent CD38 CAR further comprises a hinge domain (such as a CD8α hinge domain) located between the C-terminus of the extracellular antigen binding domain and the N-terminus of the transmembrane domain. In some embodiments, the multivalent CD38 CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ. In some embodiments, the multivalent CD38 CAR is bivalent. In some embodiments, the multivalent CD38 CAR is trivalent. In some embodiments, the extracellular antigen binding domain further comprises a third anti-CD38 sdAb that specifically binds to an epitope that is different from the first and the second anti-CD38 sdAb. Any of the anti-CD38 sdAbs can be used to construct the multivalent CD38 CAR.

In some embodiments, there is provided a multivalent CD38 CAR comprising a polypeptide having at least about any one of 85%, 86%, 87%, 88%, 89%, 90%, 91%, 92%, 93%, 94%, 95%, 96%, 97%, 98%, 99%, or 100% sequence identity to the amino acid sequence of SEQ ID NO: 200 or SEQ ID NO: 201. In some embodiments, there is provided a multivalent CD38 CAR comprising the amino acid sequence of SEQ ID NO: 200 or SEQ ID NO: 201. Also provided is a polypeptide comprising the amino acid sequence of SEQ ID NO: 200 or SEQ ID NO: 201.

In some embodiments, there is provided an isolated nucleic acid encoding any of the multivalent CD38 CARs provided herein. In some embodiments, there is provided an isolated nucleic acid having at least about any one of 85%, 86%, 87%, 88%, 89%, 90%, 91%, 92%, 93%, 94%, 95%, 96%, 97%, 98%, 99%, or 100% sequence identity to the nucleic acid sequence of SEQ ID NO: 204 or SEQ ID NO: 205. In some embodiments, there is provided an isolated nucleic acid comprising the nucleic acid sequence of SEQ ID NO: 204 or SEQ ID NO: 205. In some embodiments, the isolated nucleic acid is a DNA. In some embodiments, the isolated nucleic acid is an RNA. In some embodiments, there is provided a vector comprising any one of the nucleic acids encoding the multivalent CD38 CARs described above. In some embodiments, the vector is an expression vector. In some embodiments, the vector is a viral vector, such as a lentiviral vector.

3. Other Exemplary Multivalent CARs

In some embodiments, there is provided a multivalent CAR targeting CD19 (also referred herein as "multivalent CD19 CAR") comprising: (a) an extracellular antigen binding domain comprising a plurality (such as 2, 3, or more) of an anti-CD19 sdAb; (b) a transmembrane domain; and (c) an intracellular signaling domain. In some embodiments, the anti-CD19 sdAb is camelid, chimeric, human, or humanized. In some embodiments, the plurality of the anti-CD19 sdAb is fused to each other via peptide bonds or peptide linkers. In some embodiments, each peptide linker is no more than about 50 (such as no more than about any one of 35, 25, 20, 15, 10, or 5) amino acids long. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the multivalent CD19 CAR further comprises a hinge domain (such as a CD8α hinge domain) located between the C-terminus of the extracellular antigen binding domain and the N-terminus of the transmembrane domain. In some embodiments, the multivalent CD19 CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ. In some embodiments, the multivalent CD19 CAR is bivalent. In some embodiments, the multivalent CD19 CAR is trivalent. Any of the anti-CD19 sdAbs can be used to construct the multivalent CD19 CAR.

In some embodiments, there is provided a multivalent CAR targeting CD20 (also referred herein as "multivalent CD20 CAR") comprising: (a) an extracellular antigen binding domain comprising a plurality (such as 2, 3, or more) of an anti-CD20 sdAb; (b) a transmembrane domain; and (c) an intracellular signaling domain. In some embodiments, the anti-CD20 sdAb is camelid, chimeric, human, or humanized. In some embodiments, the plurality of the anti-CD20 sdAb is fused to each other via peptide bonds or peptide linkers. In some embodiments, each peptide linker is no more than about 50 (such as no more than about any one of 35, 25, 20, 15, 10, or 5) amino acids long. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the multivalent CD20 CAR further comprises a hinge domain (such as a CD8α hinge domain) located between the C-terminus of the extracellular antigen binding domain and the N-terminus of the transmembrane domain. In some embodiments, the multivalent CD20 CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ. In some embodiments, the multivalent CD20 CAR is bivalent. In some embodiments, the multivalent CD20 CAR is trivalent. Any of the anti-CD20 sdAbs can be used to construct the multivalent CD20 CAR.

In some embodiments, there is provided a multivalent CAR targeting CD22 (also referred herein as "multivalent CD22 CAR") comprising: (a) an extracellular antigen binding domain comprising a plurality (such as 2, 3, or more) of an anti-CD22 sdAb; (b) a transmembrane domain; and (c) an intracellular signaling domain. In some embodiments, the anti-CD22 sdAb is camelid, chimeric, human, or humanized. In some embodiments, the plurality of the anti-CD22 sdAb is fused to each other via peptide bonds or peptide linkers. In some embodiments, each peptide linker is no more than about 50 (such as no more than about any one of 35, 25, 20, 15, 10, or 5) amino acids long. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the multivalent CD22 CAR further comprises a hinge domain (such as a CD8α hinge domain) located between the C-terminus of the extracellular antigen binding domain and the N-terminus of the transmembrane domain. In some embodiments, the multivalent CD22 CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ. In some embodiments, the multivalent CD22 CAR is bivalent. In some embodiments, the multivalent CD22 CAR is trivalent.

multispecific CAR has more than two binding sites for at least one antigen. Each antigen binding site may comprise a single-domain antibody. For example, in some embodiments, the multispecific chimeric antigen receptor is a bispecific CAR comprising an extracellular antigen binding domain comprising two different sdAbs each specifically binding to an antigen. In some embodiments, the multispecific CAR is a trispecific CAR comprising an extracellular antigen binding domain comprising three different sdAbs each specifically binding to an antigen.

In some embodiments, there is provided a multispecific (such as bispecific) chimeric antigen receptor (CAR) comprising a polypeptide comprising: (a) an extracellular antigen binding domain comprising a first single-domain antibody (sdAb) specifically binding to a first antigen (such as a first tumor antigen) and a second single-domain antibody (sdAb) specifically binding to a second antigen (such as a second tumor antigen); (b) a transmembrane domain; and (c) an intracellular signaling domain, wherein the first antigen is different from the second antigen. In some embodiments, the first antigen and/or the second antigen is selected from the group consisting of CD19, CD20, CD22, CD33, CD38, BCMA, CS1, ROR1, GPC3, CD123, IL-13R, CD138, c-Met, EGFRvIII, GD-2, NY-ESO-1, MAGE A3, and glycolipid F77. In some embodiments, the first sdAb and/or the second sdAb is camelid, chimeric, human, or humanized. In some embodiments, the first single-domain antibody and the second single-domain antibody are fused to each other via a peptide bond or a peptide linker. In some embodiments, the peptide linker is no more than about 50 (such as no more than about any one of 35, 25, 20, 15, 10, or 5) amino acids long. In some embodiments, the transmembrane domain is selected from the group consisting of CD8α, CD4, CD28, CD137, CD80, CD86, CD152 and PD1. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodi-

TABLE 5

Exemplary monospecific, multivalent CAR.

| | | | Extracellular Antigen binding domain | | | | | | | | Intracellular signaling | |
|---|---|---|---|---|---|---|---|---|---|---|---|---|
| CAR | Ex. AA SEQ ID | Ex. NA SEQ ID | SP | sdAb #1 | Lnk. #1 SEQ ID | sdAb #2 | Lnk. #2 SEQ ID | sdAb #3 | Hinge | TM | CO1 | Prim. |
| GSI5014 | 198 | 202 | CD8α | 269A37346 | 144 | 269A37346 | NA | NA | CD8α | CD8α | CD137 | CD3ζ |
| GSI5015 | 199 | 203 | CD8α | 269A37346 | 144 | 269A37346 | 144 | 269A37346 | CD8α | CD8α | CD137 | CD3ζ |
| GSI5016 | 200 | 204 | CD8α | 38A37717 | 144 | 38A37717 | NA | NA | CD8α | CD8α | CD137 | CD3ζ |
| GSI5017 | 201 | 205 | CD8α | 38A37717 | 144 | 38A37717 | 144 | 38A37717 | CD8α | CD8α | CD137 | CD3ζ |
| GSI5021 | 265 | 271 | CD8α | 269A37353 | 144 | 269A37917 | NA | NA | CD8α | CD8α | CD137 | CD3ζ |
| GSI5022 | 266 | 272 | CD8α | 269A37353 | 149 | 269A37917 | NA | NA | CD8α | CD8α | CD137 | CD3ζ |
| GSI5023 | 267 | 273 | CD8α | 269A37353 | 151 | 269A37917 | NA | NA | CD8α | CD8α | CD137 | CD3ζ |
| GSI5024 | 268 | 274 | CD8α | 269A37917 | 145 | 269A37353 | NA | NA | CD8α | CD8α | CD137 | CD3ζ |
| GSI5025 | 269 | 275 | CD8α | 269A37917 | 149 | 269A37353 | NA | NA | CD8α | CD8α | CD137 | CD3ζ |
| GSI5026 | 270 | 276 | CD8α | 269A37917 | 150 | 269A37353 | NA | NA | CD8α | CD8α | CD137 | CD3ζ |

Multispecific Chimeric Antigen Receptor

The present application further provides multispecific chimeric antigen receptors targeting two or more (such as about any one of 2, 3, 4, 5, 6, or more) different antigens. In some embodiments, the multispecific CAR has one antigen binding site for each antigen. In some embodiments, the ments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the multispecific CAR further comprises a hinge domain (such as a CD8α hinge domain) located between the C-terminus of the extracellular antigen binding domain and the N-terminus of the transmembrane domain. In some embodiments, the multispecific CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ. In some embodiments, the polypeptide comprises from the N-terminus to the C-terminus: a CD8α signal peptide, the extracellular antigen binding domain, a CD8α hinge domain, a CD28 transmembrane domain, a co-stimulatory signaling domain derived from CD28, and a primary intracellular signaling domain derived from CD3ζ.

Depending on the desired antigen to be targeted, the CARs of the present application can be engineered to include the appropriate single-domain antibodies that are specific to the desired antigens. Any one or more of the anti-CD19, anti-CD20, anti-BCMA, or anti-CD38 antibodies described herein may be used in the extracellular antigen binding domain in the CARs of the present applications. The single-domain antibodies can be arranged in any suitable order. For example, the first single-domain antibody is fused at the N-terminus or the C-terminus of the second single-domain antibody. A suitable peptide linker may be placed between different single-domain antibodies to avoid steric hindrance between the single-domain antibodies. A list of exemplary bispecific chimeric antigen receptors, exemplary sequences, constructs and vectors thereof are shown in Table 6.

1. BCMA×CD38 CAR

In some embodiments, the CAR of the present application is a bispecific CAR simultaneously targeting BCMA and CD38. For example, the BCMA and CD38 can be used as candidates for targeting antigens expressed on multiple myeloma cells.

In some embodiments, there is provided a multispecific (such as bispecific) chimeric antigen receptor targeting BCMA and CD38 (also referred herein as "BCMA×CD38 CAR") comprising a polypeptide comprising: (a) an extracellular antigen binding domain comprising a first single-domain antibody (sdAb) specifically binding to BCMA and a second single-domain antibody specifically binding to CD38; (b) a transmembrane domain; and (c) an intracellular signaling domain. In some embodiments, the first sdAb and/or the second sdAb is camelid, chimeric, human, or humanized. In some embodiments, the first single-domain antibody and the second single-domain antibody are fused to each other via a peptide bond or a peptide linker. In some embodiments, the first sdAb is fused at the N-terminus of the second sdAb. In some embodiments, the first sdAb is fused at the C-terminus of the second sdAb. In some embodiments, the peptide linker is no more than about 50 (such as no more than about any one of 35, 25, 20, 15, 10, or 5) amino acids long. In some embodiments, the peptide linker comprises an amino acid sequence selected from the group consisting of SEQ ID NOs: 144-151. In some embodiments, the transmembrane domain is selected from the group consisting of CD8α, CD4, CD28, CD137, CD80, CD86, CD152 and PD1. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the BCMA×CD38 CAR further comprises a hinge domain (such as a CD8α hinge domain) located between the C-terminus of the extracellular antigen binding domain and the N-terminus of the transmembrane domain. In some embodiments, the BCMA×CD38 CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ.

In some embodiments, there is provided a multispecific (such as bispecific) chimeric antigen receptor targeting BCMA and CD38 (also referred herein as "BCMA×CD38 CAR") comprising a polypeptide comprising: (a) an extracellular antigen binding domain comprising an anti-BCMA single-domain antibody and an anti-CD38 single-domain antibody; (b) a transmembrane domain; and (c) an intracellular signaling domain, wherein the anti-BCMA single-domain antibody comprises a CDR1 comprising the amino acid sequence of SEQ ID NO:7, a CDR2 comprising the amino acid sequence of SEQ ID NO:18, and a CDR3 comprising the amino acid sequence of SEQ ID NO:29; and wherein the anti-CD38 antibody comprises a CDR1 comprising the amino acid sequence of SEQ ID NO:44, a CDR2 comprising the amino acid sequence of SEQ ID NO:56, and a CDR3 comprising the amino acid sequence of SEQ ID NO:68. In some embodiments, the anti-BCMA sdAb and/or the anti-CD38 sdAb is camelid, chimeric, human, or humanized. In some embodiments, the anti-BCMA sdAbs comprises a $V_HH$ domain comprising the amino acid sequence of SEQ ID NO:78. In some embodiments, the anti-CD38 sdAbs comprises a $V_HH$ domain comprising the amino acid sequence of SEQ ID NO:93. In some embodiments, the anti-BCMA sdAb and the anti-CD38 sdAb are fused to each other via a peptide bond or a peptide linker. In some embodiments, the anti-BCMA sdAb is fused at the N-terminus of the anti-CD38 sdAb. In some embodiments, the first anti-BCMA is fused at the C-terminus of the anti-CD38 sdAb. In some embodiments, the peptide linker is no more than about 50 (such as no more than about any one of 35, 25, 20, 15, 10, or 5) amino acids long. In some embodiments, the peptide linker comprises an amino acid sequence selected from the group consisting of SEQ ID NOs: 144-151. In some embodiments, the transmembrane domain is selected from the group consisting of CD8α, CD4, CD28, CD137, CD80, CD86, CD152 and PD1. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the BCMA×CD38 CAR further comprises a hinge domain (such as a CD8α hinge domain) located between the C-terminus of the extracellular antigen binding domain and the N-terminus of the transmembrane domain. In some embodiments, the BCMA×CD38 CAR further comprises a signal peptide (such as a CD8α signal peptide) located at the N-terminus of the polypeptide.

In some embodiments, there is provided a BCMA×CD38 CAR comprising a polypeptide comprising from the N-terminus to the C-terminus: a CD8α signal peptide, an anti-CD38 single-domain antibody, a peptide linker, an anti-BCMA single-domain antibody, a CD8α hinge domain, a CD8α transmembrane domain, a co-stimulatory signaling domain derived from CD137, and a primary intracellular signaling domain derived from CD3ζ; wherein the anti-BCMA single-domain antibody comprises a CDR1 comprising the amino acid sequence of SEQ ID NO:7, a CDR2 comprising the amino acid sequence of SEQ ID NO: 18, and a CDR3 comprising the amino acid sequence of SEQ ID NO:29; and wherein the anti-CD38 antibody comprises a CDR1 comprising the amino acid sequence of SEQ ID NO:44, a CDR2 comprising the amino acid sequence of SEQ ID NO: 56, and a CDR3 comprising the amino acid sequence of SEQ ID NO:68. In some embodiments, the peptide linker is no more than about 50 (such as no more than about any one of 35, 25, 20, 15, 10, or 5) amino acids long. In some embodiments, the peptide linker comprises an amino acid sequence selected from the group consisting of SEQ ID NOs: 144-151. In some embodiments, the BCMA×CD38 CAR comprising a polypeptide having at least about any one of 85%, 86%, 87%, 88%, 89%, 90%, 91%, 92%, 93%, 94%, 95%, 96%, 97%, 98%, 99%, or 100% sequence identity to an amino acid sequence selected from the group consisting of SEQ ID NOs: 207-211. In some embodiments, there is provided a BCMA×CD38 CAR comprising an amino acid sequence selected from the group consisting of SEQ ID NOs: 207-211. Also provided is a polypeptide comprising an amino acid sequence selected from the group consisting of SEQ ID NOs: 207-211.

In some embodiments, there is provided a BCMA×CD38 CAR comprising a polypeptide comprising from the N-terminus to the C-terminus: a CD8α signal peptide, an anti-BCMA single-domain antibody, a peptide linker, an anti-CD38 single-domain antibody, a CD8α hinge domain, a CD8α transmembrane domain, a co-stimulatory signaling domain derived from CD137, and a primary intracellular signaling domain derived from CD3ζ; wherein the anti-BCMA single-domain antibody comprises a CDR1 comprising the amino acid sequence of SEQ ID NO:7, a CDR2 comprising the amino acid sequence of SEQ ID NO: 18, and a CDR3 comprising the amino acid sequence of SEQ ID NO:29; and wherein the anti-CD38 antibody comprises a CDR1 comprising the amino acid sequence of SEQ ID NO:44, a CDR2 comprising the amino acid sequence of SEQ ID NO:56, and a CDR3 comprising the amino acid sequence of SEQ ID NO:68. In some embodiments, the peptide linker is no more than about 50 (such as no more than about any one of 35, 25, 20, 15, 10, or 5) amino acids long. In some embodiments, the peptide linker comprises an amino acid sequence selected from the group consisting of SEQ ID NOs: 144-151. In some embodiments, the BCMA×CD38 CAR comprising a polypeptide having at least about any one of 85%, 86%, 87%, 88%, 89%, 90%, 91%, 92%, 93%, 94%, 95%, 96%, 97%, 98%, 99%, or 100% sequence identity to an amino acid sequence selected from the group consisting of SEQ ID NOs: 212-216. In some embodiments, there is provided a BCMA×CD38 CAR comprising t an amino acid sequence selected from the group consisting of SEQ ID NOs: 212-216. Also provided is a polypeptide comprising an amino acid sequence selected from the group consisting of SEQ ID NOs: 212-216.

In some embodiments, there is provided an isolated nucleic acid encoding any of the BCMA×CD38 CAR provided herein. In some embodiments, there is provided an isolated nucleic acid having at least about any one of 85%, 86%, 87%, 88%, 89%, 90%, 91%, 92%, 93%, 94%, 95%, 96%, 97%, 98%, 99%, or 100% sequence identity to a nucleic acid sequence selected from the group consisting of SEQ ID NOs:218-227. In some embodiments, there is provided an isolated nucleic acid comprising a nucleic acid sequence selected from the group consisting of SEQ ID NOs:218-227. In some embodiments, the isolated nucleic acid is a DNA. In some embodiments, the isolated nucleic acid is an RNA. In some embodiments, there is provided a vector comprising any one of the nucleic acids encoding the BCMA×CD38 CARs described above. In some embodiments, the vector is an expression vector. In some embodiments, the vector is a viral vector, such as a lentiviral vector.

2. CD19×CD20 CAR

In some embodiments, B cell differentiation antigens such as CD19 and CD20 are candidates for target antigens in B cell lymphoma. Some of these antigens have been used as targets for passive immunotherapy with monoclonal antibodies with limited success. In some embodiments, the CAR of the present application is a bispecific CAR simultaneously targeting CD19 and CD20.

In some embodiments, there is provided a multispecific (such as bispecific) chimeric antigen receptor targeting CD19 and CD20 (also referred herein as "CD19×CD20 CAR") comprising a polypeptide comprising: (a) an extracellular antigen binding domain comprising a first single-domain antibody (sdAb) specifically binding to CD19 and a second single-domain antibody specifically binding to CD20; (b) a transmembrane domain; and (c) an intracellular signaling domain. In some embodiments, the first sdAb and/or the second sdAb is camelid, chimeric, human, or humanized. In some embodiments, the first single-domain antibody and the second single-domain antibody are fused to each other via a peptide bond or a peptide linker. In some embodiments, the first sdAb is fused at the N-terminus of the second sdAb. In some embodiments, the first sdAb is fused at the C-terminus of the second sdAb. In some embodiments, the peptide linker is no more than about 50 (such as no more than about any one of 35, 25, 20, 15, 10, or 5) amino acids long. In some embodiments, the peptide linker comprises an amino acid sequence selected from the group consisting of SEQ ID NOs: 144-151. In some embodiments, the transmembrane domain is selected from the group consisting of CD8α, CD4, CD28, CD137, CD80, CD86, CD152 and PD1. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the CD19×CD20 CAR further comprises a hinge domain (such as a CD8α hinge domain) located between the C-terminus of the extracellular antigen binding domain and the N-terminus of the transmembrane domain. In some embodiments, the CD19×CD20 CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD28 transmembrane domain, a co-stimulatory signaling domain derived from CD28, and a primary intracellular signaling domain derived from CD3ζ.

In some embodiments, there is provided a multispecific (such as bispecific) chimeric antigen receptor targeting CD19 and CD20 (also referred herein as "CD19×CD20 CAR") comprising a polypeptide comprising: (a) an extracellular antigen binding domain comprising an anti-CD19 single-domain antibody and an anti-CD20 single-domain antibody; (b) a transmembrane domain; and (c) an intracellular signaling domain, wherein the anti-CD19 single-domain antibody comprises a CDR1 comprising the amino acid sequence of SEQ ID NO:1, a CDR2 comprising the amino acid sequence of SEQ ID NO:2, and a CDR3 comprising the amino acid sequence of SEQ ID NO:3; and wherein the anti-CD20 antibody comprises a CDR1 comprising the amino acid sequence of SEQ ID NO:4, a CDR2 comprising the amino acid sequence of SEQ ID NO:5, and a CDR3 comprising the amino acid sequence of SEQ ID NO:6. In some embodiments, the anti-CD19 sdAb and/or the anti-CD20 sdAb is camelid, chimeric, human, or humanized. In some embodiments, the anti-CD19 sdAbs comprises a $V_HH$ domain comprising the amino acid sequence of SEQ ID NO:76. In some embodiments, the anti-CD20 sdAbs comprises a $V_HH$ domain comprising the amino acid sequence of SEQ ID NO:77. In some embodiments, the anti-CD19 sdAb and the anti-CD20 sdAb are fused to each other via a peptide bond or a peptide linker. In some embodiments, the anti-CD19 sdAb is fused at the N-terminus of the anti-CD20 sdAb. In some embodiments, the first anti-CD19 is fused at the C-terminus of the anti-CD20 sdAb. In some embodiments, the peptide linker is no more than about 50 (such as no more than about any one of 35, 25, 20, 15, 10, or 5 amino acids long. In some embodiments, the peptide linker comprises the amino acid sequence of SEQ ID NOs: 146. In some embodiments, the transmembrane domain is selected from the group consisting of CD8α, CD4, CD28, CD137, CD80, CD86, CD152 and PD1. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the CD19×CD20 CAR further comprises a hinge domain (such as a CD8α hinge domain) located between the C-terminus of the extracellular antigen binding domain and the N-terminus of the transmembrane domain. In some embodiments, the CD19×CD20 CAR further comprises a signal peptide (such as a CD8α signal peptide) located at the N-terminus of the polypeptide.

In some embodiments, there is provided a CD19×CD20 CAR comprising a polypeptide comprising from the N-terminus to the C-terminus: a CD8α signal peptide, an anti-CD19 single-domain antibody, a peptide linker, an anti-CD20 single-domain antibody, a CD8α hinge domain, a CD28 transmembrane domain, a co-stimulatory signaling domain derived from CD28, and a primary intracellular signaling domain derived from CD3ζ; wherein the anti-CD19 single-domain antibody comprises a CDR1 comprising the amino acid sequence of SEQ ID NO: 1, a CDR2 comprising the amino acid sequence of SEQ ID NO:2, and a CDR3 comprising the amino acid sequence of SEQ ID NO:3; and wherein the anti-CD20 antibody comprises a CDR1 comprising the amino acid sequence of SEQ ID NO:4, a CDR2 comprising the amino acid sequence of SEQ ID NO:5, and a CDR3 comprising the amino acid sequence of SEQ ID NO:6. In some embodiments, the peptide linker is no more than about 50 (such as no more than about any one of 35, 25, 20, 15, 10, or 5 amino acids long. In some embodiments, the peptide linker comprises the amino acid sequence of SEQ ID NO: 146. In some embodiments, the CD19×CD20 CAR comprising a polypeptide having at least about any one of 85%, 86%, 87%, 88%, 89%, 90%, 91%, 92%, 93%, 94%, 95%, 96%, 97%, 98%, 99%, or 100% sequence identity to the amino acid sequence of SEQ ID NO: 206. In some embodiments, there is provided a CD19× CD20 CAR comprising the amino acid sequence of SEQ ID NO: 206. Also provided is a polypeptide comprising the amino acid sequence of SEQ ID NO: 206.

In some embodiments, there is provided an isolated nucleic acid encoding any of the CD19×CD20 CARs provided herein. In some embodiments, there is provided an isolated nucleic acid having at least about any one of 85%, 86%, 87%, 88%, 89%, 90%, 91%, 92%, 93%, 94%, 95%, 96%, 97%, 98%, 99%, or 100% sequence identity to the nucleic acid sequence of SEQ ID NO:217. In some embodiments, there is provided an isolated nucleic acid comprising the nucleic acid sequence of SEQ ID NO:217. In some embodiments, the isolated nucleic acid is a DNA. In some embodiments, the isolated nucleic acid is an RNA. In some embodiments, there is provided a vector comprising any one of the nucleic acids encoding the CD19×CD20 CARs described above. In some embodiments, the vector is an expression vector. In some embodiments, the vector is a viral vector, such as a lentiviral vector.

Currently, immunotherapies targeting CD19 have seen remarkable results in clinical trials. CD19 CAR-T cell-based clinical trials of short-term ALL treatment can achieve about 90% complete remission efficacy. However, approximately 10% of patients were found relapse after a few months' treatment. The main reason was that CD19 was lost during maturation of B cells to plasma cells and the residual tumor cells produced the CD19 antigen loss escape variants. The CD19×CD20 CARs described herein may simultaneously target CD19 and CD20 tumor surface antigens, which may enhance systemic T cell antitumor activity, and reduce the target escape phenomena which caused at least 30% of leukemia relapse after CAR therapy.

3. Other Exemplary Multispecific CARs

In some embodiments, there is provided a multispecific (such as bispecific) chimeric antigen receptor targeting CD19 and CD22 (also referred herein as "CD19×CD22 CAR") comprising a polypeptide comprising: (a) an extracellular antigen binding domain comprising an anti-CD19 single-domain antibody and an anti-CD22 single-domain antibody; (b) a transmembrane domain; and (c) an intracellular signaling domain. In some embodiments, the anti-CD19 sdAb and/or the anti-CD22 sdAb is camelid, chimeric, human, or humanized. In some embodiments, the anti-CD22 single-domain antibody and anti-CD22 single-domain antibody are fused to each other via a peptide bond or a peptide linker. In some embodiments, the anti-CD19 sdAb is fused at the N-terminus of the anti-CD22 sdAb. In some embodiments, the anti-CD19 sdAb is fused at the C-terminus of the anti-CD22 sdAb. In some embodiments, the peptide linker is no more than about 50 (such as no more than about any one of 35, 25, 20, 15, 10, or 5) amino acids long. In some embodiments, the peptide linker comprises an amino acid sequence selected from the group consisting of SEQ ID NOs: 144-151. In some embodiments, the transmembrane domain is selected from the group consisting of CD8α, CD4, CD28, CD137, CD80, CD86, CD152 and PD1. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the CD19×CD22 CAR further comprises a hinge domain (such as a CD8α hinge domain) located between the C-terminus of the extracellular antigen binding domain and the N-terminus of the transmembrane domain. In some embodiments, the CD19×CD22 CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ. In some embodiments, the polypeptide comprises from the N-terminus to the C-terminus: a CD8α signal peptide, the extracellular antigen binding domain, a CD8α hinge domain, a CD28 transmembrane domain, a co-stimulatory signaling domain derived from CD28, and a primary intracellular signaling domain derived from CD3ζ. In some embodiments, the anti-CD19 single-domain antibody comprises a CDR1 comprising the amino acid sequence of SEQ ID NO: 1, a CDR2 comprising the amino acid sequence of SEQ ID NO:2, and a CDR3 comprising the amino acid sequence of SEQ ID NO:3.

In some embodiments, there is provided a multispecific (such as bispecific) chimeric antigen receptor targeting CD19 and BCMA (also referred herein as "CD19×BCMA CAR") comprising a polypeptide comprising: (a) an extracellular antigen binding domain comprising an anti-CD19 single-domain antibody and an anti-BCMA single-domain antibody; (b) a transmembrane domain; and (c) an intracellular signaling domain. In some embodiments, the anti-CD19 sdAb and/or the anti-BCMA sdAb is camelid, chimeric, human, or humanized. In some embodiments, the anti-BCMA single-domain antibody and anti-BCMA single-domain antibody are fused to each other via a peptide bond or a peptide linker. In some embodiments, the anti-CD19 sdAb is fused at the N-terminus of the anti-BCMA sdAb. In some embodiments, the anti-CD19 sdAb is fused at the C-terminus of the anti-BCMA sdAb. In some embodiments, the peptide linker is no more than about 50 (such as no more than about any one of 35, 25, 20, 15, 10, or 5) amino acids long. In some embodiments, the peptide linker comprises an amino acid sequence selected from the group consisting of SEQ ID NOs: 144-151. In some embodiments, the transmembrane domain is selected from the group consisting of CD8α, CD4, CD28, CD137, CD80, CD86, CD152 and PD1. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the CD19×BCMA CAR further comprises a hinge domain (such as a CD8α hinge domain) located between the C-terminus of the extracellular antigen binding domain and the N-terminus of the transmembrane domain. In some embodiments, the CD19×BCMA CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ. In some embodiments, the polypeptide comprises from the N-terminus to the C-terminus: a CD8α signal peptide, the extracellular antigen binding domain, a CD8α hinge domain, a CD28 transmembrane domain, a co-stimulatory signaling domain derived from CD28, and a primary intracellular signaling domain derived from CD3ζ. In some embodiments, the anti-CD19 single-domain antibody comprises a CDR1 comprising the amino acid sequence of SEQ ID NO:1, a CDR2 comprising the amino acid sequence of SEQ ID NO:2, and a CDR3 comprising the amino acid sequence of SEQ ID NO:3.

TABLE 6

Exemplary bispecific CARs.

| CAR | Ex. AA SEQ ID | Ex. NA SEQ ID | SP | Extracellular Antigen binding domain | | | Hinge | TM | CO1 | Intra. |
| | | | | sdAb #1 | Linker SEQ ID | sdAb#2 | | | | |
| --- | --- | --- | --- | --- | --- | --- | --- | --- | --- | --- |
| CD19 × CD20 | 206 | 217 | CD8α | CD19 V$_H$H | 146 | CD20 V$_H$H | CD8α | CD28 | CD28 | CD3ζ |
| GSI5001 | 207 | 218 | CD8α | 38A37717 | 144 | 269A37346 | CD8α | CD8α | CD137 | CD3ζ |
| GSI5002 | 208 | 219 | CD8α | 38A37717 | 145 | 269A37346 | CD8α | CD8α | CD137 | CD3ζ |
| GSI5003 | 209 | 220 | CD8α | 38A37717 | 146 | 269A37346 | CD8α | CD8α | CD137 | CD3ζ |
| GSI5004 | 210 | 221 | CD8α | 38A37717 | 147 | 269A37346 | CD8α | CD8α | CD137 | CD3ζ |
| GSI5005 | 211 | 222 | CD8α | 38A37717 | 148 | 269A37346 | CD8α | CD8α | CD137 | CD3ζ |
| GSI5006 | 212 | 223 | CD8α | 269A37346 | 144 | 38A37717 | CD8α | CD8α | CD137 | CD3ζ |

TABLE 6-continued

Exemplary bispecific CARs.

| CAR | Ex. AA SEQ ID | Ex. NA SEQ ID | SP | Extracellular Antigen binding domain | | | Hinge | TM | CO1 | Intra. |
| | | | | sdAb #1 | Linker SEQ ID | sdAb#2 | | | | |
|---|---|---|---|---|---|---|---|---|---|---|
| GSI5007 | 213 | 224 | CD8α | 269A37346 | 145 | 38A37717 | CD8α | CD8α | CD137 | CD3ζ |
| GSI5008 | 214 | 225 | CD8α | 269A37346 | 146 | 38A37717 | CD8α | CD8α | CD137 | CD3ζ |
| GSI5009 | 215 | 226 | CD8α | 269A37346 | 147 | 38A37717 | CD8α | CD8α | CD137 | CD3ζ |
| GSI5010 | 216 | 227 | CD8α | 269A37346 | 148 | 38A37717 | CD8α | CD8α | CD137 | CD3ζ |

Extracellular Antigen Binding Domain

The extracellular antigen binding domain of the CARs described herein comprises one or more (such as any one of 1, 2, 3, 4, 5, 6 or more) single-domain antibodies. The single-domain antibodies can be fused to each other directly via peptide bonds, or via peptide linkers.

1. Single-Domain Antibodies

The CARs of the present application comprise an extracellular antigen binding domain comprising one or more single-domain antibodies. The sdAbs may be of the same of different origins, and of the same or different sizes. Exemplary sdAbs include, but are not limited to, heavy chain variable domains from heavy-chain only antibodies (e.g., $V_HH$ or $V_{NAR}$), binding molecules naturally devoid of light chains, single domains (such as $V_H$ or $V_L$) derived from conventional 4-chain antibodies, humanized heavy-chain only antibodies, human single-domain antibodies produced by transgenic mice or rats expressing human heavy chain segments, and engineered domains and single domain scaffolds other than those derived from antibodies. Any sdAbs known in the art or developed by the inventors, including the single-domain antibodies described in Section II of the present application, may be used to construct the CARs described herein. The sdAbs may be derived from any species including, but not limited to mouse, rat, human, camel, llama, lamprey, fish, shark, goat, rabbit, and bovine. Single-domain antibodies contemplated herein also include naturally occurring single-domain antibody molecules from species other than Camelidae and sharks.

In some embodiments, the sdAb is derived from a naturally occurring single-domain antigen binding molecule known as heavy chain antibody devoid of light chains (also referred herein as "heavy chain only antibodies"). Such single domain molecules are disclosed in WO 94/04678 and Hamers-Casterman, C. et al. (1993) Nature 363:446-448, for example. For clarity reasons, the variable domain derived from a heavy chain molecule naturally devoid of light chain is known herein as a $V_HH$ to distinguish it from the conventional $V_H$ of four chain immunoglobulins. Such a $V_HH$ molecule can be derived from antibodies raised in Camelidae species, for example, camel, llama, vicuna, dromedary, alpaca and guanaco. Other species besides Camelidae may produce heavy chain molecules naturally devoid of light chain, and such $V_HHs$ are within the scope of the present application.

$V_HH$ molecules from Camelids are about 10 times smaller than IgG molecules. They are single polypeptides and can be very stable, resisting extreme pH and temperature conditions. Moreover, they can be resistant to the action of proteases which is not the case for conventional 4-chain antibodies. Furthermore, in vitro expression of $V_HH$ s produces high yield, properly folded functional $V_HHs$. In addition, antibodies generated in Camelids can recognize epitopes other than those recognized by antibodies generated in vitro through the use of antibody libraries or via immunization of mammals other than Camelids (see, for example, WO9749805). As such, multispecific or multivalent CARs comprising one or more $V_HH$ domains may interact more efficiently with targets than multispecific or multivalent CARs comprising antigen binding fragments derived from conventional 4-chain antibodies. Since $V_HHs$ are known to bind into 'unusual' epitopes such as cavities or grooves, the affinity of CARs comprising such $V_HHs$ may be more suitable for therapeutic treatment than conventional multispecific polypeptides.

In some embodiments, the sdAb is derived from a variable region of the immunoglobulin found in cartilaginous fish. For example, the sdAb can be derived from the immunoglobulin isotype known as Novel Antigen Receptor (NAR) found in the serum of shark. Methods of producing single domain molecules derived from a variable region of NAR ("IgNARs") are described in WO 03/014161 and Streltsov (2005) Protein Sci. 14:2901-2909.

In some embodiments, the sdAb is recombinant, CDR-grafted, humanized, camelized, de-immunized and/or in vitro generated (e.g., selected by phage display). In some embodiments, the amino acid sequence of the framework regions may be altered by "camelization" of specific amino acid residues in the framework regions. Camelization refers to the replacing or substitution of one or more amino acid residues in the amino acid sequence of a (naturally occurring) $V_H$ domain from a conventional 4-chain antibody by one or more of the amino acid residues that occur at the corresponding position(s) in a $V_HH$ domain of a heavy chain antibody. This can be performed in a manner known per se, which will be clear to the skilled person, for example on the basis of the further description herein. Such "camelizing" substitutions are preferably inserted at amino acid positions that form and/or are present at the $V_H$-$V_L$ interface, and/or at the so-called Camelidae hallmark residues, as defined herein (see for example WO 94/04678, Davies and Riechmann FEBS Letters 339: 285-290, 1994; Davies and Riechmann Protein Engineering 9 (6): 531-537, 1996; Riechmann J. Mol. Biol. 259: 957-969, 1996; and Riechmann and Muyldermans J. Immunol. Meth. 231: 25-38, 1999).

In some embodiments, the sdAb is a human single-domain antibody produced by transgenic mice or rats expressing human heavy chain segments. See, e.g., US20090307787A1, U.S. Pat. No. 8,754,287, US20150289489A1, US20100122358A1, and WO2004049794. In some embodiments, the sdAb is affinity matured.

In some embodiments, naturally occurring $V_HH$ domains against a particular antigen or target, can be obtained from (naïve or immune) libraries of Camelid $V_HH$ sequences. Such methods may or may not involve screening such a library using said antigen or target, or at least one part, fragment, antigenic determinant or epitope thereof using one or more screening techniques known per se. Such libraries and techniques are for example described in WO 99/37681, WO 01/90190, WO 03/025020 and WO 03/035694. Alternatively, improved synthetic or semi-synthetic libraries derived from (naïve or immune) $V_HH$ libraries may be used, such as $V_HH$ libraries obtained from (naïve or immune) $V_HH$ libraries by techniques such as random mutagenesis and/or CDR shuffling, as for example described in WO 00/43507.

In some embodiments, the single-domain antibodies are generated from conventional four-chain antibodies. See, for example, EP 0 368 684, Ward et al. (Nature 1989 Oct. 12; 341 (6242): 544-6), Holt et al., Trends Biotechnol., 2003, 21(11):484-490; WO 06/030220; and WO 06/003388.

2. Antigens

The antigen(s) targeted by the CARs of the present application are cell surface molecules. The single-domain antibodies may be chosen to recognize an antigen that acts as a cell surface marker on target cells associated with a special disease state. In some embodiments, the antigen (such as the first antigen and/or the second antigen) is a tumor antigen. In some embodiments, the multispecific CARs target two or more tumor antigens. In some embodiments, the tumor antigen is associated with a B cell malignancy. Tumors express a number of proteins that can serve as a target antigen for an immune response, particularly T cell mediated immune responses. The antigens targeted by the CAR may be antigens on a single diseased cell or antigens that are expressed on different cells that each contribute to the disease. The antigens targeted by the CAR may be directly or indirectly involved in the diseases.

Tumor antigens are proteins that are produced by tumor cells that can elicit an immune response, particularly T-cell mediated immune responses. The selection of the targeted antigen of the invention will depend on the particular type of cancer to be treated. Exemplary tumor antigens include, for example, a glioma-associated antigen, carcinoembryonic antigen (CEA), β-human chorionic gonadotropin, alphafetoprotein (AFP), lectin-reactive AFP, thyroglobulin, RAGE-1, MN-CAIX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-la, p53, prostein, PSMA, HER2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin.

In some embodiments, the tumor antigen comprises one or more antigenic cancer epitopes associated with a malignant tumor. Malignant tumors express a number of proteins that can serve as target antigens for an immune attack. These molecules include but are not limited to tissue-specific antigens such as MART-I, tyrosinase and gp100 in melanoma and prostatic acid phosphatase (PAP) and prostate-specific antigen (PSA) in prostate cancer. Other target molecules belong to the group of transformation-related molecules such as the oncogene HER2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma.

In some embodiments, the tumor antigen is a tumor-specific antigen (TSA) or a tumor-associated antigen (TAA). A TSA is unique to tumor cells and does not occur on other cells in the body. A TAA associated antigen is not unique to a tumor cell, and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development, when the immune system is immature, and unable to respond or they may be antigens that are normally present at extremely low levels on normal cells, but which are expressed at much higher levels on tumor cells.

Non-limiting examples of TSA or TAA antigens include the following: Differentiation antigens such as MART-1/MelanA (MART-I), gp 100 (Pmel 17), tyrosinase, TRP-1, TRP-2 and tumor-specific multilineage antigens such as MAGE-1, MAGE-3, BAGE, GAGE-1, GAGE-2, pl5; overexpressed embryonic antigens such as CEA; overexpressed oncogenes and mutated tumor-suppressor genes such as p53, Ras, HER2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, pl85erbB2, pl80erbB-3, c-met, nm-23HI, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS 1, SDCCAG16, TA-90\Mac-2 binding protein\cyclophilin C-associated protein, TAAL6, TAG72, TLP, and TPS.

In some embodiments, the antigen (such as the first antigen and/or the second antigen) are selected from the group consisting of CD19, CD20, CD22, CD33, CD38, BCMA, CS1, ROR1, GPC3, CD123, IL-13R, CD138, c-Met, EGFRvIII, GD-2, NY-ESO-1, MAGE A3, and glycolipid F77.

3. Peptide Linkers

The various single-domain antibodies in the multispecific or multivalent CARs described herein may be fused to each other via peptide linkers. In some embodiments, the single-domain antibodies are directly fused to each other without any peptide linkers. The peptide linkers connecting different single-domain antibodies may be the same or different. Different domains of the CARs may also be fused to each other via peptide linkers.

Each peptide linker in a CAR may have the same or different length and/or sequence depending on the structural and/or functional features of the single-domain antibodies and/or the various domains. Each peptide linker may be selected and optimized independently. The length, the degree of flexibility and/or other properties of the peptide linker(s) used in the CARs may have some influence on properties, including but not limited to the affinity, specificity or avidity for one or more particular antigens or epitopes. For example, longer peptide linkers may be selected to ensure that two adjacent domains do not sterically interfere with one another. For example, in a multivalent or multispecific CAR of the present application that comprise single-domain antibodies directed against a multimeric antigen, the length and flexibility of the peptide linkers are preferably such that it allows each single-domain antibody in the multivalent CAR to bind to the antigenic determinant on each of the subunits of the multimer. In some embodiments, a short peptide linker may be disposed between the transmembrane domain and the intracellular signaling domain of a CAR. In some embodiment, a peptide linker comprises flexible residues (such as glycine and serine) so that the adjacent domains are free to move relative to each other. For example, a glycine-serine doublet can be a suitable peptide linker.

The peptide linker can be of any suitable length. In some embodiments, the peptide linker is at least about any of 1, 2, 3, 4, 5, 6, 7, 8, 9, 10, 11, 12, 13, 14, 15, 16, 17, 18, 19, 20, 25, 30, 35, 40, 50, 75, 100 or more amino acids long. In some embodiments, the peptide linker is no more than about any of 100, 75, 50, 40, 35, 30, 25, 20, 19, 18, 17, 16, 15, 14, 13, 12, 11, 10, 9, 8, 7, 6, 5 or fewer amino acids long. In some embodiments, the length of the peptide linker is any of about 1 amino acid to about 10 amino acids, about 1 amino acids to about 20 amino acids, about 1 amino acid to about 30 amino acids, about 5 amino acids to about 15 amino acids, about 10 amino acids to about 25 amino acids, about 5 amino acids to about 30 amino acids, about 10 amino acids to about 30 amino acids long, about 30 amino acids to about 50 amino acids, about 50 amino acids to about 100 amino acids, or about 1 amino acid to about 100 amino acids.

The peptide linker may have a naturally occurring sequence, or a non-naturally occurring sequence. For example, a sequence derived from the hinge region of heavy chain only antibodies may be used as the linker. See, for example, WO1996/34103. In some embodiments, the peptide linker is a flexible linker. Exemplary flexible linkers include glycine polymers $(G)_n$, glycine-serine polymers (including, for example, $(GS)_n$, $(GSGGS)_n$, $(GGGS)_n$, and $(GGGGS)_n$, where n is an integer of at least one), glycine-alanine polymers, alanine-serine polymers, and other flexible linkers known in the art. In some embodiments, the peptide linker comprises the amino acid sequence GGGGS (SEQ ID NO: 144), $(GGGGS)_2$ (SEQ ID NO: 145), $(GGGS)_4$ (SEQ ID NO: 146), GGGGSGGGGSGGGGGGSGSGGGS (SEQ ID NO: 147), GGGGSGGGGSGGGGGSGSGGGGSGGGGSGGGGS (SEQ ID NO: 148), $(GGGGS)_3$ (SEQ ID NO: 149), $(GGGGS)_4$ (SEQ ID NO: 150), or $(GGGGS)_3$ (SEQ ID NO: 151).

Transmembrane Domain

The CARs of the present application comprise a transmembrane domain that can be directly or indirectly fused to the extracellular antigen binding domain. The transmembrane domain may be derived either from a natural or from a synthetic source. As used herein, a "transmembrane domain" refers to any protein structure that is thermodynamically stable in a cell membrane, preferably a eukaryotic cell membrane. Transmembrane domains compatible for use in the CARs described herein may be obtained from a naturally occurring protein. Alternatively, it can be a synthetic, non-naturally occurring protein segment, e.g., a hydrophobic protein segment that is thermodynamically stable in a cell membrane.

Transmembrane domains are classified based on the three dimensional structure of the transmembrane domain. For example, transmembrane domains may form an alpha helix, a complex of more than one alpha helix, a beta-barrel, or any other stable structure capable of spanning the phospholipid bilayer of a cell. Furthermore, transmembrane domains may also or alternatively be classified based on the transmembrane domain topology, including the number of passes that the transmembrane domain makes across the membrane and the orientation of the protein. For example, single-pass membrane proteins cross the cell membrane once, and multi-pass membrane proteins cross the cell membrane at least twice (e.g., 2, 3, 4, 5, 6, 7 or more times). Membrane proteins may be defined as Type I, Type II or Type II depending upon the topology of their termini and membrane-passing segment(s) relative to the inside and outside of the cell. Type I membrane proteins have a single membrane-spanning region and are oriented such that the N-terminus of the protein is present on the extracellular side of the lipid bilayer of the cell and the C-terminus of the protein is present on the cytoplasmic side. Type II membrane proteins also have a single membrane-spanning region but are oriented such that the C-terminus of the protein is present on the extracellular side of the lipid bilayer of the cell and the N-terminus of the protein is present on the cytoplasmic side. Type II membrane proteins have multiple membrane-spanning segments and may be further sub-classified based on the number of transmembrane segments and the location of N- and C-termini.

In some embodiments, the transmembrane domain of the CAR described herein is derived from a Type I single-pass membrane protein. In some embodiments, transmembrane domains from multi-pass membrane proteins may also be compatible for use in the CARs described herein. Multi-pass membrane proteins may comprise a complex (at least 2, 3, 4, 5, 6, 7 or more) alpha helices or a beta sheet structure. Preferably, the N-terminus and the C-terminus of a multipass membrane protein are present on opposing sides of the lipid bilayer, e.g., the N-terminus of the protein is present on the cytoplasmic side of the lipid bilayer and the C-terminus of the protein is present on the extracellular side.

In some embodiments, the transmembrane domain of the CAR comprises a transmembrane domain chosen from the transmembrane domain of an alpha, beta or zeta chain of a T-cell receptor, CD28, CD3ζ epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CD1 la, CD18), ICOS (CD278), 4-1BB (CD137), GITR, CD40, BAFFR, HVEM (LIGHTR), SLAMF7, NKp80 (KLRF1), CD160, CD19, IL-2R beta, IL-2R gamma, IL-7R a, ITGA1, VLA1, CD49a, ITGA4, IA4, CD49D, ITGA6, VLA-6, CD49f, ITGAD, CD1 ld, ITGAE, CD103, ITGAL, CD1 la, LFA-1, ITGAM, CD1 lb, ITGAX, CD1 lc, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRT AM, Ly9 (CD229), CD160 (BY55), PSGL1, CDIOO (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and/or NKG2C. In some embodiments, the transmembrane domain is derived from a molecule selected from the group consisting of CD8c, CD4, CD28, CD137, CD80, CD86, CD152 and PD1.

In some embodiments, the transmembrane domain is derived from CD28. In some embodiments, the transmembrane domain is a transmembrane domain of CD28 comprising the amino acid sequence of SEQ ID NO: 133. In some embodiments, the transmembrane domain of CD28 is encoded by the nucleic acid sequence of SEQ ID NO: 135.

In some embodiments, the transmembrane domain is derived from CD8α. In some embodiments, the transmembrane domain is a transmembrane domain of CD8α comprising the amino acid sequence of SEQ ID NO: 132. In some embodiments, the transmembrane domain of CD8α is encoded by the nucleic acid sequence of SEQ ID NO: 134.

Transmembrane domains for use in the CARs described herein can also comprise at least a portion of a synthetic, non-naturally occurring protein segment. In some embodiments, the transmembrane domain is a synthetic, non-naturally occurring alpha helix or beta sheet. In some embodiments, the protein segment is at least approximately 20 amino acids, e.g., at least 18, 19, 20, 21, 22, 23, 24, 25, 26, 27, 28, 29, 30, or more amino acids. Examples of synthetic transmembrane domains are known in the art, for example in U.S. Pat. No. 7,052,906 B1 and PCT Publication No. WO 2000/032776 A2, the relevant disclosures of which are incorporated by reference herein.

The transmembrane domain may comprise a transmembrane region and a cytoplasmic region located at the C-terminal side of the transmembrane domain. The cytoplasmic region of the transmembrane domain may comprise three or more amino acids and, in some embodiments, helps to orient the transmembrane domain in the lipid bilayer. In some embodiments, one or more cysteine residues are present in the transmembrane region of the transmembrane domain. In some embodiments, one or more cysteine residues are present in the cytoplasmic region of the transmembrane domain. In some embodiments, the cytoplasmic region of the transmembrane domain comprises positively charged amino acids. In some embodiments, the cytoplasmic region of the transmembrane domain comprises the amino acids arginine, serine, and lysine.

In some embodiments, the transmembrane region of the transmembrane domain comprises hydrophobic amino acid residues. In some embodiments, the transmembrane domain of the CAR comprises an artificial hydrophobic sequence. For example, a triplet of phenylalanine, tryptophan and valine may be present at the C terminus of the transmembrane domain. In some embodiments, the transmembrane region comprises mostly hydrophobic amino acid residues, such as alanine, leucine, isoleucine, methionine, phenylalanine, tryptophan, or valine. In some embodiments, the transmembrane region is hydrophobic. In some embodiments, the transmembrane region comprises a poly-leucine-alanine sequence. The hydropathy, or hydrophobic or hydrophilic characteristics of a protein or protein segment, can be assessed by any method known in the art, for example the Kyte and Doolittle hydropathy analysis.

Intracellular Signaling Domain

The CARs of the present application comprise an intracellular signaling domain. The intracellular signaling domain is responsible for activation of at least one of the normal effector functions of the immune effector cell expressing the CARs. The term "effector function" refers to a specialized function of a cell. Effector function of a T cell, for example, may be cytolytic activity or helper activity including the secretion of cytokines. Thus the term "cytoplasmic signaling domain" refers to the portion of a protein which transduces the effector function signal and directs the cell to perform a specialized function. While usually the entire cytoplasmic signaling domain can be employed, in many cases it is not necessary to use the entire chain. To the extent that a truncated portion of the cytoplasmic signaling domain is used, such truncated portion may be used in place of the intact chain as long as it transduces the effector function signal. The term cytoplasmic signaling domain is thus meant to include any truncated portion of the cytoplasmic signaling domain sufficient to transduce the effector function signal.

In some embodiments, the intracellular signaling domain comprises a primary intracellular signaling domain of an immune effector cell. In some embodiments, the CAR comprises an intracellular signaling domain consisting essentially of a primary intracellular signaling domain of an immune effector cell. "Primary intracellular signaling domain" refers to cytoplasmic signaling sequence that acts in a stimulatory manner to induce immune effector functions. In some embodiments, the primary intracellular signaling domain contains a signaling motif known as immunoreceptor tyrosine-based activation motif, or ITAM. An "ITAM," as used herein, is a conserved protein motif that is generally present in the tail portion of signaling molecules expressed in many immune cells. The motif may comprises two repeats of the amino acid sequence YxxL/I separated by 6-8 amino acids, wherein each x is independently any amino acid, producing the conserved motif YxxL/Ix(6-8)YxxL/I. ITAMs within signaling molecules are important for signal transduction within the cell, which is mediated at least in part by phosphorylation of tyrosine residues in the ITAM following activation of the signaling molecule. ITAMs may also function as docking sites for other proteins involved in signaling pathways. Exemplary ITAM-containing primary cytoplasmic signaling sequences include those derived from CD3ζ, FcR gamma(FCER1G), FcR beta (Fc Epsilon Rib), CD3ζ gamma, CD3ζ delta, CD3 epsilon, CD5, CD22, CD79a, CD79b, and CD66d.

In some embodiments, the primary intracellular signaling domain is derived from CD3ζ. In some embodiments, the intracellular signaling domain consists of the cytoplasmic signaling domain of CD3ζ. In some embodiments, the primary intracellular signaling domain is a cytoplasmic signaling domain of wildtype CD3ζ. In some embodiments, the primary intracellular signaling domain of wildtype CD3ζ comprises the amino acid sequence of SEQ ID NO: 140. In some embodiments, the primary intracellular signaling domain of wildtype CD3ζ is encoded by the nucleic acid of SEQ ID NO: 142. In some embodiments, the primary intracellular signaling domain is a functional mutant of the cytoplasmic signaling domain of CD3ζ containing one or more mutations, such as Q65K. In some embodiments, the primary intracellular signaling domain of mutant CD3ζ comprises the amino acid sequence of SEQ ID NO: 141. In some embodiments, the primary intracellular signaling domain of mutant CD3ζ is encoded by the nucleic acid of SEQ ID NO: 143.

Co-Stimulatory Signaling Domain

Many immune effector cells require co-stimulation, in addition to stimulation of an antigen-specific signal, to promote cell proliferation, differentiation and survival, as well as to activate effector functions of the cell. In some embodiments, the CAR comprises at least one co-stimulatory signaling domain. The term "co-stimulatory signaling domain," as used herein, refers to at least a portion of a protein that mediates signal transduction within a cell to induce an immune response such as an effector function. The co-stimulatory signaling domain of the chimeric receptor described herein can be a cytoplasmic signaling domain from a co-stimulatory protein, which transduces a signal and modulates responses mediated by immune cells, such as T cells, NK cells, macrophages, neutrophils, or eosinophils. "Co-stimulatory signaling domain" can be the cytoplasmic portion of a co-stimulatory molecule. The term "co-stimulatory molecule" refers to a cognate binding partner on an immune cell (such as T cell) that specifically binds with a co-stimulatory ligand, thereby mediating a co-stimulatory response by the immune cell, such as, but not limited to, proliferation and survival.

In some embodiments, the intracellular signaling domain comprises a single co-stimulatory signaling domain. In some embodiments, the intracellular signaling domain comprises two or more (such as about any of 2, 3, 4, or more) co-stimulatory signaling domains. In some embodiments, the intracellular signaling domain comprises two or more of the same co-stimulatory signaling domains, for example, two copies of the co-stimulatory signaling domain of CD28. In some embodiments, the intracellular signaling domain comprises two or more co-stimulatory signaling domains from different co-stimulatory proteins, such as any two or more co-stimulatory proteins described herein. In some embodiments, the intracellular signaling domain comprises a primary intracellular signaling domain (such as cytoplasmic signaling domain of CD3ζ) and one or more co-stimulatory signaling domains. In some embodiments, the one or more co-stimulatory signaling domains and the primary intracellular signaling domain (such as cytoplasmic signaling domain of CD3ζ) are fused to each other via optional peptide linkers. The primary intracellular signaling domain, and the one or more co-stimulatory signaling domains may be arranged in any suitable order. In some embodiments, the one or more co-stimulatory signaling domains are located between the transmembrane domain and the primary intracellular signaling domain (such as cytoplasmic signaling domain of CD3ζ). Multiple co-stimulatory signaling domains may provide additive or synergistic stimulatory effects.

Activation of a co-stimulatory signaling domain in a host cell (e.g., an immune cell) may induce the cell to increase or decrease the production and secretion of cytokines, phagocytic properties, proliferation, differentiation, survival, and/or cytotoxicity. The co-stimulatory signaling domain of any co-stimulatory molecule may be compatible for use in the CARs described herein. The type(s) of co-stimulatory signaling domain is selected based on factors such as the type of the immune effector cells in which the effector molecules would be expressed (e.g., T cells, NK cells, macrophages, neutrophils, or eosinophils) and the desired immune effector function (e.g., ADCC effect). Examples of co-stimulatory signaling domains for use in the CARs can be the cytoplasmic signaling domain of co-stimulatory proteins, including, without limitation, members of the B7/CD28 family (e.g., B7-1/CD80, B7-2/CD86, B7-H1/PD-L1, B7-H2, B7-H3, B7-H4, B7-H6, B7-H7, BTLA/CD272, CD28, CTLA-4, Gi24/VISTA/B7-H5, ICOS/CD278, PD-1, PD-L2/B7-DC, and PDCD6); members of the TNF superfamily (e.g., 4-1BB/TNFSF9/CD137, 4-1BB Ligand/TNFSF9, BAFF/BLyS/TNFSF13B, BAFF R/TNFRSF13C, CD27/TNFRSF7, CD27 Ligand/TNFSF7, CD30/TNFRSF8, CD30 Ligand/TNFSF8, CD40/TNFRSF5, CD40/TNFSF5, CD40 Ligand/TNFSF5, DR3/TNFRSF25, GITR/TNFRSF18, GITR Ligand/TNFSF18, HVEM/TNFRSF14, LIGHT/TNFSF14, Lymphotoxin-alpha/TNF-beta, OX40/TNFRSF4, OX40 Ligand/TNFSF4, RELT/TNFRSF19L, TACI/TNFRSF13B, TL1A/TNFSF15, TNF-alpha, and TNF RII/TNFRSF1B); members of the SLAM family (e.g., 2B4/CD244/SLAMF4, BLAME/SLAMF8, CD2, CD2F-10/SLAMF9, CD48/SLAMF2, CD58/LFA-3, CD84/SLAMF5, CD229/SLAMF3, CRACC/SLAMF7, NTB-A/SLAMF6, and SLAM/CD150); and any other co-stimulatory molecules, such as CD2, CD7, CD53, CD82/Kai-1, CD90/Thy1, CD96, CD160, CD200, CD300a/LMIR1, HLA Class I, HLA-DR, Ikaros, Integrin alpha 4/CD49d, Integrin alpha 4 beta 1, Integrin alpha 4 beta 7/LPAM-1, LAG-3, TCL1A, TCL1B, CRTAM, DAP12, Dectin-1/CLEC7A, DPPIV/CD26, EphB6, TIM-1/KIM-1/HAVCR, TIM-4, TSLP, TSLP R, lymphocyte function associated antigen-1 (LFA-1), and NKG2C.

In some embodiments, the one or more co-stimulatory signaling domains are selected from the group consisting of CD27, CD28, 4-1BB, OX40, CD30, CD40, CD3, lymphocyte function-associated antigen-1(LFA-1), CD2, CD7, LIGHT, NKG2C, B7-H3 and ligands that specially bind to CD83.

In some embodiments, the intracellular signaling domain in the CAR of the present application comprises a co-stimulatory signaling domain derived from CD28. In some embodiments, the intracellular signaling domain comprises a cytoplasmic signaling domain of CD3ζ and a co-stimulatory signaling domain of CD28. In some embodiments, the intracellular signaling domain comprises a co-stimulatory signaling domain of CD28 comprising the amino acid sequence of SEQ ID NO: 136. In some embodiments, the co-stimulatory signaling domain of CD28 is encoded by the nucleic acid sequence of SEQ ID NO: 138. In some embodiments, the intracellular signaling domain is encoded by the nucleic acid sequence of SEQ ID NO: 228.

In some embodiments, the intracellular signaling domain in the CAR of the present application comprises a co-stimulatory signaling domain derived from CD137 (i.e., 4-1BB). In some embodiments, the intracellular signaling domain comprises a cytoplasmic signaling domain of CD3ζ and a co-stimulatory signaling domain of CD137. In some embodiments, the intracellular signaling domain comprises a co-stimulatory signaling domain of CD137 comprising the amino acid sequence of SEQ ID NO: 137. In some embodiments, the co-stimulatory signaling domain of CD137 is encoded by the nucleic acid sequence of SEQ ID NO: 139.

In some embodiments, the intracellular signaling domain in the CAR of the present application comprises a co-stimulatory signaling domain of CD28 and a co-stimulatory signaling domain of CD137. In some embodiments, the intracellular signaling domain comprises a cytoplasmic signaling domain of CD3ζ, a co-stimulatory signaling domain of CD28, and a co-stimulatory signaling domain of CD137. In some embodiments, the intracellular signaling domain comprises a polypeptide comprising from the N-terminus to the C-terminus: a co-stimulatory signaling domain of CD28, a co-stimulatory signaling domain of CD137, and a cytoplasmic signaling domain of CD3ζ. In some embodiments, the intracellular signaling domain comprises a co-stimulatory signaling domain of CD28 comprising the amino acid sequence of SEQ ID NO: 136. In some embodiments, the co-stimulatory signaling domain of CD28 is encoded by the nucleic acid sequence of SEQ ID NO: 138. In some embodiments, the intracellular signaling domain comprises a co-stimulatory signaling domain of CD137 comprising the amino acid sequence of SEQ ID NO: 137. In some embodiments, the co-stimulatory signaling domain of CD137 is encoded by the nucleic acid sequence of SEQ ID NO: 139.

Also within the scope of the present disclosure are variants of any of the co-stimulatory signaling domains described herein, such that the co-stimulatory signaling domain is capable of modulating the immune response of the immune cell. In some embodiments, the co-stimulatory signaling domains comprises up to 10 amino acid residue variations (e.g., 1, 2, 3, 4, 5, or 8) as compared to a wild-type counterpart. Such co-stimulatory signaling domains comprising one or more amino acid variations may be referred to as variants. Mutation of amino acid residues of the co-stimulatory signaling domain may result in an increase in signaling transduction and enhanced stimulation of immune responses relative to co-stimulatory signaling domains that do not comprise the mutation. Mutation of amino acid residues of the co-stimulatory signaling domain may result in a decrease in signaling transduction and reduced stimulation of immune responses relative to co-stimulatory signaling domains that do not comprise the mutation.

Hinge Region

The CARs of the present application may comprise a hinge domain that is located between the extracellular antigen binding domain and the transmembrane domain. A hinge domain is an amino acid segment that is generally found between two domains of a protein and may allow for flexibility of the protein and movement of one or both of the domains relative to one another. Any amino acid sequence that provides such flexibility and movement of the extracellular antigen binding domain relative to the transmembrane domain of the effector molecule can be used.

The hinge domain may contain about 10-100 amino acids, e.g., about any one of 15-75 amino acids, 20-50 amino acids, or 30-60 amino acids. In some embodiments, the hinge domain may be at least about any one of 10, 11, 12, 13, 14, 15, 16, 17, 18, 19, 20, 21, 22, 23, 24, 25, 26, 27, 28, 29, 30, 35, 40, 45, 50, 55, 60, 65, 70, or 75 amino acids in length.

In some embodiments, the hinge domain is a hinge domain of a naturally occurring protein. Hinge domains of any protein known in the art to comprise a hinge domain are compatible for use in the chimeric receptors described herein. In some embodiments, the hinge domain is at least a portion of a hinge domain of a naturally occurring protein and confers flexibility to the chimeric receptor. In some embodiments, the hinge domain is derived from CD8α. In some embodiments, the hinge domain is a portion of the hinge domain of CD8α, e.g., a fragment containing at least 15 (e.g., 20, 25, 30, 35, or 40) consecutive amino acids of the hinge domain of CD8α. In some embodiments, the hinge domain of CD8α comprises the amino acid sequence of SEQ ID NO: 130. In some embodiments, the hinge domain of CD8α is encoded by the nucleic acid sequence of SEQ ID NO: 131.

Hinge domains of antibodies, such as an IgG, IgA, IgM, IgE, or IgD antibodies, are also compatible for use in the pH-dependent chimeric receptor systems described herein. In some embodiments, the hinge domain is the hinge domain that joins the constant domains CH1 and CH2 of an antibody. In some embodiments, the hinge domain is of an antibody and comprises the hinge domain of the antibody and one or more constant regions of the antibody. In some embodiments, the hinge domain comprises the hinge domain of an antibody and the CH3 constant region of the antibody. In some embodiments, the hinge domain comprises the hinge domain of an antibody and the CH2 and CH3 constant regions of the antibody. In some embodiments, the antibody is an IgG, IgA, IgM, IgE, or IgD antibody. In some embodiments, the antibody is an IgG antibody. In some embodiments, the antibody is an IgG, IgG2, IgG3, or IgG4 antibody. In some embodiments, the hinge region comprises the hinge region and the CH2 and CH3 constant regions of an IgG1 antibody. In some embodiments, the hinge region comprises the hinge region and the CH3 constant region of an IgG1 antibody.

Non-naturally occurring peptides may also be used as hinge domains for the chimeric receptors described herein. In some embodiments, the hinge domain between the C-terminus of the extracellular ligand-binding domain of an Fc receptor and the N-terminus of the transmembrane domain is a peptide linker, such as a (G×S)n linker, wherein x and n, independently can be an integer between 3 and 12, including 3, 4, 5, 6, 7, 8, 9, 10, 11, 12, or more.

Signal Peptide

The CARs of the present application may comprise a signal peptide (also known as a signal sequence) at the N-terminus of the polypeptide. In general, signal peptides are peptide sequences that target a polypeptide to the desired site in a cell. In some embodiments, the signal peptide targets the effector molecule to the secretory pathway of the cell and will allow for integration and anchoring of the effector molecule into the lipid bilayer. Signal peptides including signal sequences of naturally occurring proteins or synthetic, non-naturally occurring signal sequences, which are compatible for use in the CARs described herein will be evident to one of skill in the art. In some embodiments, the signal peptide is derived from a molecule selected from the group consisting of CD8α, GM-CSF receptor α, and IgG1 heavy chain. In some embodiments, the signal peptide is derived from CD8α. In some embodiments, the signal peptide of CD8α comprises the amino acid sequence of SEQ ID NO: 127. In some embodiments, the signal peptide of CD8α is encoded by the nucleic acid sequence of SEQ ID NO: 128 or SEQ ID NO: 129.

IV. Engineered Immune Effector Cells

Further provided in the present application are host cells (such as immune effector cells) comprising any one of the CARs described herein.

Thus, in some embodiments, there is provided an engineered immune effector cell (such as T cell) comprising a multispecific (such as bispecific) chimeric antigen receptor (CAR) comprising a polypeptide comprising: (a) an extracellular antigen binding domain comprising a first single-domain antibody (sdAb) specifically binding to a first antigen (such as a first tumor antigen) and a second single-domain antibody (sdAb) specifically binding to a second antigen (such as a second tumor antigen); (b) a transmembrane domain; and (c) an intracellular signaling domain, wherein the first antigen is different from the second antigen. In some embodiments, the first antigen and/or the second antigen is selected from the group consisting of CD19, CD20, CD22, CD33, CD38, BCMA, CS1, ROR1, GPC3, CD123, IL-13R, CD138, c-Met, EGFRvIII, GD-2, NY-ESO-1, MAGE A3, and glycolipid F77. In some embodiments, the first sdAb and/or the second sdAb is camelid, chimeric, human, or humanized. In some embodiments, the first single-domain antibody and the second single-domain antibody are fused to each other via a peptide bond or a peptide linker. In some embodiments, the peptide linker is no more than about 50 (such as no more than about any one of 35, 25, 20, 15, 10, or 5) amino acids long. In some embodiments, the transmembrane domain is selected from the group consisting of CD8α, CD4, CD28, CD137, CD80, CD86, CD152 and PD1. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the multispecific CAR further comprises a hinge domain (such as a CD8α hinge domain) located between the C-terminus of the extracellular antigen binding domain and the N-terminus of the transmembrane domain. In some embodiments, the multispecific CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD28 transmembrane domain, a first co-stimulatory signaling domain derived from CD28, a second co-stimulatory signaling domain derived from CD137, and a primary intracellular signaling domain derived from CD3ζ. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ. In some embodiments, the polypeptide comprises from the N-terminus to the C-terminus: a CD8α signal peptide, the extracellular antigen binding domain, a CD8α hinge domain, a CD28 transmembrane domain, a co-stimulatory signaling domain derived from CD28, and a primary intracellular signaling domain derived from CD3ζ. In some embodiments, the engineered immune effector cell is a T cell, an NK cell, a peripheral blood mononuclear cell (PBMC), a hematopoietic stem cell, a pluripotent stem cell, or an embryonic stem cell. In some embodiments, the engineered immune effector cell is autologous. In some embodiments, the engineered immune effector cell is allogenic.

In some embodiments, there is provided an engineered immune effector cell (such as T cell) comprising a BCMA×CD38 CAR comprising a polypeptide comprising: (a) an extracellular antigen binding domain comprising an anti-BCMA single-domain antibody and an anti-CD38 single-domain antibody; (b) a transmembrane domain; and (c) an intracellular signaling domain. In some embodiments, the anti-BCMA sdAb and/or the anti-CD38 sdAb is camelid, chimeric, human, or humanized. In some embodiments, the anti-BCMA single-domain antibody and the anti-CD38 single-domain antibody are fused to each other via a peptide bond or a peptide linker. In some embodiments, the anti-BCMA sdAb is fused at the N-terminus of the anti-CD38 sdAb. In some embodiments, the anti-BCMA sdAb is fused at the C-terminus of the anti-CD38 sdAb. In some embodiments, the peptide linker is no more than about 50 (such as no more than about any one of 35, 25, 20, 15, 10, or 5) amino acids long. In some embodiments, the peptide linker comprises an amino acid sequence selected from the group consisting of SEQ ID NOs: 144-151. In some embodiments, the transmembrane domain is selected from the group consisting of CD8α, CD4, CD28, CD137, CD80, CD86, CD152 and PD1. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the BCMA×CD38 CAR further comprises a hinge domain (such as a CD8α hinge domain) located between the C-terminus of the extracellular antigen binding domain and the N-terminus of the transmembrane domain. In some embodiments, the BCMA×CD38 CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8 hinge domain, a CD8α transmembrane domain, a co-stimulatory signaling domain derived from CD137, and a primary intracellular signaling domain derived from CD3ζ. In some embodiments, the anti-BCMA single-domain antibody comprises a CDR1 comprising the amino acid sequence of SEQ ID NO:7, a CDR2 comprising the amino acid sequence of SEQ ID NO:18, and a CDR3 comprising the amino acid sequence of SEQ ID NO:29. In some embodiments, the anti-CD38 antibody comprises a CDR1 comprising the amino acid sequence of SEQ ID NO:44, a CDR2 comprising the amino acid sequence of SEQ ID NO:56, and a CDR3 comprising the amino acid sequence of SEQ ID NO:68. In some embodiments, the BCMA×CD38 CAR comprises an amino acid sequence selected from the group consisting of SEQ ID NOs: 207-216. In some embodiments, the engineered immune effector cell is a T cell, an NK cell, a peripheral blood mononuclear cell (PBMC), a hematopoietic stem cell, a pluripotent stem cell, or an embryonic stem cell. In some embodiments, the engineered immune effector cell is autologous. In some embodiments, the engineered immune effector cell is allogenic.

In some embodiments, there is provided an engineered immune effector cell (such as T cell) comprising a CD19×CD20 CAR comprising a polypeptide comprising: (a) an extracellular antigen binding domain comprising an anti-CD19 single-domain antibody and an anti-CD20 single-domain antibody; (b) a transmembrane domain; and (c) an intracellular signaling domain. In some embodiments, the anti-CD19 sdAb and/or the anti-CD20 sdAb is camelid, chimeric, human, or humanized. In some embodiments, the anti-CD20 single-domain antibody and anti-CD20 single-domain antibody are fused to each other via a peptide bond or a peptide linker. In some embodiments, the anti-CD19 sdAb is fused at the N-terminus of the anti-CD20 sdAb. In some embodiments, the anti-CD19 sdAb is fused at the C-terminus of the anti-CD20 sdAb. In some embodiments, the peptide linker is no more than about 50 (such as no more than about any one of 35, 25, 20, 15, 10, or 5) amino acids long. In some embodiments, the peptide linker comprises an amino acid sequence selected from the group consisting of SEQ ID NOs: 144-151. In some embodiments, the transmembrane domain is selected from the group consisting of CD8α, CD4, CD28, CD137, CD80, CD86, CD152 and PD1. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the CD19×CD20 CAR further comprises a hinge domain (such as a CD8α hinge domain) located between the C-terminus of the extracellular antigen binding domain and the N-terminus of the transmembrane domain. In some embodiments, the CD19×CD20 CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD28 transmembrane domain, a co-stimulatory signaling domain derived from CD28, and a primary intracellular signaling domain derived from CD3ζ. In some embodiments, the anti-CD19 single-domain antibody comprises a CDR1 comprising the amino acid sequence of SEQ ID NO:1, a CDR2 comprising the amino acid sequence of SEQ ID NO:2, and a CDR3 comprising the amino acid sequence of SEQ ID NO:3. In some embodiments, the anti-CD20 antibody comprises a CDR1 comprising the amino acid sequence of SEQ ID NO:4, a CDR2 comprising the amino acid sequence of SEQ ID NO:5, and a CDR3 comprising the amino acid sequence of SEQ ID NO:6. In some embodiments, the CD19×CD20 CAR comprises the amino acid sequence of SEQ ID NO: 206. In some embodiments, the engineered immune effector cell is a T cell, an NK cell, a peripheral blood mononuclear cell (PBMC), a hematopoietic stem cell, a pluripotent stem cell, or an embryonic stem cell. In some embodiments, the engineered immune effector cell is autologous. In some embodiments, the engineered immune effector cell is allogenic.

In some embodiments, there is provided an engineered immune effector cell (such as T cell) comprising a CD19×CD22 CAR comprising a polypeptide comprising: (a) an extracellular antigen binding domain comprising an anti-CD19 single-domain antibody and an anti-CD22 single-domain antibody; (b) a transmembrane domain; and (c) an intracellular signaling domain. In some embodiments, the anti-CD19 sdAb and/or the anti-CD22 sdAb is camelid, chimeric, human, or humanized. In some embodiments, the anti-CD22 single-domain antibody and anti-CD22 single-domain antibody are fused to each other via a peptide bond or a peptide linker. In some embodiments, the anti-CD19 sdAb is fused at the N-terminus of the anti-CD22 sdAb. In some embodiments, the anti-CD19 sdAb is fused at the C-terminus of the anti-CD22 sdAb. In some embodiments, the peptide linker is no more than about 50 (such as no more than about any one of 35, 25, 20, 15, 10, or 5) amino acids long. In some embodiments, the peptide linker comprises an amino acid sequence selected from the group consisting of SEQ ID NOs: 144-151. In some embodiments, the transmembrane domain is selected from the group consisting of CD8α, CD4, CD28, CD137, CD80, CD86, CD152 and PD1. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the CD19×CD22 CAR further comprises a hinge domain (such as a CD8α hinge domain) located between the C-terminus of the extracellular antigen binding domain and the N-terminus of the transmembrane domain. In some embodiments, the CD19×CD22 CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD28 transmembrane domain, a co-stimulatory signaling domain derived from CD28, and a primary intracellular signaling domain derived from CD3ζ. In some embodiments, the anti-CD19 single-domain antibody comprises a CDR1 comprising the amino acid sequence of SEQ ID NO:1, a CDR2 comprising the amino acid sequence of SEQ ID NO:2, and a CDR3 comprising the amino acid sequence of SEQ ID NO:3. In some embodiments, the engineered immune effector cell is a T cell, an NK cell, a peripheral blood mononuclear cell (PBMC), a hematopoietic stem cell, a pluripotent stem cell, or an embryonic stem cell. In some embodiments, the engineered immune effector cell is autologous. In some embodiments, the engineered immune effector cell is allogenic.

In some embodiments, there is provided an engineered immune effector cell (such as T cell) comprising a CD19×BCMA CAR comprising a polypeptide comprising: (a) an extracellular antigen binding domain comprising an anti-CD19 single-domain antibody and an anti-BCMA single-domain antibody; (b) a transmembrane domain; and (c) an intracellular signaling domain. In some embodiments, the anti-CD19 sdAb and/or the anti-BCMA sdAb is camelid, chimeric, human, or humanized. In some embodiments, the anti-BCMA single-domain antibody and anti-BCMA single-domain antibody are fused to each other via a peptide bond or a peptide linker. In some embodiments, the anti-CD19 sdAb is fused at the N-terminus of the anti-BCMA sdAb. In some embodiments, the anti-CD19 sdAb is fused at the C-terminus of the anti-BCMA sdAb. In some embodiments, the peptide linker is no more than about 50 (such as no more than about any one of 35, 25, 20, 15, 10, or 5) amino acids long. In some embodiments, the peptide linker comprises an amino acid sequence selected from the group consisting of SEQ ID NOs: 144-151. In some embodiments, the transmembrane domain is selected from the group consisting of CD8α, CD4, CD28, CD137, CD80, CD86, CD152 and PD1. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the CD19×BCMA CAR further comprises a hinge domain (such as a CD8α hinge domain) located between the C-terminus of the extracellular antigen binding domain and the N-terminus of the transmembrane domain. In some embodiments, the CD19×BCMA CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ. In some embodiments, the polypeptide comprises from the N-terminus to the C-terminus: a CD8α signal peptide, the extracellular antigen binding domain, a CD8α hinge domain, a CD28 transmembrane domain, a co-stimulatory signaling domain derived from CD28, and a primary intracellular signaling domain derived from CD3ζ. In some embodiments, the anti-CD19 single-domain antibody comprises a CDR1 comprising the amino acid sequence of SEQ ID NO: 1, a CDR2 comprising the amino acid sequence of SEQ ID NO:2, and a CDR3 comprising the amino acid sequence of SEQ ID NO:3. In some embodiments, the engineered immune effector cell is a T cell, an NK cell, a peripheral blood mononuclear cell (PBMC), a hematopoietic stem cell, a pluripotent stem cell, or an embryonic stem cell. In some embodiments, the engineered immune effector cell is autologous. In some embodiments, the engineered immune effector cell is allogenic.

In some embodiments, there is provided an engineered immune effector cell (such as T cell) comprising a multivalent chimeric antigen receptor comprising a polypeptide comprising: (a) an extracellular antigen binding domain comprising a plurality of single-domain antibodies (sdAbs) specifically binding to an antigen (such as a tumor antigen); (b) a transmembrane domain; and (c) an intracellular signaling domain. In some embodiments, the antigen is selected from the group consisting of CD19, CD20, CD22, CD33, CD38, BCMA, CS1, ROR1, GPC3, CD123, IL-13R, CD138, c-Met, EGFRvIII, GD-2, NY-ESO-1, MAGE A3, and glycolipid F77. In some embodiments, the plurality of sdAbs is camelid, chimeric, human, or humanized. In some embodiments, the plurality of single-domain antibodies is fused to each other via peptide bonds or peptide linkers. In some embodiments, each peptide linker is no more than about 50 (such as no more than about any one of 35, 25, 20, 15, 10, or 5) amino acids long. In some embodiments, the transmembrane domain is selected from the group consisting of CD8α, CD4, CD28, CD137, CD80, CD86, CD152 and PD1. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the multivalent CAR further comprises a hinge domain (such as a CD8α hinge domain) located between the C-terminus of the extracellular antigen binding domain and the N-terminus of the transmembrane domain. In some embodiments, the multivalent CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ. In some embodiments, the multivalent CAR is monospecific. In some embodiments, the multivalent CAR is multispecific, such as bispecific. In some embodiments, the multivalent CAR comprises an amino acid sequence selected from the group consisting of SEQ ID NOs: 198-201.

In some embodiments, there is provided an engineered immune effector cell (such as T cell) comprising a multivalent chimeric antigen receptor comprising a polypeptide comprising: (a) an extracellular antigen binding domain comprising a first single-domain antibody specifically binding to a first epitope of an antigen (such as a tumor antigen), and a second single-domain antibody specifically binding to a second epitope of the antigen; (b) a transmembrane domain; and (c) an intracellular signaling domain, wherein the first epitope and the second epitope are different. In some embodiments, the antigen is selected from the group consisting of CD19, CD20, CD22, CD33, CD38, BCMA, CS1, ROR1, GPC3, CD123, IL-13R, CD138, c-Met, EGFRvIII, GD-2, NY-ESO-1, MAGE A3, and glycolipid F77. In some embodiments, the first sdAb and/or the second sdAb is camelid, chimeric, human, or humanized. In some embodiments, the first single-domain antibody and the second single-domain antibody are fused to each other via a peptide bond or a peptide linker. In some embodiments, the peptide linker is no more than about 50 (such as no more than about any one of 35, 25, 20, 15, 10, or 5) amino acids long. In some embodiments, the transmembrane domain is selected from the group consisting of CD8α, CD4, CD28, CD137, CD80, CD86, CD152 and PD1. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the multivalent CAR further comprises a hinge domain (such as a CD8α hinge domain) located between the C-terminus of the extracellular antigen binding domain and the N-terminus of the transmembrane domain. In some embodiments, the multivalent CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ. In some embodiments, the engineered immune effector cell is a T cell, an NK cell, a peripheral blood mononuclear cell (PBMC), a hematopoietic stem cell, a pluripotent stem cell, or an embryonic stem cell. In some embodiments, the engineered immune effector cell is autologous. In some embodiments, the engineered immune effector cell is allogenic.

In some embodiments, there is provided an engineered immune effector cell (such as T cell) comprising a CD19 chimeric antigen receptor comprising a polypeptide comprising: (a) an extracellular antigen binding domain comprising an anti-CD19 sdAb; (b) a transmembrane domain; and (c) an intracellular signaling domain, wherein the anti-CD19 sdAb comprises the amino acid sequence of SEQ ID NO:1, a CDR2 comprising the amino acid sequence of SEQ ID NO:2, and a CDR3 comprising the amino acid sequence of SEQ ID NO:3. In some embodiments, the anti-CD19 sdAb is camelid, chimeric, human, or humanized. In some embodiments, the anti-CD19 sdAb comprises a $V_H H$ domain comprising the amino acid sequence of SEQ ID NO: 76. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the CD19 CAR further comprises a hinge domain (such as a CD8α hinge domain) located between the C-terminus of the extracellular antigen binding domain and the N-terminus of the transmembrane domain. In some embodiments, the CD19 CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD28 transmembrane domain, a co-stimulatory signaling domain derived from CD28, and a primary intracellular signaling domain derived from CD3ζ. In some embodiments, the CD19 CAR comprises the amino acid sequence of SEQ ID NO: 248. In some embodiments, the engineered immune effector cell is a T cell, an NK cell, a peripheral blood mononuclear cell (PBMC), a hematopoietic stem cell, a pluripotent stem cell, or an embryonic stem cell. In some embodiments, the engineered immune effector cell is autologous. In some embodiments, the engineered immune effector cell is allogenic.

In some embodiments, there is provided an engineered immune effector cell (such as T cell) comprising a CD20 CAR comprising a polypeptide comprising: (a) an extracellular antigen binding domain comprising an anti-CD20 sdAb; (b) a transmembrane domain; and (c) an intracellular signaling domain, wherein the anti-CD20 sdAb comprises the amino acid sequence of SEQ ID NO:4, a CDR2 comprising the amino acid sequence of SEQ ID NO:5, and a CDR3 comprising the amino acid sequence of SEQ ID NO:6. In some embodiments, the anti-CD20 sdAb is camelid, chimeric, human, or humanized. In some embodiments, the anti-CD20 sdAb further comprises an FR1 comprising the amino acid sequence of SEQ ID NO: 244, an FR2 comprising the amino acid sequence of SEQ ID NO: 245, an FR3 comprising the amino acid sequence of SEQ ID NO: 246, and/or an FR4 comprising the amino acid sequence of SEQ ID NO: 247. In some embodiments, the anti-CD20 sdAb comprises a $V_HH$ domain comprising the amino acid sequence of SEQ ID NO: 77. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the CD20 CAR further comprises a hinge domain (such as a CD8α hinge domain) located between the C-terminus of the extracellular antigen binding domain and the N-terminus of the transmembrane domain. In some embodiments, the CD20 CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD28 transmembrane domain, a co-stimulatory signaling domain derived from CD28, and a primary intracellular signaling domain derived from CD3ζ. In some embodiments, the CD20 CAR comprises the amino acid sequence of SEQ ID NO: 249. In some embodiments, the engineered immune effector cell is a T cell, an NK cell, a peripheral blood mononuclear cell (PBMC), a hematopoietic stem cell, a pluripotent stem cell, or an embryonic stem cell. In some embodiments, the engineered immune effector cell is autologous. In some embodiments, the engineered immune effector cell is allogenic.

In some embodiments, there is provided an engineered immune effector cell (such as T cell) comprising a BCMA CAR comprising a polypeptide comprising: (a) an extracellular antigen binding domain comprising an anti-BCMA sdAb; (b) a transmembrane domain; and (c) an intracellular signaling domain, wherein the anti-BCMA sdAb comprises any one of the following:

(12) a CDR1 comprising the amino acid sequence of SEQ ID NO:7; a CDR2 comprising the amino acid sequence of SEQ ID NO: 18; and a CDR3 comprising the amino acid sequence of SEQ ID NO:29;

(13) a CDR1 comprising the amino acid sequence of SEQ ID NO:8; a CDR2 comprising the amino acid sequence of SEQ ID NO: 19; and a CDR3 comprising the amino acid sequence of SEQ ID NO:30;

(14) a CDR1 comprising the amino acid sequence of SEQ ID NO:9; a CDR2 comprising the amino acid sequence of SEQ ID NO:20; and a CDR3 comprising the amino acid sequence of SEQ ID NO:31;

(15) a CDR1 comprising the amino acid sequence of SEQ ID NO: 10; a CDR2 comprising the amino acid sequence of SEQ ID NO:21; and a CDR3 comprising the amino acid sequence of SEQ ID NO:32;

(16) a CDR1 comprising the amino acid sequence of SEQ ID NO: 11; a CDR2 comprising the amino acid sequence of SEQ ID NO:22; and a CDR3 comprising the amino acid sequence of SEQ ID NO:33;

(17) a CDR1 comprising the amino acid sequence of SEQ ID NO: 12; a CDR2 comprising the amino acid sequence of SEQ ID NO:23; and a CDR3 comprising the amino acid sequence of SEQ ID NO:34;

(18) a CDR1 comprising the amino acid sequence of SEQ ID NO: 13; a CDR2 comprising the amino acid sequence of SEQ ID NO:24; and a CDR3 comprising the amino acid sequence of SEQ ID NO:35;

(19) a CDR1 comprising the amino acid sequence of SEQ ID NO: 14; a CDR2 comprising the amino acid sequence of SEQ ID NO:25; and a CDR3 comprising the amino acid sequence of SEQ ID NO:36;

(20) a CDR1 comprising the amino acid sequence of SEQ ID NO: 15; a CDR2 comprising the amino acid sequence of SEQ ID NO:26; and a CDR3 comprising the amino acid sequence of SEQ ID NO:37;

(21) a CDR1 comprising the amino acid sequence of SEQ ID NO: 16; a CDR2 comprising the amino acid sequence of SEQ ID NO:27; and a CDR3 comprising the amino acid sequence of SEQ ID NO:38; or

(22) a CDR1 comprising the amino acid sequence of SEQ ID NO: 17; a CDR2 comprising the amino acid sequence of SEQ ID NO:28; and a CDR3 comprising the amino acid sequence of SEQ ID NO:39.

In some embodiments, the anti-BCMA sdAb is camelid, chimeric, human, or humanized. In some embodiments, the anti-BCMA sdAb comprises a $V_HH$ domain comprising an amino acid sequence from the group consisting of SEQ ID NO:78-88. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the BCMA CAR further comprises a hinge domain (such as a CD8α hinge domain) located between the C-terminus of the extracellular antigen binding domain and the N-terminus of the transmembrane domain. In some embodiments, the BCMA CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen-binding domain, a CD8α hinge domain, a CD28 transmembrane domain, a first co-stimulatory signaling domain derived from CD28, a second co-stimulatory signaling domain derived from CD137, and a primary intracellular signaling domain derived from CD3ζ. In some embodiments, the polypeptide comprises from the N-terminus to the C-terminus: a CD8α signal peptide, the extracellular antigen binding domain, a CD8 hinge domain, a CD8α transmembrane domain, a co-stimulatory signaling domain derived from CD137, and a primary intracellular signaling domain derived from CD3ζ. In some embodiments, the BCMA CAR comprises an amino acid sequence selected from the group consisting of SEQ ID NO: 152-162. In some embodiments, the engineered immune effector cell is a T cell, an NK cell, a peripheral blood mononuclear cell (PBMC), a hematopoietic stem cell, a pluripotent stem cell, or an embryonic stem cell. In some embodiments, the engineered immune effector cell is autologous. In some embodiments, the engineered immune effector cell is allogenic.

In some embodiments, there is provided an engineered immune effector cell (such as T cell) comprising a CD38 CAR comprising a polypeptide comprising: (a) an extracellular antigen binding domain comprising an anti-CD38 sdAb; (b) a transmembrane domain; and (c) an intracellular signaling domain, wherein the anti-BCMA sdAb comprises any one of the following:

(13) a CDR1 comprising the amino acid sequence of SEQ ID NO:40; a CDR2 comprising the amino acid sequence of SEQ ID NO: 52; and a CDR3 comprising the amino acid sequence of SEQ ID NO:64;
(14) a CDR1 comprising the amino acid sequence of SEQ ID NO:41; a CDR2 comprising the amino acid sequence of SEQ ID NO:53; and a CDR3 comprising the amino acid sequence of SEQ ID NO:65;
(15) a CDR1 comprising the amino acid sequence of SEQ ID NO:42; a CDR2 comprising the amino acid sequence of SEQ ID NO:54; and a CDR3 comprising the amino acid sequence of SEQ ID NO:66;
(16) a CDR1 comprising the amino acid sequence of SEQ ID NO:43; a CDR2 comprising the amino acid sequence of SEQ ID NO:55; and a CDR3 comprising the amino acid sequence of SEQ ID NO:67;
(17) a CDR1 comprising the amino acid sequence of SEQ ID NO:44; a CDR2 comprising the amino acid sequence of SEQ ID NO:56; and a CDR3 comprising the amino acid sequence of SEQ ID NO:68;
(18) a CDR1 comprising the amino acid sequence of SEQ ID NO:45; a CDR2 comprising the amino acid sequence of SEQ ID NO:57; and a CDR3 comprising the amino acid sequence of SEQ ID NO:69;
(19) a CDR1 comprising the amino acid sequence of SEQ ID NO:46; a CDR2 comprising the amino acid sequence of SEQ ID NO:58; and a CDR3 comprising the amino acid sequence of SEQ ID NO:70;
(20) a CDR1 comprising the amino acid sequence of SEQ ID NO:47; a CDR2 comprising the amino acid sequence of SEQ ID NO:59; and a CDR3 comprising the amino acid sequence of SEQ ID NO:71;
(21) a CDR1 comprising the amino acid sequence of SEQ ID NO:48; a CDR2 comprising the amino acid sequence of SEQ ID NO:60; and a CDR3 comprising the amino acid sequence of SEQ ID NO:72;
(22) a CDR1 comprising the amino acid sequence of SEQ ID NO:49; a CDR2 comprising the amino acid sequence of SEQ ID NO:61; and a CDR3 comprising the amino acid sequence of SEQ ID NO:73;
(23) a CDR1 comprising the amino acid sequence of SEQ ID NO:50; a CDR2 comprising the amino acid sequence of SEQ ID NO:62; and a CDR3 comprising the amino acid sequence of SEQ ID NO:74; or
(24) a CDR1 comprising the amino acid sequence of SEQ ID NO:51; a CDR2 comprising the amino acid sequence of SEQ ID NO:63; and a CDR3 comprising the amino acid sequence of SEQ ID NO:75.

In some embodiments, the anti-CD38 sdAb is camelid, chimeric, human, or humanized. In some embodiments, the anti-CD38 sdAb comprises a $V_H$H domain comprising an amino acid sequence from the group consisting of SEQ ID NO:89-100. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the CD38 CAR further comprises a hinge domain (such as a CD8α hinge domain) located between the C-terminus of the extracellular antigen binding domain and the N-terminus of the transmembrane domain. In some embodiments, the CD38 CAR further comprises a signal peptide (such as a CD8α signal peptide) located at the N-terminus of the polypeptide. In some embodiments, the polypeptide comprises from the N-terminus to the C-terminus: a CD8α signal peptide, the anti-CD38 sdAb, a CD8α hinge domain, a CD28 transmembrane domain, a first co-stimulatory signaling domain derived from CD28, a second co-stimulatory signaling domain derived from CD137, and a primary intracellular signaling domain derived from CD3ζ. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ. In some embodiments, there is provided a CD38 CAR comprising an amino acid sequence selected from the group consisting of SEQ ID NO: 163-174. In some embodiments, the engineered immune effector cell is a T cell, an NK cell, a peripheral blood mononuclear cell (PBMC), a hematopoietic stem cell, a pluripotent stem cell, or an embryonic stem cell. In some embodiments, the engineered immune effector cell is autologous. In some embodiments, the engineered immune effector cell is allogenic.

Figure 1E:
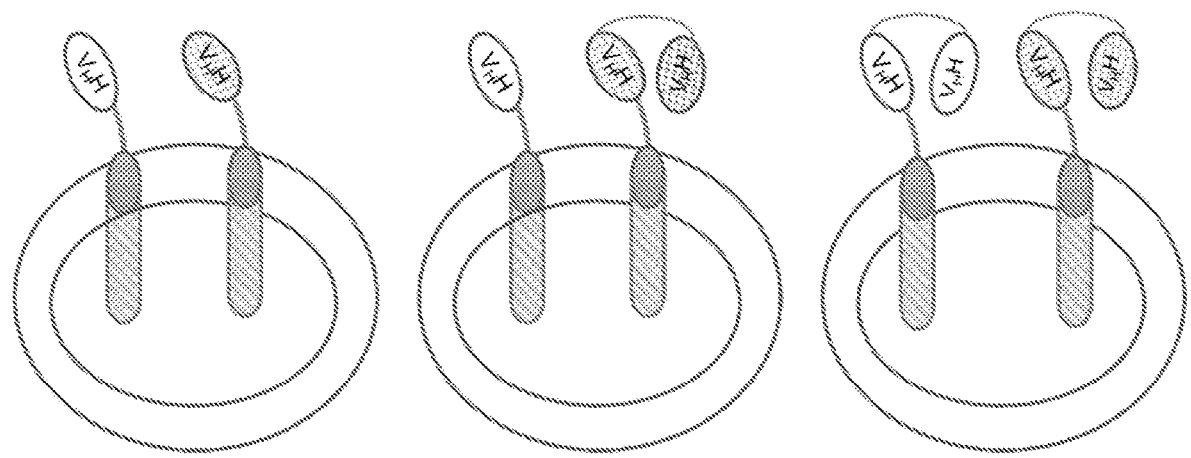
FIG. 1E shows exemplary engineered immune effector cells co-expressing two different $V_HH$-based CARs. The exemplary engineered immune effector cell in the left panel co-expresses two different monospecific, monovalent CARs. The exemplary engineered immune effector cell in the middle panel co-expresses a monospecific, monovalent CAR and a bispecific or bivalent CAR. The exemplary engineered immune effector cell in the right panel co-expresses two different bispecific or bivalent CARs. The CARs may recognize different antigens.

Also provided are engineered immune effector cells comprising (or expressing) two or more different CARs. Any two or more of the CARs described herein may be expressed in combination. The CARs may target different antigens, thereby providing synergistic or additive effects. As the single-domain antibodies in the extracellular antigen binding domains of the CARs have only single antigen variable chains (such as heavy chains), such CAR-expressing cells do not have variable chain mispairing problems, as seen in engineered immune effector cells co-expressing two or more scFv-based CARs. Exemplary engineered immune effector cells co-expressing two $V_HH$-based CARs are illustrated in FIG. 1E. One of skill in the art would recognize that CARs based on other sdAbs or having other structures as described herein may be co-expressed in the engineered immune effector cells as well. The two or more CARs may be encoded on the same vector or different vectors.

The engineered immune effector cell may further express one or more therapeutic proteins and/or immunomodulators, such as immune checkpoint inhibitors. See, for example, International Patent Application NOs. PCT/CN2016/073489 and PCT/CN2016/087855, which are incorporated herein by reference in their entirety.

Vectors

The present application provides vectors for cloning and expressing any one of the CARs described herein. In some embodiments, the vector is suitable for replication and integration in eukaryotic cells, such as mammalian cells. In some embodiments, the vector is a viral vector. Examples of viral vectors include, but are not limited to, adenoviral vectors, adeno-associated virus vectors, lentiviral vector, retroviral vectors, vaccinia vector, herpes simplex viral vector, and derivatives thereof. Viral vector technology is well known in the art and is described, for example, in Sambrook et al. (2001, Molecular Cloning: A Laboratory Manual, Cold Spring Harbor Laboratory, New York), and in other virology and molecular biology manuals.

A number of viral based systems have been developed for gene transfer into mammalian cells. For example, retroviruses provide a convenient platform for gene delivery systems. The heterologous nucleic acid can be inserted into a vector and packaged in retroviral particles using techniques known in the art. The recombinant virus can then be isolated and delivered to the engineered mammalian cell in vitro or ex vivo. A number of retroviral systems are known in the art. In some embodiments, adenovirus vectors are used. A number of adenovirus vectors are known in the art. In some embodiments, lentivirus vectors are used. In some embodiments, self-inactivating lentiviral vectors are used. For example, self-inactivating lentiviral vectors carrying the immunomodulator (such as immune checkpoint inhibitor) coding sequence and/or self-inactivating lentiviral vectors carrying chimeric antigen receptors can be packaged with protocols known in the art. The resulting lentiviral vectors can be used to transduce a mammalian cell (such as primary human T cells) using methods known in the art. Vectors derived from retroviruses such as lentivirus are suitable tools to achieve long-term gene transfer, because they allow long-term, stable integration of a transgene and its propagation in progeny cells. Lentiviral vectors also have low immunogenicity, and can transduce non-proliferating cells.

In some embodiments, the vector comprises any one of the nucleic acids encoding a CAR described herein. The nucleic acid can be cloned into the vector using any known molecular cloning methods in the art, including, for example, using restriction endonuclease sites and one or more selectable markers. In some embodiments, the nucleic acid is operably linked to a promoter. Varieties of promoters have been explored for gene expression in mammalian cells, and any of the promoters known in the art may be used in the present invention. Promoters may be roughly categorized as constitutive promoters or regulated promoters, such as inducible promoters.

In some embodiments, the nucleic acid encoding the CAR is operably linked to a constitutive promoter. Constitutive promoters allow heterologous genes (also referred to as transgenes) to be expressed constitutively in the host cells. Exemplary constitutive promoters contemplated herein include, but are not limited to, Cytomegalovirus (CMV) promoters, human elongation factors-1alpha (hEF1α), ubiquitin C promoter (UbiC), phosphoglycerokinase promoter (PGK), simian virus 40 early promoter (SV40), and chicken j-Actin promoter coupled with CMV early enhancer (CAGG). The efficiencies of such constitutive promoters on driving transgene expression have been widely compared in a huge number of studies. For example, Michael C. Milone et al compared the efficiencies of CMV, hEF1α, UbiC and PGK to drive chimeric antigen receptor expression in primary human T cells, and concluded that hEF1α promoter not only induced the highest level of transgene expression, but was also optimally maintained in the CD4 and CD8 human T cells (Molecular Therapy, 17(8): 1453-1464 (2009)). In some embodiments, the nucleic acid encoding the CAR is operably linked to a hEF1α promoter.

In some embodiments, the nucleic acid encoding the CAR is operably linked to an inducible promoter. Inducible promoters belong to the category of regulated promoters. The inducible promoter can be induced by one or more conditions, such as a physical condition, microenvironment of the engineered immune effector cell, or the physiological state of the engineered immune effector cell, an inducer (i.e., an inducing agent), or a combination thereof. In some embodiments, the inducing condition does not induce the expression of endogenous genes in the engineered mammalian cell, and/or in the subject that receives the pharmaceutical composition. In some embodiments, the inducing condition is selected from the group consisting of: inducer, irradiation (such as ionizing radiation, light), temperature (such as heat), redox state, tumor environment, and the activation state of the engineered mammalian cell.

In some embodiments, the vector also contains a selectable marker gene or a reporter gene to select cells expressing the CAR from the population of host cells transfected through lentiviral vectors. Both selectable markers and reporter genes may be flanked by appropriate regulatory sequences to enable expression in the host cells. For example, the vector may contain transcription and translation terminators, initiation sequences, and promoters useful for regulation of the expression of the nucleic acid sequences.

In some embodiments, the vector comprises more than one nucleic acid encoding CARs. In some embodiments, the vector comprises a nucleic acid comprising a first nucleic acid sequence encoding a first CAR and a second nucleic acid sequence encoding a second CAR, wherein the first nucleic acid is operably linked to the second nucleic acid via a third nucleic acid sequence encoding a self-cleaving peptide. In some embodiments, the self-cleaving peptide is selected from the group consisting of T2A, P2A and F2A. In some embodiments, the T2A peptide has an amino acid sequence of SEQ ID NO: 254. In some embodiments, the T2A peptide is encoded by the nucleic acid sequence of SEQ ID NO: 255. In some embodiments, there is provided an isolated nucleic acid encoding a BCMA CAR and a CD38 CAR, comprising the nucleic acid sequence of SEQ ID NO: 239.

Immune Effector Cells

"Immune effector cells" are immune cells that can perform immune effector functions. In some embodiments, the immune effector cells express at least FcγRIII and perform ADCC effector function. Examples of immune effector cells which mediate ADCC include peripheral blood mononuclear cells (PBMC), natural killer (NK) cells, monocytes, cytotoxic T cells, neutrophils, and eosinophils.

In some embodiments, the immune effector cells are T cells. In some embodiments, the T cells are CD4+/CD8−, CD4−/CD8+, CD4+/CD8+, CD4−/CD8−, or combinations thereof. In some embodiments, the T cells produce IL-2, TFN, and/or TNF upon expressing the CAR and binding to the target cells, such as CD20+ or CD19+ tumor cells. In some embodiments, the CD8+ T cells lyse antigen-specific target cells upon expressing the CAR and binding to the target cells.

In some embodiments, the immune effector cells are NK cells. In other embodiments, the immune effector cells can be established cell lines, for example, NK-92 cells.

In some embodiments, the immune effector cells are differentiated from a stem cell, such as a hematopoietic stem cell, a pluripotent stem cell, an iPS, or an embryonic stem cell.

The engineered immune effector cells are prepared by introducing the CARs into the immune effector cells, such as T cells. In some embodiments, the CAR is introduced to the immune effector cells by transfecting any one of the isolated nucleic acids or any one of the vectors described in Section III. In some embodiments, the CAR is introduced to the immune effector cells by inserting proteins into the cell membrane while passing cells through a microfluidic system, such as CELL SQUEEZE® (see, for example, U.S. Patent Application Publication No. 20140287509).

Methods of introducing vectors or isolated nucleic acids into a mammalian cell are known in the art. The vectors described can be transferred into an immune effector cell by physical, chemical, or biological methods.

Physical methods for introducing the vector into an immune effector cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001) Molecular Cloning: A Laboratory Manual, Cold Spring Harbor Laboratory, New York. In some embodiments, the vector is introduced into the cell by electroporation.

Biological methods for introducing the vector into an immune effector cell include the use of DNA and RNA vectors. Viral vectors have become the most widely used method for inserting genes into mammalian, e.g., human cells.

Chemical means for introducing the vector into an immune effector cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro is a liposome (e.g., an artificial membrane vesicle).

In some embodiments, RNA molecules encoding any of the CARs described herein may be prepared by a conventional method (e.g., in vitro transcription) and then introduced into the immune effector cells via known methods such as mRNA electroporation. See, e.g., Rabinovich et al., Human Gene Therapy 17:1027-1035.

In some embodiments, the transduced or transfected immune effector cell is propagated ex vivo after introduction of the vector or isolated nucleic acid. In some embodiments, the transduced or transfected immune effector cell is cultured to propagate for at least about any of 1 day, 2 days, 3 days, 4 days, 5 days, 6 days, 7 days, 10 days, 12 days, or 14 days. In some embodiments, the transduced or transfected immune effector cell is further evaluated or screened to select the engineered mammalian cell.

Reporter genes may be used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al. FEBS Letters 479: 79-82 (2000)). Suitable expression systems are well known and may be prepared using known techniques or obtained commercially.

Other methods to confirm the presence of the nucleic acid encoding the CARs in the engineered immune effector cell, include, for example, molecular biological assays well known to those of skill in the art, such as Southern and Northern blotting, RT-PCR and PCR; biochemical assays, such as detecting the presence or absence of a particular peptide, e.g., by immunological methods (such as ELISAs and Western blots).

1. Sources of T Cells

Prior to expansion and genetic modification of the T cells, a source of T cells is obtained from an individual. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In some embodiments, any number of T cell lines available in the art, may be used. In some embodiments, T cells can be obtained from a unit of blood collected from a subject using any number of techniques known to the skilled artisan, such as Ficoll™ separation. In some embodiments, cells from the circulating blood of an individual are obtained by apheresis. The apheresis product typically contains lymphocytes, including T cells, monocytes, granulocytes, B cells, other nucleated white blood cells, red blood cells, and platelets. In some embodiments, the cells collected by apheresis may be washed to remove the plasma fraction and to place the cells in an appropriate buffer or media for subsequent processing steps. In some embodiments, the cells are washed with phosphate buffered saline (PBS). In some embodiments, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the apheresis sample may be removed and the cells directly resuspended in culture media.

In some embodiments, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as CD3+, CD28+, CD4+, CD8+, CD45RA+, and CD45RO+ T cells, can be further isolated by positive or negative selection techniques. For example, in some embodiments, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In some embodiments, the time period is about 30 minutes. In a further embodiment, the time period ranges from 30 minutes to 36 hours or longer and all integer values there between. In a further embodiment, the time period is at least 1, 2, 3, 4, 5, or 6 hours. In some embodiments, the time period is 10 to 24 hours. In some embodiments, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3ζ and/or anti-CD28 antibodies on the beads or other surface, subpopulations of T cells can be preferentially selected for or against at culture initiation or at other desired time points. The skilled artisan would recognize that multiple rounds of selection can also be used. In some embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD1 lb, CD16, HLA-DR, and CD8. In certain embodiments, it may be desirable to enrich for or positively select for regulatory T cells which typically express CD4+, CD25+, CD62Lhi, GITR+, and FoxP3+. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of CD8+ T cells that normally have weaker CD28 expression.

In some embodiments, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In some embodiments, the concentration of cells used is $5 \times 10^6$/ml. In some embodiments, the concentration used can be from about $1 \times 10^5$/ml to $1 \times 10^6$/ml, and any integer value in between.

In some embodiments, the cells may be incubated on a rotator for varying lengths of time at varying speeds at either 2-10° C., or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1 per minute and stored in the vapor phase of a liquid nitrogen storage tank. Other methods of controlled freezing may be used as well as uncontrolled freezing immediately at −20° C. or in liquid nitrogen.

In some embodiments, cryopreserved cells are thawed and washed as described herein and allowed to rest for one hour at room temperature prior to activation.

Also contemplated in the present application is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3ζ antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun 73:316-321, 1991; Bierer et al., Curr. Opin. Immun. 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In some embodiments, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

2. Activation and Expansion of T Cells

Whether prior to or after genetic modification of the T cells with the CARs described herein, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, T cells can be expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3ζ antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3ζ antibody and an anti-CD28 antibody, under conditions appropriate for stimulating proliferation of the T cells. To stimulate proliferation of either CD4+ T cells or CD8+ T cells, an anti-CD3ζ antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In some embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In some embodiments, the T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3ζ and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In some embodiments, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-$\gamma$, IL-4, IL-7, GM-CSF, I-10, IL-12, IL-15, TGF$\beta$, and TNF-$\alpha$ or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, $\alpha$-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$). T cells that have been exposed to varied stimulation times may exhibit different characteristics. For example, typical blood or apheresed peripheral blood mononuclear cell products have a helper T cell population (TH, CD4+) that is greater than the cytotoxic or suppressor T cell population (TC, CD8). Ex vivo expansion of T cells by stimulating CD3$\zeta$ and CD28 receptors produces a population of T cells that prior to about days 8-9 consists predominately of TH cells, while after about days 8-9, the population of T cells comprises an increasingly greater population of TC cells. Accordingly, depending on the purpose of treatment, infusing a subject with a T cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

V. Pharmaceutical Compositions

Further provided by the present application are pharmaceutical compositions comprising any one of the single-domain antibodies (such as anti-CD19, anti-CD20, anti-BCMA, or anti-CD38 sdAbs), or any one of the engineered immune effector cells comprising any one of the CARs as described herein, and a pharmaceutically acceptable carrier. Pharmaceutical compositions can be prepared by mixing a single-domain antibody, or a plurality of engineered immune effector cells having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions.

Acceptable carriers, excipients, or stabilizers are nontoxic to recipients at the dosages and concentrations employed, and include buffers, antioxidants including ascorbic acid, methionine, Vitamin E, sodium metabisulfite; preservatives, isotonicifiers, stabilizers, metal complexes (e.g. Zn-protein complexes); chelating agents such as EDTA and/or nonionic surfactants.

Buffers are used to control the pH in a range which optimizes the therapeutic effectiveness, especially if stability is pH dependent. Buffers are preferably present at concentrations ranging from about 50 mM to about 250 mM. Suitable buffering agents for use with the present invention include both organic and inorganic acids and salts thereof. For example, citrate, phosphate, succinate, tartrate, fumarate, gluconate, oxalate, lactate, acetate. Additionally, buffers may comprise histidine and trimethylamine salts such as Tris.

Preservatives are added to retard microbial growth, and are typically present in a range from 0.2%-1.0% (w/v). Suitable preservatives for use with the present invention include octadecyldimethylbenzyl ammonium chloride; hexamethonium chloride; benzalkonium halides (e.g., chloride, bromide, iodide), benzethonium chloride; thimerosal, phenol, butyl or benzyl alcohol; alkyl parabens such as methyl or propyl paraben; catechol; resorcinol; cyclohexanol, 3-pentanol, and m-cresol.

Tonicity agents, sometimes known as "stabilizers" are present to adjust or maintain the tonicity of liquid in a composition. When used with large, charged biomolecules such as proteins and antibodies, they are often termed "stabilizers" because they can interact with the charged groups of the amino acid side chains, thereby lessening the potential for inter and intra-molecular interactions. Tonicity agents can be present in any amount between 0.1% to 25% by weight, preferably 1 to 5%, taking into account the relative amounts of the other ingredients. Preferred tonicity agents include polyhydric sugar alcohols, preferably trihydric or higher sugar alcohols, such as glycerin, erythritol, arabitol, xylitol, sorbitol and mannitol.

Additional excipients include agents which can serve as one or more of the following: (1) bulking agents, (2) solubility enhancers, (3) stabilizers and (4) and agents preventing denaturation or adherence to the container wall. Such excipients include: polyhydric sugar alcohols (enumerated above); amino acids such as alanine, glycine, glutamine, asparagine, histidine, arginine, lysine, ornithine, leucine, 2-phenylalanine, glutamic acid, threonine, etc.; organic sugars or sugar alcohols such as sucrose, lactose, lactitol, trehalose, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, $\alpha$-monothioglycerol and sodium thio sulfate; low molecular weight proteins such as human serum albumin, bovine serum albumin, gelatin or other immunoglobulins; hydrophilic polymers such as polyvinylpyrrolidone; monosaccharides (e.g., xylose, mannose, fructose, glucose; disaccharides (e.g., lactose, maltose, sucrose); trisaccharides such as raffinose; and polysaccharides such as dextrin or dextran.

Non-ionic surfactants or detergents (also known as "wetting agents") are present to help solubilize the therapeutic agent as well as to protect the therapeutic protein against agitation-induced aggregation, which also permits the formulation to be exposed to shear surface stress without causing denaturation of the active therapeutic protein or antibody. Non-ionic surfactants are present in a range of about 0.05 mg/ml to about 1.0 mg/ml, preferably about 0.07 mg/ml to about 0.2 mg/ml.

Suitable non-ionic surfactants include polysorbates (20, 40, 60, 65, 80, etc.), polyoxamers (184, 188, etc.), PLURONIC® polyols, TRITON®, polyoxyethylene sorbitan monoethers (TWEEN®-20, TWEEN®-80, etc.), lauromacrogol 400, polyoxyl 40 stearate, polyoxyethylene hydrogenated castor oil 10, 50 and 60, glycerol monostearate, sucrose fatty acid ester, methyl celluose and carboxymethyl cellulose. Anionic detergents that can be used include sodium lauryl sulfate, dioctyle sodium sulfosuccinate and dioctyl sodium sulfonate. Cationic detergents include benzalkonium chloride or benzethonium chloride.

In order for the pharmaceutical compositions to be used for in vivo administration, they must be sterile. The pharmaceutical composition may be rendered sterile by filtration through sterile filtration membranes. The pharmaceutical compositions herein generally are placed into a container having a sterile access port, for example, an intravenous solution bag or vial having a stopper pierceable by a hypodermic injection needle.

The route of administration is in accordance with known and accepted methods, such as by single or multiple bolus or infusion over a long period of time in a suitable manner, e.g., injection or infusion by subcutaneous, intravenous, intraperitoneal, intramuscular, intraarterial, intralesional or intraarticular routes, topical administration, inhalation or by sustained release or extended-release means.

Sustained-release preparations may be prepared. Suitable examples of sustained-release preparations include semipermeable matrices of solid hydrophobic polymers containing the antagonist, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and. ethyl-L-glutamate, non-degradable ethylene-vinyl acetate, degradable lactic acid-glycolic acid copolymers such as the LUPRON DEPOTr (injectable microspheres composed of lactic acid-glycolic acid copolymer and leuprolide acetate), and poly-D-(−)-3-hydroxybutyric acid.

The pharmaceutical compositions described herein may also contain more than one active compound or agent as necessary for the particular indication being treated, preferably those with complementary activities that do not adversely affect each other. Alternatively, or in addition, the composition may comprise a cytotoxic agent, chemotherapeutic agent, cytokine, immunosuppressive agent, or growth inhibitory agent. Such molecules are suitably present in combination in amounts that are effective for the purpose intended.

The active ingredients may also be entrapped in microcapsules prepared, for example, by coascervation techniques or by interfacial polymerization, for example, hydroxymethylcellulose or gelatin-microcapsules and poly-(methyl-methacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 18th edition.

VI. Methods of Treating Cancer

The present application further relates to methods and compositions for use in cell immunotherapy. In some embodiments, the cell immunotherapy is for treating cancer, including but not limited to hematological malignancies and solid tumors. Any of the single-domain antibodies, chimeric antigen receptors, and engineered immune effector cells described herein may be used in the method of treating cancer. The CARs described herein may be useful for treating tumors having antigen loss escape mutations, and for reducing resistance to existing therapies. In some embodiments, the methods and compositions described herein may be used for treating other diseases that are associated with the antigens specifically recognized by the single-domain antibodies or CARs, including, for example, autoimmune diseases.

In some embodiments, there is provided a method of treating a cancer in an individual (such as a human individual), comprising administering to the individual an effective amount of a pharmaceutical composition comprising: (1) an engineered immune effector cell (such as T cell) comprising a multispecific (such as bispecific) chimeric antigen receptor (CAR) comprising a polypeptide comprising: (a) an extracellular antigen binding domain comprising a first single-domain antibody (sdAb) specifically binding to a first antigen (such as a first tumor antigen) and a second single-domain antibody (sdAb) specifically binding to a second antigen (such as a second tumor antigen); (b) a transmembrane domain; and (c) an intracellular signaling domain, wherein the first antigen is different from the second antigen; and (2) a pharmaceutically acceptable carrier. In some embodiments, the first antigen and/or the second antigen is selected from the group consisting of CD19, CD20, CD22, CD33, CD38, BCMA, CS1, ROR1, GPC3, CD123, IL-13R, CD138, c-Met, EGFRvIII, GD-2, NY-ESO-1, MAGE A3, and glycolipid F77. In some embodiments, the first sdAb and/or the second sdAb is camelid, chimeric, human, or humanized. In some embodiments, the first single-domain antibody and the second single-domain antibody are fused to each other via a peptide bond or a peptide linker. In some embodiments, the peptide linker is no more than about 50 (such as no more than about any one of 35, 25, 20, 15, 10, or 5) amino acids long. In some embodiments, the transmembrane domain is selected from the group consisting of CD8α, CD4, CD28, CD137, CD80, CD86, CD152 and PD1. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the multispecific CAR further comprises a hinge domain (such as a CD8α hinge domain) located between the C-terminus of the extracellular antigen binding domain and the N-terminus of the transmembrane domain. In some embodiments, the multispecific CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD28 transmembrane domain, a first co-stimulatory signaling domain derived from CD28, a second co-stimulatory signaling domain derived from CD137, and a primary intracellular signaling domain derived from CD3ζ. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ. In some embodiments, the polypeptide comprises from the N-terminus to the C-terminus: a CD8α signal peptide, the extracellular antigen binding domain, a CD8α hinge domain, a CD28 transmembrane domain, a co-stimulatory signaling domain derived from CD28, and a primary intracellular signaling domain derived from CD3ζ. In some embodiments, the engineered immune effector cell is autologous. In some embodiments, the engineered immune effector cell is allogenic. In some embodiments, the cancer is a liquid cancer, such as multiple myeloma, acute lymphoblastic leukemia, or chronic lymphocytic leukemia. In some embodiments, the cancer is a solid cancer.

In some embodiments, there is provided a method of treating a cancer in an individual (such as a human individual), comprising administering to the individual an effective amount of a pharmaceutical composition comprising: (1) an engineered immune effector cell (such as T cell) comprising a BCMA×CD38 CAR comprising a polypeptide comprising: (a) an extracellular antigen binding domain comprising an anti-BCMA single-domain antibody and an anti-CD38 single-domain antibody; (b) a transmembrane domain; and (c) an intracellular signaling domain; and (2) a pharmaceutically acceptable carrier. In some embodiments, the anti-BCMA sdAb and/or the anti-CD38 sdAb is camelid, chimeric, human, or humanized. In some embodiments, the anti-BCMA single-domain antibody and the anti-CD38 single-domain antibody are fused to each other via a peptide bond or a peptide linker. In some embodiments, the anti-BCMA sdAb is fused at the N-terminus of the anti-CD38 sdAb. In some embodiments, the anti-BCMA sdAb is fused at the C-terminus of the anti-CD38 sdAb. In some embodiments, the peptide linker is no more than about 50 (such as no more than about any one of 35, 25, 20, 15, 10, or 5) amino acids long. In some embodiments, the peptide linker comprises an amino acid sequence selected from the group consisting of SEQ ID NOs: 144-151. In some embodiments, the transmembrane domain is selected from the group consisting of CD8α, CD4, CD28, CD137, CD80, CD86, CD152 and PD1. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the BCMA×CD38 CAR further comprises a hinge domain (such as a CD8α hinge domain) located between the C-terminus of the extracellular antigen binding domain and the N-terminus of the transmembrane domain. In some embodiments, the BCMA×CD38 CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ. In some embodiments, the anti-BCMA single-domain antibody comprises a CDR1 comprising the amino acid sequence of SEQ ID NO:7, a CDR2 comprising the amino acid sequence of SEQ ID NO:18, and a CDR3 comprising the amino acid sequence of SEQ ID NO:29. In some embodiments, the anti-CD38 antibody comprises a CDR1 comprising the amino acid sequence of SEQ ID NO:44, a CDR2 comprising the amino acid sequence of SEQ ID NO: 56, and a CDR3 comprising the amino acid sequence of SEQ ID NO:68. In some embodiments, the BCMA×CD38 CAR comprises an amino acid sequence selected from the group consisting of SEQ ID NOs: 207-216. In some embodiments, the engineered immune effector cell is autologous. In some embodiments, the engineered immune effector cell is allogenic. In some embodiments, the cancer is a liquid cancer. In some embodiments, the liquid cancer is multiple myeloma.

In some embodiments, there is provided a method of treating a cancer in an individual (such as a human individual), comprising administering to the individual an effective amount of a pharmaceutical composition comprising: (1) a CD19×CD20 CAR comprising a polypeptide comprising: (a) an extracellular antigen binding domain comprising an anti-CD19 single-domain antibody and an anti-CD20 single-domain antibody; (b) a transmembrane domain; and (c) an intracellular signaling domain; and (2) a pharmaceutically acceptable carrier. In some embodiments, the anti-CD19 sdAb and/or the anti-CD20 sdAb is camelid, chimeric, human, or humanized. In some embodiments, the anti-CD20 single-domain antibody and anti-CD20 single-domain antibody are fused to each other via a peptide bond or a peptide linker. In some embodiments, the anti-CD19 sdAb is fused at the N-terminus of the anti-CD20 sdAb. In some embodiments, the anti-CD19 sdAb is fused at the C-terminus of the anti-CD20 sdAb. In some embodiments, the peptide linker is no more than about 50 (such as no more than about any one of 35, 25, 20, 15, 10, or 5) amino acids long. In some embodiments, the peptide linker comprises an amino acid sequence selected from the group consisting of SEQ ID NOs: 144-151. In some embodiments, the transmembrane domain is selected from the group consisting of CD8α, CD4, CD28, CD137, CD80, CD86, CD152 and PD1. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the CD19×CD20 CAR further comprises a hinge domain (such as a CD8α hinge domain) located between the C-terminus of the extracellular antigen binding domain and the N-terminus of the transmembrane domain.

In some embodiments, the CD19×CD20 CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD28 transmembrane domain, a co-stimulatory signaling domain derived from CD28, and a primary intracellular signaling domain derived from CD3ζ. In some embodiments, the anti-CD19 single-domain antibody comprises a CDR1 comprising the amino acid sequence of SEQ ID NO:1, a CDR2 comprising the amino acid sequence of SEQ ID NO:2, and a CDR3 comprising the amino acid sequence of SEQ ID NO:3. In some embodiments, the anti-CD20 antibody comprises a CDR1 comprising the amino acid sequence of SEQ ID NO:4, a CDR2 comprising the amino acid sequence of SEQ ID NO:5, and a CDR3 comprising the amino acid sequence of SEQ ID NO:6. In some embodiments, the CD19×CD20 CAR comprises the amino acid sequence of SEQ ID NO: 206. In some embodiments, the engineered immune effector cell is autologous. In some embodiments, the engineered immune effector cell is allogenic. In some embodiments, the cancer is a liquid cancer. In some embodiments, the liquid cancer is B-cell lymphoma.

In some embodiments, there is provided a method of treating a cancer in an individual (such as a human individual), comprising administering to the individual an effective amount of a pharmaceutical composition comprising: (1) an engineered immune effector cell (such as T cell) comprising a multivalent chimeric antigen receptor comprising a polypeptide comprising: (a) an extracellular antigen binding domain comprising a plurality of single-domain antibodies (sdAbs) specifically binding to an antigen (such as a tumor antigen); (b) a transmembrane domain; and (c) an intracellular signaling domain; and (2) a pharmaceutically acceptable carrier. In some embodiments, the antigen is selected from the group consisting of CD19, CD20, CD22, CD33, CD38, BCMA, CS1, ROR1, GPC3, CD123, IL-13R, CD138, c-Met, EGFRvIII, GD-2, NY-ESO-1, MAGE A3, and glycolipid F77. In some embodiments, the plurality of sdAbs is camelid, chimeric, human, or humanized. In some embodiments, the plurality of single-domain antibodies is fused to each other via peptide bonds or peptide linkers. In some embodiments, each peptide linker is no more than about 50 (such as no more than about any one of 35, 25, 20, 15, 10, or 5) amino acids long. In some embodiments, the transmembrane domain is selected from the group consisting of CD8α, CD4, CD28, CD137, CD80, CD86, CD152 and PD1. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the multivalent CAR further comprises a hinge domain (such as a CD8α hinge domain) located between the C-terminus of the extracellular antigen binding domain and the N-terminus of the transmembrane domain. In some embodiments, the multivalent CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ. In some embodiments, the multivalent CAR comprises an amino acid sequence selected from the group consisting of SEQ ID NOs: 198-201, and 265-270. In some embodiments, the engineered immune effector cell is autologous. In some embodiments, the engineered immune effector cell is allogenic. In some embodiments, the cancer is a liquid cancer, such as multiple myeloma, acute lymphoblastic leukemia, or chronic lymphocytic leukemia. In some embodiments, the cancer is a solid cancer.

In some embodiments, there is provided a method of treating a cancer in an individual (such as a human individual), comprising administering to the individual an effective amount of a pharmaceutical composition comprising: (1) an engineered immune effector cell (such as T cell) comprising a multivalent chimeric antigen receptor comprising a polypeptide comprising: (a) an extracellular antigen binding domain comprising a first single-domain antibody specifically binding to a first epitope of an antigen (such as a tumor antigen), and a second single-domain antibody specifically binding to a second epitope of the antigen; (b) a transmembrane domain; and (c) an intracellular signaling domain, wherein the first epitope and the second epitope are different; and (2) a pharmaceutically acceptable carrier. In some embodiments, the antigen is selected from the group consisting of CD19, CD20, CD22, CD33, CD38, BCMA, CS1, ROR1, GPC3, CD123, IL-13R, CD138, c-Met, EGFRvIII, GD-2, NY-ESO-1, MAGE A3, and glycolipid F77. In some embodiments, the first sdAb and/or the second sdAb is camelid, chimeric, human, or humanized. In some embodiments, the first single-domain antibody and the second single-domain antibody are fused to each other via a peptide bond or a peptide linker. In some embodiments, the peptide linker is no more than about 50 (such as no more than about any one of 35, 25, 20, 15, 10, or 5) amino acids long. In some embodiments, the transmembrane domain is selected from the group consisting of CD8α, CD4, CD28, CD137, CD80, CD86, CD152 and PD1. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the multivalent CAR further comprises a hinge domain (such as a CD8α hinge domain) located between the C-terminus of the extracellular antigen binding domain and the N-terminus of the transmembrane domain. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ. In some embodiments, the engineered immune effector cell is autologous. In some embodiments, the engineered immune effector cell is allogenic. In some embodiments, the cancer is a liquid cancer, such as multiple myeloma, acute lymphoblastic leukemia, or chronic lymphocytic leukemia. In some embodiments, the cancer is a solid cancer.

In some embodiments, there is provided a method of treating a cancer in an individual (such as a human individual), comprising administering to the individual an effective amount of a pharmaceutical composition comprising: (1) an engineered immune effector cell (such as T cell) comprising a CD19 chimeric antigen receptor comprising a polypeptide comprising: (a) an extracellular antigen binding domain comprising an anti-CD19 sdAb; (b) a transmembrane domain; and (c) an intracellular signaling domain, wherein the anti-CD19 sdAb comprises the amino acid sequence of SEQ ID NO: 1, a CDR2 comprising the amino acid sequence of SEQ ID NO:2, and a CDR3 comprising the amino acid sequence of SEQ ID NO:3; and (2) a pharmaceutically acceptable carrier. In some embodiments, the anti-CD19 sdAb is camelid, chimeric, human, or humanized. In some embodiments, the anti-CD19 sdAb comprises a $V_H$H domain comprising the amino acid sequence of SEQ ID NO: 76. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the CD19 CAR further comprises a hinge domain (such as a CD8α hinge domain) located between the C-terminus of the extracellular antigen binding domain and the N-terminus of the transmembrane domain. In some embodiments, the CD19 CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD28 transmembrane domain, a first co-stimulatory signaling domain derived from CD28, a second co-stimulatory signaling domain derived from CD137, and a primary intracellular signaling domain derived from CD3ζ. In some embodiments, the CD19 CAR comprises the amino acid sequence of SEQ ID NO: 248. In some embodiments, the engineered immune effector cell is autologous. In some embodiments, the engineered immune effector cell is allogenic. In some embodiments, the cancer is a liquid cancer, such as multiple myeloma, acute lymphoblastic leukemia, or chronic lymphocytic leukemia. In some embodiments, the cancer is a solid cancer.

In some embodiments, there is provided a method of treating a cancer in an individual (such as a human individual), comprising administering to the individual an effective amount of a pharmaceutical composition comprising: (1) an engineered immune effector cell (such as T cell) comprising a CD20 CAR comprising a polypeptide comprising: (a) an extracellular antigen binding domain comprising an anti-CD20 sdAb; (b) a transmembrane domain; and (c) an intracellular signaling domain, wherein the anti-CD20 sdAb comprises the amino acid sequence of SEQ ID NO:4, a CDR2 comprising the amino acid sequence of SEQ ID NO:5, and a CDR3 comprising the amino acid sequence of SEQ ID NO:6; and (2) a pharmaceutically acceptable carrier. In some embodiments, the anti-CD20 sdAb is camelid, chimeric, human, or humanized. In some embodiments, the anti-CD20 sdAb further comprises an FR1 comprising the amino acid sequence of SEQ ID NO: 244, an FR2 comprising the amino acid sequence of SEQ ID NO: 245, an FR3 comprising the amino acid sequence of SEQ ID NO: 246, and/or an FR4 comprising the amino acid sequence of SEQ ID NO: 247. In some embodiments, the anti-CD20 sdAb comprises a $V_H$H domain comprising the amino acid sequence of SEQ ID NO: 77. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the CD20 CAR further comprises a hinge domain (such as a CD8α hinge domain) located between the C-terminus of the extracellular antigen binding domain and the N-terminus of the transmembrane domain. In some embodiments, the CD20 CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD28 transmembrane domain, a first co-stimulatory signaling domain derived from CD28, a second co-stimulatory signaling domain derived from CD137, and a primary intracellular signaling domain derived from CD3ζ. In some embodiments, the CD20 CAR comprises the amino acid sequence of SEQ ID NO: 249. In some embodiments, the CD20 CAR comprises the amino acid sequence of SEQ ID NO: 249. In some embodiments, the engineered immune effector cell is autologous. In some embodiments, the engineered immune effector cell is allogenic. In some embodiments, the cancer is a liquid cancer, such as multiple myeloma, acute lymphoblastic leukemia, or chronic lymphocytic leukemia. In some embodiments, the cancer is a solid cancer.

In some embodiments, there is provided a method of treating a cancer in an individual (such as a human individual), comprising administering to the individual an effective amount of a pharmaceutical composition comprising: (1) an engineered immune effector cell (such as T cell) comprising a BCMA CAR comprising a polypeptide comprising: (a) an extracellular antigen binding domain comprising an anti-BCMA sdAb; (b) a transmembrane domain; and (c) an intracellular signaling domain; and (2) a pharmaceutically acceptable carrier, wherein the anti-BCMA sdAb comprises any one of the following:

(23) a CDR1 comprising the amino acid sequence of SEQ ID NO:7; a CDR2 comprising the amino acid sequence of SEQ ID NO: 18; and a CDR3 comprising the amino acid sequence of SEQ ID NO:29;

(24) a CDR1 comprising the amino acid sequence of SEQ ID NO:8; a CDR2 comprising the amino acid sequence of SEQ ID NO: 19; and a CDR3 comprising the amino acid sequence of SEQ ID NO:30;

(25) a CDR1 comprising the amino acid sequence of SEQ ID NO:9; a CDR2 comprising the amino acid sequence of SEQ ID NO:20; and a CDR3 comprising the amino acid sequence of SEQ ID NO:31;

(26) a CDR1 comprising the amino acid sequence of SEQ ID NO: 10; a CDR2 comprising the amino acid sequence of SEQ ID NO:21; and a CDR3 comprising the amino acid sequence of SEQ ID NO:32;

(27) a CDR1 comprising the amino acid sequence of SEQ ID NO: 11; a CDR2 comprising the amino acid sequence of SEQ ID NO:22; and a CDR3 comprising the amino acid sequence of SEQ ID NO:33;

(28) a CDR1 comprising the amino acid sequence of SEQ ID NO: 12; a CDR2 comprising the amino acid sequence of SEQ ID NO:23; and a CDR3 comprising the amino acid sequence of SEQ ID NO:34;

(29) a CDR1 comprising the amino acid sequence of SEQ ID NO: 13; a CDR2 comprising the amino acid sequence of SEQ ID NO:24; and a CDR3 comprising the amino acid sequence of SEQ ID NO:35;

(30) a CDR1 comprising the amino acid sequence of SEQ ID NO: 14; a CDR2 comprising the amino acid sequence of SEQ ID NO:25; and a CDR3 comprising the amino acid sequence of SEQ ID NO:36;

(31) a CDR1 comprising the amino acid sequence of SEQ ID NO: 15; a CDR2 comprising the amino acid sequence of SEQ ID NO:26; and a CDR3 comprising the amino acid sequence of SEQ ID NO:37;

(32) a CDR1 comprising the amino acid sequence of SEQ ID NO: 16; a CDR2 comprising the amino acid sequence of SEQ ID NO:27; and a CDR3 comprising the amino acid sequence of SEQ ID NO:38; or

(33) a CDR1 comprising the amino acid sequence of SEQ ID NO: 17; a CDR2 comprising the amino acid sequence of SEQ ID NO:28; and a CDR3 comprising the amino acid sequence of SEQ ID NO:39.

In some embodiments, the anti-BCMA sdAb is camelid, chimeric, human, or humanized. In some embodiments, the anti-BCMA sdAb comprises a $V_HH$ domain comprising an amino acid sequence from the group consisting of SEQ ID NO:78-88. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the BCMA CAR further comprises a hinge domain (such as a CD8α hinge domain) located between the C-terminus of the extracellular antigen binding domain and the N-terminus of the transmembrane domain. In some embodiments, the BCMA CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD28 transmembrane domain, a first co-stimulatory signaling domain derived from CD28, a second co-stimulatory signaling domain derived from CD137, and a primary intracellular signaling domain derived from CD3ζ. In some embodiments, the polypeptide comprises from the N-terminus to the C-terminus: a CD8α signal peptide, the extracellular antigen-binding domain, a CD8α hinge domain, a CD8α transmembrane domain, a co-stimulatory signaling domain derived from CD137, and a primary intracellular signaling domain derived from CD3ζ. In some embodiments, the BCMA CAR comprises an amino acid sequence selected from the group consisting of SEQ ID NO: 152-162. In some embodiments, the engineered immune effector cell is autologous. In some embodiments, the engineered immune effector cell is allogenic. In some embodiments, the cancer is a liquid cancer, such as multiple myeloma, acute lymphoblastic leukemia, or chronic lymphocytic leukemia. In some embodiments, the cancer is a solid cancer.

In some embodiments, there is provided a method of treating a cancer in an individual (such as a human individual), comprising administering to the individual an effective amount of a pharmaceutical composition comprising: (1) an engineered immune effector cell (such as T cell) comprising a CD38 CAR comprising a polypeptide comprising: (a) an extracellular antigen binding domain comprising an anti-CD38 sdAb; (b) a transmembrane domain; and (c) an intracellular signaling domain; and (2) a pharmaceutically acceptable carrier, wherein the anti-BCMA sdAb comprises any one of the following:

(25) a CDR1 comprising the amino acid sequence of SEQ ID NO:40; a CDR2 comprising the amino acid sequence of SEQ ID NO: 52; and a CDR3 comprising the amino acid sequence of SEQ ID NO:64;

(26) a CDR1 comprising the amino acid sequence of SEQ ID NO:41; a CDR2 comprising the amino acid sequence of SEQ ID NO:53; and a CDR3 comprising the amino acid sequence of SEQ ID NO:65;

(27) a CDR1 comprising the amino acid sequence of SEQ ID NO:42; a CDR2 comprising the amino acid sequence of SEQ ID NO:54; and a CDR3 comprising the amino acid sequence of SEQ ID NO:66;

(28) a CDR1 comprising the amino acid sequence of SEQ ID NO:43; a CDR2 comprising the amino acid sequence of SEQ ID NO:55; and a CDR3 comprising the amino acid sequence of SEQ ID NO:67;

(29) a CDR1 comprising the amino acid sequence of SEQ ID NO:44; a CDR2 comprising the amino acid sequence of SEQ ID NO:56; and a CDR3 comprising the amino acid sequence of SEQ ID NO:68;

(30) a CDR1 comprising the amino acid sequence of SEQ ID NO:45; a CDR2 comprising the amino acid sequence of SEQ ID NO:57; and a CDR3 comprising the amino acid sequence of SEQ ID NO:69;

(31) a CDR1 comprising the amino acid sequence of SEQ ID NO:46; a CDR2 comprising the amino acid sequence of SEQ ID NO:58; and a CDR3 comprising the amino acid sequence of SEQ ID NO:70;

(32) a CDR1 comprising the amino acid sequence of SEQ ID NO:47; a CDR2 comprising the amino acid sequence of SEQ ID NO:59; and a CDR3 comprising the amino acid sequence of SEQ ID NO:71;

(33) a CDR1 comprising the amino acid sequence of SEQ ID NO:48; a CDR2 comprising the amino acid sequence of SEQ ID NO:60; and a CDR3 comprising the amino acid sequence of SEQ ID NO:72;

(34) a CDR1 comprising the amino acid sequence of SEQ ID NO:49; a CDR2 comprising the amino acid sequence of SEQ ID NO:61; and a CDR3 comprising the amino acid sequence of SEQ ID NO:73;

(35) a CDR1 comprising the amino acid sequence of SEQ ID NO:50; a CDR2 comprising the amino acid sequence of SEQ ID NO:62; and a CDR3 comprising the amino acid sequence of SEQ ID NO:74; or

(36) a CDR1 comprising the amino acid sequence of SEQ ID NO:51; a CDR2 comprising the amino acid sequence of SEQ ID NO:63; and a CDR3 comprising the amino acid sequence of SEQ ID NO:75.

In some embodiments, the anti-CD38 sdAb is camelid, chimeric, human, or humanized. In some embodiments, the anti-CD38 sdAb comprises a V$_H$H domain comprising an amino acid sequence from the group consisting of SEQ ID NO:89-100. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof. In some embodiments, the CD38 CAR further comprises a hinge domain (such as a CD8α hinge domain) located between the C-terminus of the extracellular antigen binding domain and the N-terminus of the transmembrane domain. In some embodiments, the CD38 CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD28 transmembrane domain, a first co-stimulatory signaling domain derived from CD28, a second co-stimulatory signaling domain derived from CD137, and a primary intracellular signaling domain derived from CD3ζ. In some embodiments, the polypeptide comprises from the N-terminus to the C-terminus: a CD8α signal peptide, the extracellular antigen-binding domain, a CD8α hinge domain, a CD8α transmembrane domain, a co-stimulatory signaling domain derived from CD137, and a primary intracellular signaling domain derived from CD3ζ. In some embodiments, the CD38 CAR comprises an amino acid sequence selected from the group consisting of SEQ ID NO: 163-174. In some embodiments, the engineered immune effector cell is autologous. In some embodiments, the engineered immune effector cell is allogenic. In some embodiments, the cancer is a liquid cancer, such as multiple myeloma, acute lymphoblastic leukemia, or chronic lymphocytic leukemia. In some embodiments, the cancer is a solid cancer.

In some embodiments, there is provided a method of treating a disease (such as cancer) in an individual (such as a human individual), comprising administering to the individual an effective amount of a pharmaceutical composition comprising an anti-CD19 single-domain antibody and a pharmaceutically acceptable carrier, wherein the anti-CD19 single-domain antibody comprising three CDRs comprising: (a) a CDR1 comprising the amino acid sequence of SEQ ID NO: 1; (b) a CDR2 comprising the amino acid sequence of SEQ ID NO: 2; and (c) a CDR3 comprising the amino acid sequence of SEQ ID NO: 3. In some embodiments, the anti-CD19 sdAb comprises the amino acid sequence of SEQ ID NO: 76.

In some embodiments, there is provided a method of treating a disease (such as cancer) in an individual (such as a human individual), comprising administering to the individual an effective amount of a pharmaceutical composition comprising an anti-CD19 single-domain antibody and a pharmaceutically acceptable carrier, wherein the anti-CD20 single-domain antibody comprising three CDRs comprising: (a) a CDR1 comprising the amino acid sequence of SEQ ID NO: 4; (b) a CDR2 comprising the amino acid sequence of SEQ ID NO: 5; and (c) a CDR3 comprising the amino acid sequence of SEQ ID NO: 6. In some embodiments, the anti-CD20 sdAb comprises the amino acid sequence of SEQ ID NO: 77.

In some embodiments, there is provided a method of treating a disease (such as cancer) in an individual (such as a human individual), comprising administering to the individual an effective amount of a pharmaceutical composition comprising an anti-BCMA single-domain antibody and a pharmaceutically acceptable carrier, wherein the anti-BCMA sdAb comprises any one of the following:
(1) a CDR1 comprising the amino acid sequence of SEQ ID NO:7; a CDR2 comprising the amino acid sequence of SEQ ID NO: 18; and a CDR3 comprising the amino acid sequence of SEQ ID NO:29;
(2) a CDR1 comprising the amino acid sequence of SEQ ID NO:8; a CDR2 comprising the amino acid sequence of SEQ ID NO: 19; and a CDR3 comprising the amino acid sequence of SEQ ID NO:30;
(3) a CDR1 comprising the amino acid sequence of SEQ ID NO:9; a CDR2 comprising the amino acid sequence of SEQ ID NO:20; and a CDR3 comprising the amino acid sequence of SEQ ID NO:31;
(4) a CDR1 comprising the amino acid sequence of SEQ ID NO:10; a CDR2 comprising the amino acid sequence of SEQ ID NO:21; and a CDR3 comprising the amino acid sequence of SEQ ID NO:32;
(5) a CDR1 comprising the amino acid sequence of SEQ ID NO: 11; a CDR2 comprising the amino acid sequence of SEQ ID NO:22; and a CDR3 comprising the amino acid sequence of SEQ ID NO:33;
(6) a CDR1 comprising the amino acid sequence of SEQ ID NO:12; a CDR2 comprising the amino acid sequence of SEQ ID NO:23; and a CDR3 comprising the amino acid sequence of SEQ ID NO:34;
(7) a CDR1 comprising the amino acid sequence of SEQ ID NO: 13; a CDR2 comprising the amino acid sequence of SEQ ID NO:24; and a CDR3 comprising the amino acid sequence of SEQ ID NO:35;
(8) a CDR1 comprising the amino acid sequence of SEQ ID NO:14; a CDR2 comprising the amino acid sequence of SEQ ID NO:25; and a CDR3 comprising the amino acid sequence of SEQ ID NO:36;
(9) a CDR1 comprising the amino acid sequence of SEQ ID NO:15; a CDR2 comprising the amino acid sequence of SEQ ID NO:26; and a CDR3 comprising the amino acid sequence of SEQ ID NO:37;
(10) a CDR1 comprising the amino acid sequence of SEQ ID NO: 16; a CDR2 comprising the amino acid sequence of SEQ ID NO:27; and a CDR3 comprising the amino acid sequence of SEQ ID NO:38; or
(11) a CDR1 comprising the amino acid sequence of SEQ ID NO: 17; a CDR2 comprising the amino acid sequence of SEQ ID NO:28; and a CDR3 comprising the amino acid sequence of SEQ ID NO:39.
In some embodiments, the anti-BCMA sdAb comprises an amino acid sequence selected from the group consisting of SEQ ID NOs: 78-88.

In some embodiments, there is provided a method of treating a disease (such as cancer) in an individual (such as a human individual), comprising administering to the individual an effective amount of a pharmaceutical composition comprising an anti-CD38 single-domain antibody and a pharmaceutically acceptable carrier, wherein the anti-CD38 sdAb comprises any one of the following: a CDR1 comprising the amino acid sequence of SEQ ID NO:40; a CDR2 comprising the amino acid sequence of SEQ ID NO:52; and a CDR3 comprising the amino acid sequence of SEQ ID NO:64;
(1) a CDR1 comprising the amino acid sequence of SEQ ID NO:41; a CDR2 comprising the amino acid sequence of SEQ ID NO:53; and a CDR3 comprising the amino acid sequence of SEQ ID NO:65;
(2) a CDR1 comprising the amino acid sequence of SEQ ID NO:42; a CDR2 comprising the amino acid sequence of SEQ ID NO:54; and a CDR3 comprising the amino acid sequence of SEQ ID NO:66;
(3) a CDR1 comprising the amino acid sequence of SEQ ID NO:43; a CDR2 comprising the amino acid sequence of SEQ ID NO:55; and a CDR3 comprising the amino acid sequence of SEQ ID NO:67;
(4) a CDR1 comprising the amino acid sequence of SEQ ID NO:44; a CDR2 comprising the amino acid sequence of SEQ ID NO:56; and a CDR3 comprising the amino acid sequence of SEQ ID NO:68;
(5) a CDR1 comprising the amino acid sequence of SEQ ID NO:45; a CDR2 comprising the amino acid sequence of SEQ ID NO:57; and a CDR3 comprising the amino acid sequence of SEQ ID NO:69;
(6) a CDR1 comprising the amino acid sequence of SEQ ID NO:46; a CDR2 comprising the amino acid sequence of SEQ ID NO:58; and a CDR3 comprising the amino acid sequence of SEQ ID NO:70;
(7) a CDR1 comprising the amino acid sequence of SEQ ID NO:47; a CDR2 comprising the amino acid sequence of SEQ ID NO:59; and a CDR3 comprising the amino acid sequence of SEQ ID NO:71;
(8) a CDR1 comprising the amino acid sequence of SEQ ID NO:48; a CDR2 comprising the amino acid sequence of SEQ ID NO:60; and a CDR3 comprising the amino acid sequence of SEQ ID NO:72;
(9) a CDR1 comprising the amino acid sequence of SEQ ID NO:49; a CDR2 comprising the amino acid sequence of SEQ ID NO:61; and a CDR3 comprising the amino acid sequence of SEQ ID NO:73;
(10) a CDR1 comprising the amino acid sequence of SEQ ID NO: 50; a CDR2 comprising the amino acid sequence of SEQ ID NO:62; and a CDR3 comprising the amino acid sequence of SEQ ID NO:74; or
(11) a CDR1 comprising the amino acid sequence of SEQ ID NO:51; a CDR2 comprising the amino acid sequence of SEQ ID NO:63; and a CDR3 comprising the amino acid sequence of SEQ ID NO:75.

In some embodiments, the anti-CD38 sdAb comprises an amino acid sequence selected from the group consisting of SEQ ID NOs: 89-100.

The methods described herein are suitable for treating various cancers, including both solid cancer and liquid cancer. The methods are applicable to cancers of all stages, including early stage, advanced stage and metastatic cancer. The methods described herein may be used as a first therapy, second therapy, third therapy, or combination therapy with other types of cancer therapies known in the art, such as chemotherapy, surgery, radiation, gene therapy, immunotherapy, bone marrow transplantation, stem cell transplantation, targeted therapy, cryotherapy, ultrasound therapy, photodynamic therapy, radio-frequency ablation or the like, in an adjuvant setting or a neoadjuvant setting.

Administration of the pharmaceutical compositions may be carried out in any convenient manner, including by injection, ingestion, transfusion, implantation or transplantation. The compositions may be administered to a patient transarterially, subcutaneously, intradermally, intratumorally, intranodally, intramedullary, intramuscularly, intravenously, or intraperitoneally. In some embodiments, the pharmaceutical composition is administered systemically. In some embodiments, the pharmaceutical composition is administered to an individual by infusion, such as intravenous infusion. Infusion techniques for immunotherapy are known in the art (see, e.g., Rosenberg et al., New Eng. J. of Med. 319: 1676 (1988)). In some embodiments, the pharmaceutical composition is administered to an individual by intradermal or subcutaneous injection. In some embodiments, the compositions are administered by intravenous injection. In some embodiments, the compositions are injected directly into a tumor, or a lymph node. In some embodiments, the pharmaceutical composition is administered locally to a site of tumor, such as directly into tumor cells, or to a tissue having tumor cells.

Multiple myelomia (MM) is an incurable aggressive plasma malignancy, which is categorized as a B-cell neoplasia and proliferates in uncontrollably method in the bone marrow, interfering with the normal metabolic production of blood cells and causing painful bone lesions (Garfall, A. L. et al., *Discovery Med.* 2014, 17, 37). Multiple myelomia can present clinically with hypercalcemia, renal insufficiency, anemia, bony lesions, bacterial infections, hyperviscosity, and amyloidosis (Robert Z Orlowski, *Cancer Cell.* 2013, 24(3)). According to investigation and statistics, nearly 86,000 patients will be diagnosed each year with myelomia, and while about 63,000 patients die every year from the disease-related complications (Becker, 2011). Because of an aging populace, it is predicted that the number of cases of myeloma will increase year by year. Like many cancers, there is no known cause of multiple myeloma, and no cure. Some treatments for multiple myeloma are similar to treatments for other cancers, such as chemotherapy or radiation therapy, stem cell transplant or bone marrow transplant, targeted therapy or biological therapy (George, 2014). Antibody-based cell immunotherapies have demonstrated substantial clinical benefit for patients with hematological malignancies, particular in B cell Non-Hodgkin's lymphoma. There is a need for effective immunotherapeutic agent for treating multiple myelomia.

Dosages and desired drug concentration of pharmaceutical compositions of the present invention may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles laid down by Mordenti, J. and Chappell, W. "The Use of Interspecies Scaling in Toxicokinetics," In *Toxicokinetics and New Drug Development*, Yacobi et al., Eds, Pergamon Press, New York 1989, pp. 42-46. It is within the scope of the present application that different formulations will be effective for different treatments and different disorders, and that administration intended to treat a specific organ or tissue may necessitate delivery in a manner different from that to another organ or tissue.

In some embodiments, wherein the pharmaceutical composition comprises any one of the single-domain antibodies described herein, the pharmaceutical composition is administered at a dosage of about 10 ng/kg up to about 100 mg/kg of body weight of the individual or more per day, for example, at about 1 mg/kg/day to 10 mg/kg/day, depending upon the route of administration. Guidance as to particular dosages and methods of delivery is provided in the literature; see, for example, U.S. Pat. No. 4,657,760; 5,206,344; or 5,225,212.

In some embodiments, wherein the pharmaceutical composition comprises any one of the engineered immune cells described herein, the pharmaceutical composition is administered at a dosage of at least about any of $10^4$, $10^5$, $10^6$, $10^7$, $10^8$, or $10^9$ cells/kg of body weight of the individual. In some embodiments, the pharmaceutical composition is administered at a dosage of any of about $10^4$ to about $10^5$, about $10^5$ to about $10^6$, about $10^6$ to about $10^7$, about $10^7$ to about $10^8$, about $10^8$ to about $10^9$, about $10^4$ to about $10^9$, about $10^4$ to about $10^6$, about $10^6$ to about $10^8$, or about $10^5$ to about $10^7$ cells/kg of body weight of the individual.

In some embodiments, the pharmaceutical composition is administered for a single time. In some embodiments, the pharmaceutical composition is administered for multiple times (such as any of 2, 3, 4, 5, 6, or more times). In some embodiments, the pharmaceutical composition is administered once per week, once 2 weeks, once 3 weeks, once 4 weeks, once per month, once per 2 months, once per 3 months, once per 4 months, once per 5 months, once per 6 months, once per 7 months, once per 8 months, once per 9 months, or once per year. In some embodiments, the interval between administrations is about any one of 1 week to 2 weeks, 2 weeks to 1 month, 2 weeks to 2 months, 1 month to 2 months, 1 month to 3 months, 3 months to 6 months, or 6 months to a year. The optimal dosage and treatment regime for a particular patient can readily be determined by one skilled in the art of medicine by monitoring the patient for signs of disease and adjusting the treatment accordingly.

Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

VII. Kits and Articles of Manufacture

Further provided are kits, unit dosages, and articles of manufacture comprising any of the single-domain antibodies, the chimeric antigen receptors, or the engineered immune effector cells described herein. In some embodiments, a kit is provided which contains any one of the pharmaceutical compositions described herein and preferably provides instructions for its use.

The kits of the present application are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The article of manufacture can comprise a container and a label or package insert on or associated with the container. Suitable containers include, for example, bottles, vials, syringes, etc. The containers may be formed from a variety of materials such as glass or plastic. Generally, the container holds a composition which is effective for treating a disease or disorder (such as cancer) described herein, and may have a sterile access port (for example the container may be an intravenous solution bag or a vial having a stopper pierceable by a hypodermic injection needle). The label or package insert indicates that the composition is used for treating the particular condition in an individual. The label or package insert will further comprise instructions for administering the composition to the individual. The label may indicate directions for reconstitution and/or use. The container holding the pharmaceutical composition may be a multi-use vial, which allows for repeat administrations (e.g. from 2-6 administrations) of the reconstituted formulation. Package insert refers to instructions customarily included in commercial packages of therapeutic products that contain information about the indications, usage, dosage, administration, contraindications and/or warnings concerning the use of such therapeutic products. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kits or article of manufacture may include multiple unit doses of the pharmaceutical composition and instructions for use, packaged in quantities sufficient for storage and use in pharmacies, for example, hospital pharmacies and compounding pharmacies.

The examples and exemplary embodiments below are intended to be purely exemplary of the invention and should therefore not be considered to limit the invention in any way. The following examples and detailed description are offered by way of illustration and not by way of limitation.

EXEMPLARY EMBODIMENTS

Embodiment 1

In some embodiments, there is provided a chimeric antigen receptor (CAR) comprising a polypeptide comprising: (a) an extracellular antigen binding domain comprising a first single-domain antibody (sdAb) specifically binding to a first antigen and a second single-domain antibody (sdAb) specifically binding to a second antigen; (b) a transmembrane domain; and (c) an intracellular signaling domain.

Embodiment 2

In some further embodiments of embodiment 1, the first antigen is different from the second antigen.

Embodiment 3

In some further embodiments of embodiment 2, the CAR is multispecific.

Embodiment 4

In some further embodiments of embodiment 3, the CAR is bispecific.

Embodiment 5

In some further embodiments of any one of embodiments 1-4, the first sdAb is located at the N-terminus of the second sdAb.

Embodiment 6

In some further embodiments of any one of embodiments 1-4, the first sdAb is located at the C-terminus of the second sdAb.

Embodiment 7

In some further embodiments of any one of embodiments 1-6, the first antigen and the second antigen are selected from the group consisting of CD19, CD20, CD22, CD33, CD38, BCMA, CS1, ROR1, GPC3, CD123, IL-13R, CD138, c-Met, EGFRvIII, GD-2, NY-ESO-1, MAGE A3, and glycolipid F77.

Embodiment 8

In some further embodiments of embodiment 7, the first sdAb is an anti-BCMA sdAb.

Embodiment 9

In some further embodiments of embodiment 7, the first sdAb is an anti-CD38 sdAb.

Embodiment 10

In some further embodiments of embodiment 7, the first sdAb is an anti-CD19 sdAb.

Embodiment 11

In some further embodiments of embodiment 7, the first sdAb is an anti-CD20 sdAb.

Embodiment 12

In some further embodiments of embodiment 7, the first sdAb is an anti-CD22 sdAb.

Embodiment 13

In some further embodiments of embodiment 8, the CAR comprises an extracellular antigen binding domain comprising at least two copies of an anti-BCMA sdAb.

Embodiment 14

In some further embodiments of embodiment 9, the CAR comprises an extracellular antigen binding domain comprising at least two copies of an anti-CD38 sdAb.

Embodiment 15

In some further embodiments of embodiment 8 or embodiment 9, the first sdAb is an anti-BCMA sdAb, and the second sdAb is an anti-CD38 sdAb.

Embodiment 16

In some further embodiments of embodiment 8 or embodiment 10, the first sdAb is an anti-BCMA sdAb, and the second sdAb is an anti-CD19 sdAb.

Embodiment 17

In some further embodiments of embodiment 10 or embodiment 11, the first sdAb is an anti-CD19 sdAb, and the second sdAb is an anti-CD20 sdAb.

Embodiment 18

In some further embodiments of embodiment 10 or embodiment 12, the first sdAb is an anti-CD19 sdAb, and the second sdAb is an anti-CD22 sdAb.

Embodiment 19

In some further embodiments of any one of embodiments 1-14, the first antigen is the same as the second antigen.

Embodiment 20

In some further embodiments of embodiment 19, the CAR is bivalent or trivalent.

Embodiment 21

In some further embodiments of embodiment 19 or embodiment 20, the first sdAb and the second sdAb specifically bind to the same epitope.

Embodiment 22

In some further embodiments of embodiment 21, the first sdAb is the same as the second sdAb.

Embodiment 23

In some further embodiments of embodiment 19 or embodiment 20, the first sdAb and the second sdAb specifically bind to different epitopes.

Embodiment 24

In some further embodiments of any one of embodiments 8, 13, 15, 16, and 19-23, the anti-BCMA comprises any one of the following:
(1) a CDR1 comprising the amino acid sequence of SEQ ID NO:7; a CDR2 comprising the amino acid sequence of SEQ ID NO: 18; and a CDR3 comprising the amino acid sequence of SEQ ID NO:29;
(2) a CDR1 comprising the amino acid sequence of SEQ ID NO:8; a CDR2 comprising the amino acid sequence of SEQ ID NO: 19; and a CDR3 comprising the amino acid sequence of SEQ ID NO:30;
(3) a CDR1 comprising the amino acid sequence of SEQ ID NO:9; a CDR2 comprising the amino acid sequence of SEQ ID NO:20; and a CDR3 comprising the amino acid sequence of SEQ ID NO:31;
(4) a CDR1 comprising the amino acid sequence of SEQ ID NO:10; a CDR2 comprising the amino acid sequence of SEQ ID NO:21; and a CDR3 comprising the amino acid sequence of SEQ ID NO:32;
(5) a CDR1 comprising the amino acid sequence of SEQ ID NO: 11; a CDR2 comprising the amino acid sequence of SEQ ID NO:22; and a CDR3 comprising the amino acid sequence of SEQ ID NO:33;
(6) a CDR1 comprising the amino acid sequence of SEQ ID NO:12; a CDR2 comprising the amino acid sequence of SEQ ID NO:23; and a CDR3 comprising the amino acid sequence of SEQ ID NO:34;
(7) a CDR1 comprising the amino acid sequence of SEQ ID NO:13; a CDR2 comprising the amino acid sequence of SEQ ID NO:24; and a CDR3 comprising the amino acid sequence of SEQ ID NO:35;
(8) a CDR1 comprising the amino acid sequence of SEQ ID NO: 14; a CDR2 comprising the amino acid sequence of SEQ ID NO:25; and a CDR3 comprising the amino acid sequence of SEQ ID NO:36;
(9) a CDR1 comprising the amino acid sequence of SEQ ID NO:15; a CDR2 comprising the amino acid sequence of SEQ ID NO:26; and a CDR3 comprising the amino acid sequence of SEQ ID NO:37;
(10) a CDR1 comprising the amino acid sequence of SEQ ID NO: 16; a CDR2 comprising the amino acid sequence of SEQ ID NO:27; and a CDR3 comprising the amino acid sequence of SEQ ID NO:38; or
(11) a CDR1 comprising the amino acid sequence of SEQ ID NO: 17; a CDR2 comprising the amino acid sequence of SEQ ID NO:28; and a CDR3 comprising the amino acid sequence of SEQ ID NO:39.

Embodiment 25

In some further embodiments of embodiment 24, the anti-BCMA sdAb comprises a $V_HH$ domain comprising an amino acid sequence selected from the group consisting of SEQ ID NO:78-88.

Embodiment 26

In some further embodiments of any one of embodiments 9, 14, 15, and 19-23, the anti-CD38 sdAb comprises any one of the following:
(1) a CDR1 comprising the amino acid sequence of SEQ ID NO:40; a CDR2 comprising the amino acid sequence of SEQ ID NO:52; and a CDR3 comprising the amino acid sequence of SEQ ID NO:64;
(2) a CDR1 comprising the amino acid sequence of SEQ ID NO:41; a CDR2 comprising the amino acid sequence of SEQ ID NO:53; and a CDR3 comprising the amino acid sequence of SEQ ID NO:65;
(3) a CDR1 comprising the amino acid sequence of SEQ ID NO:42; a CDR2 comprising the amino acid sequence of SEQ ID NO: 54; and a CDR3 comprising the amino acid sequence of SEQ ID NO:66;
(4) a CDR1 comprising the amino acid sequence of SEQ ID NO:43; a CDR2 comprising the amino acid sequence of SEQ ID NO:55; and a CDR3 comprising the amino acid sequence of SEQ ID NO:67;
(5) a CDR1 comprising the amino acid sequence of SEQ ID NO:44; a CDR2 comprising the amino acid sequence of SEQ ID NO: 56; and a CDR3 comprising the amino acid sequence of SEQ ID NO:68;
(6) a CDR1 comprising the amino acid sequence of SEQ ID NO:45; a CDR2 comprising the amino acid sequence of SEQ ID NO:57; and a CDR3 comprising the amino acid sequence of SEQ ID NO:69;
(7) a CDR1 comprising the amino acid sequence of SEQ ID NO:46; a CDR2 comprising the amino acid sequence of SEQ ID NO:58; and a CDR3 comprising the amino acid sequence of SEQ ID NO:70;
(8) a CDR1 comprising the amino acid sequence of SEQ ID NO:47; a CDR2 comprising the amino acid sequence of SEQ ID NO:59; and a CDR3 comprising the amino acid sequence of SEQ ID NO:71;
(9) a CDR1 comprising the amino acid sequence of SEQ ID NO:48; a CDR2 comprising the amino acid sequence of SEQ ID NO:60; and a CDR3 comprising the amino acid sequence of SEQ ID NO:72;
(10) a CDR1 comprising the amino acid sequence of SEQ ID NO:49; a CDR2 comprising the amino acid sequence of SEQ ID NO:61; and a CDR3 comprising the amino acid sequence of SEQ ID NO:73;
(11) a CDR1 comprising the amino acid sequence of SEQ ID NO: 50; a CDR2 comprising the amino acid sequence of SEQ ID NO:62; and a CDR3 comprising the amino acid sequence of SEQ ID NO:74; or
(12) a CDR1 comprising the amino acid sequence of SEQ ID NO:51; a CDR2 comprising the amino acid sequence of SEQ ID NO:63; and a CDR3 comprising the amino acid sequence of SEQ ID NO:75.

Embodiment 27

In some further embodiments of embodiment 26, the anti-CD38 sdAb comprises a $V_HH$ domain comprising an amino acid sequence selected from the group consisting of SEQ ID NO:89-100.

Embodiment 28

In some further embodiments of any one of embodiments 10 and 16-23, the anti-CD19 sdAb comprise a CDR1 comprising the amino acid sequence of SEQ ID NO:1, a CDR2 comprising the amino acid sequence of SEQ ID NO:2, and a CDR3 comprising the amino acid sequence of SEQ ID NO:3.

Embodiment 29

In some further embodiments of embodiment 28, the anti-CD19 sdAb comprises a $V_HH$ domain comprising the amino acid sequence of SEQ ID NO: 76.

Embodiment 30

In some further embodiments of any one of embodiments 11, 17 and 19-23, the anti-CD20 sdAb comprise a CDR1 comprising the amino acid sequence of SEQ ID NO:4, a CDR2 comprising the amino acid sequence of SEQ ID NO:5, and a CDR3 comprising the amino acid sequence of SEQ ID NO:6.

Embodiment 31

In some further embodiments of embodiment 30, the anti-CD20 sdAb comprises a $V_HH$ domain comprising the amino acid sequence of SEQ ID NO: 77.

Embodiment 32

In some further embodiments of any one of embodiments 1-31, the first sdAb and/or the second sdAb are camelid, chimeric, human, or humanized.

Embodiment 33

In some further embodiments of any one of embodiments 1-32, the first sdAb and the second sdAb are directly fused to each other via a peptide bond.

Embodiment 34

In some further embodiments of any one of embodiments 1-32, the first sdAb and the second sdAb are fused to each other via a peptide linker.

Embodiment 35

In some further embodiments of embodiment 34, the peptide linker is no more than about 50 amino acids long.

Embodiment 36

In some further embodiments of embodiment 35, the peptide linker comprises an amino acid sequence selected from SEQ ID Nos: 144-151.

Embodiment 37

In some embodiments, there is provided an anti-CD19 single-domain antibody (sdAb) comprising a CDR1 comprising the amino acid sequence of SEQ ID NO:1, a CDR2 comprising the amino acid sequence of SEQ ID NO:2, and a CDR3 comprising the amino acid sequence of SEQ ID NO:3.

Embodiment 38

In some further embodiments of embodiment 37, the anti-CD19 sdAb comprises a $V_HH$ domain comprising the amino acid sequence of SEQ ID NO: 76.

Embodiment 39

In some embodiments, there is provided a chimeric antigen receptor comprising: (a) an extracellular antigen binding domain comprising the anti-CD19 sdAb of embodiment 37 or embodiment 38; (b) a transmembrane domain; and (c) an intracellular signaling domain.

Embodiment 40

In some embodiments, there is provided an anti-CD20 single-domain antibody (sdAb) comprising a CDR1 comprising the amino acid sequence of SEQ ID NO:4, a CDR2 comprising the amino acid sequence of SEQ ID NO:5, and a CDR3 comprising the amino acid sequence of SEQ ID NO:6.

Embodiment 41

In some further embodiments of embodiment 40, the anti-CD20 sdAb comprises a $V_HH$ domain comprising the amino acid sequence of SEQ ID NO: 77.

Embodiment 42

In some embodiments, there is provided a chimeric antigen receptor comprising: (a) an extracellular antigen binding domain comprising the anti-CD20 sdAb of embodiment 40 or embodiment 41; (b) a transmembrane domain; and (c) an intracellular signaling domain.

Embodiment 43

In some embodiments, there is provided an anti-BCMA single-domain antibody (sdAb) comprising any one of the following:
(1) a CDR1 comprising the amino acid sequence of SEQ ID NO:7; a CDR2 comprising the amino acid sequence of SEQ ID NO: 18; and a CDR3 comprising the amino acid sequence of SEQ ID NO:29;
(2) a CDR1 comprising the amino acid sequence of SEQ ID NO:8; a CDR2 comprising the amino acid sequence of SEQ ID NO: 19; and a CDR3 comprising the amino acid sequence of SEQ ID NO:30;
(3) a CDR1 comprising the amino acid sequence of SEQ ID NO:9; a CDR2 comprising the amino acid sequence of SEQ ID NO:20; and a CDR3 comprising the amino acid sequence of SEQ ID NO:31;
(4) a CDR1 comprising the amino acid sequence of SEQ ID NO: 10; a CDR2 comprising the amino acid sequence of SEQ ID NO:21; and a CDR3 comprising the amino acid sequence of SEQ ID NO:32;
(5) a CDR1 comprising the amino acid sequence of SEQ ID NO: 11; a CDR2 comprising the amino acid sequence of SEQ ID NO:22; and a CDR3 comprising the amino acid sequence of SEQ ID NO:33;
(6) a CDR1 comprising the amino acid sequence of SEQ ID NO: 12; a CDR2 comprising the amino acid sequence of SEQ ID NO:23; and a CDR3 comprising the amino acid sequence of SEQ ID NO:34;
(7) a CDR1 comprising the amino acid sequence of SEQ ID NO: 13; a CDR2 comprising the amino acid sequence of SEQ ID NO:24; and a CDR3 comprising the amino acid sequence of SEQ ID NO:35;
(8) a CDR1 comprising the amino acid sequence of SEQ ID NO: 14; a CDR2 comprising the amino acid sequence of SEQ ID NO:25; and a CDR3 comprising the amino acid sequence of SEQ ID NO:36;
(9) a CDR1 comprising the amino acid sequence of SEQ ID NO: 15; a CDR2 comprising the amino acid sequence of SEQ ID NO:26; and a CDR3 comprising the amino acid sequence of SEQ ID NO:37;
(10) a CDR1 comprising the amino acid sequence of SEQ ID NO: 16; a CDR2 comprising the amino acid sequence of SEQ ID NO:27; and a CDR3 comprising the amino acid sequence of SEQ ID NO:38; or
(11) a CDR1 comprising the amino acid sequence of SEQ ID NO: 17; a CDR2 comprising the amino acid sequence of SEQ ID NO:28; and a CDR3 comprising the amino acid sequence of SEQ ID NO:39.

Embodiment 44

In some further embodiments of embodiment 43, the anti-BCMA sdAb comprises a $V_HH$ domain comprising an amino acid sequence selected from the group consisting of SEQ ID NO:78-88.

Embodiment 45

In some embodiments, there is provided a chimeric antigen receptor comprising: (a) an extracellular antigen binding domain comprising the anti-BCMA sdAb of embodiment 43 or embodiment 44; (b) a transmembrane domain; and (c) an intracellular signaling domain.

Embodiment 46

In some embodiments, there is provided an anti-CD38 single-domain antibody (sdAb) comprising a CDR comprising any one of the following:
(1) a CDR1 comprising the amino acid sequence of SEQ ID NO:40; a CDR2 comprising the amino acid sequence of SEQ ID NO:52; and a CDR3 comprising the amino acid sequence of SEQ ID NO:64;
(2) a CDR1 comprising the amino acid sequence of SEQ ID NO:41; a CDR2 comprising the amino acid sequence of SEQ ID NO:53; and a CDR3 comprising the amino acid sequence of SEQ ID NO:65;
(3) a CDR1 comprising the amino acid sequence of SEQ ID NO:42; a CDR2 comprising the amino acid sequence of SEQ ID NO:54; and a CDR3 comprising the amino acid sequence of SEQ ID NO:66;

(4) a CDR1 comprising the amino acid sequence of SEQ ID NO:43; a CDR2 comprising the amino acid sequence of SEQ ID NO:55; and a CDR3 comprising the amino acid sequence of SEQ ID NO:67;
(5) a CDR1 comprising the amino acid sequence of SEQ ID NO:44; a CDR2 comprising the amino acid sequence of SEQ ID NO:56; and a CDR3 comprising the amino acid sequence of SEQ ID NO:68;
(6) a CDR1 comprising the amino acid sequence of SEQ ID NO:45; a CDR2 comprising the amino acid sequence of SEQ ID NO:57; and a CDR3 comprising the amino acid sequence of SEQ ID NO:69;
(7) a CDR1 comprising the amino acid sequence of SEQ ID NO:46; a CDR2 comprising the amino acid sequence of SEQ ID NO:58; and a CDR3 comprising the amino acid sequence of SEQ ID NO:70;
(8) a CDR1 comprising the amino acid sequence of SEQ ID NO:47; a CDR2 comprising the amino acid sequence of SEQ ID NO:59; and a CDR3 comprising the amino acid sequence of SEQ ID NO:71;
(9) a CDR1 comprising the amino acid sequence of SEQ ID NO:48; a CDR2 comprising the amino acid sequence of SEQ ID NO:60; and a CDR3 comprising the amino acid sequence of SEQ ID NO:72;
(10) a CDR1 comprising the amino acid sequence of SEQ ID NO:49; a CDR2 comprising the amino acid sequence of SEQ ID NO:61; and a CDR3 comprising the amino acid sequence of SEQ ID NO:73;
(11) a CDR1 comprising the amino acid sequence of SEQ ID NO: 50; a CDR2 comprising the amino acid sequence of SEQ ID NO:62; and a CDR3 comprising the amino acid sequence of SEQ ID NO:74; or
(12) a CDR1 comprising the amino acid sequence of SEQ ID NO:51; a CDR2 comprising the amino acid sequence of SEQ ID NO:63; and a CDR3 comprising the amino acid sequence of SEQ ID NO:75.

Embodiment 47

In some further embodiments of embodiment 46, the anti-BCMA sdAb comprises a $V_HH$ domain comprising an amino acid sequence selected from the group consisting of SEQ ID NO:89-100.

Embodiment 48

In some embodiments, there is provided a chimeric antigen receptor comprising: (a) an extracellular antigen binding domain comprising the anti-CD38 sdAb of embodiment 46 or embodiment 47; (b) a transmembrane domain; and (c) an intracellular signaling domain.

Embodiment 49

In some further embodiments of any one of embodiments 1-36, 39, 42, 45, and 48, the transmembrane domain is derived from a molecule selected from the group consisting of CD8α, CD4, CD28, CD137, CD80, CD86, CD152 and PD1.

Embodiment 50

In some further embodiments of embodiment 49, the transmembrane domain is derived from CD8 or CD28.

Embodiment 51

In some further embodiments of embodiment 50, the transmembrane domain comprises the amino acid sequence of SEQ ID NO: 132 or SEQ ID NO: 133.

Embodiment 52

In some further embodiments of any one of embodiments 1-36, 39, 42, 45, and 48-51, the intracellular signaling domain comprises a primary intracellular signaling domain of an immune effector cell.

Embodiment 53

In some further embodiments of embodiment 52, the primary intracellular signaling domain is derived from CD3ζ.

Embodiment 54

In some further embodiments of embodiment 53, the intracellular signaling domain comprises the amino acid sequence of SEQ ID NO: 140 or SEQ ID NO: 141.

Embodiment 55

In some further embodiments of any one of embodiments 1-36, 39, 42, 45, and 48-54, the intracellular signaling domain comprises a co-stimulatory signaling domain.

Embodiment 56

In some further embodiments of embodiment 55, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof.

Embodiment 57

In some further embodiments of embodiment 56, the co-stimulatory signaling domain comprises a cytoplasmic domain of CD28 and/or a cytoplasmic domain of CD137.

Embodiment 58

In some further embodiments of embodiment 57, the co-stimulatory signaling domain comprises the amino acid sequence of SEQ ID NO: 136 and/or SEQ ID NO: 137.

Embodiment 59

In some further embodiments of any one of embodiments 1-36, 39, 42, 45, and 48-58, the CAR further comprises a hinge domain located between the C-terminus of the extracellular antigen binding domain and the N-terminus of the transmembrane domain.

Embodiment 60

In some further embodiments of embodiment 59, the hinge domain is derived from CD8α.

Embodiment 61

In some further embodiments of embodiment 60, the hinge domain comprises the amino acid sequence of SEQ ID NO: 130.

Embodiment 62

In some further embodiments of any one of embodiments 1-36, 39, 42, 45, and 48-61, the CAR further comprises a signal peptide located at the N-terminus of the polypeptide.

Embodiment 63

In some further embodiments of embodiment 62, the signal peptide is derived from a molecule selected from the group consisting of CD8α, GM-CSF receptor α, and IgG1 heavy chain.

Embodiment 64

In some further embodiments of embodiment 63, the signal peptide is derived from CD8α.

Embodiment 65

In some further embodiments of embodiment 64, the signal peptide comprises the amino acid sequence of SEQ ID NO: 127.

Embodiment 66

In some embodiments, there is provided a chimeric antigen receptor, comprising an amino acid sequence selected from the group consisting of SEQ ID NOs: 152-174, 198-201, 206-216, 248-249, 257-260, and 265-270.

Embodiment 67

In some embodiments, there is provided a polypeptide comprising an amino acid sequence selected from the group consisting of SEQ ID NOs: 76-100, 152-174, 198-201, 206-216, 248-249, 257-260, and 265-270.

Embodiment 68

In some embodiments, there is provided an isolated nucleic acid comprising a nucleic acid sequence encoding the CAR of any one of embodiments 1-36, 39, 42, 45, and 48-66.

Embodiment 69

In some further embodiments of embodiment 68, the nucleic acid sequence is selected from the group consisting of SEQ ID NOs: 175-197, 202-205, 217-227, 250-251, 261-264, and 271-276.

Embodiment 7

In some further embodiments of embodiment 68 or embodiment 69, the isolated nucleic acid further comprises a second nucleic acid sequence encoding a second CAR, wherein the nucleic acid sequence encoding the CAR is operably linked to the second nucleic acid sequence via a third nucleic acid sequence encoding a self-cleaving peptide.

Embodiment 71

In some further embodiments of embodiment 70, the self-cleaving peptide is selected from the group consisting of T2A, P2A, and F2A.

Embodiment 72

In some further embodiments of embodiment 71, the third nucleic acid sequence is SEQ ID NO: 255.

Embodiment 73

In some further embodiments of any one of embodiments 68-72, the isolated nucleic acid is an RNA molecule.

Embodiment 74

In some embodiments, there is provided a vector comprising the isolated nucleic acid of any one of embodiments 68-72.

Embodiment 75

In some further embodiments of embodiment 74, the vector is an expression vector.

Embodiment 76

In some further embodiments of embodiment 74 or embodiment 75, the vector is a viral vector.

Embodiment 77

In some further embodiments of embodiment 76, the vector is a lentiviral vector.

Embodiment 78

In some embodiments, there is provided an engineered immune effector cell, comprising the CAR of any one of embodiments 1-36, 39, 42, 45, and 48-66, the isolated nucleic acid of any one of embodiments 68-73, or the vector of any one of embodiments 74-77.

Embodiment 79

In some further embodiments of embodiment 78, the immune effector cell is a T cell, an NK cell, a peripheral blood mononuclear cell (PBMC), a hematopoietic stem cell, a pluripotent stem cell, or an embryonic stem cell.

Embodiment 80

In some further embodiments of embodiment 79, the immune effector cell is a T cell.

Embodiment 81

In some embodiments, there is provided a pharmaceutical composition, comprising the engineered immune effector cell of any one of embodiments 78-80 and a pharmaceutically acceptable carrier.

Embodiment 82

In some embodiments, there is provided a method of treating cancer in an individual, comprising administering to the individual an effective amount of the pharmaceutical composition of embodiment 81.

Embodiment 83

In some further embodiments of embodiment 82, the engineered immune effector cell is autologous.

Embodiment 84

In some further embodiments of embodiment 82, the engineered immune effector cell is allogenic.

Embodiment 85

In some further embodiments of any one of embodiments 82-84, the cancer is liquid cancer.

Embodiment 86

In some further embodiments of embodiment 85, the cancer is multiple myeloma, acute lymphoblastic leukemia, or chronic lymphocytic leukemia.

Embodiment 87

In some further embodiments of any one of embodiments 82-84, the cancer is solid cancer.

Embodiment 88

In some embodiments, there is provided a pharmaceutical composition, comprising the anti-CD19 sdAb of embodiment 37 or embodiment 38, and a pharmaceutically acceptable carrier.

Embodiment 89

In some embodiments, there is provided a pharmaceutical composition, comprising the anti-CD20 sdAb of embodiment 40 or embodiment 41, and a pharmaceutically acceptable carrier.

Embodiment 90

In some embodiments, there is provided a pharmaceutical composition, comprising the anti-BCMA sdAb of embodiment 43 or embodiment 44, and a pharmaceutically acceptable carrier.

Embodiment 91

In some embodiments, there is provided a pharmaceutical composition, comprising the anti-CD38 sdAb of embodiment 46 or embodiment 47, and a pharmaceutically acceptable carrier.

Embodiment 92

In some embodiments, there is provided a method of treating a disease in an individual, comprising administering to the individual an effective amount of the pharmaceutical composition of any one of embodiments 88-91.

Embodiment 93

In some further embodiments of embodiment 92, the disease is cancer.

EXAMPLES

The examples described herein are not intended to represent that the experiments below are all or the only experiments performed. Efforts have been made to ensure accuracy with respect to numbers used (for example, amounts, temperature, etc.), but some experimental errors and deviations should be accounted for. Unless indicated otherwise, parts are parts by weight, molecular weight is weight average molecular weight, temperature is in degrees Centigrade, and pressure is at or near atmospheric.

Example 1. Preparation of Single-Domain Antibodies

To develop single-domain antibodies with high binding affinity to specified antigens, llamas were immunized and a phage-display library was constructed to identify $V_HH$ leads. Distinct clones were picked at random and were classified according to the heavy chain complementarity determining region 3 (CDR3), a region that can play a major role in antigen binding.

In order to obtain the single-domain antibodies, llamas were immunized regularly with respective immunogens, which can include recombinant human BCMA protein having a C-terminal Fc tag (ACRO Biosystems, Cat No.: BC7-H5254), recombinant human CD38 protein having a C-terminal His tag (ACRO Biosystems, Cat No.: CD8-H5224), recombinant human CD19 protein having a C-terminal Fc tag (ACRO Biosystems, Cat No.: CD9-H5229) and recombinant human CD20 protein having a C-terminal Fc tag (ACRO Biosystems, Cat No.: CD0-H526a).

A process of generating anti-BCMA single-domain antibodies is described below as an example for generating single-domain antibodies against various antigens. Generation of anti-human CD38, anti-human-CD19 and anti-CD20 single-domain antibodies were performed with similar processes as described below. Other protocols for preparing single-domain antibodies have been described. See, for example, Els Pardon et al, *Nature Protocol*, 2014; 9(3): 674.

1. Animal Immunization and Immune Response Assay 1.1 Animal Immunization

Each immunogen comprising a recombinant antigen protein was mixed with adjuvant or PBS and injected to a llama. The animals were immunized by service vendor (Cedarline) for seven times, typically with 200 µg immunogen and CFA (Complete Freund's Adjuvant) each time at about 1-week to 2-week intervals. Peripheral blood samples were collected at the pre-immunization stage and after the 5th and 7th immunization. After multiple rounds of immunization, immune reactions of the llamas against the target antigen were evaluated to confirm the titer of antigen-specific single-domain antibodies. Lymphocytes were isolated by gradient centrifugation from about 100 ml of peripheral blood. The cells were supplemented with RNALATER™ and stored at −80° C. Sera were obtained by centrifugation of anti-coagulated blood samples and stored at −80° C.

1.2 IgG Fractionation

IgG-subclass fractionation was carried out according to GenScript's Standard Operating Procedure. The IgG subclasses were fractionated from terminal bleed serum using Protein G and Protein A resins. The 1 ml serum sample was loaded onto a 1 ml HITRAP® Protein G HP column, and the column was washed with 10 ml phosphate buffer (20 mM, pH 7.0). The IgG3 (MW 100,000 Da) fraction was eluted with 0.15 M NaCl, 0.58% acetic acid (pH 3.5), and the eluate was neutralized with 1 M Tris-HCl (pH 9.0) to pH 7.4.

Subsequently, the IgG1 (MW 170,000 Da) fraction was eluted with 0.1 M glycine-HCl (pH 2.7), and the eluate was neutralized with 1 M Tris-HCl (pH 8.5) to pH 7.4. The flow-through of HITRAP® Protein G HP column was then loaded onto a 1 ml HITRAP® Protein A HP column, and the column was washed with 20 ml phosphate buffer (20 mM, pH 7.0). The IgG2 (MW 100,000 Da) fraction was eluted with 0.15 M NaCl, 0.58% acetic acid (pH 4.5), and the eluate was neutralized with 1M Tris-HCl (pH 9.0) to pH 7.4. The concentrations of the purified IgG, IgG2 and IgG3 antibodies were determined by OD280, and the purity of each was assessed by both reducing and non-reducing SDS-PAGE analysis.

1.3 Immune Response Assay

Immune response of the llamas was evaluated by ELISA, in which the serum samples and purified IgGs were assayed for binding to immobilized immunogens. Sera collected pre-immunization, after 5th immunization and at terminal bleed were evaluated. The antigen (i.e., recombinant human antigen protein) was diluted in coating buffer at 4 µg/ml. The microtiter plate was coated with diluted antigen at 4° C. overnight. The plate was then washed 3 times with washing buffer followed by blocking at room temperature for 2 hours. The plate was subsequently washed 4 times with washing buffer. A series of diluted sera or IgGs were added to the plate and incubated at room temperature for 1.5 hours. The plate was then washed 4 times with washing buffer. HRP-conjugated anti-llama IgG secondary antibody was added to the plate and incubated at room temperature for 1 hour. After washing, the TMB substrate was added to each well and incubated for 10 minutes before stopping with 1 M HCl. To quantify binding, absorbance at 450 nm was measured for each well using a MK3 spectrometer.

2. $V_H$H Phage Display Library Construction 2.1 RNA Extraction

Total RNA was extracted from the isolated lymphocytes (from 1.1.1) using TRIZOL® Reagent according to the manufacturer's protocol. Quantity and quality of the total RNA were assessed by gel electrophoresis and quantified by measuring absorbance at OD260/280.

2.2 RT-PCR and $V_H$H Amplification

Total RNA was reverse transcribed into cDNA with an oligo(dT)$_{20}$ primer using PRIMESCRIPT™ 1st Strand cDNA Synthesis Kit according to the manufacturer's protocol. Six forward and two reverse specific degenerate primers were designed to amplify the $V_H$H fragments, which had two BglI restriction sites introduced. The $V_H$H fragments were amplified according to GenScript's standard operating procedure (SOP) as described below.

The variable regions of the heavy-chain immunoglobulins (i.e., $V_H$Hs) were amplified using a two-step polymerase chain reaction (PCR). In the first PCR, 100 ng of cDNA template was mixed with primers CALL001 (SEQ ID NO: 229) and CALL002 (SEQ ID NO: 230). The DNA products from the first PCR reaction were analyzed by agarose gel electrophoresis. After gel purification, the DNA products of the first PCR were used as templates in the second PCR The second PCR was performed with the primers BACK-1 (SEQ ID NO: 231), BACK-2 (SEQ ID NO: 232) and PMCF (SEQ ID NO: 233). The amplified second PCR products containing $V_H$H PCR fragments were gel purified and enzyme digested, and then inserted into phagemid plasmids. The recombinant plasmids with $V_H$H gene fragments were electro-transferred into E. coli cells in order to generate the phage display $V_H$H immune library.

The procedure of the PCR reaction has an initial denaturation step at 94° C. for 7 min, followed by 30 cycles of 94° C. for 1 min, 55° C. for 1 min, and 72° C. for 1 min; and followed by a final extension step at 72° C. for 7 min.

2.3 Phage Library Construction

The $V_H$H PCR products were obtained by amplification using different primer pairs. The PCR products were then digested with BglI and gel purified. The gel purified fragments were inserted into GenScript's in-house phagemid vector. A pilot library was constructed to optimize the ligation and transformation conditions. The optimized ligation and transformation conditions were employed to develop the phagemid library. A small portion of the transformed cells was diluted and streaked on 2×YT plates supplemented with 100 µg/ml ampicillin. The colonies were counted to calculate the library size. Positive clones were randomly picked and sequenced to assess the quality of the library. The rest of the transformed cells were streaked onto YT plates supplemented with 100 µg/ml ampicillin and 2% glucose. Lawns of colonies were scraped off the plates. A small aliquot of the cells was used for library plasmid isolation. The rest was supplemented with glycerol and stored at −80° C. as stock.

3. Phage Display Panning 3.1 Bio-Panning

The constructed $V_H$H phage library was panned against recombinant human BCMA protein and CHO cells expressing human BCMA (i.e., CHO-BCMA cells, prepared in house by Legend Biotec) respectively using a standard procedure developed by GenScript. The library stock was grown to log phase, and then the library was rescued with M13KO7 helper phage and was amplified overnight at 25° C. in a shaker. The phage was then precipitated with PEG/NaCl, re-suspended in PBS and stored at −80° C. For solid phase panning, microplate wells were coated with recombinant human BCMA protein in PBS at 4° C. overnight. For liquid phase panning, CHO-BCMA cells were blocked with blocking buffer at room temperature for 1 hour. During the coating or blocking step, phage particles were pre-incubated with the blocking buffer and Fc control protein in microplate wells. After pre-incubation, phage particles were added to the wells coated with BCMA proteins or CHO-BCMA solution respectively and incubated for 1 hour. After incubation, unbound and nonspecifically bound phages were washed away by rinsing the wells or the CHO-BCMA cells with PBST for six times supplemented with two additional PBS washes. The bound phage particles were eluted by 100 mM triethylamine (TEA), and the eluate was neutralized by 1 M Tris-HCl (pH 7.4). Half of the eluate was then used to infect exponentially growing E. coli TG1 cells ($OD_{600}$=0.4~0.6) for output titration.

3.2 Phage ELISA

Phage ELISA was performed to identify clones specific to the target antigens. Individual output phage clones were grown in 96-deep-well plate and rescued by M13KO7 helper phage overnight. To identify clones that bind to antigen proteins, 96-well ELISA microtiter plates were coated with recombinant human BCMA protein and Fc control protein respectively in coating buffer overnight at 4° C., and the plates were then blocked with blocking buffer. After blocking, approximately 50 µl per well of phage supernatant from the overnight cell culture was added to the plates for 1.5-hour incubation at 4° C. The plates were washed four times, and the HRP-conjugated anti-M13 monoclonal antibody was added to the plates for 45-minute incubation at 4° C. The plates were again washed five times and substrate solution was added to the wells for developing. Absorption at 450 nm was measured for each well.

To identify clones that bind CHO-BCMA cells, the CHO-BCMA cells were blocked with blocking buffer at room temperature for 1 hour. After blocking, approximately 20 μl per well of phage supernatant from the overnight cell culture was added to the cell solutions for 1-hour incubation at room temperature. After the cells were washed 4 times, the HRP-conjugated anti-M13 monoclonal antibody was added for 30-minute incubation at room temperature. The cells were washed five times and substrate solution was then added for developing. The absorption was measured at 450 nm.

After panning, phage ELISA positive single clones were randomly selected and DNA was prepared from output phage using plasmid extraction kits. The inserts in the plasmids were sequenced. One or more $V_HH$ sequences were obtain for each target antigen, see, for example, Table 2.

Example 2. Preparation of Monospecific $V_HH$ Chimeric Antigen Receptors

A CAR backbone sequence encoding a CAR backbone polypeptide comprising from the N-terminus to the C-terminus: a CD8α hinge domain, a CD28 transmembrane domain, a CD28 cytoplasmic domain, a CD137 cytoplasmic domain, and a CD3ζ cytoplasmic domain were chemically synthesized and cloned into a pre-modified lentiviral vector downstream and operably linked to a constitutive hEF1α promoter. The resulting CAR backbone vector was named "PLLV-hEF1α-8281373." Multi-cloning sites (MCS) in the vector allowed insertion of a nucleic acid sequence comprising a Kozak sequence (SEQ ID NO: 126) operably linked to a nucleic acid sequence encoding a CD8α signal peptide fused to the N-terminus of a $V_HH$ fragment into the PLLV-hEF1α-8281373 vector, upstream and operably linked to the CAR backbone sequence.

To construct a monospecific CAR having a single $V_HH$ domain using the PLLV-hEF1α-8281373 backbone, the nucleic acid sequence encoding the $V_HH$ domain was operably linked to the 3' of the nucleic acid sequence encoding the CD8α signal peptide. The fusion nucleic acid sequence was chemically synthesized and cloned into the PLLV-hEF1α-8281373 CAR backbone via the EcoRI (SEQ ID NO: 234: 5'-GAATTC-3') and SpeI (SEQ ID NO:235: 5'-ACTAGT-3') restriction sites by molecular cloning techniques known in the art. Table 4 lists the vectors that were constructed to express the exemplary monospecific, monovalent anti-BCMA and anti-CD38 CARs.

For ease of further inserting additional sequences, such as a nucleotide encoding a second $V_HH$, when designing a monospecific CAR construct (e.g., anti-BCMA or anti-CD38), restriction sites including HpaI (SEQ ID NO: 236: 5'-GTTAAC-3'), MluI (SEQ ID NO: 237: 5'-ACGCGT-3'), NsiI (SEQ ID NO: 238: 5'-ATGCAT-3') sites were included between the CD8α signal peptide nucleic acid sequence and the $V_HH$ nucleic acid sequence.

The lentivirus packaging plasmid mixture including pCMV-AR-8.74 and pMD2.G (Addgene #12259) was pre-mixed with the vectors PLLV-hEF1α-8281373 having $V_HH$ fragments (Table 4) at a pre-optimized ratio with polyetherimide (PEI), then mixed properly and incubated at room temperature for 5 minutes. The transfection mix was then added dropwise to the HEK293 cells and mixed gently. Afterwards, cells were incubated overnight in a 37° C. and 5% $CO_2$ cell incubator. The supernatants were collected after centrifugation at 4° C., 500 g for 10 min.

The virus-containing supernatants were filtered through a 0.45 μm PES filter, followed by ultra-centrifugation for lentivirus concentration. After ultra-centrifugation, the supernatants were carefully discarded and the virus pellets were rinsed cautiously with pre-chilled DPBS. The virus was aliquoted properly, then stored at −80° C. immediately. The virus titer was determined by p24 based on HTRF kit developed by GenScript.

PBMC Preparation

Leukocytes were collected from healthy donors by apheresis, and cell concentration was adjusted to $5\times10^6$ cells/ml in R10 medium. Leukocytes were then mixed with 0.9% NaCl solution at 1:1 (v/v) ratio. 3 ml lymphoprep medium was added to a 15 ml centrifuge tube, and 6 ml of diluted lymphocyte mix was slowly layered on top of the lymphoprep medium. The lymphocyte mix was centrifuged at 800 g for 30 minutes without brakes at 20° C. Lymphocyte buffy coat was then collected with a 200 μl pipette. The harvested fraction was diluted at least 6 folds with 0.9% NaCl or R10 to reduce density of the solution. The harvested fraction was then centrifuged at 250 g for 10 minutes at 20° C. The supernatant was aspirated completely, and 10 ml of R10 was added to the cell pellet to resuspend the cell pellet. The mixture was further centrifuged at 250 g for 10 minutes at 20° C. The supernatant was again aspirated. 2 ml of 37° C. pre-warmed R10 with 100 IU/ml IL-2 was added to the cell pellet, and the cell pellet was re-suspended softly. The cell number was determined following Trypan Blue staining, and this PBMC sample was ready for later experiments.

T Cell Purification

Human T cells were purified from PBMCs using Miltenyi Pan T cell isolation kit (Cat #130-096-535), following manufacturer's protocol as described below. Cell number was first determined and the cell suspension was centrifuged at 300 g for 10 minutes. The supernatant was then aspirated completely, and the cell pellets were re-suspended in 40 μl buffer per $10^7$ total cells. 10 μl of Pan T Cell Biotin-Antibody Cocktail was added per $10^7$ total cells, mixed thoroughly and incubated for about 5 minutes in the refrigerator (2~8° C.). 30 μl of buffer was then added per $10^7$ cells. 20 μl of Pan T Cell MicroBead Cocktail was added per $10^7$ cells. The cell suspension mixture was mixed well and incubated for an additional 10 minutes in the refrigerator (2~8° C.). A minimum of 500 μl is required for magnetic separation. For magnetic separation, an LS column was placed in the magnetic field of a suitable MACS Separator. The column was prepared by rinsing with 3 ml of buffer. The cell suspension was then applied onto the column, and flow-through containing the unlabeled cells was collected, which represented the enriched T cell fractions. Additional T cells were collected by washing the column with 3 ml of buffer and collecting unlabeled cells that pass through. These unlabeled cells again represented the enriched T cells, and were combined with the flow-through from previous step. The pooled enriched T cells were then centrifuged and re-suspended in R10-100 IU/ml IL-2.

The prepared T cells were subsequently pre-activated for 48-96 hours with human T cell activation/expansion kit (Miltenyi #130-091-441) according to manufacturer's protocol in which anti-CD3/CD28 MACSiBead particles were added at a bead-to-cell ratio of 1:2.

The pre-activated T cells were transduced with lentivirus stock in the presence of 7 μg/ml polybrene with centrifugation at 1200 g, 32° C. for 1.5 h. The transduced cells were then transferred to the cell culture incubator for transgene expression under suitable conditions.

On day 3 or day 7 post-transduction, transduced T cells were harvested and co-incubated with tumor cells at an effector (CAR-T) to target cell ratio of 20:1 for 20 hours. Target cells were either human multiple myeloma cell line RPMI8226.Luc or human glioblastoma cell line U87MG.Luc cells, both cell lines engineered in house to express firefly luciferase. To assay the cytotoxicity of CAR-T on tumor cells, One-glo luminescent luciferase assay reagents (Promega #E6110) were prepared according to manufacturer's protocol and added to the co-cultured cells to detect the remaining luciferase activity in the well. Since luciferase is expressed only in RPMI8226.Luc or U87MG.Luc cells, the remaining luciferase activity in the well correlates directly to the number of viable target cells in the well. The maximum luciferase activity was obtained by adding culture media to target cells in absence of effector cells. The minimum luciferase activity was determined by adding Triton X-100 at a final concentration of 1% at the time when the cytotoxicity assays were initiated. The specific cytotoxicity was calculated by the formula: Specific Cytotoxicity %=100%*(1−(RLUsample−RLUmin)/(RLUmax−RLUmin)).

Figure 2A:
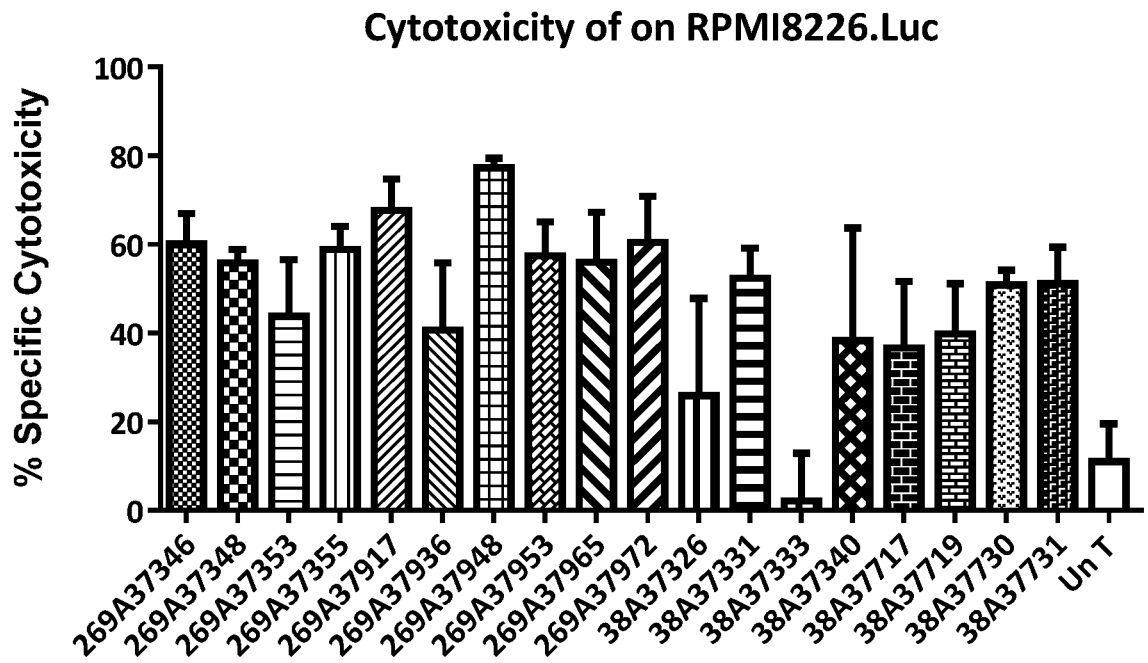
FIG. 2A shows results of an in vitro cytotoxicity assay of T cells expressing exemplary monospecific CARs comprising various anti-BCMA (i.e., anti-CD269) or anti-CD38 single-domain antibodies against multiple myeloma cell line RPMI8226.Luc.
Figure 2B:
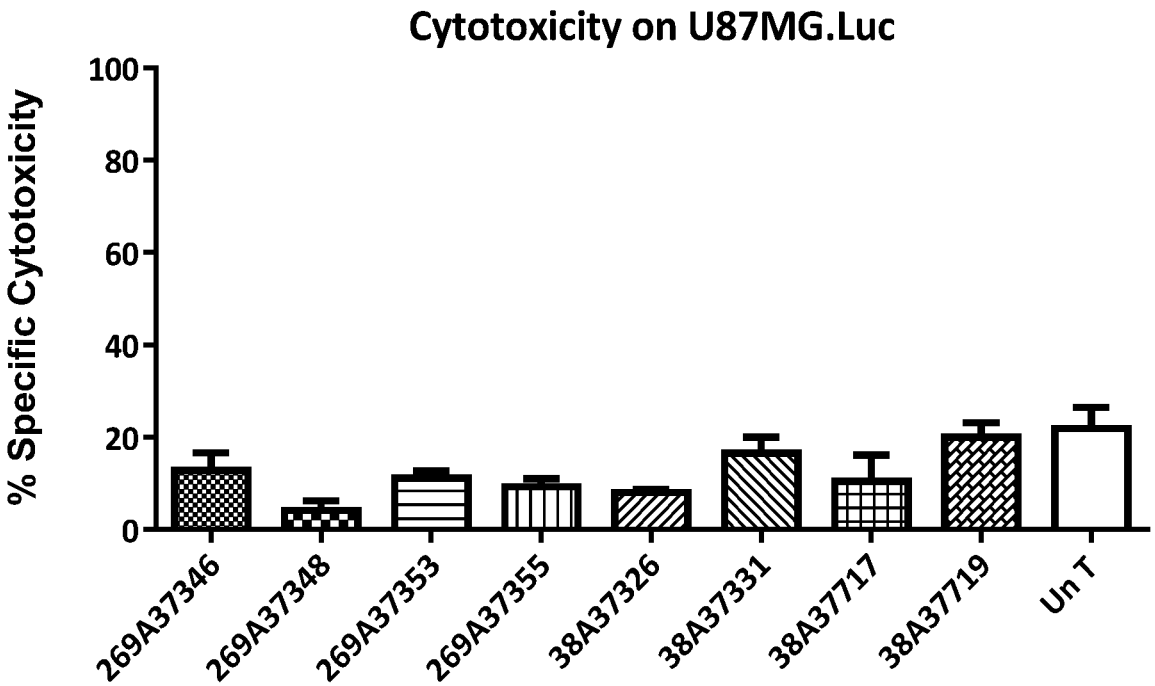
FIG. 2B shows results of an in vitro cytotoxicity assay of T cells expressing exemplary monospecific CARs comprising various anti-BCMA (i.e., anti-CD269) or anti-CD38 single-domain antibodies against glioblastoma cell line U87MG.Luc.

Monospecific CAR clones targeting BCMA (CD269) were coded starting with the digits "269" while monospecific CAR clones targeting CD38 were similarly coded starting with the digits "38." As shown in FIG. 2A, the selected clones exhibited different levels of cytotoxicity on multiple myeloma cell line RPMI8226.Luc cells, with over 60% monospecific $V_HH$-based CAR-Ts showing >50% cytotoxicity against RPMI8226.Luc cells. Clones 269A37346, 269A37348, 269A37353, 269A37355, 38A37326, 38A37331, 38A37717, and 38A37719 based CAR-T were selected for further testing. In particular, clones 269A37346, 269A37348, 267A37353, 269A37355, 38A37326, 38A37331, 38A37717 based CAR-T exhibited potent cytotoxicity on multiple myeloma cell line RPMI8226.Luc cells with more than 20%-30% increase in RPMI8226.Luc cell killing by CAR-T treatment as compared with untransduced control T cells (UnT). Nevertheless, such cytotoxicity increase did not occur on human glioblastoma cell line U87MG.Luc cells (see FIG. 2B). No significant cytotoxicity effects were detected on U87MG.Luc by these monospecific $V_HH$-based CAR-T cells as compared to UnT controls. The observation above indicated that some of these clones might be target specific and potent on BCMA or CD38 positive cells.

Example 3. Preparation of Exemplary Bispecific or Multivalent Chimeric Antigen Receptors Potentially potent clones as described in Example 2 could also be favorable candidates for generating bispecific or multivalent $V_HH$-based CARs. Two representative $V_HH$ clones (anti-BCMA $V_HH$ clone 269A37346 and anti-CD38 $V_HH$ clone 38A37717) were selected to construct various exemplary CAR constructs.

BCMA×CD38 $V_HH$-based CARs can be generated by combining BCMA specific $V_HH$ and CD38 specific $V_HH$ via a suitable peptide linker (e.g. Gly-Ser polymer) followed by a CAR signal domain backbone vector. Exemplary bispecific BCMA×CD38 CAR constructs (GSI5001 to GSI5010) are listed in Table 6. First, the amino acid sequence of anti-BCMA $V_HH$ and anti-CD38 $V_HH$ were connected together via a Gly-Ser linker that could be of different lengths. Then the linked amino acid sequence was placed after the CD8α signal peptide sequence. This combined sequence including Kozak-CD8α signal peptide-bispecific $V_HH$ was directly synthesized and cloned into a PLLV-hEF1α-81373 CAR backbone via EcoRI and SpeI restriction sites, by regular molecular cloning protocols known in the art. The CAR backbone sequence encodes a CAR backbone polypeptide comprising from the N-terminus to the C-terminus: a CD8α hinge domain, a CD8α transmembrane domain, a CD137 cytoplasmic domain, and a CD3ζ cytoplasmic domain were chemically synthesized and cloned into a pre-modified lentiviral vector downstream and operably linked to a constitutive hEF1α promoter. The resulting CAR backbone vector was named "PLLV-hEF1α-81373."

Additionally, an exemplary co-expression vector encoding BCMA CAR and CD38 CAR were constructed by combining BCMA specific $V_HH$-based CAR and CD38 specific $V_HH$-based CAR in a single CAR vector via a suitable splice based linker (T2A, P2A, or F2A). For example, the GSI5013 construct has a nucleic acid sequence of SEQ ID NO: 239. The nucleic acid sequence in GSI5013 encodes from the 5' to the 3': CD8α signal peptide, 38A37717 $V_HH$, CD8α hinge domain, CD8α transmembrane domain, CD137 co-stimulatory domain, CD3C cytoplasmic signaling domain, T2A, CD8α signal peptide, 269A37346 $V_HH$, CD8α hinge domain, CD8α transmembrane domain, CD137 co-stimulatory domain, and CD3ζ cytoplasmic signaling domain.

Multivalent $V_HH$ CARs can be constructed by introducing a nucleic acid sequencing encoding multiple copies of a single $V_HH$ fused to each other by peptide linkers into a CAR signal domain backbone vector. Exemplary monovalent multivalent CAR constructs (GSI5014, GSI5015, GSI5016, GSI5017) are listed in Table 5. These constructs were prepared by linking 2-3 copies of $V_HH$ by Glycine-serine linker followed by directly synthesizing this linked sequence in combination with Kozak-CD8α signal peptide nucleic acid sequence, and cloning into the PLLV-hEF1α-81373 CAR backbone via EcoRI and SpeI restriction sites. As controls, single copy $V_HH$ were also cloned into the same PLLV-hEF1α-81373 CAR backbone by identical methods (GSI5011 and GSI5012, listed in Table 4).

Lentiviral vectors carrying CAR genes of GSI5001 to GSI5017 were packaged and titrated with protocols as described in Example 2. Using protocols described in Example 2, human PBMCs were prepared from peripheral bloods of volunteers for further isolation of primary human T cells using Miltenyi human PanT cell isolation kits. The purified T cells were pre-activated and expanded using Miltenyi anti-CD3/CD28 micro-beads as described in Example 2. The pre-activated T cells were then transduced with lentivirus stock in the presence of 7 µg/ml polybrene by centrifugation at 1200 g, 32° C. for 1.5 h. The transduced cells were then transferred to the cell culture incubator for transgene expression under suitable conditions.

On day 3 post transduction, transduced T cells were harvested and co-incubated with tumor cells at an effector (CAR-T) to target cell ratio of 20:1 for 20 hours. To assay the cytotoxicity of CAR-T on tumor cells, One-glo luminescent luciferase assay reagents (Promega #E6110) were added to the co-cultured cells and the specific cytotoxicity for each CAR-T was measured as described in Example 2.

The copy numbers of integrated CAR genes for each group was determined by a semi-quantitative PCR (q-PCR) assay. Briefly, genomic DNA from each group of CAR-T was prepared with Gentra Puregene Cell Kit (Qiagen). The concentration of genomic DNA was determined by Nanodrop, and 10 ng genomic DNA sample was processed for a standardized q-PCR assay with SYBR Green Realtime PCR Master mix plus (Toyobo) on ABI #7300 q-PCR instrument using CAR specific primers (forward primer 137P2F (SEQ ID NO: 252): 5'-GTCCTTCTCCTGTCACTGGTTAT-3'; and reverse primer 137P2R (SEQ ID NO: 253): 5'-TCTTCTCTTCTGGAAATCGGCA-3'). The relative copy number of each integrated CAR gene was calculated based on a standard curve established using plasmid containing target sequences.

As shown in Table 7 below, the copy numbers for each CAR-T preparation were determined and the data suggested high target gene integration into the genome of the T cells.

TABLE 7

| Genome integration copy numbers. | |
|---|---|
| CAR-T cells with constructs | Copies/ng gDNA |
| GSI5001 | 18257060 |
| GSI5002 | 15105810 |
| GSI5003 | 17307510 |
| GSI5004 | 2735165 |
| GSI5005 | Not processed |
| GSI5006 | 6692277 |
| GSI5007 | 6929693 |
| GSI5008 | 15549250 |
| GSI5009 | 10602720 |
| GSI5010 | 7353348 |
| GSI5011 | 3089537 |
| GSI5012 | 650551.3 |
| GSS005 | 1070972 |
| GSI005 | 321521 |
| UnT | 72.77 |
| water | 117 |

Figure 3A:
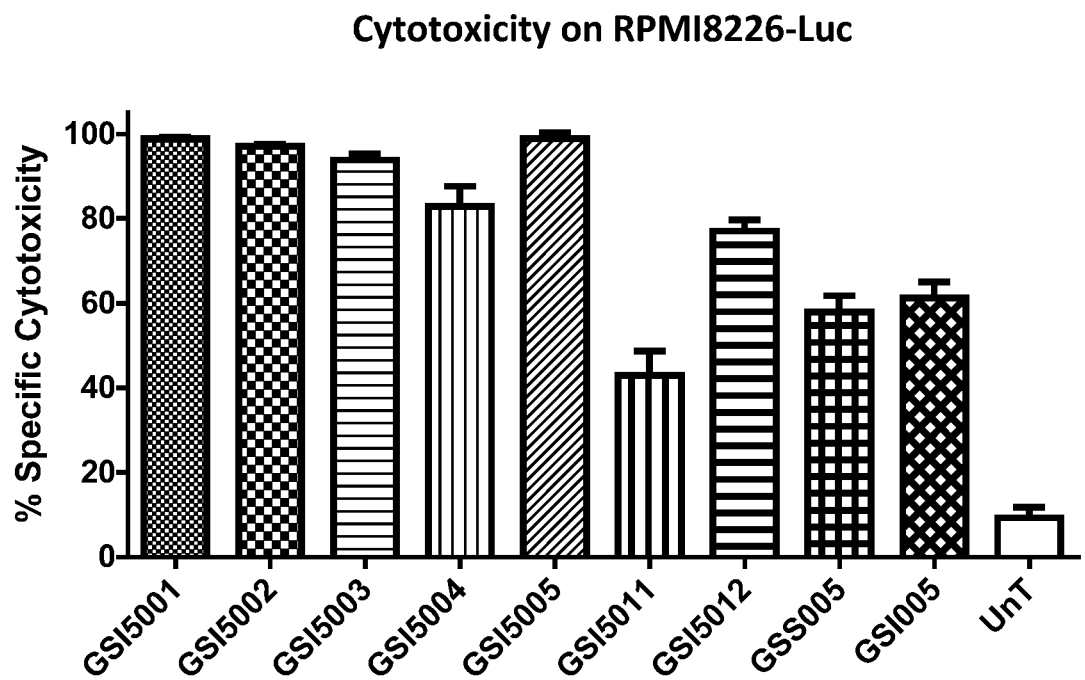
FIG. 3A shows results of an in vitro cytotoxicity assay of T cells expressing exemplary bispecific CARs against multiple myeloma cell line RPMI8226.Luc.
Figure 3B:
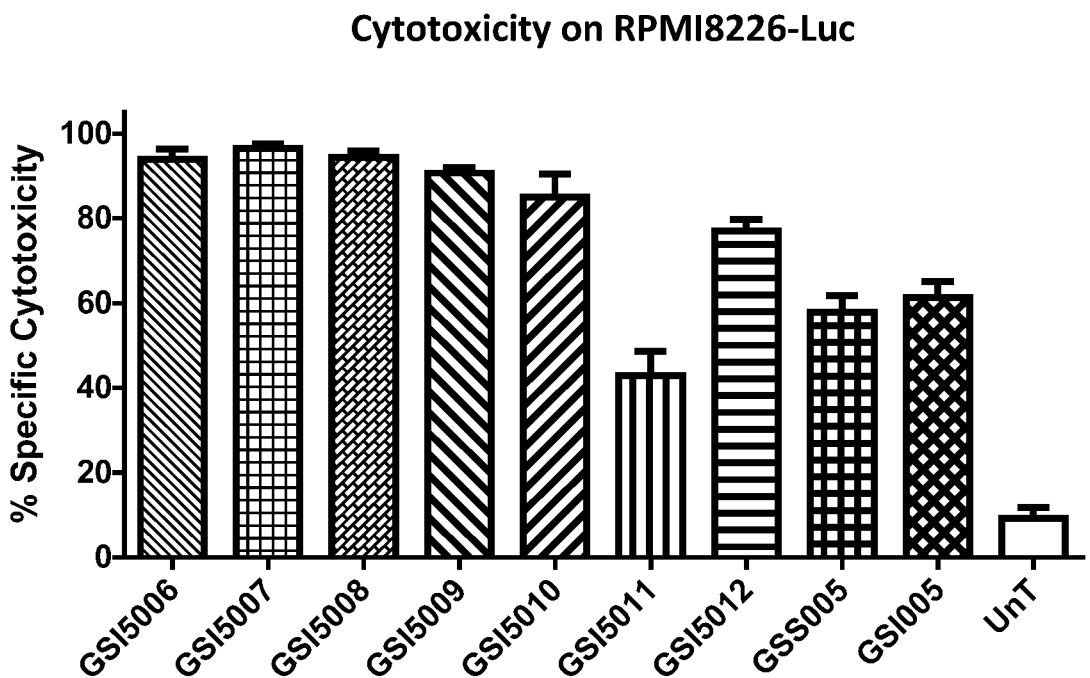
FIG. 3B shows results of an in vitro cytotoxicity assay of T cells expressing exemplary bispecific CARs against multiple myeloma cell line RPMI8226.Luc.

As illustrated in FIGS. 3A-3B, mono-specific $V_HH$ CAR against BCMA (GSI5011) and mono-specific $V_HH$ CAR against CD38 (GSI5012) showed potent cytotoxicity on multiple myeloma cell line RPMI8226.Luc. With GSI5011 CAR, 42.98±2.86% RPMI8226.Luc cells were lyzed, and with GS15012, 61.25±1.92% RPMI8226.Luc cells were lyzed, as compared with the non-specific lysis by untransduced control T cells (UnT, 9.25±1.11%).

The bispecific CARs GSI5001-GSI5010 elicited potent specific lysis of multiple myeloma cell line RPMI8226.Luc as compared to untransduced control T cells (UnT). As shown in FIGS. 3A and 3B, the specific percentage of lysis of RPMI8226.Luc cells was 98.91±0.17% for GSI5001-expressing CAR-T cells, 97.10±0.26% for GSI5002-expressing CAR-T cells, 93.85±0.69% for GSI5003-expressing CAR-T cells, 82.81±2.40% for GS15004-expressing CAR-T cells, 98.95±0.66% for GSI5005-expressing CAR-T cells, 93.91±1.25% for GSI5006-expressing CAR-T cells, 96.49:1.05% for GSI5007-expressing CAR-T cells, 94.41±0.75% for GSI5008-expressing CAR-T cells, 90.72±0.62% for GSI5009-expressing CAR-T cells, and 85.05±2.69% for GSI5010-expressing CAR-T cells, as compared to the non-specific lysis by untransduced control T cells (UnT, 9.25±1.11%). These results also implicated that the shorter Gly-Ser linker seemed to be showing slightly better cytotoxicity performance on target tumor cells. Further studies could be performed under sub-optimal assay conditions to study such effects. Moreover, the order of anti-BCMA $V_HH$ and anti-CD38 $V_HH$ in the vector did not show significant influence on the final cytotoxicity performance on RPMI8226.Luc cells. Two scFv-based CAR-T cells were also prepared in the assay, in which GSS005 was an anti-BCMA scFv-based CAR while GSI005 was an anti-CD38 scFv-based CAR Both GSS005 and GSI005 showed potent specific lysis against RPMI8226.Luc cells as well (57.94±1.91% for GSS5005, 61.25±1.92% for GSI005).

Figure 4:
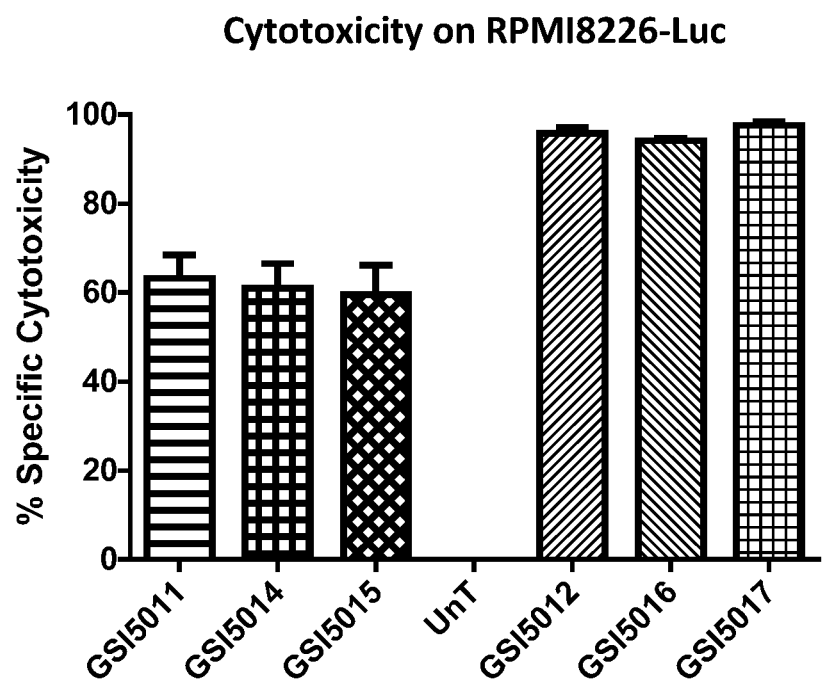
FIG. 4 shows results of an in vitro cytotoxicity assay of T cells expressing exemplary bispecific CARs against multiple myeloma cell line RPMI8226.Luc.

Engineered T cells with BCMA-specific monovalent CAR (GSI5011), BCMA specific bivalent CAR (GSI5012) or BCMA specific trivalent CAR (GSI5013) engineered T cells, and engineered T cells with CD38-specific monovalent CAR (GSI5012), CD38 specific bivalent CAR (GSI5016) or CD38 specific trivalent CAR (GSI5017) were prepared and cytotoxicity assays were performed on RPMI8226.Luc cells as described above. As shown in FIG. 4, the specific percentage lysis of RPMI8226.Luc cells were 63.25±2.64% by GSI5011-expressing CAR-T cells, 61.04±2.75% by GSI5014-expressing CAR-T cells, and 59.57±2.64% by GSI5015-expressing CAR-T cells, as compared to 0.05/02.33% by untransduced control T cells (UnT). Also, as depicted in FIG. 4, the specific lysis of RPMI8226.Luc cells by anti-CD38 $V_HH$ CAR-T were 95.79±0.62% by GSI5012-expressing CAR-T cells, 94.16±0.31% by GSI5016-expressing CAR-T cells, and 97.61±0.77% by GSI5015-expressing CAR-T cells, as compared to 57.92%/2.88% by untransduced control T cells (UnT). The data suggested that these CARs with different antigen binding modalities had potent antitumor activity against BCMA positive cells.

Figure 5:
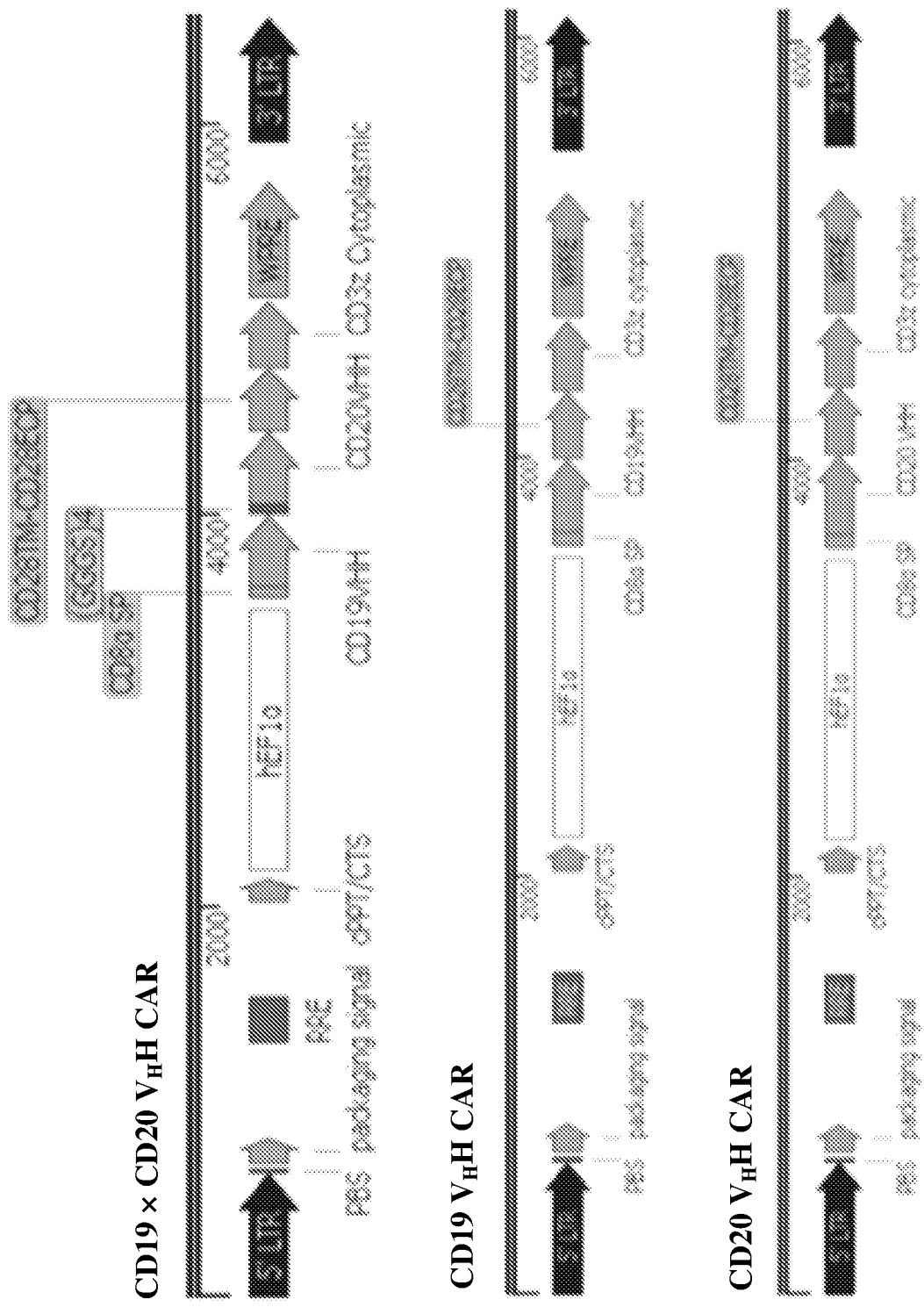
FIG. 5 shows constructs of an exemplary bispecific CAR targeting CD19 and CD20, an exemplary monospecific CAR targeting CD19, and an exemplary monospecific CAR targeting CD20.

Example 4. Preparation, In Vitro and In Vivo Assays of an Exemplary CD19×CD20 CAR Exemplary anti-CD19 sdAb and anti-CD20 sdAb were obtained by similar procedures as in Example 1. These single-domain antibodies are listed in Table 2. Monospecific CD19 CAR based on the CD19 $V_HH$ and monospecific CD20 CAR based on CD20 $V_HH$ were prepared as described in Example 2, and listed in Table 4. An exemplary bispecific CD19×CD20 CAR based on the CD19 $V_HH$ and CD20 $V_HH$ was constructed as described in Example 3, and listed in Table 6. The CAR backbone vector used for constructing the exemplary CD19 CAR, CD20 CAR and the CD19×CD20 CAR encodes from the N-terminus to the C-terminus: a CD8α signal peptide, CD8α hinge domain, a CD28 transmembrane domain, cytoplasmic domain of CD28, and cytoplasmic domain of CD3ζ. FIG. 5 shows the constructs of the CD19 CAR, the CD20 CAR and the bispecific CD19×CD20 CAR. Engineered CAR-T cells expressing the CD19 CAR, the CD20 CAR or the bispecific CD19×CD20 CAR were prepared as described in Example 2.

Cytotoxicity of the CAR-T cells were determined in a 4 h co-culture assay. In the experiments, the prepared CAR-T cells were centrifugally collected, then diluted to desired concentrations by DPBS with 10% human AB serum, and cultured on 96 well-plates. Raji tumor cells, known to exhibit strong expression of CD19 and CD20, were labeled with Calcein-AM (BD Biosciences). The labeled CAR-T cells and Raji cells were cultured at an effector to target ratio of 10:1 at 37° C. for 4 h. Subsequently, the cytotoxicity of CAR-T cells was detected by FACS.

Figure 6:
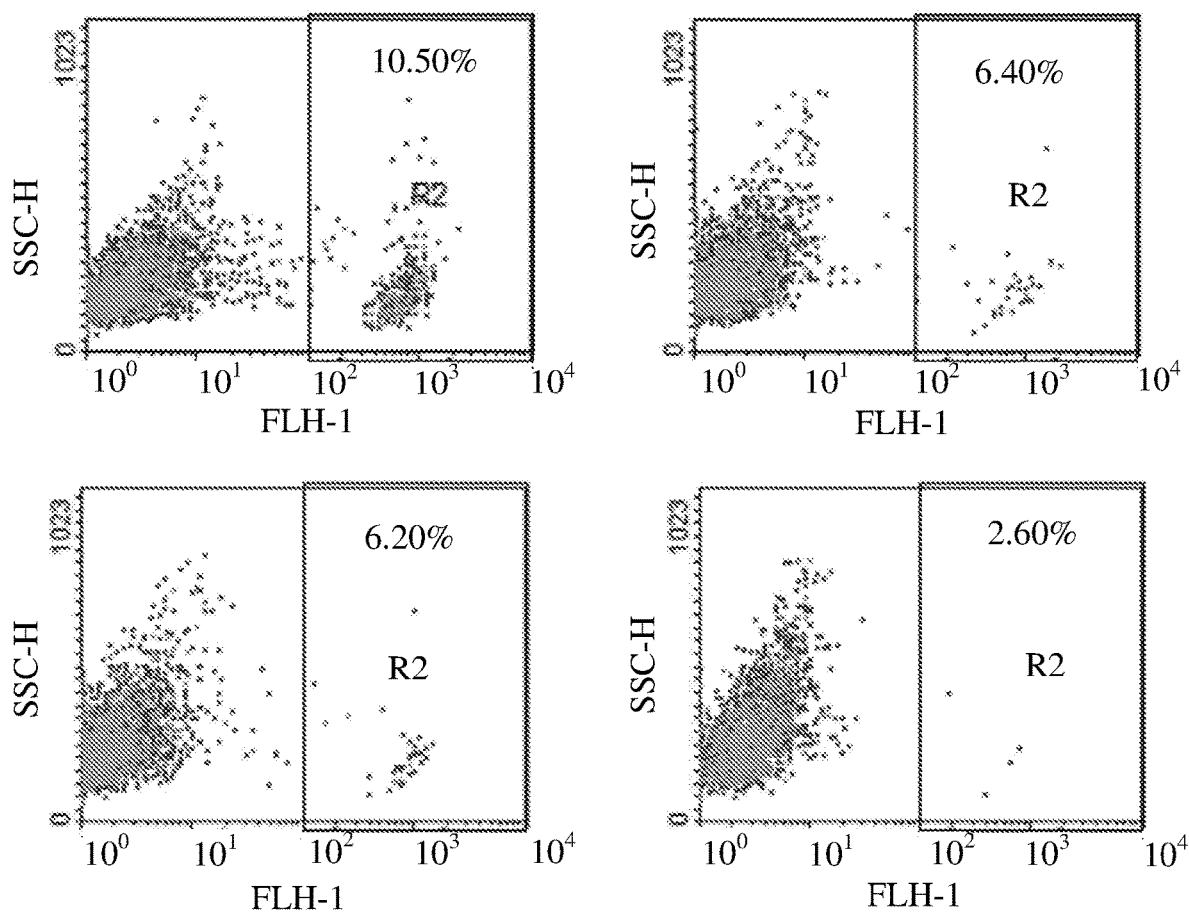
FIG. 6 shows results of an in vitro cytotoxicity assay for various T cells. Top left panel shows results of untransduced control T cells. Top right panel shows results of T cells expressing an exemplary CD19 CAR. Bottom left panel shows results of T cells expressing an exemplary CD20 CAR. Bottom right panel shows results of T cells expressing an exemplary bispecific CD19×CD20 CAR.

As shown in FIG. 6 top left panel, there was no significant Raji cell lysis by untransduced T cells. The cytotoxicity on Raji cells was around 40% either by CD19 (39%, top right panel) or CD20 (41%, bottom left panel) monospecific $V_HH$ CAR-T cells. When the same CD19 $V_HH$ and CD20 $V_HH$ were fused to serve as the extracellular antigen binding domain in the same construct, i.e. in the CD19×CD20 bispecific CAR-T cells, the cytotoxicity of the Raji tumor cells (75.24%) were enhanced as compared to mono-specific CD19 $V_HH$ CAR-T or CD20 $V_HH$ CAR-T cells (FIG. 6 bottom right panel).

Mouse Tumor Model Studies

NOG mice were infused with 4×10⁶ Raji cells per mouse through tail vein injection. After 10 days, the mice were divided evenly into four groups at random, where each group was injected with equivalent doses of untransduced T cells, CD19 CAR-T cells, CD20 CAR-T cells, or CD19×CD20 bispecific CAR-T cells respectively, and observed continuously for 5 weeks.

Figure 7:
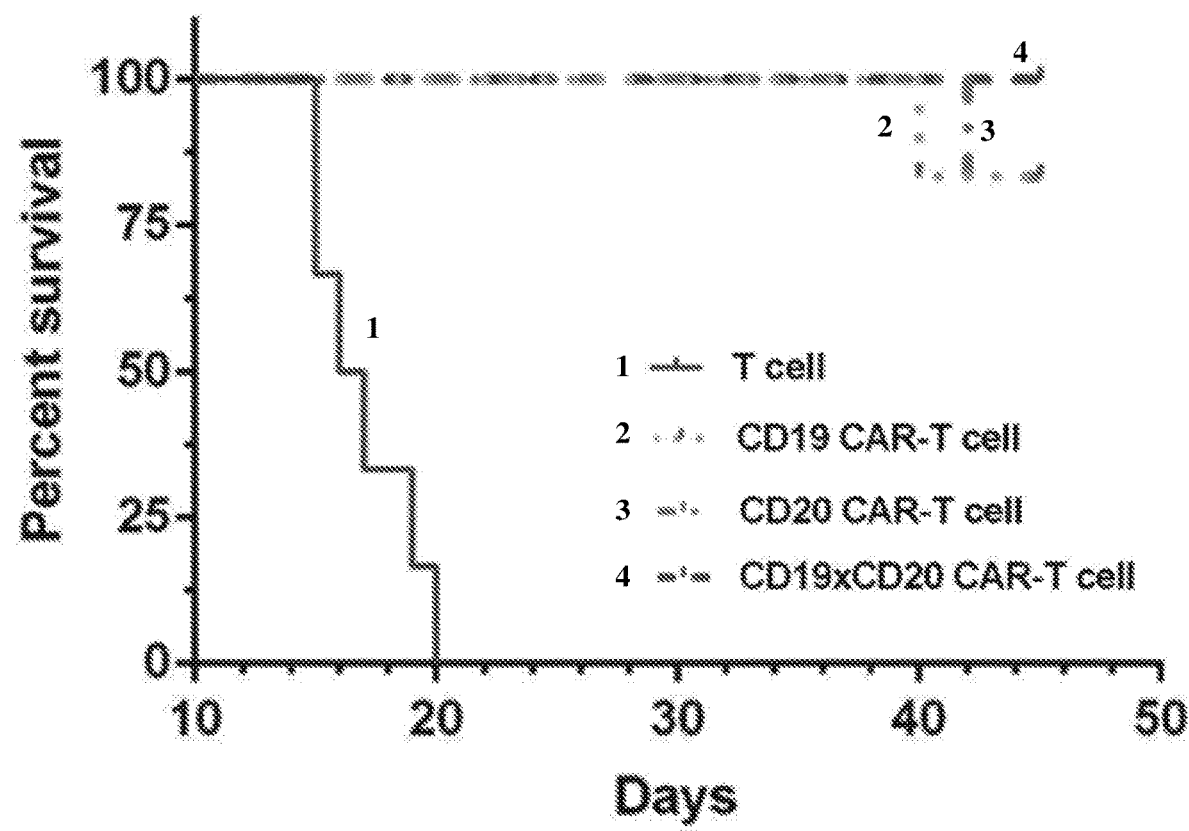
FIG. 7 shows results of an in vivo antitumor assay of T cells expressing an exemplary bispecific CAR targeting CD19 and CD20.

As shown in FIG. 7, the in vivo survival data suggested that the overall survival rate for mice treated with CD19×CD20 bispecific CARs was higher than that with CD19 or CD20 mono-specific CAR-T cells.

Example 5. Preparation of Exemplary Monospecific, Bivalent CARs Having Two Different BCMA Binding Domains Potential $V_HH$ clones as described in Example 2 could also be used to generate monospecific, multivalent CARs having two or more different target binding domains in the extracellular antigen binding domain. Two representative anti-BCMA sdAb clones (clone 269A37353 and clone 269A37917) were selected to construct various exemplary monospecific, bivalent CAR constructs in the present example.

BCMA targeting bivalent CARs (i.e., bivalent BCMA CARs) can be generated by fusing two different BCMA-specific $V_HH$ domains via a suitable peptide linker (e.g. Gly-Ser polymer), and subsequently inserting the fusion construct into a CAR signal domain backbone vector. Exemplary bivalent BCMA CAR constructs (GSI5021-GSI5026) having two different BCMA binding domains 269A37353 and 269A37917 are listed in Table 5. Peptide linkers of various lengths were used in different constructs. Constructs GSI5021-GSI5023 each encoded from the N-terminus to the C-terminus: CD8α signal peptide, 269A37353, peptide linker, 269A37917, CD8α hinge, CD8α transmembrane domain, cytoplasmic domain of CD137, and cytoplasmic domain of human CD3ζ. Constructs GSI5024-GSI5026 each encoded from the N-terminus to the C-terminus: CD8α signal peptide, 269A37917, peptide linker, 269A37353, CD8α hinge, CD8α transmembrane domain, cytoplasmic domain of CD137, and cytoplasmic domain of human CD3ζ. Each construct was further fused to a Kozak sequence at the 5' to provide the full coding sequence. The full coding sequence was directly synthesized and cloned into a PLLV-hEF1α-81373 CAR backbone via EcoRI and SpeI restriction sites using common molecular cloning protocols known in the art. By contrast, monospecific, monovalent CARs (GSI5019 and GSI5020, listed in Table 4) having the same CAR signal domain backbone were constructed using similar methods.

Lentiviral vectors carrying each of the CAR constructs GSI5019-GSI5026 were packaged and titrated with protocols as described in Example 2. Using protocols described in Example 2, human PBMCs were prepared from peripheral blood samples from volunteers for further isolation of primary human T cells using Miltenyi human PanT cell isolation kits. The purified T cells were pre-activated and expanded using Miltenyi anti-CD3/CD28 micro-beads as described in Example 2.

The pre-activated T cells were then transduced with lentivirus stock in the presence of 7 μg/ml polybrene by centrifugation at 1200 g, 32° C. for 1.5 h. The transduced cells were then transferred to the cell culture incubator for transgene expression under suitable conditions.

On day 3 post transduction, transduced T cells were harvested and co-incubated with tumor cells (RPMI8226.Luc cells or U87MG.Luc cells) at an effector (CAR-T) to target cell ratio of 20:1 for 20 hours. RPMI8226.Luc cells are multiple myeloma cells expressing luciferase, and are BCMA positive. U87MG.Luc cells are glioblastoma cells expressing luciferase, and are BCMA negative. To assay the cytotoxicity of the CAR-Ts on tumor cells, One-glo luminescent luciferase assay reagents (Promega #E6110) were added to the co-cultured cells and the specific cytotoxicity for each CAR-T was measured as described in Example 2.

Figure 8A:
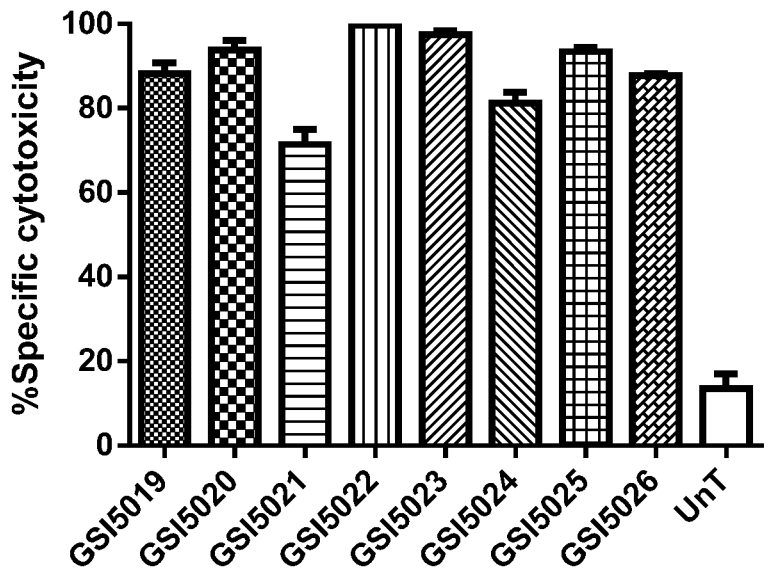
FIG. 8A shows results of an in vitro cytotoxicity assay of T cells expressing exemplary monospecific, bivalent CARs against multiple myeloma cell line RPMI8226.Luc. The CARs each comprise an extracellular antigen binding domain comprising two different anti-BCMA (i.e., anti-CD269) sdAbs.
Figure 8B:
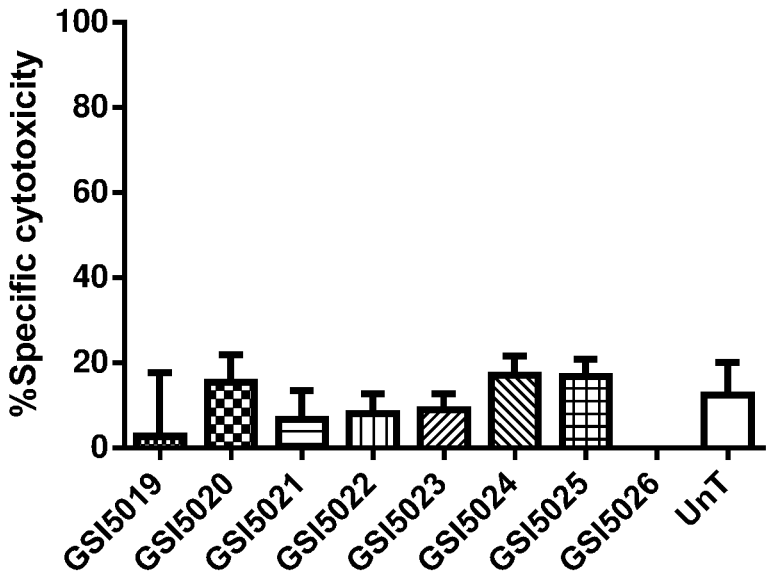
FIG. 8B shows results of an in vitro cytotoxicity assay of T cells expressing exemplary monospecific, bivalent CARs against glioblastoma cell line U87MG.Luc. The CARs each comprise an extracellular antigen binding domain comprising two different anti-BCMA (i.e., anti-CD269) sdAbs.

As shown in FIG. 8A, the specific percentage of lysis of RPMI8226.Luc cells were 88.21±1.29% by GSI5019-expressing CAR-T cells, 93.84±1.13% by GSI5020-expressing CAR-T cells, 71.45±1.79% by GSI5021-expressing CAR-T cells, 99.80±0.45% by GSI5022-expressing CAR-T cells, 97.46±0.50% by GSI5023-expressing CAR-T cells, 81.29±1.27% by GSI5024-expressing CAR-T cells, 93.50±0.47% by GSI5025-expressing CAR-T cells, 87.83±0.23% by GSI5026-expressing CAR-T cells, respectively, as compared to 13.49%±1.75% by untransduced control T cells (UnT). Also, as depicted in FIG. 8B, the specific percentage of lysis of BCMA-negative cell line U87MG.Luc was 2.84±7.41% by GSI5019-expressing CAR-T cells, 15.50±2.24% by GSI5020-expressing CAR-T cells, 6.74±3.37% by GSI5021-expressing CAR-T cells, 8.03±2.36% by GSI5022-expressing CAR-T cells, 9.00±1.88% by GSI5023-expressing CAR-T cells, 17.03±2.27% by GSI5024-expressing CAR-T cells, 16.81±1.98% by GSI5025-expressing CAR-T cells, −11.55±5.43% by GSI5026-expressing CAR-T cells, as compared to 12.49%±3.79% by untransduced control T cells (UnT). The data suggests that the multivalent CARs with different antigen-binding modalities had potent antitumor activity against BCMA positive cells, but not against BCMA negative cells.

The invention claimed is:

1. A chimeric antigen receptor (CAR) comprising a polypeptide comprising, (a) an extracellular antigen binding domain comprising a first single domain antibody (sdAb) specifically binding to a first epitope of BCMA and a second sdAb specifically binding to a second epitope of BCMA, wherein each of the first and second sdAb is a V$_H$H domain, and wherein the first sdAb comprises the amino acid sequence of SEQ ID NO: 87 and the second sdAb comprises the amino acid sequence of SEQ ID NO: 80;

(b) a transmembrane domain; and (c) an intracellular signaling domain.

2. The CAR according to claim 1, wherein the extracellular antigen binding domain has a C-terminus and an N-terminus, and the transmembrane domain has a C terminus and an N-terminus, and wherein the CAR further comprises a hinge domain located between the C-terminus of the extracellular antigen binding domain and the N-terminus of the transmembrane domain.

3. The CAR according to claim 2, wherein the CAR further comprise a signal peptide located upstream of its N-terminus.

4. The CAR according to claim 1, wherein the first sdAb and the second sdAb are directly fused to each other via a peptide bond.

5. The CAR according to claim 1, wherein the first sdAb and the second sdAb are linked to each other via a peptide linker.

6. The CAR according to claim 5, wherein the peptide linker comprises no more than 50 amino acid residues.

7. The CAR according to claim 1, wherein the CAR comprises the amino acid sequence of SEQ ID NO: 265.

8. An isolated nucleic acid comprising a nucleic acid sequence encoding the CAR of claim 1.

9. A vector comprising the isolated nucleic acid of claim 8.

10. An engineered immune effector cell comprising the CAR of claim 1.

11. An engineered immune effector cell according to claim 10, wherein the immune effector cell is a T cell.

12. A pharmaceutical composition, comprising the engineered immune effector cell of claim 11, and a pharmaceutically acceptable carrier.

13. The CAR of claim 1, wherein the first sdAb is located at the N-terminus of the second sdAb.

14. The CAR of claim 1, wherein the first sdAb is located at the C-terminus of the second sdAb.

15. The CAR of claim 1, wherein the transmembrane domain is derived from a molecule selected from the group consisting of CD8α, CD4, CD28, CD137, CD80, CD86, CD152 and PD1.

16. The CAR of 1, wherein the intracellular signaling domain comprises a primary intracellular signaling domain of an immune effector cell.

17. The CAR of claim 16, wherein the primary intracellular signaling domain is derived from CD3ζ.

18. The CAR of claim 1, wherein the intracellular signaling domain comprises a co-stimulatory signaling domain.

19. The CAR of claim 18, wherein the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, Ligands of CD83 and combinations thereof.

20. The CAR of claim 1, wherein the CAR comprises the amino acid sequence of SEQ ID NO: 266.

21. The CAR of claim 1, wherein the CAR comprises the amino acid sequence of SEQ ID NO: 267.

22. The CAR of claim 1, wherein the CAR comprises the amino acid sequence of SEQ ID NO: 268.

23. The CAR of claim 1, wherein the CAR comprises the amino acid sequence of SEQ ID NO: 269.

24. The CAR of claim 1, wherein the CAR comprises the amino acid sequence of SEQ ID NO: 270.

* * * * *

SEQUENCE LISTING

```
<160> NUMBER OF SEQ ID NOS: 277

<210> SEQ ID NO 1
<211> LENGTH: 5
<212> TYPE: PRT
<213> ORGANISM: Artificial Sequence
<220> FEATURE:
<223> OTHER INFORMATION: CD19 single-domain antibody VHH CDR1

<400> SEQUENCE: 1

Ile Asn Arg Met Gly
```

<210> SEQ ID NO 2
<211> LENGTH: 16
<212> TYPE: PRT
<213> ORGANISM: Artificial Sequence
<220> FEATURE:
<223> OTHER INFORMATION: CD19 single-domain antibody VHH CDR2

<400> SEQUENCE: 2

Ser Ile Thr Val Arg Gly Ile Thr Asn Tyr Ala Asp Ser Val Lys Gly
1               5                   10                  15

<210> SEQ ID NO 3
<211> LENGTH: 9
<212> TYPE: PRT
<213> ORGANISM: Artificial Sequence
<220> FEATURE:
<223> OTHER INFORMATION: CD19 single-domain antibody VHH CDR3

<400> SEQUENCE: 3

Val Ser Ser Asn Arg Asp Pro Asp Tyr
1               5

<210> SEQ ID NO 4
<211> LENGTH: 5
<212> TYPE: PRT
<213> ORGANISM: Artificial Sequence
<220> FEATURE:
<223> OTHER INFORMATION: CD20 single-domain antibody VHH CDR1

<400> SEQUENCE: 4

Ile Gly Thr Met Gly
1               5

<210> SEQ ID NO 5
<211> LENGTH: 17
<212> TYPE: PRT
<213> ORGANISM: Artificial Sequence
<220> FEATURE:
<223> OTHER INFORMATION: CD20 single-domain antibody VHH CDR2

<400> SEQUENCE: 5

Ala Ile Arg Trp Ser Thr Gly Gly Thr Arg Tyr Ala Asp Ser Val Lys
1               5                   10                  15

Gly

<210> SEQ ID NO 6
<211> LENGTH: 20
<212> TYPE: PRT
<213> ORGANISM: Artificial Sequence
<220> FEATURE:
<223> OTHER INFORMATION: CD20 single-domain antibody VHH CDR3

<400> SEQUENCE: 6

Asp Arg Leu Ser Leu Asp Leu Ser Gly Arg Tyr His Tyr Asn Pro Ala
1               5                   10                  15

Val Tyr Asp Tyr
            20

<210> SEQ ID NO 7
<211> LENGTH: 11
<212> TYPE: PRT
<213> ORGANISM: Artificial Sequence
<220> FEATURE:
<223> OTHER INFORMATION: BCMA 269A37346 VHH CDR1

```
<400> SEQUENCE: 7

Ser Gly Phe Thr Leu Asp Tyr Tyr Ala Ile Gly
1               5                   10

<210> SEQ ID NO 8
<211> LENGTH: 11
<212> TYPE: PRT
<213> ORGANISM: Artificial Sequence
<220> FEATURE:
<223> OTHER INFORMATION: BCMA 269A37348 VHH CDR1

<400> SEQUENCE: 8

Ser Gly Arg Thr Phe Ser Thr Tyr Gly Met Ala
1               5                   10

<210> SEQ ID NO 9
<211> LENGTH: 8
<212> TYPE: PRT
<213> ORGANISM: Artificial Sequence
<220> FEATURE:
<223> OTHER INFORMATION: BCMA 269A37917 VHH CDR1

<400> SEQUENCE: 9

Ser Gly Arg Thr Phe Thr Met Gly
1               5

<210> SEQ ID NO 10
<211> LENGTH: 11
<212> TYPE: PRT
<213> ORGANISM: Artificial Sequence
<220> FEATURE:
<223> OTHER INFORMATION: BCMA 269A37355 VHH CDR1

<400> SEQUENCE: 10

Ser Gly Gly Ile Phe Val Ile Asn Ala Met Gly
1               5                   10

<210> SEQ ID NO 11
<211> LENGTH: 11
<212> TYPE: PRT
<213> ORGANISM: Artificial Sequence
<220> FEATURE:
<223> OTHER INFORMATION: BCMA 269A37915 VHH CDR1

<400> SEQUENCE: 11

Ser Gly Arg Thr Phe Ser Ser Ile Val Met Gly
1               5                   10

<210> SEQ ID NO 12
<211> LENGTH: 11
<212> TYPE: PRT
<213> ORGANISM: Artificial Sequence
<220> FEATURE:
<223> OTHER INFORMATION: BCMA 269A37936 VHH CDR1

<400> SEQUENCE: 12

Ser Gly Phe Thr Phe Asp Arg Ala Val Ile Val
1               5                   10

<210> SEQ ID NO 13
<211> LENGTH: 11
<212> TYPE: PRT
<213> ORGANISM: Artificial Sequence
<220> FEATURE:
<223> OTHER INFORMATION: BCMA 269A37953 VHH CDR1
```

```
<400> SEQUENCE: 13

Ser Thr Tyr Thr Val Asn Ser Asp Val Met Gly
1               5                   10

<210> SEQ ID NO 14
<211> LENGTH: 11
<212> TYPE: PRT
<213> ORGANISM: Artificial Sequence
<220> FEATURE:
<223> OTHER INFORMATION: BCMA 269A37965 VHH CDR1

<400> SEQUENCE: 14

Ser Gly Ala Thr Leu Thr Asn Asp His Met Ala
1               5                   10

<210> SEQ ID NO 15
<211> LENGTH: 11
<212> TYPE: PRT
<213> ORGANISM: Artificial Sequence
<220> FEATURE:
<223> OTHER INFORMATION: BCMA 269A37972 VHH CDR1

<400> SEQUENCE: 15

Ser Gly Gly Thr Leu Ser Lys Asn Thr Val Ala
1               5                   10

<210> SEQ ID NO 16
<211> LENGTH: 11
<212> TYPE: PRT
<213> ORGANISM: Artificial Sequence
<220> FEATURE:
<223> OTHER INFORMATION: BCMA 269A37353 VHH CDR1

<400> SEQUENCE: 16

Ser Glu His Thr Phe Ser Ser His Val Met Gly
1               5                   10

<210> SEQ ID NO 17
<211> LENGTH: 11
<212> TYPE: PRT
<213> ORGANISM: Artificial Sequence
<220> FEATURE:
<223> OTHER INFORMATION: BCMA 269A37948 VHH CDR1

<400> SEQUENCE: 17

Ser Gly Arg Ala Phe Ser Thr Tyr Phe Met Ala
1               5                   10

<210> SEQ ID NO 18
<211> LENGTH: 17
<212> TYPE: PRT
<213> ORGANISM: Artificial Sequence
<220> FEATURE:
<223> OTHER INFORMATION: BCMA 269A37346 VHH CDR2

<400> SEQUENCE: 18

Cys Ile Ser Arg Ser Asp Gly Ser Thr Tyr Tyr Ala Asp Ser Val Lys
1               5                   10                  15
Gly

<210> SEQ ID NO 19
<211> LENGTH: 19
<212> TYPE: PRT
<213> ORGANISM: Artificial Sequence
<220> FEATURE:
<223> OTHER INFORMATION: BCMA 269A37348 VHH CDR2
```

<400> SEQUENCE: 19

Ser Lys Ala Ser Met Asn Tyr Ser Gly Arg Thr Tyr Tyr Ala Asp Ser
1               5                   10                  15

Val Lys Gly

<210> SEQ ID NO 20
<211> LENGTH: 17
<212> TYPE: PRT
<213> ORGANISM: Artificial Sequence
<220> FEATURE:
<223> OTHER INFORMATION: BCMA 269A37917 VHH CDR2

<400> SEQUENCE: 20

Ala Ile Ser Leu Ser Pro Thr Leu Ala Tyr Tyr Ala Glu Ser Val Lys
1               5                   10                  15

Gly

<210> SEQ ID NO 21
<211> LENGTH: 16
<212> TYPE: PRT
<213> ORGANISM: Artificial Sequence
<220> FEATURE:
<223> OTHER INFORMATION: BCMA 269A37355 VHH CDR2

<400> SEQUENCE: 21

Ser Ile Arg Gly Leu Gly Arg Thr Asn Tyr Asp Asp Ser Val Lys Gly
1               5                   10                  15

<210> SEQ ID NO 22
<211> LENGTH: 17
<212> TYPE: PRT
<213> ORGANISM: Artificial Sequence
<220> FEATURE:
<223> OTHER INFORMATION: BCMA 269A37915 VHH CDR2

<400> SEQUENCE: 22

Ala Ile Met Trp Asn Asp Gly Ile Thr Tyr Leu Gln Asp Ser Val Lys
1               5                   10                  15

Gly

<210> SEQ ID NO 23
<211> LENGTH: 17
<212> TYPE: PRT
<213> ORGANISM: Artificial Sequence
<220> FEATURE:
<223> OTHER INFORMATION: BCMA 269A37936 VHH CDR2

<400> SEQUENCE: 23

Phe Ile Lys Pro Ser Asp Gly Thr Ile Tyr Tyr Ile Asp Ser Leu Lys
1               5                   10                  15

Gly

<210> SEQ ID NO 24
<211> LENGTH: 17
<212> TYPE: PRT
<213> ORGANISM: Artificial Sequence
<220> FEATURE:
<223> OTHER INFORMATION: BCMA 269A37953 VHH CDR2

<400> SEQUENCE: 24

Ala Ile Met Trp Asn Asp Gly Ile Thr Tyr Leu Gln Asp Ser Val Lys
1               5                   10                  15

Gly

<210> SEQ ID NO 25
<211> LENGTH: 17
<212> TYPE: PRT
<213> ORGANISM: Artificial Sequence
<220> FEATURE:
<223> OTHER INFORMATION: BCMA 269A37965 VHH CDR2

<400> SEQUENCE: 25

Ala Ile Asp Trp Ser Gly Arg Thr Thr Asn Tyr Ala Asp Pro Val Glu
1               5                   10                  15

Gly

<210> SEQ ID NO 26
<211> LENGTH: 17
<212> TYPE: PRT
<213> ORGANISM: Artificial Sequence
<220> FEATURE:
<223> OTHER INFORMATION: BCMA 269A37972 VHH CDR2

<400> SEQUENCE: 26

Ser Ile Thr Trp Asp Gly Arg Thr Thr Tyr Tyr Ala Asp Ser Val Lys
1               5                   10                  15

Gly

<210> SEQ ID NO 27
<211> LENGTH: 17
<212> TYPE: PRT
<213> ORGANISM: Artificial Sequence
<220> FEATURE:
<223> OTHER INFORMATION: BCMA 269A37353 VHH CDR2

<400> SEQUENCE: 27

Val Ile Gly Trp Arg Asp Ile Ser Thr Ser Tyr Ala Asp Ser Val Lys
1               5                   10                  15

Gly

<210> SEQ ID NO 28
<211> LENGTH: 17
<212> TYPE: PRT
<213> ORGANISM: Artificial Sequence
<220> FEATURE:
<223> OTHER INFORMATION: BCMA 269A37948 VHH CDR2

<400> SEQUENCE: 28

Gly Ile Ala Trp Ser Gly Gly Ser Thr Ala Tyr Ala Asp Ser Val Lys
1               5                   10                  15

Gly

<210> SEQ ID NO 29
<211> LENGTH: 14
<212> TYPE: PRT
<213> ORGANISM: Artificial Sequence
<220> FEATURE:
<223> OTHER INFORMATION: BCMA 269A37346 VHH CDR3

<400> SEQUENCE: 29

Ala Gly Ala Asp Cys Ser Gly Tyr Leu Arg Asp Tyr Glu Phe
1               5                   10

<210> SEQ ID NO 30
<211> LENGTH: 18
<212> TYPE: PRT

```
<213> ORGANISM: Artificial Sequence
<220> FEATURE:
<223> OTHER INFORMATION: BCMA 269A37348 VHH CDR3

<400> SEQUENCE: 30

Ala Gly Thr Gly Cys Ser Thr Tyr Gly Cys Phe Asp Ala Gln Ile Ile
1               5                   10                  15

Asp Tyr

<210> SEQ ID NO 31
<211> LENGTH: 13
<212> TYPE: PRT
<213> ORGANISM: Artificial Sequence
<220> FEATURE:
<223> OTHER INFORMATION: BCMA 269A37917 VHH CDR3

<400> SEQUENCE: 31

Ala Asp Arg Lys Ser Val Met Ser Ile Arg Pro Asp Tyr
1               5                   10

<210> SEQ ID NO 32
<211> LENGTH: 13
<212> TYPE: PRT
<213> ORGANISM: Artificial Sequence
<220> FEATURE:
<223> OTHER INFORMATION: BCMA 269A37355 VHH CDR3

<400> SEQUENCE: 32

Val Tyr Val Thr Leu Leu Gly Gly Val Asn Arg Asp Tyr
1               5                   10

<210> SEQ ID NO 33
<211> LENGTH: 11
<212> TYPE: PRT
<213> ORGANISM: Artificial Sequence
<220> FEATURE:
<223> OTHER INFORMATION: BCMA 269A37915 VHH CDR3

<400> SEQUENCE: 33

Ala Ser Lys Gly Arg Tyr Ser Glu Tyr Glu Tyr
1               5                   10

<210> SEQ ID NO 34
<211> LENGTH: 17
<212> TYPE: PRT
<213> ORGANISM: Artificial Sequence
<220> FEATURE:
<223> OTHER INFORMATION: BCMA 269A37936 VHH CDR3

<400> SEQUENCE: 34

Ala Ser Pro Glu Asp Trp Tyr Thr Asp Trp Ile Asp Trp Ser Ile Tyr
1               5                   10                  15

Arg

<210> SEQ ID NO 35
<211> LENGTH: 11
<212> TYPE: PRT
<213> ORGANISM: Artificial Sequence
<220> FEATURE:
<223> OTHER INFORMATION: BCMA 269A37953 VHH CDR3

<400> SEQUENCE: 35

Ala Ser Lys Gly Arg Tyr Ser Glu Tyr Glu Tyr
1               5                   10
```

```
<210> SEQ ID NO 36
<211> LENGTH: 12
<212> TYPE: PRT
<213> ORGANISM: Artificial Sequence
<220> FEATURE:
<223> OTHER INFORMATION: BCMA 269A37965 VHH CDR3

<400> SEQUENCE: 36

Val Leu Arg Ala Trp Ile Ser Tyr Asp Asn Asp Tyr
1               5                   10

<210> SEQ ID NO 37
<211> LENGTH: 12
<212> TYPE: PRT
<213> ORGANISM: Artificial Sequence
<220> FEATURE:
<223> OTHER INFORMATION: BCMA 269A37972 VHH CDR3

<400> SEQUENCE: 37

Asp Leu Gly Lys Trp Pro Ala Gly Pro Ala Asp Tyr
1               5                   10

<210> SEQ ID NO 38
<211> LENGTH: 11
<212> TYPE: PRT
<213> ORGANISM: Artificial Sequence
<220> FEATURE:
<223> OTHER INFORMATION: BCMA 269A37353 VHH CDR3

<400> SEQUENCE: 38

Ala Arg Arg Ile Asp Ala Ala Asp Phe Asp Ser
1               5                   10

<210> SEQ ID NO 39
<211> LENGTH: 11
<212> TYPE: PRT
<213> ORGANISM: Artificial Sequence
<220> FEATURE:
<223> OTHER INFORMATION: BCMA 269A37948 VHH CDR3

<400> SEQUENCE: 39

Ser Arg Gly Ile Glu Val Glu Glu Phe Gly Ala
1               5                   10

<210> SEQ ID NO 40
<211> LENGTH: 11
<212> TYPE: PRT
<213> ORGANISM: Artificial Sequence
<220> FEATURE:
<223> OTHER INFORMATION: CD38 38A37333 VHH CDR1

<400> SEQUENCE: 40

Ser Gly Leu Thr Phe Ser Ser Tyr Pro Met Met
1               5                   10

<210> SEQ ID NO 41
<211> LENGTH: 11
<212> TYPE: PRT
<213> ORGANISM: Artificial Sequence
<220> FEATURE:
<223> OTHER INFORMATION: CD38 38A37336 VHH CDR1

<400> SEQUENCE: 41

Ser Gly Phe Thr Phe Ser Ser Asn Trp Met Tyr
1               5                   10

<210> SEQ ID NO 42
```

-continued

```
<211> LENGTH: 11
<212> TYPE: PRT
<213> ORGANISM: Artificial Sequence
<220> FEATURE:
<223> OTHER INFORMATION: CD38 38A37699 VHH CDR1

<400> SEQUENCE: 42

Ser Gly Arg Ile Phe Ser Ile Asn Ala Met Gly
1               5                   10

<210> SEQ ID NO 43
<211> LENGTH: 14
<212> TYPE: PRT
<213> ORGANISM: Artificial Sequence
<220> FEATURE:
<223> OTHER INFORMATION: CD38 38A37331 VHH CDR1

<400> SEQUENCE: 43

Ser Gly Ser Ile Phe Lys Val Phe Arg Val Phe Ala Met Ser
1               5                   10

<210> SEQ ID NO 44
<211> LENGTH: 11
<212> TYPE: PRT
<213> ORGANISM: Artificial Sequence
<220> FEATURE:
<223> OTHER INFORMATION: CD38 38A37717 VHH CDR1

<400> SEQUENCE: 44

Thr Gly Lys Val Phe Ser Ile Tyr Asp Met Gly
1               5                   10

<210> SEQ ID NO 45
<211> LENGTH: 11
<212> TYPE: PRT
<213> ORGANISM: Artificial Sequence
<220> FEATURE:
<223> OTHER INFORMATION: CD38 38A37719 VHH CDR1

<400> SEQUENCE: 45

Ser Ala Ser Ile Phe Thr Arg Leu Pro Met Gly
1               5                   10

<210> SEQ ID NO 46
<211> LENGTH: 9
<212> TYPE: PRT
<213> ORGANISM: Artificial Sequence
<220> FEATURE:
<223> OTHER INFORMATION: CD38 38A37330 VHH CDR1

<400> SEQUENCE: 46

Ser Gly Arg Ala Tyr Ala Thr Met Ala
1               5

<210> SEQ ID NO 47
<211> LENGTH: 11
<212> TYPE: PRT
<213> ORGANISM: Artificial Sequence
<220> FEATURE:
<223> OTHER INFORMATION: CD38 38A37334 VHH CDR1

<400> SEQUENCE: 47

Ser Gly Leu Thr Phe Ser Ser Tyr Ile Met Gly
1               5                   10

<210> SEQ ID NO 48
<211> LENGTH: 11
```

```
<212> TYPE: PRT
<213> ORGANISM: Artificial Sequence
<220> FEATURE:
<223> OTHER INFORMATION: CD38 38A37730 VHH CDR1

<400> SEQUENCE: 48

Ser Gln Gly Ile Phe Thr Ile Asn Ala Met Gly
1               5                   10

<210> SEQ ID NO 49
<211> LENGTH: 11
<212> TYPE: PRT
<213> ORGANISM: Artificial Sequence
<220> FEATURE:
<223> OTHER INFORMATION: CD38 38A37340 VHH CDR1

<400> SEQUENCE: 49

Ser Gly Arg Thr Phe Ser Ser Tyr Ala Met Ala
1               5                   10

<210> SEQ ID NO 50
<211> LENGTH: 11
<212> TYPE: PRT
<213> ORGANISM: Artificial Sequence
<220> FEATURE:
<223> OTHER INFORMATION: CD38 38A37731 VHH CDR1

<400> SEQUENCE: 50

Ser Gly Thr Ile Val Ser Ile Ser Thr Met Gly
1               5                   10

<210> SEQ ID NO 51
<211> LENGTH: 8
<212> TYPE: PRT
<213> ORGANISM: Artificial Sequence
<220> FEATURE:
<223> OTHER INFORMATION: CD38 38A37326 VHH CDR1

<400> SEQUENCE: 51

Ser Gly Arg Thr Tyr Ala Met Gly
1               5

<210> SEQ ID NO 52
<211> LENGTH: 17
<212> TYPE: PRT
<213> ORGANISM: Artificial Sequence
<220> FEATURE:
<223> OTHER INFORMATION: CD38 38A37333 VHH CDR2

<400> SEQUENCE: 52

Arg Ile Ser Asp Ser Gly Gly Tyr Thr Asn Tyr Asp Ser Val Lys
1               5                   10                  15

Gly

<210> SEQ ID NO 53
<211> LENGTH: 17
<212> TYPE: PRT
<213> ORGANISM: Artificial Sequence
<220> FEATURE:
<223> OTHER INFORMATION: CD38 38A37336 VHH CDR2

<400> SEQUENCE: 53

Thr Ile Ser Thr Asp Gly Arg Gly Thr Tyr Tyr Lys Asp Ser Val Lys
1               5                   10                  15

Gly
```

```
<210> SEQ ID NO 54
<211> LENGTH: 16
<212> TYPE: PRT
<213> ORGANISM: Artificial Sequence
<220> FEATURE:
<223> OTHER INFORMATION: CD38 38A37699 VHH CDR2

<400> SEQUENCE: 54

Ala Ile Ser Thr Ala Gly Ser Thr Asn Tyr Gly Asp Ser Val Lys Gly
1               5                   10                  15

<210> SEQ ID NO 55
<211> LENGTH: 16
<212> TYPE: PRT
<213> ORGANISM: Artificial Sequence
<220> FEATURE:
<223> OTHER INFORMATION: CD38 38A37331 VHH CDR2

<400> SEQUENCE: 55

Ser Ile Ser Ser Gly Glu Thr Thr Thr Tyr Ala Asp Ser Val Lys Gly
1               5                   10                  15

<210> SEQ ID NO 56
<211> LENGTH: 16
<212> TYPE: PRT
<213> ORGANISM: Artificial Sequence
<220> FEATURE:
<223> OTHER INFORMATION: CD38 38A37717 VHH CDR2

<400> SEQUENCE: 56

Glu Ile Thr Ser Ser Gly Thr Thr His Tyr Asp Asp Phe Val Ser Gly
1               5                   10                  15

<210> SEQ ID NO 57
<211> LENGTH: 16
<212> TYPE: PRT
<213> ORGANISM: Artificial Sequence
<220> FEATURE:
<223> OTHER INFORMATION: CD38 38A37719 VHH CDR2

<400> SEQUENCE: 57

Gly Ile Val Pro Ser Gly Arg Ile Asn Tyr Ala Asp Ser Val Lys Gly
1               5                   10                  15

<210> SEQ ID NO 58
<211> LENGTH: 17
<212> TYPE: PRT
<213> ORGANISM: Artificial Sequence
<220> FEATURE:
<223> OTHER INFORMATION: CD38 38A37330 VHH CDR2

<400> SEQUENCE: 58

His Leu Arg Val Ser Gly Asp Thr Thr Tyr Tyr Thr Asp Ser Val Lys
1               5                   10                  15
Gly

<210> SEQ ID NO 59
<211> LENGTH: 16
<212> TYPE: PRT
<213> ORGANISM: Artificial Sequence
<220> FEATURE:
<223> OTHER INFORMATION: CD38 38A37334 VHH CDR2

<400> SEQUENCE: 59

Glu Ile Ser Ser Gly Gly Met Thr Ser Tyr Ala Asp Ser Val Lys Gly
1               5                   10                  15
```

<210> SEQ ID NO 60
<211> LENGTH: 16
<212> TYPE: PRT
<213> ORGANISM: Artificial Sequence
<220> FEATURE:
<223> OTHER INFORMATION: CD38 38A37730 VHH CDR2

<400> SEQUENCE: 60

Glu Val Ser Ser Gly Gly Arg Thr Asp Tyr Ala Asp Ser Val Lys Gly
1               5                   10                  15

<210> SEQ ID NO 61
<211> LENGTH: 17
<212> TYPE: PRT
<213> ORGANISM: Artificial Sequence
<220> FEATURE:
<223> OTHER INFORMATION: CD38 38A37340 VHH CDR2

<400> SEQUENCE: 61

Ser Ile Ser Thr Ser Gly Gly Ile Thr Asp Tyr Ala Asp Ser Val Lys
1               5                   10                  15

Gly

<210> SEQ ID NO 62
<211> LENGTH: 16
<212> TYPE: PRT
<213> ORGANISM: Artificial Sequence
<220> FEATURE:
<223> OTHER INFORMATION: CD38 38A37731 VHH CDR2

<400> SEQUENCE: 62

Thr Ile Thr Arg Arg Gly Arg Thr Asn Tyr Thr Asp Ser Val Lys Gly
1               5                   10                  15

<210> SEQ ID NO 63
<211> LENGTH: 16
<212> TYPE: PRT
<213> ORGANISM: Artificial Sequence
<220> FEATURE:
<223> OTHER INFORMATION: CD38 38A37326 VHH CDR2

<400> SEQUENCE: 63

Thr Ile Ser Gly Ala Gly Asn Thr Lys Tyr Ala Asp Ser Val Lys Gly
1               5                   10                  15

<210> SEQ ID NO 64
<211> LENGTH: 6
<212> TYPE: PRT
<213> ORGANISM: Artificial Sequence
<220> FEATURE:
<223> OTHER INFORMATION: CD38 38A37333 VHH CDR3

<400> SEQUENCE: 64

Ile Leu Gly Leu Pro Thr
1               5

<210> SEQ ID NO 65
<211> LENGTH: 18
<212> TYPE: PRT
<213> ORGANISM: Artificial Sequence
<220> FEATURE:
<223> OTHER INFORMATION: CD38 38A37336 VHH CDR3

<400> SEQUENCE: 65

Lys Glu Pro Arg Val Leu Met Ala Tyr Leu Arg Asn Leu Gly Asp Phe

```
1               5                  10                  15
Gly Ser

<210> SEQ ID NO 66
<211> LENGTH: 8
<212> TYPE: PRT
<213> ORGANISM: Artificial Sequence
<220> FEATURE:
<223> OTHER INFORMATION: CD38 38A37699 VHH CDR3

<400> SEQUENCE: 66

Leu Asn Phe Pro Pro Tyr Val Tyr
1               5

<210> SEQ ID NO 67
<211> LENGTH: 9
<212> TYPE: PRT
<213> ORGANISM: Artificial Sequence
<220> FEATURE:
<223> OTHER INFORMATION: CD38 38A37331 VHH CDR3

<400> SEQUENCE: 67

Ala Asp His Thr Phe Thr Gly Asp Phe
1               5

<210> SEQ ID NO 68
<211> LENGTH: 8
<212> TYPE: PRT
<213> ORGANISM: Artificial Sequence
<220> FEATURE:
<223> OTHER INFORMATION: CD38 38A37717 VHH CDR3

<400> SEQUENCE: 68

Asn His Val Phe Gly Gly Ser Tyr
1               5

<210> SEQ ID NO 69
<211> LENGTH: 8
<212> TYPE: PRT
<213> ORGANISM: Artificial Sequence
<220> FEATURE:
<223> OTHER INFORMATION: CD38 38A37719 VHH CDR3

<400> SEQUENCE: 69

Ala Asp Thr Phe Pro Leu Pro Thr
1               5

<210> SEQ ID NO 70
<211> LENGTH: 19
<212> TYPE: PRT
<213> ORGANISM: Artificial Sequence
<220> FEATURE:
<223> OTHER INFORMATION: CD38 38A37330 VHH CDR3

<400> SEQUENCE: 70

Gly Pro Tyr Gly Ile Leu Ala Ala Ala Arg Val Ser Asn Pro Gly Asn
1               5                  10                  15

Tyr Asp Tyr

<210> SEQ ID NO 71
<211> LENGTH: 16
<212> TYPE: PRT
<213> ORGANISM: Artificial Sequence
<220> FEATURE:
<223> OTHER INFORMATION: CD38 38A37334 VHH CDR3
```

```
<400> SEQUENCE: 71

Ala Pro Glu Arg Gly Ser Ile Trp Tyr Ser Arg Tyr Glu Tyr Lys Tyr
1               5                   10                  15

<210> SEQ ID NO 72
<211> LENGTH: 13
<212> TYPE: PRT
<213> ORGANISM: Artificial Sequence
<220> FEATURE:
<223> OTHER INFORMATION: CD38 38A37730 VHH CDR3

<400> SEQUENCE: 72

Val Ser Gly Trp His Val Phe Val Gly Asp Arg Ile Val
1               5                   10

<210> SEQ ID NO 73
<211> LENGTH: 14
<212> TYPE: PRT
<213> ORGANISM: Artificial Sequence
<220> FEATURE:
<223> OTHER INFORMATION: CD38 38A37340 VHH CDR3

<400> SEQUENCE: 73

Ala Arg Thr Trp Tyr Leu Arg Thr Ser Leu Gln Tyr Asp Tyr
1               5                   10

<210> SEQ ID NO 74
<211> LENGTH: 14
<212> TYPE: PRT
<213> ORGANISM: Artificial Sequence
<220> FEATURE:
<223> OTHER INFORMATION: CD38 38A37731 VHH CDR3

<400> SEQUENCE: 74

Ala Glu Val Gln Leu Asp Ile Trp Ala Ser Ala Tyr Asp Tyr
1               5                   10

<210> SEQ ID NO 75
<211> LENGTH: 11
<212> TYPE: PRT
<213> ORGANISM: Artificial Sequence
<220> FEATURE:
<223> OTHER INFORMATION: CD38 38A37326 VHH CDR3

<400> SEQUENCE: 75

Ala Gly Lys Trp Phe Pro Ala Ala Asn Glu Tyr
1               5                   10

<210> SEQ ID NO 76
<211> LENGTH: 117
<212> TYPE: PRT
<213> ORGANISM: Artificial Sequence
<220> FEATURE:
<223> OTHER INFORMATION: CD19 single-domain antibody VHH

<400> SEQUENCE: 76

Gln Val Lys Leu Glu Glu Ser Gly Gly Glu Leu Val Gln Pro Gly Gly
1               5                   10                  15

Pro Leu Arg Leu Ser Cys Ala Ala Ser Gly Asn Ile Phe Ser Ile Asn
            20                  25                  30

Arg Met Gly Trp Tyr Arg Gln Ala Pro Gly Lys Gln Arg Ala Phe Val
        35                  40                  45

Ala Ser Ile Thr Val Arg Gly Ile Thr Asn Tyr Ala Asp Ser Val Lys
    50                  55                  60
```

```
Gly Arg Phe Thr Ile Ser Val Asp Lys Ser Lys Asn Thr Ile Tyr Leu
 65                  70                  75                  80

Gln Met Asn Ala Leu Lys Pro Glu Asp Thr Ala Val Tyr Tyr Cys Asn
                 85                  90                  95

Ala Val Ser Ser Asn Arg Asp Pro Asp Tyr Trp Gly Gln Gly Thr Gln
            100                 105                 110

Val Thr Val Ser Ser
            115

<210> SEQ ID NO 77
<211> LENGTH: 129
<212> TYPE: PRT
<213> ORGANISM: Artificial Sequence
<220> FEATURE:
<223> OTHER INFORMATION: CD20 single-domain antibody VHH

<400> SEQUENCE: 77

Pro Val Gln Leu Val Glu Ser Gly Gly Gly Leu Val Gln Ala Gly Asp
  1               5                  10                  15

Ser Leu Arg Leu Ser Cys Ala Ala Ser Gly Arg Thr Phe Gly Ile Gly
                 20                  25                  30

Thr Met Gly Trp Phe Arg Gln Pro Pro Gly Lys Glu Arg Glu Phe Val
             35                  40                  45

Ala Ala Ile Arg Trp Ser Thr Gly Gly Thr Arg Tyr Ala Asp Ser Val
 50                  55                  60

Lys Gly Arg Phe Thr Ile Ser Arg Asp Asn Ala Lys Leu Thr Val Asp
 65                  70                  75                  80

Leu Gln Met Asp Ser Leu Lys Pro Glu Asp Thr Ala Val Tyr Tyr Cys
                 85                  90                  95

Ala Ala Asp Arg Leu Ser Leu Asp Leu Ser Gly Arg Tyr His Tyr Asn
            100                 105                 110

Pro Ala Val Tyr Asp Tyr Trp Gly Gln Gly Thr Gln Val Thr Val Ser
            115                 120                 125

Ser

<210> SEQ ID NO 78
<211> LENGTH: 122
<212> TYPE: PRT
<213> ORGANISM: Artificial Sequence
<220> FEATURE:
<223> OTHER INFORMATION: BCMA 269A37346 VHH

<400> SEQUENCE: 78

Gln Val Gln Leu Val Glu Ser Gly Gly Gly Leu Val Gln Pro Gly Gly
  1               5                  10                  15

Ser Leu Arg Leu Ser Cys Glu Ala Ser Gly Phe Thr Leu Asp Tyr Tyr
                 20                  25                  30

Ala Ile Gly Trp Phe Arg Gln Ala Pro Gly Lys Glu Arg Glu Gly Val
             35                  40                  45

Ile Cys Ile Ser Arg Ser Asp Gly Ser Thr Tyr Tyr Ala Asp Ser Val
 50                  55                  60

Lys Gly Arg Phe Thr Ile Ser Arg Asp Asn Ala Lys Lys Thr Val Tyr
 65                  70                  75                  80

Leu Gln Met Ile Ser Leu Lys Pro Glu Asp Thr Ala Ala Tyr Tyr Cys
                 85                  90                  95

Ala Ala Gly Ala Asp Cys Ser Gly Tyr Leu Arg Asp Tyr Glu Phe Arg
            100                 105                 110
```

```
Gly Gln Gly Thr Gln Val Thr Val Ser Ser
        115                 120
```

```
<210> SEQ ID NO 79
<211> LENGTH: 128
<212> TYPE: PRT
<213> ORGANISM: Artificial Sequence
<220> FEATURE:
<223> OTHER INFORMATION: BCMA 269A37348 VHH

<400> SEQUENCE: 79

Gln Val Lys Leu Glu Glu Ser Gly Gly Arg Leu Val Gln Pro Arg Gly
1               5                   10                  15

Ser Leu Arg Leu Ser Cys Ala Gly Ser Gly Arg Thr Phe Ser Thr Tyr
            20                  25                  30

Gly Met Ala Trp Phe Arg Gln Ala Pro Gly Lys Glu Arg Glu Phe Val
        35                  40                  45

Ala Ser Lys Ala Ser Met Asn Tyr Ser Gly Arg Thr Tyr Tyr Ala Asp
    50                  55                  60

Ser Val Lys Gly Arg Phe Thr Ile Ala Arg Asp Asn Ala Lys Asn Met
65                  70                  75                  80

Val Phe Leu Gln Met Asn Asn Leu Lys Pro Glu Asp Thr Ala Val Tyr
                85                  90                  95

Tyr Cys Ala Ala Gly Thr Gly Cys Ser Thr Tyr Gly Cys Phe Asp Ala
            100                 105                 110

Gln Ile Ile Asp Tyr Trp Gly Lys Gly Thr Leu Val Thr Val Ser Ser
        115                 120                 125
```

```
<210> SEQ ID NO 80
<211> LENGTH: 118
<212> TYPE: PRT
<213> ORGANISM: Artificial Sequence
<220> FEATURE:
<223> OTHER INFORMATION: BCMA 269A37917 VHH

<400> SEQUENCE: 80

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Thr Met Gly
            20                  25                  30

Trp Phe Arg Gln Ala Pro Gly Lys Glu Arg Glu Phe Val Ala Ala Ile
        35                  40                  45

Ser Leu Ser Pro Thr Leu Ala Tyr Tyr Ala Glu Ser Val Lys Gly Arg
    50                  55                  60

Phe Thr Ile Ser Arg Asp Asn Ala Lys Asn Thr Val Val Leu Gln Met
65                  70                  75                  80

Asn Ser Leu Lys Pro Glu Asp Thr Ala Leu Tyr Tyr Cys Ala Ala Asp
                85                  90                  95

Arg Lys Ser Val Met Ser Ile Arg Pro Asp Tyr Trp Gly Gln Gly Thr
            100                 105                 110

Gln Val Thr Val Ser Ser
        115
```

```
<210> SEQ ID NO 81
<211> LENGTH: 120
<212> TYPE: PRT
<213> ORGANISM: Artificial Sequence
<220> FEATURE:
<223> OTHER INFORMATION: BCMA 269A37355 VHH
```

-continued

```
<400> SEQUENCE: 81

Ala Val Gln Leu Val Asp Ser Gly Gly Gly Leu Val Gln Pro Gly Gly
1               5                   10                  15

Ser Leu Arg Leu Ser Cys Val Ala Ser Gly Gly Ile Phe Val Ile Asn
            20                  25                  30

Ala Met Gly Trp Tyr Arg Gln Ala Pro Gly Lys Gln Arg Glu Leu Val
        35                  40                  45

Ala Ser Ile Arg Gly Leu Gly Arg Thr Asn Tyr Asp Asp Ser Val Lys
    50                  55                  60

Gly Arg Phe Thr Ile Ser Arg Asp Asn Ala Asn Asn Thr Val Tyr Leu
65                  70                  75                  80

Gln Met Asn Ser Leu Glu Pro Glu Asp Thr Ala Val Tyr Tyr Cys Thr
                85                  90                  95

Val Tyr Val Thr Leu Leu Gly Gly Val Asn Arg Asp Tyr Trp Gly Gln
            100                 105                 110

Gly Thr Gln Val Thr Val Ser Ser
        115                 120

<210> SEQ ID NO 82
<211> LENGTH: 119
<212> TYPE: PRT
<213> ORGANISM: Artificial Sequence
<220> FEATURE:
<223> OTHER INFORMATION: BCMA 269A37915 VHH

<400> SEQUENCE: 82

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Ile
            20                  25                  30

Val Met Gly Trp Phe Arg Gln Ala Pro Gly Lys Glu Arg Glu Phe Val
        35                  40                  45

Gly Ala Ile Met Trp Asn Asp Gly Ile Thr Tyr Leu Gln Asp Ser Val
    50                  55                  60

Lys Gly Arg Phe Thr Ile Phe Arg Asp Asn Ala Lys Asn Thr Val Tyr
65                  70                  75                  80

Leu Gln Met Asn Ser Leu Lys Leu Glu Asp Thr Ala Val Tyr Tyr Cys
                85                  90                  95

Ala Ala Ser Lys Gly Arg Tyr Ser Glu Tyr Glu Tyr Trp Gly Gln Gly
            100                 105                 110

Thr Gln Val Thr Val Ser Ser
        115

<210> SEQ ID NO 83
<211> LENGTH: 128
<212> TYPE: PRT
<213> ORGANISM: Artificial Sequence
<220> FEATURE:
<223> OTHER INFORMATION: BCMA 269A37936 VHH

<400> SEQUENCE: 83

Glu Val Gln Leu Val Glu Ser Gly Gly Gly Val Val Gln Ala Gly Gly
1               5                   10                  15

Ser Leu Thr Val Ser Cys Thr Ala Ser Gly Phe Thr Phe Asp Arg Ala
            20                  25                  30

Val Ile Val Trp Phe Arg Gln Ala Pro Gly Lys Gly Arg Glu Gly Val
        35                  40                  45
```

```
Ser Phe Ile Lys Pro Ser Asp Gly Thr Ile Tyr Tyr Ile Asp Ser Leu
    50                  55                  60

Lys Gly Arg Phe Thr Ile Ser Ser Asp Ile Ala Lys Asn Thr Val Tyr
 65                  70                  75                  80

Leu Gln Met Lys Ser Leu Glu Ser Glu Asp Ser Ala Val Tyr Tyr Cys
                 85                  90                  95

Ala Ala Ser Pro Glu Asp Trp Tyr Thr Asp Trp Ile Asp Trp Ser Ile
                100                 105                 110

Tyr Arg Trp Gln His Trp Gly Gln Gly Thr Gln Val Thr Val Ser Ser
            115                 120                 125
```

<210> SEQ ID NO 84
<211> LENGTH: 119
<212> TYPE: PRT
<213> ORGANISM: Artificial Sequence
<220> FEATURE:
<223> OTHER INFORMATION: BCMA 269A37953 VHH

<400> SEQUENCE: 84

```
Glu Val Gln Leu Val Glu Ser Gly Gly Gly Met Val Gln Ala Gly Asp
 1               5                  10                  15

Ser Leu Arg Leu Ser Cys Val Gly Ser Thr Tyr Thr Val Asn Ser Asp
             20                  25                  30

Val Met Gly Trp Phe Arg Gln Ala Pro Gly Lys Glu Arg Glu Phe Val
         35                  40                  45

Gly Ala Ile Met Trp Asn Asp Gly Ile Thr Tyr Leu Gln Asp Ser Val
     50                  55                  60

Lys Gly Arg Phe Thr Ile Phe Arg Asp Asn Ala Lys Asn Thr Val Tyr
 65                  70                  75                  80

Leu Gln Met Asn Ser Leu Lys Leu Glu Asp Thr Ala Val Tyr Tyr Cys
                 85                  90                  95

Ala Ala Ser Lys Gly Arg Tyr Ser Glu Tyr Glu Tyr Trp Gly Gln Gly
                100                 105                 110

Thr Gln Val Thr Val Ser Ser
            115
```

<210> SEQ ID NO 85
<211> LENGTH: 120
<212> TYPE: PRT
<213> ORGANISM: Artificial Sequence
<220> FEATURE:
<223> OTHER INFORMATION: BCMA 269A37965 VHH

<400> SEQUENCE: 85

```
Ala Val Gln Leu Val Glu Ser Gly Gly Gly Leu Val Gln Ala Gly Asp
 1               5                  10                  15

Ser Leu Arg Leu Ser Cys Thr Ala Ser Gly Ala Thr Leu Thr Asn Asp
             20                  25                  30

His Met Ala Trp Phe Arg Gln Ala Pro Gly Lys Gly Arg Glu Phe Val
         35                  40                  45

Ala Ala Ile Asp Trp Ser Gly Arg Thr Thr Asn Tyr Ala Asp Pro Val
     50                  55                  60

Glu Gly Arg Phe Thr Ile Ser Arg Asn Asn Ala Lys Asn Thr Val Tyr
 65                  70                  75                  80

Leu Glu Met Asn Ser Leu Lys Leu Glu Asp Thr Ala Val Tyr Tyr Cys
                 85                  90                  95

Ala Val Leu Arg Ala Trp Ile Ser Tyr Asp Asn Asp Tyr Trp Gly Gln
                100                 105                 110
```

```
Gly Thr Gln Val Thr Val Ser Ser
        115                 120

<210> SEQ ID NO 86
<211> LENGTH: 120
<212> TYPE: PRT
<213> ORGANISM: Artificial Sequence
<220> FEATURE:
<223> OTHER INFORMATION: BCMA 269A37972 VHH

<400> SEQUENCE: 86

Gln Val Gln Leu Val Glu Ser Gly Gly Gly Leu Val Gln Ala Gly Gly
1               5                   10                  15

Ser Leu Arg Leu Ser Cys Ala Ala Ser Gly Gly Thr Leu Ser Lys Asn
            20                  25                  30

Thr Val Ala Trp Phe Arg Gln Ala Pro Gly Lys Glu Arg Gly Phe Val
        35                  40                  45

Ala Ser Ile Thr Trp Asp Gly Arg Thr Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Val Cys
                85                  90                  95

Ala Asp Leu Gly Lys Trp Pro Ala Gly Pro Ala Asp Tyr Trp Gly Gln
            100                 105                 110

Gly Thr Gln Val Thr Val Ser Ser
        115                 120

<210> SEQ ID NO 87
<211> LENGTH: 119
<212> TYPE: PRT
<213> ORGANISM: Artificial Sequence
<220> FEATURE:
<223> OTHER INFORMATION: BCMA 269A37353 VHH

<400> SEQUENCE: 87

Gln Val Lys Leu Glu Glu Ser Gly Gly Gly Leu Val Gln Ala Gly Arg
1               5                   10                  15

Ser Leu Arg Leu Ser Cys Ala Ala Ser Glu His Thr Phe Ser Ser His
            20                  25                  30

Val Met Gly Trp Phe Arg Gln Ala Pro Gly Lys Glu Arg Glu Ser Val
        35                  40                  45

Ala Val Ile Gly Trp Arg Asp Ile Ser Thr Ser Tyr Ala Asp Ser Val
    50                  55                  60

Lys Gly Arg Phe Thr Ile Ser Arg Asp Asn Ala Lys Lys Thr Leu Tyr
65                  70                  75                  80

Leu Gln Met Asn Ser Leu Lys Pro Glu Asp Thr Ala Val Tyr Tyr Cys
                85                  90                  95

Ala Ala Arg Arg Ile Asp Ala Ala Asp Phe Asp Ser Trp Gly Gln Gly
            100                 105                 110

Thr Gln Val Thr Val Ser Ser
        115

<210> SEQ ID NO 88
<211> LENGTH: 119
<212> TYPE: PRT
<213> ORGANISM: Artificial Sequence
<220> FEATURE:
<223> OTHER INFORMATION: BCMA 269A37948 VHH
```

<400> SEQUENCE: 88

Ala Val Gln Leu Val Glu Ser Gly Gly Gly Leu Val Gln Ala Gly Asp
1               5                   10                  15

Ser Leu Arg Leu Thr Cys Thr Ala Ser Gly Arg Ala Phe Ser Thr Tyr
            20                  25                  30

Phe Met Ala Trp Phe Arg Gln Ala Pro Gly Lys Glu Arg Glu Phe Val
        35                  40                  45

Ala Gly Ile Ala Trp Ser Gly Ser Thr Ala Tyr Ala Asp Ser Val
50                  55                  60

Lys Gly Arg Phe Thr Ile Ser Arg Asp Asn Ala Lys Asn Thr Val Tyr
65                  70                  75                  80

Leu Gln Met Asn Ser Leu Lys Ser Glu Asp Thr Ala Val Tyr Tyr Cys
                85                  90                  95

Ala Ser Arg Gly Ile Glu Val Glu Glu Phe Gly Ala Trp Gly Gln Gly
                100                 105                 110

Thr Gln Val Thr Val Ser Ser
            115

<210> SEQ ID NO 89
<211> LENGTH: 114
<212> TYPE: PRT
<213> ORGANISM: Artificial Sequence
<220> FEATURE:
<223> OTHER INFORMATION: CD38 38A37333 VHH

<400> SEQUENCE: 89

Asp Val Gln Leu Val Glu Ser Gly Gly Gly Leu Val Gln Pro Gly Gly
1               5                   10                  15

Ser Leu Arg Leu Ser Cys Val Ala Ser Gly Leu Thr Phe Ser Ser Tyr
            20                  25                  30

Pro Met Met Trp Val Arg Gln Ala Pro Gly Lys Gly Leu Glu Trp Val
        35                  40                  45

Ser Arg Ile Ser Asp Ser Gly Gly Tyr Thr Asn Tyr Asp Asp Ser Val
50                  55                  60

Lys Gly Arg Phe Thr Ile Ser Arg Asp Asn Ala Lys Asn Thr Leu Tyr
65                  70                  75                  80

Leu Gln Met Asn Ser Leu Thr Pro Glu Asp Thr Ala Val Tyr Tyr Cys
                85                  90                  95

Arg Ile Leu Gly Leu Pro Thr Thr Gly Gln Gly Thr Gln Val Thr Val
                100                 105                 110

Ser Ser

<210> SEQ ID NO 90
<211> LENGTH: 126
<212> TYPE: PRT
<213> ORGANISM: Artificial Sequence
<220> FEATURE:
<223> OTHER INFORMATION: CD38 38A37336 VHH

<400> SEQUENCE: 90

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Trp Met Tyr Trp Val Arg Gln Ala Pro Gly Lys Gly Leu Glu Trp Val
        35                  40                  45

Ala Thr Ile Ser Thr Asp Gly Arg Gly Thr Tyr Tyr Lys Asp Ser Val
 50                  55                  60

Lys Gly Arg Phe Thr Val Ser Arg Asp Asn Ala Met Ser Thr Leu Leu
 65                  70                  75                  80

Leu Gln Met Asn Asn Leu Lys Ser Glu Asp Thr Ala Val Tyr Tyr Cys
                 85                  90                  95

Ala Lys Glu Pro Arg Val Leu Met Ala Tyr Leu Arg Asn Leu Gly Asp
            100                 105                 110

Phe Gly Ser Trp Gly Gln Gly Thr Gln Val Thr Val Ser Ser
        115                 120                 125

<210> SEQ ID NO 91
<211> LENGTH: 115
<212> TYPE: PRT
<213> ORGANISM: Artificial Sequence
<220> FEATURE:
<223> OTHER INFORMATION: CD38 38A37699 VHH

<400> SEQUENCE: 91

Gln Val Gln Leu Val Glu Ser Gly Gly Gly Leu Val Gln Ala Gly Gly
 1               5                  10                  15

Ser Leu Arg Leu Ser Cys Ala Ser Gly Arg Ile Phe Ser Ile Asn
             20                  25                  30

Ala Met Gly Trp Tyr Arg Gln Ala Pro Gly Lys Gln Arg Glu Leu Val
         35                  40                  45

Ala Ala Ile Ser Thr Ala Gly Ser Thr Asn Tyr Gly Asp Ser Val Lys
     50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Asn
                 85                  90                  95

Leu Asn Phe Pro Pro Tyr Val Tyr Trp Gly Gln Gly Thr Gln Val Thr
            100                 105                 110

Val Ser Ser
        115

<210> SEQ ID NO 92
<211> LENGTH: 119
<212> TYPE: PRT
<213> ORGANISM: Artificial Sequence
<220> FEATURE:
<223> OTHER INFORMATION: CD38 38A37331 VHH

<400> SEQUENCE: 92

Gln Val Lys Leu Glu Glu Ser Gly Gly Gly Leu Val Gln Pro Gly Glu
 1               5                  10                  15

Ser Leu Arg Leu Ser Cys Ser Ala Ser Gly Ser Ile Phe Lys Val Phe
             20                  25                  30

Arg Val Phe Ala Met Ser Trp Tyr Arg Gln Gly Pro Gly Lys Gln Arg
         35                  40                  45

Glu Leu Val Ala Ser Ile Ser Ser Gly Glu Thr Thr Thr Tyr Ala Asp
     50                  55                  60

Ser Val Lys Gly Arg Phe Thr Ile Ser Arg Asp Asn Ala Lys Asn Thr
 65                  70                  75                  80

Ala Tyr Leu Gln Met Asp Ser Leu Lys Pro Glu Asp Thr Ala Val Tyr
                 85                  90                  95

Tyr Cys Asn Ala Asp His Thr Phe Thr Gly Asp Phe Trp Gly Gln Gly
            100                 105                 110

Thr Gln Val Thr Val Ser Ser
        115

<210> SEQ ID NO 93
<211> LENGTH: 116
<212> TYPE: PRT
<213> ORGANISM: Artificial Sequence
<220> FEATURE:
<223> OTHER INFORMATION: CD38 38A37717 VHH

<400> SEQUENCE: 93

Glu Val Gln Leu Val Glu Ser Gly Gly Gly Leu Val Gln Ala Gly Gly
1               5                   10                  15

Ser Leu Arg Leu Ser Cys Ile Ala Thr Gly Lys Val Phe Ser Ile Tyr
            20                  25                  30

Asp Met Gly Trp Tyr Arg Gln Ala Pro Gly Lys Gln Arg Glu Leu Val
        35                  40                  45

Ala Glu Ile Thr Ser Ser Gly Thr Thr His Tyr Asp Asp Phe Val Ser
    50                  55                  60

Gly Arg Phe Thr Ile Ser Arg Asp Asn Ala Lys Asn Thr Val Tyr Leu
65                  70                  75                  80

Gln Met Asn Thr Leu Lys Ala Glu Asp Thr Ala Val Tyr Tyr Cys Arg
                85                  90                  95

Ala Asn His Val Phe Gly Gly Ser Tyr Trp Gly Gln Gly Thr Gln Val
            100                 105                 110

Thr Val Ser Ser
        115

<210> SEQ ID NO 94
<211> LENGTH: 115
<212> TYPE: PRT
<213> ORGANISM: Artificial Sequence
<220> FEATURE:
<223> OTHER INFORMATION: CD38 38A37719 VHH

<400> SEQUENCE: 94

Gln Val Lys Leu Glu Glu Ser Gly Gly Gly Ser Val Gln Thr Gly Gly
1               5                   10                  15

Ser Leu Arg Leu Ser Cys Ala Ala Ser Ala Ser Ile Phe Thr Arg Leu
            20                  25                  30

Pro Met Gly Trp Tyr Arg Gln Ala Pro Gly Lys Gln Arg Glu Leu Val
        35                  40                  45

Val Gly Ile Val Pro Ser Gly Arg Ile Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Arg Pro Glu Asp Thr Ala Val Tyr Tyr Cys Arg
                85                  90                  95

Ala Asp Thr Phe Pro Leu Pro Thr Trp Gly Gln Gly Thr Gln Val Thr
            100                 105                 110

Val Ser Ser
        115

<210> SEQ ID NO 95
<211> LENGTH: 126
<212> TYPE: PRT
<213> ORGANISM: Artificial Sequence
<220> FEATURE:
<223> OTHER INFORMATION: CD38 38A37330 VHH -continued

<400> SEQUENCE: 95

Gln Val Gln Leu Val Glu Ser Gly Gly Gly Leu Val Gln Ala Gly Asp
1               5                   10                  15

Ser Leu Arg Leu Ser Cys Ala Ala Ser Gly Arg Ala Tyr Ala Thr Met
            20                  25                  30

Ala Trp Phe Arg Gln Ala Pro Gly Lys Glu Arg Glu Phe Val Ala His
        35                  40                  45

Leu Arg Val Ser Gly Asp Thr Thr Tyr Tyr Thr Asp Ser Val Lys Gly
    50                  55                  60

Arg Phe Thr Ile Ser Arg Asp Asn Ala Lys Asn Thr Ala Tyr Leu Gln
65                  70                  75                  80

Met Asn Met Leu Lys Pro Glu Asp Thr Ala Val Tyr Tyr Cys Ala Ala
                85                  90                  95

Gly Pro Tyr Gly Ile Leu Ala Ala Ala Arg Val Ser Asn Pro Gly Asn
            100                 105                 110

Tyr Asp Tyr Trp Gly Gln Gly Thr Gln Val Thr Val Ser Ser
        115                 120                 125

<210> SEQ ID NO 96
<211> LENGTH: 123
<212> TYPE: PRT
<213> ORGANISM: Artificial Sequence
<220> FEATURE:
<223> OTHER INFORMATION: CD38 38A37334 VHH

<400> SEQUENCE: 96

Glu Val Gln Leu Val Glu Ser Gly Gly Gly Leu Val Gln Ala Gly Gly
1               5                   10                  15

Ser Leu Arg Leu Ser Cys Ala Ala Ser Gly Leu Thr Phe Ser Ser Tyr
            20                  25                  30

Ile Met Gly Trp Phe Arg Gln Ala Pro Gly Glu Glu Arg Glu Leu Val
        35                  40                  45

Ala Glu Ile Ser Ser Gly Gly Met Thr Ser Tyr Ala Asp Ser Val Lys
    50                  55                  60

Gly Arg Phe Thr Ile Ser Arg Asp Asn Ala Lys Lys Thr Gly Tyr Leu
65                  70                  75                  80

Gln Met Asn Ser Leu Lys Pro Glu Asp Thr Ala Val Tyr Tyr Cys Ala
                85                  90                  95

Ala Pro Glu Arg Gly Ser Ile Trp Tyr Ser Arg Tyr Glu Tyr Lys Tyr
            100                 105                 110

Trp Gly Gln Gly Thr Gln Val Thr Val Ser Ser
        115                 120

<210> SEQ ID NO 97
<211> LENGTH: 120
<212> TYPE: PRT
<213> ORGANISM: Artificial Sequence
<220> FEATURE:
<223> OTHER INFORMATION: CD38 38A37730 VHH

<400> SEQUENCE: 97

Ala Val Gln Leu Val Asp Ser Gly Gly Gly Leu Ala Gln Thr Gly Gly
1               5                   10                  15

Ser Leu Arg Leu Ser Cys Ala Ala Ser Gln Gly Ile Phe Thr Ile Asn
            20                  25                  30

Ala Met Gly Trp Tyr Arg Gln Val Pro Gly Lys Gln Arg Glu Leu Val
        35                  40                  45

```
Ala Glu Val Ser Ser Gly Gly Arg Thr Asp Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Gly Val Tyr Tyr Cys Arg
                 85                  90                  95

Val Ser Gly Trp His Val Phe Val Gly Asp Arg Ile Val Trp Gly Gln
             100                 105                 110

Gly Thr Leu Val Thr Val Ser Ser
             115                 120

<210> SEQ ID NO 98
<211> LENGTH: 123
<212> TYPE: PRT
<213> ORGANISM: Artificial Sequence
<220> FEATURE:
<223> OTHER INFORMATION: CD38 38A37340 VHH

<400> SEQUENCE: 98

Asp Val Gln Leu Val Glu Ser Gly Gly Gly Leu Val Gln Ala Gly Asp
 1               5                  10                  15

Ser Leu Arg Leu Ser Cys Ala Ala Ser Gly Arg Thr Phe Ser Ser Tyr
                 20                  25                  30

Ala Met Ala Trp Phe Arg Gln Ala Pro Gly Lys Glu Arg Glu Ile Val
                 35                  40                  45

Ser Ser Ile Ser Thr Ser Gly Gly Ile Thr Asp Tyr Ala Asp Ser Val
 50                  55                  60

Lys Gly Arg Phe Thr Ile Ser Lys Asp Ser Ala Lys Met Asn Thr Val
 65                  70                  75                  80

Tyr Leu Gln Met Asn Ser Leu Glu Pro Glu Asp Thr Ala Val Tyr Tyr
                 85                  90                  95

Cys Ala Ala Arg Thr Trp Tyr Leu Arg Thr Ser Leu Gly Tyr Asp Tyr
             100                 105                 110

Trp Gly Gln Gly Thr Gln Val Thr Val Ser Ser
             115                 120

<210> SEQ ID NO 99
<211> LENGTH: 121
<212> TYPE: PRT
<213> ORGANISM: Artificial Sequence
<220> FEATURE:
<223> OTHER INFORMATION: CD38 38A37731 VHH

<400> SEQUENCE: 99

Gln Val Lys Leu Glu Glu Ser Gly Gly Gly Leu Val Gln Ala Gly Gly
 1               5                  10                  15

Ser Leu Arg Leu Ser Cys Val Ala Ser Gly Thr Ile Val Ser Ile Ser
                 20                  25                  30

Thr Met Gly Trp Tyr Arg Gln Ala Pro Gly Lys Gln Arg Glu Leu Val
                 35                  40                  45

Ala Thr Ile Thr Arg Arg Gly Arg Thr Asn Tyr Thr Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Asn
                 85                  90                  95

Ala Glu Val Gln Leu Asp Ile Trp Ala Ser Ala Tyr Asp Tyr Trp Gly
```

```
                      100                 105                 110
Gln Gly Thr Gln Val Thr Val Ala Ser
            115                 120

<210> SEQ ID NO 100
<211> LENGTH: 115
<212> TYPE: PRT
<213> ORGANISM: Artificial Sequence
<220> FEATURE:
<223> OTHER INFORMATION: CD38 38A37326 VHH

<400> SEQUENCE: 100

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Tyr Ala Met Gly
            20                  25                  30

Trp Tyr Arg Gln Ala Pro Gly Lys Gln Arg Asp Leu Val Ala Thr Ile
        35                  40                  45

Ser Gly Ala Gly Asn Thr Lys Tyr Ala Asp Ser Val Lys Gly Arg Phe
    50                  55                  60

Thr Ile Ser Arg Asp Asn Ala Lys Asn Thr Met Tyr Leu Gln Met Asn
65                  70                  75                  80

Ser Leu Lys Pro Glu Asp Thr Ala Val Tyr Tyr Cys Ala Ala Gly Lys
                85                  90                  95

Trp Phe Pro Ala Ala Asn Glu Tyr Trp Gly Gln Gly Thr Gln Val Thr
            100                 105                 110

Val Ser Ser
        115

<210> SEQ ID NO 101
<211> LENGTH: 351
<212> TYPE: DNA
<213> ORGANISM: Artificial Sequence
<220> FEATURE:
<223> OTHER INFORMATION: CD19 single-domain antibody VHH

<400> SEQUENCE: 101
caggtaaagc tggaggagtc tgggggagaa ttggtgcagc ctggggggcc tctgagactc      60
tcctgtgcag cctcgggaaa catcttcagt atcaatcgca tgggctggta ccgccaggct     120
ccagggaagc agcgcgcgtt cgtcgcatct attactgttc gtggtataac aaactatgca     180
gactccgtga agggccgatt caccatttct gtagacaagt ccaaaaacac gatttatctg     240
cagatgaacg cactcaaacc tgaggacacg gccgtctatt attgtaatgc agtgtcttca     300
aacagggacc ccgactactg ggccaggggg acccaggtca ccgtctcctc a              351

<210> SEQ ID NO 102
<211> LENGTH: 387
<212> TYPE: DNA
<213> ORGANISM: Artificial Sequence
<220> FEATURE:
<223> OTHER INFORMATION: CD20 single-domain antibody VHH

<400> SEQUENCE: 102
ccggtgcagc tggtggagtc tgggggaggc ttggtgcagg ctggggattc tctgagactc      60
tcctgtgctg cctctggacg caccttcggt attggtacca tgggctggtt ccgccaacct     120
ccagggaagg agcgtgaatt tgtagcagct attaggtgga gtactggtgg cactcgctat     180
gcagactccg tgaagggccg attcaccatc tcccgagaca cgccaagct cacggtagat     240
```

-continued

```
ctgcaaatgg acagcctgaa acctgaagac acggccgttt attactgtgc agcagataga      300
ctgtcccttg atttaagtgg tcgttaccac tacaaccccg ccgtgtatga ctattggggc      360
caggggaccc aggtcaccgt ctcctca                                          387
```

<210> SEQ ID NO 103
<211> LENGTH: 366
<212> TYPE: DNA
<213> ORGANISM: Artificial Sequence
<220> FEATURE:
<223> OTHER INFORMATION: BCMA 269A37346 VHH

<400> SEQUENCE: 103

```
caggtgcagc tggtggagtc tgggggaggc ttggtgcagc ctggggggttc tctgaggctc      60 tcctgtgaag cctctggatt cactttggat tattatgcca taggctggtt ccgccaggcc     120
ccagggaagg agcgcgaggg ggtcatatgt attagtagaa gtgatggtag cacatactat     180
gcagactccg tgaagggccg attcaccatc tccagagaca cgccaagaa acggtgtat      240 ctgcaaatga tcagcctgaa acctgaggac acggccgctt attactgtgc agcaggggcc     300
gattgttcgg ggtacctacg agattatgag ttccggggc aggggaccca ggtcaccgtc     360
tcctca                                                                366
```

<210> SEQ ID NO 104
<211> LENGTH: 384
<212> TYPE: DNA
<213> ORGANISM: Artificial Sequence
<220> FEATURE:
<223> OTHER INFORMATION: BCMA 269A37348 VHH

<400> SEQUENCE: 104

```
caggtaaagc tggaggagtc tgggggacga ttggtgcagc caaggggctc tctgagactc      60
tcctgtgcag gctctggacg cactttcagt acctatggta tggcctggtt ccgccaggct     120
ccagggaagg agcgtgagtt cgtagcgtct aaagcatcga tgaattacag cggtagaaca     180
tactatgcag actccgtgaa gggccgattc accatcgcca gagacaacgc caagaacatg     240
gtgtttctgc aaatgaacaa cctgaagcct gaggacacgg ccgtttatta ctgtgcagcg     300
ggcactggat gctcaacata tgggtgtttt gacgcccaga taatagacta ctggggcaaa     360
gggaccctgg tcaccgtctc ctca                                            384
```

<210> SEQ ID NO 105
<211> LENGTH: 354
<212> TYPE: DNA
<213> ORGANISM: Artificial Sequence
<220> FEATURE:
<223> OTHER INFORMATION: BCMA 269A37917 VHH

<400> SEQUENCE: 105

```
gaggtgcagc tggtggagtc tgggggaggc ttggtgcagg ctgggggtc tctgagactc       60 tcctgtgcag cctctggacg caccttcacc atgggtggt ccgtcaggc tccagggaag      120 gagcgtgagt ttgtagcagc tattagtttg agtcctactt tagcatatta tgcagagtcc     180
gtgaagggcc gattcaccat cagccgagac aacgccaaga acacgtggt tttgcaaatg     240 aacagcctga aacctgagga cacggccctt tattactgtg cagcagaccg gaaatcagta     300
atgtctattc ggcccgacta ctggggccag gggacccagg tcaccgtctc ctca           354
```

<210> SEQ ID NO 106
<211> LENGTH: 360

<212> TYPE: DNA
<213> ORGANISM: Artificial Sequence
<220> FEATURE:
<223> OTHER INFORMATION: BCMA 269A37355 VHH

<400> SEQUENCE: 106

```
gccgtgcagc tggtggattc tgggggaggc ttggtgcagc ctgggggtc tctgagactc      60
tcctgtgtag cctctggagg tatcttcgtc atcaatgcca tgggctggta ccgccaggct    120
ccaggaaagc agcgcgagtt ggtcgcatct attcgtggac taggcagaac aaactatgac    180
gactccgtga agggccgatt caccatctcc agagacaacg ccaacaacac ggtgtatctg    240
cagatgaaca gcctggaacc tgaggacacg gccgtctact actgtacagt ctacgttaca    300
ctacttggtg gggttaatag ggactactgg ggccagggga cccaggtcac cgtctcctca    360
```

<210> SEQ ID NO 107
<211> LENGTH: 357
<212> TYPE: DNA
<213> ORGANISM: Artificial Sequence
<220> FEATURE:
<223> OTHER INFORMATION: BCMA 269A37915 VHH

<400> SEQUENCE: 107

```
gaggtgcagc tggtggagtc tgggggagga ttggtgcagg ctgggggctc tctgagactc      60
tcctgtgcag cctctggacg gaccttcagt agcattgtca tgggctggtt ccgccaggct    120
ccagggaagg agcgtgagtt tgtaggagcg attatgtgga atgatggtat tacatacttg    180
caagactccg tgaagggccg atttaccatc ttcagagaca atgccaagaa cacggtgtat    240
ctgcaaatga acagcctgaa acttgaggat acggccgttt attactgtgc agcatccaag    300
ggtagatact cggaatatga gtactggggc caggggaccc aggtcaccgt ctcctca      357
```

<210> SEQ ID NO 108
<211> LENGTH: 384
<212> TYPE: DNA
<213> ORGANISM: Artificial Sequence
<220> FEATURE:
<223> OTHER INFORMATION: BCMA 269A37936 VHH

<400> SEQUENCE: 108

```
gaggtgcagc tggtggagtc tgggggaggc gtggtgcagg ctgggggtc tctgacagtc      60
tcctgtacag cctctggatt cactttcgac cgtgctgtca tagtctggtt ccgccaggcc    120
cccgggaagg gccgtgaggg ggtctcattt attaaaccta gtgatggcac catatactac    180
attgactccc tgaagggccg attcacgatc tccagtgaca tcgccaagaa tacggtatat    240
ctgcaaatga aaagtctgga atcggaggac tcggccgttt attactgtgc ggcctcgcct    300
gaggactggt acacggattg gatcgactgg agtatatatc ggtggcagca ctggggccag    360
gggacccagg tcactgtctc ctca                                           384
```

<210> SEQ ID NO 109
<211> LENGTH: 357
<212> TYPE: DNA
<213> ORGANISM: Artificial Sequence
<220> FEATURE:
<223> OTHER INFORMATION: BCMA 269A37953 VHH

<400> SEQUENCE: 109

```
gaggtgcagc tggtggagtc tgggggagga atggtgcagg ctggggactc tctgagacta      60
tcctgtgtgc agtctactta caccgtcaat agcgatgtca tgggctggtt ccgccaggct    120
```

```
ccagggaagg agcgtgagtt tgtaggagcg attatgtgga atgatggtat tacatacttg    180
caagactccg tgaagggccg atttaccatc ttcagagaca acgccaagaa cacggtgtat    240
ctgcaaatga acagcctgaa acttgaggat acggccgttt attactgtgc agcatccaag    300
ggtagatact cggaatatga gtactggggc caggggaccc aggtcaccgt ctcctca       357
```

<210> SEQ ID NO 110
<211> LENGTH: 360
<212> TYPE: DNA
<213> ORGANISM: Artificial Sequence
<220> FEATURE:
<223> OTHER INFORMATION: BCMA 269A37965 VHH

<400> SEQUENCE: 110

```
gcggtgcagc tggtggagtc tgggggagga ttggtgcagg ctggggactc tctgagactc    60
tcctgtacag cctctggtgc aaccttgact aacgatcaca tggcatggtt ccgccaggct    120
ccagggaagg ggcgtgaatt tgtagcagct attgactgga gtggtcgtac cacaaattac    180
gcagaccccg tagagggccg attcaccatc tccagaaaca cgccaagaa cacggtgtat    240 ctggaaatga acagcctgaa acttgaggac acggccgttt attactgtgc ggtcctccgc    300
gcttggatct catatgacaa tgactactgg ggccagggga cccaggtcac cgtctcctca    360
```

<210> SEQ ID NO 111
<211> LENGTH: 360
<212> TYPE: DNA
<213> ORGANISM: Artificial Sequence
<220> FEATURE:
<223> OTHER INFORMATION: BCMA 269A37972 VHH

<400> SEQUENCE: 111

```
caggtgcagc tggtggagtc tgggggagga ttggtgcagg ctgggggctc tctgagactc    60
tcctgtgcag cctctggagg caccttaagt aaaaataccg tggcttggtt ccgccaggct    120
ccagggaagg agcgtgggtt tgtagcgtct attacctggg atggtcgtac gacatactat    180
gcagactccg tgaagggccg attcaccatc tccagagaca acgccaagaa cacagtgtat    240
ctgcaaatga acagcctgaa acctgaggat acggccgttt atgtctgtgc agacttaggg    300
aaatggcctg cgggcccggc ggactactgg ggccagggga cccaggtcac cgtctcctca    360
```

<210> SEQ ID NO 112
<211> LENGTH: 357
<212> TYPE: DNA
<213> ORGANISM: Artificial Sequence
<220> FEATURE:
<223> OTHER INFORMATION: BCMA 269A37353 VHH

<400> SEQUENCE: 112

```
caggtaaagc tggaggagtc tgggggaggc ttggtgcagg ctgggcggtc tctgagactc    60
tcctgtgcag cctctgaaca caccttcagt agccatgtca tggctgtt ccgccaggct     120 ccagggaagg agcgtgagtc tgttgcagtt attggctgga gagatattag cacaagctat    180
gcagactccg tgaagggccg attcaccatc tccagagaca acgccaagaa gacgctgtat    240
ctgcaaatga atagcctgaa acctgaggac acggccgttt actactgtgc agcacgtcgg    300
atcgacgcag ctgactttga ttcctggggg caggggaccc aggtcaccgt ctcctcg       357
```

<210> SEQ ID NO 113
<211> LENGTH: 357
<212> TYPE: DNA
<213> ORGANISM: Artificial Sequence

<220> FEATURE:
<223> OTHER INFORMATION: BCMA 269A37948 VHH

<400> SEQUENCE: 113

```
gcggtgcagc tggtggagtc tgggggagga ttggtgcagg ctggggactc tctgagactc      60
acctgtacag cctctggacg cgccttcagt acctatttca tggcctggtt ccgccaggct     120
ccagggaagg agcgtgagtt tgtagcagga attgcatgga gtggtggtag cacggcgtat     180
gcagactccg tgaagggccg attcaccatc tccagagaca cgccaagaa cacggtgtat      240
ctgcaaatga acagcctgaa atctgaggac acggccgttt attactgtgc cagcagggg      300
attgaggtcg aagagtttgg tgcctggggc caggggaccc aggtcaccgt ctcgtcg        357
```

<210> SEQ ID NO 114
<211> LENGTH: 342
<212> TYPE: DNA
<213> ORGANISM: Artificial Sequence
<220> FEATURE:
<223> OTHER INFORMATION: CD38 38A37333 VHH

<400> SEQUENCE: 114

```
gatgtgcagc tggtggagtc tgggggaggc ttggtgcagc ctgggggtc tctgagactc       60
tcctgtgtag cctctggatt gaccttcagt agctaccca tgatgtggt ccgccaggct      120
ccaggaaagg ggctcgagtg ggtctcacgt attagcgata gtggtggtta cacaaactat     180
gacgactccg tgaagggccg attcaccatc tccagagaca cgccaagaa cacgctgtat      240
ctgcaaatga acagcctgac acctgaggac acggccgtgt attactgtag aatcctgggg     300
ttgcccacca cgggccaggg gacccaggtc accgtctcct ca                        342
```

<210> SEQ ID NO 115
<211> LENGTH: 378
<212> TYPE: DNA
<213> ORGANISM: Artificial Sequence
<220> FEATURE:
<223> OTHER INFORMATION: CD38 38A37336 VHH

<400> SEQUENCE: 115

```
gaggtgcagc tggtggagtc tgggggaggc ctggtgcagc ctgggggtc tctgagactc      60
tcctgtgcag cctctggatt caccttcagt agcaactgga tgtattgggt ccgtcaggct    120
ccagggaagg ggctcgagtg ggtcgcaact attagtactg atggtcgtgg aacatactat    180
aaagactctg tgaagggccg attcaccgtc tccagagaca cgccatgag tacgctgctt    240
ctgcaaatga acaatctgaa atctgaagat acggccgtgt attattgtgc aaaagagccg    300
agggtgttga tggcttacct gcggaacctg ggtgactttg gttcctgggg ccaggggacc    360
caggtcaccg tctcctcg                                                   378
```

<210> SEQ ID NO 116
<211> LENGTH: 345
<212> TYPE: DNA
<213> ORGANISM: Artificial Sequence
<220> FEATURE:
<223> OTHER INFORMATION: CD38 38A37699 VHH

<400> SEQUENCE: 116

```
caggtgcagc tggtggagtc tgggggaggc ttggtgcagg ctggggggtc tctgagactc      60
tcctgtgcag cctctggaag gatcttcagt atcaatgcca tggcctggta ccgccaggct    120
ccagggaagc agcgcgagtt ggtcgccgct attagtacgg ctggtagcac aaactatgga    180
```

```
gactccgtga agggccgatt caccatctcc agagacaacg ccaagaacac ggtgtatctg      240
caaatgaaca gcctgaaacc tgaggacaca gctgtttatt actgtaattt aaattttccc      300
ccgtatgtgt actggggcca ggggacccag gtcaccgtct cctca                      345
```

```
<210> SEQ ID NO 117
<211> LENGTH: 357
<212> TYPE: DNA
<213> ORGANISM: Artificial Sequence
<220> FEATURE:
<223> OTHER INFORMATION: CD38 38A37331 VHH

<400> SEQUENCE: 117
caggtaaagc tggaggagtc tgggggaggt ctggtgcagc ctggggagtc tctgagactc      60
tcctgttcag cctctggaag catcttcaaa gttttcagag tctttgccat gagctggtac      120
cgccagggtc ccgggaaaca gcgcgagttg gtcgcatcca ttagtagtgg cgagaccaca      180
acctatgcag actccgtgaa gggccgattc accatctcca gagacaacgc caagaatacg      240
gcgtatctgc aaatgacag cctgaaacct gaggacacgc cgtctatta ctgtaatgcg        300 gatcacacct ttacaggaga cttctggggc caggggaccc aggtcaccgt ctcctca         357
```

```
<210> SEQ ID NO 118
<211> LENGTH: 348
<212> TYPE: DNA
<213> ORGANISM: Artificial Sequence
<220> FEATURE:
<223> OTHER INFORMATION: CD38 38A37717 VHH

<400> SEQUENCE: 118
gaggtgcagc tggtggaaag cggggggga ctggtgcagg caggcgggtc actgagactg       60
tcatgtatcg caactgggaa ggtgtttagc atctacgaca tgggctggta taggcaggca     120
ccaggaaagc agagggagct ggtggccgag atcaccagct ccggcaccac acactacgac     180
gatttcgtgt ctggccggtt taccatcagc agagacaacg ccaagaatac agtgtatctg     240
cagatgaaca ccctgaaggc cgaggataca gccgtgtact attgccgggc taatcacgtc     300
ttcggcggct cctactgggg gcagggaact caggtcactg tgtcatcc                  348
```

```
<210> SEQ ID NO 119
<211> LENGTH: 345
<212> TYPE: DNA
<213> ORGANISM: Artificial Sequence
<220> FEATURE:
<223> OTHER INFORMATION: CD38 38A37719 VHH

<400> SEQUENCE: 119
caggtaaagc tggaggagtc tgggggaggc tcggtgcaga ctggggggtc tctgagactc      60
tcctgtgcag cctctgcaag catcttcact aggctgccca tgggctggta ccgccaggct     120
ccagggaagc agcgcgagtt ggtcgtaggc attgttccta gtggtaggat aaactatgca     180
gactccgtga agggccgatt caccatctcc agagacaacg ccaagaacac ggtgtatctg     240
caaatgaaca gcctgcgccc tgaggacaca gccgtctatt actgccgcgc cgataccttc     300
cccttgccca cctggggcca ggggacccag gtcaccgtct cctca                      345
```

```
<210> SEQ ID NO 120
<211> LENGTH: 378
<212> TYPE: DNA
<213> ORGANISM: Artificial Sequence
<220> FEATURE:
<223> OTHER INFORMATION: CD38 38A37330 VHH
```

<400> SEQUENCE: 120

```
caggtgcagc tggtggagtc tgggggagga ttggtgcagg ctggggactc tctgagactc      60
tcctgtgcag cctctggacg cgcctacgct acgatggcct ggttccgcca ggctccaggg     120
aaggagcgtg agtttgtagc acatctgcgc gtgagtggtg ataccactta ctatacagac     180
tccgtgaagg gccgattcac catctccaga gacaacgcca agaacacggc gtatctgcaa     240
atgaacatgt tgaaacctga ggacacggcc gtttattact gtgcagcggg accgtatggc     300
attcttgccg ctgccagggt cagtaatcca ggaaattatg attattgggg ccaggggacc     360
caggtcaccg tctcctca                                                    378
```

<210> SEQ ID NO 121
<211> LENGTH: 369
<212> TYPE: DNA
<213> ORGANISM: Artificial Sequence
<220> FEATURE:
<223> OTHER INFORMATION: CD38 38A37334 VHH

<400> SEQUENCE: 121

```
gaggtgcagc tggtggagtc tgggggagga ttggtgcagg ctgggggctc tctgagactc      60
tcctgtgcag cctctggact caccttcagt agttatatta tgggctggtt ccgccaggct     120
ccaggcgagg agcgcgagtt ggtcgcggaa attagtagcg gtggtatgac atcgtatgca     180
gactccgtga agggccgatt caccatctcc agagacaacg ccaagaagac ggggtatctg     240
caaatgaaca gcctgaaacc tgaggacacg gccgtttact attgtgcagc ccctgagagg     300
ggtagtatct ggtacagccg ctacgaatat aagtactggg gccaggggac caggtcacc      360
gtctcctca                                                              369
```

<210> SEQ ID NO 122
<211> LENGTH: 360
<212> TYPE: DNA
<213> ORGANISM: Artificial Sequence
<220> FEATURE:
<223> OTHER INFORMATION: CD38 38A37730 VHH

<400> SEQUENCE: 122

```
gccgtgcagc tggtggattc tgggggaggc ttggcgcaga ctgggggggtc tctgagactc      60
tcctgtgcag cctctcaagg gatcttcact atcaatgcca tgggctggta ccgccaggtt     120
ccagggaagc agcgggagtt ggtcgcagaa gttagtagtg gtggccgcac agactatgca     180
gactccgtga agggccgatt caccatctcc agagacaacg ccaagaacac ggtgtacctg     240
caaatgaaca gcctgaaacc tgaggacaca ggcgtctatt attgtcgagt ttctggatgg     300
catgtgtttg tcggtgaccg catagtttgg ggccagggca ccctggtcac tgtctcctca     360
```

<210> SEQ ID NO 123
<211> LENGTH: 369
<212> TYPE: DNA
<213> ORGANISM: Artificial Sequence
<220> FEATURE:
<223> OTHER INFORMATION: CD38 38A37340 VHH

<400> SEQUENCE: 123

```
gatgtgcagc tggtggagtc tgggggagga ttggtgcagg ctggggactc tctgagactc      60
tcctgtgcag cctctggacg caccttcagt agctatgcca tggcctggtt ccgccaggct     120
ccagggaagg agcgtgagat tgtttcgtct atcagtacca gtggtggtat cacagactat     180
```

-continued

```
gcagactccg tgaagggccg attcaccatc tccaaagaca gcgcgaagat gaacacggtg        240
tatctgcaaa tgaatagcct agaacctgag gacacggccg tttactactg tgcggcccgt        300
acatggtacc ttcgtacttc tctccaatat gactattggg gccaggggac ccaggtcacc        360
gtctcctca                                                                369
```

<210> SEQ ID NO 124
<211> LENGTH: 363
<212> TYPE: DNA
<213> ORGANISM: Artificial Sequence
<220> FEATURE:
<223> OTHER INFORMATION: CD38 38A37731 VHH

<400> SEQUENCE: 124

```
caggtaaagc tggaggagtc tgggggaggc ttggtgcagg ctgggggtc tctgagactc         60 tcctgtgtag cctctggaac catcgtcagt atcagtacca tgggctggta ccgccaggct        120
ccagggaagc agcgcgagtt ggtcgcgact ataaccaggc gtggacgcac gaactataca        180
gactccgtga agggccgatt caccatctcc agagacaacc caaaaacac ggtgtatctg        240 caaatgaaca gcctgaaacc tgaggacaca gccgtctatt actgtaatgc agaggtgcaa        300
ctggatatat gggcatctgc gtatgactac tggggccagg gacccaggt caccgtcgcc        360 tca                                                                     363
```

<210> SEQ ID NO 125
<211> LENGTH: 345
<212> TYPE: DNA
<213> ORGANISM: Artificial Sequence
<220> FEATURE:
<223> OTHER INFORMATION: CD38 38A37326 VHH

<400> SEQUENCE: 125

```
gaggtgcagc tggtggagtc tgggggagga ttggtgcagg ctggggggctc tctgagactc       60 tcctgtgcag cctctggacg cacctatgcc atgggctggt atcgccaggc tccagggaag       120
cagcgcgact tggtcgcaac tattagtggt gcgggtaaca caaagtatgc agactccgtg       180
aagggccgat tcaccatctc cagagacaac gccaagaaca caatgtatct gcaaatgaac       240
agcctgaaac ctgaggacac ggccgtttat tactgtgccg cgggtaaatg gttccctgct       300
gcgaatgagt actggggcca ggggacccag gtcaccgtct cctca                       345
```

<210> SEQ ID NO 126
<211> LENGTH: 9
<212> TYPE: DNA
<213> ORGANISM: Artificial Sequence
<220> FEATURE:
<223> OTHER INFORMATION: Kozak nucleic acid sequence

<400> SEQUENCE: 126

```
gccgccacc                                                               9
```

<210> SEQ ID NO 127
<211> LENGTH: 21
<212> TYPE: PRT
<213> ORGANISM: Artificial Sequence
<220> FEATURE:
<223> OTHER INFORMATION: CD8alpha signal peptide

<400> SEQUENCE: 127

```
Met Ala Leu Pro Val Thr Ala Leu Leu Leu Pro Leu Ala Leu Leu Leu
1               5                   10                  15
```

His Ala Ala Arg Pro
            20

<210> SEQ ID NO 128
<211> LENGTH: 63
<212> TYPE: DNA
<213> ORGANISM: Artificial Sequence
<220> FEATURE:
<223> OTHER INFORMATION: CD8alpha signal peptide nucleic acid sequence 1

<400> SEQUENCE: 128
atggccttac cagtgaccgc cttgctcctg ccgctggcct tgctgctcca cgccgccagg    60
ccg                                                                 63

<210> SEQ ID NO 129
<211> LENGTH: 63
<212> TYPE: DNA
<213> ORGANISM: Artificial Sequence
<220> FEATURE:
<223> OTHER INFORMATION: CD8alpha signal peptide nucleic acid sequence 2

<400> SEQUENCE: 129
atggctctgc ccgtcactgc tctgctgctg cccctggctc tgctgctgca cgccgcaaga    60
ccc                                                                 63

<210> SEQ ID NO 130
<211> LENGTH: 45
<212> TYPE: PRT
<213> ORGANISM: Artificial Sequence
<220> FEATURE:
<223> OTHER INFORMATION: CD8alpha hinge

<400> SEQUENCE: 130

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 131
<211> LENGTH: 135
<212> TYPE: DNA
<213> ORGANISM: Artificial Sequence
<220> FEATURE:
<223> OTHER INFORMATION: CD8alpha hinge

<400> SEQUENCE: 131
accacgacgc cagcgccgcg accaccaaca ccggcgccca ccatcgcgtc gcagcccctg    60
tccctgcgcc cagaggcgtg ccggccagcg gcggggggcg cagtgcacac gagggggctg   120
gacttcgcct gtgat                                                   135

<210> SEQ ID NO 132
<211> LENGTH: 24
<212> TYPE: PRT
<213> ORGANISM: Artificial Sequence
<220> FEATURE:
<223> OTHER INFORMATION: CD8alpha transmembrane

<400> SEQUENCE: 132

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 133
<211> LENGTH: 27
<212> TYPE: PRT
<213> ORGANISM: Artificial Sequence
<220> FEATURE:
<223> OTHER INFORMATION: CD28 transmembrane

<400> SEQUENCE: 133

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 134
<211> LENGTH: 72
<212> TYPE: DNA
<213> ORGANISM: Artificial Sequence
<220> FEATURE:
<223> OTHER INFORMATION: CD8alpha transmembrane

<400> SEQUENCE: 134
atctacatct gggcgccctt ggccgggact tgtggggtcc ttctcctgtc actggttatc      60 acccttact gc                                                          72

<210> SEQ ID NO 135
<211> LENGTH: 81
<212> TYPE: DNA
<213> ORGANISM: Artificial Sequence
<220> FEATURE:
<223> OTHER INFORMATION: CD28 transmembrane

<400> SEQUENCE: 135
ttttgggtgc tggtggtggt tgtggagtc ctggcttgct atagcttgct agtaacagtg       60
gcctttatta ttttctgggt g                                               81

<210> SEQ ID NO 136
<211> LENGTH: 41
<212> TYPE: PRT
<213> ORGANISM: Artificial Sequence
<220> FEATURE:
<223> OTHER INFORMATION: CD28 cytoplasmic aa sequence

<400> SEQUENCE: 136

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 137
<211> LENGTH: 42
<212> TYPE: PRT
<213> ORGANISM: Artificial Sequence
<220> FEATURE:
<223> OTHER INFORMATION: CD137 cytoplasmic domain

<400> SEQUENCE: 137

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 138
<211> LENGTH: 123
<212> TYPE: DNA
<213> ORGANISM: Artificial Sequence
<220> FEATURE:
<223> OTHER INFORMATION: CD28 cytoplasmic na sequence

<400> SEQUENCE: 138
aggagtaaga ggagcaggct cctgcacagt gactacatga acatgactcc ccgccgcccc    60
gggcccaccc gcaagcatta ccagccctat gccccaccac gcgacttcgc agcctatcgc   120
tcc                                                                 123

<210> SEQ ID NO 139
<211> LENGTH: 126
<212> TYPE: DNA
<213> ORGANISM: Artificial Sequence
<220> FEATURE:
<223> OTHER INFORMATION: CD137 cytoplasmic domain

<400> SEQUENCE: 139
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                              126

<210> SEQ ID NO 140
<211> LENGTH: 113
<212> TYPE: PRT
<213> ORGANISM: Artificial Sequence
<220> FEATURE:
<223> OTHER INFORMATION: wt CD3z cytoplasmic domain

<400> SEQUENCE: 140

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
            35                  40                  45

Pro Gln Arg Arg Lys Asn Pro Gln Glu Gly Leu Tyr Asn Glu Leu Gln
        50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 141
<211> LENGTH: 113
<212> TYPE: PRT
<213> ORGANISM: Artificial Sequence
<220> FEATURE:
<223> OTHER INFORMATION: Q65K CD3z cytoplasmic domain

<400> SEQUENCE: 141

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 142
<211> LENGTH: 336
<212> TYPE: DNA
<213> ORGANISM: Artificial Sequence
<220> FEATURE:
<223> OTHER INFORMATION: wt CD3z cytoplasmic domain

<400> SEQUENCE: 142

```
agagtgaagt tcagcaggag cgcagacgcc cccgcgtacc agcagggcca gaaccagctc    60
tataacgagc tcaatctagg acgaagagag gagtacgatg ttttggacaa gagacgtggc   120
cgggaccctg agatggggggg aaagccgaga aggaagaacc ctcaggaagg cctgtacaat   180
gaactgcaga aagataagat ggcggaggcc tacagtgaga ttgggatgaa aggcgagcgc   240
cggagggggca aggggcacga tggcctttac cagggtctca gtacagccac caaggacacc   300
tacgacgccc ttcacatgca ggccctgccc cctcgc                              336
```

<210> SEQ ID NO 143
<211> LENGTH: 336
<212> TYPE: DNA
<213> ORGANISM: Artificial Sequence
<220> FEATURE:
<223> OTHER INFORMATION: Q65K CD3z cytoplasmic domain

<400> SEQUENCE: 143

```
agagtgaagt tcagcaggag cgcagacgcc cccgcgtaca agcagggcca gaaccagctc    60
tataacgagc tcaatctagg acgaagagag gagtacgatg ttttggacaa gagacgtggc   120
cgggaccctg agatggggggg aaagccgaga aggaagaacc ctcaggaagg cctgtacaat   180
gaactgcaga aagataagat ggcggaggcc tacagtgaga ttgggatgaa aggcgagcgc   240
cggagggggca aggggcacga tggcctttac cagggtctca gtacagccac caaggacacc   300
tacgacgccc ttcacatgca ggccctgccc cctcgc                              336
```

<210> SEQ ID NO 144
<211> LENGTH: 5
<212> TYPE: PRT
<213> ORGANISM: Artificial Sequence
<220> FEATURE:
<223> OTHER INFORMATION: linker sequence 1

<400> SEQUENCE: 144

Gly Gly Gly Gly Ser
1               5

<210> SEQ ID NO 145
<211> LENGTH: 10
<212> TYPE: PRT
<213> ORGANISM: Artificial Sequence
<220> FEATURE:
<223> OTHER INFORMATION: linker sequence 2

<400> SEQUENCE: 145

Gly Gly Gly Gly Ser Gly Gly Gly Gly Ser
1               5                   10

<210> SEQ ID NO 146
<211> LENGTH: 16
<212> TYPE: PRT
<213> ORGANISM: Artificial Sequence
<220> FEATURE:
<223> OTHER INFORMATION: linker sequence 3

<400> SEQUENCE: 146

Gly Gly Gly Ser Gly Gly Gly Ser Gly Gly Gly Ser Gly Gly Gly Ser
1               5                   10                  15

<210> SEQ ID NO 147
<211> LENGTH: 24
<212> TYPE: PRT
<213> ORGANISM: Artificial Sequence
<220> FEATURE:
<223> OTHER INFORMATION: linker sequence 4

<400> SEQUENCE: 147

Gly Gly Gly Gly Ser Gly Gly Gly Gly Ser Gly Gly Gly Gly Gly
1               5                   10                  15

Ser Gly Ser Gly Gly Gly Gly Ser
            20

<210> SEQ ID NO 148
<211> LENGTH: 34
<212> TYPE: PRT
<213> ORGANISM: Artificial Sequence
<220> FEATURE:
<223> OTHER INFORMATION: linker sequence 5

<400> SEQUENCE: 148

Gly Gly Gly Gly Ser Gly Gly Gly Ser Gly Gly Gly Gly Gly
1               5                   10                  15

Ser Gly Ser Gly Gly Gly Gly Ser Gly Gly Gly Ser Gly Gly Gly
            20                  25                  30

Gly Ser

<210> SEQ ID NO 149
<211> LENGTH: 15
<212> TYPE: PRT
<213> ORGANISM: Artificial Sequence
<220> FEATURE:
<223> OTHER INFORMATION: Linker sequence 6

<400> SEQUENCE: 149

Gly Gly Gly Gly Ser Gly Gly Gly Gly Ser Gly Gly Gly Gly Ser
1               5                   10                  15

<210> SEQ ID NO 150
<211> LENGTH: 20

```
<212> TYPE: PRT
<213> ORGANISM: Artificial Sequence
<220> FEATURE:
<223> OTHER INFORMATION: Linker sequence 7

<400> SEQUENCE: 150

Gly Gly Gly Gly Ser Gly Gly Gly Ser Gly Gly Gly Gly Ser Gly
1               5                   10                  15

Gly Gly Gly Ser
            20

<210> SEQ ID NO 151
<211> LENGTH: 25
<212> TYPE: PRT
<213> ORGANISM: Artificial Sequence
<220> FEATURE:
<223> OTHER INFORMATION: Linker sequence 8

<400> SEQUENCE: 151

Gly Gly Gly Gly Ser Gly Gly Gly Ser Gly Gly Gly Gly Ser Gly
1               5                   10                  15

Gly Gly Gly Ser Gly Gly Gly Gly Ser
            20                  25

<210> SEQ ID NO 152
<211> LENGTH: 420
<212> TYPE: PRT
<213> ORGANISM: Artificial Sequence
<220> FEATURE:
<223> OTHER INFORMATION: BCMA 269A37346 CAR

<400> SEQUENCE: 152

Met Ala Leu Pro Val Thr Ala Leu Leu Leu Pro Leu Ala Leu Leu Leu
1               5                   10                  15

His Ala Ala Arg Pro Val Asn Arg Thr Arg Arg Met His Gln Val Gln
            20                  25                  30

Leu Val Glu Ser Gly Gly Gly Leu Val Gln Pro Gly Gly Ser Leu Arg
        35                  40                  45

Leu Ser Cys Glu Ala Ser Gly Phe Thr Leu Asp Tyr Tyr Ala Ile Gly
    50                  55                  60

Trp Phe Arg Gln Ala Pro Gly Lys Glu Arg Glu Gly Val Ile Cys Ile
65                  70                  75                  80

Ser Arg Ser Asp Gly Ser Thr Tyr Tyr Ala Asp Ser Val Lys Gly Arg
                85                  90                  95

Phe Thr Ile Ser Arg Asp Asn Ala Lys Lys Thr Val Tyr Leu Gln Met
            100                 105                 110

Ile Ser Leu Lys Pro Glu Asp Thr Ala Ala Tyr Tyr Cys Ala Ala Gly
        115                 120                 125

Ala Asp Cys Ser Gly Tyr Leu Arg Asp Tyr Glu Phe Arg Gly Gln Gly
    130                 135                 140

Thr Gln Val Thr Val Ser Ser Thr Thr Thr Pro Ala Pro Arg
145                 150                 155                 160

Pro Pro Thr Pro Ala Pro Thr Ile Ala Ser Gln Pro Leu Ser Leu Arg
                165                 170                 175

Pro Glu Ala Cys Arg Pro Ala Ala Gly Gly Ala Val His Thr Arg Gly
            180                 185                 190

Leu Asp Phe Ala Cys Asp Phe Trp Val Leu Val Val Val Gly Gly Val
        195                 200                 205

Leu Ala Cys Tyr Ser Leu Leu Val Thr Val Ala Phe Ile Ile Phe Trp
```

-continued

```
            210                 215                 220
Val Arg Ser Lys Arg Ser Arg Leu Leu His Ser Asp Tyr Met Asn Met
225                 230                 235                 240

Thr Pro Arg Arg Pro Gly Pro Thr Arg Lys His Tyr Gln Pro Tyr Ala
                245                 250                 255

Pro Pro Arg Asp Phe Ala Ala Tyr Arg Ser Lys Arg Gly Arg Lys Lys
                260                 265                 270

Leu Leu Tyr Ile Phe Lys Gln Pro Phe Met Arg Pro Val Gln Thr Thr
                275                 280                 285

Gln Glu Glu Asp Gly Cys Ser Cys Arg Phe Pro Glu Glu Glu Glu Gly
            290                 295                 300

Gly Cys Glu Leu Arg Val Lys Phe Ser Arg Ser Ala Asp Ala Pro Ala
305                 310                 315                 320

Tyr Lys Gln Gly Gln Asn Gln Leu Tyr Asn Glu Leu Asn Leu Gly Arg
                325                 330                 335

Arg Glu Glu Tyr Asp Val Leu Asp Lys Arg Arg Gly Arg Asp Pro Glu
                340                 345                 350

Met Gly Gly Lys Pro Arg Arg Lys Asn Pro Gln Glu Gly Leu Tyr Asn
            355                 360                 365

Glu Leu Gln Lys Asp Lys Met Ala Glu Ala Tyr Ser Glu Ile Gly Met
370                 375                 380

Lys Gly Glu Arg Arg Arg Gly Lys Gly His Asp Gly Leu Tyr Gln Gly
385                 390                 395                 400

Leu Ser Thr Ala Thr Lys Asp Thr Tyr Asp Ala Leu His Met Gln Ala
                405                 410                 415

Leu Pro Pro Arg
            420

<210> SEQ ID NO 153
<211> LENGTH: 426
<212> TYPE: PRT
<213> ORGANISM: Artificial Sequence
<220> FEATURE:
<223> OTHER INFORMATION: BCMA 269A37348 CAR

<400> SEQUENCE: 153

Met Ala Leu Pro Val Thr Ala Leu Leu Leu Pro Leu Ala Leu Leu Leu
1               5                   10                  15

His Ala Ala Arg Pro Val Asn Arg Thr Arg Arg Met His Gln Val Lys
                20                  25                  30

Leu Glu Glu Ser Gly Gly Arg Leu Val Gln Pro Arg Gly Ser Leu Arg
            35                  40                  45

Leu Ser Cys Ala Gly Ser Gly Arg Thr Phe Ser Thr Tyr Gly Met Ala
        50                  55                  60

Trp Phe Arg Gln Ala Pro Gly Lys Glu Arg Glu Phe Val Ala Ser Lys
65                  70                  75                  80

Ala Ser Met Asn Tyr Ser Gly Arg Thr Tyr Tyr Ala Asp Ser Val Lys
                85                  90                  95

Gly Arg Phe Thr Ile Ala Arg Asp Asn Ala Lys Asn Met Val Phe Leu
                100                 105                 110

Gln Met Asn Asn Leu Lys Pro Glu Asp Thr Ala Val Tyr Tyr Cys Ala
            115                 120                 125

Ala Gly Thr Gly Cys Ser Thr Tyr Gly Cys Phe Asp Ala Gln Ile Ile
        130                 135                 140

Asp Tyr Trp Gly Lys Gly Thr Leu Val Thr Val Ser Ser Thr Ser Thr
```

```
                145                 150                 155                 160
Thr Thr Pro Ala Pro Arg Pro Thr Pro Ala Pro Thr Ile Ala Ser
                    165                 170                 175

Gln Pro Leu Ser Leu Arg Pro Glu Ala Cys Arg Pro Ala Ala Gly Gly
                180                 185                 190

Ala Val His Thr Arg Gly Leu Asp Phe Ala Cys Asp Phe Trp Val Leu
            195                 200                 205

Val Val Val Gly Gly Val Leu Ala Cys Tyr Ser Leu Leu Val Thr Val
        210                 215                 220

Ala Phe Ile Ile Phe Trp Val Arg Ser Lys Arg Ser Arg Leu Leu His
225                 230                 235                 240

Ser Asp Tyr Met Asn Met Thr Pro Arg Arg Pro Gly Pro Thr Arg Lys
                    245                 250                 255

His Tyr Gln Pro Tyr Ala Pro Pro Arg Asp Phe Ala Ala Tyr Arg Ser
                260                 265                 270

Lys Arg Gly Arg Lys Lys Leu Leu Tyr Ile Phe Lys Gln Pro Phe Met
            275                 280                 285

Arg Pro Val Gln Thr Thr Gln Glu Glu Asp Gly Cys Ser Cys Arg Phe
        290                 295                 300

Pro Glu Glu Glu Glu Gly Gly Cys Glu Leu Arg Val Lys Phe Ser Arg
305                 310                 315                 320

Ser Ala Asp Ala Pro Ala Tyr Lys Gln Gly Gln Asn Gln Leu Tyr Asn
                    325                 330                 335

Glu Leu Asn Leu Gly Arg Arg Glu Glu Tyr Asp Val Leu Asp Lys Arg
                340                 345                 350

Arg Gly Arg Asp Pro Glu Met Gly Gly Lys Pro Arg Arg Lys Asn Pro
            355                 360                 365

Gln Glu Gly Leu Tyr Asn Glu Leu Gln Lys Asp Lys Met Ala Glu Ala
        370                 375                 380

Tyr Ser Glu Ile Gly Met Lys Gly Glu Arg Arg Arg Gly Lys Gly His
385                 390                 395                 400

Asp Gly Leu Tyr Gln Gly Leu Ser Thr Ala Thr Lys Asp Thr Tyr Asp
                    405                 410                 415

Ala Leu His Met Gln Ala Leu Pro Pro Arg
                420                 425

<210> SEQ ID NO 154
<211> LENGTH: 416
<212> TYPE: PRT
<213> ORGANISM: Artificial Sequence
<220> FEATURE:
<223> OTHER INFORMATION: BCMA 269A37917 CAR

<400> SEQUENCE: 154

Met Ala Leu Pro Val Thr Ala Leu Leu Leu Pro Leu Ala Leu Leu Leu
1               5                   10                  15

His Ala Ala Arg Pro Val Asn Arg Thr Arg Met His Glu Val Gln
                20                  25                  30

Leu Val Glu Ser Gly Gly Gly Leu Val Gln Ala Gly Gly Ser Leu Arg
            35                  40                  45

Leu Ser Cys Ala Ala Ser Gly Arg Thr Phe Thr Met Gly Trp Phe Arg
        50                  55                  60

Gln Ala Pro Gly Lys Glu Arg Glu Phe Val Ala Ala Ile Ser Leu Ser
65                  70                  75                  80

Pro Thr Leu Ala Tyr Tyr Ala Glu Ser Val Lys Gly Arg Phe Thr Ile
```

```
                    85                  90                  95

Ser Arg Asp Asn Ala Lys Asn Thr Val Val Leu Gln Met Asn Ser Leu
                100                 105                 110

Lys Pro Glu Asp Thr Ala Leu Tyr Tyr Cys Ala Ala Asp Arg Lys Ser
            115                 120                 125

Val Met Ser Ile Arg Pro Asp Tyr Trp Gly Gln Gly Thr Gln Val Thr
        130                 135                 140

Val Ser Ser Thr Ser Thr Thr Thr Pro Ala Pro Arg Pro Pro Thr Pro
145                 150                 155                 160

Ala Pro Thr Ile Ala Ser Gln Pro Leu Ser Leu Arg Pro Glu Ala Cys
                165                 170                 175

Arg Pro Ala Ala Gly Gly Ala Val His Thr Arg Gly Leu Asp Phe Ala
            180                 185                 190

Cys Asp Phe Trp Val Leu Val Val Val Gly Gly Val Leu Ala Cys Tyr
        195                 200                 205

Ser Leu Leu Val Thr Val Ala Phe Ile Ile Phe Trp Val Arg Ser Lys
210                 215                 220

Arg Ser Arg Leu Leu His Ser Asp Tyr Met Asn Met Thr Pro Arg Arg
225                 230                 235                 240

Pro Gly Pro Thr Arg Lys His Tyr Gln Pro Tyr Ala Pro Pro Arg Asp
                245                 250                 255

Phe Ala Ala Tyr Arg Ser Lys Arg Gly Arg Lys Lys Leu Leu Tyr Ile
            260                 265                 270

Phe Lys Gln Pro Phe Met Arg Pro Val Gln Thr Thr Gln Glu Glu Asp
        275                 280                 285

Gly Cys Ser Cys Arg Phe Pro Glu Glu Glu Glu Gly Gly Cys Glu Leu
                295                 300

Arg Val Lys Phe Ser Arg Ser Ala Asp Ala Pro Ala Tyr Lys Gln Gly
305                 310                 315                 320

Gln Asn Gln Leu Tyr Asn Glu Leu Asn Leu Gly Arg Arg Glu Glu Tyr
                325                 330                 335

Asp Val Leu Asp Lys Arg Arg Gly Arg Asp Pro Glu Met Gly Gly Lys
            340                 345                 350

Pro Arg Arg Lys Asn Pro Gln Glu Gly Leu Tyr Asn Glu Leu Gln Lys
        355                 360                 365

Asp Lys Met Ala Glu Ala Tyr Ser Glu Ile Gly Met Lys Gly Glu Arg
                375                 380

Arg Arg Gly Lys Gly His Asp Gly Leu Tyr Gln Gly Leu Ser Thr Ala
385                 390                 395                 400

Thr Lys Asp Thr Tyr Asp Ala Leu His Met Gln Ala Leu Pro Pro Arg
                405                 410                 415

<210> SEQ ID NO 155
<211> LENGTH: 418
<212> TYPE: PRT
<213> ORGANISM: Artificial Sequence
<220> FEATURE:
<223> OTHER INFORMATION: BCMA 269A37355 CAR

<400> SEQUENCE: 155

Met Ala Leu Pro Val Thr Ala Leu Leu Leu Pro Leu Ala Leu Leu Leu
1               5                   10                  15

His Ala Ala Arg Pro Val Asn Arg Thr Arg Arg Met His Ala Val Gln
                20                  25                  30

Leu Val Asp Ser Gly Gly Gly Leu Val Gln Pro Gly Gly Ser Leu Arg
```

Note: Position 290 appears before "Gly Cys Ser Cys..." — reading as "Gly Cys Ser Cys Arg Phe Pro Glu Glu Glu Glu Gly Gly Cys Glu Leu" with position marker 290 under Gly and 295 under Arg, 300 under Gly.

```
            35                  40                  45
Leu Ser Cys Val Ala Ser Gly Gly Ile Phe Val Ile Asn Ala Met Gly
 50                  55                  60

Trp Tyr Arg Gln Ala Pro Gly Lys Gln Arg Glu Leu Val Ala Ser Ile
 65                  70                  75                  80

Arg Gly Leu Gly Arg Thr Asn Tyr Asp Asp Ser Val Lys Gly Arg Phe
                 85                  90                  95

Thr Ile Ser Arg Asp Asn Ala Asn Asn Thr Val Tyr Leu Gln Met Asn
            100                 105                 110

Ser Leu Glu Pro Glu Asp Thr Ala Val Tyr Tyr Cys Thr Val Tyr Val
        115                 120                 125

Thr Leu Leu Gly Gly Val Asn Arg Asp Tyr Trp Gly Gln Gly Thr Gln
    130                 135                 140

Val Thr Val Ser Ser Thr Ser Thr Thr Thr Pro Ala Pro Arg Pro Pro
145                 150                 155                 160

Thr Pro Ala Pro Thr Ile Ala Ser Gln Pro Leu Ser Leu Arg Pro Glu
                165                 170                 175

Ala Cys Arg Pro Ala Ala Gly Gly Ala Val His Thr Arg Gly Leu Asp
            180                 185                 190

Phe Ala Cys Asp Phe Trp Val Leu Val Val Val Gly Gly Val Leu Ala
        195                 200                 205

Cys Tyr Ser Leu Leu Val Thr Val Ala Phe Ile Ile Phe Trp Val Arg
    210                 215                 220

Ser Lys Arg Ser Arg Leu Leu His Ser Asp Tyr Met Asn Met Thr Pro
225                 230                 235                 240

Arg Arg Pro Gly Pro Thr Arg Lys His Tyr Gln Pro Tyr Ala Pro Pro
                245                 250                 255

Arg Asp Phe Ala Ala Tyr Arg Ser Lys Arg Gly Arg Lys Lys Leu Leu
            260                 265                 270

Tyr Ile Phe Lys Gln Pro Phe Met Arg Pro Val Gln Thr Thr Gln Glu
        275                 280                 285

Glu Asp Gly Cys Ser Cys Arg Phe Pro Glu Glu Glu Glu Gly Gly Cys
    290                 295                 300

Glu Leu Arg Val Lys Phe Ser Arg Ser Ala Asp Ala Pro Ala Tyr Lys
305                 310                 315                 320

Gln Gly Gln Asn Gln Leu Tyr Asn Glu Leu Asn Leu Gly Arg Arg Glu
                325                 330                 335

Glu Tyr Asp Val Leu Asp Lys Arg Arg Gly Arg Asp Pro Glu Met Gly
            340                 345                 350

Gly Lys Pro Arg Arg Lys Asn Pro Gln Glu Gly Leu Tyr Asn Glu Leu
        355                 360                 365

Gln Lys Asp Lys Met Ala Glu Ala Tyr Ser Glu Ile Gly Met Lys Gly
    370                 375                 380

Glu Arg Arg Arg Gly Lys Gly His Asp Gly Leu Tyr Gln Gly Leu Ser
385                 390                 395                 400

Thr Ala Thr Lys Asp Thr Tyr Asp Ala Leu His Met Gln Ala Leu Pro
                405                 410                 415

Pro Arg

<210> SEQ ID NO 156
<211> LENGTH: 417
<212> TYPE: PRT
<213> ORGANISM: Artificial Sequence
<220> FEATURE:
```

<223> OTHER INFORMATION: BCMA 269A37915 CAR

<400> SEQUENCE: 156

```
Met Ala Leu Pro Val Thr Ala Leu Leu Leu Pro Leu Ala Leu Leu Leu
1               5                   10                  15

His Ala Ala Arg Pro Val Asn Arg Thr Arg Arg Met His Glu Val Gln
            20                  25                  30

Leu Val Glu Ser Gly Gly Gly Leu Val Gln Ala Gly Gly Ser Leu Arg
        35                  40                  45

Leu Ser Cys Ala Ala Ser Gly Arg Thr Phe Ser Ser Ile Val Met Gly
    50                  55                  60

Trp Phe Arg Gln Ala Pro Gly Lys Glu Arg Glu Phe Val Gly Ala Ile
65                  70                  75                  80

Met Trp Asn Asp Gly Ile Thr Tyr Leu Gln Asp Ser Val Lys Gly Arg
                85                  90                  95

Phe Thr Ile Phe Arg Asp Asn Ala Lys Asn Thr Val Tyr Leu Gln Met
            100                 105                 110

Asn Ser Leu Lys Leu Glu Asp Thr Ala Val Tyr Tyr Cys Ala Ala Ser
        115                 120                 125

Lys Gly Arg Tyr Ser Glu Tyr Glu Tyr Trp Gly Gln Gly Thr Gln Val
    130                 135                 140

Thr Val Ser Ser Thr Ser Thr Thr Thr Pro Ala Pro Arg Pro Pro Thr
145                 150                 155                 160

Pro Ala Pro Thr Ile Ala Ser Gln Pro Leu Ser Leu Arg Pro Glu Ala
                165                 170                 175

Cys Arg Pro Ala Ala Gly Gly Ala Val His Thr Arg Gly Leu Asp Phe
            180                 185                 190

Ala Cys Asp Phe Trp Val Leu Val Val Gly Gly Val Leu Ala Cys
        195                 200                 205

Tyr Ser Leu Leu Val Thr Val Ala Phe Ile Ile Phe Trp Val Arg Ser
    210                 215                 220

Lys Arg Ser Arg Leu Leu His Ser Asp Tyr Met Asn Met Thr Pro Arg
225                 230                 235                 240

Arg Pro Gly Pro Thr Arg Lys His Tyr Gln Pro Tyr Ala Pro Pro Arg
                245                 250                 255

Asp Phe Ala Ala Tyr Arg Ser Lys Arg Gly Arg Lys Lys Leu Leu Tyr
            260                 265                 270

Ile Phe Lys Gln Pro Phe Met Arg Pro Val Gln Thr Thr Gln Glu Glu
        275                 280                 285

Asp Gly Cys Ser Cys Arg Phe Pro Glu Glu Glu Glu Gly Gly Cys Glu
    290                 295                 300

Leu Arg Val Lys Phe Ser Arg Ser Ala Asp Ala Pro Ala Tyr Lys Gln
305                 310                 315                 320

Gly Gln Asn Gln Leu Tyr Asn Glu Leu Asn Leu Gly Arg Arg Glu Glu
                325                 330                 335

Tyr Asp Val Leu Asp Lys Arg Arg Gly Arg Asp Pro Glu Met Gly Gly
            340                 345                 350

Lys Pro Arg Arg Lys Asn Pro Gln Glu Gly Leu Tyr Asn Glu Leu Gln
        355                 360                 365

Lys Asp Lys Met Ala Glu Ala Tyr Ser Glu Ile Gly Met Lys Gly Glu
    370                 375                 380

Arg Arg Arg Gly Lys Gly His Asp Gly Leu Tyr Gln Gly Leu Ser Thr
385                 390                 395                 400
```

```
Ala Thr Lys Asp Thr Tyr Asp Ala Leu His Met Gln Ala Leu Pro Pro
                405                 410                 415

Arg

<210> SEQ ID NO 157
<211> LENGTH: 426
<212> TYPE: PRT
<213> ORGANISM: Artificial Sequence
<220> FEATURE:
<223> OTHER INFORMATION: BCMA 269A37936 CAR

<400> SEQUENCE: 157

Met Ala Leu Pro Val Thr Ala Leu Leu Leu Pro Leu Ala Leu Leu Leu
1               5                   10                  15

His Ala Ala Arg Pro Val Asn Arg Thr Arg Arg Met His Glu Val Gln
                20                  25                  30

Leu Val Glu Ser Gly Gly Gly Val Gln Ala Gly Gly Ser Leu Thr
            35                  40                  45

Val Ser Cys Thr Ala Ser Gly Phe Thr Phe Asp Arg Ala Val Ile Val
    50                  55                  60

Trp Phe Arg Gln Ala Pro Gly Lys Gly Arg Glu Gly Val Ser Phe Ile
65                  70                  75                  80

Lys Pro Ser Asp Gly Thr Ile Tyr Tyr Ile Asp Ser Leu Lys Gly Arg
                85                  90                  95

Phe Thr Ile Ser Ser Asp Ile Ala Lys Asn Thr Val Tyr Leu Gln Met
            100                 105                 110

Lys Ser Leu Glu Ser Glu Asp Ser Ala Val Tyr Tyr Cys Ala Ala Ser
        115                 120                 125

Pro Glu Asp Trp Tyr Thr Asp Trp Ile Asp Trp Ser Ile Tyr Arg Trp
130                 135                 140

Gln His Trp Gly Gln Gly Thr Gln Val Thr Val Ser Ser Thr Ser Thr
145                 150                 155                 160

Thr Thr Pro Ala Pro Arg Pro Pro Thr Pro Ala Pro Thr Ile Ala Ser
                165                 170                 175

Gln Pro Leu Ser Leu Arg Pro Glu Ala Cys Arg Pro Ala Ala Gly Gly
            180                 185                 190

Ala Val His Thr Arg Gly Leu Asp Phe Ala Cys Asp Phe Trp Val Leu
        195                 200                 205

Val Val Val Gly Gly Val Leu Ala Cys Tyr Ser Leu Leu Val Thr Val
210                 215                 220

Ala Phe Ile Ile Phe Trp Val Arg Ser Lys Arg Ser Arg Leu Leu His
225                 230                 235                 240

Ser Asp Tyr Met Asn Met Thr Pro Arg Arg Pro Gly Pro Thr Arg Lys
                245                 250                 255

His Tyr Gln Pro Tyr Ala Pro Pro Arg Asp Phe Ala Ala Tyr Arg Ser
            260                 265                 270

Lys Arg Gly Arg Lys Lys Leu Leu Tyr Ile Phe Lys Gln Pro Phe Met
        275                 280                 285

Arg Pro Val Gln Thr Thr Gln Glu Glu Asp Gly Cys Ser Cys Arg Phe
290                 295                 300

Pro Glu Glu Glu Glu Gly Gly Cys Glu Leu Arg Val Lys Phe Ser Arg
305                 310                 315                 320

Ser Ala Asp Ala Pro Ala Tyr Lys Gln Gly Gln Asn Gln Leu Tyr Asn
                325                 330                 335

Glu Leu Asn Leu Gly Arg Arg Glu Glu Tyr Asp Val Leu Asp Lys Arg
```

```
                    340                 345                 350
Arg Gly Arg Asp Pro Glu Met Gly Gly Lys Pro Arg Arg Lys Asn Pro
            355                 360                 365

Gln Glu Gly Leu Tyr Asn Glu Leu Gln Lys Asp Lys Met Ala Glu Ala
    370                 375                 380

Tyr Ser Glu Ile Gly Met Lys Gly Glu Arg Arg Arg Gly Lys Gly His
385                 390                 395                 400

Asp Gly Leu Tyr Gln Gly Leu Ser Thr Ala Thr Lys Asp Thr Tyr Asp
            405                 410                 415

Ala Leu His Met Gln Ala Leu Pro Pro Arg
            420                 425
```

<210> SEQ ID NO 158
<211> LENGTH: 417
<212> TYPE: PRT
<213> ORGANISM: Artificial Sequence
<220> FEATURE:
<223> OTHER INFORMATION: BCMA 269A37953 CAR

<400> SEQUENCE: 158

```
Met Ala Leu Pro Val Thr Ala Leu Leu Leu Pro Leu Ala Leu Leu Leu
1               5                   10                  15

His Ala Ala Arg Pro Val Asn Arg Thr Arg Met His Glu Val Gln
            20                  25                  30

Leu Val Glu Ser Gly Gly Gly Met Val Gln Ala Gly Asp Ser Leu Arg
        35                  40                  45

Leu Ser Cys Val Gln Ser Thr Tyr Thr Val Asn Ser Asp Val Met Gly
    50                  55                  60

Trp Phe Arg Gln Ala Pro Gly Lys Glu Arg Glu Phe Val Gly Ala Ile
65                  70                  75                  80

Met Trp Asn Asp Gly Ile Thr Tyr Leu Gln Asp Ser Val Lys Gly Arg
                85                  90                  95

Phe Thr Ile Phe Arg Asp Asn Ala Lys Asn Thr Val Tyr Leu Gln Met
            100                 105                 110

Asn Ser Leu Lys Leu Glu Asp Thr Ala Val Tyr Tyr Cys Ala Ala Ser
        115                 120                 125

Lys Gly Arg Tyr Ser Glu Tyr Glu Tyr Trp Gly Gln Gly Thr Gln Val
    130                 135                 140

Thr Val Ser Ser Thr Ser Thr Thr Thr Pro Ala Pro Arg Pro Pro Thr
145                 150                 155                 160

Pro Ala Pro Thr Ile Ala Ser Gln Pro Leu Ser Leu Arg Pro Glu Ala
                165                 170                 175

Cys Arg Pro Ala Ala Gly Gly Ala Val His Thr Arg Gly Leu Asp Phe
            180                 185                 190

Ala Cys Asp Phe Trp Val Leu Val Val Gly Gly Val Leu Ala Cys
        195                 200                 205

Tyr Ser Leu Leu Val Thr Val Ala Phe Ile Ile Phe Trp Val Arg Ser
    210                 215                 220

Lys Arg Ser Arg Leu Leu His Ser Asp Tyr Met Asn Met Thr Pro Arg
225                 230                 235                 240

Arg Pro Gly Pro Thr Arg Lys His Tyr Gln Pro Tyr Ala Pro Pro Arg
                245                 250                 255

Asp Phe Ala Ala Tyr Arg Ser Lys Arg Gly Arg Lys Lys Leu Leu Tyr
            260                 265                 270

Ile Phe Lys Gln Pro Phe Met Arg Pro Val Gln Thr Thr Gln Glu Glu
```

```
                275                 280                 285
Asp Gly Cys Ser Cys Arg Phe Pro Glu Glu Glu Gly Gly Cys Glu
    290                 295                 300

Leu Arg Val Lys Phe Ser Arg Ser Ala Asp Ala Pro Ala Tyr Lys Gln
305                 310                 315                 320

Gly Gln Asn Gln Leu Tyr Asn Glu Leu Asn Leu Gly Arg Arg Glu Glu
                325                 330                 335

Tyr Asp Val Leu Asp Lys Arg Arg Gly Arg Asp Pro Glu Met Gly Gly
                340                 345                 350

Lys Pro Arg Arg Lys Asn Pro Gln Glu Gly Leu Tyr Asn Glu Leu Gln
                355                 360                 365

Lys Asp Lys Met Ala Glu Ala Tyr Ser Glu Ile Gly Met Lys Gly Glu
                370                 375                 380

Arg Arg Arg Gly Lys Gly His Asp Gly Leu Tyr Gln Gly Leu Ser Thr
385                 390                 395                 400

Ala Thr Lys Asp Thr Tyr Asp Ala Leu His Met Gln Ala Leu Pro Pro
                405                 410                 415

Arg

<210> SEQ ID NO 159
<211> LENGTH: 418
<212> TYPE: PRT
<213> ORGANISM: Artificial Sequence
<220> FEATURE:
<223> OTHER INFORMATION: BCMA 269A37965 CAR

<400> SEQUENCE: 159

Met Ala Leu Pro Val Thr Ala Leu Leu Leu Pro Leu Ala Leu Leu Leu
1               5                   10                  15

His Ala Ala Arg Pro Val Asn Arg Thr Arg Met His Ala Val Gln
                20                  25                  30

Leu Val Glu Ser Gly Gly Gly Leu Val Gln Ala Gly Asp Ser Leu Arg
                35                  40                  45

Leu Ser Cys Thr Ala Ser Gly Ala Thr Leu Thr Asn Asp His Met Ala
    50                  55                  60

Trp Phe Arg Gln Ala Pro Gly Lys Gly Arg Glu Phe Val Ala Ala Ile
65                  70                  75                  80

Asp Trp Ser Gly Arg Thr Thr Asn Tyr Ala Asp Pro Val Glu Gly Arg
                85                  90                  95

Phe Thr Ile Ser Arg Asn Asn Ala Lys Asn Thr Val Tyr Leu Glu Met
                100                 105                 110

Asn Ser Leu Lys Leu Glu Asp Thr Ala Val Tyr Tyr Cys Ala Val Leu
            115                 120                 125

Arg Ala Trp Ile Ser Tyr Asp Asn Asp Tyr Trp Gly Gln Gly Thr Gln
    130                 135                 140

Val Thr Val Ser Ser Thr Ser Thr Thr Thr Pro Ala Pro Arg Pro Pro
145                 150                 155                 160

Thr Pro Ala Pro Thr Ile Ala Ser Gln Pro Leu Ser Leu Arg Pro Glu
                165                 170                 175

Ala Cys Arg Pro Ala Ala Gly Gly Ala Val His Thr Arg Gly Leu Asp
                180                 185                 190

Phe Ala Cys Asp Phe Trp Val Leu Val Val Val Gly Gly Val Leu Ala
            195                 200                 205

Cys Tyr Ser Leu Leu Val Thr Val Ala Phe Ile Ile Phe Trp Val Arg
    210                 215                 220
```

Ser Lys Arg Ser Arg Leu Leu His Ser Asp Tyr Met Asn Met Thr Pro
225                 230                 235                 240

Arg Arg Pro Gly Pro Thr Arg Lys His Tyr Gln Pro Tyr Ala Pro Pro
            245                 250                 255

Arg Asp Phe Ala Ala Tyr Arg Ser Lys Arg Gly Arg Lys Lys Leu Leu
            260                 265                 270

Tyr Ile Phe Lys Gln Pro Phe Met Arg Pro Val Gln Thr Thr Gln Glu
        275                 280                 285

Glu Asp Gly Cys Ser Cys Arg Phe Pro Glu Glu Glu Glu Gly Gly Cys
    290                 295                 300

Glu Leu Arg Val Lys Phe Ser Arg Ser Ala Asp Ala Pro Ala Tyr Lys
305                 310                 315                 320

Gln Gly Gln Asn Gln Leu Tyr Asn Glu Leu Asn Leu Gly Arg Arg Glu
                325                 330                 335

Glu Tyr Asp Val Leu Asp Lys Arg Arg Gly Arg Asp Pro Glu Met Gly
            340                 345                 350

Gly Lys Pro Arg Arg Lys Asn Pro Gln Glu Gly Leu Tyr Asn Glu Leu
        355                 360                 365

Gln Lys Asp Lys Met Ala Glu Ala Tyr Ser Glu Ile Gly Met Lys Gly
    370                 375                 380

Glu Arg Arg Arg Gly Lys Gly His Asp Gly Leu Tyr Gln Gly Leu Ser
385                 390                 395                 400

Thr Ala Thr Lys Asp Thr Tyr Asp Ala Leu His Met Gln Ala Leu Pro
                405                 410                 415

Pro Arg

<210> SEQ ID NO 160
<211> LENGTH: 418
<212> TYPE: PRT
<213> ORGANISM: Artificial Sequence
<220> FEATURE:
<223> OTHER INFORMATION: BCMA 269A37972 CAR

<400> SEQUENCE: 160

Met Ala Leu Pro Val Thr Ala Leu Leu Leu Pro Leu Ala Leu Leu Leu
1               5                   10                  15

His Ala Ala Arg Pro Val Asn Arg Thr Arg Met His Gln Val Gln
            20                  25                  30

Leu Val Glu Ser Gly Gly Gly Leu Val Gln Ala Gly Gly Ser Leu Arg
            35                  40                  45

Leu Ser Cys Ala Ala Ser Gly Gly Thr Leu Ser Lys Asn Thr Val Ala
    50                  55                  60

Trp Phe Arg Gln Ala Pro Gly Lys Glu Arg Gly Phe Val Ala Ser Ile
65                  70                  75                  80

Thr Trp Asp Gly Arg Thr Thr Tyr Tyr Ala Asp Ser Val Lys Gly Arg
                85                  90                  95

Phe Thr Ile Ser Arg Asp Asn Ala Lys Asn Thr Val Tyr Leu Gln Met
            100                 105                 110

Asn Ser Leu Lys Pro Glu Asp Thr Ala Val Tyr Val Cys Ala Asp Leu
        115                 120                 125

Gly Lys Trp Pro Ala Gly Pro Ala Asp Tyr Trp Gly Gln Gly Thr Gln
    130                 135                 140

Val Thr Val Ser Ser Thr Ser Thr Thr Pro Ala Pro Arg Pro Pro
145                 150                 155                 160

Thr Pro Ala Pro Thr Ile Ala Ser Gln Pro Leu Ser Leu Arg Pro Glu
              165                 170                 175

Ala Cys Arg Pro Ala Ala Gly Gly Ala Val His Thr Arg Gly Leu Asp
        180                 185                 190

Phe Ala Cys Asp Phe Trp Val Leu Val Val Val Gly Gly Val Leu Ala
            195                 200                 205

Cys Tyr Ser Leu Leu Val Thr Val Ala Phe Ile Ile Phe Trp Val Arg
210                 215                 220

Ser Lys Arg Ser Arg Leu Leu His Ser Asp Tyr Met Asn Met Thr Pro
225                 230                 235                 240

Arg Arg Pro Gly Pro Thr Arg Lys His Tyr Gln Pro Tyr Ala Pro Pro
                245                 250                 255

Arg Asp Phe Ala Ala Tyr Arg Ser Lys Arg Gly Arg Lys Lys Leu Leu
            260                 265                 270

Tyr Ile Phe Lys Gln Pro Phe Met Arg Pro Val Gln Thr Thr Gln Glu
            275                 280                 285

Glu Asp Gly Cys Ser Cys Arg Phe Pro Glu Glu Glu Glu Gly Gly Cys
        290                 295                 300

Glu Leu Arg Val Lys Phe Ser Arg Ser Ala Asp Ala Pro Ala Tyr Lys
305                 310                 315                 320

Gln Gly Gln Asn Gln Leu Tyr Asn Glu Leu Asn Leu Gly Arg Arg Glu
                325                 330                 335

Glu Tyr Asp Val Leu Asp Lys Arg Arg Gly Arg Asp Pro Glu Met Gly
            340                 345                 350

Gly Lys Pro Arg Arg Lys Asn Pro Gln Glu Gly Leu Tyr Asn Glu Leu
        355                 360                 365

Gln Lys Asp Lys Met Ala Glu Ala Tyr Ser Glu Ile Gly Met Lys Gly
    370                 375                 380

Glu Arg Arg Arg Gly Lys Gly His Asp Gly Leu Tyr Gln Gly Leu Ser
385                 390                 395                 400

Thr Ala Thr Lys Asp Thr Tyr Asp Ala Leu His Met Gln Ala Leu Pro
                405                 410                 415

Pro Arg

<210> SEQ ID NO 161
<211> LENGTH: 417
<212> TYPE: PRT
<213> ORGANISM: Artificial Sequence
<220> FEATURE:
<223> OTHER INFORMATION: BCMA 269A37353 CAR

<400> SEQUENCE: 161

Met Ala Leu Pro Val Thr Ala Leu Leu Leu Pro Leu Ala Leu Leu Leu
1               5                   10                  15

His Ala Ala Arg Pro Val Asn Arg Thr Arg Arg Met His Gln Val Lys
                20                  25                  30

Leu Glu Glu Ser Gly Gly Gly Leu Val Gln Ala Gly Arg Ser Leu Arg
            35                  40                  45

Leu Ser Cys Ala Ala Ser Glu His Thr Phe Ser Ser His Val Met Gly
        50                  55                  60

Trp Phe Arg Gln Ala Pro Gly Lys Glu Arg Glu Ser Val Ala Val Ile
65                  70                  75                  80

Gly Trp Arg Asp Ile Ser Thr Ser Tyr Ala Asp Ser Val Lys Gly Arg
                85                  90                  95

Phe Thr Ile Ser Arg Asp Asn Ala Lys Lys Thr Leu Tyr Leu Gln Met 100                 105                 110
Asn Ser Leu Lys Pro Glu Asp Thr Ala Val Tyr Tyr Cys Ala Ala Arg
            115                 120                 125

Arg Ile Asp Ala Ala Asp Phe Asp Ser Trp Gly Gln Gly Thr Gln Val
        130                 135                 140

Thr Val Ser Ser Thr Ser Thr Thr Pro Ala Pro Arg Pro Pro Thr
145                 150                 155                 160

Pro Ala Pro Thr Ile Ala Ser Gln Pro Leu Ser Leu Arg Pro Glu Ala
                165                 170                 175

Cys Arg Pro Ala Ala Gly Gly Ala Val His Thr Arg Gly Leu Asp Phe
            180                 185                 190

Ala Cys Asp Phe Trp Val Leu Val Val Gly Gly Val Leu Ala Cys
        195                 200                 205

Tyr Ser Leu Leu Val Thr Val Ala Phe Ile Ile Phe Trp Val Arg Ser
    210                 215                 220

Lys Arg Ser Arg Leu Leu His Ser Asp Tyr Met Asn Met Thr Pro Arg
225                 230                 235                 240

Arg Pro Gly Pro Thr Arg Lys His Tyr Gln Pro Tyr Ala Pro Pro Arg
                245                 250                 255

Asp Phe Ala Ala Tyr Arg Ser Lys Arg Gly Arg Lys Lys Leu Leu Tyr
            260                 265                 270

Ile Phe Lys Gln Pro Phe Met Arg Pro Val Gln Thr Thr Gln Glu Glu
        275                 280                 285

Asp Gly Cys Ser Cys Arg Phe Pro Glu Glu Glu Glu Gly Gly Cys Glu
    290                 295                 300

Leu Arg Val Lys Phe Ser Arg Ser Ala Asp Ala Pro Ala Tyr Lys Gln
305                 310                 315                 320

Gly Gln Asn Gln Leu Tyr Asn Glu Leu Asn Leu Gly Arg Arg Glu Glu
                325                 330                 335

Tyr Asp Val Leu Asp Lys Arg Arg Gly Arg Asp Pro Glu Met Gly Gly
            340                 345                 350

Lys Pro Arg Arg Lys Asn Pro Gln Glu Gly Leu Tyr Asn Glu Leu Gln
        355                 360                 365

Lys Asp Lys Met Ala Glu Ala Tyr Ser Glu Ile Gly Met Lys Gly Glu
    370                 375                 380

Arg Arg Arg Gly Lys Gly His Asp Gly Leu Tyr Gln Gly Leu Ser Thr
385                 390                 395                 400

Ala Thr Lys Asp Thr Tyr Asp Ala Leu His Met Gln Ala Leu Pro Pro
                405                 410                 415

Arg

<210> SEQ ID NO 162
<211> LENGTH: 417
<212> TYPE: PRT
<213> ORGANISM: Artificial Sequence
<220> FEATURE:
<223> OTHER INFORMATION: BCMA 269A37948 CAR

<400> SEQUENCE: 162

Met Ala Leu Pro Val Thr Ala Leu Leu Leu Pro Leu Ala Leu Leu Leu
1               5                   10                  15

His Ala Ala Arg Pro Val Asn Arg Thr Arg Met His Ala Val Gln
            20                  25                  30

Leu Val Glu Ser Gly Gly Gly Leu Val Gln Ala Gly Asp Ser Leu Arg
        35                  40                  45

```
Leu Thr Cys Thr Ala Ser Gly Arg Ala Phe Ser Thr Tyr Phe Met Ala
 50                  55                  60

Trp Phe Arg Gln Ala Pro Gly Lys Glu Arg Glu Phe Val Ala Gly Ile
 65                  70                  75                  80

Ala Trp Ser Gly Gly Ser Thr Ala Tyr Ala Asp Ser Val Lys Gly Arg
                 85                  90                  95

Phe Thr Ile Ser Arg Asp Asn Ala Lys Asn Thr Val Tyr Leu Gln Met
                100                 105                 110

Asn Ser Leu Lys Ser Glu Asp Thr Ala Val Tyr Tyr Cys Ala Ser Arg
            115                 120                 125

Gly Ile Glu Val Glu Glu Phe Gly Ala Trp Gly Gln Gly Thr Gln Val
130                 135                 140

Thr Val Ser Ser Thr Ser Thr Thr Thr Pro Ala Pro Arg Pro Pro Thr
145                 150                 155                 160

Pro Ala Pro Thr Ile Ala Ser Gln Pro Leu Ser Leu Arg Pro Glu Ala
                165                 170                 175

Cys Arg Pro Ala Ala Gly Gly Ala Val His Thr Arg Gly Leu Asp Phe
                180                 185                 190

Ala Cys Asp Phe Trp Val Leu Val Val Val Gly Gly Val Leu Ala Cys
            195                 200                 205

Tyr Ser Leu Leu Val Thr Val Ala Phe Ile Ile Phe Trp Val Arg Ser
210                 215                 220

Lys Arg Ser Arg Leu Leu His Ser Asp Tyr Met Asn Met Thr Pro Arg
225                 230                 235                 240

Arg Pro Gly Pro Thr Arg Lys His Tyr Gln Pro Tyr Ala Pro Pro Arg
                245                 250                 255

Asp Phe Ala Ala Tyr Arg Ser Lys Arg Gly Arg Lys Lys Leu Leu Tyr
                260                 265                 270

Ile Phe Lys Gln Pro Phe Met Arg Pro Val Gln Thr Thr Gln Glu Glu
            275                 280                 285

Asp Gly Cys Ser Cys Arg Phe Pro Glu Glu Glu Glu Gly Gly Cys Glu
290                 295                 300

Leu Arg Val Lys Phe Ser Arg Ser Ala Asp Ala Pro Ala Tyr Lys Gln
305                 310                 315                 320

Gly Gln Asn Gln Leu Tyr Asn Glu Leu Asn Leu Gly Arg Arg Glu Glu
                325                 330                 335

Tyr Asp Val Leu Asp Lys Arg Arg Gly Arg Asp Pro Glu Met Gly Gly
                340                 345                 350

Lys Pro Arg Arg Lys Asn Pro Gln Glu Gly Leu Tyr Asn Glu Leu Gln
            355                 360                 365

Lys Asp Lys Met Ala Glu Ala Tyr Ser Glu Ile Gly Met Lys Gly Glu
370                 375                 380

Arg Arg Arg Gly Lys Gly His Asp Gly Leu Tyr Gln Gly Leu Ser Thr
385                 390                 395                 400

Ala Thr Lys Asp Thr Tyr Asp Ala Leu His Met Gln Ala Leu Pro Pro
                405                 410                 415

Arg

<210> SEQ ID NO 163
<211> LENGTH: 411
<212> TYPE: PRT
<213> ORGANISM: Artificial Sequence
<220> FEATURE:
<223> OTHER INFORMATION: CD38 38A37333 CAR
```

<400> SEQUENCE: 163

| | | | | | | | | | | | | | | |
|---|---|---|---|---|---|---|---|---|---|---|---|---|---|---|
|Met|Ala|Leu|Pro|Val|Thr|Ala|Leu|Leu|Pro|Leu|Ala|Leu|Leu|Leu|
|1| | | |5| | | | |10| | | | |15|

His Ala Ala Arg Pro Val Asn Asp Val Gln Leu Val Glu Ser Gly Gly
              20                  25              30

Gly Leu Val Gln Pro Gly Gly Ser Leu Arg Leu Ser Cys Val Ala Ser
    35                40                45

Gly Leu Thr Phe Ser Ser Tyr Pro Met Met Trp Val Arg Gln Ala Pro
   50                55                60

Gly Lys Gly Leu Glu Trp Val Ser Arg Ile Ser Asp Ser Gly Gly Tyr
65              70                75            80

Thr Asn Tyr Asp Asp Ser Val Lys Gly Arg Phe Thr Ile Ser Arg Asp
        85              90            95

Asn Ala Lys Asn Thr Leu Tyr Leu Gln Met Asn Ser Leu Thr Pro Glu
        100            105            110

Asp Thr Ala Val Tyr Tyr Cys Arg Ile Leu Gly Leu Pro Thr Thr Gly
     115              120              125

Gln Gly Thr Gln Val Thr Val Ser Ser Thr Arg Arg Met His Thr Ser
   130               135              140

Thr Thr Thr Pro Ala Pro Arg Pro Pro Thr Pro Ala Pro Thr Ile Ala
145              150                155            160

Ser Gln Pro Leu Ser Leu Arg Pro Glu Ala Cys Arg Pro Ala Ala Gly
            165              170            175

Gly Ala Val His Thr Arg Gly Leu Asp Phe Ala Cys Asp Phe Trp Val
        180            185            190

Leu Val Val Val Gly Gly Val Leu Ala Cys Tyr Ser Leu Leu Val Thr
     195              200            205

Val Ala Phe Ile Ile Phe Trp Val Arg Ser Lys Arg Ser Arg Leu Leu
   210               215              220

His Ser Asp Tyr Met Asn Met Thr Pro Arg Arg Pro Gly Pro Thr Arg
225              230              235            240

Lys His Tyr Gln Pro Tyr Ala Pro Pro Arg Asp Phe Ala Ala Tyr Arg
            245              250            255

Ser Lys Arg Gly Arg Lys Lys Leu Leu Tyr Ile Phe Lys Gln Pro Phe
        260            265            270

Met Arg Pro Val Gln Thr Thr Gln Glu Glu Asp Gly Cys Ser Cys Arg
     275              280              285

Phe Pro Glu Glu Glu Glu Gly Gly Cys Glu Leu Arg Val Lys Phe Ser
   290               295              300

Arg Ser Ala Asp Ala Pro Ala Tyr Lys Gln Gly Gln Asn Gln Leu Tyr
305              310                315            320

Asn Glu Leu Asn Leu Gly Arg Arg Glu Glu Tyr Asp Val Leu Asp Lys
            325              330            335

Arg Arg Gly Arg Asp Pro Glu Met Gly Gly Lys Pro Arg Arg Lys Asn
        340            345            350

Pro Gln Glu Gly Leu Tyr Asn Glu Leu Gln Lys Asp Lys Met Ala Glu
     355              360             365

Ala Tyr Ser Glu Ile Gly Met Lys Gly Glu Arg Arg Arg Gly Lys Gly
   370               375              380

His Asp Gly Leu Tyr Gln Gly Leu Ser Thr Ala Thr Lys Asp Thr Tyr
385              390              395            400

Asp Ala Leu His Met Gln Ala Leu Pro Pro Arg

-continued

```
                    405                 410

<210> SEQ ID NO 164
<211> LENGTH: 423
<212> TYPE: PRT
<213> ORGANISM: Artificial Sequence
<220> FEATURE:
<223> OTHER INFORMATION: CD38 38A37336 CAR

<400> SEQUENCE: 164

Met Ala Leu Pro Val Thr Ala Leu Leu Leu Pro Leu Ala Leu Leu Leu
1               5                   10                  15

His Ala Ala Arg Pro Val Asn Glu Val Gln Leu Val Glu Ser Gly Gly
            20                  25                  30

Gly Leu Val Gln Pro Gly Gly Ser Leu Arg Leu Ser Cys Ala Ala Ser
        35                  40                  45

Gly Phe Thr Phe Ser Ser Asn Trp Met Tyr Trp Val Arg Gln Ala Pro
    50                  55                  60

Gly Lys Gly Leu Glu Trp Val Ala Thr Ile Ser Thr Asp Gly Arg Gly
65                  70                  75                  80

Thr Tyr Tyr Lys Asp Ser Val Lys Gly Arg Phe Thr Val Ser Arg Asp
                85                  90                  95

Asn Ala Met Ser Thr Leu Leu Leu Gln Met Asn Asn Leu Lys Ser Glu
            100                 105                 110

Asp Thr Ala Val Tyr Tyr Cys Ala Lys Glu Pro Arg Val Leu Met Ala
        115                 120                 125

Tyr Leu Arg Asn Leu Gly Asp Phe Gly Ser Trp Gly Gln Gly Thr Gln
    130                 135                 140

Val Thr Val Ser Ser Thr Arg Arg Met His Thr Ser Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Phe Trp Val Leu Val Val Val
        195                 200                 205

Gly Gly Val Leu Ala Cys Tyr Ser Leu Leu Val Thr Val Ala Phe Ile
    210                 215                 220

Ile Phe Trp Val Arg Ser Lys Arg Ser Arg Leu Leu His Ser Asp Tyr
225                 230                 235                 240

Met Asn Met Thr Pro Arg Arg Pro Gly Pro Thr Arg Lys His Tyr Gln
                245                 250                 255

Pro Tyr Ala Pro Pro Arg Asp Phe Ala Ala Tyr Arg Ser Lys Arg Gly
            260                 265                 270

Arg Lys Lys Leu Leu Tyr Ile Phe Lys Gln Pro Phe Met Arg Pro Val
        275                 280                 285

Gln Thr Thr Gln Glu Glu Asp Gly Cys Ser Cys Arg Phe Pro Glu Glu
    290                 295                 300

Glu Glu Gly Gly Cys Glu Leu Arg Val Lys Phe Ser Arg Ser Ala Asp
305                 310                 315                 320

Ala Pro Ala Tyr Lys Gln Gly Gln Asn Gln Leu Tyr Asn Glu Leu Asn
                325                 330                 335

Leu Gly Arg Arg Glu Glu Tyr Asp Val Leu Asp Lys Arg Arg Gly Arg
            340                 345                 350

Asp Pro Glu Met Gly Gly Lys Pro Arg Arg Lys Asn Pro Gln Glu Gly
```

```
                355                 360                 365
Leu Tyr Asn Glu Leu Gln Lys Asp Lys Met Ala Glu Ala Tyr Ser Glu
        370                 375                 380

Ile Gly Met Lys Gly Glu Arg Arg Arg Gly Lys Gly His Asp Gly Leu
385                 390                 395                 400

Tyr Gln Gly Leu Ser Thr Ala Thr Lys Asp Thr Tyr Asp Ala Leu His
                405                 410                 415

Met Gln Ala Leu Pro Pro Arg
            420

<210> SEQ ID NO 165
<211> LENGTH: 412
<212> TYPE: PRT
<213> ORGANISM: Artificial Sequence
<220> FEATURE:
<223> OTHER INFORMATION: CD38 38A37699 CAR

<400> SEQUENCE: 165

Met Ala Leu Pro Val Thr Ala Leu Leu Leu Pro Leu Ala Leu Leu Leu
1               5                   10                  15

His Ala Ala Arg Pro Val Asn Gln Val Gln Leu Val Glu Ser Gly Gly
            20                  25                  30

Gly Leu Val Gln Ala Gly Gly Ser Leu Arg Leu Ser Cys Ala Ala Ser
        35                  40                  45

Gly Arg Ile Phe Ser Ile Asn Ala Met Gly Trp Tyr Arg Gln Ala Pro
    50                  55                  60

Gly Lys Gln Arg Glu Leu Val Ala Ala Ile Ser Thr Ala Gly Ser Thr
65                  70                  75                  80

Asn Tyr Gly Asp Ser Val Lys Gly Arg Phe Thr Ile Ser Arg Asp Asn
                85                  90                  95

Ala Lys Asn Thr Val Tyr Leu Gln Met Asn Ser Leu Lys Pro Glu Asp
            100                 105                 110

Thr Ala Val Tyr Tyr Cys Asn Leu Asn Phe Pro Pro Tyr Val Tyr Trp
        115                 120                 125

Gly Gln Gly Thr Gln Val Thr Val Ser Ser Thr Arg Arg Met His Thr
    130                 135                 140

Ser Thr Thr Thr Pro Ala Pro Arg Pro Pro Thr Pro Ala Pro Thr Ile
145                 150                 155                 160

Ala Ser Gln Pro Leu Ser Leu Arg Pro Glu Ala Cys Arg Pro Ala Ala
                165                 170                 175

Gly Gly Ala Val His Thr Arg Gly Leu Asp Phe Ala Cys Asp Phe Trp
            180                 185                 190

Val Leu Val Val Val Gly Gly Val Leu Ala Cys Tyr Ser Leu Leu Val
        195                 200                 205

Thr Val Ala Phe Ile Ile Phe Trp Val Arg Ser Lys Arg Ser Arg Leu
    210                 215                 220

Leu His Ser Asp Tyr Met Asn Met Thr Pro Arg Arg Pro Gly Pro Thr
225                 230                 235                 240

Arg Lys His Tyr Gln Pro Tyr Ala Pro Pro Arg Asp Phe Ala Ala Tyr
                245                 250                 255

Arg Ser Lys Arg Gly Arg Lys Lys Leu Leu Tyr Ile Phe Lys Gln Pro
            260                 265                 270

Phe Met Arg Pro Val Gln Thr Thr Gln Glu Glu Asp Gly Cys Ser Cys
        275                 280                 285

Arg Phe Pro Glu Glu Glu Glu Gly Gly Cys Glu Leu Arg Val Lys Phe
```

```
            290                 295                 300
Ser Arg Ser Ala Asp Ala Pro Ala Tyr Lys Gln Gly Gln Asn Gln Leu
305                 310                 315                 320

Tyr Asn Glu Leu Asn Leu Gly Arg Arg Glu Glu Tyr Asp Val Leu Asp
                325                 330                 335

Lys Arg Arg Gly Arg Asp Pro Glu Met Gly Gly Lys Pro Arg Arg Lys
                340                 345                 350

Asn Pro Gln Glu Gly Leu Tyr Asn Glu Leu Gln Lys Asp Lys Met Ala
            355                 360                 365

Glu Ala Tyr Ser Glu Ile Gly Met Lys Gly Glu Arg Arg Arg Gly Lys
        370                 375                 380

Gly His Asp Gly Leu Tyr Gln Gly Leu Ser Thr Ala Thr Lys Asp Thr
385                 390                 395                 400

Tyr Asp Ala Leu His Met Gln Ala Leu Pro Pro Arg
                405                 410

<210> SEQ ID NO 166
<211> LENGTH: 416
<212> TYPE: PRT
<213> ORGANISM: Artificial Sequence
<220> FEATURE:
<223> OTHER INFORMATION: CD38 38A37331 CAR

<400> SEQUENCE: 166

Met Ala Leu Pro Val Thr Ala Leu Leu Leu Pro Leu Ala Leu Leu Leu
1               5                   10                  15

His Ala Ala Arg Pro Val Asn Gln Val Lys Leu Glu Glu Ser Gly Gly
                20                  25                  30

Gly Leu Val Gln Pro Gly Glu Ser Leu Arg Leu Ser Cys Ser Ala Ser
            35                  40                  45

Gly Ser Ile Phe Lys Val Phe Arg Val Phe Ala Met Ser Trp Tyr Arg
        50                  55                  60

Gln Gly Pro Gly Lys Gln Arg Glu Leu Val Ala Ser Ile Ser Ser Gly
65                  70                  75                  80

Glu Thr Thr Thr Tyr Ala Asp Ser Val Lys Gly Arg Phe Thr Ile Ser
                85                  90                  95

Arg Asp Asn Ala Lys Asn Thr Ala Tyr Leu Gln Met Asp Ser Leu Lys
                100                 105                 110

Pro Glu Asp Thr Ala Val Tyr Tyr Cys Asn Ala Asp His Thr Phe Thr
            115                 120                 125

Gly Asp Phe Trp Gly Gln Gly Thr Gln Val Thr Val Ser Ser Thr Arg
        130                 135                 140

Arg Met His Thr Ser Thr Thr Thr Pro Ala Pro Arg Pro Pro Thr Pro
145                 150                 155                 160

Ala Pro Thr Ile Ala Ser Gln Pro Leu Ser Leu Arg Pro Glu Ala Cys
                165                 170                 175

Arg Pro Ala Ala Gly Gly Ala Val His Thr Arg Gly Leu Asp Phe Ala
                180                 185                 190

Cys Asp Phe Trp Val Leu Val Val Gly Gly Val Leu Ala Cys Tyr
        195                 200                 205

Ser Leu Leu Val Thr Val Ala Phe Ile Ile Phe Trp Val Arg Ser Lys
        210                 215                 220

Arg Ser Arg Leu Leu His Ser Asp Tyr Met Asn Met Thr Pro Arg Arg
225                 230                 235                 240

Pro Gly Pro Thr Arg Lys His Tyr Gln Pro Tyr Ala Pro Pro Arg Asp
```

```
                    245                 250                 255
Phe Ala Ala Tyr Arg Ser Lys Arg Gly Arg Lys Lys Leu Leu Tyr Ile
                260                 265                 270

Phe Lys Gln Pro Phe Met Arg Pro Val Gln Thr Thr Gln Glu Glu Asp
            275                 280                 285

Gly Cys Ser Cys Arg Phe Pro Glu Glu Glu Glu Gly Cys Glu Leu
        290                 295                 300

Arg Val Lys Phe Ser Arg Ser Ala Asp Ala Pro Ala Tyr Lys Gln Gly
305                 310                 315                 320

Gln Asn Gln Leu Tyr Asn Glu Leu Asn Leu Gly Arg Arg Glu Glu Tyr
                325                 330                 335

Asp Val Leu Asp Lys Arg Arg Gly Arg Asp Pro Glu Met Gly Gly Lys
            340                 345                 350

Pro Arg Arg Lys Asn Pro Gln Glu Gly Leu Tyr Asn Glu Leu Gln Lys
        355                 360                 365

Asp Lys Met Ala Glu Ala Tyr Ser Glu Ile Gly Met Lys Gly Glu Arg
370                 375                 380

Arg Arg Gly Lys Gly His Asp Gly Leu Tyr Gln Gly Leu Ser Thr Ala
385                 390                 395                 400

Thr Lys Asp Thr Tyr Asp Ala Leu His Met Gln Ala Leu Pro Pro Arg
                405                 410                 415
```

<210> SEQ ID NO 167
<211> LENGTH: 413
<212> TYPE: PRT
<213> ORGANISM: Artificial Sequence
<220> FEATURE:
<223> OTHER INFORMATION: CD38 38A37717 CAR

<400> SEQUENCE: 167

```
Met Ala Leu Pro Val Thr Ala Leu Leu Leu Pro Leu Ala Leu Leu Leu
1               5                   10                  15

His Ala Ala Arg Pro Val Asn Glu Val Gln Leu Val Glu Ser Gly Gly
            20                  25                  30

Gly Leu Val Gln Ala Gly Gly Ser Leu Arg Leu Ser Cys Ile Ala Thr
        35                  40                  45

Gly Lys Val Phe Ser Ile Tyr Asp Met Gly Trp Tyr Arg Gln Ala Pro
    50                  55                  60

Gly Lys Gln Arg Glu Leu Val Ala Glu Ile Thr Ser Ser Gly Thr Thr
65                  70                  75                  80

His Tyr Asp Asp Phe Val Ser Gly Arg Phe Thr Ile Ser Arg Asp Asn
                85                  90                  95

Ala Lys Asn Thr Val Tyr Leu Gln Met Asn Thr Leu Lys Ala Glu Asp
            100                 105                 110

Thr Ala Val Tyr Tyr Cys Arg Ala Asn His Val Phe Gly Gly Ser Tyr
        115                 120                 125

Trp Gly Gln Gly Thr Gln Val Thr Val Ser Ser Thr Arg Arg Met His
    130                 135                 140

Thr Ser Thr Thr Thr Pro Ala Pro Arg Pro Pro Thr Pro Ala Pro Thr
145                 150                 155                 160

Ile Ala Ser Gln Pro Leu Ser Leu Arg Pro Glu Ala Cys Arg Pro Ala
                165                 170                 175

Ala Gly Gly Ala Val His Thr Arg Gly Leu Asp Phe Ala Cys Asp Phe
            180                 185                 190

Trp Val Leu Val Val Val Gly Gly Val Leu Ala Cys Tyr Ser Leu Leu
```

```
            195                 200                 205
Val Thr Val Ala Phe Ile Ile Phe Trp Val Arg Ser Lys Arg Ser Arg
210                 215                 220

Leu Leu His Ser Asp Tyr Met Asn Met Thr Pro Arg Arg Pro Gly Pro
225                 230                 235                 240

Thr Arg Lys His Tyr Gln Pro Tyr Ala Pro Pro Arg Asp Phe Ala Ala
                245                 250                 255

Tyr Arg Ser Lys Arg Gly Arg Lys Lys Leu Leu Tyr Ile Phe Lys Gln
                260                 265                 270

Pro Phe Met Arg Pro Val Gln Thr Thr Gln Glu Glu Asp Gly Cys Ser
            275                 280                 285

Cys Arg Phe Pro Glu Glu Glu Glu Gly Gly Cys Glu Leu Arg Val Lys
            290                 295                 300

Phe Ser Arg Ser Ala Asp Ala Pro Ala Tyr Lys Gln Gly Gln Asn Gln
305                 310                 315                 320

Leu Tyr Asn Glu Leu Asn Leu Gly Arg Arg Glu Glu Tyr Asp Val Leu
                325                 330                 335

Asp Lys Arg Arg Gly Arg Asp Pro Glu Met Gly Gly Lys Pro Arg Arg
                340                 345                 350

Lys Asn Pro Gln Glu Gly Leu Tyr Asn Glu Leu Gln Lys Asp Lys Met
            355                 360                 365

Ala Glu Ala Tyr Ser Glu Ile Gly Met Lys Gly Glu Arg Arg Arg Gly
            370                 375                 380

Lys Gly His Asp Gly Leu Tyr Gln Gly Leu Ser Thr Ala Thr Lys Asp
385                 390                 395                 400

Thr Tyr Asp Ala Leu His Met Gln Ala Leu Pro Pro Arg
                405                 410

<210> SEQ ID NO 168
<211> LENGTH: 412
<212> TYPE: PRT
<213> ORGANISM: Artificial Sequence
<220> FEATURE:
<223> OTHER INFORMATION: CD38 38A37719 CAR

<400> SEQUENCE: 168

Met Ala Leu Pro Val Thr Ala Leu Leu Leu Pro Leu Ala Leu Leu Leu
1               5                   10                  15

His Ala Ala Arg Pro Val Asn Gln Val Lys Leu Glu Glu Ser Gly Gly
                20                  25                  30

Gly Ser Val Gln Thr Gly Gly Ser Leu Arg Leu Ser Cys Ala Ala Ser
            35                  40                  45

Ala Ser Ile Phe Thr Arg Leu Pro Met Gly Trp Tyr Arg Gln Ala Pro
50                  55                  60

Gly Lys Gln Arg Glu Leu Val Val Gly Ile Val Pro Ser Gly Arg Ile
65                  70                  75                  80

Asn Tyr Ala Asp Ser Val Lys Gly Arg Phe Thr Ile Ser Arg Asp Asn
                85                  90                  95

Ala Lys Asn Thr Val Tyr Leu Gln Met Asn Ser Leu Arg Pro Glu Asp
                100                 105                 110

Thr Ala Val Tyr Tyr Cys Arg Ala Asp Thr Phe Pro Leu Pro Thr Trp
            115                 120                 125

Gly Gln Gly Thr Gln Val Thr Val Ser Ser Thr Arg Arg Met His Thr
        130                 135                 140

Ser Thr Thr Thr Pro Ala Pro Arg Pro Pro Thr Pro Ala Pro Thr Ile
```

```
            145                 150                 155                 160
Ala Ser Gln Pro Leu Ser Leu Arg Pro Glu Ala Cys Arg Pro Ala Ala
                165                 170                 175

Gly Gly Ala Val His Thr Arg Gly Leu Asp Phe Ala Cys Asp Phe Trp
            180                 185                 190

Val Leu Val Val Val Gly Gly Val Leu Ala Cys Tyr Ser Leu Leu Val
        195                 200                 205

Thr Val Ala Phe Ile Ile Phe Trp Val Arg Ser Lys Arg Ser Arg Leu
    210                 215                 220

Leu His Ser Asp Tyr Met Asn Met Thr Pro Arg Arg Pro Gly Pro Thr
225                 230                 235                 240

Arg Lys His Tyr Gln Pro Tyr Ala Pro Pro Arg Asp Phe Ala Ala Tyr
                245                 250                 255

Arg Ser Lys Arg Gly Arg Lys Lys Leu Leu Tyr Ile Phe Lys Gln Pro
            260                 265                 270

Phe Met Arg Pro Val Gln Thr Thr Gln Glu Glu Asp Gly Cys Ser Cys
        275                 280                 285

Arg Phe Pro Glu Glu Glu Glu Gly Gly Cys Glu Leu Arg Val Lys Phe
    290                 295                 300

Ser Arg Ser Ala Asp Ala Pro Ala Tyr Lys Gln Gly Gln Asn Gln Leu
305                 310                 315                 320

Tyr Asn Glu Leu Asn Leu Gly Arg Arg Glu Glu Tyr Asp Val Leu Asp
                325                 330                 335

Lys Arg Arg Gly Arg Asp Pro Glu Met Gly Gly Lys Pro Arg Arg Lys
            340                 345                 350

Asn Pro Gln Glu Gly Leu Tyr Asn Glu Leu Gln Lys Asp Lys Met Ala
        355                 360                 365

Glu Ala Tyr Ser Glu Ile Gly Met Lys Gly Glu Arg Arg Arg Gly Lys
    370                 375                 380

Gly His Asp Gly Leu Tyr Gln Gly Leu Ser Thr Ala Thr Lys Asp Thr
385                 390                 395                 400

Tyr Asp Ala Leu His Met Gln Ala Leu Pro Pro Arg
                405                 410

<210> SEQ ID NO 169
<211> LENGTH: 423
<212> TYPE: PRT
<213> ORGANISM: Artificial Sequence
<220> FEATURE:
<223> OTHER INFORMATION: CD38 38A37330 CAR

<400> SEQUENCE: 169

Met Ala Leu Pro Val Thr Ala Leu Leu Leu Pro Leu Ala Leu Leu Leu
1               5                   10                  15

His Ala Ala Arg Pro Val Asn Gln Val Gln Leu Val Glu Ser Gly Gly
            20                  25                  30

Gly Leu Val Gln Ala Gly Asp Ser Leu Arg Leu Ser Cys Ala Ala Ser
        35                  40                  45

Gly Arg Ala Tyr Ala Thr Met Ala Trp Phe Arg Gln Ala Pro Gly Lys
    50                  55                  60

Glu Arg Glu Phe Val Ala His Leu Arg Val Ser Gly Asp Thr Thr Tyr
65                  70                  75                  80

Tyr Thr Asp Ser Val Lys Gly Arg Phe Thr Ile Ser Arg Asp Asn Ala
                85                  90                  95

Lys Asn Thr Ala Tyr Leu Gln Met Asn Met Leu Lys Pro Glu Asp Thr
```

```
                100                 105                 110
Ala Val Tyr Tyr Cys Ala Ala Gly Pro Tyr Gly Ile Leu Ala Ala Ala
            115                 120                 125

Arg Val Ser Asn Pro Gly Asn Tyr Asp Tyr Trp Gly Gln Gly Thr Gln
        130                 135                 140

Val Thr Val Ser Ser Thr Arg Arg Met His Thr Ser Thr Thr Thr Pro
145                 150                 155                 160

Ala Pro Arg Pro Pro Thr Pro Ala Pro Thr Ile Ala Ser Gln Pro Leu
                165                 170                 175

Ser Leu Arg Pro Glu Ala Cys Arg Pro Ala Ala Gly Gly Ala Val His
            180                 185                 190

Thr Arg Gly Leu Asp Phe Ala Cys Asp Phe Trp Val Leu Val Val Val
        195                 200                 205

Gly Gly Val Leu Ala Cys Tyr Ser Leu Leu Val Thr Val Ala Phe Ile
210                 215                 220

Ile Phe Trp Val Arg Ser Lys Arg Ser Arg Leu Leu His Ser Asp Tyr
225                 230                 235                 240

Met Asn Met Thr Pro Arg Arg Pro Gly Pro Thr Arg Lys His Tyr Gln
                245                 250                 255

Pro Tyr Ala Pro Pro Arg Asp Phe Ala Ala Tyr Arg Ser Lys Arg Gly
            260                 265                 270

Arg Lys Lys Leu Leu Tyr Ile Phe Lys Gln Pro Phe Met Arg Pro Val
        275                 280                 285

Gln Thr Thr Gln Glu Glu Asp Gly Cys Ser Cys Arg Phe Pro Glu Glu
    290                 295                 300

Glu Glu Gly Gly Cys Glu Leu Arg Val Lys Phe Ser Arg Ser Ala Asp
305                 310                 315                 320

Ala Pro Ala Tyr Lys Gln Gly Gln Asn Gln Leu Tyr Asn Glu Leu Asn
                325                 330                 335

Leu Gly Arg Arg Glu Glu Tyr Asp Val Leu Asp Lys Arg Arg Gly Arg
            340                 345                 350

Asp Pro Glu Met Gly Gly Lys Pro Arg Arg Lys Asn Pro Gln Glu Gly
        355                 360                 365

Leu Tyr Asn Glu Leu Gln Lys Asp Lys Met Ala Glu Ala Tyr Ser Glu
    370                 375                 380

Ile Gly Met Lys Gly Glu Arg Arg Arg Gly Lys Gly His Asp Gly Leu
385                 390                 395                 400

Tyr Gln Gly Leu Ser Thr Ala Thr Lys Asp Thr Tyr Asp Ala Leu His
                405                 410                 415

Met Gln Ala Leu Pro Pro Arg
                420

<210> SEQ ID NO 170
<211> LENGTH: 420
<212> TYPE: PRT
<213> ORGANISM: Artificial Sequence
<220> FEATURE:
<223> OTHER INFORMATION: CD38 38A37334 CAR

<400> SEQUENCE: 170

Met Ala Leu Pro Val Thr Ala Leu Leu Leu Pro Leu Ala Leu Leu Leu
1               5                   10                  15

His Ala Ala Arg Pro Val Asn Glu Val Gln Leu Val Glu Ser Gly Gly
            20                  25                  30

Gly Leu Val Gln Ala Gly Gly Ser Leu Arg Leu Ser Cys Ala Ala Ser
```

```
                35                  40                  45
Gly Leu Thr Phe Ser Ser Tyr Ile Met Gly Trp Phe Arg Gln Ala Pro
 50                  55                  60
Gly Glu Glu Arg Glu Leu Val Ala Glu Ile Ser Ser Gly Gly Met Thr
 65                  70                  75                  80
Ser Tyr Ala Asp Ser Val Lys Gly Arg Phe Thr Ile Ser Arg Asp Asn
                 85                  90                  95
Ala Lys Lys Thr Gly Tyr Leu Gln Met Asn Ser Leu Lys Pro Glu Asp
                100                 105                 110
Thr Ala Val Tyr Tyr Cys Ala Ala Pro Glu Arg Gly Ser Ile Trp Tyr
                115                 120                 125
Ser Arg Tyr Glu Tyr Lys Tyr Trp Gly Gln Gly Thr Gln Val Thr Val
                130                 135                 140
Ser Ser Thr Arg Arg Met His Thr Ser Thr Thr Thr Pro Ala Pro Arg
145                 150                 155                 160
Pro Pro Thr Pro Ala Pro Thr Ile Ala Ser Gln Pro Leu Ser Leu Arg
                165                 170                 175
Pro Glu Ala Cys Arg Pro Ala Ala Gly Gly Ala Val His Thr Arg Gly
                180                 185                 190
Leu Asp Phe Ala Cys Asp Phe Trp Val Leu Val Val Val Gly Gly Val
                195                 200                 205
Leu Ala Cys Tyr Ser Leu Leu Val Thr Val Ala Phe Ile Ile Phe Trp
                210                 215                 220
Val Arg Ser Lys Arg Ser Arg Leu Leu His Ser Asp Tyr Met Asn Met
225                 230                 235                 240
Thr Pro Arg Arg Pro Gly Pro Thr Arg Lys His Tyr Gln Pro Tyr Ala
                245                 250                 255
Pro Pro Arg Asp Phe Ala Ala Tyr Arg Ser Lys Arg Gly Arg Lys Lys
                260                 265                 270
Leu Leu Tyr Ile Phe Lys Gln Pro Phe Met Arg Pro Val Gln Thr Thr
                275                 280                 285
Gln Glu Glu Asp Gly Cys Ser Cys Arg Phe Pro Glu Glu Glu Glu Gly
290                 295                 300
Gly Cys Glu Leu Arg Val Lys Phe Ser Arg Ser Ala Asp Ala Pro Ala
305                 310                 315                 320
Tyr Lys Gln Gly Gln Asn Gln Leu Tyr Asn Glu Leu Asn Leu Gly Arg
                325                 330                 335
Arg Glu Glu Tyr Asp Val Leu Asp Lys Arg Arg Gly Arg Asp Pro Glu
                340                 345                 350
Met Gly Gly Lys Pro Arg Arg Lys Asn Pro Gln Glu Gly Leu Tyr Asn
                355                 360                 365
Glu Leu Gln Lys Asp Lys Met Ala Glu Ala Tyr Ser Glu Ile Gly Met
                370                 375                 380
Lys Gly Glu Arg Arg Arg Gly Lys Gly His Asp Gly Leu Tyr Gln Gly
385                 390                 395                 400
Leu Ser Thr Ala Thr Lys Asp Thr Tyr Asp Ala Leu His Met Gln Ala
                405                 410                 415
Leu Pro Pro Arg
            420

<210> SEQ ID NO 171
<211> LENGTH: 417
<212> TYPE: PRT
<213> ORGANISM: Artificial Sequence
```

<220> FEATURE:
<223> OTHER INFORMATION: CD38 38A37730 CAR

<400> SEQUENCE: 171

Met Ala Leu Pro Val Thr Ala Leu Leu Leu Pro Leu Ala Leu Leu Leu
1               5                   10                  15

His Ala Ala Arg Pro Val Asn Ala Val Gln Leu Val Asp Ser Gly Gly
            20                  25                  30

Gly Leu Ala Gln Thr Gly Gly Ser Leu Arg Leu Ser Cys Ala Ala Ser
        35                  40                  45

Gln Gly Ile Phe Thr Ile Asn Ala Met Gly Trp Tyr Arg Gln Val Pro
    50                  55                  60

Gly Lys Gln Arg Glu Leu Val Ala Glu Val Ser Ser Gly Gly Arg Thr
65                  70                  75                  80

Asp Tyr Ala Asp Ser Val Lys Gly Arg Phe Thr Ile Ser Arg Asp Asn
                85                  90                  95

Ala Lys Asn Thr Val Tyr Leu Gln Met Asn Ser Leu Lys Pro Glu Asp
            100                 105                 110

Thr Gly Val Tyr Tyr Cys Arg Val Ser Gly Trp His Val Phe Val Gly
        115                 120                 125

Asp Arg Ile Val Trp Gly Gln Gly Thr Leu Val Thr Val Ser Ser Thr
    130                 135                 140

Arg Arg Met His Thr Ser Thr Thr Thr Pro Ala Pro Arg Pro Pro Thr
145                 150                 155                 160

Pro Ala Pro Thr Ile Ala Ser Gln Pro Leu Ser Leu Arg Pro Glu Ala
                165                 170                 175

Cys Arg Pro Ala Ala Gly Gly Ala Val His Thr Arg Gly Leu Asp Phe
            180                 185                 190

Ala Cys Asp Phe Trp Val Leu Val Val Val Gly Gly Val Leu Ala Cys
        195                 200                 205

Tyr Ser Leu Leu Val Thr Val Ala Phe Ile Ile Phe Trp Val Arg Ser
    210                 215                 220

Lys Arg Ser Arg Leu Leu His Ser Asp Tyr Met Asn Met Thr Pro Arg
225                 230                 235                 240

Arg Pro Gly Pro Thr Arg Lys His Tyr Gln Pro Tyr Ala Pro Pro Arg
                245                 250                 255

Asp Phe Ala Ala Tyr Arg Ser Lys Arg Gly Arg Lys Lys Leu Leu Tyr
            260                 265                 270

Ile Phe Lys Gln Pro Phe Met Arg Pro Val Gln Thr Thr Gln Glu Glu
        275                 280                 285

Asp Gly Cys Ser Cys Arg Phe Pro Glu Glu Glu Glu Gly Gly Cys Glu
    290                 295                 300

Leu Arg Val Lys Phe Ser Arg Ser Ala Asp Ala Pro Ala Tyr Lys Gln
305                 310                 315                 320

Gly Gln Asn Gln Leu Tyr Asn Glu Leu Asn Leu Gly Arg Arg Glu Glu
                325                 330                 335

Tyr Asp Val Leu Asp Lys Arg Arg Gly Arg Asp Pro Glu Met Gly Gly
            340                 345                 350

Lys Pro Arg Arg Lys Asn Pro Gln Glu Gly Leu Tyr Asn Glu Leu Gln
        355                 360                 365

Lys Asp Lys Met Ala Glu Ala Tyr Ser Glu Ile Gly Met Lys Gly Glu
    370                 375                 380

Arg Arg Arg Gly Lys Gly His Asp Gly Leu Tyr Gln Gly Leu Ser Thr
385                 390                 395                 400

Ala Thr Lys Asp Thr Tyr Asp Ala Leu His Met Gln Ala Leu Pro Pro
            405                 410                 415
Arg

<210> SEQ ID NO 172
<211> LENGTH: 420
<212> TYPE: PRT
<213> ORGANISM: Artificial Sequence
<220> FEATURE:
<223> OTHER INFORMATION: CD38 38A37340 CAR

<400> SEQUENCE: 172

Met Ala Leu Pro Val Thr Ala Leu Leu Leu Pro Leu Ala Leu Leu Leu
1               5                   10                  15

His Ala Ala Arg Pro Val Asn Asp Val Gln Leu Val Glu Ser Gly Gly
            20                  25                  30

Gly Leu Val Gln Ala Gly Asp Ser Leu Arg Leu Ser Cys Ala Ala Ser
        35                  40                  45

Gly Arg Thr Phe Ser Ser Tyr Ala Met Ala Trp Phe Arg Gln Ala Pro
    50                  55                  60

Gly Lys Glu Arg Glu Ile Val Ser Ser Ile Ser Thr Ser Gly Gly Ile
65                  70                  75                  80

Thr Asp Tyr Ala Asp Ser Val Lys Gly Arg Phe Thr Ile Ser Lys Asp
                85                  90                  95

Ser Ala Lys Met Asn Thr Val Tyr Leu Gln Met Asn Ser Leu Glu Pro
            100                 105                 110

Glu Asp Thr Ala Val Tyr Tyr Cys Ala Ala Arg Thr Trp Tyr Leu Arg
        115                 120                 125

Thr Ser Leu Gln Tyr Asp Tyr Trp Gly Gln Gly Thr Gln Val Thr Val
    130                 135                 140

Ser Ser Thr Arg Arg Met His Thr Ser Thr Thr Pro Ala Pro Arg
145                 150                 155                 160

Pro Pro Thr Pro Ala Pro Thr Ile Ala Ser Gln Pro Leu Ser Leu Arg
                165                 170                 175

Pro Glu Ala Cys Arg Pro Ala Ala Gly Gly Ala Val His Thr Arg Gly
            180                 185                 190

Leu Asp Phe Ala Cys Asp Phe Trp Val Leu Val Val Val Gly Gly Val
        195                 200                 205

Leu Ala Cys Tyr Ser Leu Leu Val Thr Val Ala Phe Ile Ile Phe Trp
    210                 215                 220

Val Arg Ser Lys Arg Ser Arg Leu Leu His Ser Asp Tyr Met Asn Met
225                 230                 235                 240

Thr Pro Arg Arg Pro Gly Pro Thr Arg Lys His Tyr Gln Pro Tyr Ala
                245                 250                 255

Pro Pro Arg Asp Phe Ala Ala Tyr Arg Ser Lys Arg Gly Arg Lys Lys
            260                 265                 270

Leu Leu Tyr Ile Phe Lys Gln Pro Phe Met Arg Pro Val Gln Thr Thr
        275                 280                 285

Gln Glu Glu Asp Gly Cys Ser Cys Arg Phe Pro Glu Glu Glu Glu Gly
    290                 295                 300

Gly Cys Glu Leu Arg Val Lys Phe Ser Arg Ser Ala Asp Ala Pro Ala
305                 310                 315                 320

Tyr Lys Gln Gly Gln Asn Gln Leu Tyr Asn Glu Leu Asn Leu Gly Arg
                325                 330                 335

```
Arg Glu Glu Tyr Asp Val Leu Asp Lys Arg Arg Gly Arg Asp Pro Glu
                340                 345                 350

Met Gly Gly Lys Pro Arg Arg Lys Asn Pro Gln Glu Gly Leu Tyr Asn
            355                 360                 365

Glu Leu Gln Lys Asp Lys Met Ala Glu Ala Tyr Ser Glu Ile Gly Met
        370                 375                 380

Lys Gly Glu Arg Arg Arg Gly Lys Gly His Asp Gly Leu Tyr Gln Gly
385                 390                 395                 400

Leu Ser Thr Ala Thr Lys Asp Thr Tyr Asp Ala Leu His Met Gln Ala
                405                 410                 415

Leu Pro Pro Arg
            420

<210> SEQ ID NO 173
<211> LENGTH: 418
<212> TYPE: PRT
<213> ORGANISM: Artificial Sequence
<220> FEATURE:
<223> OTHER INFORMATION: CD38 38A37731 CAR

<400> SEQUENCE: 173

Met Ala Leu Pro Val Thr Ala Leu Leu Leu Pro Leu Ala Leu Leu Leu
1               5                   10                  15

His Ala Ala Arg Pro Val Asn Gln Val Lys Leu Glu Glu Ser Gly Gly
                20                  25                  30

Gly Leu Val Gln Ala Gly Gly Ser Leu Arg Leu Ser Cys Val Ala Ser
            35                  40                  45

Gly Thr Ile Val Ser Ile Ser Thr Met Gly Trp Tyr Arg Gln Ala Pro
        50                  55                  60

Gly Lys Gln Arg Glu Leu Val Ala Thr Ile Thr Arg Arg Gly Arg Thr
65                  70                  75                  80

Asn Tyr Thr Asp Ser Val Lys Gly Arg Phe Thr Ile Ser Arg Asp Asn
                85                  90                  95

Ala Lys Asn Thr Val Tyr Leu Gln Met Asn Ser Leu Lys Pro Glu Asp
            100                 105                 110

Thr Ala Val Tyr Tyr Cys Asn Ala Glu Val Gln Leu Asp Ile Trp Ala
        115                 120                 125

Ser Ala Tyr Asp Tyr Trp Gly Gln Gly Thr Gln Val Thr Val Ala Ser
130                 135                 140

Thr Arg Arg Met His Thr Ser Thr Thr Thr Pro Ala Pro Arg Pro Pro
145                 150                 155                 160

Thr Pro Ala Pro Thr Ile Ala Ser Gln Pro Leu Ser Leu Arg Pro Glu
                165                 170                 175

Ala Cys Arg Pro Ala Ala Gly Gly Ala Val His Thr Arg Gly Leu Asp
            180                 185                 190

Phe Ala Cys Asp Phe Trp Val Leu Val Val Val Gly Gly Val Leu Ala
        195                 200                 205

Cys Tyr Ser Leu Leu Val Thr Val Ala Phe Ile Ile Phe Trp Val Arg
    210                 215                 220

Ser Lys Arg Ser Arg Leu Leu His Ser Asp Tyr Met Asn Met Thr Pro
225                 230                 235                 240

Arg Arg Pro Gly Pro Thr Arg Lys His Tyr Gln Pro Tyr Ala Pro Pro
                245                 250                 255

Arg Asp Phe Ala Ala Tyr Arg Ser Lys Arg Gly Arg Lys Lys Leu Leu
            260                 265                 270
```

```
Tyr Ile Phe Lys Gln Pro Phe Met Arg Pro Val Gln Thr Gln Glu
            275                 280                 285

Glu Asp Gly Cys Ser Cys Arg Phe Pro Glu Glu Glu Gly Gly Cys
290                 295                 300

Glu Leu Arg Val Lys Phe Ser Arg Ser Ala Asp Ala Pro Ala Tyr Lys
305                 310                 315                 320

Gln Gly Gln Asn Gln Leu Tyr Asn Glu Leu Asn Leu Gly Arg Arg Glu
                325                 330                 335

Glu Tyr Asp Val Leu Asp Lys Arg Arg Gly Arg Asp Pro Glu Met Gly
                340                 345                 350

Gly Lys Pro Arg Arg Lys Asn Pro Gln Glu Gly Leu Tyr Asn Glu Leu
            355                 360                 365

Gln Lys Asp Lys Met Ala Glu Ala Tyr Ser Glu Ile Gly Met Lys Gly
370                 375                 380

Glu Arg Arg Arg Gly Lys Gly His Asp Gly Leu Tyr Gln Gly Leu Ser
385                 390                 395                 400

Thr Ala Thr Lys Asp Thr Tyr Asp Ala Leu His Met Gln Ala Leu Pro
                405                 410                 415

Pro Arg

<210> SEQ ID NO 174
<211> LENGTH: 412
<212> TYPE: PRT
<213> ORGANISM: Artificial Sequence
<220> FEATURE:
<223> OTHER INFORMATION: CD38 38A37326 CAR

<400> SEQUENCE: 174

Met Ala Leu Pro Val Thr Ala Leu Leu Leu Pro Leu Ala Leu Leu Leu
1               5                   10                  15

His Ala Ala Arg Pro Val Asn Glu Val Gln Leu Val Glu Ser Gly Gly
                20                  25                  30

Gly Leu Val Gln Ala Gly Gly Ser Leu Arg Leu Ser Cys Ala Ala Ser
            35                  40                  45

Gly Arg Thr Tyr Ala Met Gly Trp Tyr Arg Gln Ala Pro Gly Lys Gln
50                  55                  60

Arg Asp Leu Val Ala Thr Ile Ser Gly Ala Gly Asn Thr Lys Tyr Ala
65                  70                  75                  80

Asp Ser Val Lys Gly Arg Phe Thr Ile Ser Arg Asp Asn Ala Lys Asn
                85                  90                  95

Thr Met Tyr Leu Gln Met Asn Ser Leu Lys Pro Glu Asp Thr Ala Val
            100                 105                 110

Tyr Tyr Cys Ala Ala Gly Lys Trp Phe Pro Ala Ala Asn Glu Tyr Trp
        115                 120                 125

Gly Gln Gly Thr Gln Val Thr Val Ser Ser Thr Arg Arg Met His Thr
130                 135                 140

Ser Thr Thr Thr Pro Ala Pro Arg Pro Pro Thr Pro Ala Pro Thr Ile
145                 150                 155                 160

Ala Ser Gln Pro Leu Ser Leu Arg Pro Glu Ala Cys Arg Pro Ala Ala
                165                 170                 175

Gly Gly Ala Val His Thr Arg Gly Leu Asp Phe Ala Cys Asp Phe Trp
            180                 185                 190

Val Leu Val Val Val Gly Gly Val Leu Ala Cys Tyr Ser Leu Leu Val
        195                 200                 205

Thr Val Ala Phe Ile Ile Phe Trp Val Arg Ser Lys Arg Ser Arg Leu
```

```
                 210                 215                 220

Leu His Ser Asp Tyr Met Asn Met Thr Pro Arg Arg Pro Gly Pro Thr
225                 230                 235                 240

Arg Lys His Tyr Gln Pro Tyr Ala Pro Pro Arg Asp Phe Ala Ala Tyr
                245                 250                 255

Arg Ser Lys Arg Gly Arg Lys Lys Leu Leu Tyr Ile Phe Lys Gln Pro
            260                 265                 270

Phe Met Arg Pro Val Gln Thr Thr Gln Glu Glu Asp Gly Cys Ser Cys
        275                 280                 285

Arg Phe Pro Glu Glu Glu Glu Gly Gly Cys Glu Leu Arg Val Lys Phe
290                 295                 300

Ser Arg Ser Ala Asp Ala Pro Ala Tyr Lys Gln Gly Gln Asn Gln Leu
305                 310                 315                 320

Tyr Asn Glu Leu Asn Leu Gly Arg Arg Glu Glu Tyr Asp Val Leu Asp
                325                 330                 335

Lys Arg Arg Gly Arg Asp Pro Glu Met Gly Gly Lys Pro Arg Arg Lys
            340                 345                 350

Asn Pro Gln Glu Gly Leu Tyr Asn Glu Leu Gln Lys Asp Lys Met Ala
        355                 360                 365

Glu Ala Tyr Ser Glu Ile Gly Met Lys Gly Glu Arg Arg Arg Gly Lys
    370                 375                 380

Gly His Asp Gly Leu Tyr Gln Gly Leu Ser Thr Ala Thr Lys Asp Thr
385                 390                 395                 400

Tyr Asp Ala Leu His Met Gln Ala Leu Pro Pro Arg
                405                 410

<210> SEQ ID NO 175
<211> LENGTH: 1263
<212> TYPE: DNA
<213> ORGANISM: Artificial Sequence
<220> FEATURE:
<223> OTHER INFORMATION: BCMA 269A37346 CAR

<400> SEQUENCE: 175
atggccttac cagtgaccgc cttgctcctg ccgctggcct tgctgctcca cgccgccagg     60
ccggttaacc gcacgcgtcg catgcatcag gtgcagctgg tggagtctgg gggaggcttg    120
gtgcagcctg ggggttctct gaggctctcc tgtgaagcct ctggattcac tttggattat    180
tatgccatag gctggttccg ccaggcccca gggaaggagc gcgaggggt catatgtatt     240 agtagaagtg atggtagcac atactatgca gactccgtga aggccgatt caccatctcc    300 agagacaacg ccaagaaaac ggtgtatctg caaatgatca gcctgaaacc tgaggacacg    360
gccgcttatt actgtgcagc aggggccgat tgttcgggt acctacgaga ttatgagttc    420 cggggcagg ggacccaggt caccgtctcc tcaactagta ccacgacgcc agcgccgcga     480
ccaccaacac cggcgcccac catcgcgtcg cagcccctgt ccctgcgccc agaggcgtgc    540
cggccagcgg cggggggcgc agtgcacacg agggggctgg acttcgcctg tgattttttgg   600 gtgctggtgg tggttggtgg agtcctggct tgctatagct tgctagtaac agtggccttt    660
attattttct gggtgaggag taagaggagc aggctcctgc acagtgacta catgaacatg    720
actccccgcc gccccgggcc cacccgcaag cattaccagc cctatgcccc accacgcgac    780
ttcgcagcct atcgctccaa acggggcaga aagaaactcc tgtatatatt caaacaacca    840
tttatgagac agtacaaac tactcaagag gaagatggct gtagctgccg atttccagaa     900
gaagaagaag aggatgtga actgagagtg aagttcagca ggagcgcaga cgccccgcg     960
```

| | |
|---|---|
| tacaagcagg gccagaacca gctctataac gagctcaatc taggacgaag agaggagtac | 1020 |
| gatgttttgg acaagagacg tggccgggac cctgagatgg ggggaaagcc gagaaggaag | 1080 |
| aaccctcagg aaggcctgta caatgaactg cagaaagata agatggcgga ggcctacagt | 1140 |
| gagattggga tgaaaggcga gcgccggagg ggcaaggggc acgatggcct ttaccagggt | 1200 |
| ctcagtacag ccaccaagga cacctacgac gcccttcaca tgcaggccct gccccctcgc | 1260 |
| tga | 1263 |

<210> SEQ ID NO 176
<211> LENGTH: 1281
<212> TYPE: DNA
<213> ORGANISM: Artificial Sequence
<220> FEATURE:
<223> OTHER INFORMATION: BCMA 269A37348 CAR

<400> SEQUENCE: 176

| | |
|---|---|
| atggccttac cagtgaccgc cttgctcctg ccgctggcct tgctgctcca cgccgccagg | 60 |
| ccggttaacc gcacgcgtcg catgcatcag gtaaagctgg aggagtctgg gggacgattg | 120 |
| gtgcagccaa ggggctctct gagactctcc tgtgcaggct ctggacgcac tttcagtacc | 180 |
| tatggtatgg cctggttccg ccaggctcca gggaaggagc gtgagttcgt agcgtctaaa | 240 |
| gcatcgatga attacagcgg tagaacatac tatgcagact ccgtgaaggg ccgattcacc | 300 |
| atcgccagag acaacgccaa gaacatggtg tttctgcaaa tgaacaacct gaagcctgag | 360 |
| gacacggccg tttattactg tgcagcgggc actggatgct caacatatgg tgttttgac | 420 |
| gcccagataa tagactactg gggcaaaggg accctggtca ccgtctcctc aactagtacc | 480 |
| acgacgccag cgccgcgacc accaacaccg gcgcccacca tcgcgtcgca gcccctgtcc | 540 |
| ctgcgcccag aggcgtgccg gccagcggcg ggggcgcag tgcacacgag ggggctggac | 600 |
| ttcgcctgtg atttttgggt gctggtggtg gttggtggag tcctggcttg ctatagcttg | 660 |
| ctagtaacag tggcctttat tattttctgg gtgaggagta gaggagcag gctcctgcac | 720 |
| agtgactaca tgaacatgac tccccgccgc cccgggccca cccgcaagca ttaccagccc | 780 |
| tatgccccac cacgcgactt cgcagcctat cgctccaaac ggggcagaaa gaaactcctg | 840 |
| tatatattca acaaccatt tatgagacca gtacaaacta ctcaagagga agatggctgt | 900 |
| agctgccgat ttccagaaga agaagaagga ggatgtgaac tgagagtgaa gttcagcagg | 960 |
| agcgcagacg cccccgcgta caagcagggc cagaaccagc tctataacga gctcaatcta | 1020 |
| ggacgaagag aggagtacga tgttttggac aagagacgtg gccgggaccc tgagatgggg | 1080 |
| ggaaagccga aggaagaa ccctcaggaa ggcctgtaca atgaactgca gaaagataag | 1140 |
| atggcggagg cctacagtga gattgggatg aaaggcgagc gccggagggg caaggggcac | 1200 |
| gatggccttt accagggtct cagtacagcc accaaggaca cctacgacgc ccttcacatg | 1260 |
| caggccctgc cccctcgctg a | 1281 |

<210> SEQ ID NO 177
<211> LENGTH: 1251
<212> TYPE: DNA
<213> ORGANISM: Artificial Sequence
<220> FEATURE:
<223> OTHER INFORMATION: BCMA 269A37917 CAR

<400> SEQUENCE: 177

| | |
|---|---|
| atggccttac cagtgaccgc cttgctcctg ccgctggcct tgctgctcca cgccgccagg | 60 |

```
ccggttaacc gcacgcgtcg catgcatgag gtgcagctgg tggagtctgg gggaggcttg    120
gtgcaggctg gggggtctct gagactctcc tgtgcagcct ctggacgcac cttcaccatg    180
gggtggttcc gtcaggctcc agggaaggag cgtgagtttg tagcagctat tagtttgagt    240
cctactttag catattatgc agagtccgtg aagggccgat tcaccatcag ccagacaac     300 gccaagaaca cggtggtttt gcaaatgaac agcctgaaac ctgaggacac ggccctttat    360
tactgtgcag cagaccggaa atcagtaatg tctattcggc ccgactactg gggcagggg    420 acccaggtca ccgtctcctc aactagtacc acgacgccag cgccgcgacc accaacaccg    480
gcgcccacca tcgcgtcgca gcccctgtcc ctgcgcccag aggcgtgccg gccagcggcg    540
gggggcgcag tgcacacgag ggggctggac ttcgcctgtg attttttggt gctggtggtg    600
gttggtggag tcctggcttg ctatagcttg ctagtaacag tggcctttat tattttctgg    660
gtgaggagta agaggagcag gctcctgcac agtgactaca tgaacatgac tccccgccgc    720
cccgggccca cccgcaagca ttaccagccc tatgccccac cacgcgactt cgcagcctat    780
cgctccaaac ggggcagaaa gaaactcctg tatatattca acaaccatt tatgagacca    840 gtacaaacta ctcaagagga agatggctgt agctgccgat tccagaaga agaagaagga    900 ggatgtgaac tgagagtgaa gttcagcagg agcgcagacg cccccgcgta caagcagggc    960
cagaaccagc tctataacga gctcaatcta ggacgaagag aggagtacga tgttttggac   1020
aagagacgtg gccgggaccc tgagatgggg ggaaagccga aaggaagaa ccctcaggaa    1080 ggcctgtaca atgaactgca gaaagataag atggcggagg cctacagtga gattgggatg   1140
aaaggcgagc gccggagggg caaggggcac gatggccttt accagggtct cagtacagcc   1200
accaaggaca cctacgacgc ccttcacatg caggccctgc cccctcgctg a             1251
```

<210> SEQ ID NO 178
<211> LENGTH: 1257
<212> TYPE: DNA
<213> ORGANISM: Artificial Sequence
<220> FEATURE:
<223> OTHER INFORMATION: BCMA 269A37355 CAR

<400> SEQUENCE: 178

```
atggccttac cagtgaccgc cttgctcctg ccgctggcct tgctgctcca cgccgccagg    60
ccggttaacc gcacgcgtcg catgcatgcc gtgcagctgg tggattctgg gggaggcttg   120
gtgcagcctg gggggtctct gagactctcc tgtgtagcct ctggaggtat cttcgtcatc   180
aatgccatgg gctggtaccg ccaggctcca ggaaagcagc gcgagttggt cgcatctatt   240
cgtggactag gcagaacaaa ctatgacgac tccgtgaagg gccgattcac catctccaga   300
gacaacgcca acaacacggt gtatctgcag atgaacagcc tggaacctga ggacacggcc   360
gtctactact gtacagtcta cgttacacta cttggtgggg ttaataggga ctactgggc    420 caggggaccc aggtcaccgt ctcctcaact agtaccacga cgccagcgcc gcgaccacca   480
acaccggcgc ccaccatcgc gtcgcagccc ctgtccctgc gcccagaggc gtgccggcca   540
gcggcggggg cgcagtgca cacgagggg ctggacttcg cctgtgattt ttgggtgctg     600
gtggtggttg gtggagtcct ggcttgctat agcttgctag taacagtggc ctttattatt   660
ttctgggtga ggagtaagag gagcaggctc ctgcacagtg actacatgaa catgactccc   720
cgccgccccg ggcccacccg caagcattac cagccctatg ccccaccacg cgacttcgca   780
gcctatcgct ccaaacgggg cagaaagaaa ctcctgtata tattcaaaca accatttatg   840
agaccagtac aaactactca gaggaagat ggctgtagct gccgatttcc agaagaagaa    900
```

```
gaaggaggat gtgaactgag agtgaagttc agcaggagcg cagacgcccc cgcgtacaag    960
cagggccaga accagctcta taacgagctc aatctaggac gaagagagga gtacgatgtt   1020
ttggacaaga gacgtggccg ggaccctgag atggggggaa agccgagaag gaagaaccct   1080
caggaaggcc tgtacaatga actgcagaaa gataagatgg cggaggccta cagtgagatt   1140
gggatgaaag gcgagcgccg gaggggcaag gggcacgatg gcctttacca gggtctcagt   1200
acagccacca aggacaccta cgacgcccct cacatgcagg ccctgccccc tcgctga     1257
```

<210> SEQ ID NO 179
<211> LENGTH: 1254
<212> TYPE: DNA
<213> ORGANISM: Artificial Sequence
<220> FEATURE:
<223> OTHER INFORMATION: BCMA 269A37915 CAR

<400> SEQUENCE: 179

```
atggccttac cagtgaccgc cttgctcctg ccgctggcct tgctgctcca cgccgccagg     60
ccggttaacc gcacgcgtcg catgcatgag gtgcagctgg tggagtctgg gggaggattg    120
gtgcaggctg ggggctctct gagactctcc tgtgcagcct ctggacggac cttcagtagc    180
attgtcatgg gctggttccg ccaggctcca gggaaggagc gtgagtttgt aggagcgatt    240
atgtggaatg atggtattac atacttgcaa gactccgtga agggccgatt taccatcttc    300
agagacaatg ccaagaacac ggtgtatctg caaatgaaca gcctgaaact tgaggatacg    360
gccgtttatt actgtgcagc atccaagggt agatactcgg aatatgagta ctggggccag    420
gggacccagg tcaccgtctc ctcaactagt accacgacgc cagcgccgcg accaccaaca    480
ccggcgccca ccatcgcgtc gcagcccctg tccctgcgcc cagaggcgtg ccggccagcg    540
gcggggggcg cagtgcacac gagggggctg gacttcgcct gtgattttg ggtgctggtg    600 gtggttggtg gagtcctggc ttgctatagc ttgctagtaa cagtggcctt tattattttc    660
tgggtgagga gtaagaggag caggctcctg cacagtgact acatgaacat gactccccgc    720
cgccccgggc ccacccgcaa gcattaccag ccctatgccc caccacgcga cttcgcagcc    780
tatcgctcca acggggcag aaagaaactc ctgtatatat tcaaacaacc atttatgaga    840
ccagtacaaa ctactcaaga ggaagatggc tgtagctgcc gatttccaga agaagaagaa    900
ggaggatgtg aactgagagt gaagttcagc aggagcgcag acgccccgc gtacaagcag    960 ggccagaacc agctctataa cgagctcaat ctaggacgaa gagaggagta cgatgttttg   1020
gacaagagac gtggccggga ccctgagatg ggggaaagc cgagaaggaa gaaccctcag   1080
gaaggcctgt acaatgaact gcagaaagat aagatggcgg aggcctacag tgagattggg   1140
atgaaaggcg agcgccggag gggcaagggg cacgatggcc tttaccaggg tctcagtaca   1200
gccaccaagg acacctacga cgcccttcac atgcaggccc tgcccctcg ctga         1254
```

<210> SEQ ID NO 180
<211> LENGTH: 1281
<212> TYPE: DNA
<213> ORGANISM: Artificial Sequence
<220> FEATURE:
<223> OTHER INFORMATION: BCMA 269A37936 CAR

<400> SEQUENCE: 180

```
atggccttac cagtgaccgc cttgctcctg ccgctggcct tgctgctcca cgccgccagg     60
ccggttaacc gcacgcgtcg catgcatgag gtgcagctgg tggagtctgg gggaggcgtg    120
```

| | |
|---|---|
| gtgcaggctg gggggtctct gacagtctcc tgtacagcct ctggattcac tttcgaccgt | 180 |
| gctgtcatag tctggttccg ccaggccccc gggaagggcc gtgaggggt ctcatttatt | 240 |
| aaacctagtg atggcaccat atactacatt gactccctga agggccgatt cacgatctcc | 300 |
| agtgacatcg ccaagaatac ggtatatctg caaatgaaaa gtctggaatc ggaggactcg | 360 |
| gccgtttatt actgtgcggc ctcgcctgag gactggtaca cggattggat cgactggagt | 420 |
| atatatcggt ggcagcactg gggccagggg acccaggtca ctgtctcctc aactagtacc | 480 |
| acgacgccag cgccgcgacc accaacaccg gcgcccacca tcgcgtcgca gcccctgtcc | 540 |
| ctgcgcccag aggcgtgccg gccagcggcg ggggcgcag tgcacacgag ggggctggac | 600 |
| ttcgcctgtg atttttgggt gctggtggtg gttggtggag tcctggcttg ctatagcttg | 660 |
| ctagtaacag tggcctttat tattttctgg gtgaggagta agaggagcag gctcctgcac | 720 |
| agtgactaca tgaacatgac tccccgccgc cccgggccca cccgcaagca ttaccagccc | 780 |
| tatgccccac cacgcgactt cgcagcctat cgctccaaac ggggcagaaa gaaactcctg | 840 |
| tatatattca acaaccatt tatgagacca gtacaaacta ctcaagagga agatggctgt | 900 |
| agctgccgat ttccagaaga agaagaagga ggatgtgaac tgagagtgaa gttcagcagg | 960 |
| agcgcagacg ccccgcgta caagcagggc cagaaccagc tctataacga gctcaatcta | 1020 |
| ggacgaagag aggagtacga tgttttggac aagagacgtg gccgggaccc tgagatgggg | 1080 |
| ggaaagccga aaggaagaa ccctcaggaa ggcctgtaca tgaactgca gaaagataag | 1140 |
| atggcggagg cctacagtga gattgggatg aaaggcgagc gccggagggg caaggggcac | 1200 |
| gatggccttt accagggtct cagtacagcc accaaggaca cctacgacgc ccttcacatg | 1260 |
| caggccctgc cccctcgctg a | 1281 |

<210> SEQ ID NO 181
<211> LENGTH: 1254
<212> TYPE: DNA
<213> ORGANISM: Artificial Sequence
<220> FEATURE:
<223> OTHER INFORMATION: BCMA 269A37953 CAR

<400> SEQUENCE: 181

| | |
|---|---|
| atggccttac cagtgaccgc cttgctcctg ccgctggcct tgctgctcca cgccgccagg | 60 |
| ccggttaacc gcacgcgtcg catgcatgag gtgcagctgg tggagtctgg gggaggaatg | 120 |
| gtgcaggctg gggactctct gagactatcc tgtgtgcagt ctacttacac cgtcaatagc | 180 |
| gatgtcatgg gctggttccg ccaggctcca gggaaggagc gtgagtttgt aggagcgatt | 240 |
| atgtggaatg atggtattac atacttgcaa gactccgtga agggccgatt taccatcttc | 300 |
| agagacaacg ccaagaacac ggtgtatctg caaatgaaca gcctgaaact tgaggatacg | 360 |
| gccgtttatt actgtgcagc atccaagggt agatactcgg aatatgagta ctggggccag | 420 |
| gggacccagg tcaccgtctc ctcaactagt accacgacgc cagcgccgcg accaccaaca | 480 |
| ccggcgccca ccatcgcgtc gcagcccctg tcctgcgcc agaggcgtg ccggccagcg | 540 |
| gcggggggcg cagtgcacac gaggggggctg gacttcgcct gtgatttttg ggtgctggtg | 600 |
| gtggttggtg gagtcctggc ttgctatagc ttgctagtaa cagtggcctt tattattttc | 660 |
| tgggtgagga gtaagaggag caggctcctg cacagtgact acatgaacat gactccccgc | 720 |
| cgccccgggc ccacccgcaa gcattaccag ccctatgccc caccacgcga cttcgcagcc | 780 |
| tatcgctcca acggggcag aaagaaactc ctgtatatat tcaaacaacc atttatgaga | 840 |
| ccagtacaaa ctactcaaga ggaagatggc tgtagctgcc gatttccaga agaagaagaa | 900 |

```
ggaggatgtg aactgagagt gaagttcagc aggagcgcag acgccccgc gtacaagcag      960 ggccagaacc agctctataa cgagctcaat ctaggacgaa gagaggagta cgatgttttg     1020
gacaagagac gtggccggga ccctgagatg gggggaaagc cgagaaggaa gaaccctcag    1080
gaaggcctgt acaatgaact gcagaaagat aagatggcgg aggcctacag tgagattggg    1140
atgaaaggcg agcgccggag gggcaagggg cacgatggcc tttaccaggg tctcagtaca   1200
gccaccaagg acacctacga cgcccttcac atgcaggccc tgcccctcg ctga           1254
```

<210> SEQ ID NO 182
<211> LENGTH: 1257
<212> TYPE: DNA
<213> ORGANISM: Artificial Sequence
<220> FEATURE:
<223> OTHER INFORMATION: BCMA 269A37965 CAR

<400> SEQUENCE: 182

```
atggccttac cagtgaccgc cttgctcctg ccgctggcct tgctgctcca cgccgccagg      60
ccggttaacc gcacgcgtcg catgcatgcg gtgcagctgg tggagtctgg gggaggattg    120
gtgcaggctg gggactctct gagactctcc tgtacagcct ctggtgcaac cttgactaac    180
gatcacatgg catggttccg ccaggctcca gggaaggggc gtgaatttgt agcagctatt    240
gactggagtg gtcgtaccac aaattacgca gaccccgtag agggccgatt caccatctcc    300
agaaacaacg ccaagaacac ggtgtatctg gaaatgaaca gcctgaaact tgaggacacg    360
gccgtttatt actgtgcggt cctccgcgct tggatctcat atgacaatga ctactgggc    420 caggggaccc aggtcaccgt ctcctcaact agtaccacga cgccagcgcc gcgaccacca    480
acaccggcgc ccaccatcgc gtcgcagccc ctgtccctgc gcccagaggc gtgccggcca    540
gcggcggggg gcgcagtgca cacgaggggg ctggacttcg cctgtgattt ttgggtgctg    600
gtggtggttg gtggagtcct ggcttgctat agcttgctag taacagtggc ctttattatt    660
ttctgggtga ggagtaagag gagcaggctc ctgcacagtg actacatgaa catgactccc    720
cgccgccccg ggcccacccg caagcattac cagccctatg ccccaccacg cgacttcgca    780
gcctatcgct ccaaacgggg cagaaagaaa ctcctgtata tattcaaaca accatttatg    840
agaccagtac aaactactca agaggaagat ggctgtagct gccgatttcc agaagaagaa    900
gaaggaggat gtgaactgag agtgaagttc agcaggagcg cagacgcccc cgcgtacaag    960
cagggccaga accagctcta taacgagctc aatctaggac gaagagagga gtacgatgtt    1020
ttggacaaga cgtggccgg gaccctgag atgggggaa agccgagaag gaagaaccct      1080
caggaaggcc tgtacaatga actgcagaaa gataagatgg cggaggccta cagtgagatt    1140
gggatgaaag cgagcgccg gaggggcaag gggcacgatg gcctttacca gggtctcagt    1200
acagccacca aggacaccta cgacgccctt cacatgcagg ccctgccccc tcgctga       1257
```

<210> SEQ ID NO 183
<211> LENGTH: 1257
<212> TYPE: DNA
<213> ORGANISM: Artificial Sequence
<220> FEATURE:
<223> OTHER INFORMATION: BCMA 269A37972 CAR

<400> SEQUENCE: 183

```
atggccttac cagtgaccgc cttgctcctg ccgctggcct tgctgctcca cgccgccagg      60
ccggttaacc gcacgcgtcg catgcatcag gtgcagctgg tggagtctgg gggaggattg    120
```
gtgcaggctg ggggctctct gagactctcc tgtgcagcct ctggaggcac cttaagtaaa    180
aataccgtgg cttggttccg ccaggctcca gggaaggagc gtgggtttgt agcgtctatt    240
acctgggatg gtcgtacgac atactatgca gactccgtga agggccgatt caccatctcc    300
agagacaacg ccaagaacac agtgtatctg caaatgaaca gcctgaaacc tgaggatacg    360
gccgtttatg tctgtgcaga cttagggaaa tggcctgcgg gcccggcgga ctactgggc    420 cagggggaccc aggtcaccgt ctcctcaact agtaccacga cgccagcgcc gcgaccacca    480
acaccggcgc ccaccatcgc gtcgcagccc ctgtccctgc gcccagaggc gtgccggcca    540
gcggcggggg gcgcagtgca cacgagggggg ctggacttcg cctgtgattt ttgggtgctg    600
gtggtggttg gtggagtcct ggcttgctat agcttgctag taacagtggc ctttattatt    660
ttctgggtga ggagtaagag gagcaggctc ctgcacagtg actacatgaa catgactccc    720
cgccgccccg ggcccacccg caagcattac cagccctatg ccccaccacg cgacttcgca    780
gcctatcgct ccaaacgggg cagaaagaaa ctcctgtata tattcaaaca accatttatg    840
agaccagtac aaactactca agaggaagat ggctgtagct gccgatttcc agaagaagaa    900
gaaggaggat gtgaactgag agtgaagttc agcaggagcg cagacgcccc cgcgtacaag    960
cagggccaga accagctcta taacgagctc aatctaggac gaagagagga gtacgatgtt    1020
ttggacaaga gacgtggccg ggaccctgag atgggggggaa agccgagaag gaagaaccct    1080
caggaaggcc tgtacaatga actgcagaaa gataagatgg cggaggccta cagtgagatt    1140
gggatgaaag gcgagcgccg gaggggcaag gggcacgatg gcctttacca gggtctcagt    1200
acagccacca aggacaccta cgacgcccctt cacatgcagg ccctgccccc tcgctga    1257

<210> SEQ ID NO 184
<211> LENGTH: 1254
<212> TYPE: DNA
<213> ORGANISM: Artificial Sequence
<220> FEATURE:
<223> OTHER INFORMATION: BCMA 269A37353 CAR

<400> SEQUENCE: 184
atggccttac cagtgaccgc cttgctcctg ccgctggcct tgctgctcca cgccgccagg     60
ccggttaacc gcacgcgtcg catgcatcag gtaaagctgg aggagtctgg gggaggcttg    120
gtgcaggctg ggcggtctct gagactctcc tgtgcagcct ctgaacacac cttcagtagc    180
catgtcatgg gctggttccg ccaggctcca gggaaggagc gtgagtctgt tgcagttatt    240
ggctggagag atattagcac aagctatgca gactccgtga agggccgatt caccatctcc    300
agagacaacg ccaagaagac gctgtatctg caaatgaata gcctgaaacc tgaggacacg    360
gccgtttact actgtgcagc acgtcggatc gacgcagctg actttgattc ctgggggcag    420
gggacccagg tcaccgtctc ctcgactagt accacgacgc cagcgccgcg accaccaaca    480
ccggcgccca catcgcgtc gcagcccctg tccctgcgcc cagaggcgtg ccggccagcg    540 gcgggggggcg cagtgcacac gaggggggctg acttcgcct gtgattttttg ggtgctggtg    600 gtggttggtg gagtcctggc ttgctatagc ttgctagtaa cagtggcctt tattattttc    660
tgggtgagga gtaagaggag caggctcctg cacagtgact acatgaacat gactccccgc    720
cgccccgggc ccacccgcaa gcattaccag ccctatgccc caccacgcga cttcgcagcc    780
tatcgctcca acggggcag aaagaaactc ctgtatatat tcaaacaacc atttatgaga    840
ccagtacaaa ctactcaaga ggaagatggc tgtagctgcc gatttccaga agaagaa    900 ggaggatgtg aactgagagt gaagttcagc aggagcgcag acgcccccgc gtacaagcag    960

```
ggccagaacc agctctataa cgagctcaat ctaggacgaa gagaggagta cgatgttttg    1020
gacaagagac gtggccggga ccctgagatg ggggggaaagc cgagaaggaa gaaccctcag   1080
gaaggcctgt acaatgaact gcagaaagat aagatggcgg aggcctacag tgagattggg   1140
atgaaaggcg agcgccggag gggcaagggg cacgatggcc tttaccaggg tctcagtaca   1200
gccaccaagg acacctacga cgcccttcac atgcaggccc tgcccctcg ctga          1254
```

<210> SEQ ID NO 185
<211> LENGTH: 1254
<212> TYPE: DNA
<213> ORGANISM: Artificial Sequence
<220> FEATURE:
<223> OTHER INFORMATION: BCMA 269A37948 CAR

<400> SEQUENCE: 185

```
atggccttac cagtgaccgc cttgctcctg ccgctggcct tgctgctcca cgccgccagg    60
ccggttaacc gcacgcgtcg catgcatgcg gtgcagctgg tggagtctgg ggaggattg    120 gtgcaggctg gggactctct gagactcacc tgtacagcct ctggacgcgc cttcagtacc   180
tatttcatgg cctggttccg ccaggctcca gggaaggagc gtgagtttgt agcaggaatt   240
gcatggagtg gtggtagcac ggcgtatgca gactccgtga agggccgatt caccatctcc   300
agagacaacg ccaagaacac ggtgtatctg caaatgaaca gcctgaaatc tgaggacacg   360
gccgtttatt actgtgccag caggggggatt gaggtcgaag agtttggtgc ctggggccag   420
gggacccagg tcaccgtctc gtcgactagt accacgacgc cagcgccgcg accaccaaca   480
ccggcgccca ccatcgcgtc gcagcccctg tccctgcgcc cagaggcgtg ccggccagcg   540
gcggggggcg cagtgcacac gagggggctg gacttcgcct gtgattttg ggtgctggtg    600 gtggttggtg gagtcctggc ttgctatagc ttgctagtaa cagtggcctt tattattttc   660
tgggtgagga gtaagaggag caggctcctg cacagtgact acatgaacat gactccccgc   720
cgccccgggc ccacccgcaa gcattaccag ccctatgccc caccacgcga cttcgcagcc   780
tatcgctcca aacggggcag aaagaaactc ctgtatatat tcaaacaacc atttatgaga   840
ccagtacaaa ctactcaaga ggaagatggc tgtagctgcc gatttccaga agaagaagaa   900
ggaggatgtg aactgagagt gaagttcagc aggagcgcag acgccccccgc gtacaagcag   960 ggccagaacc agctctataa cgagctcaat ctaggacgaa gagaggagta cgatgttttg   1020
gacaagagac gtggccggga ccctgagatg ggggggaaagc cgagaaggaa gaaccctcag   1080
gaaggcctgt acaatgaact gcagaaagat aagatggcgg aggcctacag tgagattggg   1140
atgaaaggcg agcgccggag gggcaagggg cacgatggcc tttaccaggg tctcagtaca   1200
gccaccaagg acacctacga cgcccttcac atgcaggccc tgcccctcg ctga          1254
```

<210> SEQ ID NO 186
<211> LENGTH: 1236
<212> TYPE: DNA
<213> ORGANISM: Artificial Sequence
<220> FEATURE:
<223> OTHER INFORMATION: CD38 38A37333 CAR

<400> SEQUENCE: 186

```
atggccttac cagtgaccgc cttgctcctg ccgctggcct tgctgctcca cgccgccagg    60
ccggttaacg atgtgcagct ggtggagtct gggggaggct tggtgcagcc tggggggtct   120
ctgagactct cctgtgtagc ctctggattg accttcagta gctaccccat gatgtgggtc   180
```

| | |
|---|---|
| cgccaggctc caggaaaggg gctcgagtgg gtctcacgta ttagcgatag tggtggttac | 240 |
| acaaactatg cgactccgt gaagggccga ttcaccatct ccagagacaa cgccaagaac | 300 |
| acgctgtatc tgcaaatgaa cagcctgaca cctgaggaca cggccgtgta ttactgtaga | 360 |
| atcctggggt tgcccaccac gggccagggg acccaggtca ccgtctcctc aacgcgtcgc | 420 |
| atgcatacta gtaccacgac gccagcgccg cgaccaccaa caccggcgcc caccatcgcg | 480 |
| tcgcagcccc tgtccctgcg cccagaggcg tgccggccag cggcgggggg cgcagtgcac | 540 |
| acgagggggc tggacttcgc ctgtgatttt tgggtgctgg tggtggttgg tggagtcctg | 600 |
| gcttgctata gcttgctagt aacagtggcc tttattattt tctgggtgag gagtaagagg | 660 |
| agcaggctcc tgcacagtga ctacatgaac atgactcccc gccgcccgg gcccacccgc | 720 |
| aagcattacc agccctatgc cccaccacgc gacttcgcag cctatcgctc aaacggggc | 780 |
| agaaagaaac tcctgtatat attcaaacaa ccatttatga gaccagtaca aactactcaa | 840 |
| gaggaagatg gctgtagctg ccgatttcca gaagaagaag aaggaggatg tgaactgaga | 900 |
| gtgaagttca gcaggagcgc agacgccccc gcgtacaagc agggccagaa ccagctctat | 960 |
| aacgagctca atctaggacg aagagaggag tacgatgttt tggacaagag acgtggccgg | 1020 |
| gaccctgaga tggggggaaa gccgagaagg aagaaccctc aggaaggcct gtacaatgaa | 1080 |
| ctgcagaaag ataagatggc ggaggcctac agtgagattg ggatgaaagg cgagcgccgg | 1140 |
| aggggcaagg ggcacgatgg cctttaccag ggtctcagta cagccaccaa ggacacctac | 1200 |
| gacgcccttc acatgcaggc cctgccccct cgctga | 1236 |

<210> SEQ ID NO 187
<211> LENGTH: 1272
<212> TYPE: DNA
<213> ORGANISM: Artificial Sequence
<220> FEATURE:
<223> OTHER INFORMATION: CD38 38A37336 CAR

<400> SEQUENCE: 187

| | |
|---|---|
| atggccttac cagtgaccgc cttgctcctg ccgctggcct tgctgctcca cgccgccagg | 60 |
| ccggttaacg aggtgcagct ggtggagtct gggggaggcc tggtgcagcc tggggggtct | 120 |
| ctgagactct cctgtgcagc ctctggattc accttcagta gcaactggat gtattgggtc | 180 |
| cgtcaggctc cagggaaggg gctcgagtgg gtcgcaacta ttagtactga tggtcgtgga | 240 |
| acatactata agactctgt gaagggccga ttcaccgtct ccagagacaa cgccatgagt | 300 |
| acgctgcttc tgcaaatgaa caatctgaaa tctgaagata cggccgtgta ttattgtgca | 360 |
| aaagagccga gggtgttgat ggcttacctg cggaacctgg gtgactttgg ttcctggggc | 420 |
| caggggaccc aggtcaccgt ctcctcgacg cgtcgcatgc atactagtac cacgacgcca | 480 |
| gcgccgcgac caccaacacc ggcgcccacc atcgcgtcgc agcccctgtc cctgcgccca | 540 |
| gaggcgtgcc ggccagcggc ggggggcgca gtgcacacga gggggctgga cttcgcctgt | 600 |
| gattttggg tgctggtggt ggttggtgga gtcctggctt gctatagctt gctagtaaca | 660 |
| gtggccttta ttttttctg ggtgaggagt aagaggagca ggctcctgca cagtgactac | 720 |
| atgaacatga ctccccgccg ccccgggccc acccgcaagc attaccagcc ctatgcccca | 780 |
| ccacgcgact tcgcagccta tcgctccaaa cggggcagaa agaaactcct gtatatattc | 840 |
| aaacaaccat ttatgagacc agtacaaact actcaagagg aagatggctg tagctgccga | 900 |
| tttccagaag aagaagaagg aggatgtgaa ctgagtga agttcagcag gagcgcagac | 960 |
| gccccgcgt acaagcaggg ccagaaccag ctctataacg agctcaatct aggacgaaga | 1020 |

| | |
|---|---|
| gaggagtacg atgttttgga caagagacgt ggccgggacc ctgagatggg gggaaagccg | 1080 |
| agaaggaaga accctcagga aggcctgtac aatgaactgc agaaagataa gatggcggag | 1140 |
| gcctacagtg agattgggat gaaaggcgag cgccggaggg gcaaggggca cgatggcctt | 1200 |
| taccagggtc tcagtacagc caccaaggac acctacgacg cccttcacat gcaggccctg | 1260 |
| cccctcgct ga | 1272 |

<210> SEQ ID NO 188
<211> LENGTH: 1239
<212> TYPE: DNA
<213> ORGANISM: Artificial Sequence
<220> FEATURE:
<223> OTHER INFORMATION: CD38 38A37669 CAR

<400> SEQUENCE: 188

| | |
|---|---|
| atggccttac cagtgaccgc cttgctcctg ccgctggcct tgctgctcca cgccgccagg | 60 |
| ccggttaacc aggtgcagct ggtggagtct gggggaggct tggtgcaggc tggggggtct | 120 |
| ctgagactct cctgtgcagc ctctggaagg atcttcagta tcaatgccat gggctggtac | 180 |
| cgccaggctc cagggaagca gcgcgagttg gtcgccgcta ttagtacggc tggtagcaca | 240 |
| aactatggag actccgtgaa gggccgattc accatctcca gagacaacgc caagaacacg | 300 |
| gtgtatctgc aaatgaacag cctgaaacct gaggacacag ctgtttatta ctgtaattta | 360 |
| aattttcccc gtatgtgta ctggggccag gggacccagg tcaccgtctc ctcaacgcgt | 420 |
| cgcatgcata ctagtaccac gacgccagcg ccgcgaccac caacaccggc gcccaccatc | 480 |
| gcgtcgcagc ccctgtccct gcgcccagag gcgtgccggc cagcggcggg gggcgcagtg | 540 |
| cacacgaggg ggctggactt cgcctgtgat ttttgggtgc tggtggtggt tgtgggagtc | 600 |
| ctggcttgct atagcttgct agtaacagtg gcctttatta ttttctgggt gaggagtaag | 660 |
| aggagcaggc tcctgcacag tgactacatg aacatgactc cccgccgccc cgggcccacc | 720 |
| cgcaagcatt accagcccta tgccccacca cgcgacttcg cagcctatcg ctccaaacgg | 780 |
| ggcagaaaga aactcctgta tatattcaaa caaccattta tgagaccagt acaaactact | 840 |
| caagaggaag atggctgtag ctgccgattt ccagaagaag aagaaggagg atgtgaactg | 900 |
| agagtgaagt tcagcaggag cgcagacgcc ccgcgtaca agcagggcca gaaccagctc | 960 |
| tataacgagc tcaatctagg acgaagagag gagtacgatg ttttggacaa gagacgtggc | 1020 |
| cgggaccctg agatggggg aaagccgaga aggaagaacc ctcaggaagg cctgtacaat | 1080 |
| gaactgcaga aagataagat ggcggaggcc tacagtgaga ttgggatgaa aggcgagcgc | 1140 |
| cggaggggca aggggcacga tggcctttac agggtctca gtacagccac caaggacacc | 1200 |
| tacgacgccc ttcacatgca ggccctgccc ctcgctga | 1239 |

<210> SEQ ID NO 189
<211> LENGTH: 1251
<212> TYPE: DNA
<213> ORGANISM: Artificial Sequence
<220> FEATURE:
<223> OTHER INFORMATION: CD38 38A37331 CAR

<400> SEQUENCE: 189

| | |
|---|---|
| atggccttac cagtgaccgc cttgctcctg ccgctggcct tgctgctcca cgccgccagg | 60 |
| ccggttaacc aggtaaagct ggaggagtct gggggaggtc tggtgcagcc tggggagtct | 120 |
| ctgagactct cctgttcagc ctctggaagc atcttcaaag ttttcagagt ctttgccatg | 180 |

| | |
|---|---|
| agctggtacc gccagggtcc cgggaaacag cgcgagttgg tcgcatccat tagtagtggc | 240 |
| gagaccacaa cctatgcaga ctccgtgaag ggccgattca ccatctccag agacaacgcc | 300 |
| aagaatacgg cgtatctgca aatggacagc ctgaaacctg aggacacggc cgtctattac | 360 |
| tgtaatgcgg atcacacctt tacaggagac ttctggggcc aggggaccca ggtcaccgtc | 420 |
| tcctcaacgc gtcgcatgca tactagtacc acgacgccag cgccgcgacc accaacaccg | 480 |
| gcgcccacca tcgcgtcgca gcccctgtcc ctgcgcccag aggcgtgccg gccagcggcg | 540 |
| gggggcgcag tgcacacgag ggggctggac ttcgcctgtg attttgggt gctggtggtg | 600 |
| gttggtggag tcctggcttg ctatagcttg ctagtaacag tggcctttat tattttctgg | 660 |
| gtgaggagta agaggagcag gctcctgcac agtgactaca tgaacatgac tccccgccgc | 720 |
| cccgggccca cccgcaagca ttaccagccc tatgccccac cacgcgactt cgcagcctat | 780 |
| cgctccaaac ggggcagaaa gaaactcctg tatatattca acaaccatt tatgagacca | 840 |
| gtacaaacta ctcaagagga agatggctgt agctgccgat ttccagaaga agaagaagga | 900 |
| ggatgtgaac tgagagtgaa gttcagcagg agcgcagacg cccccgcgta caagcagggc | 960 |
| cagaaccagc tctataacga gctcaatcta ggacgaagag aggagtacga tgttttggac | 1020 |
| aagagacgtg gccgggaccc tgagatgggg ggaaagccga aaggaagaa ccctcaggaa | 1080 |
| ggcctgtaca atgaactgca gaaagataag atggcggagg cctacagtga gattgggatg | 1140 |
| aaaggcgagc gccggagggg caaggggcac gatggccttt accagggtct cagtacagcc | 1200 |
| accaaggaca cctacgacgc ccttcacatg caggccctgc cccctcgctg a | 1251 |

<210> SEQ ID NO 190
<211> LENGTH: 1242
<212> TYPE: DNA
<213> ORGANISM: Artificial Sequence
<220> FEATURE:
<223> OTHER INFORMATION: CD38 38A37717 CAR

<400> SEQUENCE: 190

| | |
|---|---|
| atggccttac cagtgaccgc cttgctcctg ccgctggcct tgctgctcca cgccgccagg | 60 |
| ccggttaacg aggtgcagct ggtggaaagc ggggggggac tggtgcaggc aggcgggtca | 120 |
| ctgagactgt catgtatcgc aactgggaag gtgtttagca tctacgacat gggctggtat | 180 |
| aggcaggcac caggaaagca gagggagctg gtggccgaga tcaccagctc cggcaccaca | 240 |
| cactacgacg atttcgtgtc tggccggttt accatcagca gagacaacgc caagaataca | 300 |
| gtgtatctgc agatgaacac cctgaaggcc gaggatacag ccgtgtacta ttgccgggct | 360 |
| aatcacgtct tcggcggctc ctactggggg cagggaactc aggtcactgt gtcatccacg | 420 |
| cgtcgcatgc atactagtac cacgacgcca gcgccgcgac caccaacacc ggcgcccacc | 480 |
| atcgcgtcgc agcccctgtc cctgcgccca gaggcgtgcc ggccagcggc ggggggcgca | 540 |
| gtgcacacga ggggctgga cttcgcctgt gattttggg tgctggtggt ggttggtgga | 600 |
| gtcctggctt gctatagctt gctagtaaca gtggccttta ttattttctg ggtgaggagt | 660 |
| aagaggagca ggctcctgca cagtgactac atgaacatga ctccccgccg ccccgggccc | 720 |
| acccgcaagc attaccagcc ctatgcccca ccacgcgact cgcagccta cgctccaaa | 780 |
| cggggcagaa agaaactcct gtatatattc aacaaccat ttatgagacc agtacaaact | 840 |
| actcaagagg aagatggctg tagctgccga tttccagaag aagaagaagg aggatgtgaa | 900 |
| ctgagagtga agttcagcag gagcgcagac gcccccgcgt acaagcaggg ccagaaccag | 960 |
| ctctataacg agctcaatct aggacgaaga gaggagtacg atgttttgga caagagacgt | 1020 |

```
ggccgggacc ctgagatggg gggaaagccg agaaggaaga accctcagga aggcctgtac    1080
aatgaactgc agaaagataa gatggcggag gcctacagtg agattgggat gaaaggcgag    1140
cgccggaggg gcaaggggca cgatggcctt taccagggtc tcagtacagc caccaaggac    1200
acctacgacg cccttcacat gcaggccctg ccccctcgct ga                      1242
```

<210> SEQ ID NO 191
<211> LENGTH: 1239
<212> TYPE: DNA
<213> ORGANISM: Artificial Sequence
<220> FEATURE:
<223> OTHER INFORMATION: CD38 38A37719 CAR

<400> SEQUENCE: 191

```
atggccttac cagtgaccgc cttgctcctg ccgctggcct tgctgctcca cgccgccagg     60
ccggttaacc aggtaaagct ggaggagtct gggggaggct cggtgcagac tgggggtct    120 ctgagactct cctgtgcagc ctctgcaagc atcttcacta ggctgcccat gggctggtac    180
cgccaggctc cagggaagca gcgcgagttg gtcgtaggca ttgttcctag tggtaggata    240
aactatgcag actccgtgaa gggccgattc accatctcca gagacaacgc caagaacacg    300
gtgtatctgc aaatgaacag cctgcgccct gaggacacag ccgtctatta ctgccgcgcc    360
gataccttcc ccttgcccac ctggggccag gggacccagg tcaccgtctc ctcaacgcgt    420
cgcatgcata ctagtaccac gacgccagcg ccgcgaccac caacaccggc gcccaccatc    480
gcgtcgcagc ccctgtccct gcgcccagag gcgtgccggc cagcggcggg gggcgcagtg    540
cacacgaggg ggctggactt cgcctgtgat ttttgggtgc tggtggtggt tggtggagtc    600
ctggcttgct atagcttgct agtaacagtg gcctttatta ttttctgggt gaggagtaag    660
aggagcaggc tcctgcacag tgactacatg aacatgactc ccgccgcccc gggccccacc    720
cgcaagcatt accagcccta tgccccacca cgcgacttcg cagcctatcg ctccaaacgg    780
ggcagaaaga aactcctgta tatattcaaa caaccattta tgagaccagt acaaactact    840
caagaggaag atggctgtag ctgccgattt ccagaagaag aagaaggagg atgtgaactg    900
agagtgaagt tcagcaggag cgcagacgcc ccgcgtaca gcagggcca gaaccagctc    960 tataacgagc tcaatctagg acgaagagag gagtacgatg ttttggacaa gagacgtggc   1020
cgggaccctg agatgggggg aaagccgaga aggaagaacc tcaggaagg cctgtacaat   1080 gaactgcaga agataagat ggcggaggcc tacagtgaga ttgggatgaa aggcgagcgc   1140
cggaggggca aggggcacga tggcctttac cagggtctca gtacagccac caaggacacc   1200
tacgacgccc ttcacatgca ggccctgccc ctcgctga                           1239
```

<210> SEQ ID NO 192
<211> LENGTH: 1272
<212> TYPE: DNA
<213> ORGANISM: Artificial Sequence
<220> FEATURE:
<223> OTHER INFORMATION: CD38 38A37330 CAR

<400> SEQUENCE: 192

```
atggccttac cagtgaccgc cttgctcctg ccgctggcct tgctgctcca cgccgccagg     60
ccggttaacc aggtgcagct ggtggagtct gggggaggat tggtgcaggc tgggactct    120 ctgagactct cctgtgcagc ctctggacgc gcctacgcta cgatggcctg gttccgccag    180
gctccaggga aggagcgtga gtttgtagca catctgcgcg tgagtggtga taccacttac    240
```

| | |
|---|---|
| tatacagact ccgtgaaggg ccgattcacc atctccagag acaacgccaa gaacacggcg | 300 |
| tatctgcaaa tgaacatgtt gaaacctgag gacacggccg tttattactg tgcagcggga | 360 |
| ccgtatggca ttcttgccgc tgccagggtc agtaatccag gaaattatga ttattgggc | 420 |
| caggggaccc aggtcaccgt ctcctcaacg cgtcgcatgc atactagtac cacgacgcca | 480 |
| gcgccgcgac caccaacacc ggcgcccacc atcgcgtcgc agcccctgtc cctgcgccca | 540 |
| gaggcgtgcc ggccagcggc gggggcgca gtgcacacga gggggctgga cttcgcctgt | 600 |
| gattttggg tgctggtggt ggttggtgga gtcctggctt gctatagctt gctagtaaca | 660 |
| gtggccttta ttattttctg ggtgaggagt aagaggagca ggctcctgca cagtgactac | 720 |
| atgaacatga ctccccgccg ccccgggccc accgcaagc attaccagcc ctatgcccca | 780 |
| ccacgcgact tcgcagccta tcgctccaaa cggggcagaa agaaactcct gtatatattc | 840 |
| aaacaaccat ttatgagacc agtacaaact actcaagagg aagatggctg tagctgccga | 900 |
| tttccagaag aagaagaagg aggatgtgaa ctgagagtga agttcagcag gagcgcagac | 960 |
| gcccccgcgt acaagcaggg ccagaaccag ctctataacg agctcaatct aggacgaaga | 1020 |
| gaggagtacg atgttttgga caagagacgt ggccgggacc ctgagatggg gggaaagccg | 1080 |
| agaaggaaga accctcagga aggcctgtac aatgaactgc agaaagataa gatggcggag | 1140 |
| gcctacagtg agattgggat gaaaggcgag cgccggaggg gcaaggggca cgatggcctt | 1200 |
| taccagggtc tcagtacagc caccaaggac acctacgacg cccttcacat gcaggccctg | 1260 |
| ccccctcgct ga | 1272 |

<210> SEQ ID NO 193
<211> LENGTH: 1263
<212> TYPE: DNA
<213> ORGANISM: Artificial Sequence
<220> FEATURE:
<223> OTHER INFORMATION: CD38 38A37334 CAR

<400> SEQUENCE: 193

| | |
|---|---|
| atggccttac cagtgaccgc cttgctcctg ccgctggcct tgctgctcca cgccgccagg | 60 |
| ccggttaacg aggtgcagct ggtggagtct gggggaggat tggtgcaggc tggggggctct | 120 |
| ctgagactct cctgtgcagc ctctggactc accttcagta gttatattat gggctggttc | 180 |
| cgccaggctc caggcgagga gcgcgagttg gtcgcggaaa ttagtagcgg tggtatgaca | 240 |
| tcgtatgcag actccgtgaa gggccgattc accatctcca gagacaacgc caagaagacg | 300 |
| gggtatctgc aaatgaacag cctgaaacct gaggacacgg ccgtttacta ttgtgcagcc | 360 |
| cctgagaggg gtagtatctg gtacagccgc tacgaatata gtactgggg ccaggggacc | 420 |
| caggtcaccg tctcctcaac gcgtcgcatg catactagta ccacgacgcc agcgccgcga | 480 |
| ccaccaacac cggcgcccac catcgcgtcg cagcccctgt ccctgcgccc agaggcgtgc | 540 |
| cggcagcgg cggggggcgc agtgcacacg aggggctgg acttcgcctg tgattttttgg | 600 |
| gtgctggtgg tggttggtgg agtcctggct tgctatagct tgctagtaac agtggccttt | 660 |
| attattttct gggtgaggag taagaggagc aggctcctgc acagtgacta catgaacatg | 720 |
| actccccgcc gccccgggcc caccgcaag cattaccagc cctatgcccc accacgcgac | 780 |
| ttcgcagcct atcgctccaa acggggcaga agaaactcc tgtatatatt caaacaacca | 840 |
| tttatgagac cagtacaaac tactcaagag gaagatggct gtagctgccg atttccagaa | 900 |
| gaagaagaag aggatgtgaa ctgagagtg aagttcagca ggagcgcaga cgcccccgcg | 960 |
| tacaagcagg gccagaacca gctctataac gagctcaatc taggacgaag agaggagtac | 1020 |

| | | |
|---|---|---|
| gatgttttgg acaagagacg tggccgggac cctgagatgg ggggaaagcc gagaaggaag | 1080 |
| aaccctcagg aaggcctgta caatgaactg cagaaagata agatggcgga ggcctacagt | 1140 |
| gagattggga tgaaggcgga gcgccggagg ggcaaggggc acgatggcct ttaccagggt | 1200 |
| ctcagtacag ccaccaagga cacctacgac gcccttcaca tgcaggccct gccccctcgc | 1260 |
| tga | 1263 |

<210> SEQ ID NO 194
<211> LENGTH: 1254
<212> TYPE: DNA
<213> ORGANISM: Artificial Sequence
<220> FEATURE:
<223> OTHER INFORMATION: CD38 38A37730 CAR

<400> SEQUENCE: 194

| | |
|---|---|
| atggccttac cagtgaccgc cttgctcctg ccgctggcct tgctgctcca cgccgccagg | 60 |
| ccggttaacg ccgtgcagct ggtggattct gggggaggct tggcgcagac tgggggtgtct | 120 |
| ctgagactct cctgtgcagc ctctcaaggg atcttcacta tcaatgccat gggctggtac | 180 |
| cgccaggttc cagggaagca gcgggagttg gtcgcagaag ttagtagtgg tggccgcaca | 240 |
| gactatgcag actccgtgaa gggccgattc accatctcca gagacaacgc caagaacacg | 300 |
| gtgtacctgc aaatgaacag cctgaaacct gaggacacag cgtctatta ttgtcgagtt | 360 |
| tctggatggc atgtgtttgt cggtgaccgc atagtttggg gccagggcac cctggtcact | 420 |
| gtctcctcaa cgcgtcgcat gcatactagt accacgacgc cagcgccgcg accaccaaca | 480 |
| ccggcgccca ccatcgcgtc gcagcccctg tccctgcgcc cagaggcgtg ccggccagcg | 540 |
| gcggggggcg cagtgcacac gagggggctg gacttcgcct gtgattttttg ggtgctggtg | 600 |
| gtggttggtg gagtcctggc ttgctatagc ttgctagtaa cagtggcctt tattattttc | 660 |
| tgggtgagga gtaagaggag caggctcctg cacagtgact acatgaacat gactccccgc | 720 |
| cgccccgggc ccacccgcaa gcattaccag ccctatgccc caccacgcga cttcgcagcc | 780 |
| tatcgctcca acggggcag aaagaaactc ctgtatatat tcaaacaacc atttatgaga | 840 |
| ccagtacaaa ctactcaaga ggaagatggc tgtagctgcc gatttccaga agaagaagaa | 900 |
| ggaggatgtg aactgagagt gaagttcagc aggagcgcag acgccccccgc gtacaagcag | 960 |
| ggccagaacc agctctataa cgagctcaat ctaggacgaa gagaggagta cgatgttttg | 1020 |
| gacaagagac gtggccggga ccctgagatg gggggaaagc cgagaaggaa gaaccctcag | 1080 |
| gaaggcctgt acaatgaact gcagaaagat aagatggcgg aggcctacag tgagattggg | 1140 |
| atgaaggcg agcgccggag gggcaagggg cacgatggcc tttaccaggg tctcagtaca | 1200 |
| gccaccaagg acacctacga cgcccttcac atgcaggccc tgccccctcg ctga | 1254 |

<210> SEQ ID NO 195
<211> LENGTH: 1263
<212> TYPE: DNA
<213> ORGANISM: Artificial Sequence
<220> FEATURE:
<223> OTHER INFORMATION: CD38 38A37340 CAR

<400> SEQUENCE: 195

| | |
|---|---|
| atggccttac cagtgaccgc cttgctcctg ccgctggcct tgctgctcca cgccgccagg | 60 |
| ccggttaacg atgtgcagct ggtggagtct gggggaggat tggtgcaggc tggggactct | 120 |
| ctgagactct cctgtgcagc ctctggacgc accttcagta gctatgccat ggcctggttc | 180 |

```
cgccaggctc cagggaagga gcgtgagatt gtttcgtcta tcagtaccag tggtggtatc    240
acagactatg cagactccgt gaagggccga ttcaccatct ccaaagacag cgcgaagatg    300
aacacggtgt atctgcaaat gaatagccta gaacctgagg acacggccgt ttactactgt    360
gcggcccgta catggtacct tcgtacttct ctccaatatg actattgggg ccaggggacc    420
caggtcaccg tctcctcaac gcgtcgcatg catactagta ccacgacgcc agcgccgcga    480
ccaccaacac cggcgcccac catcgcgtcg cagcccctgt ccctgcgccc agaggcgtgc    540
cggccagcgg cgggggcgc agtgcacacg agggggctgg acttcgcctg tgattttgg     600 gtgctggtgg tggttggtgg agtcctggct tgctatagct tgctagtaac agtggccttt    660
attattttct gggtgaggag taagaggagc aggctcctgc acagtgacta catgaacatg    720
actccccgcc gccccgggcc cacccgcaag cattaccagc cctatgcccc accacgcgac    780
ttcgcagcct atcgctccaa acgggcaga aagaaactcc tgtatatatt caaacaacca    840
tttatgagac cagtacaaac tactcaagag gaagatggct gtagctgccg atttccagaa    900
gaagaagaag gaggatgtga actgagagtg aagttcagca ggagcgcaga cgcccccgcg    960
tacaagcagg gccagaacca gctctataac gagctcaatc taggacgaag agaggagtac   1020
gatgttttgg acaagagacg tggccgggac cctgagatgg gggaaaagcc gagaaggaag   1080
aaccctcagg aaggcctgta caatgaactg cagaaagata gatggcgga ggcctacagt     1140 gagattggga tgaaaggcga gcgccggagg ggcaaggggc acgatggcct ttaccagggt   1200
ctcagtacag ccaccaagga cacctacgac gcccttcaca tgcaggccct gccccctcgc   1260
tga                                                                  1263
```

<210> SEQ ID NO 196
<211> LENGTH: 1257
<212> TYPE: DNA
<213> ORGANISM: Artificial Sequence
<220> FEATURE:
<223> OTHER INFORMATION: CD38 38A37731 CAR

<400> SEQUENCE: 196

```
atggccttac cagtgaccgc cttgctcctg ccgctggcct tgctgctcca cgccgccagg     60
ccggttaacc aggtaaagct ggaggagtct gggggaggct tggtgcaggc tgggggtct    120 ctgagactct cctgtgtagc ctctggaacc atcgtcagta tcagtaccat gggctggtac    180
cgccaggctc cagggaagca gcgcgagttg gtcgcgacta taaccaggcg tggacgcacg    240
aactatacag actccgtgaa gggccgattc accatctcca gagacaacgc caaaaacacg    300
gtgtatctgc aaatgaacag cctgaaacct gaggacacag ccgtctatta ctgtaatgca    360
gaggtgcaac tggatatatg ggcatctgcg tatgactact ggggccaggg gacccaggtc    420
accgtcgcct caacgcgtcg catgcatact agtaccacga cgccagcgcc gcgaccacca    480
acaccggcgc ccaccatcgc gtcgcagccc ctgtccctgc gcccagaggc gtgccggcca    540
gcggcggggg gcgcagtgca cacgaggggg ctggacttcg cctgtgattt ttgggtgctg    600
gtggtggttg gtggagtcct ggcttgctat agcttgctag taacagtggc ctttattatt    660
ttctgggtga ggagtaagag gagcaggctc ctgcacagtg actacatgaa catgactccc    720
cgccgccccg ggcccacccg caagcattac cagccctatg ccccaccacg cgacttcgca    780
gcctatcgct ccaaacgggg cagaaagaaa ctcctgtata tattcaaaca accatttatg    840
agaccagtac aaactactca agaggaagat ggctgtagct gccgatttcc agaagaagaa    900
gaaggaggat gtgaactgag agtgaagttc agcaggagcg cagacgcccc cgcgtacaag    960
```

```
cagggccaga accagctcta taacgagctc aatctaggac gaagagagga gtacgatgtt    1020
ttggacaaga gacgtggccg ggaccctgag atgggggggaa agccgagaag gaagaaccct    1080
caggaaggcc tgtacaatga actgcagaaa gataagatgg cggaggccta cagtgagatt    1140
gggatgaaag gcgagcgccg gaggggcaag gggcacgatg gcctttacca gggtctcagt    1200
acagccacca aggacaccta cgacgccctt cacatgcagg ccctgccccc tcgctga       1257
```

<210> SEQ ID NO 197
<211> LENGTH: 1239
<212> TYPE: DNA
<213> ORGANISM: Artificial Sequence
<220> FEATURE:
<223> OTHER INFORMATION: CD38 38A37326 CAR

<400> SEQUENCE: 197

```
atggcctta  cagtgaccgc cttgctcctg ccgctggcct tgctgctcca cgccgccagg      60
ccggttaacg aggtgcagct ggtggagtct gggggaggat tggtgcaggc tgggggctct    120
ctgagactct cctgtgcagc ctctggacgc acctatgcca tgggctggta tcgccaggct    180
ccagggaagc agcgcgactt ggtcgcaact attagtggtg cgggtaacac aaagtatgca    240
gactccgtga agggccgatt caccatctcc agagacaacg ccaagaacac aatgtatctg    300
caaatgaaca gcctgaaacc tgaggacacg gccgtttatt actgtgccgc gggtaaatgg    360
ttccctgctg cgaatgagta ctggggccag gggacccagg tcaccgtctc ctcaacgcgt    420
cgcatgcata ctagtaccac gacgccagcg ccgcgaccac caacaccggc gcccaccatc    480
gcgtcgcagc ccctgtccct gcgcccagag gcgtgccggc cagcggcggg gggcgcagtg    540
cacacgaggg ggctggactt cgcctgtgat ttttgggtgc tggtggtggt tgtggagtc    600 ctggcttgct atagcttgct agtaacagtg gcctttatta ttttctgggt gaggagtaag    660
aggagcaggc tcctgcacag tgactacatg aacatgactc cccgccgccc cgggcccacc    720
cgcaagcatt accagcccta tgccccacca cgcgacttcg cagcctatcg ctccaaacgg    780
ggcagaaaga aactcctgta tatattcaaa caaccattta tgagaccagt acaaactact    840
caagaggaag atggctgtag ctgccgattt ccagaagaag aagaaggagg atgtgaactg    900
agagtgaagt tcagcaggag cgcagacgcc ccgcgtaca gcagggcca gaaccagctc    960 tataacgagc tcaatctagg acgaagagag gagtacgatg ttttggacaa gagacgtggc    1020
cgggaccctg agatgggggg aaagccgaga aggaagaacc ctcaggaagg cctgtacaat    1080
gaactgcaga aagataagat ggcggaggcc tacagtgaga ttgggatgaa aggcgagcgc    1140
cggaggggca aggggcacga tggccttac agggtctca gtacagccac caaggacacc    1200
tacgacgccc ttcacatgca ggccctgccc cctcgctga                          1239
```

<210> SEQ ID NO 198
<211> LENGTH: 495
<212> TYPE: PRT
<213> ORGANISM: Artificial Sequence
<220> FEATURE:
<223> OTHER INFORMATION: BCMAx2 269A37946 GSI5014 CAR

<400> SEQUENCE: 198

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

-continued

```
Val Gln Pro Gly Gly Ser Leu Arg Leu Ser Cys Glu Ala Ser Gly Phe
         35                  40                  45

Thr Leu Asp Tyr Tyr Ala Ile Gly Trp Phe Arg Gln Ala Pro Gly Lys
 50                  55                  60

Glu Arg Glu Gly Val Ile Cys Ile Ser Arg Ser Asp Gly Ser Thr Tyr
 65                  70                  75                  80

Tyr Ala Asp Ser Val Lys Gly Arg Phe Thr Ile Ser Arg Asp Asn Ala
                 85                  90                  95

Lys Lys Thr Val Tyr Leu Gln Met Ile Ser Leu Lys Pro Glu Asp Thr
            100                 105                 110

Ala Ala Tyr Tyr Cys Ala Ala Gly Ala Asp Cys Ser Gly Tyr Leu Arg
            115                 120                 125

Asp Tyr Glu Phe Arg Gly Gln Gly Thr Gln Val Thr Val Ser Ser Gly
        130                 135                 140

Gly Gly Gly Ser Gln Val Gln Leu Val Glu Ser Gly Gly Gly Leu Val
145                 150                 155                 160

Gln Pro Gly Gly Ser Leu Arg Leu Ser Cys Glu Ala Ser Gly Phe Thr
                165                 170                 175

Leu Asp Tyr Tyr Ala Ile Gly Trp Phe Arg Gln Ala Pro Gly Lys Glu
            180                 185                 190

Arg Glu Gly Val Ile Cys Ile Ser Arg Ser Asp Gly Ser Thr Tyr Tyr
        195                 200                 205

Ala Asp Ser Val Lys Gly Arg Phe Thr Ile Ser Arg Asp Asn Ala Lys
    210                 215                 220

Lys Thr Val Tyr Leu Gln Met Ile Ser Leu Lys Pro Glu Asp Thr Ala
225                 230                 235                 240

Ala Tyr Tyr Cys Ala Ala Gly Ala Asp Cys Ser Gly Tyr Leu Arg Asp
                245                 250                 255

Tyr Glu Phe Arg Gly Gln Gly Thr Gln Val Thr Val Ser Ser Thr Ser
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Lys Arg Gly Arg Lys Lys Leu Leu Tyr Ile Phe
            340                 345                 350

Lys Gln Pro Phe Met Arg Pro Val Gln Thr Thr Gln Glu Glu Asp Gly
        355                 360                 365

Cys Ser Cys Arg Phe Pro Glu Glu Glu Glu Gly Gly Cys Glu Leu Arg
    370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
        435                 440                 445

Lys Met Ala Glu Ala Tyr Ser Glu Ile Gly Met Lys Gly Glu Arg Arg
```

```
                450            455           460
Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495

<210> SEQ ID NO 199
<211> LENGTH: 622
<212> TYPE: PRT
<213> ORGANISM: Artificial Sequence
<220> FEATURE:
<223> OTHER INFORMATION: BCMAx3 269A37946 GSI5015 CAR

<400> SEQUENCE: 199

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
                20                  25                  30

Val Gln Pro Gly Gly Ser Leu Arg Leu Ser Cys Glu Ala Ser Gly Phe
            35                  40                  45

Thr Leu Asp Tyr Tyr Ala Ile Gly Trp Phe Arg Gln Ala Pro Gly Lys
        50                  55                  60

Glu Arg Glu Gly Val Ile Cys Ile Ser Arg Ser Asp Gly Ser Thr Tyr
65                  70                  75                  80

Tyr Ala Asp Ser Val Lys Gly Arg Phe Thr Ile Ser Arg Asp Asn Ala
                85                  90                  95

Lys Lys Thr Val Tyr Leu Gln Met Ile Ser Leu Lys Pro Glu Asp Thr
            100                 105                 110

Ala Ala Tyr Tyr Cys Ala Ala Gly Ala Asp Cys Ser Gly Tyr Leu Arg
        115                 120                 125

Asp Tyr Glu Phe Arg Gly Gln Gly Thr Gln Val Thr Val Ser Ser Gly
    130                 135                 140

Gly Gly Gly Ser Gln Val Gln Leu Val Glu Ser Gly Gly Gly Leu Val
145                 150                 155                 160

Gln Pro Gly Gly Ser Leu Arg Leu Ser Cys Glu Ala Ser Gly Phe Thr
                165                 170                 175

Leu Asp Tyr Tyr Ala Ile Gly Trp Phe Arg Gln Ala Pro Gly Lys Glu
            180                 185                 190

Arg Glu Gly Val Ile Cys Ile Ser Arg Ser Asp Gly Ser Thr Tyr Tyr
        195                 200                 205

Ala Asp Ser Val Lys Gly Arg Phe Thr Ile Ser Arg Asp Asn Ala Lys
    210                 215                 220

Lys Thr Val Tyr Leu Gln Met Ile Ser Leu Lys Pro Glu Asp Thr Ala
225                 230                 235                 240

Ala Tyr Tyr Cys Ala Ala Gly Ala Asp Cys Ser Gly Tyr Leu Arg Asp
                245                 250                 255

Tyr Glu Phe Arg Gly Gln Gly Thr Gln Val Thr Val Ser Ser Gly Gly
            260                 265                 270

Gly Gly Ser Gln Val Gln Leu Val Glu Ser Gly Gly Gly Leu Val Gln
        275                 280                 285

Pro Gly Gly Ser Leu Arg Leu Ser Cys Glu Ala Ser Gly Phe Thr Leu
    290                 295                 300

Asp Tyr Tyr Ala Ile Gly Trp Phe Arg Gln Ala Pro Gly Lys Glu Arg
305                 310                 315                 320

Glu Gly Val Ile Cys Ile Ser Arg Ser Asp Gly Ser Thr Tyr Tyr Ala
```

```
                        325                 330                 335
Asp Ser Val Lys Gly Arg Phe Thr Ile Ser Arg Asp Asn Ala Lys Lys
                340                 345                 350

Thr Val Tyr Leu Gln Met Ile Ser Leu Lys Pro Glu Asp Thr Ala Ala
            355                 360                 365

Tyr Tyr Cys Ala Ala Gly Ala Asp Cys Ser Gly Tyr Leu Arg Asp Tyr
        370                 375                 380

Glu Phe Arg Gly Gln Gly Thr Gln Val Thr Val Ser Ser Thr Ser Thr
385                 390                 395                 400

Thr Thr Pro Ala Pro Arg Pro Pro Thr Pro Ala Pro Thr Ile Ala Ser
                405                 410                 415

Gln Pro Leu Ser Leu Arg Pro Glu Ala Cys Arg Pro Ala Ala Gly Gly
            420                 425                 430

Ala Val His Thr Arg Gly Leu Asp Phe Ala Cys Asp Ile Tyr Ile Trp
        435                 440                 445

Ala Pro Leu Ala Gly Thr Cys Gly Val Leu Leu Leu Ser Leu Val Ile
    450                 455                 460

Thr Leu Tyr Cys Lys Arg Gly Arg Lys Lys Leu Leu Tyr Ile Phe Lys
465                 470                 475                 480

Gln Pro Phe Met Arg Pro Val Gln Thr Thr Gln Glu Glu Asp Gly Cys
                485                 490                 495

Ser Cys Arg Phe Pro Glu Glu Glu Gly Gly Cys Glu Leu Arg Val
            500                 505                 510

Lys Phe Ser Arg Ser Ala Asp Ala Pro Ala Tyr Gln Gln Gly Gln Asn
        515                 520                 525

Gln Leu Tyr Asn Glu Leu Asn Leu Gly Arg Arg Glu Glu Tyr Asp Val
    530                 535                 540

Leu Asp Lys Arg Arg Gly Arg Asp Pro Glu Met Gly Gly Lys Pro Arg
545                 550                 555                 560

Arg Lys Asn Pro Gln Glu Gly Leu Tyr Asn Glu Leu Gln Lys Asp Lys
                565                 570                 575

Met Ala Glu Ala Tyr Ser Glu Ile Gly Met Lys Gly Glu Arg Arg Arg
            580                 585                 590

Gly Lys Gly His Asp Gly Leu Tyr Gln Gly Leu Ser Thr Ala Thr Lys
        595                 600                 605

Asp Thr Tyr Asp Ala Leu His Met Gln Ala Leu Pro Pro Arg
    610                 615                 620

<210> SEQ ID NO 200
<211> LENGTH: 483
<212> TYPE: PRT
<213> ORGANISM: Artificial Sequence
<220> FEATURE:
<223> OTHER INFORMATION: CD38x2 38A37717 GSI5016 CAR

<400> SEQUENCE: 200

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Ala Gly Gly Ser Leu Arg Leu Ser Cys Ile Ala Thr Gly Lys
        35                  40                  45

Val Phe Ser Ile Tyr Asp Met Gly Trp Tyr Arg Gln Ala Pro Gly Lys
    50                  55                  60

Gln Arg Glu Leu Val Ala Glu Ile Thr Ser Ser Gly Thr Thr His Tyr
```

```
                65                  70                  75                  80
Asp Asp Phe Val Ser Gly Arg Phe Thr Ile Ser Arg Asp Asn Ala Lys
                        85                  90                  95
Asn Thr Val Tyr Leu Gln Met Asn Thr Leu Lys Ala Glu Asp Thr Ala
                        100                 105                 110
Val Tyr Tyr Cys Arg Ala Asn His Val Phe Gly Gly Ser Tyr Trp Gly
                        115                 120                 125
Gln Gly Thr Gln Val Thr Val Ser Ser Gly Gly Gly Ser Glu Val
                130                 135                 140
Gln Leu Val Glu Ser Gly Gly Gly Leu Val Gln Ala Gly Gly Ser Leu
145                 150                 155                 160
Arg Leu Ser Cys Ile Ala Thr Gly Lys Val Phe Ser Ile Tyr Asp Met
                        165                 170                 175
Gly Trp Tyr Arg Gln Ala Pro Gly Lys Gln Arg Glu Leu Val Ala Glu
                        180                 185                 190
Ile Thr Ser Ser Gly Thr Thr His Tyr Asp Asp Phe Val Ser Gly Arg
                        195                 200                 205
Phe Thr Ile Ser Arg Asp Asn Ala Lys Asn Thr Val Tyr Leu Gln Met
                210                 215                 220
Asn Thr Leu Lys Ala Glu Asp Thr Ala Val Tyr Tyr Cys Arg Ala Asn
225                 230                 235                 240
His Val Phe Gly Gly Ser Tyr Trp Gly Gln Gly Thr Gln Val Thr Val
                        245                 250                 255
Ser Ser Thr Ser Thr Thr Thr Pro Ala Pro Arg Pro Pro Thr Pro Ala
                        260                 265                 270
Pro Thr Ile Ala Ser Gln Pro Leu Ser Leu Arg Pro Glu Ala Cys Arg
                        275                 280                 285
Pro Ala Ala Gly Gly Ala Val His Thr Arg Gly Leu Asp Phe Ala Cys
                        290                 295                 300
Asp Ile Tyr Ile Trp Ala Pro Leu Ala Gly Thr Cys Gly Val Leu Leu
305                 310                 315                 320
Leu Ser Leu Val Ile Thr Leu Tyr Cys Lys Arg Gly Arg Lys Lys Leu
                        325                 330                 335
Leu Tyr Ile Phe Lys Gln Pro Phe Met Arg Pro Val Gln Thr Thr Gln
                        340                 345                 350
Glu Glu Asp Gly Cys Ser Cys Arg Phe Pro Glu Glu Glu Glu Gly Gly
                        355                 360                 365
Cys Glu Leu Arg Val Lys Phe Ser Arg Ser Ala Asp Ala Pro Ala Tyr
                        370                 375                 380
Gln Gln Gly Gln Asn Gln Leu Tyr Asn Glu Leu Asn Leu Gly Arg Arg
385                 390                 395                 400
Glu Glu Tyr Asp Val Leu Asp Lys Arg Arg Gly Arg Asp Pro Glu Met
                        405                 410                 415
Gly Gly Lys Pro Arg Arg Lys Asn Pro Gln Glu Gly Leu Tyr Asn Glu
                        420                 425                 430
Leu Gln Lys Asp Lys Met Ala Glu Ala Tyr Ser Glu Ile Gly Met Lys
                        435                 440                 445
Gly Glu Arg Arg Arg Gly Lys Gly His Asp Gly Leu Tyr Gln Gly Leu
                        450                 455                 460
Ser Thr Ala Thr Lys Asp Thr Tyr Asp Ala Leu His Met Gln Ala Leu
465                 470                 475                 480
Pro Pro Arg
```

<210> SEQ ID NO 201
<211> LENGTH: 604
<212> TYPE: PRT
<213> ORGANISM: Artificial Sequence
<220> FEATURE:
<223> OTHER INFORMATION: CD38x3 38A37717 GSI5017 CAR

<400> SEQUENCE: 201

```
Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Ala Gly Gly Ser Leu Arg Leu Ser Cys Ile Ala Thr Gly Lys
        35                  40                  45

Val Phe Ser Ile Tyr Asp Met Gly Trp Tyr Arg Gln Ala Pro Gly Lys
    50                  55                  60

Gln Arg Glu Leu Val Ala Glu Ile Thr Ser Ser Gly Thr Thr His Tyr
65                  70                  75                  80

Asp Asp Phe Val Ser Gly Arg Phe Thr Ile Ser Arg Asp Asn Ala Lys
                85                  90                  95

Asn Thr Val Tyr Leu Gln Met Asn Thr Leu Lys Ala Glu Asp Thr Ala
            100                 105                 110

Val Tyr Tyr Cys Arg Ala Asn His Val Phe Gly Gly Ser Tyr Trp Gly
        115                 120                 125

Gln Gly Thr Gln Val Thr Val Ser Ser Gly Gly Gly Ser Glu Val
130                 135                 140

Gln Leu Val Glu Ser Gly Gly Gly Leu Val Gln Ala Gly Gly Ser Leu
145                 150                 155                 160

Arg Leu Ser Cys Ile Ala Thr Gly Lys Val Phe Ser Ile Tyr Asp Met
                165                 170                 175

Gly Trp Tyr Arg Gln Ala Pro Gly Lys Gln Arg Glu Leu Val Ala Glu
            180                 185                 190

Ile Thr Ser Ser Gly Thr Thr His Tyr Asp Asp Phe Val Ser Gly Arg
        195                 200                 205

Phe Thr Ile Ser Arg Asp Asn Ala Lys Asn Thr Val Tyr Leu Gln Met
    210                 215                 220

Asn Thr Leu Lys Ala Glu Asp Thr Ala Val Tyr Tyr Cys Arg Ala Asn
225                 230                 235                 240

His Val Phe Gly Gly Ser Tyr Trp Gly Gln Gly Thr Gln Val Thr Val
                245                 250                 255

Ser Ser Gly Gly Gly Gly Ser Glu Val Gln Leu Val Glu Ser Gly Gly
            260                 265                 270

Gly Leu Val Gln Ala Gly Gly Ser Leu Arg Leu Ser Cys Ile Ala Thr
        275                 280                 285

Gly Lys Val Phe Ser Ile Tyr Asp Met Gly Trp Tyr Arg Gln Ala Pro
    290                 295                 300

Gly Lys Gln Arg Glu Leu Val Ala Glu Ile Thr Ser Ser Gly Thr Thr
305                 310                 315                 320

His Tyr Asp Asp Phe Val Ser Gly Arg Phe Thr Ile Ser Arg Asp Asn
                325                 330                 335

Ala Lys Asn Thr Val Tyr Leu Gln Met Asn Thr Leu Lys Ala Glu Asp
            340                 345                 350

Thr Ala Val Tyr Tyr Cys Arg Ala Asn His Val Phe Gly Gly Ser Tyr
        355                 360                 365
```

```
Trp Gly Gln Gly Thr Gln Val Thr Val Ser Ser Thr Ser Thr Thr Thr
    370                 375                 380
Pro Ala Pro Arg Pro Pro Thr Pro Ala Pro Thr Ile Ala Ser Gln Pro
385                 390                 395                 400
Leu Ser Leu Arg Pro Glu Ala Cys Arg Pro Ala Ala Gly Gly Ala Val
                405                 410                 415
His Thr Arg Gly Leu Asp Phe Ala Cys Asp Ile Tyr Ile Trp Ala Pro
            420                 425                 430
Leu Ala Gly Thr Cys Gly Val Leu Leu Leu Ser Leu Val Ile Thr Leu
        435                 440                 445
Tyr Cys Lys Arg Gly Arg Lys Lys Leu Leu Tyr Ile Phe Lys Gln Pro
    450                 455                 460
Phe Met Arg Pro Val Gln Thr Thr Gln Glu Glu Asp Gly Cys Ser Cys
465                 470                 475                 480
Arg Phe Pro Glu Glu Glu Glu Gly Gly Cys Glu Leu Arg Val Lys Phe
                485                 490                 495
Ser Arg Ser Ala Asp Ala Pro Ala Tyr Gln Gln Gly Gln Asn Gln Leu
            500                 505                 510
Tyr Asn Glu Leu Asn Leu Gly Arg Arg Glu Glu Tyr Asp Val Leu Asp
        515                 520                 525
Lys Arg Arg Gly Arg Asp Pro Glu Met Gly Gly Lys Pro Arg Arg Lys
    530                 535                 540
Asn Pro Gln Glu Gly Leu Tyr Asn Glu Leu Gln Lys Asp Lys Met Ala
545                 550                 555                 560
Glu Ala Tyr Ser Glu Ile Gly Met Lys Gly Glu Arg Arg Arg Gly Lys
                565                 570                 575
Gly His Asp Gly Leu Tyr Gln Gly Leu Ser Thr Ala Thr Lys Asp Thr
            580                 585                 590
Tyr Asp Ala Leu His Met Gln Ala Leu Pro Pro Arg
        595                 600

<210> SEQ ID NO 202
<211> LENGTH: 1488
<212> TYPE: DNA
<213> ORGANISM: Artificial Sequence
<220> FEATURE:
<223> OTHER INFORMATION: BCMAx2 269A37946 GSI5014 CAR

<400> SEQUENCE: 202
atggctctgc ccgtcactgc tctgctgctg cccctggctc tgctgctgca cgctgctcgc      60
cctcaggtcc agctggtgga aagcggagga ggcctggtgc agccaggagg cagcctgagg     120
ctgtcctgcg aggcctctgg cttcaccctg gactactatg ccatcggctg gtttaggcag     180
gcacctggaa aggagaggga gggagtgatc tgtatctctc gcagcgacgg cagcacatac     240
tatgccgatt ccgtgaaggg ccggttcacc atcagcagag acaacgccaa gaagacagtg     300
tacctgcaga tgatctccct gaagcctgag gataccgcag catactattg cgcagcagga     360
gcagactgta gcggatacct gagggattat gagtttaggg acagggaac ccaggtgaca     420 gtgagctccg gaggaggagg ctcccaggtg cagctggtgg agtctggagg cggcctggtg     480
cagcctggag gcagcctgag actgagctgt gaagcttccg gatttaccct ggactactat     540
gcaatcggat ggtttaggca ggcaccagga aaggagagag aaggcgtgat ctgtatctcc     600
agatctgacg gctctacata ctatgccgat agtgtcaaag acggttcac catctctaga     660 gataatgcca agaagacagt ctatctgcag atgattagcc tgaagcccga ggacacagcc     720
```

-continued

| | |
|---|---|
| gcctattact gcgcagcagg agcagattgt agtgggtatc tgagggacta tgagtttcgg | 780 |
| gggcagggga cacaggtgac agtgagttct actagtacca cgacgccagc gccgcgacca | 840 |
| ccaacaccgg cgcccaccat cgcgtcgcag cccctgtccc tgcgcccaga ggcgtgccgg | 900 |
| ccagcggcgg ggggcgcagt gcacacgagg gggctggact tcgcctgtga tatctacatc | 960 |
| tgggcgccct tggccgggac ttgtggggtc cttctcctgt cactggttat caccctttac | 1020 |
| tgcaaacggg gcagaaagaa actcctgtat atattcaaac aaccatttat gagaccagta | 1080 |
| caaactactc aagaggaaga tggctgtagc tgccgatttc agaagaaga agaaggagga | 1140 |
| tgtgaactga gagtgaagtt cagcaggagc gcagacgccc ccgcgtacca gcagggccag | 1200 |
| aaccagctct ataacgagct caatctagga cgaagagagg agtacgatgt tttggacaag | 1260 |
| agacgtggcc gggaccctga gatgggggga aagccgagaa ggaagaaccc tcaggaaggc | 1320 |
| ctgtacaatg aactgcagaa agataagatg gcggaggcct acagtgagat tgggatgaaa | 1380 |
| ggcgagcgcc ggaggggcaa ggggcacgat ggcctttacc agggtctcag tacagccacc | 1440 |
| aaggacacct acgacgccct tcacatgcag gccctgcccc ctcgctaa | 1488 |

<210> SEQ ID NO 203
<211> LENGTH: 1869
<212> TYPE: DNA
<213> ORGANISM: Artificial Sequence
<220> FEATURE:
<223> OTHER INFORMATION: BCMAx3 269A37946 GSI5015 CAR

<400> SEQUENCE: 203

| | |
|---|---|
| atggctctgc ccgtcactgc tctgctgctg cctctggccc tgctgctgca cgccgcacgc | 60 |
| cctcaggtcc agctggtcga gtcaggagga ggcctggtgc agccaggagg ctccctgcgg | 120 |
| ctgtcttgcg aggccagcgg cttcaccctg gactactatg ccatcggctg gtttaggcag | 180 |
| gcacctggaa aggagaggga gggagtgatc tgtatctcca gatctgacgg ctccacatac | 240 |
| tatgccgatt ctgtgaaggg ccggttcacc atctctagag acaacgccaa gaagacagtg | 300 |
| tacctgcaga tgatcagcct gaagcccgag ataccgcag catactattg cgcagcagga | 360 |
| gcagactgtt ccggatacct gagggattat gagtttaggg gacagggaac ccaggtgaca | 420 |
| gtgagctccg gaggaggagg ctcccaggtg cagctggtgg agtctggagg cggcctggtg | 480 |
| cagcctggag gctccctgag gctgtcttgc gaggcaagcg gcttcaccct ggattactat | 540 |
| gcaatcggat ggtttaggca ggcaccagga aaggagagag aaggcgtgat ctgtatcagc | 600 |
| cgctccgacg gcagtaccta ctatgccgat tccgtcaaag gccggttcac catctccaga | 660 |
| gacaatgcca agaagacagt ctatctgcag atgatctctc tgaagcctga ggatacagcc | 720 |
| gcctattact gtgccgcagg agcagactgt agtggctatc tgagagatta tgagtttcgc | 780 |
| ggccagggca cccaggtgac agtgtctagc ggaggaggag gcagccaggt ccagctggtg | 840 |
| gaatccggcg gaggcctggt gcagcccggc ggctccctga ctgtcctg tgaagcctcc | 900 |
| ggatttactc tggattatta cgctattgga tggttcagac aggcccctgg caaagaaaga | 960 |
| gaagggtga tctgtatctc tcggagcgac ggctctacat actatgccga tagcgtcaag | 1020 |
| ggaagattta ccatctccag agataatgcc aagaagacag tgtatctgca gatgatttcc | 1080 |
| ctgaagcccg aggacactgc cgcctattac tgtgcagcag gagcagattg tagcgggtat | 1140 |
| ctgcgggatt atgaatttag gacagggc actcaggtga cagtctcaag cactagtacc | 1200 |
| acgacgccag cgccgcgacc accaacaccg gcgcccacca tcgcgtcgca gcccctgtcc | 1260 |
| ctgcgcccag aggcgtgccg gccagcggcg ggggcgcag tgcacacgag ggggctggac | 1320 |

-continued

```
ttcgcctgtg atatctacat ctgggcgccc ttggccggga cttgtggggt ccttctcctg    1380
tcactggtta tcacccttta ctgcaaacgg ggcagaaaga aactcctgta tatattcaaa    1440
caaccattta tgagaccagt acaaactact caagaggaag atggctgtag ctgccgattt    1500
ccagaagaag aagaaggagg atgtgaactg agagtgaagt tcagcaggag cgcagacgcc    1560
cccgcgtacc agcagggcca gaaccagctc tataacgagc tcaatctagg acgaagagag    1620
gagtacgatg ttttggacaa gagacgtggc cgggaccctg agatgggggg aaagccgaga    1680
aggaagaacc ctcaggaagg cctgtacaat gaactgcaga agataagat ggcggaggcc     1740 tacagtgaga ttgggatgaa aggcgagcgc cggaggggca aggggcacga tggcctttac    1800
cagggtctca gtacagccac caaggacacc tacgacgccc ttcacatgca ggccctgccc    1860
cctcgctaa                                                           1869
```

<210> SEQ ID NO 204
<211> LENGTH: 1452
<212> TYPE: DNA
<213> ORGANISM: Artificial Sequence
<220> FEATURE:
<223> OTHER INFORMATION: CD38x2 38A37717 GSI5016 CAR

<400> SEQUENCE: 204

```
atggccctgc ctgtcaccgc tctgctgctg cctctggccc tgctgctgca cgctgctaga     60
cccgaagtcc agctggtcga agtgggggga ggcctggtgc aggcaggagg cagcctgagg    120
ctgtcctgca tcgccaccgg caaggtgttc agcatctacg acatgggatg gtataggcag    180
gcaccaggaa agcagagaga gctggtggcc gagatcacaa gctccggcac cacacactac    240
gacgatttcg tgtccggccg gtttaccatc tctagagaca cgccaagaa tacagtgtat    300 ctgcagatga acaccctgaa ggccgaggat acagccgtgt actattgccg ggccaatcac    360
gtgttcggag atcctactg gggacaggga acccaggtga cagtgtctag cggaggagga    420
ggatctgagg tgcagctggt ggagagcgga ggcggcctgg tgcaggccgg aggctctctg    480
agactgagct gtattgctac cggcaaggtg ttttctatct acgatatggg ctggtatagg    540
caggcacctg gaaagcagag ggagctggtg gctgaaatca cctcctctgg aactaccccat    600 tacgacgatt tcgtgagcgg caggtttacc atctcccgcg ataatgctaa aaacaccgtc    660
tacctgcaga tgaatactct gaaagctgaa gacacagccg tgtactattg tcgggctaac    720
catgtcttcg ggggctccta ttgggggcag ggaactcagg tcaccgtgtc atcaactagt    780
accacgacgc cagcgccgcg accaccaaca ccggcgccca ccatcgcgtc gcagcccctg    840
tccctgcgcc cagaggcgtg ccggccagcg gcggggggcg cagtgcacac gaggggggctg    900 gacttcgcct gtgatatcta catctgggcg cccttggccg gacttgtgg ggtccttctc    960 ctgtcactgg ttatcaccct ttactgcaaa cggggcagaa agaaactcct gtatatattc    1020
aaacaaccat ttatgagacc agtacaaact actcaagagg aagatggctg tagctgccga    1080
tttccagaag aagaagaagg aggatgtgaa ctgagagtga agttcagcag gagcgcagac    1140 gccccccgcgt accagcaggg ccagaaccag ctctataacg agctcaatct aggacgaaga    1200
gaggagtacg atgttttgga caagagacgt ggccgggacc tgagatgggg ggaaagccg     1260 agaaggaaga accctcagga aggcctgtac aatgaactgc agaaagataa gatggcggag    1320
gcctacagtg agattgggat gaaaggcgag cgccggaggg gcaaggggca cgatggcctt    1380
taccagggtc tcagtacagc caccaaggac acctacgacg cccttcacat gcaggccctg    1440
```

| cccctcgct aa | 1452 |

<210> SEQ ID NO 205
<211> LENGTH: 1815
<212> TYPE: DNA
<213> ORGANISM: Artificial Sequence
<220> FEATURE:
<223> OTHER INFORMATION: CD38x3 38A37717 GSI5017 CAR

<400> SEQUENCE: 205

| | |
|---|---|
| atggctctgc ctgtcaccgc actgctgctg cccctggccc tgctgctgca cgccgcaaga | 60 |
| cctgaagtcc agctggtcga atccggagga ggcctggtgc aggcaggagg ctccctgcgg | 120 |
| ctgtcttgca tcgccaccgg caaggtgttc agcatctacg catgggctg gtataggcag | 180 |
| gcaccaggaa agcagaggga gctggtggcc gagatcacaa gctccggcac acacactac | 240 |
| gacgatttcg tgtccggccg gtttaccatc tctagagaca cgccaagaa tacagtgtat | 300 |
| ctgcagatga cacccctgaa ggccgaggat acagccgtgt actattgccg ggccaatcac | 360 |
| gtgttcggag atcttactg gggacaggga acccaggtga cagtgtctag cggaggagga | 420 |
| ggatccgagg tgcagctggt ggagtctgga ggcggcctgg tgcaggccgg aggcagcctg | 480 |
| agactgtcct gtattgctac cggcaaggtg ttttccatct acgatatggg ctggtatcgg | 540 |
| caggcccctg gcaagcagag agagctggtg gctgaaatca catcctctgg aactacccat | 600 |
| tacgacgatt tcgtgagcgg caggtttacc atctcccgcg ataatgctaa aaacaccgtc | 660 |
| tacctgcaga tgaatactct gaaagctgaa gacaccgctg tgtactattg cagagctaac | 720 |
| catgtgttcg gaggaagcta ttggggccag ggcactcagg tgacagtgag ctccggcggc | 780 |
| ggcggcagtg aagtgcagct ggtggagtcc ggagggggcc tggtgcaggc cggcggctct | 840 |
| ctgcgcctga gctgtattgc aactggaaaa gtgttttcca tttatgatat gggatggtac | 900 |
| agacaggccc tgggaaaaca gagagagctg gtggcagaaa tcacctctag tggaactacc | 960 |
| cactatgatg atttcgtgtc tggccggttt accatcagca gggataatgc taaaaacact | 1020 |
| gtctacctgc agatgaacac tctgaaagct gaagataccg ccgtgtacta ttgtagggct | 1080 |
| aaccatgtct ttgggggtc atactggggg caggggactc aggtcaccgt ctcatccact | 1140 |
| agtaccacga cgccagcgcc gcgaccacca acaccggcgc ccaccatcgc gtcgcagccc | 1200 |
| ctgtccctgc gcccagaggc gtgccggcca cggcggggg gcgcagtgca cacgagggg | 1260 |
| ctggacttcg cctgtgatat ctacatctgg gcgcccttgg ccgggacttg tggggtcctt | 1320 |
| ctcctgtcac tggttatcac cctttactgc aaacggggca gaaagaaact cctgtatata | 1380 |
| ttcaaacaac catttatgag accagtacaa actactcaag aggaagatgg ctgtagctgc | 1440 |
| cgatttccag aagaagaaga aggaggatgt gaactgagag tgaagttcag caggagcgca | 1500 |
| gacgccccg cgtaccagca gggccagaac cagctctata acgagctcaa tctaggacga | 1560 |
| agagaggagt acgatgtttt ggacaagaga cgtggccggg accctgagat gggggggaaag | 1620 |
| ccgagaagga gaaccctca ggaaggcctg tacaatgaac tgcagaaaga taagatggcg | 1680 |
| gaggcctaca gtgagattgg gatgaaaggc gagcgccgga ggggcaaggg gcacgatggc | 1740 |
| ctttaccagg gtctcagtac agccaccaag gacacctacg acgccttca catgcaggcc | 1800 |
| ctgccccctc gctaa | 1815 |

<210> SEQ ID NO 206
<211> LENGTH: 502
<212> TYPE: PRT
<213> ORGANISM: Artificial Sequence
<220> FEATURE:
<223> OTHER INFORMATION: CD19XCD20 single-domain antibody-based bispecific CAR

<400> SEQUENCE: 206

```
Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Glu Leu
            20                  25                  30

Val Gln Pro Gly Gly Pro Leu Arg Leu Ser Cys Ala Ala Ser Gly Asn
        35                  40                  45

Ile Phe Ser Ile Asn Arg Met Gly Trp Tyr Arg Gln Ala Pro Gly Lys
50                  55                  60

Gln Arg Ala Phe Val Ala Ser Ile Thr Val Arg Gly Ile Thr Asn Tyr
65                  70                  75                  80

Ala Asp Ser Val Lys Gly Arg Phe Thr Ile Ser Val Asp Lys Ser Lys
                85                  90                  95

Asn Thr Ile Tyr Leu Gln Met Asn Ala Leu Lys Pro Glu Asp Thr Ala
            100                 105                 110

Val Tyr Tyr Cys Asn Ala Val Ser Ser Asn Arg Asp Pro Asp Tyr Trp
        115                 120                 125

Gly Gln Gly Thr Gln Val Thr Val Ser Ser Gly Gly Gly Ser Gly Gly
    130                 135                 140

Gly Ser Gly Gly Gly Ser Gly Gly Ser Pro Val Gln Leu Val Glu
145                 150                 155                 160

Ser Gly Gly Gly Leu Val Gln Ala Gly Asp Ser Leu Arg Leu Ser Cys
                165                 170                 175

Ala Ala Ser Gly Arg Thr Phe Gly Ile Gly Thr Met Gly Trp Phe Arg
            180                 185                 190

Gln Pro Pro Gly Lys Glu Arg Glu Phe Val Ala Ala Ile Arg Trp Ser
        195                 200                 205

Thr Gly Gly Thr Arg Tyr Ala Asp Ser Val Lys Gly Arg Phe Thr Ile
210                 215                 220

Ser Arg Asp Asn Ala Lys Leu Thr Val Asp Leu Gln Met Asp Ser Leu
225                 230                 235                 240

Lys Pro Glu Asp Thr Ala Val Tyr Tyr Cys Ala Ala Asp Arg Leu Ser
                245                 250                 255

Leu Asp Leu Ser Gly Arg Tyr His Tyr Asn Pro Ala Val Tyr Asp Tyr
            260                 265                 270

Trp Gly Gln Gly Thr Gln Val Thr Val Ser Ser Ile Glu Val Met Tyr
        275                 280                 285

Pro Pro Pro Tyr Leu Asp Asn Glu Lys Ser Asn Gly Thr Ile Ile His
290                 295                 300

Val Lys Gly Lys His Leu Cys Pro Ser Pro Leu Phe Pro Gly Pro Ser
305                 310                 315                 320

Lys Pro Phe Trp Val Leu Val Val Val Gly Gly Val Leu Ala Cys Tyr
                325                 330                 335

Ser Leu Leu Val Thr Val Ala Phe Ile Ile Phe Trp Val Arg Ser Lys
            340                 345                 350

Arg Ser Arg Leu Leu His Ser Asp Tyr Met Asn Met Thr Pro Arg Arg
        355                 360                 365

Pro Gly Pro Thr Arg Lys His Tyr Gln Pro Tyr Ala Pro Pro Arg Asp
370                 375                 380

Phe Ala Ala Tyr Arg Ser Arg Val Lys Phe Ser Arg Ser Ala Asp Ala
```

```
385                 390                 395                 400

Pro Ala Tyr Gln Gln Gly Gln Asn Gln Leu Tyr Asn Glu Leu Asn Leu
                405                 410                 415

Gly Arg Arg Glu Glu Tyr Asp Val Leu Asp Lys Arg Gly Arg Asp
                420                 425                 430     Asp

Pro Glu Met Gly Gly Lys Pro Arg Arg Lys Asn Pro Gln Glu Gly Leu
                435                 440                 445

Tyr Asn Glu Leu Gln Lys Asp Lys Met Ala Glu Ala Tyr Ser Glu Ile
450                 455                 460

Gly Met Lys Gly Glu Arg Arg Arg Gly Lys Gly His Asp Gly Leu Tyr
465                 470                 475                 480

Gln Gly Leu Ser Thr Ala Thr Lys Asp Thr Tyr Asp Ala Leu His Met
                485                 490                 495

Gln Ala Leu Pro Pro Arg
                500

<210> SEQ ID NO 207
<211> LENGTH: 489
<212> TYPE: PRT
<213> ORGANISM: Artificial Sequence
<220> FEATURE:
<223> OTHER INFORMATION: CD38xBCMA 38A37717 269A37346 GSI5001 CAR

<400> SEQUENCE: 207

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
                20                  25                  30

Val Gln Ala Gly Gly Ser Leu Arg Leu Ser Cys Ile Ala Thr Gly Lys
            35                  40                  45

Val Phe Ser Ile Tyr Asp Met Gly Trp Tyr Arg Gln Ala Pro Gly Lys
        50                  55                  60

Gln Arg Glu Leu Val Ala Glu Ile Thr Ser Ser Gly Thr Thr His Tyr
65                  70                  75                  80

Asp Asp Phe Val Ser Gly Arg Phe Thr Ile Ser Arg Asp Asn Ala Lys
                85                  90                  95

Asn Thr Val Tyr Leu Gln Met Asn Thr Leu Lys Ala Glu Asp Thr Ala
                100                 105                 110

Val Tyr Tyr Cys Arg Ala Asn His Val Phe Gly Gly Ser Tyr Trp Gly
            115                 120                 125

Gln Gly Thr Gln Val Thr Val Ser Ser Gly Gly Gly Ser Gln Val
        130                 135                 140

Gln Leu Val Glu Ser Gly Gly Gly Leu Val Gln Pro Gly Gly Ser Leu
145                 150                 155                 160

Arg Leu Ser Cys Glu Ala Ser Gly Phe Thr Leu Asp Tyr Tyr Ala Ile
                165                 170                 175

Gly Trp Phe Arg Gln Ala Pro Gly Lys Glu Arg Glu Gly Val Ile Cys
            180                 185                 190

Ile Ser Arg Ser Asp Gly Ser Thr Tyr Tyr Ala Asp Ser Val Lys Gly
        195                 200                 205

Arg Phe Thr Ile Ser Arg Asp Asn Ala Lys Lys Thr Val Tyr Leu Gln
        210                 215                 220

Met Ile Ser Leu Lys Pro Glu Asp Thr Ala Ala Tyr Tyr Cys Ala Ala
225                 230                 235                 240

Gly Ala Asp Cys Ser Gly Tyr Leu Arg Asp Tyr Glu Phe Arg Gly Gln
```

```
                    245                 250                 255
Gly Thr Gln Val Thr Val Ser Ser Thr Ser Thr Thr Thr Pro Ala Pro
            260                 265                 270

Arg Pro Pro Thr Pro Ala Pro Thr Ile Ala Ser Gln Pro Leu Ser Leu
        275                 280                 285

Arg Pro Glu Ala Cys Arg Pro Ala Ala Gly Gly Ala Val His Thr Arg
    290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Lys
                325                 330                 335

Arg Gly Arg Lys Lys Leu Leu Tyr Ile Phe Lys Gln Pro Phe Met Arg
            340                 345                 350

Pro Val Gln Thr Thr Gln Glu Glu Asp Gly Cys Ser Cys Arg Phe Pro
        355                 360                 365

Glu Glu Glu Glu Gly Gly Cys Glu Leu Arg Val Lys Phe Ser Arg Ser
    370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
        435                 440                 445

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485

<210> SEQ ID NO 208
<211> LENGTH: 494
<212> TYPE: PRT
<213> ORGANISM: Artificial Sequence
<220> FEATURE:
<223> OTHER INFORMATION: CD38xBCMA 38A37717 269A37346 GSI5002 CAR

<400> SEQUENCE: 208

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Ala Gly Gly Ser Leu Arg Leu Ser Cys Ile Ala Thr Gly Lys
        35                  40                  45

Val Phe Ser Ile Tyr Asp Met Gly Trp Tyr Arg Gln Ala Pro Gly Lys
    50                  55                  60

Gln Arg Glu Leu Val Ala Glu Ile Thr Ser Ser Gly Thr Thr His Tyr
65                  70                  75                  80

Asp Asp Phe Val Ser Gly Arg Phe Thr Ile Ser Arg Asp Asn Ala Lys
                85                  90                  95

Asn Thr Val Tyr Leu Gln Met Asn Thr Leu Lys Ala Glu Asp Thr Ala
            100                 105                 110

Val Tyr Tyr Cys Arg Ala Asn His Val Phe Gly Gly Ser Tyr Trp Gly
```

```
            115                 120                 125
Gln Gly Thr Gln Val Thr Val Ser Ser Gly Gly Gly Ser Gly Gly
            130                 135                 140
Gly Gly Ser Gln Val Gln Leu Val Glu Ser Gly Gly Leu Val Gln
145                 150                 155                 160
Pro Gly Gly Ser Leu Arg Leu Ser Cys Glu Ala Ser Gly Phe Thr Leu
                165                 170                 175
Asp Tyr Tyr Ala Ile Gly Trp Phe Arg Gln Ala Pro Gly Lys Glu Arg
            180                 185                 190
Glu Gly Val Ile Cys Ile Ser Arg Ser Asp Gly Ser Thr Tyr Tyr Ala
            195                 200                 205
Asp Ser Val Lys Gly Arg Phe Thr Ile Ser Arg Asp Asn Ala Lys Lys
210                 215                 220
Thr Val Tyr Leu Gln Met Ile Ser Leu Lys Pro Glu Asp Thr Ala Ala
225                 230                 235                 240
Tyr Tyr Cys Ala Ala Gly Ala Asp Cys Ser Gly Tyr Leu Arg Asp Tyr
                245                 250                 255
Glu Phe Arg Gly Gln Gly Thr Gln Val Thr Val Ser Ser Thr Ser Thr
            260                 265                 270
Thr Thr Pro Ala Pro Arg Pro Pro Thr Pro Ala Pro Thr Ile Ala Ser
            275                 280                 285
Gln Pro Leu Ser Leu Arg Pro Glu Ala Cys Arg Pro Ala Ala Gly Gly
            290                 295                 300
Ala Val His Thr Arg Gly Leu Asp Phe Ala Cys Asp Ile Tyr Ile Trp
305                 310                 315                 320
Ala Pro Leu Ala Gly Thr Cys Gly Val Leu Leu Leu Ser Leu Val Ile
                325                 330                 335
Thr Leu Tyr Cys Lys Arg Gly Arg Lys Lys Leu Leu Tyr Ile Phe Lys
            340                 345                 350
Gln Pro Phe Met Arg Pro Val Gln Thr Thr Gln Glu Glu Asp Gly Cys
            355                 360                 365
Ser Cys Arg Phe Pro Glu Glu Glu Glu Gly Gly Cys Glu Leu Arg Val
            370                 375                 380
Lys Phe Ser Arg Ser Ala Asp Ala Pro Ala Tyr Gln Gln Gly Gln Asn
385                 390                 395                 400
Gln Leu Tyr Asn Glu Leu Asn Leu Gly Arg Arg Glu Glu Tyr Asp Val
                405                 410                 415
Leu Asp Lys Arg Arg Gly Arg Asp Pro Glu Met Gly Gly Lys Pro Arg
            420                 425                 430
Arg Lys Asn Pro Gln Glu Gly Leu Tyr Asn Glu Leu Gln Lys Asp Lys
            435                 440                 445
Met Ala Glu Ala Tyr Ser Glu Ile Gly Met Lys Gly Glu Arg Arg Arg
            450                 455                 460
Gly Lys Gly His Asp Gly Leu Tyr Gln Gly Leu Ser Thr Ala Thr Lys
465                 470                 475                 480
Asp Thr Tyr Asp Ala Leu His Met Gln Ala Leu Pro Pro Arg
                485                 490

<210> SEQ ID NO 209
<211> LENGTH: 500
<212> TYPE: PRT
<213> ORGANISM: Artificial Sequence
<220> FEATURE:
<223> OTHER INFORMATION: CD38xBCMA 38A37717 269A37346 GSI5003 CAR
```

```
<400> SEQUENCE: 209

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
                20                  25                  30

Val Gln Ala Gly Gly Ser Leu Arg Leu Ser Cys Ile Ala Thr Gly Lys
            35                  40                  45

Val Phe Ser Ile Tyr Asp Met Gly Trp Tyr Arg Gln Ala Pro Gly Lys
    50                  55                  60

Gln Arg Glu Leu Val Ala Glu Ile Thr Ser Ser Gly Thr Thr His Tyr
65                  70                  75                  80

Asp Asp Phe Val Ser Gly Arg Phe Thr Ile Ser Arg Asp Asn Ala Lys
                85                  90                  95

Asn Thr Val Tyr Leu Gln Met Asn Thr Leu Lys Ala Glu Asp Thr Ala
            100                 105                 110

Val Tyr Tyr Cys Arg Ala Asn His Val Phe Gly Gly Ser Tyr Trp Gly
    115                 120                 125

Gln Gly Thr Gln Val Thr Val Ser Ser Gly Gly Gly Ser Gly Gly Gly
130                 135                 140

Ser Gly Gly Gly Ser Gly Gly Ser Gln Val Gln Leu Val Glu Ser
145                 150                 155                 160

Gly Gly Gly Leu Val Gln Pro Gly Gly Ser Leu Arg Leu Ser Cys Glu
                165                 170                 175

Ala Ser Gly Phe Thr Leu Asp Tyr Tyr Ala Ile Gly Trp Phe Arg Gln
            180                 185                 190

Ala Pro Gly Lys Glu Arg Glu Gly Val Ile Cys Ile Ser Arg Ser Asp
    195                 200                 205

Gly Ser Thr Tyr Tyr Ala Asp Ser Val Lys Gly Arg Phe Thr Ile Ser
210                 215                 220

Arg Asp Asn Ala Lys Lys Thr Val Tyr Leu Gln Met Ile Ser Leu Lys
225                 230                 235                 240

Pro Glu Asp Thr Ala Ala Tyr Tyr Cys Ala Ala Gly Ala Asp Cys Ser
                245                 250                 255

Gly Tyr Leu Arg Asp Tyr Glu Phe Arg Gly Gln Gly Thr Gln Val Thr
            260                 265                 270

Val Ser Thr Ser Thr Thr Thr Pro Ala Pro Arg Pro Pro Thr Pro
    275                 280                 285

Ala Pro Thr Ile Ala Ser Gln Pro Leu Ser Leu Arg Pro Glu Ala Cys
    290                 295                 300

Arg Pro Ala Ala Gly Gly Ala Val His Thr Arg Gly Leu Asp Phe Ala
305                 310                 315                 320

Cys Asp Ile Tyr Ile Trp Ala Pro Leu Ala Gly Thr Cys Gly Val Leu
                325                 330                 335

Leu Leu Ser Leu Val Ile Thr Leu Tyr Cys Lys Arg Gly Arg Lys Lys
            340                 345                 350

Leu Leu Tyr Ile Phe Lys Gln Pro Phe Met Arg Pro Val Gln Thr Thr
    355                 360                 365

Gln Glu Glu Asp Gly Cys Ser Cys Arg Phe Pro Glu Glu Glu Glu Gly
    370                 375                 380

Gly Cys Glu Leu Arg Val Lys Phe Ser Arg Ser Ala Asp Ala Pro Ala
385                 390                 395                 400

Tyr Gln Gln Gly Gln Asn Gln Leu Tyr Asn Glu Leu Asn Leu Gly Arg
                405                 410                 415
```

```
Arg Glu Glu Tyr Asp Val Leu Asp Lys Arg Gly Arg Asp Pro Glu
                420                 425                 430

Met Gly Gly Lys Pro Arg Arg Lys Asn Pro Gln Glu Gly Leu Tyr Asn
            435                 440                 445

Glu Leu Gln Lys Asp Lys Met Ala Glu Ala Tyr Ser Glu Ile Gly Met
450                 455                 460

Lys Gly Glu Arg Arg Arg Gly Lys Gly His Asp Gly Leu Tyr Gln Gly
465                 470                 475                 480

Leu Ser Thr Ala Thr Lys Asp Thr Tyr Asp Ala Leu His Met Gln Ala
                485                 490                 495

Leu Pro Pro Arg
            500

<210> SEQ ID NO 210
<211> LENGTH: 508
<212> TYPE: PRT
<213> ORGANISM: Artificial Sequence
<220> FEATURE:
<223> OTHER INFORMATION: CD38xBCMA 38A37717 269A37346 GSI5004 CAR

<400> SEQUENCE: 210

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Ala Gly Gly Ser Leu Arg Leu Ser Cys Ile Ala Thr Gly Lys
        35                  40                  45

Val Phe Ser Ile Tyr Asp Met Gly Trp Tyr Arg Gln Ala Pro Gly Lys
    50                  55                  60

Gln Arg Glu Leu Val Ala Glu Ile Thr Ser Ser Gly Thr Thr His Tyr
65                  70                  75                  80

Asp Asp Phe Val Ser Gly Arg Phe Thr Ile Ser Arg Asp Asn Ala Lys
                85                  90                  95

Asn Thr Val Tyr Leu Gln Met Asn Thr Leu Lys Ala Glu Asp Thr Ala
            100                 105                 110

Val Tyr Tyr Cys Arg Ala Asn His Val Phe Gly Gly Ser Tyr Trp Gly
        115                 120                 125

Gln Gly Thr Gln Val Thr Val Ser Ser Gly Gly Gly Ser Gly Gly
    130                 135                 140

Gly Gly Ser Gly Gly Gly Gly Gly Ser Gly Ser Gly Gly Gly Gly
145                 150                 155                 160

Ser Gln Val Gln Leu Val Glu Ser Gly Gly Gly Leu Val Gln Pro Gly
                165                 170                 175

Gly Ser Leu Arg Leu Ser Cys Glu Ala Ser Gly Phe Thr Leu Asp Tyr
            180                 185                 190

Tyr Ala Ile Gly Trp Phe Arg Gln Ala Pro Gly Lys Glu Arg Glu Gly
        195                 200                 205

Val Ile Cys Ile Ser Arg Ser Asp Gly Ser Thr Tyr Tyr Ala Asp Ser
    210                 215                 220

Val Lys Gly Arg Phe Thr Ile Ser Arg Asp Asn Ala Lys Lys Thr Val
225                 230                 235                 240

Tyr Leu Gln Met Ile Ser Leu Lys Pro Glu Asp Thr Ala Ala Tyr Tyr
                245                 250                 255

Cys Ala Ala Gly Ala Asp Cys Ser Gly Tyr Leu Arg Asp Tyr Glu Phe
            260                 265                 270
```

```
Arg Gly Gln Gly Thr Gln Val Thr Val Ser Ser Thr Thr Thr
            275                 280                 285

Pro Ala Pro Arg Pro Pro Thr Pro Ala Pro Thr Ile Ala Ser Gln Pro
290                 295                 300

Leu Ser Leu Arg Pro Glu Ala Cys Arg Pro Ala Ala Gly Gly Ala Val
305                 310                 315                 320

His Thr Arg Gly Leu Asp Phe Ala Cys Asp Ile Tyr Ile Trp Ala Pro
            325                 330                 335

Leu Ala Gly Thr Cys Gly Val Leu Leu Leu Ser Leu Val Ile Thr Leu
            340                 345                 350

Tyr Cys Lys Arg Gly Arg Lys Lys Leu Leu Tyr Ile Phe Lys Gln Pro
            355                 360                 365

Phe Met Arg Pro Val Gln Thr Thr Gln Glu Glu Asp Gly Cys Ser Cys
370                 375                 380

Arg Phe Pro Glu Glu Glu Glu Gly Gly Cys Glu Leu Arg Val Lys Phe
385                 390                 395                 400

Ser Arg Ser Ala Asp Ala Pro Ala Tyr Gln Gln Gly Gln Asn Gln Leu
            405                 410                 415

Tyr Asn Glu Leu Asn Leu Gly Arg Arg Glu Glu Tyr Asp Val Leu Asp
            420                 425                 430

Lys Arg Arg Gly Arg Asp Pro Glu Met Gly Gly Lys Pro Arg Arg Lys
            435                 440                 445

Asn Pro Gln Glu Gly Leu Tyr Asn Glu Leu Gln Lys Asp Lys Met Ala
            450                 455                 460

Glu Ala Tyr Ser Glu Ile Gly Met Lys Gly Glu Arg Arg Arg Gly Lys
465                 470                 475                 480

Gly His Asp Gly Leu Tyr Gln Gly Leu Ser Thr Ala Thr Lys Asp Thr
            485                 490                 495

Tyr Asp Ala Leu His Met Gln Ala Leu Pro Pro Arg
            500                 505

<210> SEQ ID NO 211
<211> LENGTH: 518
<212> TYPE: PRT
<213> ORGANISM: Artificial Sequence
<220> FEATURE:
<223> OTHER INFORMATION: CD38xBCMA 38A37717 269A37346 GSI5005 CAR

<400> SEQUENCE: 211

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Ala Gly Gly Ser Leu Arg Leu Ser Cys Ile Ala Thr Gly Lys
        35                  40                  45

Val Phe Ser Ile Tyr Asp Met Gly Trp Tyr Arg Gln Ala Pro Gly Lys
    50                  55                  60

Gln Arg Glu Leu Val Ala Glu Ile Thr Ser Ser Gly Thr Thr His Tyr
65                  70                  75                  80

Asp Asp Phe Val Ser Gly Arg Phe Thr Ile Ser Arg Asp Asn Ala Lys
                85                  90                  95

Asn Thr Val Tyr Leu Gln Met Asn Thr Leu Lys Ala Glu Asp Thr Ala
            100                 105                 110

Val Tyr Tyr Cys Arg Ala Asn His Val Phe Gly Gly Ser Tyr Trp Gly
        115                 120                 125
```

Gln Gly Thr Gln Val Thr Val Ser Ser Gly Gly Gly Ser Gly Gly
        130                 135                 140

Gly Gly Ser Gly Gly Gly Gly Gly Ser Gly Ser Gly Gly Gly Gly
145                 150                 155                 160

Ser Gly Gly Gly Ser Gly Gly Gly Ser Gln Val Gln Leu Val
                165                 170                 175

Glu Ser Gly Gly Gly Leu Val Gln Pro Gly Gly Ser Leu Arg Leu Ser
            180                 185                 190

Cys Glu Ala Ser Gly Phe Thr Leu Asp Tyr Tyr Ala Ile Gly Trp Phe
        195                 200                 205

Arg Gln Ala Pro Gly Lys Glu Arg Glu Gly Val Ile Cys Ile Ser Arg
    210                 215                 220

Ser Asp Gly Ser Thr Tyr Tyr Ala Asp Ser Val Lys Gly Arg Phe Thr
225                 230                 235                 240

Ile Ser Arg Asp Asn Ala Lys Lys Thr Val Tyr Leu Gln Met Ile Ser
                245                 250                 255

Leu Lys Pro Glu Asp Thr Ala Ala Tyr Tyr Cys Ala Ala Gly Ala Asp
            260                 265                 270

Cys Ser Gly Tyr Leu Arg Asp Tyr Glu Phe Arg Gly Gln Gly Thr Gln
        275                 280                 285

Val Thr Val Ser Ser Thr Ser Thr Thr Thr Pro Ala Pro Arg Pro Pro
    290                 295                 300

Thr Pro Ala Pro Thr Ile Ala Ser Gln Pro Leu Ser Leu Arg Pro Glu
305                 310                 315                 320

Ala Cys Arg Pro Ala Ala Gly Gly Ala Val His Thr Arg Gly Leu Asp
                325                 330                 335

Phe Ala Cys Asp Ile Tyr Ile Trp Ala Pro Leu Ala Gly Thr Cys Gly
            340                 345                 350

Val Leu Leu Leu Ser Leu Val Ile Thr Leu Tyr Cys Lys Arg Gly Arg
        355                 360                 365

Lys Lys Leu Leu Tyr Ile Phe Lys Gln Pro Phe Met Arg Pro Val Gln
    370                 375                 380

Thr Thr Gln Glu Glu Asp Gly Cys Ser Cys Arg Phe Pro Glu Glu Glu
385                 390                 395                 400

Glu Gly Gly Cys Glu Leu Arg Val Lys Phe Ser Arg Ser Ala Asp Ala
                405                 410                 415

Pro Ala Tyr Gln Gln Gly Gln Asn Gln Leu Tyr Asn Glu Leu Asn Leu
            420                 425                 430

Gly Arg Arg Glu Glu Tyr Asp Val Leu Asp Lys Arg Arg Gly Arg Asp
        435                 440                 445

Pro Glu Met Gly Gly Lys Pro Arg Arg Lys Asn Pro Gln Glu Gly Leu
    450                 455                 460

Tyr Asn Glu Leu Gln Lys Asp Lys Met Ala Glu Ala Tyr Ser Glu Ile
465                 470                 475                 480

Gly Met Lys Gly Glu Arg Arg Arg Gly Lys Gly His Asp Gly Leu Tyr
                485                 490                 495

Gln Gly Leu Ser Thr Ala Thr Lys Asp Thr Tyr Asp Ala Leu His Met
            500                 505                 510

Gln Ala Leu Pro Pro Arg
        515

<210> SEQ ID NO 212
<211> LENGTH: 489

```
<212> TYPE: PRT
<213> ORGANISM: Artificial Sequence
<220> FEATURE:
<223> OTHER INFORMATION: BCMAxCD38 269A37346 38A37717 GSI5006 CAR

<400> SEQUENCE: 212
```

| | | | | | | | | | | | | | | | |
|---|---|---|---|---|---|---|---|---|---|---|---|---|---|---|---|
| Met | Ala | Leu | Pro | Val | Thr | Ala | Leu | Leu | Leu | Pro | Leu | Ala | Leu | Leu | Leu |
| 1 | | | | 5 | | | | | 10 | | | | | 15 | |
| His | Ala | Ala | Arg | Pro | Gln | Val | Gln | Leu | Val | Glu | Ser | Gly | Gly | Gly | Leu |
| | | | 20 | | | | | 25 | | | | | 30 | | |
| Val | Gln | Pro | Gly | Gly | Ser | Leu | Arg | Leu | Ser | Cys | Glu | Ala | Ser | Gly | Phe |
| | | 35 | | | | | 40 | | | | | 45 | | | |
| Thr | Leu | Asp | Tyr | Tyr | Ala | Ile | Gly | Trp | Phe | Arg | Gln | Ala | Pro | Gly | Lys |
| | 50 | | | | | 55 | | | | | 60 | | | | |
| Glu | Arg | Glu | Gly | Val | Ile | Cys | Ile | Ser | Arg | Ser | Asp | Gly | Ser | Thr | Tyr |
| 65 | | | | | 70 | | | | | 75 | | | | | 80 |
| Tyr | Ala | Asp | Ser | Val | Lys | Gly | Arg | Phe | Thr | Ile | Ser | Arg | Asp | Asn | Ala |
| | | | | 85 | | | | | 90 | | | | | 95 | |
| Lys | Lys | Thr | Val | Tyr | Leu | Gln | Met | Ile | Ser | Leu | Lys | Pro | Glu | Asp | Thr |
| | | | 100 | | | | | 105 | | | | | 110 | | |
| Ala | Ala | Tyr | Tyr | Cys | Ala | Ala | Gly | Ala | Asp | Cys | Ser | Gly | Tyr | Leu | Arg |
| | | 115 | | | | | 120 | | | | | 125 | | | |
| Asp | Tyr | Glu | Phe | Arg | Gly | Gln | Gly | Thr | Gln | Val | Thr | Val | Ser | Ser | Gly |
| | 130 | | | | | 135 | | | | | 140 | | | | |
| Gly | Gly | Gly | Ser | Glu | Val | Gln | Leu | Val | Glu | Ser | Gly | Gly | Gly | Leu | Val |
| 145 | | | | | 150 | | | | | 155 | | | | | 160 |
| Gln | Ala | Gly | Gly | Ser | Leu | Arg | Leu | Ser | Cys | Ile | Ala | Thr | Gly | Lys | Val |
| | | | | 165 | | | | | 170 | | | | | 175 | |
| Phe | Ser | Ile | Tyr | Asp | Met | Gly | Trp | Tyr | Arg | Gln | Ala | Pro | Gly | Lys | Gln |
| | | | 180 | | | | | 185 | | | | | 190 | | |
| Arg | Glu | Leu | Val | Ala | Glu | Ile | Thr | Ser | Ser | Gly | Thr | Thr | His | Tyr | Asp |
| | | 195 | | | | | 200 | | | | | 205 | | | |
| Asp | Phe | Val | Ser | Gly | Arg | Phe | Thr | Ile | Ser | Arg | Asp | Asn | Ala | Lys | Asn |
| | 210 | | | | | 215 | | | | | 220 | | | | |
| Thr | Val | Tyr | Leu | Gln | Met | Asn | Thr | Leu | Lys | Ala | Glu | Asp | Thr | Ala | Val |
| 225 | | | | | 230 | | | | | 235 | | | | | 240 |
| Tyr | Tyr | Cys | Arg | Ala | Asn | His | Val | Phe | Gly | Gly | Ser | Tyr | Trp | Gly | Gln |
| | | | | 245 | | | | | 250 | | | | | 255 | |
| Gly | Thr | Gln | Val | Thr | Val | Ser | Ser | Thr | Thr | Thr | Pro | Ala | Pro | Arg | Pro |
| | | | 260 | | | | | 265 | | | | | 270 | | |
| Pro | Thr | Pro | Ala | Pro | Thr | Ile | Ala | Ser | Gln | Pro | Leu | Ser | Leu | Arg | Pro |
| | | 275 | | | | | 280 | | | | | 285 | | | |
| Glu | Ala | Cys | Arg | Pro | Ala | Ala | Gly | Gly | Ala | Val | His | Thr | Arg | Gly | Leu |
| | 290 | | | | | 295 | | | | | 300 | | | | |
| Asp | Phe | Ala | Cys | Asp | Ile | Tyr | Ile | Trp | Ala | Pro | Leu | Ala | Gly | Thr | Cys |
| 305 | | | | | 310 | | | | | 315 | | | | | 320 |
| Gly | Val | Leu | Leu | Leu | Ser | Leu | Val | Ile | Thr | Leu | Tyr | Cys | Lys | Arg | Gly |
| | | | | 325 | | | | | 330 | | | | | 335 | |
| Arg | Lys | Lys | Leu | Leu | Tyr | Ile | Phe | Lys | Gln | Pro | Phe | Met | Arg | Pro | Val |
| | | | 340 | | | | | 345 | | | | | 350 | | |
| Gln | Thr | Thr | Gln | Glu | Glu | Asp | Gly | Cys | Ser | Cys | Arg | Phe | Pro | Glu | Glu |
| | | 355 | | | | | 360 | | | | | 365 | | | |
| Glu | Glu | Gly | Gly | Cys | Glu | Leu | Arg | Val | Lys | Phe | Ser | Arg | Ser | | |
| | 370 | | | | | 375 | | | | | 380 | | | | |

```
Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
            405                 410                 415

Gly Arg Asp Pro Glu Met Gly Gly Lys Pro Arg Arg Lys Asn Pro Gln
        420                 425                 430

Glu Gly Leu Tyr Asn Glu Leu Gln Lys Asp Lys Met Ala Glu Ala Tyr
    435                 440                 445

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485

<210> SEQ ID NO 213
<211> LENGTH: 494
<212> TYPE: PRT
<213> ORGANISM: Artificial Sequence
<220> FEATURE:
<223> OTHER INFORMATION: BCMAxCD38 269A37346 38A37717 GSI5007 CAR

<400> SEQUENCE: 213

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Pro Gly Gly Ser Leu Arg Leu Ser Cys Glu Ala Ser Gly Phe
        35                  40                  45

Thr Leu Asp Tyr Tyr Ala Ile Gly Trp Phe Arg Gln Ala Pro Gly Lys
    50                  55                  60

Glu Arg Glu Gly Val Ile Cys Ile Ser Arg Ser Asp Gly Ser Thr Tyr
65                  70                  75                  80

Tyr Ala Asp Ser Val Lys Gly Arg Phe Thr Ile Ser Arg Asp Asn Ala
                85                  90                  95

Lys Lys Thr Val Tyr Leu Gln Met Ile Ser Leu Lys Pro Glu Asp Thr
            100                 105                 110

Ala Ala Tyr Tyr Cys Ala Ala Gly Ala Asp Cys Ser Gly Tyr Leu Arg
        115                 120                 125

Asp Tyr Glu Phe Arg Gly Gln Gly Thr Gln Val Thr Val Ser Ser Gly
    130                 135                 140

Gly Gly Gly Ser Gly Gly Gly Gly Ser Glu Val Gln Leu Val Glu Ser
145                 150                 155                 160

Gly Gly Gly Leu Val Gln Ala Gly Gly Ser Leu Arg Leu Ser Cys Ile
                165                 170                 175

Ala Thr Gly Lys Val Phe Ser Ile Tyr Asp Met Gly Trp Tyr Arg Gln
            180                 185                 190

Ala Pro Gly Lys Gln Arg Glu Leu Val Ala Glu Ile Thr Ser Ser Gly
        195                 200                 205

Thr Thr His Tyr Asp Asp Phe Val Ser Gly Arg Phe Thr Ile Ser Arg
    210                 215                 220

Asp Asn Ala Lys Asn Thr Val Tyr Leu Gln Met Asn Thr Leu Lys Ala
225                 230                 235                 240

Glu Asp Thr Ala Val Tyr Tyr Cys Arg Ala Asn His Val Phe Gly Gly
                245                 250                 255
```

```
Ser Tyr Trp Gly Gln Gly Thr Gln Val Thr Val Ser Ser Thr Ser Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Leu Tyr Cys Lys Arg Gly Arg Lys Lys Leu Leu Tyr Ile Phe Lys
            340                 345                 350

Gln Pro Phe Met Arg Pro Val Gln Thr Thr Gln Glu Glu Asp Gly Cys
        355                 360                 365

Ser Cys Arg Phe Pro Glu Glu Glu Gly Gly Cys Glu Leu Arg Val
    370                 375                 380

Lys Phe Ser Arg Ser Ala Asp Ala Pro Ala Tyr Gln Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
            420                 425                 430

Arg Lys Asn Pro Gln Glu Gly Leu Tyr Asn Glu Leu Gln Lys Asp Lys
        435                 440                 445

Met Ala Glu Ala Tyr Ser Glu Ile Gly Met Lys Gly Glu Arg Arg Arg
450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490

<210> SEQ ID NO 214
<211> LENGTH: 500
<212> TYPE: PRT
<213> ORGANISM: Artificial Sequence
<220> FEATURE:
<223> OTHER INFORMATION: BCMAxCD38 269A37346 38A37717 GSI5008 CAR

<400> SEQUENCE: 214

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Pro Gly Gly Ser Leu Arg Leu Ser Cys Glu Ala Ser Gly Phe
        35                  40                  45

Thr Leu Asp Tyr Tyr Ala Ile Gly Trp Phe Arg Gln Ala Pro Gly Lys
    50                  55                  60

Glu Arg Glu Gly Val Ile Cys Ile Ser Arg Ser Asp Gly Ser Thr Tyr
65                  70                  75                  80

Tyr Ala Asp Ser Val Lys Gly Arg Phe Thr Ile Ser Arg Asp Asn Ala
                85                  90                  95

Lys Lys Thr Val Tyr Leu Gln Met Ile Ser Leu Lys Pro Glu Asp Thr
            100                 105                 110

Ala Ala Tyr Tyr Cys Ala Ala Gly Ala Asp Cys Ser Gly Tyr Leu Arg
        115                 120                 125
```

```
Asp Tyr Glu Phe Arg Gly Gln Gly Thr Gln Val Thr Val Ser Ser Gly
    130                 135                 140
Gly Gly Ser Gly Gly Ser Gly Gly Ser Gly Gly Gly Ser Glu
145                 150                 155                 160
Val Gln Leu Val Glu Ser Gly Gly Leu Val Gln Ala Gly Gly Ser
            165                 170                 175
Leu Arg Leu Ser Cys Ile Ala Thr Gly Lys Val Phe Ser Ile Tyr Asp
                180                 185                 190
Met Gly Trp Tyr Arg Gln Ala Pro Gly Lys Gln Arg Glu Leu Val Ala
        195                 200                 205
Glu Ile Thr Ser Ser Gly Thr Thr His Tyr Asp Asp Phe Val Ser Gly
    210                 215                 220
Arg Phe Thr Ile Ser Arg Asp Asn Ala Lys Asn Thr Val Tyr Leu Gln
225                 230                 235                 240
Met Asn Thr Leu Lys Ala Glu Asp Thr Ala Val Tyr Tyr Cys Arg Ala
                245                 250                 255
Asn His Val Phe Gly Gly Ser Tyr Trp Gly Gln Gly Thr Gln Val Thr
            260                 265                 270
Val Ser Ser Thr Ser Thr Thr Thr Pro Ala Pro Arg Pro Pro Thr Pro
        275                 280                 285
Ala Pro Thr Ile Ala Ser Gln Pro Leu Ser Leu Arg Pro Glu Ala Cys
    290                 295                 300
Arg Pro Ala Ala Gly Gly Ala Val His Thr Arg Gly Leu Asp Phe Ala
305                 310                 315                 320
Cys Asp Ile Tyr Ile Trp Ala Pro Leu Ala Gly Thr Cys Gly Val Leu
                325                 330                 335
Leu Leu Ser Leu Val Ile Thr Leu Tyr Cys Lys Arg Gly Arg Lys Lys
            340                 345                 350
Leu Leu Tyr Ile Phe Lys Gln Pro Phe Met Arg Pro Val Gln Thr Thr
        355                 360                 365
Gln Glu Glu Asp Gly Cys Ser Cys Arg Phe Pro Glu Glu Glu Glu Gly
    370                 375                 380
Gly Cys Glu Leu Arg Val Lys Phe Ser Arg Ser Ala Asp Ala Pro Ala
385                 390                 395                 400
Tyr Gln Gln Gly Gln Asn Gln Leu Tyr Asn Glu Leu Asn Leu Gly Arg
                405                 410                 415
Arg Glu Glu Tyr Asp Val Leu Asp Lys Arg Arg Gly Arg Asp Pro Glu
            420                 425                 430
Met Gly Gly Lys Pro Arg Arg Lys Asn Pro Gln Glu Gly Leu Tyr Asn
        435                 440                 445
Glu Leu Gln Lys Asp Lys Met Ala Glu Ala Tyr Ser Glu Ile Gly Met
    450                 455                 460
Lys Gly Glu Arg Arg Arg Gly Lys Gly His Asp Gly Leu Tyr Gln Gly
465                 470                 475                 480
Leu Ser Thr Ala Thr Lys Asp Thr Tyr Asp Ala Leu His Met Gln Ala
                485                 490                 495
Leu Pro Pro Arg
            500

<210> SEQ ID NO 215
<211> LENGTH: 510
<212> TYPE: PRT
<213> ORGANISM: Artificial Sequence
<220> FEATURE:
<223> OTHER INFORMATION: BCMAxCD38 269A37346 38A37717 GSI5009 CAR
```

-continued

```
<400> SEQUENCE: 215

Met Ala Leu Pro Val Thr Ala Leu Leu Pro Leu Ala Leu Leu Leu
1               5                   10                  15

His Ala Ala Arg Pro Gln Val Gln Leu Val Glu Ser Gly Gly Gly Leu
            20                  25                  30

Val Gln Pro Gly Gly Ser Leu Arg Leu Ser Cys Glu Ala Ser Gly Phe
        35                  40                  45

Thr Leu Asp Tyr Tyr Ala Ile Gly Trp Phe Arg Gln Ala Pro Gly Lys
    50                  55                  60

Glu Arg Glu Gly Val Ile Cys Ile Ser Arg Ser Asp Gly Ser Thr Tyr
65                  70                  75                  80

Tyr Ala Asp Ser Val Lys Gly Arg Phe Thr Ile Ser Arg Asp Asn Ala
                85                  90                  95

Lys Lys Thr Val Tyr Leu Gln Met Ile Ser Leu Lys Pro Glu Asp Thr
            100                 105                 110

Ala Ala Tyr Tyr Cys Ala Ala Gly Ala Asp Cys Ser Gly Tyr Leu Arg
        115                 120                 125

Asp Tyr Glu Phe Arg Gly Gln Gly Thr Gln Val Thr Val Ser Ser Gly
    130                 135                 140

Gly Gly Gly Ser Gly Gly Gly Gly Ser Gly Gly Gly Gly Gly Gly Ser
145                 150                 155                 160

Gly Ser Gly Gly Gly Ser Glu Val Gln Leu Val Glu Ser Gly Gly
                165                 170                 175

Gly Leu Val Gln Ala Gly Gly Ser Leu Arg Leu Ser Cys Ile Ala Thr
            180                 185                 190

Gly Lys Val Phe Ser Ile Tyr Asp Met Gly Trp Tyr Arg Gln Ala Pro
        195                 200                 205

Gly Lys Gln Arg Glu Leu Val Ala Glu Ile Thr Ser Ser Gly Thr Thr
    210                 215                 220

His Tyr Asp Asp Phe Val Ser Gly Arg Phe Thr Ile Ser Arg Asp Asn
225                 230                 235                 240

Ala Lys Asn Thr Val Tyr Leu Gln Met Asn Thr Leu Lys Ala Glu Asp
                245                 250                 255

Thr Ala Val Tyr Tyr Cys Arg Ala Asn His Val Phe Gly Gly Ser Tyr
            260                 265                 270

Trp Gly Gln Gly Thr Gln Val Thr Val Ser Ser Thr Ser Thr Ser Thr
        275                 280                 285

Thr Thr Pro Ala Pro Arg Pro Pro Thr Pro Ala Pro Thr Ile Ala Ser
    290                 295                 300

Gln Pro Leu Ser Leu Arg Pro Glu Ala Cys Arg Pro Ala Ala Gly Gly
305                 310                 315                 320

Ala Val His Thr Arg Gly Leu Asp Phe Ala Cys Asp Ile Tyr Ile Trp
                325                 330                 335

Ala Pro Leu Ala Gly Thr Cys Gly Val Leu Leu Leu Ser Leu Val Ile
            340                 345                 350

Thr Leu Tyr Cys Lys Arg Gly Arg Lys Lys Leu Leu Tyr Ile Phe Lys
        355                 360                 365

Gln Pro Phe Met Arg Pro Val Gln Thr Thr Gln Glu Glu Asp Gly Cys
    370                 375                 380

Ser Cys Arg Phe Pro Glu Glu Glu Gly Gly Cys Glu Leu Arg Val
385                 390                 395                 400

Lys Phe Ser Arg Ser Ala Asp Ala Pro Ala Tyr Gln Gln Gly Gln Asn
```

```
            405                 410                 415
Gln Leu Tyr Asn Glu Leu Asn Leu Gly Arg Arg Glu Tyr Asp Val
            420                 425                 430

Leu Asp Lys Arg Gly Arg Asp Pro Glu Met Gly Gly Lys Pro Arg
            435                 440                 445

Arg Lys Asn Pro Gln Glu Gly Leu Tyr Asn Glu Leu Gln Lys Asp Lys
            450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
                485                 490                 495

Asp Thr Tyr Asp Ala Leu His Met Gln Ala Leu Pro Pro Arg
                500                 505                 510

<210> SEQ ID NO 216
<211> LENGTH: 518
<212> TYPE: PRT
<213> ORGANISM: Artificial Sequence
<220> FEATURE:
<223> OTHER INFORMATION: BCMAxCD38 269A37346 38A37717 GSI5010 CAR

<400> SEQUENCE: 216

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Leu
                20                  25                  30

Val Gln Pro Gly Gly Ser Leu Arg Leu Ser Cys Glu Ala Ser Gly Phe
            35                  40                  45

Thr Leu Asp Tyr Tyr Ala Ile Gly Trp Phe Arg Gln Ala Pro Gly Lys
        50                  55                  60

Glu Arg Glu Gly Val Ile Cys Ile Ser Arg Ser Asp Gly Ser Thr Tyr
65                  70                  75                  80

Tyr Ala Asp Ser Val Lys Gly Arg Phe Thr Ile Ser Arg Asp Asn Ala
                85                  90                  95

Lys Lys Thr Val Tyr Leu Gln Met Ile Ser Leu Lys Pro Glu Asp Thr
            100                 105                 110

Ala Ala Tyr Tyr Cys Ala Ala Gly Ala Asp Cys Ser Gly Tyr Leu Arg
        115                 120                 125

Asp Tyr Glu Phe Arg Gly Gln Gly Thr Gln Val Thr Val Ser Ser Gly
    130                 135                 140

Gly Gly Gly Ser Gly Gly Gly Ser Gly Gly Gly Gly Gly Gly Gly Ser
145                 150                 155                 160

Gly Ser Gly Gly Gly Gly Ser Gly Gly Gly Ser Gly Gly Gly Gly
                165                 170                 175

Ser Glu Val Gln Leu Val Glu Ser Gly Gly Gly Leu Val Gln Ala Gly
            180                 185                 190

Gly Ser Leu Arg Leu Ser Cys Ile Ala Thr Gly Lys Val Phe Ser Ile
        195                 200                 205

Tyr Asp Met Gly Trp Tyr Arg Gln Ala Pro Gly Lys Gln Arg Glu Leu
    210                 215                 220

Val Ala Glu Ile Thr Ser Ser Gly Thr Thr His Tyr Asp Asp Phe Val
225                 230                 235                 240

Ser Gly Arg Phe Thr Ile Ser Arg Asp Asn Ala Lys Asn Thr Val Tyr
                245                 250                 255

Leu Gln Met Asn Thr Leu Lys Ala Glu Asp Thr Ala Val Tyr Tyr Cys
```

```
                260                 265                 270
Arg Ala Asn His Val Phe Gly Gly Ser Tyr Trp Gly Gln Gly Thr Gln
            275                 280                 285

Val Thr Val Ser Ser Thr Ser Thr Thr Thr Pro Ala Pro Arg Pro Pro
        290                 295                 300

Thr Pro Ala Pro Thr Ile Ala Ser Gln Pro Leu Ser Leu Arg Pro Glu
305                 310                 315                 320

Ala Cys Arg Pro Ala Ala Gly Gly Ala Val His Thr Arg Gly Leu Asp
                325                 330                 335

Phe Ala Cys Asp Ile Tyr Ile Trp Ala Pro Leu Ala Gly Thr Cys Gly
            340                 345                 350

Val Leu Leu Leu Ser Leu Val Ile Thr Leu Tyr Cys Lys Arg Gly Arg
        355                 360                 365

Lys Lys Leu Leu Tyr Ile Phe Lys Gln Pro Phe Met Arg Pro Val Gln
        370                 375                 380

Thr Thr Gln Glu Glu Asp Gly Cys Ser Cys Arg Phe Pro Glu Glu Glu
385                 390                 395                 400

Glu Gly Gly Cys Glu Leu Arg Val Lys Phe Ser Arg Ser Ala Asp Ala
                405                 410                 415

Pro Ala Tyr Gln Gln Gly Gln Asn Gln Leu Tyr Asn Glu Leu Asn Leu
            420                 425                 430

Gly Arg Arg Glu Glu Tyr Asp Val Leu Asp Lys Arg Arg Gly Arg Asp
        435                 440                 445

Pro Glu Met Gly Gly Lys Pro Arg Arg Lys Asn Pro Gln Glu Gly Leu
        450                 455                 460

Tyr Asn Glu Leu Gln Lys Asp Lys Met Ala Glu Ala Tyr Ser Glu Ile
465                 470                 475                 480

Gly Met Lys Gly Glu Arg Arg Arg Gly Lys Gly His Asp Gly Leu Tyr
                485                 490                 495

Gln Gly Leu Ser Thr Ala Thr Lys Asp Thr Tyr Asp Ala Leu His Met
            500                 505                 510

Gln Ala Leu Pro Pro Arg
            515

<210> SEQ ID NO 217
<211> LENGTH: 1521
<212> TYPE: DNA
<213> ORGANISM: Artificial Sequence
<220> FEATURE:
<223> OTHER INFORMATION: CD19XCD20 single-domain antibody-based
      bispecific CAR

<400> SEQUENCE: 217
gccgccacca tggccttacc agtgaccgcc ttgctcctgc cgctggcctt gctgctccac    60
gccgccaggc cgcaggtaaa gctggaggag tctggggggag aattggtgca gcctgggggg   120
cctctgagac tctcctgtgc agcctcggga aacatcttca gtatcaatcg catgggctgg   180
taccgccagg ctccagggaa gcagcgcgcg ttcgtcgcat ctattactgt tcgtggtata   240
acaaactatg cagactccgt gaagggccga ttcaccattt ctgtagacaa gtccaaaaac   300
acgatttatc tgcagatgaa cgcactcaaa cctgaggaca cggccgtcta ttattgtaat   360
gcagtgtctt caaacaggga ccccgactac tggggccagg ggacccaggt caccgtctcc   420
tcaggcggcg gcagcggcgg cggcagcggc ggcggcagcg gcggcggcag cccggtgcag   480
ctggtggagt ctgggggagg cttggtgcag gctggggatt ctctgagact ctcctgtgct   540
```

```
gcctctggac gcaccttcgg tattggtacc atgggctggt tccgccaacc tccaggaag      600
gagcgtgaat tgtagcagc tattaggtgg agtactggtg cactcgcta tgcagactcc       660
gtgaagggcc gattcaccat ctcccgagac aacgccaagc tcacggtaga tctgcaaatg    720
gacagcctga aacctgaaga cacggccgtt tattactgtg cagcagatag actgtccctt   780
gatttaagtg gtcgttacca ctacaacccc gccgtgtatg actattgggg ccaggggacc    840
caggtcaccg tctcctcaat tgaagttatg tatcctcctc cttacctaga caatgagaag   900
agcaatggaa ccattatcca tgtgaaaggg aaacaccttt gtccaagtcc cctatttccc   960
ggaccttcta gcccttttg ggtgctggtg gtggttggtg gagtcctggc ttgctatagc    1020
ttgctagtaa cagtggcctt tattattttc tgggtgagga gtaagaggag caggctcctg   1080
cacagtgact acatgaacat gactccccgc cgcccccggg ccacccgcaa gcattaccag   1140
ccctatgccc caccacgcga cttcgcagcc tatcgctcca gagtgaagtt cagcaggagc   1200
gcagacgccc ccgcgtacca gcagggccag aaccagctct ataacgagct caatctagga   1260
cgaagagagg agtacgatgt tttggacaag agacgtggcc gggaccctga gatggggggga  1320
aagccgagaa ggaagaaccc tcaggaaggc ctgtacaatg aactgcagaa agataagatg   1380
gcggaggcct acagtgagat tgggatgaaa ggcgagcgcc ggaggggcaa ggggcacgat   1440
ggcctttacc agggtctcag tacagccacc aaggacacct acgacgccct tcacatgcag   1500
gccctgcccc ctcgctgata a                                              1521

<210> SEQ ID NO 218
<211> LENGTH: 1470
<212> TYPE: DNA
<213> ORGANISM: Artificial Sequence
<220> FEATURE:
<223> OTHER INFORMATION: CD38xBCMA 38A37717 269A37346 GSI5001 CAR

<400> SEQUENCE: 218
atggctctgc ccgtcactgc tctgctgctg cccctggctc tgctgctgca cgccgcaaga    60
cccgaagtcc agctggtgga atctggcgga ggcctggtgc aggcaggagg cagcctgagg   120
ctgtcctgca tcgccaccgg caaggtgttc tccatctacg acatgggctg gtatcggcag    180
gcccccaggca agcagagaga gctggtggcc gagatcacaa gctccggcac cacacactac   240
gacgatttcg tgtctggccg gtttaccatc agcagagaca cgccaagaa tacagtgtat    300
ctgcagatga acaccctgaa ggccgaggat acagccgtgt actattgtcg ggccaatcac    360
gtgtttggag gaagctactg gggacaggga acccaggtga cagtgtctag cggaggagga    420
ggcagccagg tgcagctggt ggagtccgga ggaggcctgg tgcagccagg aggctctctg    480
aggctgagct gcgaggcatc cggattcacc ctggactact atgccatcgg ctggtttagg   540
caggcacctg gaaaggagag ggagggagtg atctgtatct ccagatctga cggctccaca   600
tactatgccg attctgtgaa gggcaggttc accatctctc gcgataacgc caagaagaca   660
gtctacctgc agatgatcag cctgaagccc gaggacaccg cagcatacta ttgcgcagca   720
ggagcagatt gtagtggcta tctgagggac tacgagttcc gagggcaggg gacacaggtg   780
accgtgagca gcactagtac cacgacgcca gcgccgcgac caccaacacc ggcgcccacc   840
atcgcgtcgc agcccctgtc cctgcgccca gaggcgtgcc ggccagcggc gggggggcgca  900
gtgcacacga gggggctgga cttcgcctgt gatatctaca tctgggcgcc cttggccggg   960
acttgtgggg tccttctcct gtcactggtt atcaccctt actgcaaacg ggcagaaaag   1020
aaactcctgt atatattcaa acaaccattt atgagaccag tacaaactac tcaagaggaa   1080
```

```
gatggctgta gctgccgatt tccagaagaa gaagaaggag gatgtgaact gagagtgaag    1140
ttcagcagga gcgcagacgc ccccgcgtac cagcagggcc agaaccagct ctataacgag    1200
ctcaatctag gacgaagaga ggagtacgat gttttggaca agagacgtgg ccgggaccct    1260
gagatggggg gaaagccgag aaggaagaac cctcaggaag gcctgtacaa tgaactgcag    1320
aaagataaga tggcggaggc ctacagtgag attgggatga aggcgagcg ccggaggggc     1380 aaggggcacg atggccttta ccagggtctc agtacagcca ccaaggacac ctacgacgcc    1440
cttcacatgc aggccctgcc ccctcgctaa                                     1470
```

<210> SEQ ID NO 219
<211> LENGTH: 1485
<212> TYPE: DNA
<213> ORGANISM: Artificial Sequence
<220> FEATURE:
<223> OTHER INFORMATION: CD38xBCMA 38A37717 269A37346 GSI5002 CAR

<400> SEQUENCE: 219

```
atggctctgc ccgtcactgc tctgctgctg cccctggctc tgctgctgca cgctgctcgc    60
cctgaagtcc agctggtcga atccggcgga ggcctggtgc aggcaggagg cagcctgagg    120
ctgtcctgca tcgccaccgg caaggtgttc tccatctacg acatgggctg gtatcggcag    180
gccccaggca gcagagaga gctggtggcc gagatcacaa gctccggcac acacactac     240 gacgatttcg tgtccggccg gtttaccatc tctagagaca cgccaagaa tacagtgtat    300 ctgcagatga cacccctgaa ggccgaggat acagccgtgt actattgtcg ggccaatcac    360
gtgtttggag gatcctactg gggacaggga acccaggtga cagtgtctag cggaggagga    420
ggatctggcg gaggaggcag ccaggtgcag ctggtggagt ctggaggagg cctggtgcag    480
ccaggaggct ctctgaggct gagctgcgag gcatccggat tcacccctgga ctactatgcc    540 atcggctggt ttaggcaggc acctggaaag gagagggagg gagtgatctg tatctccaga    600
tctgacggca gcacatacta tgccgattcc gtgaagggca ggttcaccat ctctcgcgat    660
aacgccaaga gacacagtcta cctgcagatg atcagcctga gcccgagga caccgcagca    720 tactattgcg cagcaggagc agattgtagc ggctatctga gggattatga gtttagaggg    780
cagggaacac aggtgacagt gagcagcact agtaccacga cgccagcgcc gcgaccacca    840
acaccggcgc ccaccatcgc gtcgcagccc ctgtccctgc gcccagaggc gtgccggcca    900 gcggcgggg gcgcagtgca cacgaggggg ctggacttcg cctgtgatat ctacatctgg    960
gcgcccttgg ccgggacttg tggggtcctt ctcctgtcac tggttatcac cctttactgc    1020
aaacggggca gaaagaaact cctgtatata ttcaaacaac catttatgag accagtacaa    1080
actactcaag aggaagatgg ctgtagctgc cgatttccag aagaagaaga aggaggatgt    1140
gaactgagag tgaagttcag caggagcgca gacgcccccg cgtaccagca gggccagaac    1200
cagctctata cgagctcaa tctaggacga agagaggagt acgatgtttt ggacaagaga    1260
cgtggccggg accctgagat ggggggaaag ccgagaagga agaaccctca ggaaggcctg    1320
tacaatgaac tgcagaaaga taagatggcg gaggcctaca gtgagattgg gatgaaaggc    1380
gagcgccgga ggggcaaggg gcacgatggc ctttaccagg gtctcagtac agccaccaag    1440
gacacctacg acgccttca catgcaggcc ctgccccctc gctaa                    1485
```

<210> SEQ ID NO 220
<211> LENGTH: 1503
<212> TYPE: DNA

```
<213> ORGANISM: Artificial Sequence
<220> FEATURE:
<223> OTHER INFORMATION: CD38xBCMA 38A37717 269A37346 GSI5003 CAR

<400> SEQUENCE: 220
atggccctgc ctgtcaccgc actgctgctg cccctggctc tgctgctgca cgccgcacgc     60
cctgaagtcc agctggtcga gtccggggga ggcctggtgc aggcaggagg cagcctgagg    120
ctgtcctgca tcgccaccgg caaggtgttc tccatctacg acatgggctg gtatcggcag    180
gccccaggca agcagagaga gctggtggcc gagatcacaa gctccggcac cacacactac    240
gacgatttcg tgagcggccg gtttaccatc tccagagaca cgccaagaa tacagtgtat    300
ctgcagatga acaccctgaa ggccgaggat acagccgtgt actattgtcg ggccaatcac    360
gtgtttggag atcctactg gggacaggga acccaggtga cagtgtctag cggcggcggc    420
tctggaggag gaagcggagg aggatctgga ggaggctctc aggtgcagct ggtggagagc    480
ggaggaggcc tggtgcagcc aggaggcagc ctgcggctgt cctgcgaggc ctctggcttc    540
accctggact actatgccat cggctggttt aggcaggcac ctggaaagga gagggaggga    600
gtgatctgta tctccagatc tgacggctct acatactatg ccgatagcgt gaagggcagg    660
ttcaccatct cccgcgataa cgccaagaag acagtctacc tgcagatgat ctctctgaag    720
cccgaggaca ccgcagcata ctattgcgca gcaggagcag attgtagcgg gtatctgcgg    780
gattatgagt ttagaggaca ggggacacag gtcacagtca gttccactag taccacgacg    840
ccagcgccgc gaccaccaac accggcgccc accatcgcgt cgcagcccct gtccctgcgc    900
ccagaggcgt gccggccagc ggcggggggc gcagtgcaca cgagggggct ggacttcgcc    960
tgtgatatct acatctgggc gcccttggcc gggacttgtg gggtccttct cctgtcactg   1020
gttatcaccc tttactgcaa acggggcaga aagaaactcc tgtatatatt caaacaacca   1080
tttatgagac cagtacaaac tactcaagag gaagatggct gtagctgccg atttccagaa   1140
gaagaagaag aggatgtgaa actgagagtg aagttcagca ggagcgcaga cgcccccgcg   1200
taccagcagg gccagaacca gctctataac gagctcaatc taggacgaag agaggagtac   1260
gatgttttgg acaagagacg tggccgggac cctgagatgg ggggaaagcc gagaaggaag   1320
aaccctcagg aaggcctgta caatgaactg cagaaagata gatggcggga ggcctacagt   1380
gagattggga tgaaaggcga gcgccggagg ggcaagggc acgatggcct ttaccagggt   1440
ctcagtacag ccaccaagga cacctacgac gcccttcaca tgcaggccct gccccctcgc   1500
taa                                                                 1503

<210> SEQ ID NO 221
<211> LENGTH: 1527
<212> TYPE: DNA
<213> ORGANISM: Artificial Sequence
<220> FEATURE:
<223> OTHER INFORMATION: CD38xBCMA 38A37717 269A37346 GSI5004 CAR

<400> SEQUENCE: 221
atggctctgc tgtgaccgc cctgctgctg cccctggctc tgctgctgca cgccgcacga     60
cccgaagtcc agctggtgga atctggggga ggcctggtgc aggcaggagg ctctctgagg    120
ctgagctgca tcgccaccgg caaggtgttc tctatctacg acatgggctg gtatcggcag    180
gccccaggca agcagagaga gctggtggcc gagatcacaa gctccggcac cacacactac    240
gacgatttcg tgagcggccg gtttaccatc tccagagaca cgccaagaa tacagtgtat    300
ctgcagatga acaccctgaa ggccgaggat acagccgtgt actattgtcg ggccaatcac    360
```

```
gtgtttggag gaagctactg gggacaggga acccaggtga cagtgtctag cggaggagga      420
ggatccggag gaggaggatc tggaggcggc ggcggcggct ccggctctgg cggcggcggc      480
tcccaggtgc agctggtgga gtctggagga ggcctggtgc agccaggagg ctccctgcgg      540
ctgtcttgcg aggccagcgg cttcaccctg gactactatg ccatcggctg gtttaggcag      600
gcacctggaa aggagaggga gggagtgatc tgtatcagca gatccgacgg ctctacatac      660
tatgccgata gcgtgaaggg caggttcacc atcagccgcg ataacgccaa gaagacagtc      720
tacctgcaga tgatctccct gaagcccgag gacaccgcag catactattg cgcagcagga      780
gcagattgta gcggctatct gcgggattac gagtttagag acagggcac ccaggtcacc      840 gtctcaagca ctagtaccac gacgccagcg ccgcgaccac caacaccggc gcccaccatc      900
gcgtcgcagc ccctgtccct gcgcccagag gcgtgccggc cagcggcggg gggcgcagtg      960
cacacgaggg ggctggactt cgcctgtgat atctacatct gggcgccctt ggccgggact     1020 tgtgggtcc ttctcctgtc actggttatc ccctttact gcaaacgggg cagaaagaaa     1080
ctcctgtata tattcaaaca accatttatg agaccagtac aaactactca agaggaagat     1140
ggctgtagct gccgatttcc agaagaagaa gaaggaggat gtgaactgag agtgaagttc     1200
agcaggagcg cagacgcccc cgcgtaccag cagggccaga accagctcta taacgagctc     1260
aatctaggac gaagagagga gtacgatgtt ttggacaaga cgtggccg ggaccctgag     1320 atgggggaa agccgagaag gaagaaccct caggaaggcc tgtacaatga actgcagaaa     1380
gataagatgg cggaggccta cagtgagatt gggatgaaag cgagcgccg gaggggcaag     1440 gggcacgatg gcctttacca gggtctcagt acagccacca aggacaccta cgacgccctt     1500
cacatgcagg ccctgccccc tcgctaa                                          1527

<210> SEQ ID NO 222
<211> LENGTH: 1557
<212> TYPE: DNA
<213> ORGANISM: Artificial Sequence
<220> FEATURE:
<223> OTHER INFORMATION: CD38xBCMA 38A37717 269A37346 GSI5005 CAR

<400> SEQUENCE: 222
atggctctgc ctgtcactgc tctgctgctg cccctggccc tgctgctgca cgctgctaga       60
cccgaagtcc agctggtgga gtccggcgga ggcctggtgc aggcaggagg ctctctgagg      120
ctgagctgca tcgccaccgg caaggtgttc agcatctacg acatgggctg gtatcggcag      180
gccccaggca agcagagaga gctggtggcc gagatcacaa gctccggcac acacactac      240 gacgatttcg tgagcggccg gtttaccatc tccagagaca cgccaagaa tacagtgtat      300 ctgcagatga cacccctgaa ggccgaggat acagccgtgt actattgtcg ggccaatcac      360
gtgtttggag gaagctactg gggacaggga acccaggtga cagtgtctag cggaggagga      420
ggatccggag gaggaggatc tggaggcggc ggcggcggct ccggctctgg cggcggcggc      480
agtggaggcg gcggctccgg cggcggcggc tctcaggtgc agctggtgga gtccggagga      540
ggcctggtgc agccaggagg ctccctgcgg ctgtcttgcg aggccagcgg cttcaccctg      600
gactactatg ccatcggctg gtttaggcag gcacctggaa aggagaggga gggagtgatc      660
tgtatcagca gatccgacgg ctctacatac tatgccgata gcgtgaaggg caggttcacc      720
atctcccgcg ataacgccaa gaagacagtc tacctgcaga tgatctctct gaagcccgag      780
gacaccgcag catactattg cgcagcagga gcagattgtt caggctatct gcgggattat      840
```

```
gagtttcggg gacaggggac acaggtcaca gtctccagca ctagtaccac gacgccagcg    900
ccgcgaccac caacaccggc gcccaccatc gcgtcgcagc ccctgtccct gcgcccagag    960
gcgtgccggc cagcggcggg gggcgcagtg cacacgaggg ggctggactt cgcctgtgat   1020
atctacatct gggcgcccct tggccgggac tgtggggtcc ttctcctgtc actggttatc   1080
acccttact gcaaacgggg cagaaagaaa ctcctgtata tattcaaaca accatttatg   1140
agaccagtac aaactactca agaggaagat ggctgtagct gccgatttcc agaagaagaa   1200
gaaggaggat gtgaactgag agtgaagttc agcaggagcg cagacgcccc cgcgtaccag   1260
cagggccaga accagctcta taacgagctc aatctaggac gaagagagga gtacgatgtt   1320
ttggacaaga gacgtggccg ggaccctgag atgggggaa agccgagaag gaagaaccct   1380
caggaaggcc tgtacaatga actgcagaaa gataagatgg cggaggccta cagtgagatt   1440
gggatgaaag gcgagcgccg gaggggcaag gggcacgatg gcctttacca gggtctcagt   1500
acagccacca aggacaccta cgacgcccct cacatgcagg ccctgccccc tcgctaa     1557
```

<210> SEQ ID NO 223
<211> LENGTH: 1470
<212> TYPE: DNA
<213> ORGANISM: Artificial Sequence
<220> FEATURE:
<223> OTHER INFORMATION: BCMAxCD38 269A37346 38A37717 GSI5006 CAR

<400> SEQUENCE: 223

```
atggctctgc ccgtcaccgc tctgctgctg cctctggctc tgctgctgca cgccgcccgc    60
cctcaggtcc agctggtcga gtcaggagga ggctggtgc agccaggagg cagcctgagg   120
ctgtcctgcg aggcctctgg cttcaccctg gactactatg ccatcggctg gtttaggcag   180
gcacctggaa aggagaggga gggagtgatc tgtatctccc gctctgacgg ctctacatac   240
tatgccgata gcgtgaaggg ccggttcacc atctctagag acaacgccaa gaagacagtg   300
tacctgcaga tgatcagcct gaagccgaga gataccgcag catactattg cgcagcagga   360
gcagactgtt ccggatacct gagggattat gagtttaggg gacagggaac ccaggtgaca   420
gtgagctccg gcggcggcgg cagcgaggtg cagctggtgg agtccggagg aggcctggtg   480
caggcaggag gcagcctgcg gctgtcctgc atcgccaccg gcaaggtgtt cagcatctac   540
gatatgggat ggtataggca ggcaccagga aagcagagag agctggtggc cgagatcaca   600
tctagcggca ccacacacta cgacgatttc gtgtccggcc ggtttactat ttccagggac   660
aacgccaaga atacagtgta tctgcagatg aatcccctga aggccgagga tacagccgtg   720
tactattgta gagcaaatca tgtcttcggg gggtccatt ggggcaggg cactcaggtc   780
accgtctcct caactagtac cacgacgcca gcgccgcgac caccaacacc ggcgcccacc   840
atcgcgtcgc agcccctgtc cctgcgccca gaggcgtgcc ggccagcggc ggggggcgca   900
gtgcacacga gggggctgga cttcgcctgt gatatctaca tctgggcgcc cttggccggg   960
acttgtgggg tccttctcct gtcactggtt atcaccctt actgcaaacg ggggcagaaag  1020
aaactcctgt atatattcaa acaaccattt atgagaccag tacaaactac tcaagaggaa   1080
gatggctgta gctgccgatt tccagaagaa gaagaaggag gatgtgaact gagagtgaag   1140
ttcagcagga gcgcagacgc ccccgcgtac cagcagggcc agaaccagct ctataacgag   1200
ctcaatctag gacgaagaga ggagtacgat gttttggaca agagacgtgg cccggacct   1260
gagatggggg aaagccgag aaggaagaac cctcaggaag gcctgtacaa tgaactgcag   1320
aaagataaga tggcggaggc ctacagtgag attgggatga aaggcgagcg ccggaggggc   1380
```

```
aaggggcacg atggccttta ccagggtctc agtacagcca ccaaggacac ctacgacgcc    1440
cttcacatgc aggccctgcc ccctcgctaa                                      1470

<210> SEQ ID NO 224
<211> LENGTH: 1485
<212> TYPE: DNA
<213> ORGANISM: Artificial Sequence
<220> FEATURE:
<223> OTHER INFORMATION: BCMAxCD38 269A37346 38A37717 GSI5007 CAR

<400> SEQUENCE: 224
atggctctgc ccgtcactgc tctgctgctg cctctggctc tgctgctgca cgccgctcgc      60
ccacaggtcc agctggtcga atcaggggga ggcctggtgc agccaggagg cagcctgagg     120
ctgtcctgcg aggcctctgg cttcacccct gactactatg ccatcggctg gtttaggcag     180
gcacctggaa aggagaggga gggagtgatc tgtatctccc gctctgacgg ctccacatac     240
tatgccgatt ctgtgaaggg ccggttcacc atctctagag acaacgccaa gaagacagtg     300
tacctgcaga tgatcagcct gaagccagag gataccgcag catactattg cgcagcagga     360
gcagactgtt ccggataccct gagggattat gagtttaggg gacagggaac ccaggtgaca     420
gtgagctccg gaggaggagg atctggcgga ggaggcagcg aggtgcagct ggtggagtcc     480
ggcggcggcc tggtgcaggc cggcggcagc ctgcggctgt cctgcatcgc caccggcaag     540
gtgttctcta tctacgatat gggatggtat aggcaggcac caggaaagca gagagagctg     600
gtggccgaga tcacatctag cggcaccaca cactacgacg atttcgtgag cggccggttt     660
accatctcca gagacaacgc caagaataca gtgtatctgc agatgaatac cctgaaggcc     720
gaggatacag ccgtgtacta ttgtagagcc aaccatgtct tcggcgggtc atactggggg     780
cagggaactc aggtcactgt cagcagcact agtaccacga cgccagcgcc gcgaccacca     840
acaccggcgc ccaccatcgc gtcgcagccc ctgtccctgc gcccagaggc gtgccggcca     900
gcggcggggg gcgcagtgca cacgaggggg ctggacttcg cctgtgatat ctacatctgg     960
gcgcccttgg ccgggacttg tggggtcctt ctcctgtcac tggttatcac cctttactgc    1020
aaacggggca gaaagaaact cctgtatata ttcaaacaac catttatgag accagtacaa    1080
actactcaag aggaagatgg ctgtagctgc cgatttccag aagaagaaga aggaggatgt    1140
gaactgagag tgaagttcag caggagcgca gacgcccccg cgtaccagca gggccagaac    1200
cagctctata cgagctcaa tctaggacga agagaggagt acgatgtttt ggacaagaga    1260
cgtggccggg accctgagat ggggggaaag ccgagaagga agaaccctca ggaaggcctg    1320
tacaatgaac tgcagaaaga taagatggcg gaggcctaca gtgagattgg gatgaaaggc    1380
gagcgccgga ggggcaaggg gcacgatggc ctttaccagg gtctcagtac agccaccaag    1440
gacacctacg acgcccttca catgcaggcc ctgccccctc gctaa                    1485

<210> SEQ ID NO 225
<211> LENGTH: 1503
<212> TYPE: DNA
<213> ORGANISM: Artificial Sequence
<220> FEATURE:
<223> OTHER INFORMATION: BCMAxCD38 269A37346 38A37717 GSI5008 CAR

<400> SEQUENCE: 225
atggctctgc ccgtcactgc tctgctgctg cctctggctc tgctgctgca cgccgcaagg      60
cctcaggtcc agctggtcga atcaggggga ggcctggtgc agccaggagg cagcctgagg     120
```

| | |
|---|---|
| ctgtcctgcg aggcctctgg cttcaccctg gactactatg ccatcggctg gtttaggcag | 180 |
| gcacctggaa aggagaggga gggagtgatc tgtatctccc gctctgacgg cagcacatac | 240 |
| tatgccgatt ccgtgaaggg ccggttcacc atctccagag acaacgccaa gaagacagtg | 300 |
| tacctgcaga tgatctctct gaagccagag gataccgcag catactattg cgcagcagga | 360 |
| gcagactgtt ccggatacct gagggattat gagtttaggg gacagggaac ccaggtgaca | 420 |
| gtgagctccg gaggaggaag cggaggagga tccggaggcg gctctggcgg cggcagcgag | 480 |
| gtgcagctgg tggagtccgg cggcggcctg gtgcaggccg gcggctccct gcggctgtct | 540 |
| tgcatcgcca ccggcaaggt gttcagcatc tacgatatgg gatggtatag gcaggcacca | 600 |
| ggaaagcaga gagagctggt ggccgagatc acatctagcg gcaccacaca ctacgacgat | 660 |
| ttcgtgtctg ccggtttac catcagtagg gacaacgcca agaatacagt gtatctgcag | 720 |
| atgaataccc tgaaggccga ggatacagcc gtgtactatt gtagagctaa ccatgtcttc | 780 |
| gggggtcat actgggggca gggcactcag gtcactgtct catccactag taccacgacg | 840 |
| ccagcgccgc gaccaccaac accggcgccc accatcgcgt cgcagcccct gtccctgcgc | 900 |
| ccagaggcgt gccggccagc ggcgggggc gcagtgcaca cgagggggct ggacttcgcc | 960 |
| tgtgatatct acatctgggc gcccttggcc gggacttgtg gggtccttct cctgtcactg | 1020 |
| gttatcaccc tttactgcaa acggggcaga aagaaactcc tgtatatatt caaacaacca | 1080 |
| tttatgagac cagtacaaac tactcaagag gaagatggct gtagctgccg atttccagaa | 1140 |
| gaagaagaag gaggatgtga actgagagtg aagttcagca ggagcgcaga cgcccccgcg | 1200 |
| taccagcagg gccagaacca gctctataac gagctcaatc taggacgaag agaggagtac | 1260 |
| gatgttttgg acaagagacg tggccgggac cctgagatgg ggggaaagcc gagaaggaag | 1320 |
| aaccctcagg aaggcctgta caatgaactg cagaaagata gatggcggga ggcctacagt | 1380 |
| gagattggga tgaaaggcga gcgccggagg ggcaaggggc acgatggcct ttaccagggt | 1440 |
| ctcagtacag ccaccaagga cacctacgac gcccttcaca tgcaggccct gccccctcgc | 1500 |
| taa | 1503 |

<210> SEQ ID NO 226
<211> LENGTH: 1533
<212> TYPE: DNA
<213> ORGANISM: Artificial Sequence
<220> FEATURE:
<223> OTHER INFORMATION: BCMAxCD38 269A37346 38A37717 GSI5009 CAR

<400> SEQUENCE: 226

| | |
|---|---|
| atggctctgc ccgtcaccgc actgctgctg cctctggctc tgctgctgca cgccgcaagg | 60 |
| cctcaggtcc agctggtcga atcaggggga ggcctggtgc agccaggagg ctctctgagg | 120 |
| ctgagctgcg aggcatccgg attcaccctg gactactatg ccatcggctg gtttaggcag | 180 |
| gcacctggaa aggagaggga gggagtgatc tgtatctccc gctctgacgg cagcacatac | 240 |
| tatgccgatt ccgtgaaggg ccggttcacc atcagcagag acaacgccaa gaagacagtg | 300 |
| tacctgcaga tgatctccct gaagccagag gataccgcag catactattg cgcagcagga | 360 |
| gcagactgtt ctggatacct gagggattat gagtttaggg gacagggaac ccaggtgaca | 420 |
| gtgagctccg gaggaggagg atccggcgga ggaggctctg gcggcggcgg cggcggcagc | 480 |
| ggctccggcg gcggcggctc cgaggtgcag ctggtggagt ctggaggagg cctggtgcag | 540 |
| gcaggaggct ctctgcggct gagctgcatc gccaccggca aggtgttcag catctacgat | 600 |
| atgggatggt ataggcaggc accaggaaag cagagagagc tggtggccga gatcacatct | 660 |

```
agcggcacca cacactacga cgatttcgtg tctggccggt ttactatttc cagggacaac    720
gccaagaata cagtgtatct gcagatgaat accctgaagg ccgaggatac agccgtgtac    780
tattgtagag ctaatcacgt cttcggcggc tcttattggg ggcagggaac tcaggtcact    840
gtgtcatcca ctagtactag taccacgacg ccagcgccgc gaccaccaac accggcgccc    900
accatcgcgt cgcagcccct gtccctgcgc ccagaggcgt gccggccagc ggcgggggc    960 gcagtgcaca cgagggggct ggacttcgcc tgtgatatct acatctgggc gcccttggcc   1020
gggacttgtg gggtccttct cctgtcactg gttatcaccc tttactgcaa acggggcaga   1080
aagaaactcc tgtatatatt caaacaacca tttatgagac cagtacaaac tactcaagag   1140
gaagatggct gtagctgccg atttccagaa gaagaagaag gaggatgtga actgagagtg   1200
aagttcagca ggagcgcaga cgcccccgcg taccagcagg gccagaacca gctctataac   1260
gagctcaatc taggacgaag agaggagtac gatgttttgg acaagagacg tggccgggac   1320
cctgagatgg ggggaaagcc gagaaggaag aaccctcagg aaggcctgta caatgaactg   1380
cagaaagata agatggcgga ggcctacagt gagattggga tgaaaggcga gcgccggagg   1440
ggcaaggggc acgatggcct ttaccagggt ctcagtacag ccaccaagga cacctacgac   1500
gcccttcaca tgcaggccct gccccctcgc taa                                1533

<210> SEQ ID NO 227
<211> LENGTH: 1557
<212> TYPE: DNA
<213> ORGANISM: Artificial Sequence
<220> FEATURE:
<223> OTHER INFORMATION: BCMAxCD38 269A37346 38A37717 GSI5010 CAR

<400> SEQUENCE: 227
atggctctgc ccgtcaccgc tctgctgctg ccccctggctc tgctgctgca cgctgctcgc     60
cctcaggtcc agctggtcga atcaggagga ggcctggtgc agccaggagg ctctctgagg    120
ctgagctgcg aggcatccgg attcaccctg gactactatg ccatcggctg gtttaggcag    180
gcacctggaa aggagaggga gggagtgatc tgtatctccc gctctgacgg cagcacatac    240
tatgccgatt ccgtgaaggg ccggttcacc atctccagag acaacgccaa gaagacagtg    300
tacctgcaga tgatctctct gaagccagag gataccgcag catactattg cgcagcagga    360
gcagactgta gcggataccct gagggattat gagtttaggg gacagggaac ccaggtgaca    420
gtgagctccg gaggaggagg atccggcgga ggaggctctg gaggcggcgg cggcggcagc    480
ggctcaggag gcgaggaag cggcggcggc ggctccggcg gcggcggctc tgaggtgcag    540
ctggtggaga gcggaggagg cctggtgcag gcaggaggct ctctgcggct gagctgcatc    600
gccaccggca agtgttctc catctacgat atgggatggt ataggcaggc accaggaaag    660
cagagagagc tggtggccga gatcacatct agcggcacca cactacga cgatttcgtg    720 tctggccggt ttaccatcag tagggacaac gccaagaata cagtgtatct gcagatgaat    780
accctgaagg ccgaggatac agccgtgtac tattgtagag ctaatcatgt gtttggaggg    840
tcatactggg ggcagggaac tcaggtcact gtctcatcaa ctagtaccac gacgccagcg    900
ccgcgaccac caacaccggc gcccaccatc gcgtcgcagc cctgtccct gcgcccagag    960 gcgtgccggc cagcggcggg gggcgcagtg cacacgaggg ggctggactt cgcctgtgat   1020
atctacatct gggcgccctt ggccgggact tgtggggtcc ttctcctgtc actggttatc   1080
accctttact gcaaacgggg cagaaagaaa ctcctgtata tattcaaaca accatttatg   1140
```

```
agaccagtac aaactactca agaggaagat ggctgtagct gccgatttcc agaagaagaa   1200
gaaggaggat gtgaactgag agtgaagttc agcaggagcg cagacgcccc cgcgtaccag   1260
cagggccaga accagctcta taacgagctc aatctaggac gaagagagga gtacgatgtt   1320
ttggacaaga gacgtggccg ggaccctgag atggggggaa agccgagaag gaagaacccct  1380 caggaaggcc tgtacaatga actgcagaaa gataagatgg cggaggccta cagtgagatt   1440
gggatgaaag gcgagcgccg gaggggcaag gggcacgatg gcctttacca gggtctcagt   1500
acagccacca aggacaccta cgacgccctt cacatgcagg ccctgccccc tcgctaa      1557
```

```
<210> SEQ ID NO 228
<211> LENGTH: 663
<212> TYPE: DNA
<213> ORGANISM: Artificial Sequence
<220> FEATURE:
<223> OTHER INFORMATION: CD28 TM and CD28-CD3 zeta intracellular
      signaling domain

<400> SEQUENCE: 228
```

```
attgaagtta tgtatcctcc tccttaccta gacaatgaga gagcaatgg aaccattatc    60 catgtgaaag ggaaacacct ttgtccaagt cccctatttc ccggaccttc taagcccttt   120
tgggtgctgg tggtggttgg tggagtcctg gcttgctata gcttgctagt aacagtggcc   180
tttattattt tctgggtgag gagtaagagg agcaggctcc tgcacagtga ctacatgaac   240
atgactcccc gccgccccgg gcccacccgc aagcattacc agccctatgc cccaccacgc   300
gacttcgcag cctatcgctc cagagtgaag ttcagcagga gcgcagacgc ccccgcgtac   360
cagcagggcc agaaccagct ctataacgag ctcaatctag gacgaagaga ggagtacgat   420
gttttggaca gagacgtgg ccgggaccct gagatggggg gaaagccgag aaggaagaac   480
cctcaggaag gcctgtacaa tgaactgcag aaagataaga tggcggaggc ctacagtgag   540
attgggatga aaggcgagcg ccggaggggc aaggggcacg atggccttta ccagggtctc   600
agtacagcca ccaaggacac ctacgacgcc cttcacatgc aggccctgcc ccctcgctga   660
taa                                                                 663
```

```
<210> SEQ ID NO 229
<211> LENGTH: 23
<212> TYPE: DNA
<213> ORGANISM: Artificial Sequence
<220> FEATURE:
<223> OTHER INFORMATION: upstream primer CALL001

<400> SEQUENCE: 229
```

```
gtcctggctg ctcttctaca agg                                            23
```

```
<210> SEQ ID NO 230
<211> LENGTH: 23
<212> TYPE: DNA
<213> ORGANISM: Artificial Sequence
<220> FEATURE:
<223> OTHER INFORMATION: downstream primer CALL002

<400> SEQUENCE: 230
```

```
ggtacgtgct gttgaactgt tcc                                            23
```

```
<210> SEQ ID NO 231
<211> LENGTH: 29
<212> TYPE: DNA
<213> ORGANISM: Artificial Sequence
<220> FEATURE:
```

<223> OTHER INFORMATION: upstream primer BACK-1

<400> SEQUENCE: 231
gatgtgcagc tgcaggagtc tggaggagg                                 29

<210> SEQ ID NO 232
<211> LENGTH: 29
<212> TYPE: DNA
<213> ORGANISM: Artificial Sequence
<220> FEATURE:
<223> OTHER INFORMATION: downstream primer BACK-2

<400> SEQUENCE: 232
gatgtgcagc tgcaggagtc tgggggagg                                 29

<210> SEQ ID NO 233
<211> LENGTH: 34
<212> TYPE: DNA
<213> ORGANISM: Artificial Sequence
<220> FEATURE:
<223> OTHER INFORMATION: downstream primer PMCF

<400> SEQUENCE: 233
ctagtgcggc cgctgaggag acggtgacct gggt                           34

<210> SEQ ID NO 234
<211> LENGTH: 6
<212> TYPE: DNA
<213> ORGANISM: Artificial Sequence
<220> FEATURE:
<223> OTHER INFORMATION: EcoRI restriction site

<400> SEQUENCE: 234 gaattc                                                           6

<210> SEQ ID NO 235
<211> LENGTH: 6
<212> TYPE: DNA
<213> ORGANISM: Artificial Sequence
<220> FEATURE:
<223> OTHER INFORMATION: SpeI restriction site

<400> SEQUENCE: 235 actagt                                                           6

<210> SEQ ID NO 236
<211> LENGTH: 6
<212> TYPE: DNA
<213> ORGANISM: Artificial Sequence
<220> FEATURE:
<223> OTHER INFORMATION: HpaI restriction site

<400> SEQUENCE: 236 gttaac                                                           6

<210> SEQ ID NO 237
<211> LENGTH: 6
<212> TYPE: DNA
<213> ORGANISM: Artificial Sequence
<220> FEATURE:
<223> OTHER INFORMATION: MluI restriction site

<400> SEQUENCE: 237 acgcgt                                                           6

```
<210> SEQ ID NO 238
<211> LENGTH: 6
<212> TYPE: DNA
<213> ORGANISM: Artificial Sequence
<220> FEATURE:
<223> OTHER INFORMATION: NsiI restriction site

<400> SEQUENCE: 238 atgcat                                                                        6

<210> SEQ ID NO 239
<211> LENGTH: 2307
<212> TYPE: DNA
<213> ORGANISM: Artificial Sequence
<220> FEATURE:
<223> OTHER INFORMATION: tandem BCMA, CD38 269A37346 38A37717 GSI5013
      CAR

<400> SEQUENCE: 239
atggccttac cagtgaccgc cttgctcctg ccgctggcct tgctgctcca cgccgccagg      60
ccggttaacg aggtgcagct ggtggaaagc ggggggggac tggtgcaggc aggcgggtca     120
ctgagactgt catgtatcgc aactgggaag gtgtttagca tctacgacat gggctggtat     180
aggcaggcac caggaaagca gagggagctg gtggccgaga tcaccagctc cggcaccaca     240
cactacgacg atttcgtgtc tggccggttt accatcagca gagacaacgc caagaataca     300
gtgtatctgc agatgaacac cctgaaggcc gaggatacag ccgtgtacta ttgccgggct     360
aatcacgtct tcggcggctc ctactggggg cagggaactc aggtcactgt gtcatccacg     420
cgtcgcatgc atactagtac cacgacgcca gcgccgcgac caccaacacc ggcgcccacc     480
atcgcgtcgc agcccctgtc cctgcgccca gaggcgtgcc ggccagcggc gggggcgca      540 gtgcacacga gggggctgga cttcgcctgt gatatctaca tctgggcgcc cttggccggg     600
acttgtgggg tccttctcct gtcactggtt atcacccttt actgcaaacg gggcagaaag     660
aaactcctgt atatattcaa acaaccattt atgagaccag tacaaactac tcaagaggaa     720
gatggctgta gctgccgatt ccagaagaa gaagaaggag gatgtgaact gagagtgaag     780
ttcagcagga gcgcagacgc ccccgcgtac cagcagggcc agaaccagct ctataacgag     840
ctcaatctag acgaagaga ggagtacgat gttttggaca agagacgtgg ccgggaccct     900
gagatggggg gaaagccgag aaggaagaac cctcaggaag gcctgtacaa tgaactgcag     960
aaagataaga tggcggaggc ctacagtgag attgggatga aggcgagcg ccggagggc    1020 aaggggcacg atggccttta ccagggtctc agtacagcca ccaaggacac ctacgacgcc    1080
cttcacatgc aggccctgcc ccctcgcggc agtggagagg gcagaggaag tctgctaaca    1140
tgcggtgacg tcgaggagaa tcctggccca ggatccatgg ccttaccagt gaccgccttg    1200
ctcctgccgc tggccttgct gctccacgcc gccaggccgg ttaaccgcac gcgtcgcatg    1260
catcaggtgc agctggtgga gtctggggga ggcttggtgc agcctggggg ttctctgagg    1320
ctctcctgtg aagcctctgg attcactttg gattattatg ccataggctg gttccgccag    1380
gccccaggga aggagcgcga gggggtcata tgtattagta aagtgatgg tagcacatac    1440 tatgcagact ccgtgaaggg ccgattcacc atctccagag acaacgccaa gaaaacggtg    1500
tatctgcaaa tgatcagcct gaaacctgag gacacggccg ttattactg tgcagcaggg    1560 gccgattgtt cggggtacct acgagattat gagttccggg ggcaggggac ccaggtcacc    1620
gtctcctcaa ctagtaccac gacgccagcg ccgcgaccac caacaccggc gcccaccatc    1680
gcgtcgcagc ccctgtccct gcgcccagag gcgtgccggc cagcggcggg gggcgcagtg    1740
```

```
cacacgaggg ggctggactt cgcctgtgat atctacatct gggcgccctt ggccgggact    1800
tgtggggtcc ttctcctgtc actggttatc acccttact gcaaacgggg cagaaagaaa    1860
ctcctgtata tattcaaaca accatttatg agaccagtac aaactactca agaggaagat    1920
ggctgtagct gccgatttcc agaagaagaa gaaggaggat gtgaactgag agtgaagttc    1980
agcaggagcg cagacgcccc cgcgtaccag cagggccaga accagctcta taacgagctc    2040
aatctaggac gaagagagga gtacgatgtt ttggacaaga cgtggccg ggaccctgag      2100 atgggggaa agccgagaag gaagaaccct caggaaggcc tgtacaatga actgcagaaa    2160
gataagatgg cggaggccta cagtgagatt gggatgaaag gcgagcgccg gaggggcaag    2220
gggcacgatg gcctttacca gggtctcagt acagccacca aggacaccta cgacgccctt    2280
cacatgcagg ccctgccccc tcgctaa                                        2307
```

<210> SEQ ID NO 240
<211> LENGTH: 30
<212> TYPE: PRT
<213> ORGANISM: Artificial Sequence
<220> FEATURE:
<223> OTHER INFORMATION: CD19 VHH FR1

<400> SEQUENCE: 240

Gln Val Lys Leu Glu Glu Ser Gly Gly Glu Leu Val Gln Pro Gly Gly
1               5                   10                  15

Pro Leu Arg Leu Ser Cys Ala Ala Ser Gly Asn Ile Phe Ser
            20                  25                  30

<210> SEQ ID NO 241
<211> LENGTH: 14
<212> TYPE: PRT
<213> ORGANISM: Artificial Sequence
<220> FEATURE:
<223> OTHER INFORMATION: CD19 VHH FR2

<400> SEQUENCE: 241

Trp Tyr Arg Gln Ala Pro Gly Lys Gln Arg Ala Phe Val Ala
1               5                   10

<210> SEQ ID NO 242
<211> LENGTH: 32
<212> TYPE: PRT
<213> ORGANISM: Artificial Sequence
<220> FEATURE:
<223> OTHER INFORMATION: CD19 VHH FR3

<400> SEQUENCE: 242

Arg Phe Thr Ile Ser Val Asp Lys Ser Lys Asn Thr Ile Tyr Leu Gln
1               5                   10                  15

Met Asn Ala Leu Lys Pro Glu Asp Thr Ala Val Tyr Tyr Cys Asn Ala
            20                  25                  30

<210> SEQ ID NO 243
<211> LENGTH: 11
<212> TYPE: PRT
<213> ORGANISM: Artificial Sequence
<220> FEATURE:
<223> OTHER INFORMATION: CD19 VHH FR4

<400> SEQUENCE: 243

Trp Gly Gln Gly Thr Gln Val Thr Val Ser Ser
1               5                   10

```
<210> SEQ ID NO 244
<211> LENGTH: 30
<212> TYPE: PRT
<213> ORGANISM: Artificial Sequence
<220> FEATURE:
<223> OTHER INFORMATION: CD20 VHH FR1

<400> SEQUENCE: 244

Pro Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Gly
            20                  25                  30

<210> SEQ ID NO 245
<211> LENGTH: 14
<212> TYPE: PRT
<213> ORGANISM: Artificial Sequence
<220> FEATURE:
<223> OTHER INFORMATION: CD20 VHH FR2

<400> SEQUENCE: 245

Trp Phe Arg Gln Pro Pro Gly Lys Glu Arg Glu Phe Val Ala
1               5                   10

<210> SEQ ID NO 246
<211> LENGTH: 32
<212> TYPE: PRT
<213> ORGANISM: Artificial Sequence
<220> FEATURE:
<223> OTHER INFORMATION: CD20 VHH FR3

<400> SEQUENCE: 246

Arg Phe Thr Ile Ser Arg Asp Asn Ala Lys Leu Thr Val Asp Leu Gln
1               5                   10                  15

Met Asp Ser Leu Lys Pro Glu Asp Thr Ala Val Tyr Tyr Cys Ala Ala
            20                  25                  30

<210> SEQ ID NO 247
<211> LENGTH: 11
<212> TYPE: PRT
<213> ORGANISM: Artificial Sequence
<220> FEATURE:
<223> OTHER INFORMATION: CD20 VHH FR4

<400> SEQUENCE: 247

Trp Gly Gln Gly Thr Gln Val Thr Val Ser Ser
1               5                   10

<210> SEQ ID NO 248
<211> LENGTH: 357
<212> TYPE: PRT
<213> ORGANISM: Artificial Sequence
<220> FEATURE:
<223> OTHER INFORMATION: CD19 CAR

<400> SEQUENCE: 248

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Glu Leu
            20                  25                  30

Val Gln Pro Gly Gly Pro Leu Arg Leu Ser Cys Ala Ala Ser Gly Asn
        35                  40                  45

Ile Phe Ser Ile Asn Arg Met Gly Trp Tyr Arg Gln Ala Pro Gly Lys
    50                  55                  60
```

```
Gln Arg Ala Phe Val Ala Ser Ile Thr Val Arg Gly Ile Thr Asn Tyr
 65                  70                  75                  80

Ala Asp Ser Val Lys Gly Arg Phe Thr Ile Ser Val Asp Lys Ser Lys
                 85                  90                  95

Asn Thr Ile Tyr Leu Gln Met Asn Ala Leu Lys Pro Glu Asp Thr Ala
            100                 105                 110

Val Tyr Tyr Cys Asn Ala Val Ser Ser Asn Arg Asp Pro Asp Tyr Trp
            115                 120                 125

Gly Gln Gly Thr Gln Val Thr Val Ser Ser Ile Glu Val Met Tyr Pro
        130                 135                 140

Pro Pro Tyr Leu Asp Asn Glu Lys Ser Asn Gly Thr Ile Ile His Val
145                 150                 155                 160

Lys Gly Lys His Leu Cys Pro Ser Pro Leu Phe Pro Gly Pro Ser Lys
                165                 170                 175

Pro Phe Trp Val Leu Val Val Val Gly Gly Val Leu Ala Cys Tyr Ser
            180                 185                 190

Leu Leu Val Thr Val Ala Phe Ile Ile Phe Trp Val Arg Ser Lys Arg
            195                 200                 205

Ser Arg Leu Leu His Ser Asp Tyr Met Asn Met Thr Pro Arg Arg Pro
210                 215                 220

Gly Pro Thr Arg Lys His Tyr Gln Pro Tyr Ala Pro Pro Arg Asp Phe
225                 230                 235                 240

Ala Ala Tyr Arg Ser Arg Val Lys Phe Ser Arg Ser Ala Asp Ala Pro
                245                 250                 255

Ala Tyr Gln Gln Gly Gln Asn Gln Leu Tyr Asn Glu Leu Asn Leu Gly
            260                 265                 270

Arg Arg Glu Glu Tyr Asp Val Leu Asp Lys Arg Arg Gly Arg Asp Pro
            275                 280                 285

Glu Met Gly Gly Lys Pro Arg Arg Lys Asn Pro Gln Glu Gly Leu Tyr
290                 295                 300

Asn Glu Leu Gln Lys Asp Lys Met Ala Glu Ala Tyr Ser Glu Ile Gly
305                 310                 315                 320

Met Lys Gly Glu Arg Arg Arg Gly Lys Gly His Asp Gly Leu Tyr Gln
                325                 330                 335

Gly Leu Ser Thr Ala Thr Lys Asp Thr Tyr Asp Ala Leu His Met Gln
            340                 345                 350

Ala Leu Pro Pro Arg
            355

<210> SEQ ID NO 249
<211> LENGTH: 369
<212> TYPE: PRT
<213> ORGANISM: Artificial Sequence
<220> FEATURE:
<223> OTHER INFORMATION: CD20 CAR

<400> SEQUENCE: 249

Met Ala Leu Pro Val Thr Ala Leu Leu Leu Pro Leu Ala Leu Leu Leu
 1               5                  10                  15

His Ala Ala Arg Pro Pro Val Gln Leu Val Glu Ser Gly Gly Gly Leu
                20                  25                  30

Val Gln Ala Gly Asp Ser Leu Arg Leu Ser Cys Ala Ala Ser Gly Arg
            35                  40                  45

Thr Phe Gly Ile Gly Thr Met Gly Trp Phe Arg Gln Pro Pro Gly Lys
        50                  55                  60
```

```
Glu Arg Glu Phe Val Ala Ala Ile Arg Trp Ser Thr Gly Gly Thr Arg
 65                  70                  75                  80

Tyr Ala Asp Ser Val Lys Gly Arg Phe Thr Ile Ser Arg Asp Asn Ala
                 85                  90                  95

Lys Leu Thr Val Asp Leu Gln Met Asp Ser Leu Lys Pro Glu Asp Thr
            100                 105                 110

Ala Val Tyr Tyr Cys Ala Ala Asp Arg Leu Ser Leu Asp Leu Ser Gly
        115                 120                 125

Arg Tyr His Tyr Asn Pro Ala Val Tyr Asp Tyr Trp Gly Gln Gly Thr
130                 135                 140

Gln Val Thr Val Ser Ser Ile Glu Val Met Tyr Pro Pro Pro Tyr Leu
145                 150                 155                 160

Asp Asn Glu Lys Ser Asn Gly Thr Ile Ile His Val Lys Gly Lys His
                165                 170                 175

Leu Cys Pro Ser Pro Leu Phe Pro Gly Pro Ser Lys Pro Phe Trp Val
            180                 185                 190

Leu Val Val Val Gly Gly Val Leu Ala Cys Tyr Ser Leu Leu Val Thr
        195                 200                 205

Val Ala Phe Ile Ile Phe Trp Val Arg Ser Lys Arg Ser Arg Leu Leu
210                 215                 220

His Ser Asp Tyr Met Asn Met Thr Pro Arg Arg Pro Gly Pro Thr Arg
225                 230                 235                 240

Lys His Tyr Gln Pro Tyr Ala Pro Pro Arg Asp Phe Ala Ala Tyr Arg
                245                 250                 255

Ser Arg Val Lys Phe Ser Arg Ser Ala Asp Ala Pro Ala Tyr Gln Gln
            260                 265                 270

Gly Gln Asn Gln Leu Tyr Asn Glu Leu Asn Leu Gly Arg Arg Glu Glu
        275                 280                 285

Tyr Asp Val Leu Asp Lys Arg Arg Gly Arg Asp Pro Glu Met Gly Gly
290                 295                 300

Lys Pro Arg Arg Lys Asn Pro Gln Glu Gly Leu Tyr Asn Glu Leu Gln
305                 310                 315                 320

Lys Asp Lys Met Ala Glu Ala Tyr Ser Glu Ile Gly Met Lys Gly Glu
                325                 330                 335

Arg Arg Arg Gly Lys Gly His Asp Gly Leu Tyr Gln Gly Leu Ser Thr
            340                 345                 350

Ala Thr Lys Asp Thr Tyr Asp Ala Leu His Met Gln Ala Leu Pro Pro
        355                 360                 365

Arg

<210> SEQ ID NO 250
<211> LENGTH: 1077
<212> TYPE: DNA
<213> ORGANISM: Artificial Sequence
<220> FEATURE:
<223> OTHER INFORMATION: CD19 CAR

<400> SEQUENCE: 250
atggccttac cagtgaccgc cttgctcctg ccgctggcct tgctgctcca cgccgccagg      60
ccgcaggtaa agctggagga gtctggggga gaattggtgc agcctggggg gcctctgaga     120
ctctcctgtg cagcctcggg aaacatcttc agtatcaatc gcatgggctg gtaccgccag     180
gctccaggga agcagcgcgc gttcgtcgca tctattactg ttcgtggtat aacaaactat     240
gcagactccg tgaagggccg attcaccatt tctgtagaca gtccaaaaa cacgatttat     300
```

```
ctgcagatga acgcactcaa acctgaggac acggccgtct attattgtaa tgcagtgtct    360
tcaaacaggg accccgacta ctggggccag gggacccagg tcaccgtctc ctcaattgaa    420
gttatgtatc ctcctcctta cctagacaat gagaagagca atggaaccat tatccatgtg    480
aaagggaaac acctttgtcc aagtccccta tttcccggac cttctaagcc cttttgggtg    540
ctggtggtgg ttggtggagt cctggcttgc tatagcttgc tagtaacagt ggcctttatt    600
attttctggg tgaggagtaa gaggagcagg ctcctgcaca gtgactacat gaacatgact    660
ccccgccgcc ccgggcccac ccgcaagcat taccagccct atgccccacc acgcgacttc    720
gcagcctatc gctccagagt gaagttcagc aggagcgcag acgcccccgc gtaccagcag    780
ggccagaacc agctctataa cgagctcaat ctaggacgaa gagaggagta cgatgttttg    840
gacaagagac gtggccggga ccctgagatg ggggaaagc cgagaaggaa gaaccctcag    900
gaaggcctgt acaatgaact gcagaaagat aagatggcgg aggcctacag tgagattggg    960
atgaaaggcg agcgcggag gggcaagggg cacgatggcc tttaccaggg tctcagtaca   1020
gccaccaagg acacctacga cgccttcac atgcaggccc tgcccctcg ctgataa       1077

<210> SEQ ID NO 251
<211> LENGTH: 1113
<212> TYPE: DNA
<213> ORGANISM: Artificial Sequence
<220> FEATURE:
<223> OTHER INFORMATION: CD20 CAR

<400> SEQUENCE: 251
atggccttac cagtgaccgc cttgctcctg ccgctggcct tgctgctcca cgccgccagg    60
ccgccggtgc agctggtgga gtctggggga ggcttggtgc aggctgggga ttctctgaga   120
ctctcctgtg ctgcctctgg acgcaccttc ggtattggta ccatgggctg gttccgccaa   180
cctccaggga aggagcgtga atttgtagca gctattaggt ggagtactgg tggcactcgc   240
tatgcagact ccgtgaaggg ccgattcacc atctcccgag acaacgccaa gctcacggta   300
gatctgcaaa tggacagcct gaaacctgaa gacacggccg tttattactg tgcagcagat   360
agactgtccc ttgatttaag tggtcgttac cactacaacc cgccgtgta tgactattgg    420 ggccagggga cccaggtcac cgtctcctca attgaagtta tgtatcctcc tccttaccta   480
gacaatgaga agagcaatgg aaccattatc catgtgaaag ggaaacacct tgtccaagt   540 cccctatttc ccggaccttc taagcccttt tgggtgctgg tggtggttgg tggagtcctg   600
gcttgctata gcttgctagt aacagtggcc tttattattt tctgggtgag gagtaagagg   660
agcaggctcc tgcacagtga ctacatgaac atgactcccc gccgcccgg gcccacccgc    720 aagcattacc agccctatgc cccaccacgc gacttcgcag cctatcgctc cagagtgaag   780
ttcagcagga gcgcagacgc ccccgcgtac cagcagggcc agaaccagct ctataacgag   840
ctcaatctag gacgaagaga ggagtacgat gttttggaca gagacgtgg ccgggaccct    900 gagatggggg aaagccgag aaggaagaac cctcaggaag gcctgtacaa tgaactgcag    960
aaagataaga tggcggaggc ctacagtgag attgggatga aaggcgagcg ccggagggc   1020 aaggggcacg atggccttta ccagggtctc agtacagcca ccaaggacac ctacgacgcc   1080
cttcacatgc aggccctgcc cctcgctga taa                                1113

<210> SEQ ID NO 252
<211> LENGTH: 23
<212> TYPE: DNA
```

-continued

<213> ORGANISM: Artificial Sequence
<220> FEATURE:
<223> OTHER INFORMATION: 137P2F primer

<400> SEQUENCE: 252
gtccttctcc tgtcactggt tat                                             23

<210> SEQ ID NO 253
<211> LENGTH: 23
<212> TYPE: DNA
<213> ORGANISM: Artificial Sequence
<220> FEATURE:
<223> OTHER INFORMATION: 137P2R primer

<400> SEQUENCE: 253
tcttcttctt ctggaaatcg gca                                             23

<210> SEQ ID NO 254
<211> LENGTH: 48
<212> TYPE: DNA
<213> ORGANISM: Artificial Sequence
<220> FEATURE:
<223> OTHER INFORMATION: Linker sequence 3

<400> SEQUENCE: 254
ggcggcggca gcggcggcgg cagcggcggc ggcagcggcg gcggcagc                  48

<210> SEQ ID NO 255
<211> LENGTH: 21
<212> TYPE: PRT
<213> ORGANISM: Artificial Sequence
<220> FEATURE:
<223> OTHER INFORMATION: T2A

<400> SEQUENCE: 255

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 256
<211> LENGTH: 63
<212> TYPE: DNA
<213> ORGANISM: Artificial Sequence
<220> FEATURE:
<223> OTHER INFORMATION: T2A

<400> SEQUENCE: 256
ggcagtggag agggcagagg aagtctgcta acatgcggtg acgtcgagga gaatcctggc    60
cca                                                                   63

<210> SEQ ID NO 257
<211> LENGTH: 376
<212> TYPE: PRT
<213> ORGANISM: Artificial Sequence
<220> FEATURE:
<223> OTHER INFORMATION: GSI5011 CAR 269A37346

<400> SEQUENCE: 257

Met Ala Leu Pro Val Thr Ala Leu Leu Leu Pro Leu Ala Leu Leu Leu
1               5                   10                  15

His Ala Ala Arg Pro Val Asn Arg Thr Arg Arg Met His Gln Val Gln
            20                  25                  30

Leu Val Glu Ser Gly Gly Gly Leu Val Gln Pro Gly Gly Ser Leu Arg

```
                    35                  40                  45
Leu Ser Cys Glu Ala Ser Gly Phe Thr Leu Asp Tyr Tyr Ala Ile Gly
 50                  55                  60

Trp Phe Arg Gln Ala Pro Gly Lys Glu Arg Glu Gly Val Ile Cys Ile
 65                  70                  75                  80

Ser Arg Ser Asp Gly Ser Thr Tyr Tyr Ala Asp Ser Val Lys Gly Arg
                 85                  90                  95

Phe Thr Ile Ser Arg Asp Asn Ala Lys Lys Thr Val Tyr Leu Gln Met
            100                 105                 110

Ile Ser Leu Lys Pro Glu Asp Thr Ala Ala Tyr Tyr Cys Ala Ala Gly
        115                 120                 125

Ala Asp Cys Ser Gly Tyr Leu Arg Asp Tyr Glu Phe Arg Gly Gln Gly
    130                 135                 140

Thr Gln Val Thr Val Ser Ser Thr Thr Thr Pro Ala Pro Arg
145                 150                 155                 160

Pro Pro Thr Pro Ala Pro Thr Ile Ala Ser Gln Pro Leu Ser Leu Arg
                165                 170                 175

Pro Glu Ala Cys Arg Pro Ala Ala Gly Gly Ala Val His Thr Arg Gly
            180                 185                 190

Leu Asp Phe Ala Cys Asp Ile Tyr Ile Trp Ala Pro Leu Ala Gly Thr
        195                 200                 205

Cys Gly Val Leu Leu Leu Ser Leu Val Ile Thr Leu Tyr Cys Lys Arg
    210                 215                 220

Gly Arg Lys Lys Leu Leu Tyr Ile Phe Lys Gln Pro Phe Met Arg Pro
225                 230                 235                 240

Val Gln Thr Thr Gln Glu Glu Asp Gly Cys Ser Cys Arg Phe Pro Glu
                245                 250                 255

Glu Glu Glu Gly Gly Cys Glu Leu Arg Val Lys Phe Ser Arg Ser Ala
            260                 265                 270

Asp Ala Pro Ala Tyr Gln Gln Gly Gln Asn Gln Leu Tyr Asn Glu Leu
        275                 280                 285

Asn Leu Gly Arg Arg Glu Glu Tyr Asp Val Leu Asp Lys Arg Arg Gly
    290                 295                 300

Arg Asp Pro Glu Met Gly Gly Lys Pro Arg Arg Lys Asn Pro Gln Glu
305                 310                 315                 320

Gly Leu Tyr Asn Glu Leu Gln Lys Asp Lys Met Ala Glu Ala Tyr Ser
                325                 330                 335

Glu Ile Gly Met Lys Gly Glu Arg Arg Arg Gly Lys Gly His Asp Gly
            340                 345                 350

Leu Tyr Gln Gly Leu Ser Thr Ala Thr Lys Asp Thr Tyr Asp Ala Leu
        355                 360                 365

His Met Gln Ala Leu Pro Pro Arg
    370                 375

<210> SEQ ID NO 258
<211> LENGTH: 373
<212> TYPE: PRT
<213> ORGANISM: Artificial Sequence
<220> FEATURE:
<223> OTHER INFORMATION: GSI5019 CAR 269A37353

<400> SEQUENCE: 258

Met Ala Leu Pro Val Thr Ala Leu Leu Leu Pro Leu Ala Leu Leu Leu
  1               5                  10                  15

His Ala Ala Arg Pro Val Asn Arg Thr Arg Arg Met His Gln Val Lys
```

```
                20                  25                  30
Leu Glu Glu Ser Gly Gly Gly Leu Val Gln Ala Gly Arg Ser Leu Arg
         35                  40                  45

Leu Ser Cys Ala Ala Ser Glu His Thr Phe Ser Ser His Val Met Gly
 50                  55                  60

Trp Phe Arg Gln Ala Pro Gly Lys Glu Arg Glu Ser Val Ala Val Ile
65                  70                  75                  80

Gly Trp Arg Asp Ile Ser Thr Ser Tyr Ala Asp Ser Val Lys Gly Arg
                 85                  90                  95

Phe Thr Ile Ser Arg Asp Asn Ala Lys Lys Thr Leu Tyr Leu Gln Met
             100                 105                 110

Asn Ser Leu Lys Pro Glu Asp Thr Ala Val Tyr Tyr Cys Ala Ala Arg
         115                 120                 125

Arg Ile Asp Ala Ala Asp Phe Asp Ser Trp Gly Gln Gly Thr Gln Val
     130                 135                 140

Thr Val Ser Ser Thr Ser Thr Thr Thr Pro Ala Pro Arg Pro Pro Thr
145                 150                 155                 160

Pro Ala Pro Thr Ile Ala Ser Gln Pro Leu Ser Leu Arg Pro Glu Ala
                 165                 170                 175

Cys Arg Pro Ala Ala Gly Gly Ala Val His Thr Arg Gly Leu Asp Phe
             180                 185                 190

Ala Cys Asp Ile Tyr Ile Trp Ala Pro Leu Ala Gly Thr Cys Gly Val
         195                 200                 205

Leu Leu Leu Ser Leu Val Ile Thr Leu Tyr Cys Lys Arg Gly Arg Lys
     210                 215                 220

Lys Leu Leu Tyr Ile Phe Lys Gln Pro Phe Met Arg Pro Val Gln Thr
225                 230                 235                 240

Thr Gln Glu Glu Asp Gly Cys Ser Cys Arg Phe Pro Glu Glu Glu Glu
                 245                 250                 255

Gly Gly Cys Glu Leu Arg Val Lys Phe Ser Arg Ser Ala Asp Ala Pro
             260                 265                 270

Ala Tyr Gln Gln Gly Gln Asn Gln Leu Tyr Asn Glu Leu Asn Leu Gly
         275                 280                 285

Arg Arg Glu Glu Tyr Asp Val Leu Asp Lys Arg Arg Gly Arg Asp Pro
     290                 295                 300

Glu Met Gly Gly Lys Pro Arg Arg Lys Asn Pro Gln Glu Gly Leu Tyr
305                 310                 315                 320

Asn Glu Leu Gln Lys Asp Lys Met Ala Glu Ala Tyr Ser Glu Ile Gly
                 325                 330                 335

Met Lys Gly Glu Arg Arg Arg Gly Lys Gly His Asp Gly Leu Tyr Gln
             340                 345                 350

Gly Leu Ser Thr Ala Thr Lys Asp Thr Tyr Asp Ala Leu His Met Gln
         355                 360                 365

Ala Leu Pro Pro Arg
     370

<210> SEQ ID NO 259
<211> LENGTH: 372
<212> TYPE: PRT
<213> ORGANISM: Artificial Sequence
<220> FEATURE:
<223> OTHER INFORMATION: GSI5020 CAR 269A37917

<400> SEQUENCE: 259

Met Ala Leu Pro Val Thr Ala Leu Leu Leu Pro Leu Ala Leu Leu Leu
```

```
              1               5                  10                 15
            His Ala Ala Arg Pro Val Asn Arg Thr Arg Met His Glu Val Gln
                         20                  25                  30

Leu Val Glu Ser Gly Gly Gly Leu Val Gln Ala Gly Gly Ser Leu Arg
                         35                  40                  45

Leu Ser Cys Ala Ala Ser Gly Arg Thr Phe Thr Met Gly Trp Phe Arg
                 50                  55                  60

Gln Ala Pro Gly Lys Glu Arg Glu Phe Val Ala Ile Ser Leu Ser
            65                  70                  75                  80

Pro Thr Leu Ala Tyr Tyr Ala Glu Ser Val Lys Gly Arg Phe Thr Ile
                             85                  90                  95

Ser Arg Asp Asn Ala Lys Asn Thr Val Val Leu Gln Met Asn Ser Leu
                            100                 105                 110

Lys Pro Glu Asp Thr Ala Leu Tyr Tyr Cys Ala Ala Asp Arg Lys Ser
                            115                 120                 125

Val Met Ser Ile Arg Pro Asp Tyr Trp Gly Gln Gly Thr Gln Val Thr
                        130                 135                 140

Val Ser Ser Thr Ser Thr Thr Pro Ala Pro Arg Pro Pro Thr Pro
            145                 150                 155                 160

Ala Pro Thr Ile Ala Ser Gln Pro Leu Ser Leu Arg Pro Glu Ala Cys
                            165                 170                 175

Arg Pro Ala Ala Gly Gly Ala Val His Thr Arg Gly Leu Asp Phe Ala
                        180                 185                 190

Cys Asp Ile Tyr Ile Trp Ala Pro Leu Ala Gly Thr Cys Gly Val Leu
                        195                 200                 205

Leu Leu Ser Leu Val Ile Thr Leu Tyr Cys Lys Arg Gly Arg Lys Lys
                        210                 215                 220

Leu Leu Tyr Ile Phe Lys Gln Pro Phe Met Arg Pro Val Gln Thr Thr
            225                 230                 235                 240

Gln Glu Glu Asp Gly Cys Ser Cys Arg Phe Pro Glu Glu Glu Gly
                            245                 250                 255

Gly Cys Glu Leu Arg Val Lys Phe Ser Arg Ser Ala Asp Ala Pro Ala
                        260                 265                 270

Tyr Gln Gln Gly Gln Asn Gln Leu Tyr Asn Glu Leu Asn Leu Gly Arg
                        275                 280                 285

Arg Glu Glu Tyr Asp Val Leu Asp Lys Arg Arg Gly Arg Asp Pro Glu
                        290                 295                 300

Met Gly Gly Lys Pro Arg Arg Lys Asn Pro Gln Glu Gly Leu Tyr Asn
            305                 310                 315                 320

Glu Leu Gln Lys Asp Lys Met Ala Glu Ala Tyr Ser Glu Ile Gly Met
                            325                 330                 335

Lys Gly Glu Arg Arg Arg Gly Lys Gly His Asp Gly Leu Tyr Gln Gly
                        340                 345                 350

Leu Ser Thr Ala Thr Lys Asp Thr Tyr Asp Ala Leu His Met Gln Ala
                        355                 360                 365

Leu Pro Pro Arg
                370

<210> SEQ ID NO 260
<211> LENGTH: 369
<212> TYPE: PRT
<213> ORGANISM: Artificial Sequence
<220> FEATURE:
<223> OTHER INFORMATION: GSI5012 CAR 38A37717
```

<400> SEQUENCE: 260

Met Ala Leu Pro Val Thr Ala Leu Leu Leu Pro Leu Ala Leu Leu Leu
1               5                   10                  15

His Ala Ala Arg Pro Val Asn Glu Val Gln Leu Val Glu Ser Gly Gly
            20                  25                  30

Gly Leu Val Gln Ala Gly Gly Ser Leu Arg Leu Ser Cys Ile Ala Thr
        35                  40                  45

Gly Lys Val Phe Ser Ile Tyr Asp Met Gly Trp Tyr Arg Gln Ala Pro
50                  55                  60

Gly Lys Gln Arg Glu Leu Val Ala Glu Ile Thr Ser Ser Gly Thr Thr
65                  70                  75                  80

His Tyr Asp Asp Phe Val Ser Gly Arg Phe Thr Ile Ser Arg Asp Asn
                85                  90                  95

Ala Lys Asn Thr Val Tyr Leu Gln Met Asn Thr Leu Lys Ala Glu Asp
            100                 105                 110

Thr Ala Val Tyr Tyr Cys Arg Ala Asn His Val Phe Gly Gly Ser Tyr
        115                 120                 125

Trp Gly Gln Gly Thr Gln Val Thr Val Ser Ser Thr Arg Arg Met His
130                 135                 140

Thr Ser Thr Thr Thr Pro Ala Pro Arg Pro Pro Thr Pro Ala Pro Thr
145                 150                 155                 160

Ile Ala Ser Gln Pro Leu Ser Leu Arg Pro Glu Ala Cys Arg Pro Ala
                165                 170                 175

Ala Gly Gly Ala Val His Thr Arg Gly Leu Asp Phe Ala Cys Asp Ile
            180                 185                 190

Tyr Ile Trp Ala Pro Leu Ala Gly Thr Cys Gly Val Leu Leu Leu Ser
        195                 200                 205

Leu Val Ile Thr Leu Tyr Cys Lys Arg Gly Arg Lys Lys Leu Leu Tyr
210                 215                 220

Ile Phe Lys Gln Pro Phe Met Arg Pro Val Gln Thr Thr Gln Glu Glu
225                 230                 235                 240

Asp Gly Cys Ser Cys Arg Phe Pro Glu Glu Glu Glu Gly Gly Cys Glu
                245                 250                 255

Leu Arg Val Lys Phe Ser Arg Ser Ala Asp Ala Pro Ala Tyr Gln Gln
            260                 265                 270

Gly Gln Asn Gln Leu Tyr Asn Glu Leu Asn Leu Gly Arg Arg Glu Glu
        275                 280                 285

Tyr Asp Val Leu Asp Lys Arg Arg Gly Arg Asp Pro Glu Met Gly Gly
290                 295                 300

Lys Pro Arg Arg Lys Asn Pro Gln Glu Gly Leu Tyr Asn Glu Leu Gln
305                 310                 315                 320

Lys Asp Lys Met Ala Glu Ala Tyr Ser Glu Ile Gly Met Lys Gly Glu
                325                 330                 335

Arg Arg Arg Gly Lys Gly His Asp Gly Leu Tyr Gln Gly Leu Ser Thr
            340                 345                 350

Ala Thr Lys Asp Thr Tyr Asp Ala Leu His Met Gln Ala Leu Pro Pro
        355                 360                 365

Arg

<210> SEQ ID NO 261
<211> LENGTH: 1131
<212> TYPE: DNA
<213> ORGANISM: Artificial Sequence
<220> FEATURE:

<223> OTHER INFORMATION: GSI5011 CAR 269A37346

<400> SEQUENCE: 261

```
atggccttac cagtgaccgc cttgctcctg ccgctggcct tgctgctcca cgccgccagg      60
ccggttaacc gcacgcgtcg catgcatcag gtgcagctgg tggagtctgg gggaggcttg     120
gtgcagcctg ggggttctct gaggctctcc tgtgaagcct ctggattcac tttggattat    180
tatgccatag gctggttccg ccaggcccca gggaaggagc gcgaggggt catatgtatt     240
agtagaagtg atggtagcac atactatgca gactccgtga agggccgatt caccatctcc    300
agagacaacg ccaagaaaac ggtgtatctg caaatgatca gcctgaaacc tgaggacacg    360
gccgcttatt actgtgcagc aggggccgat tgttcggggt acctacgaga ttatgagttc    420
cggggggcagg ggacccaggt caccgtctcc tcaactagta ccacgacgcc agcgccgcga    480
ccaccaacac cggcgcccac catcgcgtcg cagcccctgt ccctgcgccc agaggcgtgc    540
cggccagcgg cggggggcgc agtgcacacg aggggggctgg acttcgcctg tgatatctac    600
atctgggcgc ccttggccgg gacttgtggg gtccttctcc tgtcactggt tatcacccttt   660
tactgcaaac ggggcagaaa gaaactcctg tatatattca acaaccatt tatgagacca     720
gtacaaacta ctcaagagga gatggctgt agctgccgat ttccagaaga agaagaagga     780
ggatgtgaac tgagagtgaa gttcagcagg agcgcagacg ccccgcgta ccagcagggc     840
cagaaccagc tctataacga gctcaatcta ggacgaagag aggagtacga tgttttggac    900
aagagacgtg gccgggaccc tgagatgggg ggaaagccga aggaagaa ccctcaggaa      960
ggcctgtaca tgaactgca gaaagataag atggcggagg cctacagtga gattgggatg    1020
aaaggcgagc gccggagggg caaggggcac gatggccttt accagggtct cagtacagcc   1080
accaaggaca cctacgacgc ccttcacatg caggccctgc ccctcgcta a              1131
```

<210> SEQ ID NO 262
<211> LENGTH: 1122
<212> TYPE: DNA
<213> ORGANISM: Artificial Sequence
<220> FEATURE:
<223> OTHER INFORMATION: GSI5019 CAR 269A37353

<400> SEQUENCE: 262

```
atggccttac cagtgaccgc cttgctcctg ccgctggcct tgctgctcca cgccgccagg     60
ccggttaacc gcacgcgtcg catgcatcag gtaaagctgg aggagtctgg gggaggcttg   120
gtgcaggctg ggcggtctct gagactctcc tgtgcagcct ctgaacacac cttcagtagc    180
catgtcatgg gctggttccg ccaggctcca gggaaggagc gtgagtctgt tgcagttatt    240
ggctggagag atattagcac aagctatgca gactccgtga agggccgatt caccatctcc    300
agagacaacg ccaagaagac gctgtatctg caaatgaata gcctgaaacc tgaggacacg    360
gccgtttact actgtgcagc acgtcggatc gacgcagctg actttgattc ctggggggcag   420
gggacccagg tcaccgtctc ctcgactagt accacgacgc cagcgccgcg accaccaaca    480
ccggcgccca ccatcgcgtc gcagcccctg tccctgcgcc cagaggcgtg ccggccagcg    540
gcggggggcg cagtgcacac gaggggggctg gacttcgcct gtgatatcta catctgggcg    600
cccttggccg ggacttgtgg ggtccttctc ctgtcactgg ttatcaccct ttactgcaaa    660
cgggggcagaa agaaactcct gtatatattc aacaaccat ttatgagacc agtacaaact    720
actcaagagg aagatggctg tagctgccga tttccagaag aagaagaagg aggatgtgaa    780
ctgagagtga agttcagcag gagcgcagac gcccccgcgt accagcaggg ccagaaccag    840
```

```
ctctataacg agctcaatct aggacgaaga gaggagtacg atgttttgga caagagacgt    900
ggccgggacc ctgagatggg gggaaagccg agaaggaaga accctcagga aggcctgtac    960
aatgaactgc agaaagataa gatggcggag gcctacagtg agattgggat gaaaggcgag   1020
cgccggaggg gcaaggggca cgatggcctt taccagggtc tcagtacagc caccaaggac   1080
acctacgacg cccttcacat gcaggccctg cccctcgct aa                       1122
```

<210> SEQ ID NO 263
<211> LENGTH: 1119
<212> TYPE: DNA
<213> ORGANISM: Artificial Sequence
<220> FEATURE:
<223> OTHER INFORMATION: GSI5020 CAR 269A37917

<400> SEQUENCE: 263

```
atggccttac cagtgaccgc cttgctcctg ccgctggcct tgctgctcca cgccgccagg     60
ccggttaacc gcacgcgtcg catgcatgag gtgcagctgg tggagtctgg gggaggcttg    120
gtgcaggctg gggggtctct gagactctcc tgtgcagcct ctggacgcac cttcaccatg    180
gggtggttcc gtcaggctcc agggaaggag cgtgagtttg tagcagctat tagttttgagt   240 cctactttag catattatgc agagtccgtg aagggccgat tcaccatcag ccgagacaac    300
gccaagaaca cggtggtttt gcaaatgaac agcctgaaac ctgaggacac ggccctttat    360
tactgtgcag cagaccggaa atcagtaatg tctattcggc ccgactactg gggccagggg    420
acccaggtca ccgtctcctc aactagtacc acgacgccag cgccgcgacc accaacaccg    480
gcgcccacca tcgcgtcgca gcccctgtcc ctgcgcccag aggcgtgccg gccagcggcg    540
gggggcgcag tgcacacgag ggggctggac ttcgcctgtg atatctacat ctgggcgccc    600
ttggccggga cttgtggggt ccttctcctg tcactggtta tcacccttta ctgcaaacgg    660
ggcagaaaga aactcctgta tatattcaaa caaccattta tgagaccagt acaaactact    720
caagaggaag atggctgtag ctgccgattt ccagaagaag aagaaggagg atgtgaactg    780
agagtgaagt tcagcaggag cgcagacgcc cccgcgtacc agcagggcca gaaccagctc    840
tataacgagc tcaatctagg acgaagagag gagtacgatg ttttggacaa gagacgtggc    900
cgggaccctg agatgggggg aaagccgaga aggaagaacc ctcaggaagg cctgtacaat    960
gaactgcaga aagataagat ggcggaggcc tacagtgaga ttgggatgaa aggcgagcgc   1020
cggaggggca ggggcacga tggcctttac cagggtctca gtacagccac caaggacacc   1080
tacgacgccc ttcacatgca ggccctgccc ctcgctaa                           1119
```

<210> SEQ ID NO 264
<211> LENGTH: 1110
<212> TYPE: DNA
<213> ORGANISM: Artificial Sequence
<220> FEATURE:
<223> OTHER INFORMATION: GSI5012 CAR 38A37717

<400> SEQUENCE: 264

```
atggccttac cagtgaccgc cttgctcctg ccgctggcct tgctgctcca cgccgccagg     60
ccggttaacg aggtgcagct ggtggaaagc ggggggggac tggtgcaggc aggcgggtca    120
ctgagactgt catgtatcgc aactgggaag gtgtttagca tctacgacat gggctggtat    180
aggcaggcac aggaaagca gagggagctg gtggccgaga tcaccagctc cggcaccaca    240
cactacgacg atttcgtgtc tggccggttt accatcagca gagacaacgc caagaataca    300
```

-continued

```
gtgtatctgc agatgaacac cctgaaggcc gaggatacag ccgtgtacta ttgccgggct    360
aatcacgtct tcggcggctc ctactggggg cagggaactc aggtcactgt gtcatccacg    420
cgtcgcatgc atactagtac cacgacgcca gcgccgcgac caccaacacc ggcgcccacc    480
atcgcgtcgc agcccctgtc cctgcgccca gaggcgtgcc ggccagcggc ggggggcgca    540
gtgcacacga gggggctgga cttcgcctgt gatatctaca tctgggcgcc cttggccggg    600
acttgtgggg tccttctcct gtcactggtt atcacccttt actgcaaacg ggcagaaag    660
aaactcctgt atatattcaa acaaccattt atgagaccag tacaaactac tcaagaggaa    720
gatggctgta gctgccgatt tccagaagaa gaagaaggag gatgtgaact gagagtgaag    780
ttcagcagga gcgcagacgc ccccgcgtac cagcagggcc agaaccagct ctataacgag    840
ctcaatctag gacgaagaga ggagtacgat gttttggaca gagacgtgg ccggacccct    900
gagatggggg gaaagccgag aaggaagaac cctcaggaag gcctgtacaa tgaactgcag    960
aaagataaga tggcggaggc ctacagtgag attgggatga aggcgagcg ccggaggggc   1020
aagggggcacg atggccttta ccagggtctc agtacagcca ccaaggacac ctacgacgcc   1080
cttcacatgc aggccctgcc ccctcgctaa                                    1110
```

<210> SEQ ID NO 265
<211> LENGTH: 488
<212> TYPE: PRT
<213> ORGANISM: Artificial Sequence
<220> FEATURE:
<223> OTHER INFORMATION: GSI5021 CAR

<400> SEQUENCE: 265

```
Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Leu
            20                  25                  30

Val Gln Ala Gly Arg Ser Leu Arg Leu Ser Cys Ala Ala Ser Glu His
        35                  40                  45

Thr Phe Ser Ser His Val Met Gly Trp Phe Arg Gln Ala Pro Gly Lys
    50                  55                  60

Glu Arg Glu Ser Val Ala Val Ile Gly Trp Arg Asp Ile Ser Thr Ser
65                  70                  75                  80

Tyr Ala Asp Ser Val Lys Gly Arg Phe Thr Ile Ser Arg Asp Asn Ala
                85                  90                  95

Lys Lys Thr Leu Tyr Leu Gln Met Asn Ser Leu Lys Pro Glu Asp Thr
            100                 105                 110

Ala Val Tyr Tyr Cys Ala Ala Arg Arg Ile Asp Ala Ala Asp Phe Asp
        115                 120                 125

Ser Trp Gly Gln Gly Thr Gln Val Thr Val Ser Ser Gly Gly Gly Gly
    130                 135                 140

Ser Glu Val Gln Leu Val Glu Ser Gly Gly Gly Leu Val Gln Ala Gly
145                 150                 155                 160

Gly Ser Leu Arg Leu Ser Cys Ala Ala Ser Gly Arg Thr Phe Thr Met
                165                 170                 175

Gly Trp Phe Arg Gln Ala Pro Gly Lys Glu Arg Glu Phe Val Ala Ala
            180                 185                 190

Ile Ser Leu Ser Pro Thr Leu Ala Tyr Tyr Ala Glu Ser Val Lys Gly
        195                 200                 205

Arg Phe Thr Ile Ser Arg Asp Asn Ala Lys Asn Thr Val Val Leu Gln
    210                 215                 220
```

```
Met Asn Ser Leu Lys Pro Glu Asp Thr Ala Leu Tyr Tyr Cys Ala Ala
225                 230                 235                 240

Asp Arg Lys Ser Val Met Ser Ile Arg Pro Asp Tyr Trp Gly Gln Gly
                245                 250                 255

Thr Gln Val Thr Val Ser Ser Ser Thr Thr Thr Pro Ala Pro Arg
            260                 265                 270

Pro Pro Thr Pro Ala Pro Thr Ile Ala Ser Gln Pro Leu Ser Leu Arg
            275                 280                 285

Pro Glu Ala Cys Arg Pro Ala Ala Gly Gly Ala Val His Thr Arg Gly
        290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
                340                 345                 350

Val Gln Thr Thr Gln Glu Glu Asp Gly Cys Ser Cys Arg Phe Pro Glu
            355                 360                 365

Glu Glu Glu Gly Gly Cys Glu Leu Arg Val Lys Phe Ser Arg Ser Ala
370                 375                 380

Asp Ala Pro Ala Tyr Gln Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
                420                 425                 430

Gly Leu Tyr Asn Glu Leu Gln Lys Asp Lys Met Ala Glu Ala Tyr Ser
                435                 440                 445

Glu Ile Gly Met Lys Gly Glu Arg Arg Arg Gly Lys Gly His Asp Gly
450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485

<210> SEQ ID NO 266
<211> LENGTH: 498
<212> TYPE: PRT
<213> ORGANISM: Artificial Sequence
<220> FEATURE:
<223> OTHER INFORMATION: GSI5022 CAR

<400> SEQUENCE: 266

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Leu
                20                  25                  30

Val Gln Ala Gly Arg Ser Leu Arg Leu Ser Cys Ala Ala Ser Glu His
            35                  40                  45

Thr Phe Ser Ser His Val Met Gly Trp Phe Arg Gln Ala Pro Gly Lys
        50                  55                  60

Glu Arg Glu Ser Val Ala Val Ile Gly Trp Arg Asp Ile Ser Thr Ser
65                  70                  75                  80

Tyr Ala Asp Ser Val Lys Gly Arg Phe Thr Ile Ser Arg Asp Asn Ala
                85                  90                  95
```

```
Lys Lys Thr Leu Tyr Leu Gln Met Asn Ser Leu Lys Pro Glu Asp Thr
            100                 105                 110

Ala Val Tyr Tyr Cys Ala Ala Arg Ile Asp Ala Ala Asp Phe Asp
            115                 120             125

Ser Trp Gly Gln Gly Thr Gln Val Thr Val Ser Ser Gly Gly Gly Gly
    130                 135                 140

Ser Gly Gly Gly Gly Ser Gly Gly Gly Ser Glu Val Gln Leu Val
145                 150                 155                 160

Glu Ser Gly Gly Gly Leu Val Gln Ala Gly Gly Ser Leu Arg Leu Ser
                165                 170                 175

Cys Ala Ala Ser Gly Arg Thr Phe Thr Met Gly Trp Phe Arg Gln Ala
            180                 185                 190

Pro Gly Lys Glu Arg Glu Phe Val Ala Ala Ile Ser Leu Ser Pro Thr
            195                 200                 205

Leu Ala Tyr Tyr Ala Glu Ser Val Lys Gly Arg Phe Thr Ile Ser Arg
            210                 215                 220

Asp Asn Ala Lys Asn Thr Val Val Leu Gln Met Asn Ser Leu Lys Pro
225                 230                 235                 240

Glu Asp Thr Ala Leu Tyr Tyr Cys Ala Ala Asp Arg Lys Ser Val Met
                245                 250                 255

Ser Ile Arg Pro Asp Tyr Trp Gly Gln Gly Thr Gln Val Thr Val Ser
            260                 265                 270

Ser Thr Ser Thr Thr Thr Pro Ala Pro Arg Pro Pro Thr Pro Ala Pro
            275                 280                 285

Thr Ile Ala Ser Gln Pro Leu Ser Leu Arg Pro Glu Ala Cys Arg Pro
            290                 295                 300

Ala Ala Gly Gly Ala Val His Thr Arg Gly Leu Asp Phe Ala Cys Asp
305                 310                 315                 320

Ile Tyr Ile Trp Ala Pro Leu Ala Gly Thr Cys Gly Val Leu Leu Leu
                325                 330                 335

Ser Leu Val Ile Thr Leu Tyr Cys Lys Arg Gly Arg Lys Lys Leu Leu
            340                 345                 350

Tyr Ile Phe Lys Gln Pro Phe Met Arg Pro Val Gln Thr Thr Gln Glu
            355                 360                 365

Glu Asp Gly Cys Ser Cys Arg Phe Pro Glu Glu Glu Glu Gly Gly Cys
            370                 375                 380

Glu Leu Arg Val Lys Phe Ser Arg Ser Ala Asp Ala Pro Ala Tyr Gln
385                 390                 395                 400

Gln Gly Gln Asn Gln Leu Tyr Asn Glu Leu Asn Leu Gly Arg Arg Glu
                405                 410                 415

Glu Tyr Asp Val Leu Asp Lys Arg Arg Gly Arg Asp Pro Glu Met Gly
            420                 425                 430

Gly Lys Pro Arg Arg Lys Asn Pro Gln Glu Gly Leu Tyr Asn Glu Leu
            435                 440                 445

Gln Lys Asp Lys Met Ala Glu Ala Tyr Ser Glu Ile Gly Met Lys Gly
            450                 455                 460

Glu Arg Arg Arg Gly Lys Gly His Asp Gly Leu Tyr Gln Gly Leu Ser
465                 470                 475                 480

Thr Ala Thr Lys Asp Thr Tyr Asp Ala Leu His Met Gln Ala Leu Pro
                485                 490                 495

Pro Arg
```

<210> SEQ ID NO 267
<211> LENGTH: 508
<212> TYPE: PRT
<213> ORGANISM: Artificial Sequence
<220> FEATURE:
<223> OTHER INFORMATION: GSI5023 CAR

<400> SEQUENCE: 267

```
Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Leu
            20                  25                  30

Val Gln Ala Gly Arg Ser Leu Arg Leu Ser Cys Ala Ala Ser Glu His
        35                  40                  45

Thr Phe Ser Ser His Val Met Gly Trp Phe Arg Gln Ala Pro Gly Lys
    50                  55                  60

Glu Arg Glu Ser Val Ala Val Ile Gly Trp Arg Asp Ile Ser Thr Ser
65                  70                  75                  80

Tyr Ala Asp Ser Val Lys Gly Arg Phe Thr Ile Ser Arg Asp Asn Ala
                85                  90                  95

Lys Lys Thr Leu Tyr Leu Gln Met Asn Ser Leu Lys Pro Glu Asp Thr
            100                 105                 110

Ala Val Tyr Tyr Cys Ala Ala Arg Arg Ile Asp Ala Ala Asp Phe Asp
        115                 120                 125

Ser Trp Gly Gln Gly Thr Gln Val Thr Val Ser Ser Gly Gly Gly Gly
    130                 135                 140

Ser Gly Gly Gly Gly Ser Gly Gly Gly Gly Ser Gly Gly Gly Gly Ser
145                 150                 155                 160

Gly Gly Gly Gly Ser Glu Val Gln Leu Val Glu Ser Gly Gly Gly Leu
                165                 170                 175

Val Gln Ala Gly Gly Ser Leu Arg Leu Ser Cys Ala Ala Ser Gly Arg
            180                 185                 190

Thr Phe Thr Met Gly Trp Phe Arg Gln Ala Pro Gly Lys Glu Arg Glu
        195                 200                 205

Phe Val Ala Ala Ile Ser Leu Ser Pro Thr Leu Ala Tyr Tyr Ala Glu
    210                 215                 220

Ser Val Lys Gly Arg Phe Thr Ile Ser Arg Asp Asn Ala Lys Asn Thr
225                 230                 235                 240

Val Val Leu Gln Met Asn Ser Leu Lys Pro Glu Asp Thr Ala Leu Tyr
                245                 250                 255

Tyr Cys Ala Ala Asp Arg Lys Ser Val Met Ser Ile Arg Pro Asp Tyr
            260                 265                 270

Trp Gly Gln Gly Thr Gln Val Thr Val Ser Ser Thr Ser Thr Thr Thr
        275                 280                 285

Pro Ala Pro Arg Pro Pro Thr Pro Ala Pro Thr Ile Ala Ser Gln Pro
    290                 295                 300

Leu Ser Leu Arg Pro Glu Ala Cys Arg Pro Ala Ala Gly Gly Ala Val
305                 310                 315                 320

His Thr Arg Gly Leu Asp Phe Ala Cys Asp Ile Tyr Ile Trp Ala Pro
                325                 330                 335

Leu Ala Gly Thr Cys Gly Val Leu Leu Leu Ser Leu Val Ile Thr Leu
            340                 345                 350

Tyr Cys Lys Arg Gly Arg Lys Lys Leu Leu Tyr Ile Phe Lys Gln Pro
        355                 360                 365

Phe Met Arg Pro Val Gln Thr Thr Gln Glu Glu Asp Gly Cys Ser Cys
```

```
                370                 375                 380
Arg Phe Pro Glu Glu Glu Gly Gly Cys Glu Leu Arg Val Lys Phe
385                 390                 395                 400

Ser Arg Ser Ala Asp Ala Pro Ala Tyr Gln Gln Gly Gln Asn Gln Leu
                405                 410                 415

Tyr Asn Glu Leu Asn Leu Gly Arg Arg Glu Glu Tyr Asp Val Leu Asp
                420                 425                 430

Lys Arg Arg Gly Arg Asp Pro Glu Met Gly Gly Lys Pro Arg Arg Lys
        435                 440                 445

Asn Pro Gln Glu Gly Leu Tyr Asn Glu Leu Gln Lys Asp Lys Met Ala
        450                 455                 460

Glu Ala Tyr Ser Glu Ile Gly Met Lys Gly Glu Arg Arg Arg Gly Lys
465                 470                 475                 480

Gly His Asp Gly Leu Tyr Gln Gly Leu Ser Thr Ala Thr Lys Asp Thr
                485                 490                 495

Tyr Asp Ala Leu His Met Gln Ala Leu Pro Pro Arg
                500                 505

<210> SEQ ID NO 268
<211> LENGTH: 493
<212> TYPE: PRT
<213> ORGANISM: Artificial Sequence
<220> FEATURE:
<223> OTHER INFORMATION: GSI5024 CAR

<400> SEQUENCE: 268

Met Ala Leu Pro Val Thr Ala Leu Leu Pro Leu Ala Leu Leu Leu
1               5                   10                  15

His Ala Ala Arg Pro Glu Val Gln Leu Val Glu Ser Gly Gly Gly Leu
                20                  25                  30

Val Gln Ala Gly Gly Ser Leu Arg Leu Ser Cys Ala Ala Ser Gly Arg
            35                  40                  45

Thr Phe Thr Met Gly Trp Phe Arg Gln Ala Pro Gly Lys Glu Arg Glu
    50                  55                  60

Phe Val Ala Ala Ile Ser Leu Ser Pro Thr Leu Ala Tyr Tyr Ala Glu
65                  70                  75                  80

Ser Val Lys Gly Arg Phe Thr Ile Ser Arg Asp Asn Ala Lys Asn Thr
                85                  90                  95

Val Val Leu Gln Met Asn Ser Leu Lys Pro Glu Asp Thr Ala Leu Tyr
                100                 105                 110

Tyr Cys Ala Ala Asp Arg Lys Ser Val Met Ser Ile Arg Pro Asp Tyr
            115                 120                 125

Trp Gly Gln Gly Thr Gln Val Thr Val Ser Ser Gly Gly Gly Gly Ser
    130                 135                 140

Gly Gly Gly Gly Ser Gln Val Lys Leu Glu Glu Ser Gly Gly Gly Leu
145                 150                 155                 160

Val Gln Ala Gly Arg Ser Leu Arg Leu Ser Cys Ala Ala Ser Glu His
                165                 170                 175

Thr Phe Ser Ser His Val Met Gly Trp Phe Arg Gln Ala Pro Gly Lys
                180                 185                 190

Glu Arg Glu Ser Val Ala Val Ile Gly Trp Arg Asp Ile Ser Thr Ser
            195                 200                 205

Tyr Ala Asp Ser Val Lys Gly Arg Phe Thr Ile Ser Arg Asp Asn Ala
    210                 215                 220

Lys Lys Thr Leu Tyr Leu Gln Met Asn Ser Leu Lys Pro Glu Asp Thr
```

```
                225                 230                 235                 240
Ala Val Tyr Tyr Cys Ala Ala Arg Arg Ile Asp Ala Ala Asp Phe Asp
                245                 250                 255

Ser Trp Gly Gln Gly Thr Gln Val Thr Val Ser Ser Thr Ser Thr Thr
                260                 265                 270

Thr Pro Ala Pro Arg Pro Pro Thr Pro Ala Pro Thr Ile Ala Ser Gln
                275                 280                 285

Pro Leu Ser Leu Arg Pro Glu Ala Cys Arg Pro Ala Ala Gly Gly Ala
                290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
                340                 345                 350

Pro Phe Met Arg Pro Val Gln Thr Thr Gln Glu Glu Asp Gly Cys Ser
                355                 360                 365

Cys Arg Phe Pro Glu Glu Glu Glu Gly Gly Cys Glu Leu Arg Val Lys
                370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
                420                 425                 430

Lys Asn Pro Gln Glu Gly Leu Tyr Asn Glu Leu Gln Lys Asp Lys Met
                435                 440                 445

Ala Glu Ala Tyr Ser Glu Ile Gly Met Lys Gly Glu Arg Arg Arg Gly
                450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490

<210> SEQ ID NO 269
<211> LENGTH: 498
<212> TYPE: PRT
<213> ORGANISM: Artificial Sequence
<220> FEATURE:
<223> OTHER INFORMATION: GSI5025 CAR

<400> SEQUENCE: 269

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
                20                  25                  30

Val Gln Ala Gly Gly Ser Leu Arg Leu Ser Cys Ala Ala Ser Gly Arg
                35                  40                  45

Thr Phe Thr Met Gly Trp Phe Arg Gln Ala Pro Gly Lys Glu Arg Glu
                50                  55                  60

Phe Val Ala Ala Ile Ser Leu Ser Pro Thr Leu Ala Tyr Tyr Ala Glu
65                  70                  75                  80

Ser Val Lys Gly Arg Phe Thr Ile Ser Arg Asp Asn Ala Lys Asn Thr
                85                  90                  95

Val Val Leu Gln Met Asn Ser Leu Lys Pro Glu Asp Thr Ala Leu Tyr
```

```
            100                 105                 110
Tyr Cys Ala Ala Asp Arg Lys Ser Val Met Ser Ile Arg Pro Asp Tyr
            115                 120                 125
Trp Gly Gln Gly Thr Gln Val Thr Val Ser Ser Gly Gly Gly Gly Ser
            130                 135                 140
Gly Gly Gly Gly Ser Gly Gly Gly Ser Gln Val Lys Leu Glu Glu
145                 150                 155                 160
Ser Gly Gly Gly Leu Val Gln Ala Gly Arg Ser Leu Arg Leu Ser Cys
                165                 170                 175
Ala Ala Ser Glu His Thr Phe Ser Ser His Val Met Gly Trp Phe Arg
            180                 185                 190
Gln Ala Pro Gly Lys Glu Arg Glu Ser Val Ala Val Ile Gly Trp Arg
            195                 200                 205
Asp Ile Ser Thr Ser Tyr Ala Asp Ser Val Lys Gly Arg Phe Thr Ile
            210                 215                 220
Ser Arg Asp Asn Ala Lys Lys Thr Leu Tyr Leu Gln Met Asn Ser Leu
225                 230                 235                 240
Lys Pro Glu Asp Thr Ala Val Tyr Tyr Cys Ala Ala Arg Arg Ile Asp
                245                 250                 255
Ala Ala Asp Phe Asp Ser Trp Gly Gln Gly Thr Gln Val Thr Val Ser
            260                 265                 270
Ser Thr Ser Thr Thr Thr Pro Ala Pro Arg Pro Pro Thr Pro Ala Pro
            275                 280                 285
Thr Ile Ala Ser Gln Pro Leu Ser Leu Arg Pro Glu Ala Cys Arg Pro
            290                 295                 300
Ala Ala Gly Gly Ala Val His Thr Arg Gly Leu Asp Phe Ala Cys Asp
305                 310                 315                 320
Ile Tyr Ile Trp Ala Pro Leu Ala Gly Thr Cys Gly Val Leu Leu Leu
                325                 330                 335
Ser Leu Val Ile Thr Leu Tyr Cys Lys Arg Gly Arg Lys Lys Leu Leu
                340                 345                 350
Tyr Ile Phe Lys Gln Pro Phe Met Arg Pro Val Gln Thr Thr Gln Glu
            355                 360                 365
Glu Asp Gly Cys Ser Cys Arg Phe Pro Glu Glu Glu Glu Gly Gly Cys
370                 375                 380
Glu Leu Arg Val Lys Phe Ser Arg Ser Ala Asp Ala Pro Ala Tyr Gln
385                 390                 395                 400
Gln Gly Gln Asn Gln Leu Tyr Asn Glu Leu Asn Leu Gly Arg Arg Glu
                405                 410                 415
Glu Tyr Asp Val Leu Asp Lys Arg Arg Gly Arg Asp Pro Glu Met Gly
            420                 425                 430
Gly Lys Pro Arg Arg Lys Asn Pro Gln Glu Gly Leu Tyr Asn Glu Leu
            435                 440                 445
Gln Lys Asp Lys Met Ala Glu Ala Tyr Ser Glu Ile Gly Met Lys Gly
            450                 455                 460
Glu Arg Arg Arg Gly Lys Gly His Asp Gly Leu Tyr Gln Gly Leu Ser
465                 470                 475                 480
Thr Ala Thr Lys Asp Thr Tyr Asp Ala Leu His Met Gln Ala Leu Pro
                485                 490                 495
Pro Arg

<210> SEQ ID NO 270
<211> LENGTH: 503
```

<212> TYPE: PRT
<213> ORGANISM: Artificial Sequence
<220> FEATURE:
<223> OTHER INFORMATION: GSI5026 CAR

<400> SEQUENCE: 270

```
Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Ala Gly Gly Ser Leu Arg Leu Ser Cys Ala Ala Ser Gly Arg
        35                  40                  45

Thr Phe Thr Met Gly Trp Phe Arg Gln Ala Pro Gly Lys Glu Arg Glu
    50                  55                  60

Phe Val Ala Ala Ile Ser Leu Ser Pro Thr Leu Ala Tyr Tyr Ala Glu
65                  70                  75                  80

Ser Val Lys Gly Arg Phe Thr Ile Ser Arg Asp Asn Ala Lys Asn Thr
                85                  90                  95

Val Val Leu Gln Met Asn Ser Leu Lys Pro Glu Asp Thr Ala Leu Tyr
            100                 105                 110

Tyr Cys Ala Ala Asp Arg Lys Ser Val Met Ser Ile Arg Pro Asp Tyr
        115                 120                 125

Trp Gly Gln Gly Thr Gln Val Thr Val Ser Ser Gly Gly Gly Gly Ser
    130                 135                 140

Gly Gly Gly Gly Ser Gly Gly Gly Ser Gly Gly Gly Gly Ser Gln
145                 150                 155                 160

Val Lys Leu Glu Glu Ser Gly Gly Leu Val Gln Ala Gly Arg Ser
                165                 170                 175

Leu Arg Leu Ser Cys Ala Ala Ser Glu His Thr Phe Ser Ser His Val
            180                 185                 190

Met Gly Trp Phe Arg Gln Ala Pro Gly Lys Glu Arg Glu Ser Val Ala
        195                 200                 205

Val Ile Gly Trp Arg Asp Ile Ser Thr Ser Tyr Ala Asp Ser Val Lys
    210                 215                 220

Gly Arg Phe Thr Ile Ser Arg Asp Asn Ala Lys Lys Thr Leu Tyr Leu
225                 230                 235                 240

Gln Met Asn Ser Leu Lys Pro Glu Asp Thr Ala Val Tyr Tyr Cys Ala
                245                 250                 255

Ala Arg Arg Ile Asp Ala Ala Asp Phe Asp Ser Trp Gly Gln Gly Thr
            260                 265                 270

Gln Val Thr Val Ser Ser Thr Thr Thr Pro Ala Pro Arg Pro
        275                 280                 285

Pro Thr Pro Ala Pro Thr Ile Ala Ser Gln Pro Leu Ser Leu Arg Pro
    290                 295                 300

Glu Ala Cys Arg Pro Ala Ala Gly Gly Ala Val His Thr Arg Gly Leu
305                 310                 315                 320

Asp Phe Ala Cys Asp Ile Tyr Ile Trp Ala Pro Leu Ala Gly Thr Cys
            325                 330                 335

Gly Val Leu Leu Leu Ser Leu Val Ile Thr Leu Tyr Cys Lys Arg Gly
        340                 345                 350

Arg Lys Lys Leu Leu Tyr Ile Phe Lys Gln Pro Phe Met Arg Pro Val
    355                 360                 365

Gln Thr Thr Gln Glu Glu Asp Gly Cys Ser Cys Arg Phe Pro Glu Glu
370                 375                 380
```

Glu Glu Gly Gly Cys Glu Leu Arg Val Lys Phe Ser Arg Ser Ala Asp
385                 390                 395                 400

Ala Pro Ala Tyr Gln Gln Gly Gln Asn Gln Leu Tyr Asn Glu Leu Asn
            405                 410                 415

Leu Gly Arg Arg Glu Glu Tyr Asp Val Leu Asp Lys Arg Arg Gly Arg
            420                 425                 430

Asp Pro Glu Met Gly Gly Lys Pro Arg Arg Lys Asn Pro Gln Glu Gly
        435                 440                 445

Leu Tyr Asn Glu Leu Gln Lys Asp Lys Met Ala Glu Ala Tyr Ser Glu
    450                 455                 460

Ile Gly Met Lys Gly Glu Arg Arg Arg Gly Lys Gly His Asp Gly Leu
465                 470                 475                 480

Tyr Gln Gly Leu Ser Thr Ala Thr Lys Asp Thr Tyr Asp Ala Leu His
            485                 490                 495

Met Gln Ala Leu Pro Pro Arg
            500

<210> SEQ ID NO 271
<211> LENGTH: 1467
<212> TYPE: DNA
<213> ORGANISM: Artificial Sequence
<220> FEATURE:
<223> OTHER INFORMATION: GSI5021 CAR

<400> SEQUENCE: 271

```
atggctctgc ccgtcaccgc tctgctgctg cctctggctc tgctgctgca cgctgctcgc      60
cctcaggtca aactggaaga atctggcgga ggcctggtgc aggcaggacg agcctgcgc      120
ctgagctgcg cagcatccga gcacaccttc agctcccacg tgatgggctg gtttcggcag     180
gccccaggca aggagagaga gagcgtggcc gtgatcggct ggagggacat ctccacatct     240
tacgccgatt ccgtgaaggg ccggttcacc atcagccggg acaacgccaa gaagacactg     300
tatctgcaga tgaacagcct gaagcccgag gacaccgccg tgtactattg cgcagcaagg     360
agaatcgacg cagcagactt tgattcctgg ggccagggca cccaggtgac agtgtctagc     420
ggaggaggag gatctgaggt gcagctggtg gagagcggag gcggcctggt gcaggccgga     480
ggctctctga ggctgagctg tgcagcatcc ggaagaacct tcacaatggg ctggtttagg     540
caggcaccag gaaaggagag ggagttcgtg gcagcaatca gcctgtcccc taccctggcc     600
tactatgccg agagcgtgaa gggcaggttt accatctccc gcgataacgc caagaataca     660
gtggtgctgc agatgaactc cctgaaacct gaggacacag ccctgtacta ttgtgccgcc     720
gatcggaaga gcgtgatgag cattagacca gactattggg gcagggaac acaggtgacc     780
gtgagcagca ctagtaccac gacgccagcg ccgcgaccac caacaccggc gcccaccatc     840
gcgtcgcagc ccctgtccct gcgcccagag gcgtgccggc cagcggcggg gggcgcagtg     900
cacacgaggg ggctggactt cgcctgtgat atctacatct gggcgccctt ggccgggact     960
tgtgggtcc ttctcctgtc actggttatc ccctttact gcaaacgggg cagaaagaaa     1020
ctcctgtata tattcaaaca accatttatg agaccagtac aaactactca agaggaagat     1080
ggctgtagct ccgatttcc agaagaagaa gaaggaggat gtgaactgag agtgaagttc     1140
agcaggagcg cagacgcccc cgcgtaccag cagggccaga accagctcta taacgagctc     1200
aatctaggac gaagagagga gtacgatgtt ttgacaaga cgtggccg ggaccctgag     1260
atgggggaa agccgagaag gaagaaccct caggaaggcc tgtacaatga actgcagaaa     1320
gataagatgg cggaggccta cagtgagatt gggatgaaag gcgagcgccg gaggggcaag     1380
```

```
gggcacgatg gcctttacca gggtctcagt acagccacca aggacaccta cgacgccctt    1440
cacatgcagg ccctgccccc tcgctaa                                       1467

<210> SEQ ID NO 272
<211> LENGTH: 1497
<212> TYPE: DNA
<213> ORGANISM: Artificial Sequence
<220> FEATURE:
<223> OTHER INFORMATION: GSI5022 CAR

<400> SEQUENCE: 272
atggctctgc ctgtcaccgc tctgctgctg cctctggctc tgctgctgca cgctgctcgc      60
cctcaggtca aactggaaga agtgggggga ggcctggtgc aggcaggacg gagcctgcgc     120
ctgagctgcg cagcatccga gcacaccttc agctcccacg tgatgggctg gtttcggcag     180
gccccaggca aggagagaga gtccgtggcc gtgatcggct ggagggacat ctccacatct     240
tacgccgatt ctgtgaaggg ccggttcacc atcagcagag acaacgccaa gaagacactg     300
tatctgcaga tgaatagcct gaagcccgag gacaccgccg tgtactattg cgcagcaagg     360
agaatcgacg cagcagactt tgattcctgg ggccagggca cccaggtgac agtgtctagc     420
ggaggaggag gatctggagg aggaggaagc ggaggaggag gatccgaggt gcagctggtg     480
gagtctggag gcggcctggt gcaggccgga ggctctctga gctgagctg tgcagcatcc     540 ggaagaacct tcacaatggg ctggtttagg caggcaccag aaaggagag ggagttcgtg     600 gcagcaatca gcctgtcccc taccctggcc tactatgccg agtccgtgaa gggcaggttt     660
accatctctc gcgataacgc caagaataca gtggtgctgc agatgaacag cctgaaacct     720
gaggacacag ccctgtacta ttgtgccgcc gatcggaaga gcgtgatgag cattagaccc     780
gattattggg gacagggcac acaggtgaca gtgagtagca ctagtaccac gacgccagcg     840
ccgcgaccac caacaccggc gcccaccatc gcgtcgcagc ccctgtccct gcgcccagag     900
gcgtgccggc cagcggcggg gggcgcagtg cacgagggg gctggactt cgcctgtgat     960 atctacatct gggcgccctt ggccgggact tgtggggtcc ttctcctgtc actggttatc    1020 acccttact gcaaacgggg cagaaagaaa ctcctgtata tattcaaaca accatttatg    1080
agaccagtac aaactactca agaggaagat ggctgtagct gccgatttcc agaagaagaa    1140
gaaggaggat gtgaactgag agtgaagttc agcaggagcg cagacgcccc cgcgtaccag    1200
cagggccaga accagctcta taacgagctc aatctaggac gaagagagga gtacgatgtt    1260
ttggacaaga cgtggccg ggaccctgag atgggggaa agccgagaag gaagaaccct    1320
caggaaggcc tgtacaatga actgcagaaa gataagatgg cggaggccta cagtgagatt    1380
gggatgaaag gcgagcgccg gaggggcaag ggcacgatg gcctttacca gggtctcagt    1440
acagccacca aggacaccta cgacgccctt cacatgcagg ccctgccccc tcgctaa       1497

<210> SEQ ID NO 273
<211> LENGTH: 1527
<212> TYPE: DNA
<213> ORGANISM: Artificial Sequence
<220> FEATURE:
<223> OTHER INFORMATION: GSI5023 CAR

<400> SEQUENCE: 273
atggctctgc ccgtcaccgc actgctgctg cctctggctc tgctgctgca cgccgcaaga      60
ccacaggtca aactggaaga atcaggagga ggcctggtgc aggcaggacg gagcctgcgc     120
```

```
ctgagctgcg cagcatccga gcacaccttc agctcccacg tgatgggctg gtttcggcag      180
gccccaggca aggagagaga gtccgtggcc gtgatcggct ggaggacat  ctccacatct      240 tacgccgatt ccgtgaaggg ccggttcacc atcagccggg acaacgccaa gaagacactg      300
tatctgcaga tgaacagcct gaagcccgag gacaccgccg tgtactattg cgcagcaagg      360
agaatcgacg cagcagactt tgatagctgg ggccagggca cccaggtgac agtgtctagc      420
ggaggaggag gatctggagg aggaggaagc ggaggaggag gaagcggcgg cggcggctct      480
ggcggcggcg gcagcgaggt gcagctggtg gagagcggcg gcggcctggt gcaggccggc      540
ggctctctga ggctgagctg tgcagcatcc ggaagaacct tcacaatggg ctggtttagg      600
caggcaccag gaaaggagag ggagttcgtg gcagcaatca gcctgtcccc taccctggcc      660
tactatgccg agagcgtgaa gggcaggttt accatctccc gcgataacgc caagaataca      720
gtggtgttac aaatgaacag cctgaaacct gaggacacag ccctgtacta ttgtgccgcc      780
gatcggaaga gcgtgatgag cattagaccc gattattggg ggcagggggac acaggtgacc      840 gtgagcagca ctagtaccac gacgccagcg ccgcgaccac caacaccggc gcccaccatc      900
gcgtcgcagc ccctgtccct gcgcccagag gcgtgccggc cagcggcggg gggcgcagtg      960
cacacgaggg ggctggactt cgcctgtgat atctacatct gggcgccctt ggccgggact     1020 tgtgggggtcc ttctcctgtc actggttatc acccctttact gcaaacgggg cagaaagaaa     1080
ctcctgtata tattcaaaca accatttatg agaccagtac aaactactca agaggaagat     1140
ggctgtagct gccgatttcc agaagaagaa gaaggaggat gtgaactgag agtgaagttc     1200
agcaggagcg cagacgcccc cgcgtaccag cagggccaga accagctcta taacgagctc     1260
aatctaggac gaagagagga gtacgatgtt ttggacaaga acgtggccg  ggaccctgag     1320 atgggggaa  agccgagaag gaagaaccct caggaaggcc tgtacaatga actgcagaaa     1380
gataagatgg cggaggccta cagtgagatt gggatgaaag cgagcgccg  gaggggcaag     1440 gggcacgatg gcctttacca gggtctcagt acagccacca aggacaccta cgacgcccct     1500
cacatgcagg ccctgccccc tcgctaa                                         1527
```

<210> SEQ ID NO 274
<211> LENGTH: 1482
<212> TYPE: DNA
<213> ORGANISM: Artificial Sequence
<220> FEATURE:
<223> OTHER INFORMATION: GSI5024 CAR

<400> SEQUENCE: 274

```
atggctctgc ctgtgaccgc actgctgctg cctctggctc tgctgctgca cgccgcacga       60
cctgaagtcc agctggtgga atccggggga ggcctggtgc aggcaggagg ctccctgagg     120
ctgtcttgcg cagcaagcgg aagaaccttc acaatgggct ggtttaggca ggcaccagga     180
aaggagaggg agttcgtggc cgccatctcc ctgtctccta ccctggccta ctatgccgag     240
agcgtgaagg gcaggtttac catctcccgc gacaacgcca agaatacagt ggtgctgcag     300
atgaacagcc tgaagccaga ggacacagcc ctgtactatt gcgccgccga tcggaagtct     360
gtgatgagca tcagacccga ttactggggc cagggcaccc aggtgacagt gagctccgga     420
ggaggaggat ccggcggagg aggctctcag gtgaagctgg aggagtccgg aggcggcctg     480
gtgcaggccg acggtccct  gagactgtct tgtgccgcca gcagcacac  cttctctagc     540 cacgtgatgg gatggttcag gcaggcacct ggaaaggaga gggagtccgt ggcagtgatc     600
ggatggaggg acatcagcac atcctacgcc gattctgtga agggccggtt caccatcagc     660
```

```
agagacaacg ccaagaagac actgtattta caaatgaaca gcctgaagcc cgaggatacc    720
gccgtgtact attgtgccgc ccggcggatt gacgccgcag actttgactc atggggcag    780 ggaactcagg tgaccgtgtc ctcaactagt accacgacgc cagcgccgcg accaccaaca    840
ccggcgccca ccatcgcgtc gcagcccctg tccctgcgcc cagaggcgtg ccggccagcg    900
gcggggggcg cagtgcacac gagggggctg gacttcgcct gtgatatcta catctgggcg    960
cccttggccg ggacttgtgg ggtccttctc ctgtcactgg ttatcaccct ttactgcaaa   1020
cggggcagaa agaaactcct gtatatattc aaacaaccat ttatgagacc agtacaaact   1080
actcaagagg aagatggctg tagctgccga tttccagaag aagaagaagg aggatgtgaa   1140
ctgagagtga agttcagcag gagcgcagac gcccccgcgt accagcaggg ccagaaccag   1200
ctctataacg agctcaatct aggacgaaga gaggagtacg atgttttgga caagagacgt   1260
ggccgggacc ctgagatggg gggaaagccg agaaggaaga accctcagga aggcctgtac   1320
aatgaactgc agaaagataa gatggcggag gcctacagtg agattgggat gaaaggcgag   1380
cgccggaggg gcaaggggca cgatggcctt taccagggtc tcagtacagc caccaaggac   1440
acctacgacg cccttcacat gcaggccctg cccctcgct aa                        1482
```

<210> SEQ ID NO 275
<211> LENGTH: 1497
<212> TYPE: DNA
<213> ORGANISM: Artificial Sequence
<220> FEATURE:
<223> OTHER INFORMATION: GSI5025 CAR

<400> SEQUENCE: 275

```
atggccctgc ctgtcaccgc tctgctgctg cccctggccc tgctgctgca cgccgcacgc     60
cctgaggtcc agctggtcga gtccggggga ggcctggtgc aggcaggagg ctccctgagg    120
ctgtcttgcg cagcaagcgg aagaaccttc acaatgggct ggtttaggca ggcaccagga    180
aaggagaggg agttcgtggc cgccatctcc ctgtctccta ccctggccta ctatgccgag    240
tccgtgaagg gcaggtttac catctctcgc gacaacgcca agaatacagt ggtgctgcag    300
atgaactccc tgaagccaga ggacacagcc ctgtactatt gcgccgccga tcggaagtct    360
gtgatgagca tcagacccga ttactgggc cagggcaccc aggtgacagt gagctccgga    420
ggaggaggat ccggcggagg aggctctggc ggcggcggca gccaggtgaa gctggaggag    480
agcggaggcg gcctggtgca ggccggacgg tccctgagac tgtcttgtgc cgccagcgag    540
cacaccttct ctagccacgt gatgggatgg ttcaggcagg cacctggaaa ggagagggag    600
tctgtggccg tgatcggctg gagggacatc agcacatcct acgccgatag cgtgaagggc    660
cggttcacca tctccagaga caacgccaag aagacactgt atctgcagat gaatagcctg    720
aagcccgagg ataccgccgt gtactattgt gccgcccggc ggattgacgc cgcagatttt    780
gattcttggg gcagggaac tcaggtgacc gtgtcctcaa ctagtaccac gacgccagcg    840
ccgcgaccac caacaccggc gcccaccatc gcgtcgcagc cctgtccct gcgcccagag    900 gcgtgccggc cagcggcggg gggcgcagtg cacacgaggg ggctggactt cgcctgtgat    960
atctacatct gggcgccctt ggccgggact tgtggggtcc ttctcctgtc actggttatc   1020 acccttttact gcaaacgggg cagaaagaaa ctcctgtata tattcaaaca accatttatg   1080
agaccagtac aaactactca agaggaagat ggctgtagct gccgatttcc agaagaagaa   1140
gaaggaggat gtgaactgag agtgaagttc agcaggagcg cagacgcccc cgcgtaccag   1200
```

```
cagggccaga accagctcta taacgagctc aatctaggac gaagagagga gtacgatgtt    1260
ttggacaaga gacgtggccg ggaccctgag atgggggaa agccgagaag gaagaaccct    1320
caggaaggcc tgtacaatga actgcagaaa gataagatgg cggaggccta cagtgagatt    1380
gggatgaaag gcgagcgccg gaggggcaag gggcacgatg gcctttacca gggtctcagt    1440
acagccacca aggacaccta cgacgccctt cacatgcagg ccctgccccc tcgctaa     1497

<210> SEQ ID NO 276
<211> LENGTH: 1512
<212> TYPE: DNA
<213> ORGANISM: Artificial Sequence
<220> FEATURE:
<223> OTHER INFORMATION: GSI5026 CAR

<400> SEQUENCE: 276
atggctctgc ctgtgaccgc cctgctgctg cccctggccc tgctgctgca cgccgcacga     60
cctgaagtcc agctggtgga atctggcgga ggcctggtgc aggcaggagg ctccctgagg    120
ctgtcttgcg cagcaagcgg aagaaccttc acaatgggct ggtttaggca ggcaccagga    180
aaggagaggg agttcgtggc cgccatctcc ctgtctccta ccctggccta ctatgccgag    240
tctgtgaagg gcaggtttac catcagccgc gacaacgcca agaatacagt ggtgctgcag    300
atgaacagcc tgaagccaga ggacacagcc ctgtactatt gcgccgccga tcggaagtct    360
gtgatgagca tcagacccga ttactggggc cagggcaccc aggtgacagt gagctccgga    420
ggaggaggat ccggcggagg aggctctggc ggcggcggct ccggcggcgg cggctcccag    480
gtgaagctgg aggagtccgg aggcggcctg gtgcaggccg acggtccct gagactgtct    540 tgtgccgcca gcgagcacac cttctctagc cacgtgatgg gatggttcag gcaggcacct    600
ggaaaggaga gggagagcgt ggcagtgatc ggatggaggg acatcagcac atcctacgcc    660
gattccgtga agggccggtt caccatcagc cgggacaacg ccaagaagac actgtattta    720
caaatgaaca gcctgaagcc cgaggatacc gccgtgtact attgtgccgc ccggcggatt    780
gatgccgcag actttgatag ttggggacag gggactcagg tcaccgtcag cagcactagt    840
accacgacgc cagcgccgcg accaccaaca ccggcgccca ccatcgcgtc gcagcccctg    900
tccctgcgcc cagaggcgtg ccggccagcg gcggggggcg cagtgcacac gagggggctg    960
gacttcgcct gtgatatcta catctggcg cccttggccg ggacttgtgg ggtccttctc    1020
ctgtcactgg ttatcaccct ttactgcaaa cggggcagaa agaaactcct gtatatattc    1080
aaacaaccat ttatgagacc agtacaaact actcaagagg aagatggctg tagctgccga    1140
tttccagaag aagaagaagg aggatgtgaa ctgagagtga agttcagcag gagcgcagac    1200
gcccccgcgt accagcaggg ccagaaccag ctctataacg agctcaatct aggacgaaga    1260
gaggagtacg atgttttgga caagagacgt ggccgggacc ctgagatggg gggaaagccg    1320
agaaggaaga accctcagga aggcctgtac aatgaactgc agaaagataa gatggcggag    1380
gcctacagtg agattgggat gaaaggcgag cgccggaggg gcaaggggca cgatggcctt    1440
taccagggtc tcagtacagc caccaaggac acctacgacg cccttcacat gcaggccctg    1500
ccccctcgct aa                                                       1512

<210> SEQ ID NO 277
<211> LENGTH: 768
<212> TYPE: PRT
<213> ORGANISM: Artificial Sequence
<220> FEATURE:
<223> OTHER INFORMATION: tandem BCMA, CD38 269A37346 38A37717 GSI5013
```

CARs

<400> SEQUENCE: 277

```
Met Ala Leu Pro Val Thr Ala Leu Leu Leu Pro Leu Ala Leu Leu Leu
1               5                   10                  15

His Ala Ala Arg Pro Val Asn Glu Val Gln Leu Val Glu Ser Gly Gly
            20                  25                  30

Gly Leu Val Gln Ala Gly Gly Ser Leu Arg Leu Ser Cys Ile Ala Thr
        35                  40                  45

Gly Lys Val Phe Ser Ile Tyr Asp Met Gly Trp Tyr Arg Gln Ala Pro
    50                  55                  60

Gly Lys Gln Arg Glu Leu Val Ala Glu Ile Thr Ser Ser Gly Thr Thr
65                  70                  75                  80

His Tyr Asp Asp Phe Val Ser Gly Arg Phe Thr Ile Ser Arg Asp Asn
                85                  90                  95

Ala Lys Asn Thr Val Tyr Leu Gln Met Asn Thr Leu Lys Ala Glu Asp
            100                 105                 110

Thr Ala Val Tyr Tyr Cys Arg Ala Asn His Val Phe Gly Gly Ser Tyr
        115                 120                 125

Trp Gly Gln Gly Thr Gln Val Thr Val Ser Ser Thr Arg Arg Met His
    130                 135                 140

Thr Ser Thr Thr Thr Pro Ala Pro Arg Pro Pro Thr Pro Ala Pro Thr
145                 150                 155                 160

Ile Ala Ser Gln Pro Leu Ser Leu Arg Pro Glu Ala Cys Arg Pro Ala
                165                 170                 175

Ala Gly Gly Ala Val His Thr Arg Gly Leu Asp Phe Ala Cys Asp Ile
            180                 185                 190

Tyr Ile Trp Ala Pro Leu Ala Gly Thr Cys Gly Val Leu Leu Leu Ser
        195                 200                 205

Leu Val Ile Thr Leu Tyr Cys Lys Arg Gly Arg Lys Lys Leu Leu Tyr
    210                 215                 220

Ile Phe Lys Gln Pro Phe Met Arg Pro Val Gln Thr Thr Gln Glu Glu
225                 230                 235                 240

Asp Gly Cys Ser Cys Arg Phe Pro Glu Glu Glu Gly Gly Cys Glu
                245                 250                 255

Leu Arg Val Lys Phe Ser Arg Ser Ala Asp Ala Pro Ala Tyr Gln Gln
                260                 265                 270

Gly Gln Asn Gln Leu Tyr Asn Glu Leu Asn Leu Gly Arg Arg Glu Glu
            275                 280                 285

Tyr Asp Val Leu Asp Lys Arg Arg Gly Arg Asp Pro Glu Met Gly Gly
        290                 295                 300

Lys Pro Arg Arg Lys Asn Pro Gln Glu Gly Leu Tyr Asn Glu Leu Gln
305                 310                 315                 320

Lys Asp Lys Met Ala Glu Ala Tyr Ser Glu Ile Gly Met Lys Gly Glu
                325                 330                 335

Arg Arg Arg Gly Lys Gly His Asp Gly Leu Tyr Gln Gly Leu Ser Thr
            340                 345                 350

Ala Thr Lys Asp Thr Tyr Asp Ala Leu His Met Gln Ala Leu Pro Pro
        355                 360                 365

Arg Gly Ser Gly Glu Gly Arg Gly Ser Leu Leu Thr Cys Gly Asp Val
    370                 375                 380

Glu Glu Asn Pro Gly Pro Gly Ser Met Ala Leu Pro Val Thr Ala Leu
385                 390                 395                 400
```

Leu Leu Pro Leu Ala Leu Leu Leu His Ala Ala Arg Pro Val Asn Arg
            405                 410                 415

Thr Arg Arg Met His Gln Val Gln Leu Val Glu Ser Gly Gly Gly Leu
            420                 425                 430

Val Gln Pro Gly Gly Ser Leu Arg Leu Ser Cys Glu Ala Ser Gly Phe
            435                 440                 445

Thr Leu Asp Tyr Tyr Ala Ile Gly Trp Phe Arg Gln Ala Pro Gly Lys
            450                 455                 460

Glu Arg Glu Gly Val Ile Cys Ile Ser Arg Ser Asp Gly Ser Thr Tyr
465                 470                 475                 480

Tyr Ala Asp Ser Val Lys Gly Arg Phe Thr Ile Ser Arg Asp Asn Ala
            485                 490                 495

Lys Lys Thr Val Tyr Leu Gln Met Ile Ser Leu Lys Pro Glu Asp Thr
            500                 505                 510

Ala Ala Tyr Tyr Cys Ala Ala Gly Ala Asp Cys Ser Gly Tyr Leu Arg
            515                 520                 525

Asp Tyr Glu Phe Arg Gly Gln Gly Thr Gln Val Thr Val Ser Ser Thr
            530                 535                 540

Ser Thr Thr Thr Pro Ala Pro Arg Pro Pro Thr Pro Ala Pro Thr Ile
545                 550                 555                 560

Ala Ser Gln Pro Leu Ser Leu Arg Pro Glu Ala Cys Arg Pro Ala Ala
            565                 570                 575

Gly Gly Ala Val His Thr Arg Gly Leu Asp Phe Ala Cys Asp Ile Tyr
            580                 585                 590

Ile Trp Ala Pro Leu Ala Gly Thr Cys Gly Val Leu Leu Leu Ser Leu
            595                 600                 605

Val Ile Thr Leu Tyr Cys Lys Arg Gly Arg Lys Lys Leu Leu Tyr Ile
            610                 615                 620

Phe Lys Gln Pro Phe Met Arg Pro Val Gln Thr Thr Gln Glu Glu Asp
625                 630                 635                 640

Gly Cys Ser Cys Arg Phe Pro Glu Glu Glu Glu Gly Gly Cys Glu Leu
            645                 650                 655

Arg Val Lys Phe Ser Arg Ser Ala Asp Ala Pro Ala Tyr Gln Gln Gly
            660                 665                 670

Gln Asn Gln Leu Tyr Asn Glu Leu Asn Leu Gly Arg Arg Glu Glu Tyr
            675                 680                 685

Asp Val Leu Asp Lys Arg Arg Gly Arg Asp Pro Glu Met Gly Gly Lys
            690                 695                 700

Pro Arg Arg Lys Asn Pro Gln Glu Gly Leu Tyr Asn Glu Leu Gln Lys
705                 710                 715                 720

Asp Lys Met Ala Glu Ala Tyr Ser Glu Ile Gly Met Lys Gly Glu Arg
            725                 730                 735

Arg Arg Gly Lys Gly His Asp Gly Leu Tyr Gln Gly Leu Ser Thr Ala
            740                 745                 750

Thr Lys Asp Thr Tyr Asp Ala Leu His Met Gln Ala Leu Pro Pro Arg
            755                 760                 765